US009323888B2

(12) United States Patent
Rava et al.

(10) Patent No.: US 9,323,888 B2
(45) Date of Patent: Apr. 26, 2016

(54) DETECTING AND CLASSIFYING COPY NUMBER VARIATION

(75) Inventors: Richard P. Rava, Redwood City, CA (US); Anupama Srinivasan, Redwood City, CA (US)

(73) Assignee: Verinata Health, Inc., San Diego, CA (US)

( * ) Notice: Subject to any disclaimer, the term of this patent is extended or adjusted under 35 U.S.C. 154(b) by 810 days.

(21) Appl. No.: 13/600,043

(22) Filed: Aug. 30, 2012

(65) Prior Publication Data

US 2013/0096011 A1 Apr. 18, 2013
US 2016/0070853 A9 Mar. 10, 2016

Related U.S. Application Data

(63) Continuation-in-part of application No. 13/555,037, filed on Jul. 20, 2012, which is a continuation-in-part of application No. 13/191,366, filed on Jul. 26, 2011, which is a continuation-in-part of application No. 12/958,352, filed on Dec. 1, 2010, application No. 13/600,043, which is a continuation-in-part of application No. 13/400,028, filed on Feb. 17, 2012, now abandoned, and a continuation-in-part of application No. 13/009,708, filed on Jan. 19, 2011, now Pat. No. 8,700,341, application No. 13/600,043, which is a continuation-in-part of application No. 13/445,778, filed on Apr. 12, 2012, application No. 13/600,043, which is a continuation-in-part of application No. 12/958,347, filed on Dec. 1, 2010, now abandoned, application No. 13/600,043, which is a continuation-in-part of application No. 12/958,356, filed on Dec. 1, 2010, now abandoned, application No. 13/600,043, which is a continuation-in-part of application No. 13/482,964, filed on May 29, 2012, now abandoned, which is a continuation-in-part of application No. 12/958,353, filed on Dec. 1, 2010, application No. 13/600,043, which is a continuation-in-part of application No. PCT/US2012/031625, filed on Mar. 30, 2012, application No. 13/600,043, which is a continuation-in-part of application No. 13/087,842, filed on Apr. 15, 2011, now Pat. No. 8,532,936.

(60) Provisional application No. 61/296,464, filed on Jan. 19, 2010, provisional application No. 61/474,362, filed on Apr. 12, 2011, provisional application No. 61/296,358, filed on Jan. 19, 2010, provisional application No. 61/407,017, filed on Oct. 26, 2010, provisional application No. 61/360,837, filed on Jul. 1, 2010, provisional application No. 61/455,849, filed on Oct. 26, 2010, provisional application No. 61/469,236, filed on Mar. 30, 2011.

(51) Int. Cl.
G06F 19/22 (2011.01)
G11C 17/00 (2006.01)
G06F 15/00 (2006.01)
C12Q 1/68 (2006.01)
G06F 19/24 (2011.01)

(52) U.S. Cl.
CPC .............. *G06F 19/22* (2013.01); *C12Q 1/6809* (2013.01); *C12Q 1/6869* (2013.01); *G06F 19/24* (2013.01); *C12Q 1/6883* (2013.01); *C12Q 1/6886* (2013.01); *C12Q 2537/16* (2013.01); *C12Q 2600/106* (2013.01)

(58) Field of Classification Search
None
See application file for complete search history.

(56) References Cited

U.S. PATENT DOCUMENTS

| | | |
|---|---|---|
| 5,888,740 A | 3/1999 | Han |
| 5,994,057 A | 11/1999 | Mansfield |
| 6,258,540 B1 | 7/2001 | Lo et al. |
| 6,403,315 B1 | 6/2002 | Drmanac |
| 6,440,706 B1 | 8/2002 | Vogelstein et al. |
| 6,555,315 B1 | 4/2003 | Short |

(Continued)

FOREIGN PATENT DOCUMENTS

| | | |
|---|---|---|
| CN | 100519761 | 7/2009 |
| CN | 101849236 | 9/2010 |

(Continued)

OTHER PUBLICATIONS

Ashoor, et al., "Chromosome-selective sequencing of maternal plasma cell-free DNA for first-trimester detection of trisomy 21 and trisomy 18", American Journal of Obstetrics and Gynecology, 2012, 22.

(Continued)

*Primary Examiner* — John S Brusca
(74) *Attorney, Agent, or Firm* — Weaver Austin Villeneuve & Sampson LLP

(57) ABSTRACT

The invention provides a method for determining copy number variations (CNV) of a sequence of interest in a test sample that comprises a mixture of nucleic acids that are known or are suspected to differ in the amount of one or more sequence of interest. The method comprises a statistical approach that accounts for accrued variability stemming from process-related, interchromosomal and inter-sequencing variability. The method is applicable to determining CNV of any fetal aneuploidy, and CNVs known or suspected to be associated with a variety of medical conditions. CNV that can be determined according to the method include trisomies and monosomies of any one or more of chromosomes 1-22, X and Y, other chromosomal polysomies, and deletions and/or duplications of segments of any one or more of the chromosomes, which can be detected by sequencing only once the nucleic acids of a test sample.

24 Claims, 88 Drawing Sheets

(56) References Cited

U.S. PATENT DOCUMENTS

| | | |
|---|---|---|
| 7,252,946 B2 | 8/2007 | Szasz |
| 7,332,277 B2 | 2/2008 | Dhallan |
| 7,645,576 B2 | 1/2010 | Lo et al. |
| 7,888,017 B2 | 2/2011 | Quake et al. |
| 8,137,912 B2 | 3/2012 | Kapur et al. |
| 8,195,415 B2 | 6/2012 | Fan et al. |
| 8,318,430 B2 | 11/2012 | Chuu et al. |
| 8,532,936 B2 | 9/2013 | Rava |
| 8,551,707 B2 | 10/2013 | Oeth et al. |
| 9,260,745 B2 | 2/2016 | Rava et al. |
| 2002/0142324 A1 | 10/2002 | Wang et al. |
| 2003/0044388 A1 | 3/2003 | Dennis et al. |
| 2003/0064368 A1 | 4/2003 | Sakai et al. |
| 2003/0194704 A1 | 10/2003 | Penn et al. |
| 2004/0209299 A1 | 10/2004 | Pinter et al. |
| 2005/0221341 A1 | 10/2005 | Shimkets et al. |
| 2006/0046258 A1 | 3/2006 | Lapidus et al. |
| 2006/0121452 A1 | 6/2006 | Dhallan |
| 2006/0134599 A1 | 6/2006 | Toner et al. |
| 2006/0178835 A1 | 8/2006 | Marks |
| 2006/0257895 A1 | 11/2006 | Pinkel et al. |
| 2006/0286558 A1 | 12/2006 | Novoradovskaya et al. |
| 2007/0087345 A1 | 4/2007 | Olson-Munoz et al. |
| 2007/0134658 A1 | 6/2007 | Bohmer et al. |
| 2007/0202525 A1 | 8/2007 | Quake et al. |
| 2007/0207466 A1 | 9/2007 | Cantor et al. |
| 2008/0020390 A1 | 1/2008 | Mitchell et al. |
| 2008/0050739 A1 | 2/2008 | Stoughton et al. |
| 2008/0064098 A1 | 3/2008 | Allickson |
| 2008/0070792 A1 | 3/2008 | Stoughton et al. |
| 2008/0138809 A1 | 6/2008 | Kapur et al. |
| 2008/0193927 A1 | 8/2008 | Mann et al. |
| 2008/0220422 A1 | 9/2008 | Shoemaker |
| 2008/0299562 A1 | 12/2008 | Oeth et al. |
| 2009/0026082 A1 | 1/2009 | Rothberg et al. |
| 2009/0029377 A1 | 1/2009 | Lo et al. |
| 2009/0087847 A1 | 4/2009 | Lo et al. |
| 2009/0098547 A1 | 4/2009 | Ghosh |
| 2009/0117542 A1 | 5/2009 | Maybruck et al. |
| 2009/0170114 A1 | 7/2009 | Quake et al. |
| 2009/0215042 A1 | 8/2009 | Sella-Tavor et al. |
| 2009/0270601 A1 | 10/2009 | Benner et al. |
| 2009/0291443 A1 | 11/2009 | Stoughton et al. |
| 2009/0299645 A1 | 12/2009 | Colby et al. |
| 2009/0307181 A1 | 12/2009 | Colby et al. |
| 2009/0317817 A1 | 12/2009 | Oeth et al. |
| 2009/0317818 A1 | 12/2009 | Ehrich et al. |
| 2010/0068711 A1 | 3/2010 | Umansky et al. |
| 2010/0093835 A1 | 4/2010 | McSwiggen et al. |
| 2010/0112575 A1 | 5/2010 | Fan et al. |
| 2010/0112590 A1 | 5/2010 | Lo et al. |
| 2010/0138165 A1 | 6/2010 | Fan et al. |
| 2010/0167954 A1 | 7/2010 | Earnshaw et al. |
| 2010/0184043 A1 | 7/2010 | Mitchell et al. |
| 2010/0184075 A1 | 7/2010 | Cantor et al. |
| 2010/0216151 A1 | 8/2010 | Lapidus et al. |
| 2010/0216153 A1 | 8/2010 | Lapidus et al. |
| 2010/0285537 A1 | 11/2010 | Zimmermann |
| 2011/0003293 A1 | 1/2011 | Stoughton et al. |
| 2011/0105353 A1 | 5/2011 | Lo et al. |
| 2011/0118145 A1 | 5/2011 | Akmaev et al. |
| 2011/0177517 A1 | 7/2011 | Rava et al. |
| 2011/0201507 A1 | 8/2011 | Rava et al. |
| 2011/0224087 A1 | 9/2011 | Quake et al. |
| 2011/0230358 A1 | 9/2011 | Rava |
| 2011/0245085 A1 | 10/2011 | Rava et al. |
| 2011/0312503 A1 | 12/2011 | Chuu et al. |
| 2011/0319272 A1 | 12/2011 | Fan et al. |
| 2012/0010085 A1 | 1/2012 | Rava et al. |
| 2012/0034603 A1 | 2/2012 | Oliphant et al. |
| 2012/0034685 A1 | 2/2012 | Sparks et al. |
| 2012/0040859 A1 | 2/2012 | Sparks et al. |
| 2012/0094849 A1 | 4/2012 | Rava et al. |
| 2012/0100548 A1 | 4/2012 | Rava et al. |
| 2012/0149582 A1 | 6/2012 | Rava et al. |
| 2012/0149583 A1 | 6/2012 | Rava et al. |
| 2012/0165203 A1 | 6/2012 | Quake et al. |
| 2012/0184449 A1 | 7/2012 | Hixon et al. |
| 2012/0208710 A1 | 8/2012 | Fan et al. |
| 2012/0214678 A1 | 8/2012 | Rava et al. |
| 2012/0214680 A1 | 8/2012 | Oeth et al. |
| 2012/0237928 A1 | 9/2012 | Rava et al. |
| 2012/0238738 A1 | 9/2012 | Hendrickson |
| 2012/0270739 A1 | 10/2012 | Rava et al. |
| 2013/0029852 A1 | 1/2013 | Rava et al. |
| 2013/0034546 A1 | 2/2013 | Rava et al. |
| 2013/0096011 A1 | 4/2013 | Rava et al. |
| 2014/0038830 A1 | 2/2014 | Srinivasan et al. |
| 2014/0199691 A1 | 7/2014 | Chuu et al. |

FOREIGN PATENT DOCUMENTS

| | | |
|---|---|---|
| EP | 2 513 339 | 10/2012 |
| EP | 1981995 | 7/2013 |
| JP | 2006-508632 | 3/2006 |
| JP | 2013-509884 A | 3/2013 |
| WO | WO96/19586 | 6/1996 |
| WO | WO98/14275 | 4/1998 |
| WO | WO98/44151 | 10/1998 |
| WO | WO00/18957 | 4/2000 |
| WO | WO03/004677 | 1/2003 |
| WO | WO 03/074723 A2 | 9/2003 |
| WO | WO 03/074740 A2 | 9/2003 |
| WO | WO 2004/078999 A1 | 9/2004 |
| WO | WO 2005/039389 | 5/2005 |
| WO | WO2006/010610 | 2/2006 |
| WO | WO2006/028152 | 3/2006 |
| WO | WO2006/028153 | 3/2006 |
| WO | WO 2007/092473 | 8/2007 |
| WO | WO 2007/147074 A2 | 12/2007 |
| WO | WO 2007/147079 A2 | 12/2007 |
| WO | WO 2009/046445 | 9/2009 |
| WO | WO 2010/033578 A2 | 3/2010 |
| WO | WO2011/051283 | 5/2011 |
| WO | WO 2011/057094 A1 | 5/2011 |
| WO | WO 2011/090556 A1 | 7/2011 |
| WO | WO 2011/091046 A1 | 7/2011 |
| WO | WO 2011/091063 | 7/2011 |
| WO | WO2012/019187 | 2/2012 |
| WO | WO2012/019193 | 2/2012 |
| WO | WO2012/019198 | 2/2012 |
| WO | WO2012/019200 | 2/2012 |
| WO | WO2012/071621 | 6/2012 |
| WO | WO2012/078792 | 6/2012 |
| WO | WO2012/088348 | 6/2012 |
| WO | WO2012/103031 | 8/2012 |
| WO | WO2012/108920 | 8/2012 |
| WO | WO 2012/142334 A2 | 10/2012 |
| WO | WO 2013/015793 | 1/2013 |
| WO | WO 2014/014498 | 1/2014 |

OTHER PUBLICATIONS

Ashoor, et al., "Fetal Fraction in maternal plasma cell-free DNA at 11-13 weeks' gestation: effect of maternal and fetal factors", 2012, 7.

Bentley, et al., "Accurate whole human genome sequencing using reversible terminator chemistry", Nature, vol. 456, No. 7218, Nov. 6, 2008, 53-59.

Beroukhim, et al., "The landscape of somatic copy-number alteration across human cancers", Nature, vol. 463, Feb. 2010, 899-905.

Bianchi, et al., "Genome-Wide Fetal Aneuploidy Detection by Maternal Plasma DNA Sequencing", Obstetrics and Gynecology, vol. 119, No. 5, May 5, 2012, 890-901.

Borsting, "Multiplex PCR, amplicon size and hybridization efficiency on the NanoChip electronic microarray", Int J. Legal Med. vol. 118, 2004, 75.

Botezatu, et al., "Genetic Analysis of DNA excreted in urine: a new approach for detecting specific genomic DNA sequences from cells dying in an organism", Clin Chem. 46(8 Pt1), Aug. 2000, 1078-84.

Buck, et al., "Design Strategies and Performance of Custom DNA Sequencing Primers", Biotechniques vol. 27, 1999, 528-536.

Butler, et al., "Short tandem repeat typing technologies used in human identity testing", Biotechniques 43(4), Sep. 2003, ii-v.

(56) References Cited

OTHER PUBLICATIONS

Butler, et al., "The Development of reduced size STR amplicons as tools for analysis of degraded DNA", J. Forensic Sci 48(5), 2003, 1054-64.
Chan, et al., "Size Distributions of maternal and fetal DNA in Maternal Plasma", Clin. Chem 50(1), Jan. 2004, 88-92.
Chen, et al., "Microsatellite alterations in plasma DNA of small cell lung cancer patients", Nat Med. 2(9), 1996, 1033-5.
Chiang, et al., "High-resolution mapping of copy-number alterations with massively parallel sequencing", Nature Methods, vol. 6, No. 1 (2009), published online: doi:10.1038/nmeth.1276, Nov. 30, 2008, 99-103.
Chiu, et al., "Maternal Plasma DNA Analysis with Massively Parallel Sequencing by Ligation for Noninvasive Prenatal Diagnosis of Trisomy 21", Clinical Chemistry 56:3, 2010, 459-463.
Chiu, et al., "Non-invasive prenatal assessment of trisomy 21 by multiplexed maternal plasma DNA sequencing: large scale validity study", BMJ 342, 2011, c7401.
Chiu, et al., "Non-invasive prenatal diagnosis by single molecule counting technologies", Trends Genet. 25 (7), Jul. 2009, 324-31.
Chiu, et al., "Noninvasive prenatal diagnosis of fetal chromosomal aneuploidy by massively parallel genomic sequencing of DNA in maternal plasma", Proc Natl Acad Sci 105(51), Dec. 23, 2008, 20458-63.
Chu, et al., "Statistical model for whole genome sequencing and its application to minimally invasive of fetal genetic disease", Bioinformatics 25(10), May 15, 2009, 1244-40.
Clarke, et al., "Effects of chemotherapy and hormonal therapy for early breast cancer on recurrence and 15-year survival: an overview of randomised trials", Lancet vol. 365, 2005, 1687-1717.
Clarke, et al., "Effects of radiotherapy and of differences in the extent of surgery for early breast cancer on local recurrence and 15-year survival: an overview of the randomised trials", Lancet vol. 366, 2005, 2087-2106.
Coble, et al., "Characterization of New MiniSTR Loci to Aid Analysis of Degraded DNA", J Forensic Sci, 50(1), Jan. 2005, 43-53.
Deng, et al., "Enumeration and microfluidic chip separation of circulating fetal cells early in pregnancy from maternal blood", American journal of Obstetrics & Gynecology, vol. 199, Issue 6, Dec. 2008, S134.
Dhallan, et al., "A non-invasive test for prenatal diagnosis based on fetal DNA present in maternal blood: a preliminary study", Lancet 369(9560), Feb. 10, 2007, 474-81.
Ding, et al., "MS analysis of single-nucleotide differences in circulating nucleic acids: Application to noninvasive prenatal diagnosis", Proceedings of National Academy of Sciences 101(29), 2004, 10762-10767.
Dixon, et al., "Analysis of artificially degraded DNA using STRs and SNPs-results of a collaborative European (EDNAP) exercise", Forensic Sci Int 164(1), 2006, 33-44.
Ehrich, "Noninvasive detection of fetal trisomy 21 by sequencing of DNA in maternal blood: a study in a clinical setting", Am J Obstet Gynecol, 204(3), Mar. 2011, 205.e1-11.
Fan, et al., "Analysis of the size distributions of fetal and maternal cell-free DNA by paired-end sequencing", Clin. Chem 56(8), Aug. 1, 2010, 1279-1286.
Fan, et al., "Detection of aneuploidy with digital polymerase chain reaction", Anal Chem. 79(19), Oct. 1, 2007, 7576-9.
Fan, et al., "In principle method for noninvasive determination of the fetal genome", Nature Precedings: Nature Precedings 10.1038/npre, 2010, 5373.1.
Fan, et al., "Microfluidic digital PCR enables rapid prenatal diagnosis of fetal aneuploidy", Am J Obstet Gynecol 200(5), May 2009, 543. e1-7.
Fan, et al., "Noninvasive diagnosis of fetal aneuploidy by shotgun sequencing DNA from maternal blood", Proc Natl Acad Sci 105(42), Oct. 21, 2008, 16266-71.
Fan, et al., "Sensitivity of noninvasive prenatal detection of fetal aneuploidy from maternal plasma using shotgun sequencing is limited only by counting statistics", PLoS One 5(5), May 3, 2010, e10439.
Fan, et al., "Whole-genome molecular haplotyping of single cells", Nature Biotechnology, Advanced Online Publication, Dec. 19, 2010, 9 pages.
Frohling, et al., "Chromosomal Abnormalities in Cancer", New England Journal of Medicine, vol. 359, 2008, 722-734.
Ghanta, et al., "Non-Invasive Prenatal Detection of Trisomy 21 Using Tandem Single Nucleotide Polymorphisms", PLos ONE, vol. 5, Issue 10, e13184, Oct. 2010, 10 pages.
Goossens, et al., "Simultaneous Mutation and Copy Number Variation (CNV) Detection by Multiplex PCR-Based GS-FLX Sequencing", Human Mutation, vol. 30, Issue 3, Dec. 2008, 472-476.
Grubweiser, et al., "A new "miniSTR-multiplex" displaying reduced amplicon lengths for the analysis of degrade DNA", Int J. Legal Med 120(2), 2006, 115-20.
Hanson, et al., "Whole genome amplification strategy for forensic genetic analysis using single or few cell equivalents of genomic DNA", Anal Biochem. 346(2), Nov. 15, 2005, 246-57.
Harris, et al., "Single-Molecule DNA Sequencing of a Viral Genome", Science 320, Apr. 4, 2008, 106-109 and Suppl. Materials 1-25.
Harrison, et al., "Polymer-stimulated ligation: enhanced ligation of oligo-and polynucleotides by T4 RNA ligase in polymer solutions", Nucleic Acids Research vol. 12 No. 21 1984, 8235-51.
Hayashi, et al., "Regulation of inter-and intramolecular ligation with T4 DNA ligase in the presence of polyethylene glycol", Nucleic Acids Res. 14(19), Oct. 10, 1986, 7617-31.
Hill, et al., "Characterization of 26 new miniSTR Loci", Poster #44—17th International Symposium on Human Identification, Nashville, TN, Oct. 10-12, 2006, 1.
Hoffman, et al., "The genome-enabled electronic medical record", Journal of Biomedical Informatics 10 (2007) published online, Mar. 15, 2006, 44-46.
Huang, "Isolation of cell-free DNA from maternal plasma using manual and automated systems", Methods Mol Biol. 444, 2008, 203-8.
Hung, "Detection of circulating fetal nucleic acids: a review of methods and applications", J Clin Pathol 62(4), 4/62/2009, 308-13.
Illumina, "Preparing Samples for ChIP sequencing of DNA", E-pub at grcf.jhmi.edu/hts/protocols/11257047_ChIP_Sample_Prep.pdf., 2007, 15.
International, "The International HapMap Consortium Project", Nature 426:789-96, 2003, 8.
Jama, et al., "Quantification of cell-free fetal DNA Levels on maternal plasma by STR analysis", 2010 ACMG Annual Clinical Genetics Meeting, 2010, 2.
Jensen, et al., "Detection of Microdeletion 22q11.2 in a Fetus by Next-Generation Sequencing of Maternal Plasma", Clinical Chemistry 58:7; doi:10.1373/clinchem.2011.180794, May 4, 2012.
Jiang, et al., "FetalQuant: deducing fractional fetal DNA concentration from massively parallel sequencing of DNA in maternal plasma", Bioinformatics, vol. 28, No. 22, 2012, 2883-2890.
Jorgez, et al., "Improving Enrichment of circulating fetal DNA for genetic testing: size fractionation followed by whole gene amplification", Fetal Diagn Ther 2009, 2009, 6.
Ju, et al., "Four-Color DNA Sequencing by Synthesis Using Cleavable Florescent Nucleotide Reversible Terminators", PNAS vol. 103, No. 52, 2006, 19635-19640.
Kidd, et al., "Developing a SNP panel for forensic identification of individuals", Forensic Science International 164 ( 2006), 20-32.
Kim, et al., "rSW-seq: algorithm for detection of copy number alterations in deep sequencing data", BMC Bioinformatics, vol. 11, Aug. 18, 2010, 432.
Koide, et al., "Fragmentation of cell-free fetal DNA in plasma and urine of pregnant women", www.interscience.wiley.com, Mar. 14, 2005, 4.
Kozarewa, et al., "Amplification-free Illumina sequencing-library preparation facilitates improved mapping and assembly of GC-biased genomes", UKPMC Funders Group Author Manuscript, Oct. 1, 2009, 12.

(56) References Cited

OTHER PUBLICATIONS

Lazinski, et al., "Modified Protocol for Illumina Paired-End Library Construction", http://genomics.med.tufts.edu/documents/htseq_protocol_for_illumina_paired.pdf, Feb. 27, 2009, 10.

Leon, et al., "Free DNA in the Serum of Cancer Patients and the Effect of Therapy", Cancer Research 37, Mar. 1, 1977, 646-650.

Levy, et al., "The Diploid Genome Sequence of an Individual Human", PLoS Biology, vol. 5, Issue 10, Oct. 2007, 2113-2144.

Li, et al., "Size separation of circulatory DNA in maternal plasma permits ready detection of fetal DNA polymorphisms", Clinical Chemistry 50:6, 2004, 1002-11.

Liao, et al., "Targeted Massively parallel sequencing of maternal plasma DNA permits efficient and unbiased detection of fetal alleles", Clinical Chemistry 57:1, 2011, 92-101.

Liu, et al., "Feasibility study of using fetal DNA in maternal plasma for non-invasive prenatal diagnosis", Acta Obstet Gynecol Scand. 86(5), 2007, 535-41.

Lo, et al., "Digital PCR for the molecular detection of fetal chromosomal aneuploidy", Proc Natl Acad Sci USA. 104(32), Aug. 7, 2007, 13116-21.

Lo, et al., "Increased fetal DNA concentrations in the plasma of pregnant women carrying fetuses with trisomy 21", Clinical Chemistry 45:10, 1999, 1747-51.

Lo, et al., "Maternal plasma DNA sequencing reveals the genome-wide genetic and mutational profile of the fetus", Sci Transl Med. 2(61):, Dec. 8, 2010, 61ra91.

Lo, et al., "Noninvasive prenatal detection of fetal chromosomal aneuploidies by maternal plasma nucleic acid analysis: a review of the current state of the art", BJOG, vol. 116, 2009, 152-157.

Lo, et al., "Noninvasive prenatal diagnosis of fetal chromosomal aneuploidies by maternal plasma nucleic acid analysis", Clin Chem. 54(3), Jan. 2008, 461-466.

Lo, et al., "Prenatal diagnosis of fetal RhD Status by molecular analysis of maternal plasma", The New England Journal of Medicine, Dec. 10, 1998, 1734-1738.

Lo, et al., "Presence of fetal DNA in maternal plasma and serum", Lancet. 350(9076), Aug. 16, 1997, 485-7.

Lo, et al., "Quantitative analysis of fetal DNA in maternal plasma and serum: implications for noninvasive prenatal diagnosis", Am J Hum Genet 62(4), Apr. 1998, 768-775.

Lo, et al., "Rapid Clearance of fetal DNA from Maternal Plasma", Am J Hum Genet. 64(1), 1999, 218-24.

Lun, et al., "Microfluidics digital PCR Reveals a Higher than expected fraction of fetal DNA in maternal plasma", Clinical Chemistry, vol. 54, No. 10, 2008, 1664-1672.

Lun, "Noninvasive prenatal diagnosis of monogenic diseases by digital size selection and relative mutation dosage on DNA in maternal plasma", Proceedings of National Academy of Sciences 105(50), 2008, 19920-19925.

McKernan, et al., "Sequence and structural variation in a human genome uncovered by short-read, massively parallel ligation sequencing using two-base encoding", Genome Res. 19(9), Sep. 2009, 1527-41.

Metzker, "Sequencing technologies—the next generation", Nat Rev Genet. 11(1), Jan. 2010, 31-46.

Meyerson, et al., "Advances in understanding cancer genomes through second-generation sequencing", Nature Reviews Genetics, vol. 11, 2010, 685-696.

Mullighan, et al., "Genome-wide profiling of genetic alterations in acute lymphoblastic leukemia: recent insights and future directions.", Leukemia vol. 23, Feb. 26, 2009, 1209-1218.

Nakamoto, "Detection of Microsatellite alterations in Plasma DNA of Malignant Mucosal Melanoma Using Whole Genome Amplification", Bull Tokyo Dent Coll. May 2008; 49(2), May 2008, 77-87.

Nicklas, "A real-time multiplex SNP melting assay to discriminate individuals", J. Forensic Sci. 53(6):, Nov. 2008, 1316-24.

Norton, et al., "Non-invasive chromosomal evaluation (NICE) study: results of multicenter, prospective, cohort study for detection of fetal trisomy 21 and trisomy 18", American Journal of Obstetrics and Gynecology, doi: 10.1016/j.ajog.2012.05.021., May 21, 2012, 30 pgs.

Pakstis, et al., "Candidate SNPs for a universal individual identification panel", Hum Genet. 121(3-4), May 2007, 305-17.

Pakstis, et al., "SNPs for a universal individual identification panel", Hum Genet. 127(3):, Mar. 2010, 315-24.

Pandey, et al., "Chapter 3 Applied Biosystems SOLID Systems: Ligation-Based Sequencing", Next Generation Genome Sequencing: Towards Personalized Medicine 2008. Edited by Michael Janitz., 2008, 14.

Park, et al., "A single-tube protocol for next gen library construction increases complexity and simplifies parallel sample handling", Cancer Research 71(8): Suppl. 1, Abstract No. 4851, Apr. 15, 2011.

Pathak, et al., "Circulating Cell-Free DNA in Plasma/Serum of Lung Cancer Patients as a Potential Screening and Prognostic Tool", Clin Chem. 52(10):, Oct. 2006, 1833-42.

Pennisi, E. "Semiconductors Inspire New Sequencing Technologies", Science 327, Mar. 5, 2010, 1190.

Pertl, et al., "Detection of male and female fetal DNA in maternal plasma by multiplex fluorescent polymerase chain reaction amplification of short tandem repeats", Hum Genet. 106(1), Jan. 2000, 45-9.

Peters, D. et al., "Noninvasive Prenatal Diagnosis of a Fetal Microdeletion Syndrome", New England Journal of Medicine 365;19, Correspondence, Nov. 10, 2001, 1847-1848.

Pheiffer, et al., "Polymer-stimulated ligation: enhanced blunt- or cohesive-end ligation of DNA or deoxyribooligonucleotides by T4 DNA ligase in polymer solutions", Nucleic Acids Res.11(22), Nov. 25, 1983, 7853-71.

Pui, et al., "Acute lymphoblastic leukaemia", Lancet vol. 371, 2008, 1030-1043.

Pushkarev, et al., "Single-molecule sequencing of an individual human genome", Nat Biotechnol. 27(9):, Sep. 2009, 847-50.

Quail, et al., "A large genome center's improvements to the Illumina sequencing system", Nature Methods, 5, 2008, 1005-1010.

Schwarzenbach, et al., "Cell-free Tumor DNA in Blood Plasma as a Marker for Circulating Tumor Cells in Prostate Cancer", Clin Cancer Res. 15(3):, Feb. 1, 2009, 1032-8.

Schwarzenbach, et al., "Comparative evaluation of cell-free tumor DNA in blood and disseminated tumor cells in bone marrow of patients with primary breast cancer", Breast Cancer Res. 11(5), 2009, R71.

Sehnert, et al., "Optimal Detection of Fetal Chromosomal Abnormalities by Massively Parallel DNA Sequencing of Cell-Free Fetal DNA from Maternal Blood", Clinical Chemistry, Jul. 2011, vol. 57 No. 7, E-pub on Apr. 25, 2011 as doi:10.1373/clinchem.2011.165910., Apr. 25, 2011, 1042-1049.

Shendure, et al., "Next-generation DNA sequencing", Nature Biotechnology 26(10), 2008, 1135-1145.

Sparks, et al., "Non-invasive prenatal detection and selective analysis of cell-free DNA obtained from maternal blood: evaluation for trisomy 21 and trisomy 18", American Journal of Obstetrics and Gynecology, doi: 10.1016/j.ajog.2012.01.030, Jan. 30, 2012, 33 pages.

Su, et al., "Human Urine Contains Small, 150 to 250 Nucleotide-Sized, Soluble DNA Derived from the Circulation and May be useful in the Detection of Colorectal Cancer", J Mol Diagn. 6(2), May 2004, 101-7.

Teixeira, et al., "Multiple numerical chromosome aberrations in cancer: what are their causes and what are their consequences?", Seminars in Cancer Biology, vol. 15, Issue 1, Feb. 2005, 3-12.

Thorstenson, et al., "An Automated Hydrodynamic Process for Controlled, Unbiased DNA Shearing", Genome Research 8, 1998, 848-855.

Tong, et al., "Noninvasive Prenatal Detection of Fetal Trisomy 18 by Epigenetic Allelic Ratio Analysis in Maternal Plasma: Theoretical and Empirical Considerations", Clinical Chemistry 52:12, 2006, 2194-2202.

Tong, et al., "Noninvasive prenatal detection of trisomy 21 by an epigenetic-genetic chromosome-dosage approach", Clin Chem. 56(1), Jan. 2010, 90-8.

(56) References Cited

OTHER PUBLICATIONS

Vallone, et al., "Demonstration of rapid multiplex PCR amplification involving 16 genetic loci", Forensic Sci Int Genet. 3(1), Dec. 2008, 42-5.
Voelkerding, et al., "Digital Fetal Aneuploidy diagnosis by next-generation sequencing", Clin Chem. 56(3), Mar. 2010, 336-8.
Voelkerding, et al., "Next-Generation Sequencing: From Basic Research to Diagnostics", Clinical Chemistry 55:4, 2009, 641-658.
Vogelstein, et al., "Digital PCR", PNAS USA, vol. 96, 1999, 9236-9241.
Wheeler, et al., "The complete genome of an individual by massively parallel DNA sequencing", Nature. 452(7189), Apr. 17, 2008, 872-6.
Wright, et al., "The use of cell-free fetal nucleic acids in maternal blood for non-invasive prenatal diagnosis", Hum Reprod Update. 15(1), Jan.-Feb. 2009, 139-51.
Yamazawa, et al., "Monozygotic female twins discordant for Silver-Russell syndrome and hypomethylation of H19-DMR", J. Human Genetics, vol. 53, 2008, 950-955.
Zimmerman, et al., "Macromolecular crowding allows blunt-end ligation by DNA ligases from rat liver or *Escherichia coli*", Proc Natl Acas Sci USA. 80(19), Oct. 1983, 5852-6.
U.S. Office Action dated Apr. 18, 2013 issued in U.S. Appl. No. 13/009,708.
U.S. Final Office Action dated Sep. 13, 2013 issued in U.S. Appl. No. 13/009,708.
U.S. Notice of Allowance dated Nov. 22, 2013 issued in U.S. Appl. No. 13/009,708.
U.S. Office Action dated Feb. 24, 2014 issued in U.S. Appl. No. 12/958,347.
U.S. Office Action dated Jul. 11, 2012 issued in U.S. Appl. No. 13/461,582.
U.S. Office Action dated Oct. 8, 2014 issued in U.S. Appl. No. 13/461,582.
U.S. Office Action dated May 23, 2014 issued in U.S. Appl. No. 13/555,037.
U.S. Office Action dated Nov. 13, 2014 issued in U.S. Appl. No. 13/555,037.
U.S. Office Action dated May 22, 2014 issued in U.S. Appl. No. 13/555,010.
U.S. Office Action dated Oct. 27, 2014 issued in U.S. Appl. No. 13/555,010.
SG Search Report and Written Opinion dated Apr. 1, 2015 issued in SG Application No. 201400043-4.
European Examination Report dated Mar. 16, 2012 issued in EP Patent Application No. 10 830 939.4.
Extended European Search Report dated Apr. 7, 2015 issued in EP Patent Application No. 14192156.9.
PCT International Preliminary Report on Patentability and Written Opinion dated Aug. 2, 2012 issued in PCT Application No. PCT/US2011/021751.
European Examination Report dated May 6, 2014 issued in EP Application No. 11 735 131.2.
European Examination Report dated Nov. 4, 2014 issued in EP Application No. 11 735 131.2.
PCT International Preliminary Report on Patentability and Written Opinion dated Oct. 24, 2013 issued in International Patent Application No. PCT/US2012/033391.
Australian Examiner's First Report dated Mar. 18, 2014 issued in AU 2012242698.
Chinese First Office Action dated Sep. 28, 2014 issued in CN 201280028976.9.
European Office Action dated Feb. 5, 2014 issued in EP 12 716 939.9.
PCT International Search Report dated Dec. 12, 2013 issued in PCT Application No. PCT/US2013/023909.
PCT International Preliminary Report on Patentability dated Jan. 29, 2015 issued in PCT Application No. PCT/US2013/023909.
Angeloni D., (May 24, 2007) "Molecular analysis of deletions in human chromosome 3p21 and the role of resident cancer genes in disease", *Briefings Functional Genomics* 6(1):19-39.
Bowcock et al., (1990) "Exclusion of the Retinoblastoma Gene and Chromosome 13q as the Site of a Primary Lesion for Human Breast Cancer," *Am J Hum Genet*, 46:12.
Brosens et al., (2010) "Deletion of chromosome 4q predicts outcome in stage II colon cancer patients," *Analytical Cellular Pathology I Cellular Oncology*, 33:95-104.
Caramazza et al., (2010) "Chromosome 1 abnormalities in myeloid malignancies: a literature survey and karyotype-phenotype associations," *Eur J Hematol*, 84:191-200.
Chen et al., (2005) "Detection in Fecal DNA of Colon Cancer-Specific hylation of the Nonexpressed Vimentin Gene," *Journal of the National Cancer Institute*, 97(15):1124-1132.
Craig et al. (1990) "Ordering of cosmid clones covering the Herpes simplex virus type I (HSV-1) genome: a test case for fingerprinting by hybrisation," *Nucleic Acids Research*, 18(9):2653-2660.
Eisenmann et al., (2009) "5q—myelodysplastic syndromes: chromosome 5q genes direct a tumor-suppression network sensing actin dynamics", *Oncogene*, 28:3429-3441.
Fonatsch C., (Jun. 2010) "The role of chromosome 21 in hematology and oncology", *Genes, Chromosomes and Cancer*, 49(6):497-508.
Howe et al., (Aug. 1990) "Retinoblastoma growth suppressor and a 300-kDa protein appear to regulate cellular DNA synthesis," *PNAS (USA)* 87:5883-5887.
Illanes et al., (Sep. 2007) "Early detection of cell-free fetal DNA in maternal plasma," *Early Human Dev* 83(9):563-566.
Jongsma et al., (2002) "Molecular evidence for putative tumour suppressor genes on chromosome 13q specific to BRCA1 related ovarian and fallopian tube cancer," *J Clin Pathol: Mol Path* 55(5):305-309.
Langmead, et al., (2009) "Ultrafast and memory-efficient alignment of short DNA sequences to the human genome", *Genome Biology*, 10:R25.1-R25.10.
Margulies, M., et al., (2005) "Genome sequencing in microfabricated high-density picolitre reactors", and Supplemental Materials *Nature* 437:376-380.
Park et al., (Oct. 2008) "Unraveling the Biologic and Clinical Complexities of HER2," *Clinical Breast Cancer*, 8(5):392-401.
Redon et al., (Nov. 23, 2006), "Global Variation in copy number in the human genome," *Nature*, 444:444-454.
Rygaard et al., (1990) "Abnormalities in Structure and Expression of the Retinoblastoma Gene in Small Cell Lung Cancer Cell Lines and Xenografts in Nude Mice," *Cancer Res* 50:5312-5317.
Sambrook et al., (2001) "Molecular Cloning: A Laboratory Manual" 3rd Edition, Cold Spring Harbor Laboratory, New York.
Santalucia, John Jr., (Feb. 1998) "A unified view of polymer, dumbbell, and oligonucleotide DNA nearest-neighbor thermodynamics", *PNAS USA*, 95:1460-1465.
Sato et al., (1990) "Allelotype of Breast Cancer: Cumulative Allele Losses Promote Tumor Progression in Primary Breast Cancer," *Cancer Res.*, 50:7184-7189.
Shaikh et al. (2009) "High-resolution mapping and analysis of copy number variations in the human genome: A data resource for clinical and research applications", *Genome Res*.19:1682-1690.
Soni , (2007) "Progress toward Ultrafast DNA Sequencing Using Solid-State Nanopores", *Clin Chem* 53(11):1996-2001.
Storchova, (2008) "The consequences of tetraploidy and aneuploidy" *Journal of Cell Science*, 121(23):3859-3866.
Thoma et al., (2011) "Mechanisms of aneuploidy and its suppression by tumour suppressor proteins," *Swiss Med Weekly* 141(w13170):1-8.
Varmus H., (1984) "The Molecular Genetics of Cellular Oncogenes," *Ann Rev Genetics* 18:553-612.
Walsh et al., (2008) "Rare Structural Variants Disrupt Multiple Genes in Neurodevelopmental Pathways in Schizophrenia," *Science*, 320:539-543.
U.S. Final Office Action dated Dec. 26, 2012 issued in U.S. Appl. No. 13/461,582.
U.S. Final Office Action dated Jun. 18, 2015 issued in U.S. Appl. No. 13/461,582.
U.S. Notice of Allowance dated Jun. 16, 2015 issued in U.S. Appl. No. 13/555,037.
U.S. Notice of Allowance dated Jun. 3, 2015 issued in U.S. Appl. No. 13/555,010.

(56) References Cited

OTHER PUBLICATIONS

PCT International Search Report dated Mar. 9, 2011 issued in PCT Application No. PCT/US2011/021751.
Australian Office Action dated Aug. 29, 2013 issued in AU Application No. 2011207561.
European Search Report dated Jun. 3, 2013 issued in EP Application No. 11 735 131.2.
PCT International Search Report dated Mar. 11, 2013 issued in International Patent Application No. PCT/US2012/033391.
PCT Invitation to Pay Additional Fees dated Nov. 15, 2012 issued in International Patent Application No. PCT/US2012/033391.
Chinese Second Office Action dated Apr. 13, 2015 issued in CN 201280028976.9.
European Office Action dated Mar. 10, 2015 issued in EP 12 716 939.9.
Japanese Office Action dated Apr. 22, 2015 issued in JP 2014-505313.
Amaral, et al., (Aug. 12, 2009) "Application of massive parallel sequencing to whole genome SNP discovery in the porcine genome," BMC Genomics, Biomed Central Ltd, London, UK, 10(1):374.
Chiu et al. (Mar. 30, 2012) "Noninvasive prenatal diagnosis empowered by high-throughput sequencing," Prenatal Diagnosis 32(4):401-406.
Fan et al., (Oct. 2008) "Supporting Information", 10.1073/pnas.0808319105, PNAS 105(42):16222, 7 pages.
Lee et al., (Dec. 31, 2009) "Improving the efficiency of genomic loci capture using oligonucleotide arrays for high throughput resequencing," BMC Genomics, Biomed Central Ltd, London, UK, 10(646):1-12.
Li et al., (Jun. 1, 2009) "SNP detection for massively parallel whole-genome resequencing," Genome Research, 19(6):1124-1132.
Turner, et al., (Sep. 1, 2009) "Methods for Genomic Partitioning", Annual Review of Genomics and Human Genetics, 10(1):263-284.
U.S. Notice of Allowance dated Sep. 25, 2015 issued in U.S. Appl. No. 13/555,037.
U.S. Notice of Allowance dated Nov. 6, 2015 issued in U.S. Appl. No. 13/555,010.
U.S. Office Action dated Oct. 5, 2015 issued in U.S. Appl. No. 13/843,258.
U.S. Appl. No. 14/983,379, filed Dec. 29, 2015, Rava et al.
U.S. Appl. No. 15/017,475, filed Feb. 5, 2016, Rava et al.

Whole Chr trisomy: FF_X = FF_Trisomic Chr

Deletion Aneuploidy: FF_X > FF_Aneuploid Chr

MELISSA STUDY: Trisomy 13 samples
Whole chromosome aneuploidy for Chr13 confirmed in affected "male-fetus" samples by the near-perfect correlation between estimated FF_X and FF_13

DETECTING AND CLASSIFYING COPY NUMBER VARIATION

CROSS-REFERENCE TO RELATED APPLICATIONS

This application is a continuation-in-part of U.S. application Ser. No. 13/555,037, filed Jul. 20, 2012, which is a continuation-in-part of U.S. application Ser. No. 13/191,366, filed on Jul. 26, 2011, which is a continuation-in-part of U.S. application Ser. No. 12/958,352, filed on Dec. 1, 2010, which claims priority to U.S. Provisional Application Nos. 61/296,358 filed Jan. 19, 2010 and 61/360,837 filed Jul. 1, 2010 and 61/407,017 and 61/455,849 both filed Oct. 26, 2010, all of which are incorporated by reference in their entireties. This application is also a continuation-in-part of U.S. application Ser. No. 13/400,028, filed on Feb. 17, 2012. This application is also a continuation-in-part of U.S. application Ser. No. 13/009,708 filed Jan. 19, 2011, which claims benefit of U.S. Provisional Patent Application No. 61/296,464 filed Jan. 19, 2010, both of which are incorporated herein by reference their entireties. This application is also a continuation-in-part of U.S. application Ser. No. 13/445,778 filed Apr. 12, 2012, which claims benefit of U.S. Provisional Patent Application No. 61/474,362 filed Apr. 12, 2011, both of which are incorporated herein by reference in their entireties. This application is also a continuation-in-part of U.S. application Ser. No. 12/958,347 filed Dec. 1, 2010, which claims benefit of U.S. Provisional Patent Application Nos. 61/296,358 filed Jan. 19, 2010 and 61/360,837 filed Jul. 1, 2010 and 61/407,017 and 61/455,849 both filed Oct. 26, 2010, all of which are incorporated by reference in their entireties and for all purposes. This application is also a continuation-in-part of U.S. application Ser. No. 12/958,356 filed Dec. 1, 2010, which claims benefit of U.S. Provisional Patent Application Nos. 61/296,358 filed Jan. 19, 2010 and 61/360,837 filed Jul. 1, 2010 and 61/407,017 and 61/455,849 both filed Oct. 26, 2010, all of which are incorporated by reference in their entireties and for all purposes. This application is also a continuation-in-part of U.S. application Ser. No. 13/482,964, filed on May 29, 2012, which is a continuation-in-part of U.S. application Ser. No. 12/958,353, filed on Dec. 1, 2010. This application is also a continuation-in-part of International Application PCT/US2012/031625, filed on Mar. 30, 2012, which claims benefit of U.S. Provisional Patent Application No. 61/469,236, filed on Mar. 30, 2011. This application is also a continuation-in-part of U.S. application Ser. No. 13/087,842, filed Apr. 15, 2011, by Richard P. Rava, entitled "Normalizing Chromosomes for the Determination and Verification of Common and Rare Chromosomal Aneuploidies."

BACKGROUND

One of the critical endeavors in human medical research is the discovery of genetic abnormalities that produce adverse health consequences. In many cases, specific genes and/or critical diagnostic markers have been identified in portions of the genome that are present at abnormal copy numbers. For example, in prenatal diagnosis, extra or missing copies of whole chromosomes are frequently occurring genetic lesions. In cancer, deletion or multiplication of copies of whole chromosomes or chromosomal segments, and higher level amplifications of specific regions of the genome, are common occurrences.

Most information about copy number variation has been provided by cytogenetic resolution that has permitted recognition of structural abnormalities. Conventional procedures for genetic screening and biological dosimetry have utilized invasive procedures e.g. amniocentesis, to obtain cells for the analysis of karyotypes. Recognizing the need for more rapid testing methods that do not require cell culture, fluorescence in situ hybridization (FISH), quantitative fluorescence PCR (QF-PCR) and array-Comparative Genomic Hybridization (array-CGH) have been developed as molecular-cytogenetic methods for the analysis of copy number variations.

The advent of technologies that allow for sequencing entire genomes in relatively short time, and the discovery of circulating cell-free DNA (cfDNA) have provided the opportunity to compare genetic material originating from one chromosome to be compared to that of another without the risks associated with invasive sampling methods. However, the limitations of the existing methods, which include insufficient sensitivity stemming from the limited levels of cfDNA, and the sequencing bias of the technology stemming from the inherent nature of genomic information, underlie the continuing need for noninvasive methods that would provide any or all of the specificity, sensitivity, and applicability, to reliably diagnose copy number changes in a variety of clinical settings.

Embodiments disclosed herein fulfill some of the above needs and in particular offers an advantage in providing a reliable method that is applicable at least to the practice of noninvasive prenatal diagnostics, and to the diagnosis and monitoring of metastatic progression in cancer patients.

SUMMARY

Methods are provided for determining copy number variations (CNV) of a sequence of interest in a test sample that comprises a mixture of nucleic acids that are known or are suspected to differ in the amount of one or more sequence of interest. The method comprises a statistical approach that accounts for accrued variability stemming from process-related, interchromosomal and inter-sequencing variability. The method is applicable to determining CNV of any fetal aneuploidy, and CNVs known or suspected to be associated with a variety of medical conditions. CNV that can be determined according to the present method include trisomies and monosomies of any one or more of chromosomes 1-22, X and Y, other chromosomal polysomies, and deletions and/or duplications of segments of any one or more of the chromosomes, which can be detected by sequencing only once the nucleic acids of a test sample. Any aneuploidy can be determined from sequencing information that is obtained by sequencing only once the nucleic acids of a test sample.

In one embodiment, a method is provided for determining the presence or absence of any four or more different complete fetal chromosomal aneuploidies in a maternal test sample comprising fetal and maternal nucleic acid molecules. The steps of the method comprise (a) obtaining sequence information for the fetal and maternal nucleic acids in the maternal test sample; (b) using the sequence information to identify a number of sequence tags for each of any four or more chromosomes of interest selected from chromosomes 1-22, X and Y and to identify a number of sequence tags for a normalizing chromosome sequence for each of the any four or more chromosomes of interest; (c) using the number of sequence tags identified for each of the any four or more chromosomes of interest and the number of sequence tags identified for each normalizing chromosome to calculate a single chromosome dose for each of the any four or more chromosomes of interest; and (d) comparing each of the single chromosome doses for each of the any four or more chromosomes of interest to a threshold value for each of the four or more chromosomes of interest, and thereby determining the presence or absence of any four or more complete different fetal chromosomal aneuploidies in the maternal test sample. Step (a) can comprise sequencing at least a portion of the nucleic acid molecules of a test sample to obtain said sequence information for the fetal and maternal nucleic acid molecules of the test sample. In some embodiments, step (c) comprises calculating a single chromosome dose for each of the chromosomes of interest as the ratio of the number of sequence tags identified for each of the chromosomes of interest and the number of sequence tags identified for the normalizing chromosome sequence for each of the chromosomes of interest. In some other embodiments, step (c) comprises (i) calculating a sequence tag density ratio for each of the chromosomes of interest, by relating the number of sequence tags identified for each of the chromosomes of interest in step (b) to the length of each of the chromosomes of interest; (ii) calculating a sequence tag density ratio for each normalizing chromosome sequence by relating the number of sequence tags identified for the sequence in step (b) to the length of each normalizing chromosome; and (iii) using the sequence tag density ratios calculated in steps (i) and (ii) to calculate a single chromosome dose for each of the chromosomes of interest, wherein the chromosome dose is calculated as the ratio of the sequence tag density ratio for each of the chromosomes of interest and the sequence tag density ratio for the normalizing chromosome sequence for each of the chromosomes of interest.

In another embodiment, a method is provided for determining the presence or absence of any four or more different complete fetal chromosomal aneuploidies in a maternal test sample comprising fetal and maternal nucleic acid molecules. The steps of the method comprise (a) obtaining sequence information for the fetal and maternal nucleic acids in the maternal test sample; (b) using the sequence information to identify a number of sequence tags for each of any four or more chromosomes of interest selected from chromosomes 1-22, X and Y and to identify a number of sequence tags for a normalizing chromosome sequence for each of the any four or more chromosomes of interest; (c) using the number of sequence tags identified for each of the any four or more chromosomes of interest and the number of sequence tags identified for each normalizing chromosome to calculate a single chromosome dose for each of the any four or more chromosomes of interest; and (d) comparing each of the single chromosome doses for each of the any four or more chromosomes of interest to a threshold value for each of the four or more chromosomes of interest, and thereby determining the presence or absence of any four or more complete different fetal chromosomal aneuploidies in the maternal test sample, wherein the any four or more chromosomes of interest selected from chromosomes 1-22, X, and Y comprise at least twenty chromosomes selected from chromosomes 1-22, X, and Y, and wherein the presence or absence of at least twenty different complete fetal chromosomal aneuploidies is determined. Step (a) can comprise sequencing at least a portion of the nucleic acid molecules of a test sample to obtain said sequence information for the fetal and maternal nucleic acid molecules of the test sample. In some embodiments, step (c) comprises calculating a single chromosome dose for each of the chromosomes of interest as the ratio of the number of sequence tags identified for each of the chromosomes of interest and the number of sequence tags identified for the normalizing chromosome sequence for each of the chromosomes of interest. In some other embodiments, step (c) comprises (i) calculating a sequence tag density ratio for each of the chromosomes of interest, by relating the number of sequence tags identified for each of the chromosomes of interest in step (b) to the length of each of the chromosomes of interest; (ii) calculating a sequence tag density ratio for each normalizing chromosome sequence by relating the number of sequence tags identified for the normalizing chromosome sequence in step (b) to the length of each normalizing chromosome; and (iii) using the sequence tag density ratios calculated in steps (i) and (ii) to calculate a single chromosome dose for each of the chromosomes of interest, wherein the chromosome dose is calculated as the ratio of the sequence tag density ratio for each of the chromosomes of interest and the sequence tag density ratio for the normalizing chromosome sequence for each of the chromosomes of interest.

In another embodiment, a method is provided for determining the presence or absence of any four or more different complete fetal chromosomal aneuploidies in a maternal test sample comprising fetal and maternal nucleic acid molecules. The steps of the method comprise (a) obtaining sequence information for the fetal and maternal nucleic acids in the maternal test sample; (b) using the sequence information to identify a number of sequence tags for each of any four or more chromosomes of interest selected from chromosomes 1-22, X and Y and to identify a number of sequence tags for a normalizing chromosome sequence for each of the any four or more chromosomes of interest; (c) using the number of sequence tags identified for each of the any four or more chromosomes of interest and the number of sequence tags identified for each normalizing chromosome sequence to calculate a single chromosome dose for each of the any four or more chromosomes of interest; and (d) comparing each of the single chromosome doses for each of the any four or more chromosomes of interest to a threshold value for each of the four or more chromosomes of interest, and thereby determining the presence or absence of any four or more complete different fetal chromosomal aneuploidies in the maternal test sample, wherein the any four or more chromosomes of interest selected from chromosomes 1-22, X, and Y is all of chromosomes 1-22, X, and Y, and wherein the presence or absence of complete fetal chromosomal aneuploidies of all of chromosomes 1-22, X, and Y is determined. Step (a) can comprise sequencing at least a portion of the nucleic acid molecules of a test sample to obtain said sequence information for the fetal and maternal nucleic acid molecules of the test sample. In some embodiments, step (c) comprises calculating a single chromosome dose for each of the chromosomes of interest as the ratio of the number of sequence tags identified for each of the chromosomes of interest and the number of sequence tags identified for the normalizing chromosome sequence for each of the chromosomes of interest. In some other embodiments, step (c) comprises (i) calculating a sequence tag density ratio for each of the chromosomes of interest, by relating the number of sequence tags identified for each of the chromosomes of interest in step (b) to the length of each of the chromosomes of interest; (ii) calculating a sequence tag density ratio for each normalizing chromosome sequence by relating the number of sequence tags identified for the normalizing chromosome sequence in step (b) to the length of each normalizing chromosome; and (iii) using the sequence tag density ratios calculated in steps (i) and (ii) to calculate a single chromosome dose for each of the chromosomes of interest, wherein the chromosome dose is calculated as the ratio of the sequence tag density ratio for each of the chromosomes of interest and the sequence tag density ratio for the normalizing chromosome sequence for each of the chromosomes of interest.

In any of the embodiments above, the normalizing chromosome sequence may be a single chromosome selected from chromosomes 1-22, X, and Y. Alternatively, the normalizing chromosome sequence may be a group of chromosomes selected from chromosomes 1-22, X, and Y.

In another embodiment, a method is provided for determining the presence or absence of any one or more different complete fetal chromosomal aneuploidies in a maternal test sample comprising fetal and maternal nucleic acids. The steps of the method comprise: (a) obtaining sequence information for the fetal and maternal nucleic acids in the sample; (b) using the sequence information to identify a number of sequence tags for each of any one or more chromosomes of interest selected from chromosomes 1-22, X and Y and to identify a number of sequence tags for a normalizing segment sequence for each of any one or more chromosomes of interest; (c) using the number of sequence tags identified for each of any one or more chromosomes of interest and the number of sequence tags identified for the normalizing segment sequence to calculate a single chromosome dose for each of any one or more chromosomes of interest; and (d) comparing each of the single chromosome doses for each of any one or more chromosomes of interest to a threshold value for each of the one or more chromosomes of interest, and thereby determining the presence or absence of one or more different complete fetal chromosomal aneuploidies in the sample. Step (a) can comprise sequencing at least a portion of the nucleic acid molecules of a test sample to obtain said sequence information for the fetal and maternal nucleic acid molecules of the test sample.

In some embodiments, step (c) comprises calculating a single chromosome dose for each of the chromosomes of interest as the ratio of the number of sequence tags identified for each of the chromosomes of interest and the number of sequence tags identified for the normalizing segment sequence for each of the chromosomes of interest. In some other embodiments, step (c) comprises (i) calculating a sequence tag density ratio for each of chromosomes of interest, by relating the number of sequence tags identified for each chromosomes of interest in step (b) to the length of each of the chromosomes of interest; (ii) calculating a sequence tag density ratio for each normalizing segment sequence by relating the number of sequence tags identified for the normalizing segment sequence in step (b) to the length of each the normalizing chromosomes; and (iii) using the sequence tag density ratios calculated in steps (i) and (ii) to calculate a single chromosome dose for each of said chromosomes of interest, wherein said chromosome dose is calculated as the ratio of the sequence tag density ratio for each of the chromosomes of interest and the sequence tag density ratio for the normalizing segment sequence for each of the chromosomes of interest.

In another embodiment, a method is provided for determining the presence or absence of any one or more different complete fetal chromosomal aneuploidies in a maternal test sample comprising fetal and maternal nucleic acids. The steps of the method comprise: (a) obtaining sequence information for the fetal and maternal nucleic acids in the sample; (b) using the sequence information to identify a number of sequence tags for each of any one or more chromosomes of interest selected from chromosomes 1-22, X and Y and to identify a number of sequence tags for a normalizing segment sequence for each of any one or more chromosomes of interest; (c) using the number of sequence tags identified for each of any one or more chromosomes of interest and the number of sequence tags identified for the normalizing segment sequence to calculate a single chromosome dose for each of any one or more chromosomes of interest; and (d) comparing each of the single chromosome doses for each of any one or more chromosomes of interest to a threshold value for each of the one or more chromosomes of interest, and thereby determining the presence or absence of one or more different complete fetal chromosomal aneuploidies in the sample, wherein the any one or more chromosomes of interest selected from chromosomes 1-22, X, and Y comprise at least twenty chromosomes selected from chromosomes 1-22, X, and Y, and wherein the presence or absence of at least twenty different complete fetal chromosomal aneuploidies is determined. Step (a) can comprise sequencing at least a portion of the nucleic acid molecules of a test sample to obtain said sequence information for the fetal and maternal nucleic acid molecules of the test sample. In some embodiments, step (c) comprises calculating a single chromosome dose for each of the chromosomes of interest as the ratio of the number of sequence tags identified for each of the chromosomes of interest and the number of sequence tags identified for the normalizing segment sequence for each of the chromosomes of interest. In some other embodiments, step (c) comprises (i) calculating a sequence tag density ratio for each of chromosomes of interest, by relating the number of sequence tags identified for each chromosomes of interest in step (b) to the length of each of the chromosomes of interest; (ii) calculating a sequence tag density ratio for each normalizing segment sequence by relating the number of sequence tags identified for the normalizing segment sequence in step (b) to the length of each the normalizing chromosomes; and (iii) using the sequence tag density ratios calculated in steps (i) and (ii) to calculate a single chromosome dose for each of said chromosomes of interest, wherein said chromosome dose is calculated as the ratio of the sequence tag density ratio for each of the chromosomes of interest and the sequence tag density ratio for the normalizing segment sequence for each of the chromosomes of interest.

In another embodiment, a method is provided for determining the presence or absence of any one or more different complete fetal chromosomal aneuploidies in a maternal test sample comprising fetal and maternal nucleic acids. The steps of the method comprise: (a) obtaining sequence information for the fetal and maternal nucleic acids in the sample; (b) using the sequence information to identify a number of sequence tags for each of any one or more chromosomes of interest selected from chromosomes 1-22, X and Y and to identify a number of sequence tags for a normalizing segment sequence for each of any one or more chromosomes of interest; (c) using the number of sequence tags identified for each of any one or more chromosomes of interest and the number of sequence tags identified for the normalizing segment sequence to calculate a single chromosome dose for each of any one or more chromosomes of interest; and (d) comparing each of the single chromosome doses for each of any one or more chromosomes of interest to a threshold value for each of the one or more chromosomes of interest, and thereby determining the presence or absence of one or more different complete fetal chromosomal aneuploidies in the sample, wherein the any one or more chromosomes of interest selected from chromosomes 1-22, X, and Y is all of chromosomes 1-22, X, and Y, and wherein the presence or absence of complete fetal chromosomal aneuploidies of all of chromosomes 1-22, X, and Y is determined. Step (a) can comprise sequencing at least a portion of the nucleic acid molecules of a test sample to obtain said sequence information for the fetal and maternal nucleic acid molecules of the test sample. In some embodiments, step (c) comprises calculating a single chromosome dose for each of the chromosomes of interest as the ratio of the number of sequence tags identified for each of the chromosomes of interest and the number of sequence tags identified for the normalizing segment sequence for each of the chromosomes of interest. In some other embodiments, step (c) comprises (i) calculating a sequence tag density ratio for each of chromosomes of interest, by relating the number of sequence tags identified for each chromosomes of interest in step (b) to the length of each of the chromosomes of interest; (ii) calculating a sequence tag density ratio for each normalizing segment sequence by relating the number of sequence tags identified for the normalizing segment sequence in step (b) to the length of each the normalizing chromosomes; and (iii) using the sequence tag density ratios calculated in steps (i) and (ii) to calculate a single chromosome dose for each of said chromosomes of interest, wherein said chromosome dose is calculated as the ratio of the sequence tag density ratio for each of the chromosomes of interest and the sequence tag density ratio for the normalizing segment sequence for each of the chromosomes of interest.

In any one of the embodiments above, the different complete chromosomal aneuploidies are selected from complete chromosomal trisomies, complete chromosomal monosomies and complete chromosomal polysomies. The different complete chromosomal aneuploidies are selected from complete aneuploidies of any one of chromosome 1-22, X, and Y. For example, the said different complete fetal chromosomal aneuploidies are selected from trisomy 2, trisomy 8, trisomy 9, trisomy 20, trisomy 21, trisomy 13, trisomy 16, trisomy 18, trisomy 22, 47,XXX, 47, XYY, and monosomy X.

In any one of the embodiments above, steps (a)-(d) are repeated for test samples from different maternal subjects, and the method comprises determining the presence or absence of any four or more different complete fetal chromosomal aneuploidies in each of the test samples.

In any one of the embodiments above, the method can further comprise calculating a normalized chromosome value (NCV), wherein the NCV relates the chromosome dose to the mean of the corresponding chromosome dose in a set of qualified samples as:

$$NCV_{ij} = \frac{x_{ij} - \hat{\mu}_j}{\hat{\sigma}_j}$$

where $\hat{\mu}_j$ and $\hat{\sigma}_j$ are the estimated mean and standard deviation, respectively, for the j-th chromosome dose in a set of qualified samples, and $x_{ij}$ is the observed j-th chromosome dose for test sample i.

In another embodiment, a method is provided for determining the presence or absence of different partial fetal chromosomal aneuploidies in a maternal test sample comprising fetal and maternal nucleic acids. The steps of the method comprise: (a) obtaining sequence information for the fetal and maternal nucleic acids in the sample; (b) using the sequence information to identify a number of sequence tags for each of any one or more segments of any one or more chromosomes of interest selected from chromosomes 1-22, X, and Y and to identify a number of sequence tags for a normalizing segment sequence for each of any one or more segments of any one or more chromosomes of interest; (c) using the number of sequence tags identified for each of any one or more segments of any one or more chromosomes of interest and said number of sequence tags identified for the normalizing segment sequence to calculate a single segment dose for each of said any one or more segments of any one or more chromosomes of interest; and (d) comparing each of the single segment doses for each of any one or more segments of any one or more chromosomes of interest to a threshold value for each of any one or more chromosomal segments of any one or more chromosome of interest, and thereby determining the presence or absence of one or more different partial fetal chromosomal aneuploidies in the sample. Step (a) can comprise sequencing at least a portion of the nucleic acid molecules of a test sample to obtain said sequence information for the fetal and maternal nucleic acid molecules of the test sample.

In some embodiments, step (c) comprises calculating a single segment dose for each of any one or more segments of any one or more chromosomes of interest as the ratio of the number of sequence tags identified for each of any one or more segments of any one or more chromosomes of interest and the number of sequence tags identified for the normalizing segment sequence for each of the any one or more segments of any one or more chromosomes of interest. In some other embodiments, step (c) comprises (i) calculating a sequence tag density ratio for each of segment of interest, by relating the number of sequence tags identified for each segment of interest in step (b) to the length of each of the segment of interest; (ii) calculating a sequence tag density ratio for each normalizing segment sequence by relating the number of sequence tags identified for the normalizing segment sequence in step (b) to the length of each the normalizing segment sequence; and (iii) using the sequence tag density ratios calculated in steps (i) and (ii) to calculate a single segment dose for each segment of interest, wherein the segment dose is calculated as the ratio of the sequence tag density ratio for each of the segments of interest and the sequence tag density ratio for the normalizing segment sequence for each of the segments of interest. The method can further comprise calculating a normalized segment value (NSV), wherein the NSV relates said segment dose to the mean of the corresponding segment dose in a set of qualified samples as:

$$NSV_{ij} = \frac{x_{ij} - \hat{\mu}_j}{\hat{\sigma}_j}$$

where $\hat{\mu}_j$ and $\hat{\sigma}_j$ are the estimated mean and standard deviation, respectively, for the j-th segment dose in a set of qualified samples, and $x_{ij}$ is the observed j-th segment dose for test sample i.

In embodiments of the method described whereby a chromosome dose or a segment dose is determined using a normalizing segment sequence, the normalizing segment sequence may be a single segment of any one or more of chromosomes 1-22, X, and Y. Alternatively, the normalizing segment sequence may be a group of segments of any one or more of chromosomes 1-22, X, and Y.

Steps (a)-(d) of the method for determining the presence or absence of a partial fetal chromosomal aneuploidy are repeated for test samples from different maternal subjects, and the method comprises determining the presence or absence of different partial fetal chromosomal aneuploidies in each of said samples. Partial fetal chromosomal aneuploidies that can be determined according to the method include partial aneuploidies of any segment of any chromosome. The partial aneuploidies can be selected from partial duplications, partial multiplications, partial insertions and partial deletions. Examples of partial aneuploidies that can be determined according to the method include partial monosomy of chromosome 1, partial monosomy of chromosome 4, partial monosomy of chromosome 5, partial monosomy of chromosome 7, partial monosomy of chromosome 11, partial monosomy of chromosome 15, partial monosomy of chromosome 17, partial monosomy of chromosome 18, and partial monosomy of chromosome 22.

In any one of the embodiments described above, the test sample may be a maternal sample selected from blood, plasma, serum, urine and saliva samples. In any one of the embodiments, the test sample is may be plasma sample. The nucleic acid molecules of the maternal sample are a mixture of fetal and maternal cell-free DNA molecules. Sequencing of the nucleic acids can be performed using next generation sequencing (NGS). In some embodiments, sequencing is massively parallel sequencing using sequencing-by-synthesis with reversible dye terminators. In other embodiments, sequencing is sequencing-by-ligation. In yet other embodiments, sequencing is single molecule sequencing. Optionally, an amplification step is performed prior to sequencing.

In another embodiment, a method is provided for determining the presence or absence of any twenty or more different complete fetal chromosomal aneuploidies in a maternal plasma test sample comprising a mixture of fetal and maternal cell-free DNA molecules. The steps of the method comprise: (a) sequencing at least a portion of the cell-free DNA molecules to obtain sequence information for the fetal and maternal cell-free DNA molecules in the sample; (b) using the sequence information to identify a number of sequence tags for each of any twenty or more chromosomes of interest selected from chromosomes 1-22, X, and Y and to identify a number of sequence tags for a normalizing chromosome for each of said twenty or more chromosomes of interest; (c) using the number of sequence tags identified for each of the twenty or more chromosomes of interest and the number of sequence tags identified for each normalizing chromosome to calculate a single chromosome dose for each of the twenty or more chromosomes of interest; and (d) comparing each of the single chromosome doses for each of the twenty or more chromosomes of interest to a threshold value for each of the twenty or more chromosomes of interest, and thereby determining the presence or absence of any twenty or more different complete fetal chromosomal aneuploidies in the sample.

In another embodiment, the invention provides a method for identifying copy number variation (CNV) of a sequence of interest e.g. a clinically relevant sequence, in a test sample comprising the steps of: (a) obtaining a test sample and a plurality of qualified samples, said test sample comprising test nucleic acid molecules and said plurality of qualified samples comprising qualified nucleic acid molecules; (b) obtaining sequence information for said fetal and maternal nucleic acids in said sample; (c) based on said sequencing of said qualified nucleic acid molecules, calculating a qualified sequence dose for said qualified sequence of interest in each of said plurality of qualified samples, wherein said calculating a qualified sequence dose comprises determining a parameter for said qualified sequence of interest and at least one qualified normalizing sequence; (d) based on said qualified sequence dose, identifying at least one qualified normalizing sequence, wherein said at least one qualified normalizing sequence has the smallest variability and/or the greatest differentiability in sequence dose in said plurality of qualified samples; (e) based on said sequencing of said nucleic acid molecules in said test sample, calculating a test sequence dose for said test sequence of interest, wherein said calculating a test sequence dose comprises determining a parameter for said test sequence of interest and at least one normalizing test sequence, and wherein said at least one normalizing test sequence corresponds to said at least one qualified normalizing sequence; (f) comparing said test sequence dose to at least one threshold value; and (g) assessing said copy number variation of said sequence of interest in said test sample based on the outcome of step (f). In one embodiment, the parameter for said qualified sequence of interest and at least one qualified normalizing sequence relates the number of sequence tags mapped to said qualified sequence of interest to the number of tags mapped to said qualified normalizing sequence, and wherein said parameter for said test sequence of interest and at least one normalizing test sequence relates the number of sequence tags mapped to said test sequence of interest to the number of tags mapped to said normalizing test sequence. In some embodiments, step (b) comprises sequencing at least a portion of the qualified and test nucleic acid molecules, wherein sequencing comprises providing a plurality of mapped sequence tags for a test and a qualified sequence of interest, and for at least one test and at least one qualified normalizing sequence; sequencing at least a portion of said nucleic acid molecules of the test sample to obtain the sequence information for the fetal and maternal nucleic acid molecules of the test sample. In some embodiments, the sequencing step is performed using next generation sequencing method. In some embodiments, the sequencing method may be a massively parallel sequencing method that uses sequencing-by-synthesis with reversible dye terminators. In other embodiments, the sequencing method is sequencing-by-ligation. In some embodiments, sequencing comprises an amplification. In other embodiments, sequencing is single molecule sequencing. The CNV of a sequence of interest is an aneuploidy, which can be a chromosomal or a partial aneuploidy. In some embodiments, the chromosomal aneuploidy is selected from trisomy 2, trisomy 8, trisomy 9, trisomy 20, trisomy 16, trisomy 21, trisomy 13, trisomy 18, trisomy 22, klinefelter's syndrome, 47,XXX, 47,XYY, and monosomy X. In other embodiments, the partial aneuploidy is a partial chromosomal deletion or a partial chromosomal insertion. In some embodiments, the CNV identified by the method is a chromosomal or partial aneuploidy associated with cancer. In some embodiments, the test and qualified sample are biological fluid samples e.g. plasma samples, obtained from a pregnant subject such as a pregnant human subject. In other embodiments, a test and qualified biological fluid samples e.g. plasma samples, are obtained from a subject that is known or is suspected of having cancer.

Some methods for determining the presence or absence of a fetal chromosomal aneuploidy in a maternal test sample may include the following operations: (a) providing sequence reads from fetal and maternal nucleic acids in the maternal test sample, wherein the sequence reads are provided in an electronic format; (b) aligning the sequence reads to one or more chromosome reference sequences using a computing apparatus and thereby providing sequence tags corresponding to the sequence reads; (c) computationally identifying a number of those sequence tags that are from one or more chromosomes of interest or chromosome segments of interest and computationally identifying a number of those sequence tags that are from at least one normalizing chromosome sequence or normalizing chromosome segment sequence for each of the one or more chromosomes of interest or chromosome segments of interest; (d) computationally calculating, using said number of sequence tags identified for each of said one or more chromosomes of interest or chromosome segments of interest and said number of sequence tags identified for each said normalizing chromosome sequence or normalizing chromosome segment sequence, a single chromosome or segment dose for each of said one or more chromosomes of interest or chromosome segments of interest; and (e) comparing, using said computing apparatus, each of said single chromosome doses for each of one or more chromosomes of interest or chromosome segments of interest to a corresponding threshold value for each of said one or more chromosomes of interest or chromosome segments of interest, and thereby determining the presence or absence of at least one fetal aneuploidy in said test sample. In certain implementations, the number of sequence tags identified for each of the one or more chromosomes of interest or chromosome segments of interest is at least about 10,000, or at least about 100,000. The disclosed embodiments also provide a computer program product including a non-transitory computer readable medium on which is provided program instructions for performing the recited operations and other computational operations described herein.

In some embodiments, the chromosome reference sequences have excluded regions that are present naturally in chromosomes but which do not contribute to the number of sequence tags for any chromosome or chromosome segment. In some embodiments, a method additionally includes (i) determining whether a read under consideration aligns to a site on a chromosome reference sequence where another read from the test sample previous aligned; and (ii) determining whether to include the read under consideration in the number of sequence tags for a chromosome of interest or a chromosome segment of interest. The chromosome reference sequence may be stored on a computer readable medium.

In some embodiments, a method additionally includes sequencing at least a portion of said nucleic acid molecules of said maternal test sample to obtain said sequence information for said fetal and maternal nucleic acid molecules of said test sample. The sequencing may involve massively parallel sequencing on maternal and fetal nucleic acids from the maternal test sample to produce the sequence reads.

In some embodiments, a method further includes automatically recording, using a processor, the presence or absence of a fetal chromosomal aneuploidy as determined in (d) in a patient medical record for a human subject providing the maternal test sample. The recording may include recording chromosome doses and/or a diagnosis based said chromosome doses in a computer-readable medium. In some cases, the patient medical record is maintained by a laboratory, physician's office, a hospital, a health maintenance organization, an insurance company, or a personal medical record website. A method may further include prescribing, initiating, and/or altering treatment of a human subject from whom the maternal test sample was taken. Additionally or alternatively, the method may include ordering and/or performing one or more additional tests.

Some methods disclosed herein identify normalizing chromosome sequences or normalizing chromosome segment sequences for a chromosome or chromosome segment of interest. Some such methods include the following operations: (a) providing a plurality of qualified samples for the chromosome or chromosome segment of interest; (b) repeatedly calculating chromosome doses for the chromosome or chromosome segment of interest using multiple potential normalizing chromosome sequences or normalizing chromosome segment sequences, wherein the repeated calculation is performed with a computing apparatus; and (c) selecting a normalizing chromosome sequence or normalizing chromosome segment sequence alone or in a combination giving a smallest variability and/or a large differentiability in calculated doses for the chromosome or chromosome segment of interest.

A selected normalizing chromosome sequence or normalizing chromosome segment sequence may be part of a combination of normalizing chromosome sequences or normalizing chromosome segment sequences or it may be provided alone, and not in combination with other normalizing chromosome sequences or normalizing chromosome segment sequences.

The disclosed embodiments provide a method for classifying a copy number variation in a fetal genome. The operations of the method include: (a) receiving sequence reads from fetal and maternal nucleic acids in a maternal test sample, wherein the sequence reads are provided in an electronic format; (b) aligning the sequence reads to one or more chromosome reference sequences using a computing apparatus and thereby providing sequence tags corresponding to the sequence reads; (c) computationally identifying a number of those sequence tags that are from one or more chromosomes of interest by using the computing apparatus and determining that a first chromosome of interest in the fetus harbors a copy number variation; (d) calculating a first fetal fraction value by a first method that does not use information from the tags from the first chromosome of interest; (e) calculating a second fetal fraction value by a second method that uses information from the tags from the first chromosome; and (f) comparing the first fetal fraction value and the second fetal fraction value and using the comparison to classify the copy number variation of the first chromosome. In some embodiments, the method further includes sequencing cell free DNA from the maternal test sample to provide the sequence reads. In some embodiments, the method further includes obtaining the maternal test sample from a pregnant organism. In some embodiments, operation (b) includes using the computing apparatus to align at least about 1 million reads. In some embodiments, operation (f) can include determining whether the two fetal fraction values are approximately equal.

In some embodiments, operation (f) can further include determining that the two fetal fraction values are approximately equal, and thereby determining that a ploidy assumption implicit in the second method is true. In some embodiments, the ploidy assumption implicit in the second method is that the first chromosome of interest has a complete chromosomal aneuploidy. In some of these embodiments, the complete chromosomal aneuploidy of the first chromosome of interest is a monosomy or a trisomy.

In some embodiments, operation (f) can include determining whether the two fetal fraction values are not approximately equal, and further include analyzing the tag information for the first chromosome of interest to determine whether (i) the first chromosome of interest harbors a partial aneuploidy, or (ii) the fetus is a mosaic.

In some embodiments, this operation can also include binning the sequence for the first chromosome of interest into a plurality of portions; determining whether any of said portions contains significantly more or significantly less nucleic acid than one or more other portions; and if any of said portions contain significantly more or significantly less nucleic acid than one or more other portions, determining that the first chromosome of interest harbors a partial aneuploidy. In one embodiment, this operation can further include determining that a portion of the first chromosome of interest containing significantly more or significantly less nucleic acid than one or more other portions harbors the partial aneuploidy.

In one embodiments, operation (f) can also include binning the sequence for the first chromosome of interest into a plurality of portions; determining whether any of said portions contains significantly more or significantly less nucleic acid than one or more other portions; and if none of said portions contain significantly more or significantly less nucleic acid than one or more other portions, determining that the fetus is a mosaic.

Operation (e) can include: (a) calculating the number of sequence tags from the first chromosome of interest and at least one normalizing chromosome sequence to determine a chromosome dose; and (b) calculating the fetal fraction value from the chromosome dose using the second method. In some embodiments, this operation further includes calculating a normalized chromosome value (NCV), wherein the second method uses the normalized chromosome value, and wherein the NCV relates the chromosome dose to the mean of the corresponding chromosome dose in a set of qualified samples as:

$$NCV_{iA} = \frac{R_{iA} - \overline{R_{iU}}}{\sigma_{iU}}$$

where $\overline{R_{iU}}$ and $\sigma_{iU}$ are the estimated mean and standard deviation, respectively, for the i-th chromosome dose in the set of qualified samples, and $R_{iA}$ is the chromosome dose calculated for the chromosome of interest. In another embodiment, operation (d) further includes that the first method calculates the first fetal fraction value using information from one or more polymorphisms exhibiting an allelic imbalance in the fetal and maternal nucleic acids of the maternal test sample.

In various embodiments, if the first fetal fraction value is not approximately equal to the second fetal fraction value, the method further includes (i) determining whether the copy number variation results from a partial aneuploidy or a mosaic; and (ii) if the copy number variation results from a partial aneuploidy, determining the locus of the partial aneuploidy on the first chromosome of interest. In some embodiments, determining the locus of the partial aneuploidy on the first chromosome of interest includes categorizing the sequence tags for the first chromosome of interest into bins of blocks of nucleic acids in the first chromosome of interest; and counting the mapped tags in each bin.

Operation (e) can further include calculating the fetal fraction value by evaluating the following expression:

$$ff = 2 \times NCV_{iA} CV_{iU}$$

where ff is the second fetal fraction value, $NCV_{iA}$ is the normalized chromosome value at the i-th chromosome in an affected sample, and $CV_{iU}$ is the coefficient of variation for doses of the chromosome of interest determined in the qualified samples.

In any one of the embodiments above, the first chromosome of interest is selected from a group consisting of chromosomes 1-22, X, and Y. In any one of the above embodiments, operation (f) can classify the copy number variation into a classification selected from the group consisting of complete chromosomal insertions, complete chromosomal deletions, partial chromosomal duplications, and partial chromosomal deletions, and mosaics.

The disclosed embodiments also provide a computer program product including a non-transitory computer readable medium on which is provided program instructions for classifying a copy number variation in a fetal genome. The computer program product can include: (a) code for receiving sequence reads from fetal and maternal nucleic acids in a maternal test sample, wherein the sequence reads are provided in an electronic format; (b) code for aligning the sequence reads to one or more chromosome reference sequences using a computing apparatus and thereby providing sequence tags corresponding to the sequence reads; (c) code for computationally identifying a number of those sequence tags that are from one or more chromosomes of interest by using the computing apparatus and determining that a first chromosome of interest in the fetus harbors a copy number variation; (d) code for calculating a first fetal fraction value by a first method that does not use information from the tags from the first chromosome of interest; (e) code for calculating a second fetal fraction value by a second method that uses information from the tags from the first chromosome; and (f) code for comparing the first fetal fraction value and the second fetal fraction value and using the comparison to classify the copy number variation of the first chromosome. In some embodiments, the computer program product includes code for the various operations and methods in the any of the above embodiments of the methods disclosed.

The disclosed embodiments also provide a system for classifying a copy number variation in a fetal genome. The system includes (a) an interface for receiving at least about 10,000 sequence reads from fetal and maternal nucleic acids in a maternal test sample, wherein the sequence reads are provided in an electronic format; (b) memory for storing, at least temporarily, a plurality of said sequence reads; (c) a processor designed or configured with program instructions for: (i) aligning the sequence reads to one or more chromosome reference sequences and thereby providing sequence tags corresponding to the sequence reads; (ii) identifying a number of those sequence tags that are from one or more chromosomes of interest and determining that a first chromosome of interest in the fetus harbors a copy number variation; (iii) calculating a first fetal fraction value by a first method that does not use information from the tags from the first chromosome of interest; (iv) calculating a second fetal fraction value by a second method that uses information from the tags from the first chromosome; and (v) comparing the first fetal fraction value and the second fetal fraction value and using the comparison to classify the copy number variation of the first chromosome. According to various embodiments, the first chromosome of interest is selected from a group consisting of chromosomes 1-22, X, and Y. In some embodiments, the program instructions for (c)(v) includes program instructions for classifying the copy number variation into a classification selected from the group consisting of complete chromosomal insertions, complete chromosomal deletions, partial chromosomal duplications, and partial chromosomal deletions, and mosaics. According to various embodiments, the system can include program instructions for sequencing cell free DNA from the maternal test sample to provide the sequence reads. According to some embodiments, the program instructions for operation (c)(i) includes program instructions for using the computing apparatus to align at least about 1 million reads.

In some embodiments, the system also includes a sequencer configured to sequence the fetal and maternal nucleic acids in a maternal test sample and provide the sequence reads in electronic format. In various embodiments, the sequencer and the processor are located in separate facilities and the sequencer and the processor are linked by a network.

In various embodiments, the system also further includes an apparatus for taking the maternal test sample from a pregnant mother. According to some embodiments, the apparatus for taking the maternal test sample and the processor are located in separate facilities. In various embodiments, the system also includes an apparatus for extracting cell free DNA from the maternal test sample. In some embodiments, the apparatus for extracting cell free DNA is located in the same facility with the sequencer, and the apparatus for taking the maternal test sample is located in a remote facility.

According to some embodiments, the program instructions for comparing the first fetal fraction value and the second fetal fraction value also include program instructions for determining whether the two fetal fraction values are approximately equal.

In some embodiments, the system also includes program instructions for determining that a ploidy assumption implicit in the second method is true when the two fetal fraction values are approximately equal. In some embodiments, the ploidy assumption implicit in the second method is that the first chromosome of interest has a complete chromosomal aneuploidy. In some embodiments, the complete chromosomal aneuploidy of the first chromosome of interest is a monosomy or a trisomy.

In some embodiments, the system also includes program instructions for analyzing the tag information for the first chromosome of interest to determine whether (i) first chromosome of interest harbors a partial aneuploidy, or (ii) the fetus is a mosaic, wherein the program instructions for analyzing are configured to execute when the program instructions for comparing the first fetal fraction value and the second fetal fraction value indicate that the two fetal fraction values are not approximately equal. In some embodiments, the program instructions for analyzing the tag information for the first chromosome of interest include: program instructions for binning the sequence for the first chromosome of interest into a plurality of portions; program instructions for determining whether any of said portions contains significantly more or significantly less nucleic acid than one or more other portions; and program instructions for determining that the first chromosome of interest harbors a partial aneuploidy if any of said portions contain significantly more or significantly less nucleic acid than one or more other portions. In some embodiments, the system further includes program instructions for determining that a portion of the first chromosome of interest containing significantly more or significantly less nucleic acid than one or more other portions harbors the partial aneuploidy.

In some embodiments, the program instructions for analyzing the tag information for the first chromosome of interest include: program instructions for binning the sequence for the first chromosome of interest into a plurality of portions; program instructions for determining whether any of said portions contains significantly more or significantly less nucleic acid than one or more other portions; and program instructions for determining that the fetus is a mosaic if none of said portions contain significantly more or significantly less nucleic acid than one or more other portions.

According to various embodiments, the system can include program instructions for the second method of calculating the fetal fraction value that include: (a) program instructions for calculating the number of sequence tags from the first chromosome of interest and at least one normalizing chromosome sequence to determine a chromosome dose; and (b) program instructions for calculating the fetal fraction value from the chromosome dose using the second method.

In some embodiments, the system further includes program instructions for calculating a normalized chromosome value (NCV), wherein the program instructions for the second method include program instructions for using the normalized chromosome value, and wherein the program instructions for the NCV relate the chromosome dose to the mean of the corresponding chromosome dose in a set of qualified samples as:

$$NCV_{iA} = \frac{R_{iA} - \overline{R_{iU}}}{\sigma_{iU}}$$

where $\overline{R_{iU}}$ and $\sigma_{iU}$ are the estimated mean and standard deviation, respectively, for the i-th chromosome dose in the set of qualified samples, and $R_{iA}$ is the chromosome dose calculated for the chromosome of interest. In various embodiments, the program instructions for the first method include program instructions for calculating the first fetal fraction value using information from one or more polymorphisms exhibiting an allelic imbalance in the fetal and maternal nucleic acids of the maternal test sample.

According to various embodiments, the program instructions for the second method of calculating the fetal fraction value include program instructions for evaluating the following expression:

$$ff = 2 \times NCV_{iA} CV_{iU}$$

where ff is the second fetal fraction value, $NCV_{iA}$ is the normalized chromosome value at the i-th chromosome in an affected sample, and $CV_{iU}$ is the coefficient of variation for doses of the chromosome of interest determined in the qualified samples.

According to various embodiments, the system further includes (i) program instructions for determining whether the copy number variation results from a partial aneuploidy or a mosaic; and (ii) program instructions for if the copy number variation results from a partial aneuploidy, determining the locus of the partial aneuploidy on the first chromosome of interest, wherein the program instructions in (i) and (ii) is configured to execute when the program instructions for comparing the first fetal fraction value and the second fetal fraction value determine that the first fetal fraction value is not approximately equal to the second fetal fraction value.

In some embodiments, program instructions for determining the locus of the partial aneuploidy on the first chromosome of interest include program instructions for categorizing the sequence tags for the first chromosome of interest into bins of blocks of nucleic acids in the first chromosome of interest; and program instructions for counting the mapped tags in each bin.

In certain embodiments, methods for identifying the presence of a cancer and/or an increased risk of a cancer in a mammal (e.g., a human) are provided where the methods comprise: (a) providing sequence reads of nucleic acids in a test sample from said mammal, wherein said test sample may comprise both genomic nucleic acids from cancerous or precancerous cells and genomic nucleic acids from constitutive (germline) cells, wherein the sequence reads are provided in an electronic format; (b) aligning the sequence reads to one or more chromosome reference sequences using a computing apparatus and thereby providing sequence tags corresponding to the sequence reads; (c) computationally identifying a number of sequence tags from the fetal and maternal nucleic acids for one or more chromosomes of interest amplification of which or deletions of which are known to be associated with cancers, or chromosome segments of interest amplification(s) of which or deletions of which are known to be associated with cancers, wherein said chromosome or chromosome segments are selected from chromosomes 1-22, X, and Y and segments thereof and computationally identifying a number of sequence tags for at least one normalizing chromosome sequence or normalizing chromosome segment sequence for each of the one or more chromosomes of interest or chromosome segments of interest, wherein the number of sequence tags identified for each of the one or more chromosomes of interest or chromosome segments of interest is at least about 2,000, or at least about 5,000, or at least about 10,000; (d) computationally calculating, using said number of sequence tags identified for each of said one or more chromosomes of interest or chromosome segments of interest and said number of sequence tags identified for each said normalizing chromosome sequence or normalizing chromosome segment sequence, a single chromosome or segment dose for each of said one or more chromosomes of interest or chromosome segments of interest; and (e) comparing, using said computing apparatus, each of said single chromosome doses for each of one or more chromosomes of interest or chromosome segments of interest to a corresponding threshold value for each of said one or more chromosomes of interest or chromosome segments of interest, and thereby determining the presence or absence of aneuploidies in said sample, where the presence of said aneuploidies and/or an increased number of said is an indicator of the presence and/or increased risk of a cancer. In certain embodiments, the increased risk is as compared to the same subject at a different time (e.g., earlier in time), as compared to a reference population (e.g., optionally adjusted for gender, and/or ethnicity, and/or age, etc.), as compared to a similar subject absent exposure to certain risk factors, and the like. In certain embodiments chromosomes of interest or chromosome segments of interest comprise whole chromosomes amplifications and/or deletions of which are known to be associated with a cancer (e.g., as described herein). In certain embodiments chromosomes of interest or chromosome segments of interest comprise chromosome segments amplifications or deletions of which are known to be associated with one or more cancers. In certain embodiments the chromosome segments comprise substantially whole chromosome arms (e.g., as described herein). In certain embodiments the chromosome segments comprise whole chromosome aneuploidies. In certain embodiments the whole chromosome aneuploidies comprise a loss, while in certain other embodiments the whole chromosome aneuploidies comprise a gain (e.g., a gain or a loss as shown in Table 1). In certain embodiments the chromosomal segments of interest are substantially arm-level segments comprising a p arm or a q arm of any one or more of chromosomes 1-22, X and Y. In certain embodiments the aneuploidies comprise an amplification of a substantial arm level segment of a chromosome or a deletion of a substantial arm level segment of a chromosome. In certain embodiments the chromosomal segments of interest substantially comprise one or more arms selected from the group consisting of 1q, 3q, 4p, 4q, 5p, 5q, 6p, 6q, 7p, 7q, 8p, 8q, 9p, 9q, 10p, 10q, 12p, 12q, 13q, 14q, 16p, 17p, 17q, 18p, 18q, 19p, 19q, 20p, 20q, 21q, and/or 22q. In certain embodiments the aneuploidies comprise an amplification of one or more arms selected from the group consisting of 1q, 3q, 4p, 4q, 5p, 5q, 6p, 6q, 7p, 7q, 8p, 8q, 9p, 9q, 10p, 10q, 12p, 12q, 13q, 14q, 16p, 17p, 17q, 18p, 18q, 19p, 19q, 20p, 20q, 21q, 22q. In certain embodiments the aneuploidies comprise a deletion of one or more arms selected from the group consisting of 1p, 3p, 4p, 4q, 5q, 6q, 8p, 8q, 9p, 9q, 10p, 10q, 11p, 11q, 13q, 14q, 15q, 16q, 17p, 17q, 18p, 18q, 19p, 19q, 22q. In certain embodiments the chromosomal segments of interest are segments that comprise a region and/or a gene shown in Table 3 and/or Table 5 and/or Table 4 and/or Table 6. In certain embodiments the aneuploidies comprise an amplification of a region and/or a gene shown in Table 3 and/or Table 5. In certain embodiments the aneuploidies comprise a deletion of a region and/or a gene shown in Table 4 and/or Table 6. In certain embodiments the chromosomal segments of interest are segments known to contain one or more oncogenes and/or one or more tumor suppressor genes. In certain embodiments the aneuploidies comprise an amplification of one or more regions selected from the group consisting of 20Q13, 19q12, 1q21-1q23, 8p11-p12, and the ErbB2. In certain embodiments the aneuploidies comprise an amplification of one or more regions comprising a gene selected from the group consisting of MYC, ERBB2 (EFGR), CCND1 (Cyclin D1), FGFR1, FGFR2, HRAS, KRAS, MYB, MDM2, CCNE, KRAS, MET, ERBB1, CDK4, MYCB, ERBB2, AKT2, MDM2 and CDK4, and the like. In certain embodiments the cancer is a cancer selected from the group consisting of leukemia, ALL, brain cancer, breast cancer, colorectal cancer, dedifferentiated liposarcoma, esophageal adenocarcinoma, esophageal squamous cell cancer, GIST, glioma, HCC, hepatocellular cancer, lung cancer, lung NSC, lung SC, medulloblastoma, melanoma, MPD, myeloproliferative disorder, cervical cancer, ovarian cancer, prostate cancer, and renal cancer. In certain embodiments the biological sample comprise a sample selected from the group consisting of whole blood, a blood fraction, saliva/oral fluid, urine, a tissue biopsy, pleural fluid, pericardial fluid, cerebral spinal fluid, and peritoneal fluid. In certain embodiments the chromosome reference sequences have excluded regions that are present naturally in chromosomes but that do not contribute to the number of sequence tags for any chromosome or chromosome segment. In certain embodiments the methods further comprise determining whether a read under consideration aligns and to a site on a chromosome reference sequence where another read previous aligned; and determining whether to include the read under consideration in the number of sequence tags for a chromosome of interest or a chromosome segment of interest, wherein both determining operations are performed with the computing apparatus. In various embodiments the methods further comprise storing in a computer readable medium (e.g., a non-transitory medium), at least temporarily, sequence information for said nucleic acids in said sample. In certain embodiments step (d) comprises computationally calculating a segment dose for a selected one of segments of interest as the ratio of the number of sequence tags identified for the selected segment of interest and the number of sequence tags identified for a corresponding at least one normalizing chromosome sequence or normalizing chromosome segment sequence for the selected segment of interest. In certain embodiments the said one or more chromosome segments of interest comprise at least 5, or at least 10, or at least 15, or at least 20, or at least 50, or at least 100 different segments of interest. In certain embodiments at least 5, or at least 10, or at least 15, or at least 20, or at least 50, or at least 100 different aneuploidies are detected. In certain embodiments at least one normalizing chromosome sequence comprises one or more chromosomes selected from the group consisting of chromosomes 1-22, X, and Y. In certain embodiments said at least one normalizing chromosome sequence comprises for each segment the chromosome corresponding to the chromosome in which said segment is located. In certain embodiments the at least one normalizing chromosome sequence comprises for each segment the chromosome segment corresponding to the chromosome segment that is being normalized. In certain embodiments at least one normalizing chromosome sequence or normalizing chromosome segment sequence is a chromosome or segment selected for an associated chromosome or segment of interest by (i) identifying a plurality of qualified samples for the segment of interest; (ii) repeatedly calculating chromosome doses for the selected chromosome segment using multiple potential normalizing chromosome sequences or normalizing chromosome segment sequences; and (iii) selecting the normalizing chromosome segment sequence alone or in a combination giving the smallest variability and/or greatest differentiability in calculated chromosome doses. In certain embodiments the method further comprises calculating a normalized segment value (NSV), wherein said NSV relates said segment dose to the mean of the corresponding segment dose in a set of qualified samples as described herein. In certain embodiments the normalizing segment sequence is a single segment of any one or more of chromosomes 1-22, X, and Y. In certain embodiments the normalizing segment sequence is a group of segments of any one or more of chromosomes 1-22, X, and Y. In certain embodiments the normalizing segment comprises substantially one arm of any one or more of chromosomes 1-22, X, and Y. In certain embodiments the method further comprises sequencing at least a portion of said nucleic acid molecules of said test sample to obtain said sequence information. In certain embodiments the sequencing comprises sequencing cell free DNA from the test sample to provide the sequence information. In certain embodiments the sequencing comprises sequencing cellar DNA from the test sample to provide the sequence information. In certain embodiments the sequencing comprises massively parallel sequencing. In certain embodiments the method(s) further comprise automatically recording the presence or absence of an aneuploidy as determined in (d) in a patient medical record for a human subject providing the test sample, wherein the recording is performed using the processor. In certain embodiments the recording comprises recording the chromosome doses and/or a diagnosis based said chromosome doses in a computer-readable medium. In various embodiments the patient medical record is maintained by a laboratory, physician's office, a hospital, a health maintenance organization, an insurance company, or a personal medical record website. In certain embodiments the determination of the presence or absence and/or number of said aneuploidies comprises a component in a differential diagnosis for cancer. In certain embodiments the detection of aneuploidies indicates a positive result and said method further comprises prescribing, initiating, and/or altering treatment of a human subject from whom the test sample was taken. In certain embodiments prescribing, initiating, and/or altering treatment of a human subject from whom the test sample was taken comprises prescribing and/or performing further diagnostics to determine the presence and/or severity of a cancer. In certain embodiments the further diagnostics comprise screening a sample from said subject for a biomarker of a cancer, and/or imaging said subject for a cancer. In certain embodiments when said method indicates the presence of neoplastic cells in said mammal, treating said mammal, or causing said mammal to be treated, to remove and/or to inhibit the growth or proliferation of said neoplastic cells. In certain embodiments treating the mammal comprises surgically removing the neoplastic (e.g., tumor) cells. In certain embodiments treating the mammal comprises performing radiotherapy or causing radiotherapy to be performed on said mammal to kill the neoplastic cells. In certain embodiments treating the mammal comprises administering or causing to be administered to said mammal an anti-cancer drug (e.g., matuzumab, erbitux, vectibix, nimotuzumab, matuzumab, panitumumab, fluorouracil, capecitabine, 5-trifluoromethyl-2'-deoxyuridine, methotrexate, raltitrexed, pemetrexed, cytosine arabinoside, 6-mercaptopurine, azathioprine, 6-thioguanine, pentostatin, fludarabine, cladribine, floxuridine, cyclophosphamide, neosar, ifosfamide, thiotepa, 1,3-bis(2-chloroethyl)-1-nitosourea, 1,-(2-chloroethyl)-3-cyclohexyl-Initrosourea, hexamethylmelamine, busulfan, procarbazine, dacarbazine, chlorambucil, melphalan, cisplatin, carboplatin, oxaliplatin, bendamustine, carmustine, chloromethine, dacarbazine, fotemustine, lomustine, mannosulfan, nedaplatin, nimustine, prednimustine, ranimustine, satraplatin, semustine, streptozocin, temozolomide, treosulfan, triaziquone, triethylene melamine, thiotepa, triplatin tetranitrate, trofosfamide, uramustine, doxorubicin, daunorubicin, mitoxantrone, etoposide, topotecan, teniposide, irinotecan, camptosar, camptothecin, belotecan, rubitecan, vincristine, vinblastine, vinorelbine, vindesine, paclitaxel, docetaxel, abraxane, ixabepilone, larotaxel, ortataxel, tesetaxel, vinflunine, imatinib mesylate, sunitinib malate, sorafenib tosylate, nilotinib hydrochloride monohydrate/, tasigna, semaxanib, vandetanib, vatalanib, retinoic acid, a retinoic acid derivative, and the like).

In another embodiment, a computer program product for use in determining the presence of a cancer and/or an increased risk of a cancer in a mammal is provided. The computer program product typically comprises: (a) code for providing sequence reads of nucleic acids in a test sample from said mammal, wherein said test sample may comprise both genomic nucleic acids from cancerous or precancerous cells and genomic nucleic acids from constitutive (germline) cells, wherein the sequence reads are provided in an electronic format; (b) code for aligning the sequence reads to one or more chromosome reference sequences using a computing apparatus and thereby providing sequence tags corresponding to the sequence reads; (c) code for computationally identifying a number of sequence tags from the fetal and maternal nucleic acids for one or more chromosomes of interest amplification of which or deletions of which are known to be associated with cancers, or chromosome segments of interest amplification of which or deletions of which are known to be associated with cancers, wherein said chromosome or chromosome segments are selected from chromosomes 1-22, X, and Y and segments thereof and computationally identifying a number of sequence tags for at least one normalizing chromosome sequence or normalizing chromosome segment sequence for each of the one or more chromosomes of interest or chromosome segments of interest, wherein the number of sequence tags identified for each of the one or more chromosomes of interest or chromosome segments of interest is at least about 10,000; (d) code for computationally calculating, using said number of sequence tags identified for each of said one or more chromosomes of interest or chromosome segments of interest and said number of sequence tags identified for each said normalizing chromosome sequence or normalizing chromosome segment sequence, a single chromosome or segment dose for each of said one or more chromosomes of interest or chromosome segments of interest; and (e) code for comparing, using said computing apparatus, each of said single chromosome doses for each of one or more chromosomes of interest or chromosome segments of interest to a corresponding threshold value for each of said one or more chromosomes of interest or chromosome segments of interest, and thereby determining the presence or absence of aneuploidies in said sample, where the presence of said aneuploidies and/or an increased number of said is an indicator of the presence and/or increased risk of a cancer. In various embodiments the code provides instructions for performance of the diagnostic methods as described above (and later herein).

Methods of treating a subject for a cancer are also provided. In certain embodiments the methods comprise performing a method for identifying the presence of a cancer and/or an increased risk of a cancer in a mammal as described herein using a sample from the subject or receiving the results of such a method performed on the sample; and when the method alone, or in combination with other indicator(s) from a differential diagnosis for a cancer indicates the presence of neoplastic cells in said subject, treating the subject, or causing the subject to be treated, to remove and/or to inhibit the growth or proliferation of the neoplastic cells. In certain embodiments treating said subject comprises surgically removing the cells. In certain embodiments treating the subject comprises performing radiotherapy or causing radiotherapy to be performed on said subject to kill said neoplastic cells. In certain embodiments treating the subject comprises administering or causing to be administered to the subject an anti-cancer drug (e.g., matuzumab, erbitux, vectibix, nimotuzumab, matuzumab, panitumumab, fluorouracil, capecitabine, 5-trifluoromethyl-2'-deoxyuridine, methotrexate, raltitrexed, pemetrexed, cytosine arabinoside, 6-mercaptopurine, azathioprine, 6-thioguanine, pentostatin, fludarabine, cladribine, floxuridine, cyclophosphamide, neosar, ifosfamide, thiotepa, 1,3-bis(2-chloroethyl)-1-nitosourea, 1,-(2-chloroethyl)-3-cyclohexyl-Initrosourea, hexamethylmelamine, busulfan, procarbazine, dacarbazine, chlorambucil, melphalan, cisplatin, carboplatin, oxaliplatin, bendamustine, carmustine, chloromethine, dacarbazine, fotemustine, lomustine, mannosulfan, nedaplatin, nimustine, prednimustine, ranimustine, satraplatin, semustine, streptozocin, temozolomide, treosulfan, triaziquone, triethylene melamine, thiotepa, triplatin tetranitrate, trofosfamide, uramustine, doxorubicin, daunorubicin, mitoxantrone, etoposide, topotecan, teniposide, irinotecan, camptosar, camptothecin, belotecan, rubitecan, vincristine, vinblastine, vinorelbine, vindesine, paclitaxel, docetaxel, abraxane, ixabepilone, larotaxel, ortataxel, tesetaxel, vinflunine, imatinib mesylate, sunitinib malate, sorafenib tosylate, nilotinib hydrochloride monohydrate/, tasigna, semaxanib, vandetanib, vatalanib, retinoic acid, a retinoic acid derivative, and the like).

Methods of monitoring a treatment of a subject for a cancer are also provided. In various embodiments the methods comprise performing a method for identifying the presence of a cancer and/or an increased risk of a cancer in a mammal as described herein on a sample from the subject or receiving the results of such a method performed on the sample before or during the treatment; and; performing the method again on a second sample from the subject or receiving the results of such a method performed on the second sample at a later time during or after the treatment; where a reduced number or severity of aneuploidy (e.g., a reduced aneuploidy frequency and/or a decrease or absence of certain aneuploidies) in the second measurement (e.g., as compared to the first measurement) is an indicator of a positive course of treatment and the same or increased number or severity of aneuploidy in the second measurement (e.g., as compared to the first measurement) is an indicator of a negative course of treatment and, when said indicator is negative, adjusting said treatment regimen to a more aggressive treatment regimen and/or to a palliative treatment regimen.

Although the examples herein concern humans and the language is primarily directed to human concerns, the concepts described herein are applicable to genomes from any plant or animal.

INCORPORATION BY REFERENCE

All patents, patent applications, and other publications, including all sequences disclosed within these references, referred to herein are expressly incorporated herein by reference, to the same extent as if each individual publication, patent or patent application was specifically and individually indicated to be incorporated by reference. All documents cited are, in relevant part, incorporated herein by reference in their entireties for the purposes indicated by the context of their citation herein. However, the citation of any document is not to be construed as an admission that it is prior art with respect to the present disclosure.

BRIEF DESCRIPTION OF THE DRAWINGS

FIG. 22A) when the sequencing library was prepared according to the abbreviated protocol (ABB; ◇) and when the sequencing library was prepared according to the repair-free 2-STEP method (INSOL; □); and the percent sequence tags as a function of the size of the chromosome (FIG. 22B). FIG. 22C shows the percent of the ratio of tags mapped when libraries were prepared using the 2-STEP method to that obtained when libraries were made using the abbreviated (ABB) method as a function of the GC content of the chromosomes.

FIG. 23A shows that a greater number of tags mapped to the X chromosome when using the repair-free method (2-STEP) relative to that obtained using the abbreviated method (ABB). FIG. 23B shows that the percent tags that mapped to the Y chromosome when using the repair-free 2-STEP method was not different from that when using the abbreviated method (ABB).

FIGS. 25 and 25B are graphs showing the average (n=5) of the percent of the total number of sequence tags that mapped to each human chromosome (% ChrN.

FIG. 26A shows that a greater number of tags mapped to the X chromosome when using the repair-free methods (2-STEP and 1-STEP) relative to that obtained using the abbreviated method (ABB). FIG. 26B shows that the percent tags that mapped to the Y chromosome when using the repair-free 2-STEP and 1-STEP methods was not different from that when using the abbreviated method.

FIG. 30A) when indexed sequencing libraries were prepared on solid surface according to the 1-STEP method and sequenced as 6-plex; and the percent sequence tags obtained as a function of the size of the chromosome (FIG. 30B).

DETAILED DESCRIPTION

Figure 1:
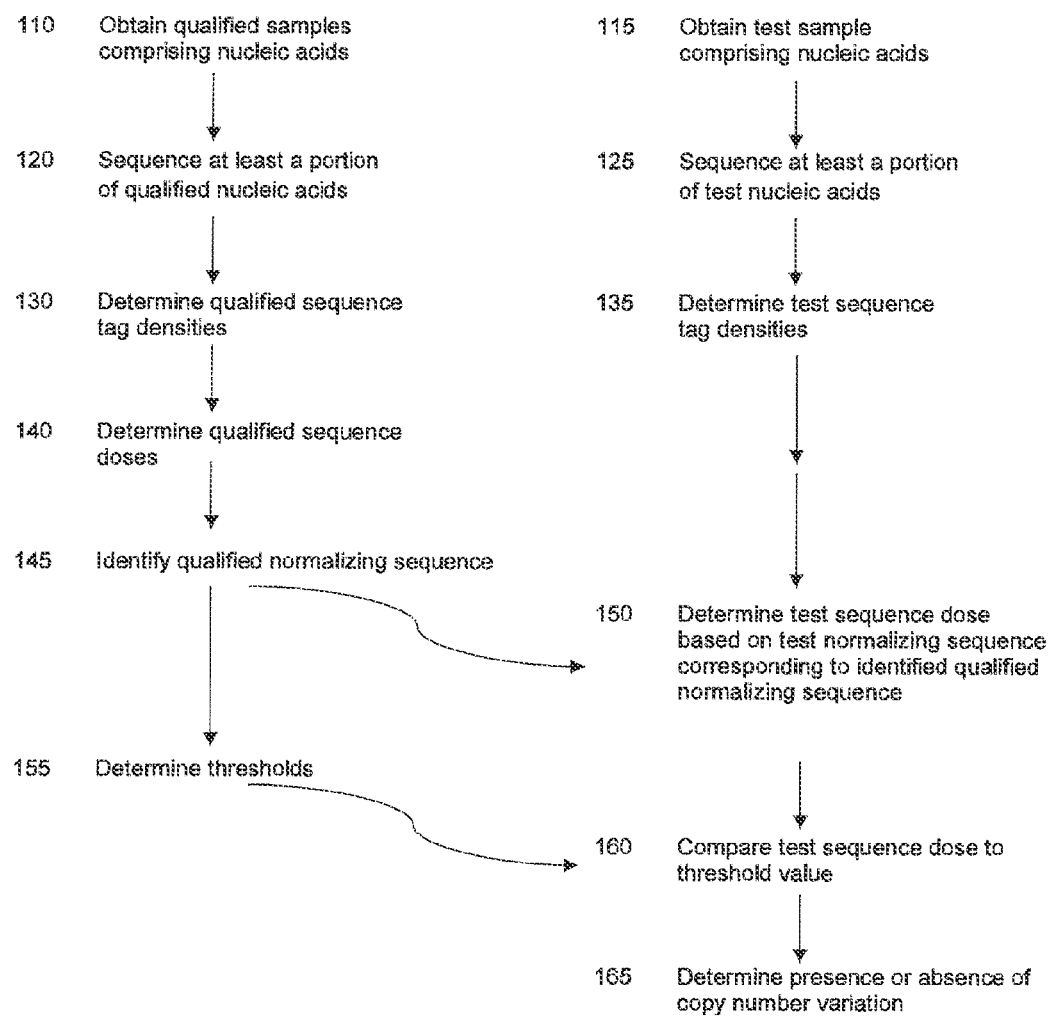
FIG. 1 is a flowchart of a method 100 for determining the presence or absence of a copy number variation in a test sample comprising a mixture of nucleic acids.

The disclosed embodiments concern methods, apparatus, and systems for determining copy number variations (CNV) of a sequence of interest in a test sample that comprises a mixture of nucleic acids that are known or are suspected to differ in the amount of one or more sequence of interest. Sequences of interest include genomic segment sequences ranging from, e.g., kilobases (kb) to megabases (Mb) to entire chromosomes that are known or are suspected to be associated with a genetic or a disease condition. Examples of sequences of interest include chromosomes associated with well-known aneuploidies e.g. trisomy 21, and segments of chromosomes that are multiplied in diseases such as cancer e.g. partial trisomy 8 in acute myeloid leukemia. CNV that can be determined according to the present method include monosomies and trisomies of any one or more of autosomes 1-22, and of sex chromosomes X and Y e.g. 45,X, 47,XXX, 47,XXY and 47,XYY, other chromosomal polysomies i.e. tetrasomy and pentasomies including but not limited to XXXX, XXXXX, XXXXY and XYYYY, and deletions and/or duplications of segments of any one or more of the chromosomes.

The methods employ a statistical approach that is implemented on machine processor(s) and accounts for accrued variability stemming from, e.g., process-related, interchromosomal (intra-run), and inter-sequencing (inter-run) variability. The methods are applicable to determining CNV of any fetal aneuploidy, and CNVs known or suspected to be associated with a variety of medical conditions.

Unless otherwise indicated, the practice of the present invention involves conventional techniques and apparatus commonly used in molecular biology, microbiology, protein purification, protein engineering, protein and DNA sequencing, and recombinant DNA fields, which are within the skill of the art. Such techniques and apparatus are known to those of skill in the art and are described in numerous texts and reference works (See e.g., Sambrook et al., "Molecular Cloning: A Laboratory Manual", Third Edition (Cold Spring Harbor), [2001]); and Ausubel et al., "Current Protocols in Molecular Biology" [1987]).

Numeric ranges are inclusive of the numbers defining the range. It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein.

Every numerical range given throughout this specification will include every narrower numerical range that falls within such broader numerical range, as if such narrower numerical ranges were all expressly written herein.

The headings provided herein are not intended to limit the disclosure.

Unless defined otherwise herein, all technical and scientific terms used herein have the same meaning as commonly understood by one of ordinary skill in the art. Various scientific dictionaries that include the terms included herein are well known and available to those in the art. Although any methods and materials similar or equivalent to those described herein find use in the practice or testing of the embodiments disclosed herein, some methods and materials are described.

The terms defined immediately below are more fully described by reference to the Specification as a whole. It is to be understood that this disclosure is not limited to the particular methodology, protocols, and reagents described, as these may vary, depending upon the context they are used by those of skill in the art.

DEFINITIONS

As used herein, the singular terms "a", "an," and "the" include the plural reference unless the context clearly indicates otherwise. Unless otherwise indicated, nucleic acids are written left to right in 5' to 3' orientation and amino acid sequences are written left to right in amino to carboxy orientation, respectively.

The term "assessing" when used herein in the context of analyzing a nucleic acid sample for CNV refers to characterizing the status of a chromosomal or segment aneuploidy by one of three types of calls: "normal" or "unaffected", "affected", and "no-call". Thresholds for calling normal and affected are typically set. A parameter related to aneuploidy is measured in a sample and the measured value is compared to the thresholds. For duplication type aneuploidies, a call of affected is made if a chromosome or segment dose (or other measured value sequence content) is above a defined threshold set for affected samples. For such aneuploidies, a call of normal is made if the chromosome or segment dose is below a threshold set for normal samples. By contrast for deletion type aneuploidies, a call of affected is made if a chromosome or segment dose is below a defined threshold for affected samples, and a call of normal is made if the chromosome or segment dose is above a threshold set for normal samples. For example, in the presence of trisomy the "normal" call is determined by the value of a parameter e.g. a test chromosome dose that is below a user-defined threshold of reliability, and the "affected" call is determined by a parameter e.g. a test chromosome dose, that is above a user-defined threshold of reliability. A "no-call" result is determined by a parameter, e.g. a test chromosome dose, that lies between the thresholds for making a "normal" or an "affected" call. The term "no-call" is used interchangeably with "unclassified".

The term "copy number variation" herein refers to variation in the number of copies of a nucleic acid sequence present in a test sample in comparison with the copy number of the nucleic acid sequence present in a qualified sample. In certain embodiments, the nucleic acid sequence is 1 kb or larger. In some cases, the nucleic acid sequence is a whole chromosome or significant portion thereof. A "copy number variant" refers to the sequence of nucleic acid in which copy-number differences are found by comparison of a sequence of interest in test sample with an expected level of the sequence of interest. For example, the level of the sequence of interest in the test sample is compared to that present in a qualified sample. Copy number variants/variations include deletions, including microdeletions, insertions, including microinsertions, duplications, multiplications, inversions, translocations and complex multi-site variants. CNVs encompass chromosomal aneuploidies and partial aneuploidies.

The term "aneuploidy" herein refers to an imbalance of genetic material caused by a loss or gain of a whole chromosome, or part of a chromosome.

The terms "chromosomal aneuploidy" and "complete chromosomal aneuploidy" herein refer to an imbalance of genetic material caused by a loss or gain of a whole chromosome, and includes germline aneuploidy and mosaic aneuploidy.

The terms "partial aneuploidy" and "partial chromosomal aneuploidy" herein refer to an imbalance of genetic material caused by a loss or gain of part of a chromosome e.g. partial monosomy and partial trisomy, and encompasses imbalances resulting from translocations, deletions and insertions.

The term "aneuploid sample" herein refers to a sample indicative of a subject whose chromosomal content is not euploid, i.e. the sample is indicative of a subject with an abnormal copy number of chromosomes or portions or chromosomes.

The term "aneuploid chromosome" herein refers to a chromosome that is known or determined to be present in a sample in an abnormal copy number.

The term "plurality" refers to more than one element. For example, the term is used herein in reference to a number of nucleic acid molecules or sequence tags that is sufficient to identify significant differences in copy number variations (e.g. chromosome doses) in test samples and qualified samples using the methods disclosed herein. In some embodiments, at least about $3\times10^6$ sequence tags, at least about $5\times10^6$ sequence tags, at least about $8\times10^6$ sequence tags, at least about $10\times10^6$ sequence tags, at least about $15\times10^6$ sequence tags, at least about $20\times10^6$ sequence tags, at least about $30\times10^6$ sequence tags, at least about $40\times10^6$ sequence tags, or at least about $50\times10^6$ sequence tags comprising between about 20 and 40 bp reads are obtained for each test sample.

The terms "polynucleotide", "nucleic acid" and "nucleic acid molecules" are used interchangeably and refer to a covalently linked sequence of nucleotides (i.e., ribonucleotides for RNA and deoxyribonucleotides for DNA) in which the 3' position of the pentose of one nucleotide is joined by a phosphodiester group to the 5' position of the pentose of the next, include sequences of any form of nucleic acid, including, but not limited to RNA and DNA molecules such as cfDNA molecules. The term "polynucleotide" includes, without limitation, single- and double-stranded polynucleotide.

The term "portion" is used herein in reference to the amount of sequence information of fetal and maternal nucleic acid molecules in a biological sample that in sum amount to less than the sequence information of 1 human genome.

The term "test sample" herein refers to a sample, typically derived from a biological fluid, cell, tissue, organ, or organism, comprising a nucleic acid or a mixture of nucleic acids comprising at least one nucleic acid sequence that is to be screened for copy number variation. In certain embodiments the sample comprises at least one nucleic acid sequence whose copy number is suspected of having undergone variation. Such samples include, but are not limited to sputum/oral fluid, amniotic fluid, blood, a blood fraction, or fine needle biopsy samples (e.g., surgical biopsy, fine needle biopsy, etc.) urine, peritoneal fluid, pleural fluid, and the like. Although the sample is often taken from a human subject (e.g., patient), the assays can be used to copy number variations (CNVs) in samples from any mammal, including, but not limited to dogs, cats, horses, goats, sheep, cattle, pigs, etc. The sample may be used directly as obtained from the biological source or following a pretreatment to modify the character of the sample. For example, such pretreatment may include preparing plasma from blood, diluting viscous fluids and so forth. Methods of pretreatment may also involve, but are not limited to, filtration, precipitation, dilution, distillation, mixing, centrifugation, freezing, lyophilization, concentration, amplification, nucleic acid fragmentation, inactivation of interfering components, the addition of reagents, lysing, etc. If such methods of pretreatment are employed with respect to the sample, such pretreatment methods are typically such that the nucleic acid(s) of interest remain in the test sample, preferably at a concentration proportional to that in an untreated test sample (e.g., namely, a sample that is not subjected to any such pretreatment method(s)). Such "treated" or "processed" samples are still considered to be biological "test" samples with respect to the methods described herein.

The term "qualified sample" herein refers to a sample comprising a mixture of nucleic acids that are present in a known copy number to which the nucleic acids in a test sample are to be compared, and it is a sample that is normal i.e. not aneuploid, for the sequence of interest. In certain embodiments, qualified samples are used for identifying one or more normalizing chromosomes or segments for a chromosome under consideration. For example, qualified samples may be used for identifying a normalizing chromosome for chromosome 21. In such case, the qualified sample is a sample that is not a trisomy 21 sample. Qualified samples may also be employed in determining thresholds for calling affected samples.

The term "training set" herein refers to a set of samples that can comprise affected and unaffected samples and are used to develop a model for analyzing test samples. The unaffected samples in a training set may be used as the qualified samples to identify normalizing sequences, e.g., normalizing chromosomes, and the chromosome doses of unaffected samples are used to set the thresholds for each of the sequences, e.g. chromosomes, of interest. The affected samples in a training set can be used to verify that affected test samples can be easily differentiated from unaffected samples.

The term "qualified nucleic acid" is used interchangeably with "qualified sequence" is a sequence against which the amount of a test sequence or test nucleic acid is compared. A qualified sequence is one present in a biological sample preferably at a known representation i.e. the amount of a qualified sequence is known. Generally, a qualified sequence is the sequence present in a "qualified sample". A "qualified sequence of interest" is a qualified sequence for which the amount is known in a qualified sample, and is a sequence that is associated with a difference in sequence representation in an individual with a medical condition.

The term "sequence of interest" herein refers to a nucleic acid sequence that is associated with a difference in sequence representation in healthy versus diseased individuals. A sequence of interest can be a sequence on a chromosome that is misrepresented i.e. over- or under-represented, in a disease or genetic condition. A sequence of interest may be a portion of a chromosome i.e. chromosome segment, or a chromosome. For example, a sequence of interest can be a chromosome that is over-represented in an aneuploidy condition, or a gene encoding a tumor-suppressor that is under-represented in a cancer. Sequences of interest include sequences that are over- or under-represented in the total population, or a sub-population of cells of a subject. A "qualified sequence of interest" is a sequence of interest in a qualified sample. A "test sequence of interest" is a sequence of interest in a test sample.

The term "normalizing sequence" herein refers to a sequence that is used to normalize the number of sequence tags mapped to a sequence of interest associated with the normalizing sequence. In some embodiments, the normalizing sequence displays a variability in the number of sequence tags that are mapped to it among samples and sequencing runs that approximates the variability of the sequence of interest for which it is used as a normalizing parameter, and that can differentiate an affected sample from one or more unaffected samples. In some implementations, the normalizing sequence best or effectively differentiates, when compared to other potential normalizing sequences such as other chromosomes, an affected sample from one or more unaffected samples. A "normalizing chromosome" or "normalizing chromosome sequence" is an example of a "normalizing sequence". A "normalizing chromosome sequence" can be composed of a single chromosome or of a group of chromosomes. A "normalizing segment" is another example of a "normalizing sequence". A "normalizing segment sequence" can be composed of a single segment of a chromosome or it can be composed of two or more segments of the same or of different chromosomes. In certain embodiments, a normalizing sequence is intended to normalize for variability such as process-related, interchromosomal (intra-run), and inter-sequencing (inter-run) variability.

The term "differentiability" herein refers to the characteristic of a normalizing chromosome that enables to distinguish one or more unaffected i.e. normal, samples from one or more affected i.e. aneuploid, samples.

The term "sequence dose" herein refers to a parameter that relates the number of sequence tags identified for a sequence of interest and the number of sequence tags identified for the normalizing sequence. In some cases, the sequence dose is the ratio of the number of sequence tags identified for a sequence of interest to the number of sequence tags identified for the normalizing sequence. In some cases, the sequence dose refers to a parameter that relates the sequence tag density of a sequence of interest to the tag density of a normalizing sequence. A "test sequence dose" is a parameter that relates the sequence tag density of a sequence of interest, e.g. chromosome 21, to that of a normalizing sequence e.g. chromosome 9, determined in a test sample. Similarly, a "qualified sequence dose" is a parameter that relates the sequence tag density of a sequence of interest to that of a normalizing sequence determined in a qualified sample.

The term "sequence tag density" herein refers to the number of sequence reads that are mapped to a reference genome sequence; e.g. the sequence tag density for chromosome 21 is the number of sequence reads generated by the sequencing method that are mapped to chromosome 21 of the reference genome. The term "sequence tag density ratio" herein refers to the ratio of the number of sequence tags that are mapped to a chromosome of the reference genome e.g. chromosome 21, to the length of the reference genome chromosome.

The term "Next Generation Sequencing (NGS)" herein refers to sequencing methods that allow for massively parallel sequencing of clonally amplified molecules and of single nucleic acid molecules. Non-limiting examples of NGS include sequencing-by-synthesis using reversible dye terminators, and sequencing-by-ligation.

The term "parameter" herein refers to a numerical value that characterizes a physical property. Frequently, a parameter numerically characterizes a quantitative data set and/or a numerical relationship between quantitative data sets. For example, a ratio (or function of a ratio) between the number of sequence tags mapped to a chromosome and the length of the chromosome to which the tags are mapped, is a parameter.

The terms "threshold value" and "qualified threshold value" herein refer to any number that is used as a cutoff to characterize a sample such as a test sample containing a nucleic acid from an organism suspected of having a medical condition. The threshold may be compared to a parameter value to determine whether a sample giving rise to such parameter value suggests that the organism has the medical condition. In certain embodiments, a qualified threshold value is calculated using a qualifying data set and serves as a limit of diagnosis of a copy number variation e.g. an aneuploidy, in an organism. If a threshold is exceeded by results obtained from methods disclosed herein, a subject can be diagnosed with a copy number variation e.g. trisomy 21. Appropriate threshold values for the methods described herein can be identified by analyzing normalizing values (e.g. chromosome doses, NCVs or NSVs) calculated for a training set of samples. Threshold values can be identified using qualified (i.e. unaffected) samples in a training set which comprises both qualified (i.e. unaffected) samples and affected samples. The samples in the training set known to have chromosomal aneuploidies (i.e. the affected samples) can be used to confirm that the chosen thresholds are useful in differentiating affected from unaffected samples in a test set (see the Examples herein). The choice of a threshold is dependent on the level of confidence that the user wishes to have to make the classification. In some embodiments, the training set used to identify appropriate threshold values comprises at least 10, at least 20, at least 30, at least 40, at least 50, at least 60, at least 70, at least 80, at least 90, at least 100, at least 200, at least 300, at least 400, at least 500, at least 600, at least 700, at least 800, at least 900, at least 1000, at least 2000, at least 3000, at least 4000, or more qualified samples. It may advantageous to use larger sets of qualified samples to improve the diagnostic utility of the threshold values.

The term "normalizing value" herein refers to a numerical value that relates the number of sequence tags identified for the sequence (e.g. chromosome or chromosome segment) of interest to the number of sequence tags identified for the normalizing sequence (e.g. normalizing chromosome or normalizing chromosome segment). For example, a "normalizing value" can be a chromosome dose as described elsewhere herein, or it can be an NCV (Normalized Chromosome Value) as described elsewhere herein, or it can be an NSV (Normalized Segment Value) as described elsewhere herein.

The term "read" refers to a sequence read from a portion of a nucleic acid sample. Typically, though not necessarily, a read represents a short sequence of contiguous base pairs in the sample. The read may be represented symbolically by the base pair sequence (in ATCG) of the sample portion. It may be stored in a memory device and processed as appropriate to determine whether it matches a reference sequence or meets other criteria. A read may be obtained directly from a sequencing apparatus or indirectly from stored sequence information concerning the sample. In some cases, a read is a. DNA sequence of sufficient length (e.g., at least about 30 bp) that can be used to identify a larger sequence or region, e.g. that can be aligned and specifically assigned to a chromosome or genomic region or gene.

The term "sequence tag" is herein used interchangeably with the term "mapped sequence tag" to refer to a sequence read that has been specifically assigned i.e. mapped, to a larger sequence e.g. a reference genome, by alignment. Mapped sequence tags are uniquely mapped to a reference genome i.e. they are assigned to a single location to the reference genome. Tags may be provided as data structures or other assemblages of data. In certain embodiments, a tag contains a read sequence and associated information for that read such as the location of the sequence in the genome, e.g., the position on a chromosome. In certain embodiments, the location is specified for a positive strand orientation. A tag may be defined to provide a limit amount of mismatch in aligning to a reference genome. Tags that can be mapped to more than one location on a reference genome i.e. tags that do not map uniquely, may not be included in the analysis.

As used herein, the terms "aligned", "alignment", or "aligning" refer to the process of comparing a read or tag to a reference sequence and thereby determining whether the reference sequence contains the read sequence. If the reference sequence contains the read, the read may be mapped to the reference sequence or, in certain embodiments, to a particular location in the reference sequence. In some cases, alignment simply tells whether or not a read is a member of a particular reference sequence (i.e., whether the read is present or absent in the reference sequence). For example, the alignment of a read to the reference sequence for human chromosome 13 will tell whether the read is present in the reference sequence for chromosome 13. A tool that provides this information may be called a set membership tester. In some cases, an alignment additionally indicates a location in the reference sequence where the read or tag maps to. For example, if the reference sequence is the whole human genome sequence, an alignment may indicate that a read is present on chromosome 13, and may further indicate that the read is on a particular strand and/or site of chromosome 13.

Aligned reads or tags are one or more sequences that are identified as a match in terms of the order of their nucleic acid molecules to a known sequence from a reference genome. Alignment can be done manually, although it is typically implemented by a computer algorithm, as it would be impossible to align reads in a reasonable time period for implementing the methods disclosed herein. One example of an algorithm from aligning sequences is the Efficient Local Alignment of Nucleotide Data (ELAND) computer program distributed as part of the Illumina Genomics Analysis pipeline. Alternatively, a Bloom filter or similar set membership tester may be employed to align reads to reference genomes. See U.S. Patent Application No. 61/552,374 filed Oct. 27, 2011 which is incorporated herein by reference in its entirety. The matching of a sequence read in aligning can be a 100% sequence match or less than 100% (non-perfect match).

As used herein, the term "reference genome" or "reference sequence" refers to any particular known genome sequence, whether partial or complete, of any organism or virus which may be used to reference identified sequences from a subject. For example, a reference genome used for human subjects as well as many other organisms is found at the National Center for Biotechnology Information at www.ncbi.nlm.nih.gov. A "genome" refers to the complete genetic information of an organism or virus, expressed in nucleic acid sequences.

In various embodiments, the reference sequence is significantly larger than the reads that are aligned to it. For example, it may be at least about 100 times larger, or at least about 1000 times larger, or at least about 10,000 times larger, or at least about $10^5$ times larger, or at least about $10^6$ times larger, or at least about $10^7$ times larger.

In one example, the reference sequence is that of a full length human genome. Such sequences may be referred to as genomic reference sequences. In another example, the reference sequence is limited to a specific human chromosome such as chromosome 13. Such sequences may be referred to as chromosome reference sequences. Other examples of reference sequences include genomes of other species, as well as chromosomes, sub-chromosomal regions (such as strands), etc. of any species.

In various embodiments, the reference sequence is a consensus sequence or other combination derived from multiple individuals. However, in certain applications, the reference sequence may be taken from a particular individual.

The term "artificial target sequences genome" herein refers to a grouping of known sequences that encompass alleles of known polymorphic sites. For example, a "SNP reference genome" is an artificial target sequences genome comprising a grouping of sequences that encompass alleles of known SNPs.

The term "clinically-relevant sequence" herein refers to a nucleic acid sequence that is known or is suspected to be associated or implicated with a genetic or disease condition. Determining the absence or presence of a clinically-relevant sequence can be useful in determining a diagnosis or confirming a diagnosis of a medical condition, or providing a prognosis for the development of a disease.

The term "derived" when used in the context of a nucleic acid or a mixture of nucleic acids, herein refers to the means whereby the nucleic acid(s) are obtained from the source from which they originate. For example, in one embodiment, a mixture of nucleic acids that is derived from two different genomes means that the nucleic acids e.g. cfDNA, were naturally released by cells through naturally occurring processes such as necrosis or apoptosis. In another embodiment, a mixture of nucleic acids that is derived from two different genomes means that the nucleic acids were extracted from two different types of cells from a subject.

The term "patient sample" herein refers to a biological sample obtained from a patient i.e. a recipient of medical attention, care or treatment. The patient sample can be any of the samples described herein. In certain embodiments, the patient sample is obtained by non-invasive procedures e.g. peripheral blood sample or a stool sample. The methods described herein need not be limited to humans. Thus, various veterinary applications are contemplated in which case the patient sample may be a sample from a non-human mammal (e.g., a feline, a porcine, an equine, a bovine, and the like).

The term "mixed sample" herein refers to a sample containing a mixture of nucleic acids, which are derived from different genomes.

The term "maternal sample" herein refers to a biological sample obtained from a pregnant subject e.g. a woman.

The term "biological fluid" herein refers to a liquid taken from a biological source and includes, for example, blood, serum, plasma, sputum, lavage fluid, cerebrospinal fluid, urine, semen, sweat, tears, saliva, and the like. As used herein, the terms "blood," "plasma" and "serum" expressly encompass fractions or processed portions thereof. Similarly, where a sample is taken from a biopsy, swab, smear, etc., the "sample" expressly encompasses a processed fraction or portion derived from the biopsy, swab, smear, etc.

The terms "maternal nucleic acids" and "fetal nucleic acids" herein refer to the nucleic acids of a pregnant female subject and the nucleic acids of the fetus being carried by the pregnant female, respectively.

As used herein, the term "corresponding to" sometimes refers to a nucleic acid sequence e.g. a gene or a chromosome, that is present in the genome of different subjects, and which does not necessarily have the same sequence in all genomes, but serves to provide the identity rather than the genetic information of a sequence of interest e.g. a gene or chromosome.

As used herein, the term "substantially cell free" encompasses preparations of the desired sample from which cell components that are normally associated with it are removed. For example, a plasma sample is rendered substantially cell free by removing blood cells e.g. red cells, which are normally associated with it. In some embodiments, substantially free samples are processed to remove cells that would otherwise contribute to the desired genetic material that is to be tested for a CNV.

As used herein, the term "fetal fraction" refers to the fraction of fetal nucleic acids present in a sample comprising fetal and maternal nucleic acid. Fetal fraction is often used to characterize the cfDNA in a mother's blood.

As used herein the term "chromosome" refers to the heredity-bearing gene carrier of a living cell which is derived from chromatin and which comprises DNA and protein components (especially histones). The conventional internationally recognized individual human genome chromosome numbering system is employed herein.

As used herein, the term "polynucleotide length" refers to the absolute number of nucleic acid molecules (nucleotides) in a sequence or in a region of a reference genome. The term "chromosome length" refers to the known length of the chromosome given in base pairs e.g. provided in the NCBI36/hg18 assembly of the human chromosome found on the world wide web at genome.ucsc.edu/cgi-bin/hgTracks?hgsid=167155613&chromInfoPage=

The term "subject" herein refers to a human subject as well as a non-human subject such as a mammal, an invertebrate, a vertebrate, a fungus, a yeast, a bacteria, and a virus. Although the examples herein concern humans and the language is primarily directed to human concerns, the concepts disclosed herein are applicable to genomes from any plant or animal, and are useful in the fields of veterinary medicine, animal sciences, research laboratories and such.

The term "condition" herein refers to "medical condition" as a broad term that includes all diseases and disorders, but can include [injuries] and normal health situations, such as pregnancy, that might affect a person's health, benefit from medical assistance, or have implications for medical treatments.

The term "complete" is used herein in reference to a chromosomal aneuploidy to refer to a gain or loss of an entire chromosome.

The term "partial" when used in reference to a chromosomal aneuploidy herein refers to a gain or loss of a portion i.e. segment, of a chromosome.

The term "mosaic" herein refers to denote the presence of two populations of cells with different karyotypes in one individual who has developed from a single fertilized egg. Mosaicism may result from a mutation during development which is propagated to only a subset of the adult cells.

The term "non-mosaic" herein refers to an organism e.g. a human fetus, composed of cells of one karyotype.

The term "using a chromosome" when used in reference to determining a chromosome dose, herein refers to using the sequence information obtained for a chromosome i.e. the number of sequence tags obtained for a chromosome.

The term "sensitivity" as used herein is equal to the number of true positives divided by the sum of true positives and false negatives.

The term "specificity" as used herein is equal to the number of true negatives divided by the sum of true negatives and false positives.

The term "hypodiploid" herein refers to a chromosome number that is one or more lower than the normal haploid number of chromosomes characteristic for the species.

A "polymorphic site" is a locus at which nucleotide sequence divergence occurs. The locus may be as small as one base pair. Illustrative markers have at least two alleles, each occurring at frequency of greater than 1%, and more typically greater than 10% or 20% of a selected population. A polymorphic site may be the site of a single nucleotide polymorphism (SNP), a small-scale multi-base deletion or insertion, a Multi-Nucleotide Polymorphism (MNP) or a Short Tandem Repeat (STR). The terms "polymorphic locus" and "polymorphic site" are herein used interchangeably.

A "polymorphic sequence" herein refers to a nucleic acid sequence e.g. a DNA sequence, that comprises one or more polymorphic sites e.g one SNP or a tandem SNP. Polymorphic sequences according to the present technology can be used to specifically differentiate between maternal and non-maternal alleles in the maternal sample comprising a mixture of fetal and maternal nucleic acids.

A "single nucleotide polymorphism" (SNP) as used herein occurs at a polymorphic site occupied by a single nucleotide, which is the site of variation between allelic sequences. The site is usually preceded by and followed by highly conserved sequences of the allele (e.g., sequences that vary in less than 1/100 or 1/1000 members of the populations). A SNP usually arises due to substitution of one nucleotide for another at the polymorphic site. A transition is the replacement of one purine by another purine or one pyrimidine by another pyrimidine. A transversion is the replacement of a purine by a pyrimidine or vice versa. SNPs can also arise from a deletion of a nucleotide or an insertion of a nucleotide relative to a reference allele. Single nucleotide polymorphisms (SNPs) are positions at which two alternative bases occur at appreciable frequency (>1%) in the human population, and are the most common type of human genetic variation.

The term "tandem SNPs" herein refers to two or more SNPs that are present within a polymorphic target nucleic acid sequence.

The term "short tandem repeat" or "STR" as used herein refers to a class of polymorphisms that occurs when a pattern of two or more nucleotides are repeated and the repeated sequences are directly adjacent to each other. The pattern can range in length from 2 to 10 base pairs (bp) (for example $(CATG)_n$ in a genomic region) and is typically in the non-coding intron region. By examining several STR loci and counting how many repeats of a specific STR sequence there are at a given locus, it is possible to create a unique genetic profile of an individual.

As used herein, the term "miniSTR" herein refers to tandem repeat of four or more base pairs that spans less than about 300 base pairs, less than about 250 base airs, less than about 200 base pairs, less than about 150 base pairs, less than about 100 base pairs, less than about 50 base pairs, or less than about 25 base pairs. "miniSTRs" are STRs that are amplifiable from cfDNA templates.

The terms "polymorphic target nucleic acid," "polymorphic sequence," "polymorphic target nucleic acid sequence" and "polymorphic nucleic acid" are used interchangeably herein to refer to a nucleic acid sequence (e.g. a DNA sequence) that comprises one or more polymorphic sites.

The term "plurality of polymorphic target nucleic acids" herein refers to a number of nucleic acid sequences each comprising at least one polymorphic site, e.g. one SNP, such that at least 1, 2, 3, 4, 5, 6, 7, 8, 9, 10, 15, 20, 25, 30, 40 or more different polymorphic sites are amplified from the polymorphic target nucleic acids to identify and/or quantify fetal alleles present in maternal samples comprising fetal and maternal nucleic acids.

The term "enrich" herein refers to the process of amplifying polymorphic target nucleic acids contained in a portion of a maternal sample, and combining the amplified product with the remainder of the maternal sample from which the portion was removed. For example, the remainder of the maternal sample can be the original maternal sample.

The term "original maternal sample" herein refers to a non-enriched biological sample obtained from a pregnant subject e.g. a woman, who serves as the source from which a portion is removed to amplify polymorphic target nucleic acids. The "original sample" can be any sample obtained from a pregnant subject, and the processed fractions thereof e.g. a purified cfDNA sample extracted from a maternal plasma sample.

The term "primer," as used herein refers to an isolated oligonucleotide which is capable of acting as a point of initiation of synthesis when placed under conditions in which synthesis of a primer extension product, which is complementary to a nucleic acid strand, is induced (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer, use of the method, and the parameters used for primer design.

The phrase "cause to be administered" refers to the actions taken by a medical professional (e.g., a physician), or a person controlling or directing medical care of a subject, that control and/or permit the administration of the agent(s)/compound(s) at issue to the subject. Causing to be administered can involve diagnosis and/or determination of an appropriate therapeutic or prophylactic regimen, and/or prescribing particular agent (s)/compounds for a subject. Such prescribing can include, for example, drafting a prescription form, annotating a medical record, and the like. Similarly, "cause to be performed", e.g., for a diagnostic procedure refers to the actions taken by a medical professional (e.g., a physician), or a person controlling or directing medical care of a subject, that control and/or permit the performance of one or more diagnostic protocols to or on the subject.

Introduction

Disclosed herein are methods, apparatus, and systems for determining copy number variations (CNV) of different sequences of interest in a test sample that comprises a mixture of nucleic acids derived from two different genomes, and which are known or are suspected to differ in the amount of one or more sequence of interest. Copy number variations determined by the methods and apparatus disclosed herein include gains or losses of entire chromosomes, alterations involving very large chromosomal segments that are microscopically visible, and an abundance of sub-microscopic copy number variation of DNA segments ranging from kilobases (kb) to megabases (Mb) in size. In various embodiments, the methods comprise a machine-implemented statistical approach that accounts for accrued variability stemming from process-related, interchromosomal and inter-sequencing variability. The method is applicable to determining CNV of any fetal aneuploidy, and CNVs known or suspected to be associated with a variety of medical conditions. CNV that can be determined according to the present method include trisomies and monosomies of any one or more of chromosomes 1-22, X and Y, other chromosomal polysomies, and deletions and/or duplications of segments of any one or more of the chromosomes, which can be detected by sequencing only once the nucleic acids of a test sample. Any aneuploidy can be determined from sequencing information that is obtained by sequencing only once the nucleic acids of a test sample.

CNV in the human genome significantly influence human diversity and predisposition to disease (Redon et al., Nature 23:444-454 [2006], Shaikh et al. Genome Res 19:1682-1690 [2009]). CNVs have been known to contribute to genetic disease through different mechanisms, resulting in either imbalance of gene dosage or gene disruption in most cases. In addition to their direct correlation with genetic disorders, CNVs are known to mediate phenotypic changes that can be deleterious. Recently, several studies have reported an increased burden of rare or de novo CNVs in complex disorders such as Autism, ADHD, and schizophrenia as compared to normal controls, highlighting the potential pathogenicity of rare or unique CNVs (Sebat et al., 316:445-449 [2007]; Walsh et al., Science 320:539-543 [2008]). CNV arise from genomic rearrangements, primarily owing to deletion, duplication, insertion, and unbalanced translocation events.

The methods and apparatus described herein may employ next generation sequencing technology (NGS), which is massively parallel sequencing. In certain embodiments, clonally amplified DNA templates or single DNA molecules are sequenced in a massively parallel fashion within a flow cell (e.g. as described in Volkerding et al. Clin Chem 55:641-658

[2009]; Metzker M Nature Rev 11:31-46 [2010]). In addition to high-throughput sequence information, NGS provides quantitative information, in that each sequence read is a countable "sequence tag" representing an individual clonal DNA template or a single DNA molecule. The sequencing technologies of NGS include pyrosequencing, sequencing-by-synthesis with reversible dye terminators, sequencing by oligonucleotide probe ligation and ion semiconductor sequencing. DNA from individual samples can be sequenced individually (i.e. singleplex sequencing) or DNA from multiple samples can be pooled and sequenced as indexed genomic molecules (i.e. multiplex sequencing) on a single sequencing run, to generate up to several hundred million reads of DNA sequences. Examples of sequencing technologies that can be used to obtain the sequence information according to the present method are described below.

In some embodiments, the methods and apparatus disclosed herein may employ the following some or all of the operations from the following sequence: obtain a nucleic acid test sample from a patient (typically by a non-invasive procedure); process the test sample in preparation for sequencing; sequence nucleic acids from the test sample to produce numerous reads (e.g., at least 10,000); align the reads to portions of a reference sequence/genome and determine the amount of DNA (e.g., the number of reads) that map to defined portions the reference sequence (e.g., to defined chromosomes or chromosome segments); calculate a dose of one or more of the defined portions by normalizing the amount of DNA mapping to the defined portions with an amount of DNA mapping to one or more normalizing chromosomes or chromosome segments selected for the defined portion; determining whether the dose indicates that the defined portion is "affected" (e.g., aneuploidy or mosaic); reporting the determination and optionally converting it to a diagnosis; using the diagnosis or determination to develop a plan of treatment, monitoring, or further testing for the patient.

Determination of Normalizing Sequences in Qualified Samples: Normalizing Chromosome Sequences and Normalizing Segment Sequences Normalizing sequences are identified using sequence information from a set of qualified samples obtained from subjects known to comprise cells having a normal copy number for any one sequence of interest e.g. a chromosome or segment thereof. Determination of normalizing sequences is outlined in steps 110, 120, 130, 140, and 145 of the embodiment of the method depicted in FIG. 1. The sequence information obtained from the qualified samples is used for determining statistically meaningful identification of chromosomal aneuploidies in test samples (step 165 FIG. 1, and Examples).

FIG. 1 provides a flow diagram 100 of an embodiment for determining a CNV of a sequence of interest e.g. a chromosome or segment thereof, in a biological sample. In some embodiments, a biological sample is obtained from a subject and comprises a mixture of nucleic acids contributed by different genomes. The different genomes can be contributed to the sample by two individuals e.g. the different genomes are contributed by the fetus and the mother carrying the fetus. Alternatively, the genomes are contributed to the sample by aneuploid cancerous cells and normal euploid cells from the same subject e.g. a plasma sample from a cancer patient.

Apart from analyzing a patient's test sample, one or more normalizing chromosomes or one or more normalizing chromosome segments are selected for each possible chromosome of interest. The normalizing chromosomes or segments are identified asynchronously from the normal testing of patient samples, which may take place in a clinical setting. In other words, the normalizing chromosomes or segments are identified prior to testing patient samples. The associations between normalizing chromosomes or segments and chromosomes or segments of interest are stored for use during testing. As explained below, such association is typically maintained over periods of time that span testing of many samples. The following discussion concerns embodiments for selecting normalizing chromosomes or chromosome segments for individual chromosomes or segments of interest.

A set of qualified samples is obtained to identify qualified normalizing sequences and to provide variance values for use in determining statistically meaningful identification of CNV in test samples. In step 110, a plurality of biological qualified samples are obtained from a plurality of subjects known to comprise cells having a normal copy number for any one sequence of interest. In one embodiment, the qualified samples are obtained from mothers pregnant with a fetus that has been confirmed using cytogenetic means to have a normal copy number of chromosomes. The biological qualified samples may be a biological fluid e.g. plasma, or any suitable sample as described below. In some embodiments, a qualified sample contains a mixture of nucleic acid molecules e.g. cfDNA molecules. In some embodiments, the qualified sample is a maternal plasma sample that contains a mixture of fetal and maternal cfDNA molecules. Sequence information for normalizing chromosomes and/or segments thereof is obtained by sequencing at least a portion of the nucleic acids e.g. fetal and maternal nucleic acids, using any known sequencing method. Preferably, any one of the Next Generation Sequencing (NGS) methods described elsewhere herein is used to sequence the fetal and maternal nucleic acids as single or clonally amplified molecules. In various embodiments, the qualified samples are processed as disclosed below prior to and during sequencing. They may be processed using apparatus, systems, and kits as disclosed herein.

In step 120, at least a portion of each of all the qualified nucleic acids contained in the qualified samples are sequenced to generate millions of sequence reads e.g. 36 bp reads, which are aligned to a reference genome, e.g. hg18. In some embodiments, the sequence reads comprise about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130 bp, about 140 bp, about 150 bp, about 200 bp, about 250 bp, about 300 bp, about 350 bp, about 400 bp, about 450 bp, or about 500 bp. It is expected that technological advances will enable single-end reads of greater than 500 bp enabling for reads of greater than about 1000 bp when paired end reads are generated. In one embodiment, the mapped sequence reads comprise 36 bp. In another embodiment, the mapped sequence reads comprise 25 bp. Sequence reads are aligned to a reference genome, and the reads that are uniquely mapped to the reference genome are known as sequence tags. In one embodiment, at least about $3 \times 10^6$ qualified sequence tags, at least about $5 \times 10^6$ qualified sequence tags, at least about $8 \times 10^6$ qualified sequence tags, at least about $10 \times 10^6$ qualified sequence tags, at least about $15 \times 10^6$ qualified sequence tags, at least about $20 \times 10^6$ qualified sequence tags, at least about $30 \times 10^6$ qualified sequence tags, at least about $40 \times 10^6$ qualified sequence tags, or at least about $50 \times 10^6$ qualified sequence tags comprising between 20 and 40 bp reads are obtained from reads that map uniquely to a reference genome.

In step 130, all the tags obtained from sequencing the nucleic acids in the qualified samples are counted to determine a qualified sequence tag density. In one embodiment the sequence tag density is determined as the number of qualified sequence tags mapped to the sequence of interest on the reference genome. In another embodiment, the qualified sequence tag density is determined as the number of qualified sequence tags mapped to a sequence of interest normalized to the length of the qualified sequence of interest to which they are mapped. Sequence tag densities that are determined as a ratio of the tag density relative to the length of the sequence of interest are herein referred to as tag density ratios. Normalization to the length of the sequence of interest is not required, and may be included as a step to reduce the number of digits in a number to simplify it for human interpretation. As all qualified sequence tags are mapped and counted in each of the qualified samples, the sequence tag density for a sequence of interest e.g. a clinically-relevant sequence, in the qualified samples is determined, as are the sequence tag densities for additional sequences from which normalizing sequences are identified subsequently.

In some embodiments, the sequence of interest is a chromosome that is associated with a complete chromosomal aneuploidy e.g. chromosome 21, and the qualified normalizing sequence is a complete chromosome that is not associated with a chromosomal aneuploidy and whose variation in sequence tag density approximates that of the sequence (i.e. chromosome) of interest e.g. chromosome 21. The selected normalizing chromosome(s) may the one or group that best approximates the variation in sequence tag density of the sequence of interest. Any one or more of chromosomes 1-22, X, and Y can be a sequence of interest, and one or more chromosomes can be identified as the normalizing sequence for each of the any one chromosomes 1-22, X and Y in the qualified samples. The normalizing chromosome can be an individual chromosome or it can be a group of chromosomes as described elsewhere herein.

In another embodiment, the sequence of interest is a segment of a chromosome associated with a partial aneuploidy, e.g. a chromosomal deletion or insertion, or unbalanced chromosomal translocation, and the normalizing sequence is a chromosomal segment (or group of segments) that is not associated with the partial aneuploidy and whose variation in sequence tag density approximates that of the chromosome segment associated with the partial aneuploidy. The selected normalizing chromosome segment(s) may the one or more that best approximates the variation in sequence tag density of the sequence of interest. Any one or more segments of any one or more chromosomes 1-22, X, and Y can be a sequence of interest.

In other embodiments, the sequence of interest is a segment of a chromosome associated with a partial aneuploidy and the normalizing sequence is a whole chromosome or chromosomes. In still other embodiments, the sequence of interest is a whole chromosome associated with an aneuploidy and the normalizing sequence is a chromosomal segment or segments that is not associated with the aneuploidy.

Whether a single sequence or a group of sequences are identified in the qualified samples as the normalizing sequence(s) for any one or more sequences of interest, the qualified normalizing sequence may be chosen to have a variation in sequence tag density that best or effectively approximates that of the sequence of interest as determined in the qualified samples. For example, a qualified normalizing sequence is a sequence that produces the smallest variability across the qualified samples when used to normalize the sequence of interest, i.e. the variability of the normalizing sequence is closest to that of the sequence of interest determined in qualified samples. Stated another way, the qualified normalizing sequence is the sequence selected to produce the least variation in sequence dose (for the sequence of interest) across the qualified samples. Thus, the process selects a sequence that when used as a normalizing chromosome is expected to produce the smallest variability in run-to-run chromosome dose for the sequence of interest.

The normalizing sequence identified in the qualified samples for any one or more sequences of interest remains the normalizing sequence of choice for determining the presence or absence of aneuploidy in test samples over days, weeks, months, and possibly years, provided that procedures needed to generate sequencing libraries, and sequencing the samples are essentially unaltered over time. As described above, normalizing sequences for determining the presence of aneuploidies are chosen for (possibly among other reasons as well) the variability in the number of sequence tags that are mapped to it among samples e.g. different samples, and sequencing runs e.g. sequencing runs that occur on the same day and/or different days, that best approximates the variability of the sequence of interest for which it is used as a normalizing parameter. Substantial alterations in these procedures will affect the number of tags that are mapped to all sequences, which in turn will determine which one or group of sequences will have a variability across samples in the same and/or in different sequencing runs, on the same day or on different days that most closely approximates that of the sequence(s) of interest, which would require that the set of normalizing sequences be re-determined. Substantial alterations in procedures include changes in the laboratory protocol used for preparing the sequencing library, which includes changes related to preparing samples for multiplex sequencing instead of singleplex sequencing, and changes in sequencing platforms, which include changes in the chemistry used for sequencing.

In some embodiments, the normalizing sequence chosen to normalize a particular sequence of interest is a sequence that best distinguishes one or more qualified, samples from one or more affected samples, which implies that the normalizing sequence is a sequence that has the greatest differentiability i.e. the differentiability of the normalizing sequence is such that it provides optimal differentiation to a sequence of interest in an affected test sample to easily distinguish the affected test sample from other unaffected samples. In other embodiments, the normalizing sequence is a sequence that has a combination of the smallest variability and the greatest differentiability.

The level of differentiability can be determined as a statistical difference between the sequence doses e.g. chromosome doses or segment doses, in a population of qualified samples and the chromosome dose(s) in one or more test samples as described below and shown in the Examples. For example, differentiability can be represented numerically as a T-test value, which represents the statistical difference between the chromosome doses in a population of qualified samples and the chromosome dose(s) in one or more test samples. Alternatively, differentiability can be represented numerically as a Normalized Chromosome Value (NCV), which is a z-score for chromosome doses as long as the distribution for the NCV is normal. Similarly, differentiability can be represented numerically as a T-test value, which represents the statistical difference between the segment doses in a population of qualified samples and the segment dose(s) in one or more test samples. In the case where chromosome segments are the sequences of interest, differentiability of segment doses can be represented numerically as a Normalized Segment Value (NSV), which is a z-score for chromosome segment doses as long as the distribution for the NSV is normal. In determining the z-score, the mean and standard deviation of chromosome or segment doses in a set of qualified samples can be used.

Alternatively, the mean and standard deviation of chromosome or segment doses in a training set comprising qualified samples and affected samples can be used. In other embodiments, the normalizing sequence is a sequence that has the smallest variability and the greatest differentiability or an optimal combination of small variability and large differentiability.

The method identifies sequences that inherently have similar characteristics and that are prone to similar variations among samples and sequencing runs, and which are useful for determining sequence doses in test samples.

Determination of Sequence Doses (i.e. Chromosome Doses or Segment Doses) in Qualified Samples In step 140, based on the calculated qualified tag densities, a qualified sequence dose i.e. a chromosome dose or a segment dose, for a sequence of interest is determined as the ratio of the sequence tag density for the sequence of interest and the qualified sequence tag density for additional sequences from which normalizing sequences are identified subsequently in step 145. The identified normalizing sequences are used subsequently to determine sequence doses in test samples.

In one embodiment, the sequence dose in the qualified samples is a chromosome dose that is calculated as the ratio of the number of sequence tags for a chromosome of interest and the number of sequence tags for a normalizing chromosome sequence in a qualified sample. The normalizing chromosome sequence can be a single chromosome, a group of chromosomes, a segment of one chromosome, or a group of segments from different chromosomes. Accordingly, a chromosome dose for a chromosome of interest is determined in a qualified sample as (i) the ratio of the number of tags for a chromosome of interest and the number of tags for a normalizing chromosome sequence composed of a single chromosome, (ii) the ratio of the number of tags for a chromosome of interest and the number of tags for a normalizing chromosome sequence composed of two or more chromosomes, (iii) the ratio of the number of tags for a chromosome of interest and the number of tags for a normalizing segment sequence composed of a single segment of a chromosome, (iv) the ratio of the number of tags for a chromosome of interest and the number of tags for a normalizing segment sequence composed of two or more segments form one chromosome, or (v) the ratio of the number of tags for a chromosome of interest and the number of tags for a normalizing segment sequence composed of two or more segments of two or more chromosomes. Examples for determining a chromosome dose for chromosome of interest 21 according to (i)-(v) are as follows: chromosome doses for chromosome of interest e.g. chromosome 21, are determined as a ratio of the sequence tag density of chromosome 21 and the sequence tag density for each of all the remaining chromosomes i.e. chromosomes 1-20, chromosome 22, chromosome X, and chromosome Y (i); chromosome doses for chromosome of interest e.g. chromosome 21, are determined as a ratio of the sequence tag density of chromosome 21 and the sequence tag density for all possible combinations of two or more remaining chromosomes (ii); chromosome doses for chromosome of interest e.g. chromosome 21, are determined as a ratio of the sequence tag density of chromosome 21 and the sequence tag density for a segment of another chromosome e.g. chromosome 9 (iii); chromosome doses for chromosome of interest e.g. chromosome 21, are determined as a ratio of the sequence tag density of chromosome 21 and the sequence tag density for two segment of one other chromosome e.g. two segments of chromosome 9 (iv); and chromosome doses for chromosome of interest e.g. chromosome 21, are determined as a ratio of the sequence tag density of chromosome 21 and the sequence tag density for two segments of two different chromosomes e.g. a segment of chromosome 9 and a segment of chromosome 14.

In another embodiment, the sequence dose in the qualified samples is a segment dose that is calculated as the ratio of the number of sequence tags for a segment of interest, that is not a whole chromosome, and the number of sequence tags for a normalizing segment sequence in a qualified sample. The normalizing segment sequence can be, for example, a whole chromosome, a group of whole chromosomes, a segment of one chromosome, or a group of segments from different chromosomes. For example, a segment dose for a segment of interest is determined in a qualified sample as (i) the ratio of the number of tags for a segment of interest and the number of tags for a normalizing segment sequence composed of a single segment of a chromosome, (ii) the ratio of the number of tags for a segment of interest and the number of tags for a normalizing segment sequence composed of two or more segments of one chromosome, or (iii) the ratio of the number of tags for a segment of interest and the number of tags for a normalizing segment sequence composed of two or more segments of two or more different chromosomes.

Chromosome doses for one or more chromosomes of interest are determined in all qualified samples, and a normalizing chromosome sequence is identified in step 145. Similarly, segment doses for one or more segments of interest are determined in all qualified samples, and a normalizing segment sequence is identified in step 145.

Identification of Normalizing Sequences from Qualified Sequence Doses

In step 145, a normalizing sequence is identified for a sequence of interest as the sequence based on the calculated sequence doses e.g., that results in the smallest variability in sequence dose for the sequence of interest across all qualified samples. The method identifies sequences that inherently have similar characteristics and that are prone to similar variations among samples and sequencing runs, and which are useful for determining sequence doses in test samples.

Normalizing sequences for one or more sequences of interest can be identified in a set of qualified samples, and the sequences that are identified in the qualified samples are used subsequently to calculate sequence doses for one or more sequences of interest in each of the test samples (step 150) to determine the presence or absence of aneuploidy in each of the test samples. The normalizing sequence identified for chromosomes or segments of interest may differ when different sequencing platforms are used and/or when differences exist in the purification of the nucleic acid that is to be sequenced and/or preparation of the sequencing library. The use of normalizing sequences according to the methods described herein provides specific and sensitive measure of a variation in copy number of a chromosome or segment thereof irrespective of sample preparation and/or sequencing platform that is used.

In some embodiments, more than one normalizing sequence is identified i.e. different normalizing sequences can be determined for one sequence of interest, and multiple sequence doses can be determined for one sequence of interest. For example, the variation, e.g. coefficient of variation, in chromosome dose for chromosome of interest 21 is least when the sequence tag density of chromosome 14 is used. However, two, three, four, five, six, seven, eight or more normalizing sequences can be identified for use in determining a sequence dose for a sequence of interest in a test sample. As an example, a second dose for chromosome 21 in any one test sample can be determined using chromosome 7, chromosome 9, chromosome 11 or chromosome 12 as the normalizing chromosome sequence as these chromosomes all have CV close to that for chromosome 14 (see Example 8, Table 10). Preferably, when a single chromosome is chosen as the normalizing chromosome sequence for a chromosome of interest, the normalizing chromosome sequence will be a chromosome that results in chromosome doses for the chromosome of interest that has the smallest variability across all samples tested e.g. qualified samples.

Normalizing Chromosome Sequence as a Normalizing Sequence for Chromosome(s)

In other embodiments, a normalizing chromosome sequence can be a single sequence or it can be a group of sequences. For example, in some embodiments, a normalizing sequence is a group of sequences e.g. a group of chromosomes, that is identified as the normalizing sequence for any or more of chromosomes 1-22, X and Y. The group of chromosomes that compose the normalizing sequence for a chromosome of interest i.e. a normalizing chromosome sequence, can be a group of two, three, four, five, six, seven, eight, nine, ten, eleven, twelve, thirteen, fourteen, fifteen, sixteen, seventeen, eighteen, nineteen, twenty, twenty-one, or twenty-two chromosomes, and including or excluding one or both of chromosomes X, and Y. The group of chromosomes that is identified as the normalizing chromosome sequence is a group of chromosomes that results in chromosome doses for the chromosome of interest that has the smallest variability across all samples tested e.g. qualified samples. Preferably, individual and groups of chromosomes are tested together for their ability to best mimic the behavior of the sequence of interest for which they are chosen as normalizing chromosome sequences.

In one embodiment, the normalizing sequence for chromosome 21 is selected from chromosome 9, chromosome 1, chromosome 2, chromosome 3, chromosome 4, chromosome 5, chromosome 6, chromosome 7, chromosome 8, chromosome 10, chromosome 11, chromosome 12, chromosome 13, chromosome 14, chromosome 15, chromosome 16, and chromosome 17. In another embodiment, the normalizing sequence for chromosome 21 is selected from chromosome 9, chromosome 1, chromosome 2, chromosome 11, chromosome 12, and chromosome 14. Alternatively, the normalizing sequence for chromosome 21 is a group of chromosomes selected from chromosome 9, chromosome 1, chromosome 2, chromosome 3, chromosome 4, chromosome 5, chromosome 6, chromosome 7, chromosome 8, chromosome 10, chromosome 11, chromosome 12, chromosome 13, chromosome 14, chromosome 15, chromosome 16, and chromosome 17. In another embodiment, the group of chromosomes is a group selected from chromosome 9, chromosome 1, chromosome 2, chromosome 11, chromosome 12, and chromosome 14.

In some embodiments, the method is further improved by using a normalizing sequence that is determined by systematic calculation of all chromosome doses using each chromosome individually and in all possible combinations with all remaining chromosomes (see Example 13). For example, a systematically determined normalizing chromosome can be determined for each chromosome of interest by systematically calculating all possible chromosome doses using one of any of chromosomes 1-22, X, and Y, and combinations of two or more of chromosomes 1-22, X, and Y to determine which single or group of chromosomes is the normalizing chromosome that results in the least variability of the chromosome dose for a chromosome of interest across a set of qualified samples (see Example 13). Accordingly, in one embodiment, the systematically calculated normalizing chromosome sequence for chromosome 21 is a group of chromosomes consisting of chromosome 4, chromosome 14, chromosome 16, chromosome 20, and chromosome 22. Single or groups of chromosomes can be determined for all chromosomes in the genome.

In one embodiment, the normalizing sequence for chromosome 18 is selected chromosome 8, chromosome 2, chromosome 3, chromosome 4, chromosome 5, chromosome 6, chromosome 7, chromosome 9, chromosome 10, chromosome 11, chromosome 12, chromosome 13, and chromosome 14. Preferably, the normalizing sequence for chromosome 18 is selected from chromosome 8, chromosome 2, chromosome 3, chromosome 5, chromosome 6, chromosome 12, and chromosome 14. Alternatively, the normalizing sequence for chromosome 18 is a group of chromosomes selected from chromosome 8, chromosome 2, chromosome 3, chromosome 4, chromosome 5, chromosome 6, chromosome 7, chromosome 9, chromosome 10, chromosome 11, chromosome 12, chromosome 13, and chromosome 14. Preferably, the group of chromosomes is a group selected from chromosome 8, chromosome 2, chromosome 3, chromosome 5, chromosome 6, chromosome 12, and chromosome 14.

In another embodiment, the normalizing sequence for chromosome 18 is determined by systematic calculation of all possible chromosome doses using each possible normalizing chromosome individually and all possible combinations of normalizing chromosomes (as explained elsewhere herein). Accordingly, in one embodiment, the normalizing sequence for chromosome 18 is a normalizing chromosome consisting of the group of chromosomes consisting of chromosome 2, chromosome 3, chromosome 5, and chromosome 7.

In one embodiment, the normalizing sequence for chromosome X is selected from chromosome 1, chromosome 2, chromosome 3, chromosome 4, chromosome 5, chromosome 6, chromosome 7, chromosome 8, chromosome 9, chromosome 10, chromosome 11, chromosome 12, chromosome 13, chromosome 14, chromosome 15, and chromosome 16. Preferably, the normalizing sequence for chromosome X is selected from chromosome 2, chromosome 3, chromosome 4, chromosome 5, chromosome 6 and chromosome 8. Alternatively, the normalizing sequence for chromosome X is a group of chromosomes selected from chromosome 1, chromosome 2, chromosome 3, chromosome 4, chromosome 5, chromosome 6, chromosome 7, chromosome 8, chromosome 9, chromosome 10, chromosome 11, chromosome 12, chromosome 13, chromosome 14, chromosome 15, and chromosome 16. Preferably, the group of chromosomes is a group selected from chromosome 2, chromosome 3, chromosome 4, chromosome 5, chromosome 6, and chromosome 8.

In another embodiment, the normalizing sequence for chromosome X is determined by systematic calculation of all possible chromosome doses using each possible normalizing chromosome individually and all possible combinations of normalizing chromosomes (as explained elsewhere herein). Accordingly, in one embodiment, the normalizing sequence for chromosome X is a normalizing chromosome consisting of the group of chromosome 4 and chromosome 8.

In one embodiment, the normalizing sequence for chromosome 13 is a chromosome selected from chromosome 2, chromosome 3, chromosome 4, chromosome 5, chromosome 6, chromosome 7, chromosome 8, chromosome 9, chromosome 10, chromosome 11, chromosome 12, chromosome 14, chromosome 18, and chromosome 21. Preferably, the normalizing sequence for chromosome 13 is a chromosome selected from chromosome 2, chromosome 3, chromosome 4, chromosome 5, chromosome 6, and chromosome 8. In another embodiment, the normalizing sequence for chromosome 13 is a group of chromosomes selected from chromosome 2, chromosome 3, chromosome 4, chromosome 5, chromosome 6, chromosome 7, chromosome 8, chromosome 9, chromosome 10, chromosome 11, chromosome 12, chromosome 14, chromosome 18, and chromosome 21. Preferably, the group of chromosomes is a group selected from chromosome 2, chromosome 3, chromosome 4, chromosome 5, chromosome 6, and chromosome 8.

In another embodiment, the normalizing sequence for chromosome 13 is determined by systematic calculation of all possible chromosome doses using each possible normalizing chromosome individually and all possible combinations of normalizing chromosomes (as explained elsewhere herein). Accordingly, in one embodiment, the normalizing sequence for chromosome 13 is a normalizing chromosome comprising the group of chromosome 4 and chromosome 5. In another embodiment, the normalizing sequence for chromosome 13 is a normalizing chromosome consisting of the group of chromosome 4 and chromosome 5.

The variation in chromosome dose for chromosome Y is greater than 30 independently of which normalizing chromosome is used in determining the chromosome Y dose. Therefore, any one chromosome, or a group of two or more chromosomes selected from chromosomes 1-22 and chromosome X can be used as the normalizing sequence for chromosome Y. In one embodiment, the at least one normalizing chromosome is a group of chromosomes consisting of chromosomes 1-22, and chromosome X. In another embodiment, the group of chromosomes consists of chromosome 2, chromosome 3, chromosome 4, chromosome 5, and chromosome 6.

In another embodiment, the normalizing sequence for chromosome Y is determined by systematic calculation of all possible chromosome doses using each possible normalizing chromosome individually and all possible combinations of normalizing chromosomes (as explained elsewhere herein). Accordingly, in one embodiment, the normalizing sequence for chromosome Y is a normalizing chromosome comprising the group of chromosomes consisting of chromosome 4 and chromosome 6. In another embodiment, the normalizing sequence for chromosome Y is a normalizing chromosome consisting of the group of chromosomes consisting of chromosome 4 and chromosome 6.

The normalizing sequence used to calculate the dose of different chromosomes of interest, or of different segments of interest can be the same or it can be a different normalizing sequence for different chromosomes or segments of interest, respectively. For example, the normalizing sequence e.g. a normalizing chromosome (one or a group) for chromosome of interest A can be the same or it can be different from the normalizing sequence e.g. a normalizing chromosome (one or a group) for chromosome of interest B.

The normalizing sequence for a complete chromosome may be a complete chromosome or a group of complete chromosomes, or it may be a segment of a chromosome, or a group of segments of one or more chromosomes.

Normalizing Segment Sequence as a Normalizing Sequence for Chromosome(s)

In another embodiment, the normalizing sequence for a chromosome can be a normalizing segment sequence. The normalizing segment sequence can be a single segment or it can be a group of segments of one chromosome, or they can be segments from two or more different chromosomes. A normalizing segment sequence can be determined by systematic calculation of all combinations of segment sequences in the genome. For example, a normalizing segment sequence for chromosome 21 can be a single segment that is bigger or smaller than the size of chromosome 21, which is approximately 47 Mbp (million base pairs), for example, the normalizing segment can be a segment from chromosome 9, which is approximately 140 Mbp. Alternatively, a normalizing sequence for chromosome 21 can be for example, a combination of segment sequences from two different chromosome e.g. from chromosome 1, and from chromosome 12.

In one embodiment, the normalizing sequence for chromosome 21 is a normalizing segment sequence of one segment or of a group of two or more segments of chromosomes 1-20, 22, X, and Y. In another embodiment, the normalizing sequence for chromosome 18 is a segment or groups segments of chromosomes 1-17, 19-22, X, and Y. In another embodiment, the normalizing sequence for chromosome 13 is a segment or groups of segments of chromosomes 1-12, 14-22, X, and Y. In another embodiment, the normalizing sequence for chromosome X is a segment or groups segments of chromosomes 1-22, and Y. In another embodiment, the normalizing sequence for chromosome Y is a segment or group of segments of chromosomes 1-22, and X. Normalizing segment sequences of single or groups of segments can be determined for all chromosomes in the genome. The two or more segments of a normalizing segment sequence can be segments from one chromosome, or the two or more segments can be segments of two or more different chromosomes. As described for normalizing chromosome sequences, a normalizing segment sequence can be the same for two or more different chromosomes.

Normalizing Segment Sequence as a Normalizing Sequence for Chromosome Segment(s)

The presence or absence of CNV of a sequence of interest can be determined when the sequence of interest is a segment of a chromosome. Variation in the copy number of a chromosome segment allows for determining the presence or absence of a partial chromosomal aneuploidy. Described below are examples of partial chromosomal aneuploidies that are associated with various fetal abnormalities and disease conditions. The segment of the chromosome can be of any length. For example, it can range from a kilobase to hundreds of megabases. The human genome occupies just over 3 billion DNA bases, which can be divided into tens, thousands, hundreds of thousands and millions of segments of different sizes of which the copy number can be determined according to the present method. The normalizing sequence for a segment of a chromosome is a normalizing segment sequence, which can be a single segment from any one of the chromosomes 1-22, X and Y, or it can be a group of segments from any one or more of chromosomes 1-22, X, and Y.

The normalizing sequence for a segment of interest is a sequence that has a variability across chromosomes and across samples that is closest to that of the segment of interest. Determination of a normalizing sequence can be performed as described for determining the normalizing sequence for a chromosome of interest when the normalizing sequence is a group of segments of any one or more of chromosomes 1-22, X and Y. A normalizing segment sequence of one or a group of segments can be identified by calculating segment doses using one, and all possible combinations of two or more segments as normalizing sequences for the segment of interest in each sample of a set of qualified samples i.e. samples known to be diploid for the segment of interest, and the normalizing sequence is determined as that providing a segment dose having the lowest variability for the segment of interest across all qualified samples, as is described above for normalizing chromosome sequences.

For example, for a segment of interest that is 1 Mb (megabase), the remaining 3 million segments (minus the 1 mg segment of interest) of the approximately 3 Gb human genome can be used individually or in combination with each other to calculate segment doses for a segment of interest in a qualified set of sample to determine which one or group of segments would serve as the normalizing segment sequence for qualified and test samples. Segments of interest can vary from about 1000 bases to tens of megabases. Normalizing segment sequences can be composed of one or more segments of the same size as that of the sequence of interest. In other embodiment, the normalizing segment sequence can be composed of segments that differ from that of the sequence of interest, and/or from each other. For example, a normalizing segment sequence for a 100,000 base long sequence can be 20,000 bases long, and comprise a combination of sequences of different lengths e.g. a 7,000+8,000+5,000 bases. As is described elsewhere herein for normalizing chromosome sequences, normalizing segment sequences can be determined by systematic calculation of all possible chromosome and/or segment doses using each possible normalizing chromosome segment individually and all possible combinations of normalizing segments (as explained elsewhere herein). Single or groups of segments can be determined for all segments and/or chromosomes in the genome.

The normalizing sequence used to calculate the dose of different chromosome segments of interest can be the same or it can be a different normalizing sequence for different chromosome segments of interest. For example, the normalizing sequence e.g. a normalizing segment (one or a group) for chromosome segment of interest A can be the same or it can be different from the normalizing sequence e.g. a normalizing segment (one or a group) for chromosome segment of interest B.

Normalizing Chromosome Sequence as a Normalizing Sequence for Chromosome Segment(s)

In another embodiment, variations in copy number of chromosome segments can be determined using a normalizing chromosome, which can be a single chromosome or a group of chromosomes as described above. The normalizing chromosome sequence can be the normalizing chromosome or group of chromosomes that are identified for the chromosome of interest in a set of qualified samples by systematically determining which one or group of chromosomes provide the lowest variability in the chromosome dose in a set of qualified samples. For example, to determine the presence or absence of a partial deletion of chromosome 7, the normalizing chromosome or group of chromosomes that is used in the analysis for the partial deletion is the chromosome or group of chromosomes that are first identified in a qualified set of samples as the normalizing sequence that provides the lowest chromosome dose for the entire chromosome 7. As is described elsewhere herein for normalizing chromosome sequences for chromosomes of interest, normalizing chromosome sequences for chromosome segments can be determined by systematic calculation of all possible chromosome doses using each possible normalizing chromosome individually and all possible combinations of normalizing chromosomes (as explained elsewhere herein). Single or groups of chromosomes can be determined for all segments of chromosomes in the genome. Examples demonstrating the use of normalizing chromosomes for determining the presence of a partial chromosomal deletion and for a partial chromosomal duplication are provided as Examples 17 and 18.

In some embodiments, determination of a CNV of a chromosome segment is performed by first subdividing the chromosome of interest into sections or bins of variable length. The bin length can be of at least about 1 kbp, at least about 10 kbp, at least about 100 kbp, at least about 1 mbp, at least about 10 mbp, or at least about 100 mbp. The smaller the bin length, the greater the resolution that is obtained to localize the CNV of the segment in the chromosome of interest.

Determining the presence or absence of a CNV of a segment of a chromosome of interest can be obtained by comparing the dose for each of the bins of the chromosome of interest in a test sample to a the mean for the corresponding bin dose determined for each bin of equivalent length in a set of qualified samples. A normalized bin value for each bin can be calculated as described above for the normalized segment value as a normalized bin value (NBV), which relates the bin dose in a test sample to the mean of the of the corresponding bin dose in a set of qualified samples. The NBV is calculated as:

$$NBV_{ij} = \frac{x_{ij} - \hat{\mu}_j}{\hat{\sigma}_j}$$

where $\hat{\mu}_j$ and $\hat{\sigma}_j$ are the estimated mean and standard deviation, respectively, for the j-th bin dose in a set of qualified samples, and $x_{ij}$ is the observed j-th bin dose for test sample i.

Determination of Aneuploidies in Test Samples

Based on the identification of the normalizing sequence(s) in qualified samples, a sequence dose is determined for a sequence of interest in a test sample comprising a mixture of nucleic acids derived from genomes that differ in one or more sequences of interest.

In step 115, a test sample is obtained from a subject suspected or known to carry a clinically-relevant CNV of a sequence of interest. The test sample may be a biological fluid e.g. plasma, or any suitable sample as described below. As explained, the sample may be obtained using a non-invasive procedure such as a simple blood draw. In some embodiments, a test sample contains a mixture of nucleic acid molecules e.g. cfDNA molecules. In some embodiments, the test sample is a maternal plasma sample that contains a mixture of fetal and maternal cfDNA molecules.

In step 125, at least a portion of the test nucleic acids in the test sample is sequenced as described for the qualified samples to generate millions of sequence reads e.g. 36 bp reads. As in step 120, the reads generated from sequencing the nucleic acids in the test sample are uniquely mapped or aligned to a reference genome to produce tags. As described in step 120, at least about $3\times10^6$ qualified sequence tags, at least about $5\times10^6$ qualified sequence tags, at least about $8\times10^6$ qualified sequence tags, at least about $10\times10^6$ qualified sequence tags, at least about $15\times10^6$ qualified sequence tags, at least about $20\times10^6$ qualified sequence tags, at least about $30\times10^6$ qualified sequence tags, at least about $40\times10^6$ qualified sequence tags, or at least about $50\times10^6$ qualified sequence tags comprising between 20 and 40 bp reads are obtained from reads that map uniquely to a reference genome. In certain embodiments, the reads produced by sequencing apparatus are provided in an electronic format. Alignment is accomplished using computational apparatus as discussed below. Individual reads are compared against the reference genome, which is often vast (millions of base pairs) to identify sites where the reads uniquely correspond with the reference genome. In some embodiments, the alignment procedure permits limited mismatch between reads and the reference genome. In some cases, 1, 2, or 3 base pairs in a read are permitted to mismatch corresponding base pairs in a reference genome, and yet a mapping is still made.

In step 135, all or most of the tags obtained from sequencing the nucleic acids in the test samples are counted to determine a test sequence tag density using a computational apparatus as described below. In some embodiments, each read is aligned to a particular region of the reference genome (a chromosome or segment in most cases), and the read is converted to a tag by appending site information to the read. As this process unfolds, the computational apparatus may keep a running count of the number of tags/reads mapping to each region of the reference genome (chromosome or segment in most cases). The counts are stored for each chromosome or segment of interest and each corresponding normalizing chromosome or segment.

In certain embodiments, the reference genome has one or more excluded regions that are part of a true biological genome but are not included in the reference genome. Reads potentially aligning to these excluded regions are not counted. Examples of excluded regions include regions of long repeated sequences, regions of similarity between X and Y chromosomes, etc.

In some embodiments, the method determines whether to count a tag more than once when multiple reads align to the same site on a reference genome or sequence. There may be occasions when two tags have the same sequence and therefore align to an identical site on a reference sequence. The method employed to count tags may under certain circumstances exclude from the count identical tags deriving from the same sequenced sample. If a disproportionate number of tags are identical in a given sample, it suggests that there is a strong bias or other defect in the procedure. Therefore, in accordance with certain embodiments, the counting method does not count tags from a given sample that are identical to tags from the sample that were previously counted.

Various criteria may be set for choosing when to disregard an identical tag from a single sample. In certain embodiments, a defined percentage of the tags that are counted must be unique. If more tags than this threshold are not unique, they are disregarded. For example, if the defined percentage requires that at least 50% are unique, identical tags are not counted until the percentage of unique tags it exceeds 50% for the sample. In other embodiments, the threshold number of unique tags is at least about 60%. In other embodiments, the threshold percentage of unique tags is at least about 75%, or at least about 90%, or at least about 95%, or at least about 98%, or at least about 99%. A threshold may be set at 90% for chromosome 21. If 30M tags are aligned to chromosome 21, then at least 27M of them must be unique. If 3M counted tags are not unique and the 30 million and first tag is not unique, it is not counted. The choice of the particular threshold or other criterion used to determine when not to count further identical tags can be selected using appropriate statistical analysis. One factor influencing this threshold or other criterion is the relative amount of sequenced sample to the size of the genome to which tags can be aligned. Other factors include the size of the reads and similar considerations.

In one embodiment, the number of test sequence tags mapped to a sequence of interest is normalized to the known length of a sequence of interest to which they are mapped to provide a test sequence tag density ratio. As described for the qualified samples, normalization to the known length of a sequence of interest is not required, and may be included as a step to reduce the number of digits in a number to simplify it for human interpretation. As all the mapped test sequence tags are counted in the test sample, the sequence tag density for a sequence of interest e.g. a clinically-relevant sequence, in the test samples is determined, as are the sequence tag densities for additional sequences that correspond to at least one normalizing sequence identified in the qualified samples.

In step 150, based on the identity of at least one normalizing sequence in the qualified samples, a test sequence dose is determined for a sequence of interest in the test sample. In various embodiments, the test sequence dose is computationally determined using by manipulating the sequence tag densities of the sequence of interest and the corresponding normalizing sequence as described herein. The computational apparatus responsible for this undertaking will electronically access the association between the sequence of interest its associated normalizing sequence, which may be stored in a database, table, graph, or be included as code in program instructions.

As described elsewhere herein, the at least one normalizing sequence can be a single sequence or a group of sequences. The sequence dose for a sequence of interest in a test sample is a ratio of the sequence tag density determined for the sequence of interest in the test sample and the sequence tag density of at least one normalizing sequence determined in the test sample, wherein the normalizing sequence in the test sample corresponds to the normalizing sequence identified in the qualified samples for the particular sequence of interest. For example, if the normalizing sequence identified for chromosome 21 in the qualified samples is determined to be a chromosome e.g. chromosome 14, then the test sequence dose for chromosome 21 (sequence of interest) is determined as the ratio of the sequence tag density for chromosome 21 in and the sequence tag density for chromosome 14 each determined in the test sample. Similarly, chromosome doses for chromosomes 13, 18, X, Y, and other chromosomes associated with chromosomal aneuploidies are determined. A normalizing sequence for a chromosome of interest can be one or a group of chromosomes, or one or a group of chromosome segments. As described previously, a sequence of interest can be part of a chromosome e.g. a chromosome segment. Accordingly, the dose for a chromosome segment can be determined as the ratio of the sequence tag density determined for the segment in the test sample and the sequence tag density for the normalizing chromosome segment in the test sample, wherein the normalizing segment in the test sample corresponds to the normalizing segment (single or a group of segments) identified in the qualified samples for the particular segment of interest. Chromosome segments can range from kilobases (kb) to megabases (Mb) in size (e.g., about 1 kb to 10 kb, or about 10 kb to 100 kb, or about 100 kb to 1 Mb).

In step 155, threshold values are derived from standard deviation values established for qualified sequence doses determined in a plurality of qualified samples and sequence doses determined for samples known to be aneuploid for a sequence of interest. Note that this operation is typically performed asynchronously with analysis of patient test samples. It may be performed, for example, concurrently with the selection of normalizing sequences from qualified samples. Accurate classification depends on the differences between probability distributions for the different classes i.e. type of aneuploidy. In some examples, thresholds are chosen from empirical distribution for each type of aneuploidy e.g. trisomy 21. Possible threshold values that were established for classifying trisomy 13, trisomy 18, trisomy 21, and monosomy X aneuploidies as described in the Examples, which describe the use of the method for determining chromosomal aneuploidies by sequencing cfDNA extracted from a maternal sample comprising a mixture of fetal and maternal nucleic acids. The threshold value that is determined to distinguish samples affected for an aneuploidy of a chromosome can be the same or can be different from the threshold that is determined to distinguish samples affected for a different aneuploidy. As is shown in the Examples, the threshold value for each chromosome of interest is determined from the variability in the dose of the chromosome of interest across samples and sequencing runs. The less variable the chromosome dose for any chromosome of interest, the narrower the spread in the dose for the chromosome of interest across all the unaffected samples, which are used to set the threshold for determining different aneuploidies.

Returning to the process flow associated with classifying a patient test sample, in step 160, the copy number variation of the sequence of interest is determined in the test sample by comparing the test sequence dose for the sequence of interest to at least one threshold value established from the qualified sequence doses. This operation may be performed by the same computational apparatus employed to measure sequence tag densities and/or calculate segment doses.

In step 165, the calculated dose for a test sequence of interest is compared to that set as the threshold values that are chosen according to a user-defined "threshold of reliability" to classify the sample as a "normal" an "affected" or a "no call". The "no call" samples are samples for which a definitive diagnosis cannot be made with reliability. Each type of affected sample (e.g., trisomy 21, partial trisomy 21, monosomy X) has its own thresholds, one for calling normal (unaffected) samples and another for calling affected samples (although in some cases the two thresholds coincide). As described elsewhere herein, under some circumstances a no-call can be converted to a call (affected or normal) if fetal fraction of nucleic acid in the test sample is sufficiently high. The classification of the test sequence may be reported by the computational apparatus employed in other operations of this process flow. In some cases, the classification is reported in an electronic format and may be displayed, emailed, texted, etc. to interest persons.

Certain embodiments provide a method for providing prenatal diagnosis of a fetal chromosomal aneuploidy in a biological sample comprising fetal and maternal nucleic acid molecules. The diagnosis is made based on obtaining sequence information sequencing at least a portion of the mixture of the fetal and maternal nucleic acid molecules derived from a biological test sample e.g. a maternal plasma sample, computing from the sequencing data a normalizing chromosome dose for one or more chromosomes of interest, and/or a normalizing segment dose for one or more segments of interest, and determining a statistically significant difference between the chromosome dose for the chromosome of interest and/or the segment dose for the segment of interest, respectively, in the test sample and a threshold value established in a plurality of qualified (normal) samples, and providing the prenatal diagnosis based on the statistical difference. As described in step 165 of the method, a diagnosis of normal or affected is made. A "no call" is provided in the event that the diagnosis for normal or affected cannot be made with confidence.

Samples and Sample Processing

Samples

Samples that are used for determining a CNV, e.g. chromosomal aneuploidies, partial aneuploidies, and the like, can include samples taken from any cell, tissue, or organ in which copy number variations for one or more sequences of interest are to be determined.

Desirably, the samples contain nucleic acids that are that are present in cells and/or nucleic acids that are "cell-free" (e.g., cfDNA).

In some embodiments it is advantageous to obtain cell-free nucleic acids e.g. cell-free DNA (cfDNA). Cell-free nucleic acids, including cell-free DNA, can be obtained by various methods known in the art from biological samples including but not limited to plasma, serum, and urine (see, e.g., Fan et al., *Proc Natl Acad Sci* 105:16266-16271 [2008]; Koide et al., *Prenatal Diagnosis* 25:604-607 [2005]; Chen et al., *Nature Med.* 2: 1033-1035 [1996]; Lo et al., Lancet 350: 485-487 [1997]; Botezatu et al., Clin Chem. 46: 1078-1084, 2000; and Su et al., J. Mol. Diagn. 6: 101-107 [2004]). To separate cell-free DNA from cells in a sample, various methods including, but not limited to fractionation, centrifugation (e.g., density gradient centrifugation), DNA-specific precipitation, or high-throughput cell sorting and/or other separation methods can be used. Commercially available kits for manual and automated separation of cfDNA are available (Roche Diagnostics, Indianapolis, Ind., Qiagen, Valencia, Calif., Macherey-Nagel, Duren, Del.). Biological samples comprising cfDNA have been used in assays to determine the presence or absence of chromosomal abnormalities e.g. trisomy 21, by sequencing assays that can detect chromosomal aneuploidies and/or various polymorphisms.

In various embodiments the cfDNA present in the sample can be enriched specifically or non-specifically prior to use (e.g., prior to preparing a sequencing library). Non-specific enrichment of sample DNA refers to the whole genome amplification of the genomic DNA fragments of the sample that can be used to increase the level of the sample DNA prior to preparing a cfDNA sequencing library. Non-specific enrichment can be the selective enrichment of one of the two genomes present in a sample that comprises more than one genome. For example, non-specific enrichment can be selective of the fetal genome in a maternal sample, which can be obtained by known methods to increase the relative proportion of fetal to maternal DNA in a sample. Alternatively, non-specific enrichment can be the non-selective amplification of both genomes present in the sample. For example, non-specific amplification can be of fetal and maternal DNA in a sample comprising a mixture of DNA from the fetal and maternal genomes. Methods for whole genome amplification are known in the art. Degenerate oligonucleotide-primed PCR (DOP), primer extension PCR technique (PEP) and multiple displacement amplification (MDA) are examples of whole genome amplification methods. In some embodiments, the sample comprising the mixture of cfDNA from different genomes is unenriched for cfDNA of the genomes present in the mixture. In other embodiments, the sample comprising the mixture of cfDNA from different genomes is non-specifically enriched for any one of the genomes present in the sample.

The sample comprising the nucleic acid(s) to which the methods described herein are applied typically comprises a biological sample ("test sample"), e.g., as described above. In some embodiments, the nucleic acid(s) to be screened for one or more CNVs is purified or isolated by any of a number of well-known methods.

Accordingly, in certain embodiments the sample comprises or consists of a purified or isolated polynucleotide, or it can comprise samples such as a tissue sample, a biological fluid sample, a cell sample, and the like. Suitable biological fluid samples include, but are not limited to blood, plasma, serum, sweat, tears, sputum, urine, sputum, ear flow, lymph, saliva, cerebrospinal fluid, ravages, bone marrow suspension, vaginal flow, transcervical lavage, brain fluid, ascites, milk, secretions of the respiratory, intestinal and genitourinary tracts, amniotic fluid, milk, and leukophoresis samples. In some embodiments, the sample is a sample that is easily obtainable by non-invasive procedures e.g. blood, plasma, serum, sweat, tears, sputum, urine, sputum, ear flow, saliva or feces. In certain embodiments the sample is a peripheral blood sample, or the plasma and/or serum fractions of a peripheral blood sample. In other embodiments, the biological sample is a swab or smear, a biopsy specimen, or a cell culture. In another embodiment, the sample is a mixture of two or more biological samples e.g. a biological sample can comprise two or more of a biological fluid sample, a tissue sample, and a cell culture sample. As used herein, the terms "blood," "plasma" and "serum" expressly encompass fractions or processed portions thereof. Similarly, where a sample is taken from a biopsy, swab, smear, etc., the "sample" expressly encompasses a processed fraction or portion derived from the biopsy, swab, smear, etc.

In certain embodiments, samples can be obtained from sources, including, but not limited to, samples from different individuals, samples from different developmental stages of the same or different individuals, samples from different diseased individuals (e.g., individuals with cancer or suspected of having a genetic disorder), normal individuals, samples obtained at different stages of a disease in an individual, samples obtained from an individual subjected to different treatments for a disease, samples from individuals subjected to different environmental factors, samples from individuals with predisposition to a pathology, samples individuals with exposure to an infectious disease agent (e.g., HIV), and the like.

In one illustrative, but non-limiting embodiment, the sample is a maternal sample that is obtained from a pregnant female, for example a pregnant woman. In this instance, the sample can be analyzed using the methods described herein to provide a prenatal diagnosis of potential chromosomal abnormalities in the fetus. The maternal sample can be a tissue sample, a biological fluid sample, or a cell sample. A biological fluid includes, as non-limiting examples, blood, plasma, serum, sweat, tears, sputum, urine, sputum, ear flow, lymph, saliva, cerebrospinal fluid, ravages, bone marrow suspension, vaginal flow, transcervical lavage, brain fluid, ascites, milk, secretions of the respiratory, intestinal and genitourinary tracts, and leukophoresis samples.

In another illustrative, but non-limiting embodiment, the maternal sample is a mixture of two or more biological samples e.g. the biological sample can comprise two or more of a biological fluid sample, a tissue sample, and a cell culture sample. In some embodiments, the sample is a sample that is easily obtainable by non-invasive procedures e.g. blood, plasma, serum, sweat, tears, sputum, urine, milk, sputum, ear flow, saliva and feces. In some embodiments, the biological sample is a peripheral blood sample, and/or the plasma and serum fractions thereof. In other embodiments, the biological sample is a swab or smear, a biopsy specimen, or a sample of a cell culture. As disclosed above, the terms "blood," "plasma" and "serum" expressly encompass fractions or processed portions thereof. Similarly, where a sample is taken from a biopsy, swab, smear, etc., the "sample" expressly encompasses a processed fraction or portion derived from the biopsy, swab, smear, etc.

In certain embodiments samples can also be obtained from in vitro cultured tissues, cells, or other polynucleotide-containing sources. The cultured samples can be taken from sources including, but not limited to, cultures (e.g., tissue or cells) maintained in different media and conditions (e.g., pH, pressure, or temperature), cultures (e.g., tissue or cells) maintained for different periods of length, cultures (e.g., tissue or cells) treated with different factors or reagents (e.g., a drug candidate, or a modulator), or cultures of different types of tissue and/or cells.

Methods of isolating nucleic acids from biological sources are well known and will differ depending upon the nature of the source. One of skill in the art can readily isolate nucleic acid(s) from a source as needed for the method described herein. In some instances, it can be advantageous to fragment the nucleic acid molecules in the nucleic acid sample. Fragmentation can be random, or it can be specific, as achieved, for example, using restriction endonuclease digestion. Methods for random fragmentation are well known in the art, and include, for example, limited DNAse digestion, alkali treatment and physical shearing. In one embodiment, sample nucleic acids are obtained from as cfDNA, which is not subjected to fragmentation.

In other illustrative embodiments, the sample nucleic acid (s) are obtained as genomic DNA, which is subjected to fragmentation into fragments of approximately 300 or more, approximately 400 or more, or approximately 500 or more base pairs, and to which NGS methods can be readily applied.

Sequencing Library Preparation

In one embodiment, the methods described herein can utilize next generation sequencing technologies (NGS), that allow multiple samples to be sequenced individually as genomic molecules (i.e. singleplex sequencing) or as pooled samples comprising indexed genomic molecules (e.g., multiplex sequencing) on a single sequencing run. These methods can generate up to several hundred million reads of DNA sequences. In various embodiments the sequences of genomic nucleic acids, and/or of indexed genomic nucleic acids can be determined using, for example, the Next Generation Sequencing Technologies (NGS) described herein. In various embodiments analysis of the massive amount of sequence data obtained using NGS can be performed using one or more processors as described herein.

In various embodiments the use of such sequencing technologies does not involve the preparation of sequencing libraries.

However, in certain embodiments the sequencing methods contemplated herein involve the preparation of sequencing libraries. In one illustrative approach, sequencing library preparation involves the production of a random collection of adapter-modified DNA fragments (e.g., polynucleotides) that are ready to be sequenced. Sequencing libraries of polynucleotides can be prepared from DNA or RNA, including equivalents, analogs of either DNA or cDNA, for example, DNA or cDNA that is complementary or copy DNA produced from an RNA template, by the action of reverse transcriptase. The polynucleotides may originate in double-stranded form (e.g., dsDNA such as genomic DNA fragments, cDNA, PCR amplification products, and the like) or, in certain embodiments, the polynucleotides may originated in single-stranded form (e.g., ssDNA, RNA, etc.) and have been converted to dsDNA form. By way of illustration, in certain embodiments, single stranded mRNA molecules may be copied into double-stranded cDNAs suitable for use in preparing a sequencing library. The precise sequence of the primary polynucleotide molecules is generally not material to the method of library preparation, and may be known or unknown. In one embodiment, the polynucleotide molecules are DNA molecules. More particularly, in certain embodiments, the polynucleotide molecules represent the entire genetic complement of an organism or substantially the entire genetic complement of an organism, and are genomic DNA molecules (e.g., cellular DNA, cell free DNA (cfDNA), etc.), that typically include both intron sequence and exon sequence (coding sequence), as well as non-coding regulatory sequences such as promoter and enhancer sequences. In certain embodiments, the primary polynucleotide molecules comprise human genomic DNA molecules, e.g. cfDNA molecules present in peripheral blood of a pregnant subject.

Preparation of sequencing libraries for some NGS sequencing platforms is facilitated by the use of polynucleotides comprising a specific range of fragment sizes. Preparation of such libraries typically involves the fragmentation of large polynucleotides (e.g. cellular genomic DNA) to obtain polynucleotides in the desired size range.

Fragmentation can be achieved by any of a number of methods known to those of skill in the art. For example, fragmentation can be achieved by mechanical means including, but not limited to nebulization, sonication and hydroshear. However mechanical fragmentation typically cleaves the DNA backbone at C—O, P—O and C—C bonds resulting in a heterogeneous mix of blunt and 3'- and 5'-overhanging ends with broken C—O, P—O and/C—C bonds (see, e.g., Alnemri and Liwack, J. Biol. Chem 265:17323-17333 [1990]; Richards and Boyer, J Mol Biol 11:327-240 [1965]) which may need to be repaired as they may lack the requisite 5'-phosphate for the subsequent enzymatic reactions e.g. ligation of sequencing adaptors, that are required for preparing DNA for sequencing.

In contrast, cfDNA, typically exists as fragments of less than about 300 base pairs and consequently, fragmentation is not typically necessary for generating a sequencing library using cfDNA samples.

Typically, whether polynucleotides are forcibly fragmented (e.g., fragmented in vitro), or naturally exist as fragments, they are converted to blunt-ended DNA having 5'-phosphates and 3'-hydroxyl. Standard protocols e.g. protocols for sequencing using, for example, the Illumina platform as described elsewhere herein, instruct users to end-repair sample DNA, to purify the end-repaired products prior to dA-tailing, and to purify the dA-tailing products prior to the adaptor-ligating steps of the library preparation.

Various embodiments, of methods of sequence library preparation described herein obviate the need to perform one or more of the steps typically mandated by standard protocols to obtain a modified DNA product that can be sequenced by NGS. An abbreviated method (ABB method), a 1-step method, and a 2-step method are described below. Consecutive dA-tailing and adaptor ligation is herein referred to as the 2-step process. Consecutive dA-tailing, adaptor ligating, and amplifying is herein referred to as the 1-step method. In various embodiments the ABB and 2-step methods can be performed in solution or on a solid surface. In certain embodiments the 1-step method is performed on a solid surface.

A comparison of a standard method e.g. Illumina, to the abbreviated method (ABB; Example 2), the 2-step and the 1-step method (Examples 3-6) for preparing DNA molecules for sequencing by NGS according to embodiments of the present invention is diagrammed in FIG. 2.

Abbreviated Preparation—ABB

In one embodiment, an abbreviated method (ABB method) for the preparation of a sequence library is provided that comprises the consecutive steps of end-repairing, dA-tailing and adaptor-ligating (ABB). In embodiments for preparing sequencing libraries that do not require the dA-tailing step (see, e.g., protocols for sequencing using Roche 454 and SOLID™3platforms) the steps of end-repairing and adaptor-ligating can exclude the purification step of the end-repaired products prior to the adaptor-ligating.

The method of preparing sequencing libraries comprising the consecutive steps of end-repairing, dA tailing and adaptor ligating is herein referred to as the abbreviated method (ABB), and was shown to generate sequencing libraries of unexpectedly improved quality while expediting the analysis of samples (see, e.g., Example 2). According to some embodiments of the method, the ABB method can be performed in solution, as exemplified herein. The ABB method can also be performed on a solid surface by first end-repairing and dA-tailing the DNA in solution, and subsequently binding it to a solid surface as is described elsewhere herein for the 1-step or 2-step preparation on a solid surface. The three enzymatic steps, including the step of ligating the adaptors to the dA-tailed DNA, are performed in the absence of polyethylene glycol. Published protocols for performing ligation reactions, including ligating adaptors to DNA, instruct users to perform ligations in the presence of polyethylene glycol. Applicants determined that the ligation of the adaptors to the dA-tailed DNA can be performed in the absence of polyethylene glycol.

In another embodiment, the preparation of the sequencing library eliminates the need for end-repairing the cfDNA prior to the dA-tailing step. Applicants have determined that cfDNA, which does not require to be fragmented, does not need be end-repaired, and the preparation of the cfDNA sequencing library according to embodiments of the present invention exclude the end-repair step and the purification steps to combine enzymatic reactions and further streamline the preparation of the DNA to be sequenced. cfDNA exists as a mixture of blunt and 3'- and 5'-overhanging ends that are generated in vivo by the action of nucleases, which cleave cellular genomic DNA into cfDNA fragments having termini with a 5'-phosphate and a 3'-hydroxyl group. Elimination of the end-repairing step selects cfDNA molecules that naturally occur as blunt-ended molecules, and of cfDNA molecules naturally having 5' overhanging ends that are filled-in by the polymerase activity of the enzyme e.g. Klenow Exo-, that is used to attach one or more deoxynucleotide to the 3'-OH as described below (dA-tailing). Elimination of the end-repair step of cfDNA selects against cfDNA molecules that have a 3'-overhanging end (3'-OH). Surprisingly, exclusion of these 3'-OH cfDNA molecules from the sequencing library does not affect the representation of genomic sequences in the library, demonstrating that the end-repair step of cfDNA molecules may be excluded from the preparation of the sequencing library (see Examples). In addition to cfDNA, other types of unrepaired polynucleotides that can be used for preparing sequencing libraries include DNA molecules resulting from reverse transcription of RNA molecules e.g. mRNA, siRNA, sRNA, and unrepaired DNA molecules that are amplicons of DNA synthesized from phosphorylated primers. When unphosphorylated primers are used, DNA that is reverse transcribed from RNA, and/or DNA that is amplified from DNA templates i.e. DNA amplicons, can also be phosphorylated subsequent to their synthesis by a polynucleotide kinase.

Figure 2:
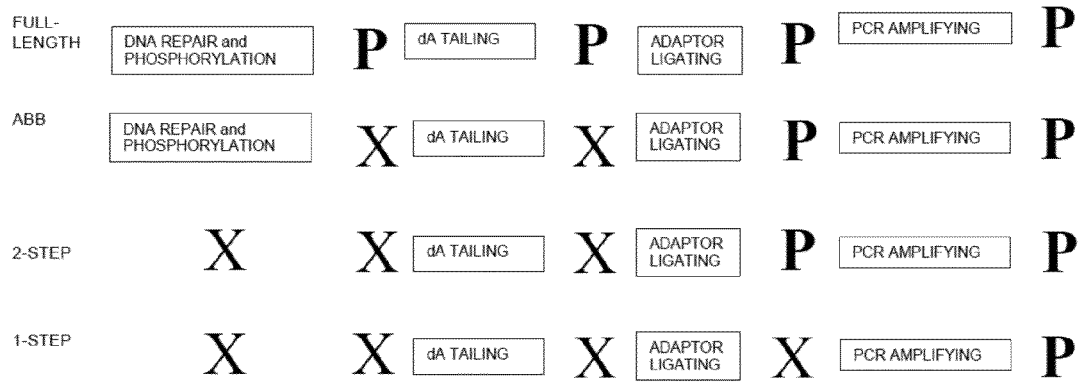
FIG. 2 depicts workflows for preparing a sequencing library according to Illumina's full-length protocol, the abbreviated protocol (ABB), the 2-STEP and 1-STEP methods as described herein. "P" represents a purification step; and "X" indicates that the purification step and or the DNA repair are excluded.

In another embodiment, unrepaired DNA is used for preparing a sequencing library according to the 2-step method, wherein end-repair of the DNA is excluded, and unrepaired DNA is subjected to the two consecutive steps of d-A tailing and adaptor ligating (see FIG. 2). The 2-step method can be performed in solution or on a solid surface. When performed in solution, the 2-step method comprises utilizing DNA obtained from a biological sample, excluding the step of end-repairing the DNA, and adding a single deoxynucleotide e.g. deoxyadenosine (A) to the 3'-ends of the polynucleotides in the sample of unrepaired DNA, for example, by the activity of certain types of DNA polymerase such as Taq polymerase or Klenow Exo-polymerase. dA-tailed products, which are compatible with 'T' overhang present on the 3' terminus of each duplex region of commercially available adaptors are ligated to the adaptors in a subsequent consecutive step. dA-tailing prevents self-ligation of both of the blunt-ended polynucleotides to favor the formation of the adaptor-ligated sequences. Thus, in some embodiments, unrepaired cfDNA is subjected to the consecutive steps of dA-tailing and adaptor-ligating, wherein the dA-tailed DNA is prepared from unrepaired DNA, and is not subjected to a purification step following the dA-tailing reaction. Double-stranded adaptors can be ligated to both ends of the dA-tailed DNA. A set of adaptors having the same sequences, or a set of two different adaptors can be utilized. In various embodiments, one or more different sets of same or different adaptors can also be used. Adaptors can comprise index sequences to enable multiplex sequencing of the library DNA. Ligation of adaptors to the dA-tailed DNA can, optionally, be performed in the absence of polyethylene glycol.

2-Step—Preparation in Solution

In various embodiments, when the 2-step process is performed in solution, the products of the adaptor ligation reaction can be purified to remove unligated adaptors, adaptors that may have ligated to one another. The purification can also select a size range of templates for cluster generation, that can, optionally, be preceded by an amplification e.g. a PCR amplification. The ligation products can be purified by any of a number of methods including, but not limited to gel electrophoresis, solid-phase reversible immobilization (SPRI), and the like. In some embodiments, the purified adaptor-ligated DNA is subjected to an amplification e.g. PCR amplification, prior to sequencing. Some sequencing platforms require that the library DNA is further subjected to another amplification. For example, the Illumina platform requires that a cluster amplification of library DNA be performed as an integral part of the sequencing according to the Illumina technology. In other embodiments, the purified adaptor-ligated DNA is denatured and the single stranded DNA molecules are attached to the flow cell of the sequencer. Thus, in some embodiments, the method for preparing a sequencing library in solution from unrepaired DNA for NGS sequencing comprises obtaining DNA molecules from a sample; and performing the consecutive steps of dA tailing and adaptor-ligating the unrepaired DNA molecules obtained from the sample.

As indicated supra, in various embodiments, these methods of library preparation are incorporated into a method of determining copy number variations (CNVs) such as aneuploidies, and the like. Accordingly, in one illustrative embodiment, a method is provided for determining the presence or absence of one or more fetal chromosomal aneuploidies comprising: (a) obtaining a maternal sample comprising a mixture of fetal and maternal cell-free DNA; (b) isolating the mixture of fetal and maternal cfDNA from said sample; (c) preparing a sequencing library from the mixture of fetal and maternal cfDNA; wherein preparing the library comprises the consecutive steps of dA-tailing and adaptor ligating the cfDNA, and wherein preparing the library excludes end-repairing the cfDNA and the preparation is performed in solution; (d) massively parallel sequencing at least a portion of the sequencing library to obtain sequence information for the fetal and maternal cfDNA in the sample; (e) storing in a computer readable medium, at least temporarily, the sequence information; (f) using the stored sequence information to computationally identify a number of sequence tags for each of one or more chromosomes of interest and for a normalizing sequence for each of any one or more chromosome of interest; (g) computationally calculating, using the number of sequence tags for each of the one or more chromosomes of interest and the number of sequence tags for the normalizing sequence for each of the one or more chromosomes of interest, a chromosome dose for each of the one or more chromosomes of interest; and (h) comparing the chromosome dose for each of the one or more chromosomes of interest to a corresponding threshold value for each of the one or more chromosomes of interest, and thereby determining the presence or absence of the fetal chromosomal aneuploidy in the sample, wherein steps (e)-(h) are performed using one or more processors. This method is exemplified in Examples 3 and 4.

2-Step and 1-Step—Solid Phase Preparation

In some embodiments, the sequencing library is prepared on a solid surface according to the 2-step method described above for the preparation of the library in solution. The preparation of the sequencing library on a solid surface according to the 2-step method comprises obtaining DNA molecules e.g. cfDNA, from a sample, and performing the consecutive steps of dA-tailing and adaptor ligating, where the adaptor-ligating is performed on a solid surface. Repaired or unrepaired DNA can be used. In some embodiments, the adaptor-ligated product is detached from the solid surface, purified, and amplified prior to sequencing. In other embodiments, the adaptor-ligated product is detached from the solid surface, purified, and not amplified prior to sequencing. In yet other embodiments, the adaptor-ligated product is amplified, detached form the solid surface, and purified. In some embodiments, the purified product is amplified. In other embodiments, the purified product is not amplified. The sequencing protocol can include an amplification e.g. cluster amplification. In various embodiments the detached adaptor-ligated product is purified prior to amplification and/or sequencing.

In certain embodiments, the sequencing library is prepared on a solid surface according to the 1-step method. In various embodiments the preparation of the sequencing library on a solid surface according to the 1-step method comprises obtaining DNA molecules e.g. cfDNA, from a sample, and performing the consecutive steps of dA-tailing, adaptor ligating, and amplifying, wherein the adaptor-ligating is performed on a solid surface. The adaptor-ligated product need not be detached prior to purification.

Figure 3:
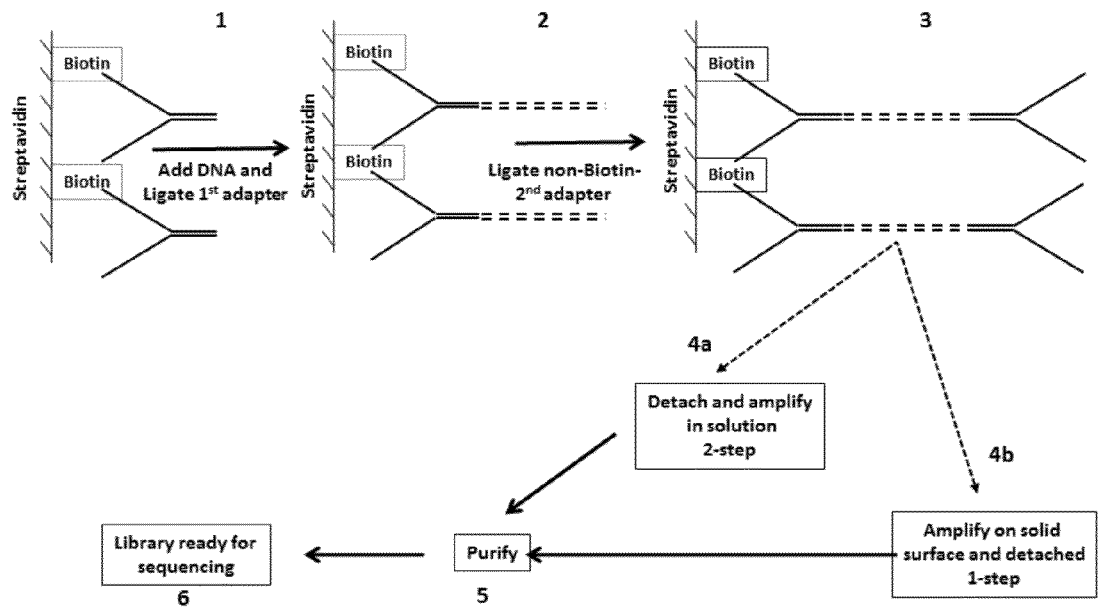
FIG. 3 depicts a workflow of embodiments of the method for preparing a sequencing library on a solid surface.

FIG. 3 depicts 2-step and 1-step methods for preparing a sequencing library on a solid surface. Either repaired or unrepaired DNA can be used for preparing a sequencing library on a solid surface. In some embodiments, unrepaired DNA is used. Examples of unrepaired DNA that can be used for preparing a sequencing library on a solid surface include without limitation cfDNA, DNA that has been reverse transcribed from RNA using phosphorylated primers, DNA that has been amplified from DNA template using phosphorylated primers i.e. phosphorylated DNA amplicons. Examples of repaired DNA that can be used for preparing a sequencing library on a solid surface include without limitation cfDNA and fragmented genomic DNA that has been blunt-ended and phosphorylated i.e. repaired, phosphorylated DNA generated by reverse transcription of RNA e.g. mRNA, sRNA, siRNA. In some illustrative embodiments, unrepaired cfDNA obtained from a maternal sample is used for preparing the sequencing library.

Preparation of a sequencing library on a solid surface comprises coating the solid surface with a first partner of a two-part conjugate, modifying a first adaptor by attaching the second partner of the two part conjugate to the adaptor, and immobilizing the adaptor on the solid surface by the binding interaction of the first and second partners of the two-part conjugate. For example, preparation of sequencing libraries on a solid surface can comprise attaching a polypeptide, polynucleotide or small molecule to an end of a library adaptor, which polypeptide, polynucleotide or small molecule is capable of forming a conjugate complex with a polypeptide, a polynucleotide or small molecule that is immobilized on a solid surface. Solid surfaces that can be used for immobilizing polypeptides, polynucleotides or small molecules include without limitation plastic, paper, membranes, filters, chips, pins or glass slides, silica or polymer beads (e.g. polypropylene, polystyrene, polycarbonate), 2D or 3D molecular scaffolds, or any support for solid-phase synthesis of polypeptides or polynucleotides.

Bonding between polypeptide-polypeptide, polypeptide-polynucleotide, polypeptide-small molecule, and polynucleotide-polynucleotide conjugates can be covalent or noncovalent. Preferably, conjugate complexes are bound by noncovalent bonds. For example, conjugates that can be used in preparing sequencing libraries on a solid surface include without limitation streptavidin-biotin conjugates, antibody-antigen conjugates, and ligand-receptor conjugates. Examples of polypeptide-polynucleotide conjugates that can be used in preparing sequencing libraries on a solid surface include without limitation DNA-binding protein-DNA conjugates. Examples of polynucleotide-polynucleotide conjugates that can be used in preparing sequencing libraries on a solid surface include without limitation oligodT-oligoA, and oligodT-oligodA. Examples of polypeptide-small molecule and polynucleotide-small molecule conjugates include streptavidin-biotin.

According to embodiments (1-step and 2-step) of the solid surface method as shown in FIG. 3, the solid surface of the vessel used for preparing the sequencing library e.g. a polypropylene PCR tube or 96-well plate, is coated with a polypeptide e.g. streptavidin. The end of a first set of adaptors is modified by attaching a small molecule e.g. a biotin molecule, and the biotinylated adaptors are bound to the streptavidin on the solid surface (1). Subsequently, the unrepaired or the repaired DNA is ligated to the streptavidin-bound biotinylated adaptor, thereby immobilizing it to the solid surface (2). The second set of adaptors is ligated to the immobilized DNA (3).

2-Step—Preparation on Solid Phase

In one embodiment, the 2-step method is performed using unrepaired DNA e.g. cfDNA, for preparing the sequencing library on a solid surface. The unrepaired DNA is dA-tailed by attaching a single nucleotide base e.g. dA, to the 3' ends of the unrepaired DNA e.g. cfDNA, strands. Optionally, multiple nucleotide bases can be attached to the unrepaired DNA. The mixture comprising the dA-tailed DNA is added to the adaptors immobilized on the solid surface, to which it is ligated. The steps of dA-tailing and adaptor-ligating the DNA are consecutive i.e. purification of the dA-tailed product is not performed (as shown in FIG. 2 for the 2-step method). As described above, the adaptors may have overhangs that are complementary to overhangs on the unrepaired DNA molecule. Subsequently, a second set of adaptors is added to the DNA-biotinylated adaptor complex to provide an adaptor-ligated DNA library. Optionally, repaired DNA is used for preparing the library. Repaired DNA can be genomic DNA that has been fragmented and subjected to in vitro enzymatic repair of 3' and 5' ends. In one embodiment, DNA e.g. maternal cfDNA, is end-repaired, dA-tailed and adaptor-ligated to adaptors immobilized on a solid surface in consecutive steps of end-repairing, dA-tailing and adaptor-ligating as described for the abbreviated method performed in solution.

In certain embodiments utilizing the 2-step process, the adaptor-ligated DNA is detached from the solid surface by chemical or physical means e.g. heat, UV light etc. (4a in FIG. 2), is purified (5 in FIG. 2), and optionally, it is subjected to an amplification in solution prior to beginning the sequencing process. In other embodiments, the adaptor-ligated DNA is not amplified. Absent amplification, the adaptors ligated to the DNA can be constructed to comprise sequences that hybridize to oligonucleotides present on the flow cell of a sequencer (Kozarewa et al., Nat Methods 6:291-295 [2009]), and an amplification that introduces sequences for hybridizing the library DNA to the flow cell of a sequencer is avoided. The library of adaptor-ligated DNA is subjected to massively parallel sequencing (6 in FIG. 2) as described for the adaptor-ligated DNA created in solution. In some embodiments, sequencing is massively parallel sequencing using sequencing-by-synthesis with reversible dye terminators. In other embodiments, sequencing is massively parallel sequencing using sequencing-by-ligation. The sequencing process may include a solid-phase amplification e.g. cluster amplification, as described elsewhere herein.

Thus, in various embodiments, the method for preparing a sequencing library on a solid surface from unrepaired DNA for NGS can comprise obtaining DNA molecules from a sample; and performing the consecutive steps of dA tailing and adaptor-ligating the unrepaired DNA molecules, where adaptor-ligating is performed on a solid phase. In certain embodiments, the adaptors can include index sequences, to allow for multiplexing the sequencing of multiple samples within a single reaction vessel e.g. a channel of a flow cell. As described above, the DNA molecules can be cfDNA molecules, they can be DNA molecules transcribed from RNA, they can be amplicons of DNA molecules, and the like.

As indicated supra, in various embodiments, these methods of library preparation are incorporated into a method of determining copy number variations (CNVs) such as aneuploidies, and the like. Thus, in some embodiments the method for preparing a sequencing library on a solid surface from unrepaired cfDNA is incorporated into a method for analyzing a maternal sample to determine the presence or absence of a fetal chromosomal aneuploidy. Accordingly, in one embodiment, a method is provided for determining the presence or absence of one or more fetal chromosomal aneuploidies comprising: (a) obtaining a maternal sample comprising a mixture of fetal and maternal cell-free DNA; (b) isolating the mixture of fetal and maternal cfDNA from said sample; (c) preparing a sequencing library from the mixture of fetal and maternal cfDNA; wherein preparing the library comprises the consecutive steps of dA-tailing and adaptor ligating the cfDNA, where preparing the library excludes end-repairing the cfDNA and the preparation is performed on a solid surface; (d) massively parallel sequencing at least a portion of the sequencing library to obtain sequence information for the fetal and maternal cfDNA in the sample; (e) storing in a computer readable medium, at least temporarily, the sequence information; (f) using the stored sequence information to computationally identify a number of sequence tags for each of one or more chromosomes of interest and for a normalizing sequence for each of any one or more chromosome of interest; (g) computationally calculating, using the number of sequence tags for each of the one or more chromosomes of interest and the number of sequence tags for the normalizing sequence for each of the one or more chromosomes of interest, a chromosome dose for each of the one or more chromosomes of interest; and (h) comparing the chromosome dose for each of the one or more chromosomes of interest to a corresponding threshold value for each of the one or more chromosomes of interest, and thereby determining the presence or absence of the fetal chromosomal aneuploidy in the sample, wherein steps (e)-(h) are performed using one or more processors. The sample can be a biological fluid sample e.g. plasma, serum, urine and saliva. In some embodiments, the sample is a maternal blood sample, or the plasma or serum fraction thereof. This method is exemplified in Example 4.

1-Step—Preparation on Solid Phase

In another embodiment, unrepaired DNA is dA-tailed, but the dA-tailed product is not purified prior to amplification such that the steps of dA-tailing, adaptor-ligating and amplifying are performed consecutively or sequentially. Consecutive dA-tailing, adaptor ligating and amplifying followed by purification prior to sequencing, is herein referred to as the 1-step process. The 1-step method can be performed on a solid surface (see, e.g., FIG. 3). The steps of attaching the first set of adaptors to a solid surface (1), ligating unrepaired and dA-tailed DNA to the surface-bound adaptors (2), and ligating the second set of adaptors to the surface-bound DNA (3), can be performed as described for the 2-step method above. In the 1-step method, however, the adaptor-ligated surface-bound DNA can be amplified while attached to the solid surface (4b in FIG. 2). Subsequently, the resulting library of adaptor-ligated DNA created on a solid surface is detached and purified (5 in FIG. 2) prior to being subjected to massively parallel sequencing as described for the adaptor-ligated DNA created in solution. In some embodiments, sequencing is massively parallel sequencing using sequencing-by-synthesis with reversible dye terminators. In other embodiments, sequencing is massively parallel sequencing using sequencing-by-ligation.

Accordingly, in some embodiments, the a method is provided for preparing a sequencing library for NGS sequencing, by performing the steps comprising obtaining DNA molecules from a sample; and performing the consecutive steps of dA-tailing, adaptor-ligating, and amplifying the DNA molecules, where the adaptor-ligating is performed on a solid surface. As described for the 2-step method, in various embodiments, the adaptors can include index sequences to allow for multiplexing the sequencing of multiple samples within a single reaction vessel e.g. a channel of a flow cell.

In some embodiments, the DNA can be repaired. The DNA molecules can be cfDNA molecules, they can be DNA molecules transcribed from RNA, or the DNA molecules can be amplicons of DNA molecules. Adaptor-ligation is performed as described above. Excess unligated adaptors can be washed from the immobilized adaptor-ligated DNA; reagents required for an amplification are added to the immobilized adaptor-ligated DNA, which is subjected to cycles of amplification e.g. PCR amplification, as is known in the art. In other embodiments, the adaptor-ligated DNA is not amplified. Absent amplification the adaptor-ligated DNA can be removed from the solid surface by chemical or physical means e.g. heat, UV light etc. Absent amplification, the adaptors ligated to the DNA can comprise sequences that hybridize to oligonucleotides present on the flow cell of the sequencer (Kozarewa et al., Nat Methods 6:291-295 [2009]).

In various embodiments the sample can be a biological fluid sample (e.g., blood, plasma, serum, urine, cerebrospinal fluid, amniotic fluid, saliva, and the like). In some embodiments the method for preparing a sequencing library on a solid surface from unrepaired cfDNA is included as a step in a method for analyzing a maternal sample to determine the presence or absence of a fetal chromosomal aneuploidy.

Accordingly, in one embodiment, a method is provided for determining the presence or absence of one or more fetal chromosomal aneuploidies comprising: (a) obtaining a maternal sample comprising a mixture of fetal and maternal cell-free DNA; (b) isolating the mixture of fetal and maternal cfDNA from said sample; (c) preparing a sequencing library from the mixture of fetal and maternal cfDNA; wherein preparing the library comprises the consecutive steps of dA-tailing, adaptor ligating, and amplifying the cfDNA, and wherein the preparation is performed on a solid surface; (d) massively parallel sequencing at least a portion of the sequencing library to obtain sequence information for the fetal and maternal cfDNA in the sample; (e) storing in a computer readable medium, at least temporarily, the sequence information; (f) using the stored sequence information to computationally identify a number of sequence tags for each of one or more chromosomes of interest and for a normalizing sequence for each of any one or more chromosome of interest; (g) computationally calculating, using the number of sequence tags for each of the one or more chromosomes of interest and the number of sequence tags for the normalizing sequence for each of the one or more chromosomes of interest, a chromosome dose for each of the one or more chromosomes of interest; and (h) comparing the chromosome dose for each of the one or more chromosomes of interest to a corresponding threshold value for each of the one or more chromosomes of interest, and thereby determining the presence or absence of the fetal chromosomal aneuploidy in the sample, wherein steps (e)-(h) are performed using one or more processors. In some embodiments, the DNA is end-repaired. In other embodiments, preparing the library excludes end-repairing the cfDNA. This method is exemplified in Examples 5 and 6.

The processes for preparing sequencing libraries as described above are applicable to methods of sample analyses including without limitation methods for determining copy number variations (CNV), and methods for determining the presence or absence of polymorphisms of any sequence of interest in samples containing single genomes and in samples containing mixtures of at least two genomes, which are known or are suspected to differ in one or more sequence of interest.

An amplification of the adaptor-ligated product prepared on a solid phase or in solution may be required to introduce to the adaptor ligated template molecules the oligonucleotide sequences that are required for hybridization to the flow cell or other surface present in some of the NGS platforms. The contents of an amplification reaction are known by one skilled in the art and include appropriate substrates (such as dNTPs), enzymes (e.g. a DNA polymerase) and buffer components required for an amplification reaction. Optionally, amplification of adaptor-ligated polynucleotides can be omitted. Generally amplification reactions require at least two amplification primers e.g. primer oligonucleotides, that can be identical or different and that can include an "adaptor-specific portion" capable of annealing to a primer-binding sequence in the polynucleotide molecule to be amplified (or the complement thereof if the template is viewed as a single strand) during the annealing step.

Once formed, the library of templates prepared according to the methods described above can be used for solid-phase nucleic acid amplification that may be required by some NGS platforms. The term "solid-phase amplification" as used herein refers to any nucleic acid amplification reaction carried out on or in association with a solid support such that all or a portion of the amplified products are immobilized on the solid support as they are formed. In particular embodiments, the term encompasses solid-phase polymerase chain reaction (solid-phase PCR) and solid phase isothermal amplification which are reactions analogous to standard solution phase amplification, except that one or both of the forward and reverse amplification primers is/are immobilized on the solid support. Solid phase PCR also includes systems such as emulsions, where one primer is anchored to a bead and the other is in free solution, and colony formation in solid phase gel matrices wherein one primer is anchored to the surface, and one is in free solution.

In various embodiments following amplification, and sequencing libraries can be analyzed by microfluidic capillary electrophoresis to ensure that the library is free of adaptor dimers or single stranded DNA. The library of template polynucleotide molecules is particularly suitable for use in solid phase sequencing methods. In addition to providing templates for solid-phase sequencing and solid-phase PCR, library templates provide templates for whole genome amplification.

Marker Nucleic Acids for Tracking and Verifying Sample Integrity

In various embodiments verification of the integrity of the samples and sample tracking can be accomplished by sequencing mixtures of sample genomic nucleic acids e.g. cfDNA, and accompanying marker nucleic acids that have been introduced into the samples, e.g., prior to processing.

Marker nucleic acids can be combined with the test sample (e.g., biological source sample) and subjected to processes that include, for example, one or more of the steps of fractionating the biological source sample e.g. obtaining an essentially cell-free plasma fraction from a whole blood sample, purifying nucleic acids from a fractionated e.g. plasma, or unfractionated biological source sample e.g. a tissue sample, and sequencing. In some embodiments, sequencing comprises preparing a sequencing library. The sequence or combination of sequences of the marker molecules that are combined with a source sample is chosen to be unique to the source sample. In some embodiments, the unique marker molecules in a sample all have the same sequence. In other embodiments, the unique marker molecules in a sample are a plurality of sequences, e.g., a combination of two, three, four, five, six, seven, eight, nine, ten, fifteen, twenty, or more different sequences.

In one embodiment, the integrity of a sample can be verified using a plurality of marker nucleic acid molecules having identical sequences. Alternatively, the identity of a sample can be verified using a plurality of marker nucleic acid molecules that have at least two, at least three, at least four, at least five, at least six, at least seven, at least eight, at least nine, at least ten, at least 11, at least 12, at least 13, at least 14, at least 15, at least 16, at least 17 m, at least 18, at least 19, at least 20, at least 25, at least 30, at least 35, at least 40, at least 50, or more different sequences. Verification of the integrity of the plurality of biological samples i.e. two or more biological samples, requires that each of the two or more samples be marked with marker nucleic acids that have sequences that are unique to each of the plurality of test sample that is being marked. For example, a first sample can be marked with a marker nucleic acid having sequence A, and a second sample can be marked with a marker nucleic acid having sequence B. Alternatively, a first sample can be marked with marker nucleic acid molecules all having sequence A, and a second sample can be marked with a mixture of sequences B and C, wherein sequences A, B and C are marker molecules having different sequences.

The marker nucleic acid(s) can be added to the sample at any stage of sample preparation that occurs prior to library preparation (if libraries are to be prepared) and sequencing. In one embodiment, marker molecules can be combined with an unprocessed source sample. For example, the marker nucleic acid can be provided in a collection tube that is used to collect a blood sample. Alternatively, the marker nucleic acids can be added to the blood sample following the blood draw. In one embodiment, the marker nucleic acid is added to the vessel that is used to collect a biological fluid sample e.g. the marker nucleic acid(s) are added to a blood collection tube that is used to collect a blood sample. In another embodiment, the marker nucleic acid(s) are added to a fraction of the biological fluid sample. For example, the marker nucleic acid is added to the plasma and/or serum fraction of a blood sample e.g. a maternal plasma sample. In yet another embodiment, the marker molecules are added to a purified sample e.g. a sample of nucleic acids that have been purified from a biological sample. For example, the marker nucleic acid is added to a sample of purified maternal and fetal cfDNA. Similarly, the marker nucleic acids can be added to a biopsy specimen prior to processing the specimen. In some embodiments, the marker nucleic acids can be combined with a carrier that delivers the marker molecules into the cells of the biological sample. Cell-delivery carriers include pH-sensitive and cationic liposomes.

In various embodiments, the marker molecules have antigenomic sequences, that are sequences that are absent from the genome of the biological source sample. In an exemplary embodiment, the marker molecules that are used to verify the integrity of a human biological source sample have sequences that are absent from the human genome. In an alternative embodiment, the marker molecules have sequences that are absent from the source sample and from any one or more other known genomes. For example, the marker molecules that are used to verify the integrity of a human biological source sample have sequences that are absent from the human genome and from the mouse genome. The alternative allows for verifying the integrity of a test sample that comprises two or more genomes. For example, the integrity of a human cell-free DNA sample obtained from a subject affected by a pathogen e.g. a bacterium, can be verified using marker molecules having sequences that are absent from both the human genome and the genome of the affecting bacterium. Sequences of genomes of numerous pathogens e.g. bacteria, viruses, yeasts, fungi, protozoa etc., are publicly available on the world wide web at ncbi.nlm.nih.gov/genomes. In another embodiment, marker molecules are nucleic acids that have sequences that are absent from any known genome. The sequences of marker molecules can be randomly generated algorithmically.

In various embodiments the marker molecules can be naturally-occurring deoxyribonucleic acids (DNA), ribonucleic acids or artificial nucleic acid analogs (nucleic acid mimics) including peptide nucleic acids (PMA), morpholino nucleic acid, locked nucleic acids, glycol nucleic acids, and threose nucleic acids, which are distinguished from naturally-occurring DNA or RNA by changes to the backbone of the molecule or DNA mimics that do not have a phosphodiester backbone. The deoxyribonucleic acids can be from naturally-occurring genomes or can be generated in a laboratory through the use of enzymes or by solid phase chemical synthesis. Chemical methods can also be used to generate the DNA mimics that are not found in nature. Derivatives of DNA are that are available in which the phosphodiester linkage has been replaced but in which the deoxyribose is retained include but are not limited to DNA mimics having backbones formed by thioformacetal or a carboxamide linkage, which have been shown to be good structural DNA mimics. Other DNA mimics include morpholino derivatives and the peptide nucleic acids (PNA), which contain an N-(2-aminoethyl)glycine-based pseudopeptide backbone (Ann Rev Biophys Biomol Struct 24:167-183 [1995]). PNA is an extremely good structural mimic of DNA (or of ribonucleic acid [RNA]), and PNA oligomers are able to form very stable duplex structures with Watson-Crick complementary DNA and RNA (or PNA) oligomers, and they can also bind to targets in duplex DNA by helix invasion (Mol Biotechnol 26:233-248 [2004]). Another good structural mimic/analog of DNA analog that can be used as a marker molecule is phosphorothioate DNA in which one of the non-bridging oxygens is replaced by a sulfur. This modification reduces the action of endo- and exonucleases 2 including 5' to 3' and 3' to 5' DNA POL 1 exonuclease, nucleases S1 and P1, RNases, serum nucleases and snake venom phosphodiesterase.

The length of the marker molecules can be distinct or indistinct from that of the sample nucleic acids i.e. the length of the marker molecules can be similar to that of the sample genomic molecules, or it can be greater or smaller than that of the sample genomic molecules. The length of the marker molecules is measured by the number of nucleotide or nucleotide analog bases that constitute the marker molecule. Marker molecules having lengths that differ from those of the sample genomic molecules can be distinguished from source nucleic acids using separation methods known in the art. For example, differences in the length of the marker and sample nucleic acid molecules can be determined by electrophoretic separation e.g. capillary electrophoresis. Size differentiation can be advantageous for quantifying and assessing the quality of the marker and sample nucleic acids. Preferably, the marker nucleic acids are shorter than the genomic nucleic acids, and of sufficient length to exclude them from being mapped to the genome of the sample. For example, as a 30 base human sequence is needed to uniquely map it to a human genome. Accordingly in certain embodiments, marker molecules used in sequencing bioassays of human samples should be at least 30 bp in length.

The choice of length of the marker molecule is determined primarily by the sequencing technology that is used to verify the integrity of a source sample. The length of the sample genomic nucleic acids being sequenced can also be considered. For example, some sequencing technologies employ clonal amplification of polynucleotides, which can require that the genomic polynucleotides that are to be clonally amplified be of a minimum length. For example, sequencing using the Illumina GAII sequence analyzer includes an in vitro clonal amplification by bridge PCR (also known as cluster amplification) of polynucleotides that have a minimum length of 110 bp, to which adaptors are ligated to provide a nucleic acid of at least 200 bp and less than 600 bp that can be clonally amplified and sequenced. In some embodiments, the length of the adaptor-ligated marker molecule is between about 200 bp and about 600 bp, between about 250 bp and 550 bp, between about 300 bp and 500 bp, or between about 350 and 450. In other embodiments, the length of the adaptor-ligated marker molecule is about 200 bp. For example, when sequencing fetal cfDNA that is present in a maternal sample, the length of the marker molecule can be chosen to be similar to that of fetal cfDNA molecules. Thus, in one embodiment, the length of the marker molecule used in an assay that comprises massively parallel sequencing of cfDNA in a maternal sample to determine the presence or absence of a fetal chromosomal aneuploidy, can be about 150 bp, about 160 bp, 170 bp, about 180 bp, about 190 bp or about 200 bp; preferably, the marker molecule is about 170 bp. Other sequencing approaches e.g. SOLiD sequencing, Polony Sequencing and 454 sequencing use emulsion PCR to clonally amplify DNA molecules for sequencing, and each technology dictates the minimum and the maximum length of the molecules that are to be amplified. The length of marker molecules to be sequenced as clonally amplified nucleic acids can be up to about 600 bp. In some embodiments, the length of marker molecules to be sequenced can be greater than 600 bp.

Single molecule sequencing technologies, that do not employ clonal amplification of molecules, and are capable of sequencing nucleic acids over a very broad range of template lengths, in most situations do not require that the molecules to be sequenced be of any specific length. However, the yield of sequences per unit mass is dependent on the number of 3' end hydroxyl groups, and thus having relatively short templates for sequencing is more efficient than having long templates. If starting with nucleic acids longer than 1000 nt, it is generally advisable to shear the nucleic acids to an average length of 100 to 200 nt so that more sequence information can be generated from the same mass of nucleic acids. Thus, the length of the marker molecule can range from tens of bases to thousands of bases. The length of marker molecules used for single molecule sequencing can be up to about 25 bp, up to about 50 bp, up to about 75 bp, up to about 100 bp, up to about 200 bp, up to about 300 bp, up to about 400 bp, up to about 500 bp, up to about 600 bp, up to about 700 bp, up to about 800 bp, up to about 900 bp, up to about 1000 bp, or more in length.

The length chosen for a marker molecule is also determined by the length of the genomic nucleic acid that is being sequenced. For example, cfDNA circulates in the human bloodstream as genomic fragments of cellular genomic DNA. Fetal cfDNA molecules found in the plasma of pregnant women are generally shorter than maternal cfDNA molecules (Chan et al., Clin Chem 50:8892 [2004]). Size fractionation of circulating fetal DNA has confirmed that the average length of circulating fetal DNA fragments is <300 bp, while maternal DNA has been estimated to be between about 0.5 and 1 Kb (Li et al., Clin Chem, 50: 1002-1011 [2004]). These findings are consistent with those of Fan et al., who determined using NGS that fetal cfDNA is rarely >340 bp (Fan et al., Clin Chem 56:1279-1286 [2010]). DNA isolated from urine with a standard silica-based method consists of two fractions, high molecular weight DNA, which originates from shed cells and low molecular weight (150-250 base pair) fraction of transrenal DNA (Tr-DNA) (Botezatu et al., Clin Chem. 46: 1078-1084, 2000; and Su et al., J Mol. Diagn. 6: 101-107, 2004). The application of newly developed technique for isolation of cell-free nucleic acids from body fluids to the isolation of transrenal nucleic acids has revealed the presence in urine of DNA and RNA fragments much shorter than 150 base pairs (U.S. Patent Application Publication No. 20080139801). In embodiments, wherein cfDNA is the genomic nucleic acid that is sequenced, marker molecules that are chosen can be up to about the length of the cfDNA. For example, the length of marker molecules used in maternal cfDNA samples to be sequenced as single nucleic acid molecules or as clonally amplified nucleic acids can be between about 100 bp and 600. In other embodiments, the sample genomic nucleic acids are fragments of larger molecules. For example, a sample genomic nucleic acid that is sequenced is fragmented cellular DNA. In embodiments, when fragmented cellular DNA is sequenced, the length of the marker molecules can be up to the length of the DNA fragments. In some embodiments, the length of the marker molecules is at least the minimum length required for mapping the sequence read uniquely to the appropriate reference genome. In other embodiments, the length of the marker molecule is the minimum length that is required to exclude the marker molecule from being mapped to the sample reference genome.

In addition, marker molecules can be used to verify samples that are not assayed by nucleic acid sequencing, and that can be verified by common biotechniques other than sequencing e.g. real-time PCR.

Sample Controls (e.g., in Process Positive Controls for Sequencing and/or Analysis).

In various embodiments marker sequences introduced into the samples, e.g., as described above, can function as positive controls to verity the verify the accuracy and efficacy of sequencing and subsequent processing and analysis.

Accordingly, compositions and method for providing an in-process positive control (IPC) for sequencing DNA in a sample are provided. In certain embodiments, positive controls are provided for sequencing cfDNA in a sample comprising a mixture of genomes are provided. An IPC can be used to relate baseline shifts in sequence information obtained from different sets of samples e.g. samples that are sequenced at different times on different sequencing runs. Thus, for example, an IPC can relate the sequence information obtained for a maternal test sample to the sequence information obtained from a set of qualified samples that were sequenced at a different time.

Similarly, in the case of segment analysis, an IPC can relate the sequence information obtained from a subject for particular segment(s) to the sequence obtained from a set of qualified samples (of similar sequences) that were sequenced at a different time. In certain embodiments an IPC can relate the sequence information obtained from a subject for particular cancer-related loci to the sequence information obtained from a set of qualified samples (e.g., from a known amplification/deletion, and the like).

In addition, IPCs can be used as markers to track sample(s) through the sequencing process. IPCs can also provide a qualitative positive sequence dose value e.g. NCV, for one or more aneuploidies of chromosomes of interest e.g. trisomy 21, trisomy 13, trisomy 18 to provide proper interpretation, and to ensure the dependability and accuracy of the data. In certain embodiments IPCs can be created to comprise nucleic acids from male and female genomes to provide doses for chromosomes X and Y in a maternal sample to determine whether the fetus is male.

The type and the number of in-process controls depends on the type or nature of the test needed. For example, for a test requiring the sequencing of DNA from a sample comprising a mixture of genomes to determine whether a chromosomal aneuploidy exists, the in-process control can comprise DNA obtained from a sample known comprising the same chromosomal aneuploidy that is being tested. In some embodiments, the IPC includes DNA from a sample known to comprise an aneuploidy of a chromosome of interest. For example, the IPC for a test to determine the presence or absence of a fetal trisomy e.g. trisomy 21, in a maternal sample comprises DNA obtained from an individual with trisomy 21. In some embodiments, the IPC comprises a mixture of DNA obtained from two or more individuals with different aneuploidies. For example, for a test to determine the presence or absence of trisomy 13, trisomy 18, trisomy 21, and monosomy X, the IPC comprises a combination of DNA samples obtained from pregnant women each carrying a fetus with one of the trisomies being tested. In addition to complete chromosomal aneuploidies, IPCs can be created to provide positive controls for tests to determine the presence or absence of partial aneuploidies.

An IPC that serves as the control for detecting a single aneuploidy can be created using a mixture of cellular genomic DNA obtained from a two subjects one being the contributor of the aneuploid genome. For example, an IPC that is created as a control for a test to determine a fetal trisomy e.g. trisomy 21, can be created by combining genomic DNA from a male or female subject carrying the trisomic chromosome with genomic DNA with a female subject known not to carry the trisomic chromosome. Genomic DNA can be extracted from cells of both subjects, and sheared to provide fragments of between about 100-400 bp, between about 150-350 bp, or between about 200-300 bp to simulate the circulating cfDNA fragments in maternal samples. The proportion of fragmented DNA from the subject carrying the aneuploidy e.g. trisomy 21, is chosen to simulate the proportion of circulating fetal cfDNA found in maternal samples to provide an IPC comprising a mixture of fragmented DNA comprising about 5%, about 10%, about 15%, about 20%, about 25%, about 30%, of DNA from the subject carrying the aneuploidy. The IPC can comprise DNA from different subjects each carrying a different aneuploidy. For example, the IPC can comprise about 80% of the unaffected female DNA, and the remaining 20% can be DNA from three different subjects each carrying a trisomic chromosome 21, a trisomic chromosome 13, and a trisomic chromosome 18. The mixture of fragmented DNA is prepared for sequencing. Processing of the mixture of fragmented DNA can comprise preparing a sequencing library, which can be sequenced using any massively parallel methods in singleplex or multiplex fashion. Stock solutions of the genomic IPC can be stored and used in multiple diagnostic tests.

Alternatively the IPC can be created using cfDNA obtained from a mother known to carry a fetus with a known chromosomal aneuploidy. For example, cfDNA can be obtained from a pregnant woman carrying a fetus with trisomy 21. The cfDNA is extracted from the maternal sample, and cloned into a bacterial vector and grown in bacteria to provide an ongoing source of the IPC. The DNA can be extracted from the bacterial vector using restriction enzymes. Alternatively, the cloned cfDNA can be amplified by e.g. PCR. The IPC DNA can be processed for sequencing in the same runs as the cfDNA from the test samples that are to be analyzed for the presence or absence of chromosomal aneuploidies.

While the creation of IPCs is described above with respect to trisomys, it will be appreciated that IPCs can be created to reflect other partial aneuploidies including for example, various segment amplification and/or deletions. Thus, for example, where various cancers are known to be associated with particular amplifications (e.g., breast cancer associated with 20Q13) IPCs can be created that incorporate those known amplifications.

Sequencing Methods

As indicated above, the prepared samples (e.g., Sequencign Libraries) are sequenced as part of the procedure for identifying copy number variation(s). Any of a number of sequencing technologies can be utilized.

Some sequencing technologies are available commercially, such as the sequencing-by-hybridization platform from Affymetrix Inc. (Sunnyvale, Calif.) and the sequencing-by-synthesis platforms from 454 Life Sciences (Bradford, Conn.), Illumina/Solexa (Hayward, Calif.) and Helicos Biosciences (Cambridge, Mass.), and the sequencing-by-ligation platform from Applied Biosystems (Foster City, Calif.), as described below. In addition to the single molecule sequencing performed using sequencing-by-synthesis of Helicos Biosciences, other single molecule sequencing technologies include, but are not limited to, the SMRT™ technology of Pacific Biosciences, the ION TORRENT™ technology, and nanopore sequencing developed for example, by Oxford Nanopore Technologies.

While the automated Sanger method is considered as a 'first generation' technology, Sanger sequencing including the automated Sanger sequencing, can also be employed in the methods described herein. Additional suitable sequencing methods include, but are not limited to nucleic acid imaging technologies e.g. atomic force microscopy (AFM) or transmission electron microscopy (TEM). Illustrative sequencing technologies are described in greater detail below.

In one illustrative, but non-limiting, embodiment, the methods described herein comprise obtaining sequence information for the nucleic acids in a test sample e.g. cfDNA in a maternal sample, cfDNA or cellular DNA in a subject being screened for a cancer, and the like, using single molecule sequencing technology of the Helicos True Single Molecule Sequencing (tSMS) technology (e.g. as described in Harris T. D. et al., Science 320:106-109 [2008]). In the tSMS technique, a DNA sample is cleaved into strands of approximately 100 to 200 nucleotides, and a polyA sequence is added to the 3' end of each DNA strand. Each strand is labeled by the addition of a fluorescently labeled adenosine nucleotide. The DNA strands are then hybridized to a flow cell, which contains millions of oligo-T capture sites that are immobilized to the flow cell surface. In certain embodiments the templates can be at a density of about 100 million templates/cm$^2$. The flow cell is then loaded into an instrument, e.g., HeliScope™ sequencer, and a laser illuminates the surface of the flow cell, revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid serves as a primer. The polymerase incorporates the labeled nucleotides to the primer in a template directed manner. The polymerase and unincorporated nucleotides are removed. The templates that have directed incorporation of the fluorescently labeled nucleotide are discerned by imaging the flow cell surface. After imaging, a cleavage step removes the fluorescent label, and the process is repeated with other fluorescently labeled nucleotides until the desired read length is achieved. Sequence information is collected with each nucleotide addition step. Whole genome sequencing by single molecule sequencing technologies excludes or typically obviates PCR-based amplification in the preparation of the sequencing libraries, and the methods allow for direct measurement of the sample, rather than measurement of copies of that sample.

In another illustrative, but non-limiting embodiment, the methods described herein comprise obtaining sequence information for the nucleic acids in the test sample e.g. cfDNA in a maternal test sample, cfDNA or cellular DNA in a subject being screened for a cancer, and the like, using the 454 sequencing (Roche) (e.g. as described in Margulies, M. et al. Nature 437:376-380 [2005]). 454 sequencing typically involves two steps. In the first step, DNA is sheared into fragments of approximately 300-800 base pairs, and the fragments are blunt-ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., Adaptor B, which contains 5'-biotin tag. The fragments attached to the beads are PCR amplified within droplets of an oil-water emulsion. The result is multiple copies of clonally amplified DNA fragments on each bead. In the second step, the beads are captured in wells (e.g., picoliter-sized wells). Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is measured and analyzed.

In another illustrative, but non-limiting, embodiment, the methods described herein comprises obtaining sequence information for the nucleic acids in the test sample e.g. cfDNA in a maternal test sample, cfDNA or cellular DNA in a subject being screened for a cancer, and the like, using the SOLiD™ technology (Applied Biosystems). In SOLiD™ sequencing-by-ligation, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide is cleaved and removed and the process is then repeated.

In another illustrative, but non-limiting, embodiment, the methods described herein comprise obtaining sequence information for the nucleic acids in the test sample e.g. cfDNA in a maternal test sample, cfDNA or cellular DNA in a subject being screened for a cancer, and the like, using the single molecule, real-time (SMRT™) sequencing technology of Pacific Biosciences. In SMRT sequencing, the continuous incorporation of dye-labeled nucleotides is imaged during DNA synthesis. Single DNA polymerase molecules are attached to the bottom surface of individual zero-mode wavelength detectors (ZMW detectors) that obtain sequence information while phospholinked nucleotides are being incorporated into the growing primer strand. A ZMW detector comprises a confinement structure that enables observation of incorporation of a single nucleotide by DNA polymerase against a background of fluorescent nucleotides that rapidly diffuse in an out of the ZMW (e.g., in microseconds). It typically takes several milliseconds to incorporate a nucleotide into a growing strand. During this time, the fluorescent label is excited and produces a fluorescent signal, and the fluorescent tag is cleaved off. Measurement of the corresponding fluorescence of the dye indicates which base was incorporated. The process is repeated to provide a sequence.

In another illustrative, but non-limiting, embodiment, the methods described herein comprise obtaining sequence information for the nucleic acids in the test sample e.g. cfDNA in a maternal test sample, cfDNA or cellular DNA in a subject being screened for a cancer, and the like, using nanopore sequencing (e.g. as described in Soni G V and Meller A. Clin Chem 53: 1996-2001 [2007]). Nanopore sequencing DNA analysis techniques are developed by a number of companies, including, for example, Oxford Nanopore Technologies (Oxford, United Kingdom), Sequenom, NABsys, and the like. Nanopore sequencing is a single-molecule sequencing technology whereby a single molecule of DNA is sequenced directly as it passes through a nanopore. A nanopore is a small hole, typically of the order of 1 nanometer in diameter. Immersion of a nanopore in a conducting fluid and application of a potential (voltage) across it results in a slight electrical current due to conduction of ions through the nanopore. The amount of current that flows is sensitive to the size and shape of the nanopore. As a DNA molecule passes through a nanopore, each nucleotide on the DNA molecule obstructs the nanopore to a different degree, changing the magnitude of the current through the nanopore in different degrees. Thus, this change in the current as the DNA molecule passes through the nanopore provides a read of the DNA sequence.

In another illustrative, but non-limiting, embodiment, the methods described herein comprises obtaining sequence information for the nucleic acids in the test sample e.g. cfDNA in a maternal test sample, cfDNA or cellular DNA in a subject being screened for a cancer, and the like, using the chemical-sensitive field effect transistor (chemFET) array (e.g., as described in U.S. Patent Application Publication No. 2009/0026082). In one example of this technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be discerned as a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

In another embodiment, the present method comprises obtaining sequence information for the nucleic acids in the test sample e.g. cfDNA in a maternal test sample, using the Halcyon Molecular's technology, which uses transmission electron microscopy (TEM). The method, termed Individual Molecule Placement Rapid Nano Transfer (IMPRNT), comprises utilizing single atom resolution transmission electron microscope imaging of high-molecular weight (150 kb or greater) DNA selectively labeled with heavy atom markers and arranging these molecules on ultra-thin films in ultra-dense (3 nm strand-to-strand) parallel arrays with consistent base-to-base spacing. The electron microscope is used to image the molecules on the films to determine the position of the heavy atom markers and to extract base sequence information from the DNA. The method is further described in PCT patent publication WO 2009/046445. The method allows for sequencing complete human genomes in less than ten minutes.

In another embodiment, the DNA sequencing technology is the Ion Torrent single molecule sequencing, which pairs semiconductor technology with a simple sequencing chemistry to directly translate chemically encoded information (A, C, G, T) into digital information (0, 1) on a semiconductor chip. In nature, when a nucleotide is incorporated into a strand of DNA by a polymerase, a hydrogen ion is released as a byproduct. Ion Torrent uses a high-density array of micro-machined wells to perform this biochemical process in a massively parallel way. Each well holds a different DNA molecule. Beneath the wells is an ion-sensitive layer and beneath that an ion sensor. When a nucleotide, for example a C, is added to a DNA template and is then incorporated into a strand of DNA, a hydrogen ion will be released. The charge from that ion will change the pH of the solution, which can be detected by Ion Torrent's ion sensor. The sequencer—essentially the world's smallest solid-state pH meter—calls the base, going directly from chemical information to digital information. The Ion personal Genome Machine (PGM™) sequencer then sequentially floods the chip with one nucleotide after another. If the next nucleotide that floods the chip is not a match. No voltage change will be recorded and no base will be called. If there are two identical bases on the DNA strand, the voltage will be double, and the chip will record two identical bases called. Direct detection allows recordation of nucleotide incorporation in seconds.

In another embodiment, the present method comprises obtaining sequence information for the nucleic acids in the test sample e.g. cfDNA in a maternal test sample, using sequencing by hybridization. Sequencing-by-hybridization comprises contacting the plurality of polynucleotide sequences with a plurality of polynucleotide probes, wherein each of the plurality of polynucleotide probes can be optionally tethered to a substrate. The substrate might be flat surface comprising an array of known nucleotide sequences. The pattern of hybridization to the array can be used to determine the polynucleotide sequences present in the sample. In other embodiments, each probe is tethered to a bead, e.g., a magnetic bead or the like. Hybridization to the beads can be determined and used to identify the plurality of polynucleotide sequences within the sample.

In another embodiment, the present method comprises obtaining sequence information for the nucleic acids in the test sample e.g. cfDNA in a maternal test sample, by massively parallel sequencing of millions of DNA fragments using Illumina's sequencing-by-synthesis and reversible terminator-based sequencing chemistry (e.g. as described in Bentley et al., Nature 6:53-59 [2009]). Template DNA can be genomic DNA e.g. cfDNA. In some embodiments, genomic DNA from isolated cells is used as the template, and it is fragmented into lengths of several hundred base pairs. In other embodiments, cfDNA is used as the template, and fragmentation is not required as cfDNA exists as short fragments. For example fetal cfDNA circulates in the bloodstream as fragments approximately 170 base pairs (bp) in length (Fan et al., Clin Chem 56:1279-1286 [2010]), and no fragmentation of the DNA is required prior to sequencing. Illumina's sequencing technology relies on the attachment of fragmented genomic DNA to a planar, optically transparent surface on which oligonucleotide anchors are bound. Template DNA is end-repaired to generate 5'-phosphorylated blunt ends, and the polymerase activity of Klenow fragment is used to add a single A base to the 3' end of the blunt phosphorylated DNA fragments. This addition prepares the DNA fragments for ligation to oligonucleotide adapters, which have an overhang of a single T base at their 3' end to increase ligation efficiency. The adapter oligonucleotides are complementary to the flow-cell anchors. Under limiting-dilution conditions, adapter-modified, single-stranded template DNA is added to the flow cell and immobilized by hybridization to the anchors. Attached DNA fragments are extended and bridge amplified to create an ultra-high density sequencing flow cell with hundreds of millions of clusters, each containing 1,000 copies of the same template. In one embodiment, the randomly fragmented genomic DNA e.g. cfDNA, is amplified using PCR before it is subjected to cluster amplification. Alternatively, an amplification-free genomic library preparation is used, and the randomly fragmented genomic DNA e.g. cfDNA is enriched using the cluster amplification alone (Kozarewa et al., Nature Methods 6:291-295 [2009]). The templates are sequenced using a robust four-color DNA sequencing-by-synthesis technology that employs reversible terminators with removable fluorescent dyes. High-sensitivity fluorescence detection is achieved using laser excitation and total internal reflection optics. Short sequence reads of about 20-40 bp e.g. 36 bp, are aligned against a repeat-masked reference genome and unique mapping of the short sequence reads to the reference genome are identified using specially developed data analysis pipeline software. Non-repeat-masked reference genomes can also be used. Whether repeat-masked or non-repeat-masked reference genomes are used, only reads that map uniquely to the reference genome are counted. After completion of the first read, the templates can be regenerated in situ to enable a second read from the opposite end of the fragments. Thus, either single-end or paired end sequencing of the DNA fragments can be used. Partial sequencing of DNA fragments present in the sample is performed, and sequence tags comprising reads of predetermined length e.g. 36 bp, are mapped to a known reference genome are counted. In one embodiment, the reference genome sequence is the NCBI36/hg18 sequence, which is available on the world wide web at genome.ucsc.edu/cgi-bin/hgGateway?org=Human&db=hg18&hgsid=166260105). Alternatively, the reference genome sequence is the GRCh37/hg19, which is available on the world wide web at genome.ucsc.edu/cgi-bin/hgGateway. Other sources of public sequence information include GenBank, dbEST, dbSTS, EMBL (the European Molecular Biology Laboratory), and the DDBJ (the DNA Databank of Japan). A number of computer algorithms are available for aligning sequences, including without limitation BLAST (Altschul et al., 1990), BLITZ (MPsrch) (Sturrock & Collins, 1993), FASTA (Person & Lipman, 1988), BOWTIE (Langmead et al., Genome Biology 10:R25.1-R25.10 [2009]), or ELAND (Illumina, Inc., San Diego, Calif., USA). In one embodiment, one end of the clonally expanded copies of the plasma cfDNA molecules is sequenced and processed by bioinformatic alignment analysis for the Illumina Genome Analyzer, which uses the Efficient Large-Scale Alignment of Nucleotide Databases (ELAND) software.

In some embodiments of the methods described herein, the mapped sequence tags comprise sequence reads of about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130, about 140 bp, about 150 bp, about 200 bp, about 250 bp, about 300 bp, about 350 bp, about 400 bp, about 450 bp, or about 500 bp. It is expected that technological advances will enable single-end reads of greater than 500 bp enabling for reads of greater than about 1000 bp when paired end reads are generated. In one embodiment, the mapped sequence tags comprise sequence reads that are 36 bp. Mapping of the sequence tags is achieved by comparing the sequence of the tag with the sequence of the reference to determine the chromosomal origin of the sequenced nucleic acid (e.g. cfDNA) molecule, and specific genetic sequence information is not needed. A small degree of mismatch (0-2 mismatches per sequence tag) may be allowed to account for minor polymorphisms that may exist between the reference genome and the genomes in the mixed sample.

A plurality of sequence tags are typically obtained per sample. In some embodiments, at least about $3 \times 10^6$ sequence tags, at least about $5 \times 10^6$ sequence tags, at least about $8 \times 10^6$ sequence tags, at least about $10 \times 10^6$ sequence tags, at least about $15 \times 10^6$ sequence tags, at least about $20 \times 10^6$ sequence tags, at least about $30 \times 10^6$ sequence tags, at least about $40 \times 10^6$ sequence tags, or at least about $50 \times 10^6$ sequence tags comprising between 20 and 40 bp reads e.g. 36 bp, are obtained from mapping the reads to the reference genome per sample. In one embodiment, all the sequence reads are mapped to all regions of the reference genome. In one embodiment, the tags that have been mapped to all regions e.g. all chromosomes, of the reference genome are counted, and the CNV i.e. the over- or under-representation of a sequence of interest e.g. a chromosome or portion thereof, in the mixed DNA sample is determined. The method does not require differentiation between the two genomes.

The accuracy required for correctly determining whether a CNV e.g. aneuploidy, is present or absent in a sample, is predicated on the variation of the number of sequence tags that map to the reference genome among samples within a sequencing run (inter-chromosomal variability), and the variation of the number of sequence tags that map to the reference genome in different sequencing runs (inter-sequencing variability). For example, the variations can be particularly pronounced for tags that map to GC-rich or GC-poor reference sequences. Other variations can result from using different protocols for the extraction and purification of the nucleic acids, the preparation of the sequencing libraries, and the use of different sequencing platforms. The present method uses sequence doses (chromosome doses, or segment doses) based on the knowledge of normalizing sequences (normalizing chromosome sequences or normalizing segment sequences), to intrinsically account for the accrued variability stemming from interchromosomal (intra-run), and inter-sequencing (inter-run) and platform-dependent variability. Chromosome doses are based on the knowledge of a normalizing chromosome sequence, which can be composed of a single chromosome, or of two or more chromosomes selected from chromosomes 1-22, X, and Y. Alternatively, normalizing chromosome sequences can be composed of a single chromosome segment, or of two or more segments of one chromosome or of two or more chromosomes. Segment doses are based on the knowledge of a normalizing segment sequence, which can be composed of a single segment of any one chromosome, or of two or more segments of any two or more of chromosomes 1-22, X, and Y.

Singleplex Sequencing

Figure 4:
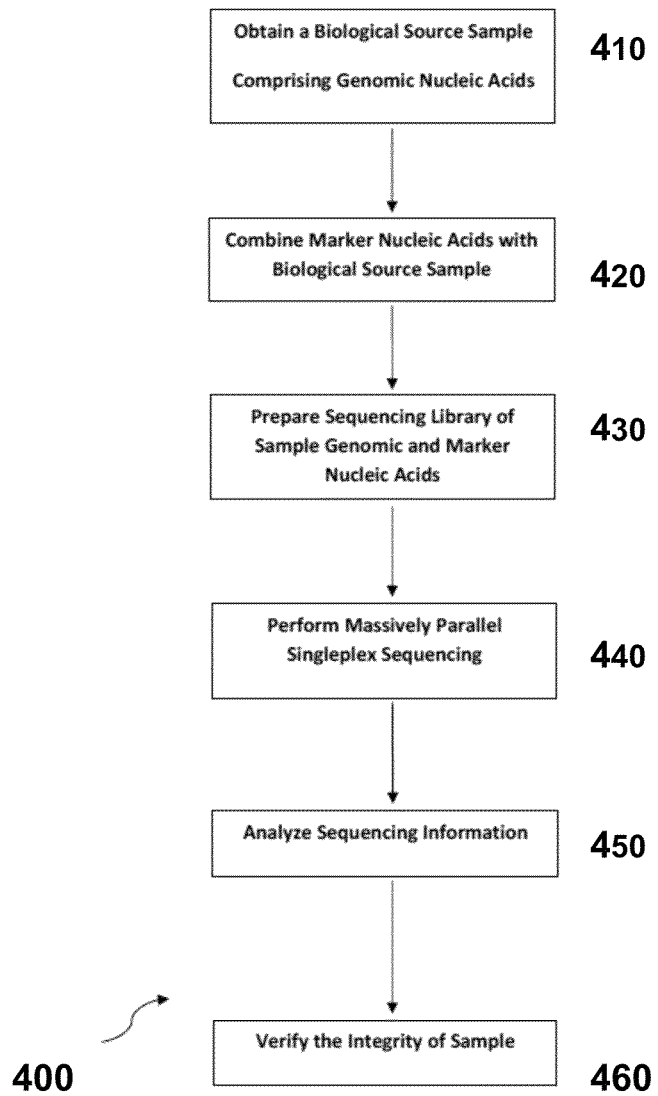
FIG. 4 illustrates a flowchart of an embodiment 400 of the method for verifying the integrity of a sample that is subjected to a multistep singleplex sequencing bioassay.

FIG. 4 illustrates a flow chart of an embodiment of the method whereby marker nucleic acids are combined with source sample nucleic acids of a single sample to assay for a genetic abnormality while determining the integrity of the biological source sample. In step 410, a biological source sample comprising genomic nucleic acids is obtained. In step 420, marker nucleic acids are combined with the biological source sample to provide a marked sample. A sequencing library of a mixture of clonally amplified source sample genomic and marker nucleic acids is prepared in step 430, and the library is sequenced in a massively parallel fashion in step 440 to provide sequencing information pertaining to the source genomic and marker nucleic acids of the sample. Massively parallel sequencing methods provide sequencing information as sequence reads, which are mapped to one or more reference genomes to generate sequence tags that can be analyzed. In step 450, all sequencing information is analyzed, and based on the sequencing information pertaining to the marker molecules, the integrity of the source sample is verified in step 460. Verification of source sample integrity is accomplished by determining a correspondence between the sequencing information obtained for the maker molecule at step 450 and the known sequence of the marker molecule that was added to the original source sample at step 420. The same process can be applied to multiple samples that are sequenced separately, with each sample comprising molecules having sequences unique to the sample i.e. one sample is marked with a unique marker molecule and it is sequenced separately from other samples in a flow cell or slide of a sequencer. If the integrity of the sample is verified, the sequencing information pertaining to the genomic nucleic acids of the sample can be analyzed to provide information e.g. about the status of the subject from which the source sample was obtained. For example, if the integrity of the sample is verified, the sequencing information pertaining to the genomic nucleic acids is analyzed to determine the presence or absence of a chromosomal abnormality. If the integrity of the sample is not verified, the sequencing information is disregarded.

The method depicted in FIG. 4 is also applicable to bioassays that comprise singleplex sequencing of single molecules e.g. tSMS by Helicos, SMRT by Pacific Biosciences, BASE by Oxford Nanopore, and other technologies such as that suggested by IBM, which do not require preparation of libraries.

Multiplex Sequencing

The large number of sequence reads that can be obtained per sequencing run permits the analysis of pooled samples i.e. multiplexing, which maximizes sequencing capacity and reduces workflow. For example, the massively parallel sequencing of eight libraries performed using the eight lane flow cell of the Illumina Genome Analyzer can be multiplexed to sequence two or more samples in each lane such that 16, 24, 32 etc. or more samples can be sequenced in a single run. Parallelizing sequencing for multiple samples i.e. multiplex sequencing, requires the incorporation of sample-specific index sequences, also known as barcodes, during the preparation of sequencing libraries. Sequencing indexes are distinct base sequences of about 5, about 10, about 15, about 20 about 25, or more bases that are added at the 3' end of the genomic and marker nucleic acid. The multiplexing system enables sequencing of hundreds of biological samples within a single sequencing run. The preparation of indexed sequencing libraries for sequencing of clonally amplified sequences can be performed by incorporating the index sequence into one of the PCR primers used for cluster amplification. Alternatively, the index sequence can be incorporated into the adaptor, which is ligated to the cfDNA prior to the PCR amplification. Indexed libraries for single molecule sequencing can be created by incorporating the index sequence at the 3' end of the marker and genomic molecule or 5' to the addition of a sequence needed for hybridization to the flow cell anchors e.g. addition of the polyA tail for single molecule sequencing using the tSMS. Sequencing of the uniquely marked indexed nucleic acids provides index sequence information that identifies samples in the pooled sample libraries, and sequence information of marker molecules correlates sequencing information of the genomic nucleic acids to the sample source. In embodiments wherein the multiple samples are sequenced individually i.e. singleplex sequencing, marker and genomic nucleic acid molecules of each sample need only be modified to contain the adaptor sequences as required by the sequencing platform and exclude the indexing sequences.

Figure 5:
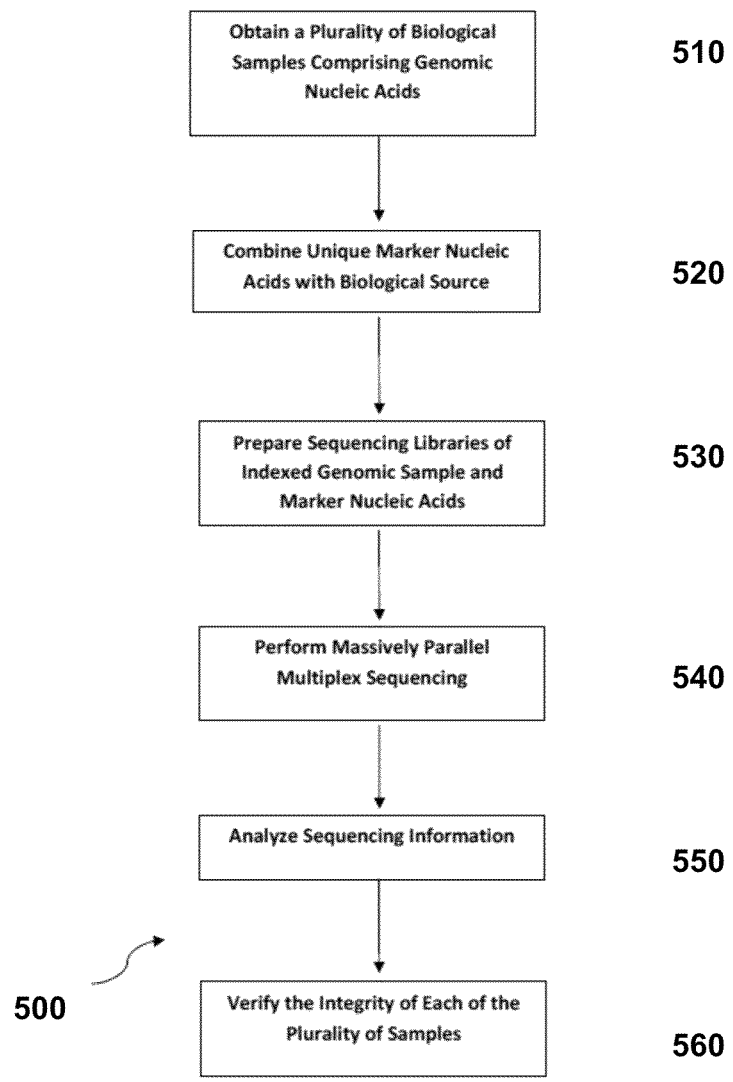
FIG. 5 illustrates a flowchart of an embodiment 500 of the method for verifying the integrity of a plurality of samples that are subjected to a multistep multiplex sequencing bioassay.

FIG. 5 provides a flowchart of an embodiment 500 of the method for verifying the integrity of samples that are subjected to a multistep multiplex sequencing bioassay i.e. nucleic acids from individual samples are combined and sequenced as a complex mixture. In step 510, a plurality of biological source samples each comprising genomic nucleic acids is obtained. In step 520, unique marker nucleic acids are combined with each of the biological source samples to provide a plurality of uniquely marked samples. A sequencing library of sample genomic and marker nucleic acids is prepared in step 530 for each of the uniquely marked samples. Library preparation of samples that are destined to undergo multiplexed sequencing comprises the incorporation of distinct indexing tags into the sample and marker nucleic acids of each of the uniquely marked samples to provide samples whose source nucleic acid sequences can be correlated with the corresponding marker nucleic acid sequences and identified in complex solutions. In embodiments of the method comprising marker molecules that can be enzymatically modified, e.g. DNA, indexing molecules can be incorporated at the 3' of the sample and marker molecules by ligating sequenceable adaptor sequences comprising the indexing sequences. In embodiments of the method comprising marker molecules that cannot be enzymatically modified, e.g. DNA analogs that do not have a phosphate backbone, indexing sequences are incorporated at the 3' of the analog marker molecules during synthesis. Sequencing libraries of two or more samples are pooled and loaded on the flow cell of the sequencer where they are sequenced in a massively parallel fashion in step 540. In step 550, all sequencing information is analyzed, and based on the sequencing information pertaining to the marker molecules; the integrity of the source sample is verified in step 560. Verification of the integrity of each of the plurality of source samples is accomplished by first grouping sequence tags associated with identical index sequences to associate the genomic and marker sequences and distinguish sequences belonging to each of the libraries made from genomic molecules of a plurality of samples. Analysis of the grouped marker and genomic sequences is then performed to verify that the sequence obtained for the marker molecules corresponds to the known unique sequence added to the corresponding source sample. If the integrity of the sample is verified, the sequencing information pertaining to the genomic nucleic acids of the sample can be analyzed to provide genetic information about the subject from which the source sample was obtained. For example, if the integrity of the sample is verified, the sequencing information pertaining to the genomic nucleic acids is analyzed to determine the presence or absence of a chromosomal abnormality. The absence of a correspondence between the sequencing information and known sequence of the marker molecule is indicative of a sample mix-up, and the accompanying sequencing information pertaining to the genomic cfDNA molecules is disregarded.

Determination of CNV for Prenatal Diagnoses

Cell-free fetal DNA and RNA circulating in maternal blood can be used for the early non-invasive prenatal diagnosis (NIPD) of an increasing number of genetic conditions, both for pregnancy management and to aid reproductive decision-making. The presence of cell-free DNA circulating in the bloodstream has been known for over 50 years. More recently, presence of small amounts of circulating fetal DNA was discovered in the maternal bloodstream during pregnancy (Lo et al., Lancet 350:485-487 [1997]). Thought to originate from dying placental cells, cell-free fetal DNA (cfDNA) has been shown to consists of short fragments typically fewer than 200 bp in length Chan et al., Clin Chem 50:88-92 [2004]), which can be discerned as early as 4 weeks gestation (Illanes et al., Early Human Dev 83:563-566 [2007]), and known to be cleared from the maternal circulation within hours of delivery (Lo et al., Am J Hum Genet. 64:218-224 [1999]). In addition to cfDNA, fragments of cell-free fetal RNA (cfRNA) can also be discerned in the maternal bloodstream, originating from genes that are transcribed in the fetus or placenta. The extraction and subsequent analysis of these fetal genetic elements from a maternal blood sample offers novel opportunities for NIPD.

The present method is a polymorphism-independent method that for use in NIPD and that does not require that the fetal cfDNA be distinguished from the maternal cfDNA to enable the determination of a fetal aneuploidy. In some embodiments, the aneuploidy is a complete chromosomal trisomy or monosomy, or a partial trisomy or monosomy. Partial aneuploidies are caused by loss or gain of part of a chromosome, and encompass chromosomal imbalances resulting from unbalanced translocations, unbalanced inversions, deletions and insertions. By far, the most common known aneuploidy compatible with life is trisomy 21 i.e. Down Syndrome (DS), which is caused by the presence of part or all of chromosome 21. Rarely, DS can be caused by an inherited or sporadic defect whereby an extra copy of all or part of chromosome 21 becomes attached to another chromosome (usually chromosome 14) to form a single aberrant chromosome. DS is associated with intellectual impairment, severe learning difficulties and excess mortality caused by long-term health problems such as heart disease. Other aneuploidies with known clinical significance include Edward syndrome (trisomy 18) and Patau Syndrome (trisomy 13), which are frequently fatal within the first few months of life. Abnormalities associated with the number of sex chromosomes are also known and include monosomy X e.g. Turner syndrome (XO), and triple X syndrome (XXX) in female births and Kleinefelter syndrome (XXY) and XYY syndrome in male births, which are all associated with various phenotypes including sterility and reduction in intellectual skills. Monosomy X [45,X] is a common cause of early pregnancy loss accounting for about 7% of spontaneous abortions. Based on the liveborn frequency of 45,X (also called Turner syndrome) of 1-2/10,000, it is estimated that less than 1% of 45,X conceptuses will survive to term. About 30% of Turners syndrome patients are mosaic with both a 45,X cell line and either a 46,XX cell line or one containing a rearranged X chromosome (Hook and Warburton 1983). The phenotype in a liveborn infant is relatively mild considering the high embryonic lethality and it has been hypothesized that possibly all liveborn females with Turner syndrome carry a cell line containing two sex chromosomes. Monosomy X can occur in females as 45,X or as 45,X/46XX, and in males as 45,X/46XY. Autosomal monosomies in human are generally suggested to be incompatible with life; however, there is quite a number of cytogenetic reports describing full monosomy of one chromosome 21 in live born children (Vosranova I et al., Molecular Cytogen. 1:13 [2008]; Joosten et al., Prenatal Diagn. 17:271-5 [1997]. The method described herein can be used to diagnose these and other chromosomal abnormalities prenatally.

According to some embodiments the methods disclosed herein can determine the presence or absence of chromosomal trisomies of any one of chromosomes 1-22, X and Y. Examples of chromosomal trisomies that can be detected according to the present method include without limitation trisomy 21 (T21; Down Syndrome), trisomy 18 (T18; Edward's Syndrome), trisomy 16 (T16), trisomy 20 (T20), trisomy 22 (T22; Cat Eye Syndrome), trisomy 15 (T15; Prader Willi Syndrome), trisomy 13 (T13; Patau Syndrome), trisomy 8 (T8; Warkany Syndrome), trisomy 9, and the XXY (Kleinefelter Syndrome), XYY, or XXX trisomies. Complete trisomies of other autosomes existing in a non-mosaic state are lethal, but can be compatible with life when present in a mosaic state. It will be appreciated that various complete trisomies, whether existing in a mosaic or non-mosaic state, and partial trisomies can be determined in fetal cfDNA according to the teachings provided herein.

Non-limiting examples of partial trisomies that can be determined by the present method include, but are not limited to, partial trisomy 1q32-44, trisomy 9 p, trisomy 4 mosaicism, trisomy 17p, partial trisomy 4q26-qter, partial 2p trisomy, partial trisomy 1q, and/or partial trisomy 6p/monosomy 6q.

The methods disclosed herein can be also used to determine chromosomal monosomy X, chromosomal monosomy 21, and partial monosomies such as, monosomy 13, monosomy 15, monosomy 16, monosomy 21, and monosomy 22, which are known to be involved in pregnancy miscarriage. Partial monosomy of chromosomes typically involved in complete aneuploidy can also be determined by the method described herein. Non-limiting examples of deletion syndromes that can be determined according to the present method include syndromes caused by partial deletions of chromosomes. Examples of partial deletions that can be determined according to the methods described herein include without limitation partial deletions of chromosomes 1, 4, 5, 7, 11, 18, 15, 13, 17, 22 and 10, which are described in the following.

1q21.1 deletion syndrome or 1q21.1 (recurrent) microdeletion is a rare aberration of chromosome 1. Next to the deletion syndrome, there is also a 1q21.1 duplication syndrome. While there is a part of the DNA missing with the deletion syndrome on a particular spot, there are two or three copies of a similar part of the DNA on the same spot with the duplication syndrome. Literature refers to both the deletion and the duplication as the 1q21.1 copy-number variations (CNV). The 1q21.1 deletion can be associated with the TAR Syndrome (Thrombocytopenia with Absent radius).

Wolf-Hirschhorn syndrome (WHS) (OMIN #194190) is a contiguous gene deletion syndrome associated with a hemizygous deletion of chromosome 4p16.3. Wolf-Hirschhorn syndrome is a congenital malformation syndrome characterized by pre- and postnatal growth deficiency, developmental disability of variable degree, characteristic craniofacial features ('Greek warrior helmet' appearance of the nose, high forehead, prominent glabella, hypertelorism, high-arched eyebrows, protruding eyes, epicanthal folds, short philtrum, distinct mouth with downturned corners, and micrognathia), and a seizure disorder.

Partial deletion of chromosome 5, also known as 5p– or 5p minus, and named Cris du Chat syndrome (OMIN#123450), is caused by a deletion of the short arm (p arm) of chromosome 5 (5p15.3-p15.2). Infants with this condition often have a high-pitched cry that sounds like that of a cat. The disorder is characterized by intellectual disability and delayed development, small head size (microcephaly), low birth weight, and weak muscle tone (hypotonia) in infancy, distinctive facial features and possibly heart defects.

Williams-Beuren Syndrome also known as chromosome 7q11.23 deletion syndrome (OMIN 194050) is a contiguous gene deletion syndrome resulting in a multisystem disorder caused by hemizygous deletion of 1.5 to 1.8 Mb on chromosome 7q11.23, which contains approximately 28 genes.

Jacobsen Syndrome, also known as 11q deletion disorder, is a rare congenital disorder resulting from deletion of a terminal region of chromosome 11 that includes band 11q24.1. It can cause intellectual disabilities, a distinctive facial appearance, and a variety of physical problems including heart defects and a bleeding disorder.

Partial monosomy of chromosome 18, known as monosomy 18p is a rare chromosomal disorder in which all or part of the short arm (p) of chromosome 18 is deleted (monosomic). The disorder is typically characterized by short stature, variable degrees of mental retardation, speech delays, malformations of the skull and facial (craniofacial) region, and/or additional physical abnormalities. Associated craniofacial defects may vary greatly in range and severity from case to case.

Conditions caused by changes in the structure or number of copies of chromosome 15 include Angelman Syndrome and Prader-Willi Syndrome, which involve a loss of gene activity in the same part of chromosome 15, the 15q11-q13 region. It will be appreciated that several translocations and microdeletions can be asymptomatic in the carrier parent, yet can cause a major genetic disease in the offspring. For example, a healthy mother who carries the 15q11-q13 microdeletion can give birth to a child with Angelman syndrome, a severe neurodegenerative disorder. Thus, the methods, apparatus and systems described herein can be used to identify such a partial deletion and other deletions in the fetus.

Partial monosomy 13q is a rare chromosomal disorder that results when a piece of the long arm (q) of chromosome 13 is missing (monosomic). Infants born with partial monosomy 13q may exhibit low birth weight, malformations of the head and face (craniofacial region), skeletal abnormalities (especially of the hands and feet), and other physical abnormalities. Mental retardation is characteristic of this condition. The mortality rate during infancy is high among individuals born with this disorder. Almost all cases of partial monosomy 13q occur randomly for no apparent reason (sporadic).

Smith-Magenis syndrome (SMS—OMIM #182290) is caused by a deletion, or loss of genetic material, on one copy of chromosome 17. This well-known syndrome is associated with developmental delay, mental retardation, congenital anomalies such as heart and kidney defects, and neurobehavioral abnormalities such as severe sleep disturbances and self-injurious behavior. Smith-Magenis syndrome (SMS) is caused in most cases (90%) by a 3.7-Mb interstitial deletion in chromosome 17p11.2.

22q11.2 deletion syndrome, also known as DiGeorge syndrome, is a syndrome caused by the deletion of a small piece of chromosome 22. The deletion (22 q11.2) occurs near the middle of the chromosome on the long arm of one of the pair of chromosome. The features of this syndrome vary widely, even among members of the same family, and affect many parts of the body. Characteristic signs and symptoms may include birth defects such as congenital heart disease, defects in the palate, most commonly related to neuromuscular problems with closure (velo-pharyngeal insufficiency), learning disabilities, mild differences in facial features, and recurrent infections. Microdeletions in chromosomal region 22q11.2 are associated with a 20 to 30-fold increased risk of schizophrenia.

Deletions on the short arm of chromosome 10 are associated with a DiGeorge Syndrome like phenotype. Partial monosomy of chromosome 10p is rare but has been observed in a portion of patients showing features of the DiGeorge Syndrome.

In one embodiment, the methods, apparatus, and systems described herein is used to determine partial monosomies including but not limited to partial monosomy of chromosomes 1, 4, 5, 7, 11, 18, 15, 13, 17, 22 and 10, e.g. partial monosomy 1q21.11, partial monosomy 4p16.3, partial monosomy 5p15.3-p15.2, partial monosomy 7q11.23, partial monosomy 11q24.1, partial monosomy 18p, partial monosomy of chromosome 15 (15q11-q13), partial monosomy 13q, partial monosomy 17p11.2, partial monosomy of chromosome 22 (22q11.2), and partial monosomy 10p can also be determined using the method.

Other partial monosomies that can be determined according to the methods described herein include unbalanced translocation t(8; 11)(p23.2;p15.5); 11q23 microdeletion; 17p11.2 deletion; 22q13.3 deletion; Xp22.3 microdeletion; 10p14 deletion; 20p microdeletion, [del(22)(q11.2q11.23)], 7q11.23 and 7q36 deletions; 1p36 deletion; 2p microdeletion; neurofibromatosis type 1 (17q11.2 microdeletion), Yq deletion; 4p16.3 microdeletion; 1p36.2 microdeletion; 11q14 deletion; 19q13.2 microdeletion; Rubinstein-Taybi (16 p13.3 microdeletion); 7p21 microdeletion; Miller-Dieker syndrome (17p13.3); and 2q37 microdeletion. Partial deletions can be small deletions of part of a chromosome, or they can be microdeletions of a chromosome where the deletion of a single gene can occur.

Several duplication syndromes caused by the duplication of part of chromosome arms have been identified (see OMIN [Online Mendelian Inheritance in Man viewed online at ncbi.nlm.nih.gov/omim]). In one embodiment, the present method can be used to determine the presence or absence of duplications and/or multiplications of segments of any one of chromosomes 1-22, X and Y. Non-limiting examples of duplications syndromes that can be determined according to the present method include duplications of part of chromosomes 8, 15, 12, and 17, which are described in the following.

8p23.1 duplication syndrome is a rare genetic disorder caused by a duplication of a region from human chromosome 8. This duplication syndrome has an estimated prevalence of 1 in 64,000 births and is the reciprocal of the 8p23.1 deletion syndrome. The 8p23.1 duplication is associated with a variable phenotype including one or more of speech delay, developmental delay, mild dysmorphism, with prominent forehead and arched eyebrows, and congenital heart disease (CHD).

Chromosome 15q Duplication Syndrome (Dup15q) is a clinically identifiable syndrome which results from duplications of chromosome 15q11-13.1 Babies with Dup15q usually have hypotonia (poor muscle tone), growth retardation; they may be born with a cleft lip and/or palate or malformations of the heart, kidneys or other organs; they show some degree of cognitive delay/disability (mental retardation), speech and language delays, and sensory processing disorders.

Pallister Killian syndrome is a result of extra #12 chromosome material. There is usually a mixture of cells (mosaicism), some with extra #12 material, and some that are normal (46 chromosomes without the extra #12 material). Babies with this syndrome have many problems including severe mental retardation, poor muscle tone, "coarse" facial features, and a prominent forehead. They tend to have a very thin upper lip with a thicker lower lip and a short nose. Other health problems include seizures, poor feeding, stiff joints, cataracts in adulthood, hearing loss, and heart defects. Persons with Pallister Killian have a shortened lifespan.

Individuals with the genetic condition designated as dup(17)(p11.2p11.2) or dup 17p carry extra genetic information (known as a duplication) on the short arm of chromosome 17. Duplication of chromosome 17p11.2 underlies Potocki-Lupski syndrome (PTLS), which is a newly recognized genetic condition with only a few dozen cases reported in the medical literature. Patients who have this duplication often have low muscle tone, poor feeding, and failure to thrive during infancy, and also present with delayed development of motor and verbal milestones. Many individuals who have PTLS have difficulty with articulation and language processing. In addition, patients may have behavioral characteristics similar to those seen in persons with autism or autism-spectrum disorders. Individuals with PTLS may have heart defects and sleep apnea. A duplication of a large region in chromosome 17p12 that includes the gene PMP22 is known to cause Charcot-Marie Tooth disease.

CNV have been associated with stillbirths. However, due to inherent limitations of conventional cytogenetics, the contribution of CNV to stillbirth is thought to be underrepresented (Harris et al., Prenatal Diagn 31:932-944 [2011]). As is shown in the examples and described elsewhere herein, the present method is capable of determining the presence of partial aneuploidies e.g. deletions and multiplications of chromosome segments, and can be used to identify and determine the presence or absence of CNV that are associated with stillbirths.

Determination of Complete Fetal Chromosomal Aneuploidies

In one embodiment, methods are provided for determining the presence or absence of any one or more different complete fetal chromosomal aneuploidies in a maternal test sample comprising fetal and maternal nucleic acid molecules. Preferably, the method determines the presence or absence of any four or more different complete chromosomal aneuploidies. The steps of the method comprise (a) obtaining sequence information for the fetal and maternal nucleic acids in the maternal test sample; and (b) using the sequence information to identify a number of sequence tags for each of any one or more chromosomes of interest selected from chromosomes 1-22, X and Y and to identify a number of sequence tags for a normalizing chromosome sequence for each of the any one or more chromosomes of interest. The normalizing chromosome sequence can be a single chromosome, or it can be a group of chromosomes selected from chromosomes 1-22, X, and Y. The method further uses in step (c) the number of sequence tags identified for each of the any one or more chromosomes of interest and the number of sequence tags identified for each normalizing chromosome sequence to calculate a single chromosome dose for each of the any one or more chromosomes of interest; and (d) compares each of the single chromosome doses for each of the any one or more chromosomes of interest to a threshold value for each of the one or more chromosomes of interest, thereby determining the presence or absence of any one or more complete different fetal chromosomal aneuploidies in the maternal test sample.

In some embodiments, step (c) comprises calculating a single chromosome dose for each chromosomes of interest as the ratio of the number of sequence tags identified for each of the chromosomes of interest and the number of sequence tags identified for the normalizing chromosome for each of the chromosomes of interest.

In other embodiments, step (c) comprises calculating a single chromosome dose for each of the chromosomes of interest as the ratio of the number of sequence tags identified for each of the chromosomes of interest and the number of sequence tags identified for the normalizing chromosome for each of the chromosomes of interest. In other embodiments, step (c) comprises calculating a sequence tag ratio for a chromosome of interest by relating the number of sequence tags obtained for the chromosome of interest to the length of the chromosome of interest, and relating the number of tags for the corresponding normalizing chromosome sequence for the chromosome of interest to the length of the normalizing chromosome sequence, and calculating a chromosome dose for the chromosome of interest as a ratio of the sequence tags density of the chromosome of interest and the sequence tag density for the normalizing sequence. The calculation is repeated for each of all chromosomes of interest. Steps (a)-(d) can be repeated for test samples from different maternal subjects.

An example of the embodiment whereby four or more complete fetal chromosomal aneuploidies are determined in a maternal test sample comprising a mixture of fetal and maternal cell-free DNA molecules, comprises: (a) sequencing at least a portion of cell-free DNA molecules to obtain sequence information for the fetal and maternal cell-free DNA molecules in the test sample; (b) using the sequence information to identify a number of sequence tags for each of any twenty or more chromosomes of interest selected from chromosomes 1-22, X, and Y and to identify a number of sequence tags for a normalizing chromosome for each of the twenty or more chromosomes of interest; (c) using the number of sequence tags identified for each of the twenty or more chromosomes of interest and the number of sequence tags identified for each the normalizing chromosome to calculate a single chromosome dose for each of the twenty or more chromosomes of interest; and (d) comparing each of the single chromosome doses for each of the twenty or more chromosomes of interest to a threshold value for each of the twenty or more chromosomes of interest, and thereby determining the presence or absence of any twenty or more different complete fetal chromosomal aneuploidies in the test sample.

In another embodiment, the method for determining the presence or absence of any one or more different complete fetal chromosomal aneuploidies in a maternal test sample as described above uses a normalizing segment sequence for determining the dose of the chromosome of interest. In this instance, the method comprises (a) obtaining sequence information for said fetal and maternal nucleic acids in said sample; (b) using said sequence information to identify a number of sequence tags for each of any one or more chromosomes of interest selected from chromosomes 1-22, X and Y and to identify a number of sequence tags for a normalizing segment sequence for each of said any one or more chromosomes of interest. The normalizing segment sequence can be a single segment of a chromosome or it can be a group of segments form one or more different chromosomes. The method further uses in step (c) the number of sequence tags identified for each of said any one or more chromosomes of interest and said number of sequence tags identified for said normalizing segment sequence to calculate a single chromosome dose for each of said any one or more chromosomes of interest; and (d) comparing each of said single chromosome doses for each of said any one or more chromosomes of interest to a threshold value for each of said one or more chromosomes of interest, and thereby determining the presence or absence of one or more different complete fetal chromosomal aneuploidies in said sample.

In some embodiments, step (c) comprises calculating a single chromosome dose for each of said chromosomes of interest as the ratio of the number of sequence tags identified for each of said chromosomes of interest and the number of sequence tags identified for said normalizing segment sequence for each of said chromosomes of interest.

In other embodiments, step (c) comprises calculating a sequence tag ratio for a chromosome of interest by relating the number of sequence tags obtained for the chromosome of interest to the length of the chromosome of interest, and relating the number of tags for the corresponding normalizing segment sequence for the chromosome of interest to the length of the normalizing segment sequence, and calculating a chromosome dose for the chromosome of interest as a ratio of the sequence tags density of the chromosome of interest and the sequence tag density for the normalizing segment sequence. The calculation is repeated for each of all chromosomes of interest. Steps (a)-(d) can be repeated for test samples from different maternal subjects.

A means for comparing chromosome doses of different sample sets is provided by determining a normalized chromosome value (NCV), which relates the chromosome dose in a test sample to the mean of the of the corresponding chromosome dose in a set of qualified samples. The NCV is calculated as:

$$NCV_{ij} = \frac{x_{ij} - \hat{\mu}_j}{\hat{\sigma}_j}$$

where $\hat{\mu}_j$ and $\hat{\sigma}_j$ the estimated mean and standard deviation, respectively, for the j-th chromosome dose in a set of qualified samples, and $x_{ij}$ is the observed j-th chromosome dose for test sample i.

In some embodiments, the presence or absence of at least one complete fetal chromosomal aneuploidy is determined. In other embodiments, the presence or absence of at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty-one, at least twenty-two, at least twenty-three, or twenty-four complete fetal chromosomal aneuploidies are determined in a sample, wherein twenty-two of the complete fetal chromosomal aneuploidies correspond to complete chromosomal aneuploidies of any one or more of the autosomes; the twenty-third and twenty fourth chromosomal aneuploidy correspond to a complete fetal chromosomal aneuploidy of chromosomes X and Y. As aneuploidies of sex chromosomes can comprise tetrasomies, pentasomies and other polysomies, the number of different complete chromosomal aneuploidies that can be determined according to the present method may be at least 24, at least 25, at least 26, at least 27, at least 28, at least 29, or at least 30 complete chromosomal aneuploidies. Thus, the number of different complete fetal chromosomal aneuploidies that are determined is related to the number of chromosomes of interest that are selected for analysis.

In one embodiment, determining the presence or absence of any one or more different complete fetal chromosomal aneuploidies in a maternal test sample as described above uses a normalizing segment sequence for one chromosome of interest, which is selected from chromosomes 1-22, X, and Y. In other embodiments, two or more chromosomes of interest are selected from any two or more of chromosomes 1, 2, 3, 4, 5, 6, 7, 8, 9, 10, 11, 12, 13, 14, 15, 16, 17, 18, 19, 20, 21, 22, X, or Y. In one embodiment, any one or more chromosomes of interest are selected from chromosomes 1-22, X, and Y comprise at least twenty chromosomes selected from chromosomes 1-22, X, and Y, and wherein the presence or absence of at least twenty different complete fetal chromosomal aneuploidies is determined. In other embodiments, any one or more chromosomes of interest selected from chromosomes 1-22, X, and Y is all of chromosomes 1-22, X, and Y, and wherein the presence or absence of complete fetal chromosomal aneuploidies of all of chromosomes 1-22, X, and Y is determined. Complete different fetal chromosomal aneuploidies that can be determined include complete chromosomal trisomies, complete chromosomal monosomies and complete chromosomal polysomies. Examples of complete fetal chromosomal aneuploidies include without limitation trisomies of any one or more of the autosomes e.g. trisomy 2, trisomy 8, trisomy 9, trisomy 20, trisomy 21, trisomy 13, trisomy 16, trisomy 18, trisomy 22; trisomies of the sex chromosomes e.g. 47,XXY, 47 XXX, and 47 XYY; tetrasomies of sex chromosomes e.g. 48,XXYY, 48,XXXY, 48XXXX, and 48,XYYY; pentasomies of sex chromosomes e.g. 49,XXXYY 49,XXXXY, 49,XXXXX, 49,XYYYY; and monosomy X. Other complete fetal chromosomal aneuploidies that can be determined according to the present method are described below.

Determination of Partial Fetal Chromosomal Aneuploidies

In another embodiment, method are provided for determining the presence or absence of any one or more different partial fetal chromosomal aneuploidies in a maternal test sample comprising fetal and maternal nucleic acid molecules. The steps of the method comprise (a) obtaining sequence information for the fetal and maternal nucleic acids in said sample; and (b) using the sequence information to identify a number of sequence tags for each of any one or more segments of any one or more chromosomes of interest selected from chromosomes 1-22, X, and Y and to identify a number of sequence tags for a normalizing segment sequence for each of said any one or more segments of any one or more chromosomes of interest. The normalizing segment sequence can be a single segment of a chromosome or it can be a group of segments form one or more different chromosomes. The method further uses in step (c) the number of sequence tags identified for each of any one or more segments of any one or more chromosomes of interest and the number of sequence tags identified for the normalizing segment sequence to calculate a single segment dose for each of any one or more segments of any one or more chromosome of interest; and (d) comparing each of the single chromosome doses for each of any one or more segments of any one or more chromosomes of interest to a threshold value for each of said any one or more chromosomal segments of any one or more chromosome of interest, and thereby determining the presence or absence of one or more different partial fetal chromosomal aneuploidies in said sample.

In some embodiments, step (c) comprises calculating a single segment dose for each of any one or more segments of any one or more chromosomes of interest as the ratio of the number of sequence tags identified for each of any one or more segments of any one or more chromosomes of interest and the number of sequence tags identified for the normalizing segment sequence for each of any one or more segments of any one or more chromosomes of interest.

In other embodiments, step (c) comprises calculating a sequence tag ratio for a segment of interest by relating the number of sequence tags obtained for the segment of interest to the length of the segment of interest, and relating the number of tags for the corresponding normalizing segment sequence for the segment of interest to the length of the normalizing segment sequence, and calculating a segment dose for the segment of interest as a ratio of the sequence tags density of the segment of interest and the sequence tag density for the normalizing segment sequence. The calculation is repeated for each of all chromosomes of interest. Steps (a)-(d) can be repeated for test samples from different maternal subjects.

A means for comparing segment doses of different sample sets is provided by determining a normalized segment value (NSV), which relates the segment dose in a test sample to the mean of the of the corresponding segment dose in a set of qualified samples. The NSV is calculated as:

$$NSV_{ij} = \frac{x_{ij} - \hat{\mu}_j}{\hat{\sigma}_j}$$

where $\hat{\mu}_j$ and $\hat{\sigma}_j$ are the estimated mean and standard deviation, respectively, for the j-th segment dose in a set of qualified samples, and $x_{ij}$ is the observed j-th segment dose for test sample i.

In some embodiments, the presence or absence of one partial fetal chromosomal aneuploidy is determined. In other embodiments, the presence or absence of two, three, four, five, six, seven, eight, nine, ten, fifteen, twenty, twenty-five, or more partial fetal chromosomal aneuplodies are determined in a sample. In one embodiment, one segment of interest selected from any one of chromosomes 1-22, X, and Y is selected from chromosomes 1-22, X, and Y. In another embodiment, two or more segments of interest selected from chromosomes 1-22, X, and Y are selected from any two or more of chromosomes 1, 2, 3, 4, 5, 6, 7, 8, 9, 10, 11, 12, 13, 14, 15, 16, 17, 18, 19, 20, 21, 22, X, or Y. In one embodiment, any one or more segments of interest are selected from chromosomes 1-22, X, and Y comprise at least one, five, ten, 15, 20, 25 or more segments selected from chromosomes 1-22, X, and Y, and wherein the presence or absence of at least one, five, ten, 15, 20, 25 different partial fetal chromosomal aneuploidies is determined. Different partial fetal chromosomal aneuploidies that can be determined include fetal chromosomal aneuploidies include partial duplications, partial multiplications, partial insertions and partial deletions. Examples of partial fetal chromosomal aneuploidies include partial monosomies and partial trisomies of autosomes. Partial monosomies of autosomes include partial monosomy of chromosome 1, partial monosomy of chromosome 4, partial monosomy of chromosome 5, partial monosomy of chromosome 7, partial monosomy of chromosome 11, partial monosomy of chromosome 15, partial monosomy of chromosome 17, partial monosomy of chromosome 18, and partial monosomy of chromosome 22. Other partial fetal chromosomal aneuploidies that can be determined according to the present method are described below.

In any one of the embodiments described above, the test sample is a maternal sample selected from blood, plasma, serum, urine and saliva samples. In some embodiments, the maternal test sample is a plasma sample. The nucleic acid molecules of the maternal sample are a mixture of fetal and maternal cell-free DNA molecules. Sequencing of the nucleic acids can be performed using next generation sequencing (NGS) as described elsewhere herein. In some embodiments, sequencing is massively parallel sequencing using sequencing-by-synthesis with reversible dye terminators. In other embodiments, sequencing is sequencing-by-ligation. In yet other embodiments, sequencing is single molecule sequencing. Optionally, an amplification step is performed prior to sequencing.

Determination of CNV of Clinical Disorders

In addition to the early determination of birth defects, the methods described herein can be applied to the determination of any abnormality in the representation of genetic sequences within the genome. A number of abnormalities in the representation of genetic sequences within the genome have been associated with various pathologies. Such pathologies include, but are not limited to cancer, infectious and autoimmune diseases, diseases of the nervous system, metabolic and/or cardiovascular diseases, and the like.

Accordingly in various embodiments use of the methods described herein in the diagnosis, and/or monitoring, and or treating such pathologies is contemplated. For example, the methods can be applied to determining the presence or absence of a disease, to monitoring the progression of a disease and/or the efficacy of a treatment regimen, to determining the presence or absence of nucleic acids of a pathogen e.g. virus; to determining chromosomal abnormalities associated with graft versus host disease (GVHD), and to determining the contribution of individuals in forensic analyses.

CNVs in Cancer

It has been shown that blood plasma and serum DNA from cancer patients contains measurable quantities of tumor DNA, that can be recovered and used as surrogate source of tumor DNA, and tumors are characterized by aneuploidy, or inappropriate numbers of gene sequences or even entire chromosomes. The determination of a difference in the amount of a given sequence i.e. a sequence of interest, in a sample from an individual can thus be used in the prognosis or diagnosis of a medical condition. In some embodiments, the present method can be used to determine the presence or absence of a chromosomal aneuploidy in a patient suspected or known to be suffering from cancer.

In certain embodiments the aneuploidy is characteristic of the genome of the subject and results in a generally increased predisposition to a cancer. In certain embodiments the aneuploidy is characteristic of particular cells (e.g., tumor cells, proto-tumor neoplastic cells, etc.) that are or have an increased predisposition to neoplasia. Particular aneuploidies are associated with particular cancers or predispositions to particular cancers as described below.

Accordingly, various embodiments of the methods described herein provide a determination of copy number variation of sequence(s) of interest e.g. clinically-relevant sequence(s), in a test sample from a subject where certain variations in copy number provide an indicator of the presence and/or a predisposition to a cancer. In certain embodiments the sample comprises a mixture of nucleic acids is derived from two or more types of cells. In one embodiment, the mixture of nucleic acids is derived from normal and cancerous cells derived from a subject suffering from a medical condition e.g. cancer.

The development of cancer is often accompanied by an alteration in number of whole chromosomes i.e. complete chromosomal aneuploidy, and/or an alteration in the number of segments of chromosomes i.e. partial aneuploidy, caused by a process known as chromosome instability (CIN) (Thoma et al., Swiss Med Weekly 2011:141:w13170). It is believed that many solid tumors, such as breast cancer, progress from initiation to metastasis through the accumulation of several genetic aberrations. [Sato et al., Cancer Res., 50: 7184-7189 [1990]; Jongsma et al., J Clin Pathol: Mol Path 55:305-309 [2002])]. Such genetic aberrations, as they accumulate, may confer proliferative advantages, genetic instability and the attendant ability to evolve drug resistance rapidly, and enhanced angiogenesis, proteolysis and metastasis. The genetic aberrations may affect either recessive "tumor suppressor genes" or dominantly acting oncogenes. Deletions and recombination leading to loss of heterozygosity (LOH) are believed to play a major role in tumor progression by uncovering mutated tumor suppressor alleles.

cfDNA has been found in the circulation of patients diagnosed with malignancies including but not limited to lung cancer (Pathak et al. Clin Chem 52:1833-1842 [2006]), prostate cancer (Schwartzenbach et al. Clin Cancer Res 15:1032-8 [2009]), and breast cancer (Schwartzenbach et al. available online at breast-cancer-research.com/content/11/5/R71 [2009]). Identification of genomic instabilities associated with cancers that can be determined in the circulating cfDNA in cancer patients is a potential diagnostic and prognostic tool. In one embodiment, methods described herein are used to determine CNV of one or more sequence(s) of interest in a sample, e.g., a sample comprising a mixture of nucleic acids derived from a subject that is suspected or is known to have cancer e.g. carcinoma, sarcoma, lymphoma, leukemia, germ cell tumors and blastoma. In one embodiment, the sample is a plasma sample derived (processed) from peripheral blood that may comprise a mixture of cfDNA derived from normal and cancerous cells. In another embodiment, the biological sample that is needed to determine whether a CNV is present is derived from a cells that, if a cancer is present, comprise a mixture of cancerous and non-cancerous cells from other biological tissues including, but not limited to biological fluids such as serum, sweat, tears, sputum, urine, sputum, ear flow, lymph, saliva, cerebrospinal fluid, ravages, bone marrow suspension, vaginal flow, transcervical lavage, brain fluid, ascites, milk, secretions of the respiratory, intestinal and genitourinary tracts, and leukophoresis samples, or in tissue biopsies, swabs, or smears. In other embodiments, the biological sample is a stool (fecal) sample.

The methods described herein are not limited to the analysis of cfDNA. It will be recognized that similar analyses can be performed on cellular DNA samples.

In various embodiments the sequence(s) of interest comprise nucleic acid sequence(s) known or is suspected to play a role in the development and/or progression of the cancer. Examples of a sequence of interest include nucleic acids sequences e.g. complete chromosomes and/or segments of chromosomes, that are amplified or deleted in cancerous cells as described below.

Total CNV Number and Risk for Cancer.

Common cancer SNPs—and by analogy common cancer CNVs may each confer only a minor increase in disease risk. However, collectively they may cause a substantially elevated risk for cancers. In this regard it is noted that germline gains and losses of large DNA segments have been reported as factors predisposing individuals to neuroblastoma, prostate and colorectal cancer, breast cancer, and BRCA1-associated ovarian cancer (see, e.g., Krepischi et al. Breast Cancer Res., 14: R24 [2012]; Diskin et al. Nature 2009, 459:987-991; Liu et al. Cancer Res 2009, 69: 2176-2179; Lucito et al. Cancer Biol Ther 2007, 6:1592-1599; Thean et al. Genes Chromosomes Cancer 2010, 49:99-106; Venkatachalam et al. Int J Cancer 2011, 129:1635-1642; and Yoshihara et al. Genes Chromosomes Cancer 2011, 50:167-177). It is noted that CNVs frequently found in the healthy population (common CNVs) are believed to have a role in cancer etiology (see, e.g., Shlien and Malkin (2009) Genome Medicine, 1(6): 62). In one study testing the hypothesis that common CNVs are associated with malignancy (Shlien et al. Proc Natl Acad Sci USA 2008, 105:11264-11269) a map of every known CNV whose locus coincides with that of bona fide cancer-related genes (as catalogued by Higgins et al. Nucleic Acids Res 2007, 35:D721-726) was created. These were termed "cancer CNVs". In an initial analysis (Shlien et al. Proc Natl Acad Sci USA 2008, 105:11264-11269), 770 healthy genomes were evaluated using the Affymetrix 500K array set, which has an average inter-probe distance of 5.8 kb. As CNVs are generally thought to be depleted in gene regions (Redon et al. (2006) Nature 2006, 444:444-454), it was surprising to find 49 cancer genes that were directly encompassed or overlapped by a CNV in more than one person in a large reference population. In the top ten genes, cancer CNVs could be found in four or more people.

It is thus believed that CNV frequency can be used as a measure of risk for cancer (see, e.g., U.S. Patent Publication No: 2010/0261183 A1). The CNV frequency can be determined simply by the constitutive genome of the organism or it can represent a fraction derived from one or more tumors (neoplastic cells) if such are present.

In certain embodiments a number of CNVs in a test sample (e.g., a sample comprising a constitutional (germline) nucleic acid) or a mixture of nucleic acids (e.g., a germline nucleic acid and nucleic acid(s) derived from neoplastic cells) is determined using the methods described herein for copy number variations. Identification of an increased number of CNVs in the test sample, e.g., in comparison to a reference value is indicative of a risk of or predisposition for cancer in the subject. It will be appreciated that the reference value may vary with a given population. It will also be appreciated that the absolute value of the increase in CNV frequency will vary depending on the resolution of the method utilized to determine CNV frequency and other parameters. Typically, an increase in CNV frequency of at least about 1.2 times the reference value been determined to indicative of risk for cancer (see, e.g., U.S. Patent Publication No: 2010/0261183 A1), for example an increase in CNV frequency of at least or about 1.5 times the reference value or greater, such as 2-4 times the reference value is an indicator of an increased risk of cancer (e.g., as compared to the normal healthy reference population).

A determination of structural variation in the genome of a mammal in comparison to a reference value is also believed to be indicative of risk of cancer. In this context, in one embodiment, the term "structural variation" is can be defined as the CNV frequency in a mammal multiplied by the average CNV size (in bp) in the mammal. Thus, high structural variation scores will result due to increased CNV frequency and/or due to the occurrence of large genomic nucleic acid deletions or duplications. Accordingly, in certain embodiments a number of CNVs in a test sample (e.g., a sample comprising a constitutional (germline) nucleic acid) is determined using the methods described herein to determine size and number of copy number variations. In certain embodiments a total structural variation score within genomic DNA of greater than about 1 megabase, or greater than about 1.1 megabases, or greater than about 1.2 megabases, or greater than about 1.3 megabases, or greater than about 1.4 megabases, or greater than about 1.5 megabases, or greater than about 1.8 megabases, or greater than about 2 megabases of DNA is indicative of risk of cancer.

It is believed these methods provide a measure of the risk of any cancer including but not limited to, acute and chronic leukemias, lymphomas, numerous solid tumors of mesenchymal or epithelial tissue, brain, breast, liver, stomach, colon cancer, B cell lymphoma, lung cancer, a bronchus cancer, a colorectal cancer, a prostate cancer, a breast cancer, a pancreas cancer, a stomach cancer, an ovarian cancer, a urinary bladder cancer, a brain or central nervous system cancer, a peripheral nervous system cancer, an esophageal cancer, a cervical cancer, a melanoma, a uterine or endometrial cancer, a cancer of the oral cavity or pharynx, a liver cancer, a kidney cancer, a biliary tract cancer, a small bowel or appendix cancer, a salivary gland cancer, a thyroid gland cancer, a adrenal gland cancer, an osteosarcoma, a chondrosarcoma, a liposarcoma, a testes cancer, and a malignant fibrous histiocytoma, and other cancers.

Full Chromosome Aneuploidies.

As indicated above, there exists a high frequency of aneuploidy in cancer. In certain studies examining the prevalence of somatic copy number alterations (SCNAs) in cancer, it has been discovered that one-quarter of the genome of a typical cancer cell is affected either by whole-arm SCNAs or by the whole-chromosome SCNAs of aneuploidy (see, e.g., Beroukhim et al. Nature 463: 899-905 [2010]). Whole-chromosome alterations are recurrently observed in several cancer types. For example, the gain of chromosome 8 is seen in 10-20% of cases of acute myeloid leukaemia (AML), as well as some solid tumours, including Ewing's Sarcoma and desmoid tumours (see, e.g., Barnard et al. *Leukemia* 10: 5-12 [1996]; Maurici et al. *Cancer Genet. Cytogenet.* 100: 106-110 [1998]; Qi et al. *Cancer Genet. Cytogenet.* 92: 147-149 [1996]; Barnard, D. R. et al. *Blood* 100: 427-434 [2002]; and the like. Illustrative, but non-limiting list of chromosome gains and losses in human cancers are shown in Table 1.

TABLE 1

Illustrative specific, recurrent chromosome gains and losses in human cancer (see, e.g., Gordon et al. (2012) *Nature Rev. Genetics*, 13: 189-203).

| Chromosome | Gains Cancer Type | Losses Cancer Type |
|---|---|---|
| 1 | Multiple myeloma Adenocarcinoma (breast) | Adenocarcinoma (kidney) |
| 2 | Hepatoblastoma Ewing's sarcoma | |
| 3 | Multiple myeloma Diffuse large B-cell lymphoma | Melanoma Adenocarcinoma (kidney) |
| 4 | Acute lymphoblastic leukaemia | Adenocarcinoma (kidney) |
| 5 | Multiple myeloma Adenocarcinoma (kidney) | |
| 6 | Acute lymphoblastic leukaemia Wilms' tumour | Adenocarcinoma (kidney) |
| 7 | Adenocarcinoma (kidney) Adenocarcinoma (intestine) | Acute myeloid leukaemia Juvenile myelomonocytic leukaemia |
| 8 | Acute myeloid leukaemia Chronic myeloid leukaemia Ewing's sarcoma | Adenocarcinoma (kidney) |
| 9 | Multiple myeloma Polycythaemia vera | |
| 10 | Acute lymphoblastic leukaemia Adenocarcinoma (uterus) | Astrocytoma Multiple myeloma |
| 11 | Multiple myeloma | |
| 12 | Chronic lymphocytic leukaemia Wilms' tumor | Multiple myeloma |
| 13 | Acute myeloid leukaemia Wilms' tumor | Multiple myeloma |
| 14 | Acute lymphoblastic leukaemia | Adenocarcinoma (kidney) Meningioma |
| 15 | Multiple myeloma | |
| 16 | Adenocarcinoma (kidney) | Multiple myeloma |
| 17 | Adenocarcinoma (kidney) Acute lymphoblastic leukaemia | |
| 18 | Acute lymphoblastic leukaemia Wilms' tumour | Adenocarcinoma (kidney) |
| 19 | Multiple myeloma Chronic myeloid leukaemia | Adenocarcinoma (Breast) Meningioma |
| 20 | Hepatoblastoma Adenocarinoma (kidney) | |
| 21 | Acute lymphoblastic leukaemia Acute megakaryoblastic leukaemia | |
| 22 | Acute lymphoblastic leukaemia | Meningioma |
| X | Acute lymphoblastic leukaemia Follicular lymphoma | |
| Y | | |

In various embodiments, the methods described herein can be used to detect and/or quantify whole chromosome aneuploidies that are associated with cancer generally, and/or that are associated with particular cancers. Thus, for example, in certain embodiments, detection and/or quantification of whole chromosome aneuploidies characterized by the gains or losses shown in Table 1 are contemplated.

Arm Level Chromosomal Segment Copy Number Variations.

Multiple studies have reported patterns of arm-level copy number variations across large numbers of cancer specimens (Lin et al. *Cancer Res* 68, 664-673 (2008); George et al. *PLoS ONE* 2, e255 (2007); Demichelis et al. *Genes Chromosomes Cancer* 48: 366-380 (2009); Beroukhim et al. *Nature.* 463 (7283): 899-905 [2010]). It has additionally been observed that the frequency of arm-level copy number variations decreases with the length of chromosome arms. Adjusted for this trend, the majority of chromosome arms exhibit strong evidence of preferential gain or loss, but rarely both, across multiple cancer lineages (see, e.g., Beroukhim et al. *Nature.* 463(7283): 899-905 [2010]).

Accordingly, in one embodiment, methods described herein are used to determine arm level CNVs (CNVs comprising one chromosomal arm or substantially one chromosomal arm) in a sample. The CNVs can be determined in a CNVs in a test sample comprising a constitutional (germline) nucleic acid and the arm level CNVs can be identified in those constitutional nucleic acids. In certain embodiments arm level CNVs are identified (if present) in a sample comprising a mixture of nucleic acids (e.g., nucleic acids derived from normal and nucleic acids derived from neoplastic cells). In certain embodiments the sample is derived from a subject that is suspected or is known to have cancer e.g. carcinoma, sarcoma, lymphoma, leukemia, germ cell tumors, blastoma, and the like. In one embodiment, the sample is a plasma sample derived (processed) from peripheral blood that may comprise a mixture of cfDNA derived from normal and cancerous cells. In another embodiment, the biological sample that is used to determine whether a CNV is present is derived from a cells that, if a cancer is present, comprise a mixture of cancerous and non-cancerous cells from other biological tissues including, but not limited to biological fluids such as serum, sweat, tears, sputum, urine, sputum, ear flow, lymph, saliva, cerebrospinal fluid, ravages, bone marrow suspension, vaginal flow, transcervical lavage, brain fluid, ascites, milk, secretions of the respiratory, intestinal and genitourinary tracts, and leukophoresis samples, or in tissue biopsies, swabs, or smears. In other embodiments, the biological sample is a stool (fecal) sample.

In various embodiments the CNVs identified as indicative of the presence of a cancer or an increased risk for a cancer include, but are not limited to the arm level CNVs listed in Table 2. As illustrated in Table 2 certain CNVs that comprise a substantial arm-level gain are indicative of the presence of a cancer or an increased risk for a certain cancers. Thus, for example, a gain in 1q is indicative of the presence or increased risk for acute lymphoblastic leukemia (ALL), breast cancer, GIST, HCC, lung NSC, medulloblastoma, melanoma, MPD, ovarian cancer, and/or prostate cancer. A gain in 3q is indicative of the presence or increased risk for Esophageal Squamous cancer, Lung SC, and/or MPD. A gain in 7q is indicative of the presence or increased risk for colorectal cancer, glioma, HCC, lung NSC, medulloblastoma, melanoma, prostate cancer, and/or renal cancer. A gain in 7p is indicative of the presence or increased risk for breast cancer, colorectal cancer, esophageal adenocarcinoma, glioma, HCC, Lung NSC, medulloblastoma, melanoma, and/or renal cancer. A gain in 20q is indicative of the presence or increased risk for breast cancer, colorectal cancer, dedifferentiated liposarcoma, esophageal adenocarcinoma, esophageal squamous, glioma cancer, HCC, lung NSC, melanoma, ovarian cancer, and/or renal cancer, and so forth.

Similarly as illustrated in Table 2 certain CNVs that comprise a substantial arm-level loss are indicative of the presence of and/or an increased risk for certain cancers. Thus, for example, a loss in 1p is indicative of the presence or increased risk for gastrointestinal stromal tumor. A loss in 4q is indicative of the presence or increased risk for colorectal cancer, esophageal adenocarcinoma, lung sc, melanoma, ovarian cancer, and/or renal cancer. a loss in 17p is indicative of the presence or increased risk for breast cancer, colorectal cancer, esophageal adenocarcinoma, HCC, lung NSC, lung SC, and/or ovarian cancer, and the like.

TABLE 2

Significant arm-level chromosomal segment copy number alterations in each of 16 cancer subtypes (breast, colorectal, dedifferentiated liposarcoma, esophageal adenocarcinoma, esophageal squamous, GIST (gastrointestinal stromal tumor), glioma, HCC (hepatocellular carcinoma), lung NSC, lung SC, medulloblastoma, melanoma, MPD (myeloproliferative disease), ovarian, prostate, acute lymphoblastic leukemia (ALL), and renal) (see, e.g., Beroukhim et al. *Nature* (2010) 463(7283): 899-905).

| Arm | Cancer Types Significantly Gained In | Cancer Types Significantly Lost In | Known Oncogene/Tumor Suppressor Gene |
|---|---|---|---|
| 1p | — | GIST | |
| 1q | ALL, Breast, GIST, HCC, Lung NSC, Medulloblastoma, Melanoma, MPD, Ovarian, Prostate | — | |
| 3p | — | Esophageal Squamous, Lung NSC, Lung SC, Renal | VHL |
| 3q | Esophageal Squamous, Lung SC, MPD | — | |
| 4p | ALL | Breast, Esophageal Adenocarcinoma, Renal | |
| 4q | ALL | Colorectal, Esophageal Adenocarcinoma, Lung SC, Melanoma, Ovarian, Renal | |
| 5p | Esophageal Squamous, HCC, Lung NSC, Lung SC, Renal | — | TERT |
| 5q | HCC, Renal | Esophageal Adenocarcinoma, Lung NSC | APC |
| 6p | ALL, HCC, Lung NSC, Melanoma | — | |
| 6q | ALL | Melanoma, Renal | |
| 7p | Breast, Colorectal, Esophageal Adenocarcinoma, Glioma, HCC, Lung NSC, Medulloblastoma, Melanoma, Renal | — | EGFR |
| 7q | Colorectal, Glioma, HCC, Lung NSC, Medulloblastoma, Melanoma, Prostate, Renal | — | BRAF, MET |
| 8p | ALL, MPD | Breast, HCC, Lung NSC, Medulloblastoma, Prostate, Renal | |
| 8q | ALL, Breast, Colorectal, Esophageal Adenocarcinoma, Esophageal Squamous, HCC, Lung NSC, MPD, Ovarian, Prostate | Medulloblastoma | MYC |
| 9p | MPD | ALL, Breast, Esophageal Adenocarcinoma, Lung NSC, Melanoma, Ovarian, Renal | CDKN2A/B |
| 9q | ALL, MPD | Lung NSC, Melanoma, Ovarian, Renal | |
| 10p | ALL | Glioma, Lung SC, Melanoma | |
| 10q | ALL | Glioma, Lung SC, Medulloblastoma, Melanoma | PTEN |
| 11p | — | Medulloblastoma | WT1 |
| 11q | — | Dedifferentiated Liposarcoma, Medulloblastoma, Melanoma | ATM |
| 12p | Colorectal, Renal | — | KRAS |
| 12q | Renal | — | |
| 13q | Colorectal | Breast, Dedifferentiated Liposarcoma, Glioma, Lung NSC, Ovarian | RB1/BRCA2 |
| 14q | ALL, Lung NSC, Lung SC, Prostate | GIST, Melanoma, Renal | |
| 15q | — | GIST, Lung NSC, Lung SC, Ovarian | |
| 16p | Breast | — | |
| 16q | — | Breast, HCC, Medulloblastoma, Ovarian, Prostate | |

TABLE 2-continued

Significant arm-level chromosomal segment copy number alterations in each of 16 cancer subtypes (breast, colorectal, dedifferentiated liposarcoma, esophageal adenocarcinoma, esophageal squamous, GIST (gastrointestinal stromal tumor), glioma, HCC (hepatocellular carcinoma), lung NSC, lung SC, medulloblastoma, melanoma, MPD (myeloproliferative disease), ovarian, prostate, acute lymphoblastic leukemia (ALL), and renal) (see, e.g., Beroukhim et al. *Nature* (2010) 463(7283): 899-905).

| Arm | Cancer Types Significantly Gained In | Cancer Types Significantly Lost In | Known Oncogene/Tumor Suppressor Gene |
|---|---|---|---|
| 17p | ALL | Breast, Colorectal, Esophageal Adenocarcinoma, HCC, Lung NSC, Lung SC, Ovarian | TP53 |
| 17q | ALL, HCC, Lung NSC, Medulloblastoma | Breast, Ovarian | ERBB2, NF1/BRCA1 |
| 18p | ALL, Medulloblastoma | Colorectal, Lung NSC | |
| 18q | ALL, Medulloblastoma | Colorectal, Esophageal Adenocarcinoma, Lung NSC | SMAD2, SMAD4 |
| 19p | Glioma | Esophageal Adenocarcinoma, Lung NSC, Melanoma, Ovarian | |
| 19q | Glioma, Lung SC | Esophageal Adenocarcinoma, Lung NSC | |
| 20p | Breast, Colorectal, Esophageal Adenocarcinoma, Esophageal Squamous, GIST, Glioma, HCC, Lung NSC, Melanoma, Renal | — | |
| 20q | Breast, Colorectal, Dedifferentiated Liposarcoma, Esophageal Adenocarcinoma, Esophageal Squamous, Glioma, HCC, Lung NSC, Melanoma, Ovarian, Renal | — | |
| 21q | ALL, GIST, MPD | — | |
| 22q | Melanoma | Breast, Colorectal, Dedifferentiated Liposarcoma, Esophageal Adenocarcinoma, GIST, Lung NSC, Lung SC, Ovarian, Prostate | NF2 |

The examples of associations between arm level copy number variations are intended to be illustrative and not limiting. Other arm level copy number variations and their cancer associations are known to those of skill in the art.

Smaller, e.g., Focal, Copy Number Variations.

As indicated above, in certain embodiments, the methods described herein can be used to determine the presence or absence of a chromosomal amplification. In some embodiments, the chromosomal amplification is the gain of one or more entire chromosomes. In other embodiments, the chromosomal amplification is the gain of one or more segments of a chromosome. In yet other embodiments, the chromosomal amplification is the gain of two or more segments of two or more chromosomes. In various embodiments, the chromosomal amplification can involve the gain of one or more oncogenes.

Dominantly acting genes associated with human solid tumors typically exert their effect by overexpression or altered expression. Gene amplification is a common mechanism leading to upregulation of gene expression. Evidence from cytogenetic studies indicates that significant amplification occurs in over 50% of human breast cancers. Most notably, the amplification of the proto-oncogene human epidermal growth factor receptor 2 (HER2) located on chromosome 17 (17(17q21-q22)), results in overexpression of HER2 receptors on the cell surface leading to excessive and dysregulated signaling in breast cancer and other malignancies (Park et al., Clinical Breast Cancer 8:392-401 [2008]). A variety of oncogenes have been found to be amplified in other human malignancies. Examples of the amplification of cellular oncogenes in human tumors include amplifications of: c-myc in promyelocytic leukemia cell line HL60, and in small-cell lung carcinoma cell lines, N-myc in primary neuroblastomas (stages III and IV), neuroblastoma cell lines, retinoblastoma cell line and primary tumors, and small-cell lung carcinoma lines and tumors, L-myc in small-cell lung carcinoma cell lines and tumors, c-myb in acute myeloid leukemia and in colon carcinoma cell lines, c-erbb in epidermoid carcinoma cell, and primary gliomas, c-K-ras-2 in primary carcinomas of lung, colon, bladder, and rectum, N-ras in mammary carcinoma cell line (Varmus H., Ann Rev Genetics 18: 553-612 (1984) [cited in Watson et al., Molecular Biology of the Gene (4th ed.; Benjamin/Cummings Publishing Co. 1987)].

Duplications of oncogenes are a common cause of many types of cancer, as is the case with P70-S6 Kinase 1 amplification and breast cancer. In such cases the genetic duplication occurs in a somatic cell and affects only the genome of the cancer cells themselves, not the entire organism, much less any subsequent offspring. Other examples of oncogenes that are amplified in human cancers include MYC, ERBB2 (EFGR), CCND1 (Cyclin D1), FGFR1 and FGFR2 in breast cancer, MYC and ERBB2 in cervical cancer, HRAS, KRAS, and MYB in colorectal cancer, MYC, CCND1 and MDM2 in esophageal cancer, CCNE, KRAS and MET in gastric cancer, ERBB1, and CDK4 in glioblastoma, CCND1, ERBB1, and MYC in head and neck cancer, CCND1 in hepatocellular cancer, MYCB in neuroblastoma, MYC, ERBB2 and AKT2 in ovarian cancer, MDM2 and CDK4 in sarcoma, and MYC in small cell lung cancer. In one embodiment, the present method can be used to determine the presence or absence of amplification of an oncogene associated with a cancer. In some embodiments, the amplified oncogene is associated with breast cancer, cervical cancer, colorectal cancer, esophageal cancer, gastric cancer, glioblastoma, head and neck cancer, hepatocellular cancer, neuroblastoma, ovarian cancer, sarcoma, and small cell lung cancer.

In one embodiment, the present method can be used to determine the presence or absence of a chromosomal deletion. In some embodiments, the chromosomal deletion is the loss of one or more entire chromosomes. In other embodiments, the chromosomal deletion is the loss of one or more segments of a chromosome. In yet other embodiments, the chromosomal deletion is the loss of two or more segments of two or more chromosomes. The chromosomal deletion can involve the loss of one or more tumor suppressor genes.

Chromosomal deletions involving tumor suppressor genes are believed to play an important role in the development and progression of solid tumors. The retinoblastoma tumor suppressor gene (Rb-1), located in chromosome 13q14, is the most extensively characterized tumor suppressor gene. The Rb-1 gene product, a 105 kDa nuclear phosphoprotein, apparently plays an important role in cell cycle regulation (Howe et al., Proc Natl Acad Sci (USA) 87:5883-5887 [1990]). Altered or lost expression of the Rb protein is caused by inactivation of both gene alleles either through a point mutation or a chromosomal deletion. Rb-i gene alterations have been found to be present not only in retinoblastomas but also in other malignancies such as osteosarcomas, small cell lung cancer (Rygaard et al., Cancer Res 50: 5312-5317 [1990])) and breast cancer. Restriction fragment length polymorphism (RFLP) studies have indicated that such tumor types have frequently lost heterozygosity at 13q suggesting that one of the Rb-1 gene alleles has been lost due to a gross chromosomal deletion (Bowcock et al., Am J Hum Genet, 46: 12 [1990]). Chromosome 1 abnormalities including duplications, deletions and unbalanced translocations involving chromosome 6 and other partner chromosomes indicate that regions of chromosome 1, in particular 1q21-1q32 and 1p11-13, might harbor oncogenes or tumor suppressor genes that are pathogenetically relevant to both chronic and advanced phases of myeloproliferative neoplasms (Caramazza et al., Eur J Hematol 84:191-200 [2010]). Myeloproliferative neoplasms are also associated with deletions of chromosome 5. Complete loss or interstitial deletions of chromosome 5 are the most common karyotypic abnormality in myelodysplastic syndromes (MDSs). Isolated del(5q)/5q-MDS patients have a more favorable prognosis than those with additional karyotypic defects, who tend to develop myeloproliferative neoplasms (MPNs) and acute myeloid leukemia. The frequency of unbalanced chromosome 5 deletions has led to the idea that 5q harbors one or more tumor-suppressor genes that have fundamental roles in the growth control of hematopoietic stem/progenitor cells (HSCs/HPCs). Cytogenetic mapping of commonly deleted regions (CDRs) centered on 5q31 and 5q32 identified candidate tumor-suppressor genes, including the ribosomal subunit RPS14, the transcription factor Egr1/Krox20 and the cytoskeletal remodeling protein, alpha-catenin (Eisenmann et al., Oncogene 28:3429-3441 [2009]). Cytogenetic and allelotyping studies of fresh tumors and tumor cell lines have shown that allelic loss from several distinct regions on chromosome 3p, including 3p25, 3p21-22, 3p21.3, 3p12-13 and 3p14, are the earliest and most frequent genomic abnormalities involved in a wide spectrum of major epithelial cancers of lung, breast, kidney, head and neck, ovary, cervix, colon, pancreas, esophagus, bladder and other organs. Several tumor suppressor genes have been mapped to the chromosome 3p region, and are thought that interstitial deletions or promoter hypermethylation precede the loss of the 3p or the entire chromosome 3 in the development of carcinomas (Angeloni D., Briefings Functional Genomics 6:19-39 [2007]).

Newborns and children with Down syndrome (DS) often present with congenital transient leukemia and have an increased risk of acute myeloid leukemia and acute lymphoblastic leukemia. Chromosome 21, harboring about 300 genes, may be involved in numerous structural aberrations, e.g., translocations, deletions, and amplifications, in leukemias, lymphomas, and solid tumors. Moreover, genes located on chromosome 21 have been identified that play an important role in tumorigenesis. Somatic numerical as well as structural chromosome 21 aberrations are associated with leukemias, and specific genes including RUNX1, TMPRSS2, and TFF, which are located in 21q, play a role in tumorigenesis (Fonatsch C Gene Chromosomes Cancer 49:497-508 [2010]).

In view of the foregoing, in various embodiments the methods described herein can be used to determine the segment CNVs that are known to comprise one or more oncogenes or tumor suppressor genes, and/or that are known to be associated with a cancer or an increased risk of cancer. In certain embodiments, the CNVs can be determined in a test sample comprising a constitutional (germline) nucleic acid and the segment can be identified in those constitutional nucleic acids. In certain embodiments segment CNVs are identified (if present) in a sample comprising a mixture of nucleic acids (e.g., nucleic acids derived from normal and nucleic acids derived from neoplastic cells). In certain embodiments the sample is derived from a subject that is suspected or is known to have cancer e.g. carcinoma, sarcoma, lymphoma, leukemia, germ cell tumors, blastoma, and the like. In one embodiment, the sample is a plasma sample derived (processed) from peripheral blood that may comprise a mixture of cfDNA derived from normal and cancerous cells. In another embodiment, the biological sample that is used to determine whether a CNV is present is derived from a cells that, if a cancer is present, comprises a mixture of cancerous and non-cancerous cells from other biological tissues including, but not limited to biological fluids such as serum, sweat, tears, sputum, urine, sputum, ear flow, lymph, saliva, cerebrospinal fluid, ravages, bone marrow suspension, vaginal flow, transcervical lavage, brain fluid, ascites, milk, secretions of the respiratory, intestinal and genitourinary tracts, and leukophoresis samples, or in tissue biopsies, swabs, or smears. In other embodiments, the biological sample is a stool (fecal) sample.

The CNVs used to determine presence of a cancer and/or increased risk for a cancer can comprise amplification or deletions.

In various embodiments the CNVs identified as indicative of the presence of a cancer or an increased risk for a cancer include one or more of the amplifications shown in Table 3.

TABLE 3

Illustrative, but non-limiting chromosomal segments characterized by amplifications that are associated with cancers. Cancer types listed are those identified in Beroukhim et al. Nature 18: 463: 899-905.

| Peak region | Length (Mb) | Cancer types identified in this analysis but not prior publications |
|---|---|---|
| chr1: 119996566-120303234 | 0.228 | Breast, Lung SC, Melanoma |
| chr1: 148661965-149063439 | 0.35 | Breast, Dedifferentiated liposarcoma, Esophageal adenocarcinoma, Hepatocellular, Lung SC, Melanoma, Ovarian, Prostate, Renal |

TABLE 3-continued

Illustrative, but non-limiting chromosomal segments characterized by amplifications that are associated with cancers. Cancer types listed are those identified in Beroukhim et al. *Nature* 18: 463: 899-905.

| Peak region | Length (Mb) | Cancer types identified in this analysis but not prior publications |
|---|---|---|
| chr1: 1-5160566 | 4.416 | Esophageal adenocarcinoma, Ovarian |
| chr1: 158317017-159953843 | 1.627 | Dedifferentiated liposarcoma, Esophageal adenocarcinoma, Prostate, Renal |
| chr1: 169549478-170484405 | 0.889 | Colorectal, Dedifferentiated liposarcoma, Prostate, Renal |
| chr1: 201678483-203358272 | 1.471 | Prostate |
| chr1: 241364021-247249719 | 5.678 | Lung NSC, Melanoma, Ovarian |
| chr1: 39907605-40263248 | 0.319 | Acute lymphoblastic leukemia, Breast, Lung NSC, Lung SC |
| chr1: 58658784-60221344 | 1.544 | Breast, Dedifferentiated liposarcoma, Lung SC |
| chr3: 170024984-173604597 | 3.496 | Breast, Esophageal adenocarcinoma, Glioma |
| chr3: 178149984-199501827 | 21.123 | Esophageal squamous, Lung NSC |
| chr3: 86250885-95164178 | 8.795 | Lung SC, Melanoma |
| chr4: 54471680-55980061 | 1.449 | Lung NSC |
| chr5: 1212750-1378766 | 0.115 | Dedifferentiated liposarcoma |
| chr5: 174477192-180857866 | 6.124 | Breast, Lung NSC |
| chr5: 45312870-49697231 | 4.206 | Lung SC |
| chr6: 1-23628840 | 23.516 | Esophageal adenocarcinoma |
| chr6: 135561194-135665525 | 0.092 | Breast, Esophageal adenocarcinoma |
| chr6: 43556800-44361368 | 0.72 | Esophageal adenocarcinoma, Hepatocellular, Ovarian |
| chr6: 63255006-65243766 | 1.988 | Esophageal adenocarcinoma, Lung NSC |
| chr7: 115981465-116676953 | 0.69 | Esophageal adenocarcinoma, Lung NSC, Melanoma, Ovarian |
| chr7: 54899301-55275419 | 0.363 | Esophageal adenocarcinoma, Esophageal squamous |
| chr7: 89924533-98997268 | 9.068 | Breast, Esophageal adenocarcinoma, Esophageal squamous, Ovarian |
| chr8: 101163387-103693879 | 2.516 | Lung NSC, Melanoma, Ovarian |
| chr8: 116186189-120600761 | 4.4 | Breast, Hepatocellular, Lung NSC, Ovarian |
| chr8: 128774432-128849112 | 0.009 | Esophageal adenocarcinoma, Esophageal squamous, Hepatocellular, Lung SC, Medulloblastoma, Myeloproliferative disorder, Ovarian |
| chr8: 140458177-146274826 | 5.784 | Lung NSC, Medulloblastoma, Melanoma, Ovarian |
| chr8: 38252951-38460772 | 0.167 | Colorectal, Esophageal adenocarcinoma, Esophageal squamous |
| chr8: 42006632-42404492 | 0.257 | Esophageal adenocarcinoma, Lung NSC, Lung SC, Ovarian, Prostate |
| chr8: 81242335-81979194 | 0.717 | Breast, Melanoma |
| chr9: 137859478-140273252 | 2.29 | Colorectal, Dedifferentiated liposarcoma |
| chr 10: 74560456-82020637 | 7.455 | Breast, Ovarian, Prostate |
| chr11: 101433436-102134907 | 0.683 | Lung NSC, Lung SC |
| chr11: 32027116-37799354 | 5.744 | Breast, Dedifferentiated liposarcoma, Lung NSC, Lung SC |
| chr11: 69098089-69278404 | 0.161 | Dedifferentiated liposarcoma, Esophageal adenocarcinoma, Hepatocellular, Lung SC, Ovarian |
| chr11: 76699529-78005085 | 1.286 | Dedifferentiated liposarcoma, Esophageal adenocarcinoma, Lung SC, Ovarian |
| chr12: 1-1311104 | 1.271 | Lung NSC |
| chr12: 25189655-25352305 | 0.112 | Acute lymphoblastic leukemia, Esophageal adenocarcinoma, Esophageal squamous, Ovarian |
| chr12: 30999223-32594050 | 1.577 | Acute lymphoblastic leukemia, Colorectal, Esophageal adenocarcinoma, Esophageal squamous, Lung NSC, Lung SC |
| chr12: 38788913-42596599 | 3.779 | Breast, Colorectal, Dedifferentiated liposarcoma, Esophageal squamous, Lung NSC, Lung SC |
| chr12: 56419524-56488685 | 0.021 | Dedifferentiated, liposarcoma, Melanoma Renal |
| chr12: 64461446-64607139 | 0.041 | Dedifferentiated liposarcoma, Renal |
| chr12: 66458200-66543552 | 0.058 | Dedifferentiated liposarcoma, Esophageal squamous, Renal |
| chr12: 67440273-67566002 | 0.067 | Breast, Dedifferentiated liposarcoma, Esophageal squamous, Melanoma, Renal |
| chr12: 68249634-68327233 | 0.06 | Breast, Dedifferentiated liposarcoma, Esophageal squamous, Renal |
| chr12: 70849987-70966467 | 0.036 | Dedifferentiated liposarcoma, Renal |
| chr12: 72596017-73080626 | 0.23 | Renal |
| chr12: 76852527-77064746 | 0.158 | Dedifferentiated liposarcoma |
| chr12: 85072329-85674601 | 0.272 | Dedifferentiated liposarcoma |
| chr12: 95089777-95350380 | 0.161 | Dedifferentiated liposarcoma |
| chr13: 108477140-110084607 | 1.6 | Breast, Esophageal adenocarcinoma, Lung NSC, Lung SC |
| chr13: 1-40829685 | 22.732 | Acute lymphoblastic leukemia, Esophageal adenocarcinoma |
| chr13: 89500014-93206506 | 3.597 | Breast, Esophageal adenocarcinoma, Medulloblastoma |
| chr14: 106074644-106368585 | 0.203 | Esophageal squamous |

TABLE 3-continued

Illustrative, but non-limiting chromosomal segments characterized by amplifications that are associated with cancers. Cancer types listed are those identified in Beroukhim et al. *Nature* 18: 463: 899-905.

| Peak region | Length (Mb) | Cancer types identified in this analysis but not prior publications |
|---|---|---|
| chr14: 1-23145193 | 3.635 | Acute lymphoblastic leukemia, Esophageal squamous, Hepatocellular, Lung SC |
| chr14: 35708407-36097605 | 0.383 | Breast, Esophageal adenocarcinoma, Esophageal squamous, Hepatocellular, Prostate |
| chr15: 96891354-97698742 | 0.778 | Breast, Colorectal, Esophageal adenocarcinoma, Lung NSC, Medulloblastoma, Melanoma |
| chr17: 18837023-19933105 | 0.815 | Breast, Hepatocellular |
| chr17: 22479313-22877776 | 0.382 | Breast, Lung NSC |
| chr17: 24112056-24310787 | 0.114 | Breast, Lung NSC |
| chr17: 35067383-35272328 | 0.149 | Colorectal, Esophageal adenocarcinoma, Esophageal squamous |
| chr17: 44673157-45060263 | 0.351 | Melanoma |
| chr17: 55144989-55540417 | 0.31 | Lung NSC, Medulloblastoma, Melanoma, Ovarian |
| chr17: 62318152-63890591 | 1.519 | Breast, Lung NSC, Melanoma, Ovarian |
| chr17: 70767943-71305641 | 0.537 | Breast, Lung NSC, Melanoma, Ovarian |
| chr18: 17749667-22797232 | 5.029 | Colorectal, Esophageal adenocarcinoma, Ovarian |
| chr19: 34975531-35098303 | 0.096 | Breast, Esophageal adenocarcinoma, Esophageal squamous |
| chr19: 43177306-45393020 | 2.17 | Lung NSC, Ovarian |
| chr19: 59066340-59471027 | 0.321 | Breast, Lung NSC, Ovarian |
| chr2: 15977811-16073001 | 0.056 | Lung SC |
| chr20: 29526118-29834552 | 0.246 | Ovarian |
| chr20: 51603033-51989829 | 0.371 | Hepatocellular, Lung NSC, Ovarian |
| chr20: 61329497-62435964 | 0.935 | Hepatocellular, Lung NSC |
| chr22: 19172385-19746441 | 0.487 | Colorectal, Melanoma, Ovarian |
| chrX: 152729030-154913754 | 1.748 | Breast, Lung NSC, Renal |
| chrX: 66436234-67090514 | 0.267 | Ovarian, Prostate |

In certain embodiments in combination with the amplifications described above (herein), or separately, the CNVs identified as indicative of the presence of a cancer or an increased risk for a cancer include one or more of the deletions shown in Table 4.

TABLE 4

Illustrative, but non-limiting chromosomal segments characterized by deletions that are associated with cancers. Cancer types listed are those identified in Beroukhim et al. *Nature* 18: 463: 899-905.

| Peak region | Length (Mb) | Cancer types identified in this analysis but not prior publications |
|---|---|---|
| chr1: 110339388-119426489 | 1p13.2 | Acute lymphoblastic leukemia, Esophageal adenocarcinoma, Lung NSC, Lung SC, Melanoma, Ovarian, Prostate |
| chr1: 223876038-247249719 | 1q43 | Acute lymphoblastic leukemia, Breast, Lung SC, Melanoma, Prostate |
| chr1: 26377344-27532551 | 1p36.11 | Breast, Esophageal adenocarcinoma, Esophageal squamous, Lung NSC, Lung SC, Medulloblastoma, Myeloproliferative disorder, Ovarian, Prostate |
| chr1: 3756302-6867390 | 1p36.31 | Acute lymphoblastic leukemia, Breast, Esophageal squamous, Hepatocellular, Lung NSC, Lung SC, Medulloblastoma, Myeloproliferative disorder, Ovarian, Prostate, Renal |
| chr1: 71284749-74440273 | 1p31.1 | Breast, Esophageal adenocarcinoma, Glioma, Hepatocellular, Lung NSC, Lung SC, Melanoma, Ovarian, Renal |
| chr2: 1-15244284 | 2p25.3 | Lung NSC, Ovarian |
| chr2: 138479322-143365272 | 2q22.1 | Breast, Colorectal, Esophageal adenocarcinoma, Esophageal squamous, Hepatocellular, Lung NSC, Ovarian, Prostate, Renal |
| chr2: 204533830-206266883 | 2q33.2 | Esophageal adenocarcinoma, Hepatocellular, Lung NSC, Medulloblastoma, Renal |
| chr2: 241477619-242951149 | 2q37.3 | Breast, Dedifferentiated liposarcoma, Esophageal adenocarcinoma, Esophageal squamous, Hepatocellular, Lung NSC, |

TABLE 4-continued

Illustrative, but non-limiting chromosomal segments characterized by deletions that are associated with cancers. Cancer types listed are those identified in Beroukhim et al. Nature 18: 463: 899-905.

| Peak region | Length (Mb) | Cancer types identified in this analysis but not prior publications |
|---|---|---|
| chr3: 116900556-120107320 | 3q13.31 | Lung SC, Medulloblastoma, Melanoma, Ovarian, Renal Dedifferentiated liposarcoma, Esophageal adenocarcinoma, Hepatocellular, Lung NSC, Melanoma, Myeloproliferative disorder, Prostate |
| chr3: 1-2121282 | 3p26.3 | Colorectal, Dedifferentiated liposarcoma, Esophageal adenocarcinoma, Lung NSC, Melanoma, Myeloproliferative disorder |
| chr3: 175446835-178263192 | 3q26.31 | Acute lymphoblastic leukemia, Dedifferentiated liposarcoma, Esophageal adenocarcinoma, Lung NSC, Melanoma, Myeloproliferative disorder, Prostate |
| chr3: 58626894-61524607 | 3p14.2 | Breast, Colorectal, Dedifferentiated liposarcoma, Esophageal adenocarcinoma, Esophageal squamous, Hepatocellular, Lung NSC, Lung SC, Medulloblastoma, Melanoma, Myeloproliferative disorder, Ovarian, Prostate, Renal |
| chr4: 1-435793 | 4p16.3 | Myeloproliferative disorder |
| chr4: 186684565-191273063 | 4q35.2 | Breast, Esophageal adenocarcinoma, Esophageal squamous, Lung NSC, Medulloblastoma, Melanoma, Prostate, Renal |
| chr4: 91089383-93486891 | 4q22.1 | Acute lymphoblastic leukemia, Esophageal adenocarcinoma, Hepatocellular, Lung NSC, Renal |
| chr5: 177541057-180857866 | 5q35.3 | Breast, Lung NSC, Myeloproliferative disorder, Ovarian |
| chr5: 57754754-59053198 | 5q11.2 | Breast, Colorectal, Dedifferentiated liposarcoma, Esophageal adenocarcinoma, Esophageal squamous, Lung SC, Melanoma, Myeloproliferative disorder, Ovarian, Prostate |
| chr5: 85837489-133480433 | 5q21.1 | Colorectal, Dedifferentiated liposarcoma, Lung NSC, Lung SC, Myeloproliferative disorder, Ovarian |
| chr6: 101000242-121511318 | 6q22.1 | Colorectal, Lung NSC, Lung SC |
| chr6: 1543157-2570302 | 6p25.3 | Colorectal, Dedifferentiated liposarcoma, Esophageal adenocarcinoma, Lung NSC, Lung SC, Ovarian, Prostate |
| chr6: 161612277-163134099 | 6q26 | Colorectal, Esophageal adenocarcinoma, Esophageal squamous, Lung NSC, Lung SC, Ovarian, Prostate |
| chr6: 76630464-105342994 | 6q16.1 | Colorectal, Hepatocellular, Lung NSC |
| chr7: 141592807-142264966 | 7q34 | Breast, Colorectal, Esophageal adenocarcinoma, Esophageal squamous, Hepatocellular, Lung NSC, Ovarian, Prostate, Renal |
| chr7: 144118814-148066271 | 7q35 | Breast, Esophageal adenocarcinoma, Esophageal squamous, Lung NSC, Melanoma, Myeloproliferative disorder, Ovarian |
| chr7: 156893473-158821424 | 7q36.3 | Breast, Esophageal adenocarcinoma, Esophageal squamous, Lung NSC, Melanoma, Myeloproliferative disorder, Ovarian, Prostate |
| chr7: 3046420-4279470 | 7p22.2 | Melanoma, Myeloproliferative disorder, Ovarian |
| chr7: 65877239-79629882 | 7q21.11 | Breast, Medulloblastoma, Melanoma, Myeloproliferative disorder, Ovarian |
| chr8: 1-392555 | 8p23.3 | Acute lymphoblastic leukemia, Breast, Myeloproliferative disorder |
| chr8: 2053441-6259545 | 8p23.2 | Acute lymphoblastic leukemia, Dedifferentiated liposarcoma, Esophageal adenocarcinoma, Esophageal squamous, Hepatocellular, Lung NSC, Myeloproliferative disorder |
| chr8: 22125332-30139123 | 8p21.2 | Acute lymphoblastic leukemia, Dedifferentiated liposarcoma, Hepatocellular, Myeloproliferative disorder, Ovarian, Renal |

TABLE 4-continued

Illustrative, but non-limiting chromosomal segments characterized by deletions that are associated with cancers. Cancer types listed are those identified in Beroukhim et al. *Nature* 18: 463: 899-905.

| Peak region | Length (Mb) | Cancer types identified in this analysis but not prior publications |
|---|---|---|
| chr8: 39008109-41238710 | 8p11.22 | Acute lymphoblastic leukemia, Breast, Dedifferentiated liposarcoma, Esophageal squamous, Hepatocellular, Lung NSC, Myeloproliferative disorder, Renal |
| chr8: 42971602-72924037 | 8q11.22 | Breast, Dedifferentiated liposarcoma, Esophageal squamous, Hepatocellular, Lung NSC, Myeloproliferative disorder, Renal |
| chr9: 1-708871 | 9p24.3 | Acute lymphoblastic leukemia, Breast, Lung NSC, Myeloproliferative disorder, Ovarian, Prostate |
| chr9: 21489625-22474701 | 9p21.3 | Colorectal, Esophageal adenocarcinoma, Esophageal squamous, Myeloproliferative disorder, Ovarian |
| chr9: 36365710-37139941 | 9p13.2 | Myeloproliferative disorder |
| chr9: 7161607-12713130 | 9p24.1 | Acute lymphoblastic leukemia, Breast, Colorectal, Esophageal adenocarcinoma, Hepatocellular, Lung SC, Medulloblastoma, Melanoma, Myeloproliferative disorder, Ovarian, Prostate, Renal |
| chr10: 1-1042949 | 10p15.3 | Colorectal, Lung NSC, Lung SC, Ovarian, Prostate, Renal |
| chr10: 129812260-135374737 | 10q26.3 | Breast, Colorectal, Glioma, Lung NSC, Lung SC, Melanoma, Ovarian, Renal |
| chr10: 52313829-53768264 | 10q11.23 | Colorectal, Lung NSC, Lung SC, Ovarian, Renal |
| chr10: 89467202-90419015 | 10q23.31 | Breast, Lung SC, Ovarian, Renal |
| chr11: 107086196-116175885 | 11q23.1 | Esophageal adenocarcinoma, Medulloblastoma, Renal |
| chr11: 1-1391954 | 11p15.5 | Breast, Dedifferentiated liposarcoma, Esophageal adenocarcinoma, Lung NSC, Medulloblastoma, Ovarian |
| chr11: 130280899-134452384 | 11q25 | Esophageal adenocarcinoma, Esophageal squamous, Hepatocellular, Lung NSC, Medulloblastoma, Renal |
| chr11: 82612034-85091467 | 11q14.1 | Melanoma, Renal |
| chr12: 11410696-12118386 | 12p13.2 | Breast, Hepatocellular, Myeloproliferative disorder, Prostate |
| chr12: 131913408-132349534 | 12q24.33 | Dedifferentiated liposarcoma, Lung NSC, Myeloproliferative disorder |
| chr12: 97551177-99047626 | 12q23.1 | Breast, Colorectal, Esophageal squamous, Lung NSC, Myeloproliferative disorder |
| chr13: 111767404-114142980 | 13q34 | Breast, Hepatocellular, Lung NSC |
| chr13: 1-23902184 | 13q12.11 | Breast, Lung SC, Ovarian |
| chr13: 46362859-48209064 | 13q14.2 | Hepatocellular, Lung SC, Myeloproliferative disorder, Prostate |
| chr13: 92308911-94031607 | 13q31.3 | Breast, Hepatocellular, Lung NSC, Renal |
| chr14: 1-29140968 | 14q11.2 | Acute lymphoblastic leukemia, Esophageal adenocarcinoma, Myeloproliferative disorder |
| chr14: 65275722-67085224 | 14q23.3 | Dedifferentiated liposarcoma, Myeloproliferative disorder |
| chr14: 80741860-106368585 | 14q32.12 | Acute lymphoblastic leukemia, Dedifferentiated liposarcoma, Melanoma, Myeloproliferative disorder |
| chr15: 1-24740084 | 15q11.2 | Acute lymphoblastic leukemia, Breast, Esophageal adenocarcinoma, Lung NSC, Myeloproliferative disorder, Ovarian |
| chr15: 35140533-43473382 | 15q15.1 | Esophageal adenocarcinoma, Lung NSC, Myeloproliferative disorder |
| chr16: 1-359092 | 16p13.3 | Esophageal adenocarcinoma, Hepatocellular, Lung NSC, Renal |
| chr16: 31854743-53525739 | 16q11.2 | Breast, Hepatocellular, Lung NSC, Melanoma, Renal |
| chr16: 5062786-7709383 | 16p13.3 | Hepatocellular, Lung NSC, Medulloblastoma, Melanoma, Myeloproliferative disorder, Ovarian, Renal |
| chr16: 76685816-78205652 | 16q23.1 | Breast, Colorectal, Esophageal adenocarcinoma, Hepatocellular, Lung NSC, Lung SC, Medulloblastoma, Renal |

TABLE 4-continued

Illustrative, but non-limiting chromosomal segments characterized by deletions that are associated with cancers. Cancer types listed are those identified in Beroukhim et al. *Nature* 18: 463: 899-905.

| Peak region | Length (Mb) | Cancer types identified in this analysis but not prior publications |
|---|---|---|
| chr16: 80759878-82408573 | 16q23.3 | Colorectal, Hepatocellular, Renal |
| chr16: 88436931-88827254 | 16q24.3 | Colorectal, Hepatocellular, Lung NSC, Prostate, Renal |
| chr17: 10675416-12635879 | 17p12 | Lung NSC, Lung SC, Myeloproliferative disorder |
| chr17: 26185485-27216066 | 17q11.2 | Breast, Colorectal, Dedifferentiated liposarcoma, Lung NSC, Lung SC, Melanoma, Myeloproliferative disorder, Ovarian |
| chr17: 37319013-37988602 | 17q21.2 | Breast, Colorectal, Dedifferentiated liposarcoma, Lung SC, Melanoma, Myeloproliferative disorder, Ovarian |
| chr17: 7471230-7717938 | 17p13.1 | Lung SC, Myeloproliferative disorder |
| chr17: 78087533-78774742 | 17q25.3 | Colorectal, Myeloproliferative disorder |
| chr18: 1-587750 | 18p11.32 | Myeloproliferative disorder |
| chr18: 46172638-49935241 | 18q21.2 | Esophageal adenocarcinoma, Lung NSC |
| chr18: 75796373-76117153 | 18q23 | Colorectal, Esophageal adenocarcinoma, Esophageal squamous, Ovarian, Prostate |
| chr19: 1-526082 | 19p13.3 | Hepatocellular, Lung NSC, Renal |
| chr19: 21788507-34401877 | 19p12 | Hepatocellular, Lung NSC, Renal |
| chr19: 52031294-53331283 | 19q13.32 | Breast, Hepatocellular, Lung NSC, Medulloblastoma, Ovarian, Renal |
| chr19: 63402921-63811651 | 19q13.43 | Breast, Colorectal, Dedifferentiated liposarcoma, Hepatocellular, Lung NSC, Medulloblastoma, Ovarian, Renal |
| chr20: 1-325978 | 20p13 | Breast, Dedifferentiated liposarcoma, Lung NSC |
| chr20: 14210829-15988895 | 20p12.1 | Esophageal adenocarcinoma, Lung NSC, Medulloblastoma, Melanoma, Myeloproliferative disorder, Prostate, Renal |
| chr21: 38584860-42033506 | 21q22.2 | Breast |
| chr22: 20517661-21169423 | 22q11.22 | Acute lymphoblastic leukemia, Esophageal adenocarcinoma |
| chr22: 45488286-49691432 | 22q13.33 | Breast, Hepatocellular, Lung NSC, Lung SC |
| chrX: 1-3243111 | Xp22.33 | Esophageal adenocarcinoma, Lung NSC, Lung SC |
| chrX: 31041721-34564697 | Xp21.2 | Acute lymphoblastic leukemia, Esophageal adenocarcinoma, Glioma |

The anuploidies identified as characteristic of various cancers (e.g., the anuploidies identified in Tables 3 and 4) may contain genes known to be implicated in cancer etiologies (e.g., tumor suppressors, oncogenes, etc.). These aneuploidies can also be probed to identify relevant but previously unknown genes.

For example Beroukhim et al. supra, assessed potential cancer-causing genes in the copy number alterations using GRAIL (Gene Relationships Among Implicated Loci$_{20}$), an algorithm that searches for functional relationships among genomic regions. GRAIL scores each gene in a collection of genomic regions for its 'relatedness' to genes in other regions based on textual similarity between published abstracts for all papers citing the genes, on the notion that some target genes will function in common pathways. These methods permit identification/characterization of genes previously not associated with the particular cancers at issue. Table 5 illustrates target genes known to be within the identified amplified segment and predicted genes, and Table 6 illustrates target genes known to be within the identified deleted segment and predicted genes.

TABLE 5

Illustrative, but non-limiting chromosomal segments and genes known or predicted to be present in regions characterized by amplification in various cancers (see, e.g., Beroukhim et al. supra.).

| Chromosome and band | Peak region | # genes | Known target | GRAIL top target |
|---|---|---|---|---|
| 8q24.21 | chr8: 128774432-128849112 | 1 | MYC | MYC |
| 11q13.2 | chr11: 69098089-69278404 | 3 | CCND1 | ORAOV1 |
| 17q12 | chr17: 35067383-35272328 | 6 | ERBB2 | ERBB2, C17orf37 |
| 12q14.1 | chr12: 56419524-56488685 | 7 | CDK4 | TSPAN31 |
| 14q13.3 | chr14: 35708407-36097605 | 3 | NKX2-1 | NKX2-1 |

TABLE 5-continued

Illustrative, but non-limiting chromosomal segments and genes known or predicted to be present in regions characterized by amplification in various cancers (see, e.g., Beroukhim et al. supra.).

| Chromosome and band | Peak region | # genes | Known target | GRAIL top target |
|---|---|---|---|---|
| 12q15 | chr12: 67440273-67566002 | 1 | MDM2 | MDM2 |
| 7p11.2 | chr7: 54899301-55275419 | 1 | EGFR | EGFR |
| 1q21.2 | chr1: 148661965-149063439 | 9 | MCL1‡ | MCL1 |
| 8p12 | chr8: 38252951-38460772 | 3 | FGFR1 | FGFR1 |
| 12p12.1 | chr12: 25189655-25352305 | 2 | KRAS | KRAS |
| 19q12 | chr19: 34975531-35098303 | 1 | CCNE1 | CCNE1 |
| 22q11.21 | chr22: 19172385-19746441 | 11 | CRKL | CRKL |
| 12q15 | chr12: 68249634-68327233 | 2 | | LRRC10 |
| 12q14.3 | chr12: 64461446-64607139 | 1 | HMGA2 | HMGA2 |
| Xq28 | chrX: 152729030-154913754 | 53 | | SPRY3 |
| 5p15.33 | chr5: 1212750-1378766 | 3 | TERT | TERT |
| 3q26.2 | chr3: 170024984-173604597 | 22 | PRKCI | PRKCI |
| 15q26.3 | chr15: 96891354-97698742 | 4 | IGF1R | IGF1R |
| 20q13.2 | chr20: 51603033-51989829 | 1 | | ZNF217 |
| 8p11.21 | chr8: 42006632-42404492 | 6 | | PLAT |
| 1p34.2 | chr1: 39907605-40263248 | 7 | MYCL1 | MYCL1 |
| 17q21.33 | chr17: 44673157-45060263 | 4 | | NGFR, PHB |
| 2p24.3 | chr2: 15977811-16073001 | 1 | MYCN | MYCN |
| 7q21.3 | chr7: 89924533-98997268 | 62 | CDK6 | CDK6 |
| 13q34 | chr13: 108477140-110084607 | 4 | | IRS2 |
| 11q14.1 | chr11: 76699529-78005085 | 14 | | GAB2 |
| 20q13.33 | chr20: 61329497-62435964 | 38 | | BIRC7 |
| 17q23.1 | chr17: 55144989-55540417 | 5 | | RPS6KB1 |
| 1p12 | chr1: 119996566-120303234 | 5 | | REG4 |
| 8q21.13 | chr8: 81242335-81979194 | 3 | | ZNF704, ZBTB10 |
| 6p21.1 | chr6: 43556800-44361368 | 18 | | VEGFA |
| 5p11 | chr5: 45312870-49697231 | 0 | | |
| 20q11.21 | chr20: 29526118-29834552 | 5 | BCL2L1‡ | BCL2L1, ID1 |
| 6q23.3 | chr6: 135561194-135665525 | 1 | MYB** | hsa-mir-548a-2 |
| 1q44 | chr1: 241364021-247249719 | 71 | | AKT3 |
| 5q35.3 | chr5: 174477192-180857866 | 92 | | FLT4 |
| 7q31.2 | chr7: 115981465-116676953 | 3 | MET | MET |
| 18q11.2 | chr18: 17749667-22797232 | 21 | | CABLES1 |
| 17q25.1 | chr17: 70767943-71305641 | 13 | | GRB2, ITGB4 |
| 1p32.1 | chr1: 58658784-60221344 | 7 | JUN | JUN |
| 17q11.2 | chr17: 24112056-24310787 | 5 | | DHRS13, FLOT2, ERAL1, PHF12 |
| 17p11.2 | chr17: 18837023-19933105 | 12 | | MAPK7 |
| 8q24.11 | chr8: 116186189-120600761 | 13 | | NOV |
| 12q15 | chr12: 66458200-66543552 | 0 | | |
| 19q13.2 | chr19: 43177306-45393020 | 60 | | LGALS7, DYRK1B |
| 11q22.2 | chr11: 101433436-102134907 | 8 | BIRC2, YAP1 | BIRC2 |
| 4q12 | chr4: 54471680-55980061 | 7 | PDGFRA, KIT | KDR, KIT |
| 12p11.21 | chr12: 30999223-32594050 | 9 | | DDX11, FAM60A |
| 3q28 | chr3: 178149984-199501827 | 143 | PIK3CA | PIK3CA |
| 1p36.33 | chr1: 1-5160566 | 77 | | TP73 |
| 17q24.2 | chr17: 62318152-63890591 | 12 | | BPTF |
| 1q23.3 | chr1: 158317017-159953843 | 52 | | PEA15 |
| 1q24.3 | chr1: 169549478-170484405 | 6 | | BAT2D1, MYOC |
| 8q22.3 | chr8: 101163387-103693879 | 14 | | RRM2B |
| 13q31.3 | chr13: 89500014-93206506 | 3 | | GPC5 |
| 12q21.1 | chr12: 70849987-70966467 | 0 | | |
| 12p13.33 | chr12: 1-1311104 | 10 | | WNK1 |
| 12q21.2 | chr12: 76852527-77064746 | 0 | | |
| 1q32.1 | chr1: 201678483-203358272 | 21 | MDM4 | MDM4 |
| 19q13.42 | chr19: 59066340-59471027 | 19 | | PRKCG, TSEN34 |
| 12q12 | chr12: 38788913-42596599 | 12 | | ADAMTS20 |
| 12q23.1 | chr12: 95089777-95350380 | 2 | | ELK3 |
| 12q21.32 | chr12: 85072329-85674601 | 0 | | |
| 10q22.3 | chr10: 74560456-82020637 | 46 | | SFTPA1B |
| 3p11.1 | chr3: 86250885-95164178 | 8 | | POU1F1 |
| 17q11.1 | chr17: 22479313-22877776 | 1 | | WSB1 |

TABLE 5-continued

Illustrative, but non-limiting chromosomal segments and genes known or predicted to be present in regions characterized by amplification in various cancers (see, e.g., Beroukhim et al. supra.).

| Chromosome and band | Peak region | # genes | Known target | GRAIL top target |
|---|---|---|---|---|
| 8q24.3 | chr8: 140458177-146274826 | 97 | | PTP4A3, MAFA, PARP10 |
| Xq12 | chrX: 66436234-67090514 | 1 | AR | AR |
| 6q12 | chr6: 63255006-65243766 | 3 | | PTP4A1 |
| 14q11.2 | chr14: 1-23145193 | 95 | | BCL2L2 |
| 9q34.3 | chr9: 137859478-140273252 | 76 | | NRARP, MRPL41, TRAF2, LHX3 |
| 6p24.1 | chr6: 1-23628840 | 95 | | E2F3 |
| 13q12.2 | chr13: 1-40829685 | 110 | | FOXO1 |
| 12q21.1 | chr12: 72596017-73080626 | 0 | | |
| 14q32.33 | chr14: 106074644-106368585 | 0 | | |
| 11p13 | chr11: 32027116-37799354 | 35 | | WT1 |

TABLE 6

Illustrative, but non-limiting chromosomal segments and genes known or predicted to be present in regions charactierzed by amplification in various cancers (see, e.g., Beroukhim et al. supra.).

| Chromosome and band | Peak region | # genes | Known target | GRAIL top target |
|---|---|---|---|---|
| 9p21.3 | chr9: 21489625-22474701 | 5 | CDKN2A/B | CDKN2A |
| 3p14.2 | chr3: 58626894-61524607 | 2 | FHIT§ | FHIT |
| 16q23.1 | chr16: 76685816-78205652 | 2 | WWOX§ | WWOX |
| 9p24.1 | chr9: 7161607-12713130 | 3 | PTPRD§ | PTPRD |
| 20p12.1 | chr20: 14210829-15988895 | 2 | MACROD2§ | FLRT3 |
| 6q26 | chr6: 161612277-163134099 | 1 | PARK2§ | PARK2 |
| 13q14.2 | chr13: 46362859-48209064 | 8 | RB1 | RB1 |
| 2q22.1 | chr2: 138479322-143365272 | 3 | LRP1B§ | LRP1B |
| 4q35.2 | chr4: 186684565-191273063 | 15 | | FRG2, TUBB4Q |
| 5q11.2 | chr5: 57754754-59053198 | 5 | PDE4D§ | PLK2, PDE4D |
| 16p13.3 | chr16: 5062786-7709383 | 2 | A2BP1§ | A2BP1 |
| 7q34 | chr7: 141592807-142264966 | 3 | TRB@ | PRSS1 |
| 2q37.3 | chr2: 241477619-242951149 | 19 | | TMEM16G, ING5 |
| 19p13.3 | chr19: 1-526082 | 10 | | GZMM, THEG, PPAP2C, C19orf20 |
| 10q23.31 | chr10: 89467202-90419015 | 4 | PTEN | PTEN |
| 8p23.2 | chr8: 2053441-6259545 | 1 | CSMD1§ | CSMD1 |
| 1p36.31 | chr1: 3756302-6867390 | 23 | | DFFB, ZBTB48, AJAP1 |
| 4q22.1 | chr4: 91089383-93486891 | 2 | | MGC48628 |
| 18q23 | chr18: 75796373-76117153 | 4 | | PARD6G |
| 6p25.3 | chr6: 1543157-2570302 | 2 | | FOXC1 |
| 19q13.43 | chr19: 63402921-63811651 | 17 | | ZNF324 |
| Xp21.2 | chrX: 31041721-34564697 | 2 | DMD§ | DMD |
| 11q25 | chr11: 130280899-134452384 | 12 | OPCML§, HNT§ | HNT |
| 13q12.11 | chr13: 1-23902184 | 29 | | LATS2 |
| 22q13.33 | chr22: 45488286-49691432 | 38 | | TUBGCP6 |
| 15q11.2 | chr15: 1-24740084 | 20 | | A26B1 |
| 22q11.22 | chr22: 20517661-21169423 | 3 | | VPREB1 |
| 10q26.3 | chr10: 129812260-135374737 | 35 | | MGMT, SYCE1 |
| 12p13.2 | chr12: 11410696-12118386 | 2 | ETV6$ | ETV6 |
| 8p23.3 | chr8: 1-392555 | 2 | | ZNF596 |
| 1p36.11 | chr1: 26377344-27532551 | 24 | | SFN |
| 11p15.5 | chr11: 1-1391954 | 49 | | RASSF7 |
| 17q11.2 | chr17: 26185485-27216066 | 10 | NF1 | NF1 |
| 11q23.1 | chr11: 107086196-116175885 | 61 | ATM | CADM1 |
| 9p24.3 | chr9: 1-708871 | 5 | | FOXD4 |

TABLE 6-continued

Illustrative, but non-limiting chromosomal segments and genes known or predicted to be present in regions charactierzed by amplification in various cancers (see, e.g., Beroukhim et al. supra.).

| Chromosome and band | Peak region | # genes | Known target | GRAIL top target |
|---|---|---|---|---|
| 10q11.23 | chr10: 52313829-53768264 | 4 | PRKG1§ | DKK1, PRKG1 |
| 15q15.1 | chr15: 35140533-43473382 | 109 | | TUBGCP4 |
| 1p13.2 | chr1: 110339388-119426489 | 81 | | MAGI3 |
| Xp22.33 | chrX: 1-3243111 | 21 | | SHOX |
| 3p26.3 | chr3: 1-2121282 | 2 | | CHL1 |
| 9p13.2 | chr9: 36365710-37139941 | 2 | PAX5 | MELK |
| 17p13.1 | chr17: 7471230-7717938 | 10 | TP53 | ATP1B2 |
| 12q24.33 | chr12: 131913408-132349534 | 7 | | CHFR |
| 7q36.3 | chr7: 156893473-158821424 | 7 | PTPRN2§ | NCAPG2 |
| 6q16.1 | chr6: 76630464-105342994 | 76 | | FUT9, C6orf165, C6orf162, GJA10 |
| 5q21.1 | chr5: 85837489-133480433 | 142 | APC | APC |
| 8p11.22 | chr8: 39008109-41238710 | 7 | | C8orf4, ZMAT4 |
| 19q13.32 | chr19: 52031294-53331283 | 25 | | BBC3 |
| 10p15.3 | chr10: 1-1042949 | 4 | | TUBB8 |
| 1p31.1 | chr1: 71284749-74440273 | 4 | NEGR1§ | NEGR1 |
| 13q31.3 | chr13: 92308911-94031607 | 2 | GPC6§ | GPC6, DCT |
| 16q11.2 | chr16: 31854743-53525739 | 37 | | RBL2 |
| 20p13 | chr20: 1-325978 | 10 | | SOX12 |
| 5q35.3 | chr5: 177541057-180857866 | 43 | | SCGB3A1 |
| 1q43 | chr1: 223876038-247249719 | 173 | RYR2§ | FH, ZNF678 |
| 16p13.3 | chr16: 1-359092 | 16 | | HBZ |
| 17q21.2 | chr17: 37319013-37988602 | 22 | | CNP |
| 2p25.3 | chr2: 1-15244284 | 51 | | MYT1L |
| 3q13.31 | chr3: 116900556-120107320 | 1 | | LSAMP |
| 7q21.11 | chr7: 65877239-79629882 | 73 | MAGI2§ | CLDN4 |
| 7q35 | chr7: 144118814-148066271 | 3 | CNTNAP2§ | CNTNAP2 |
| 14q32.12 | chr14: 80741860-106368585 | 154 | | PRIMA1 |
| 16q24.3 | chr16: 88436931-88827254 | 9 | | C16orf3 |
| 3q26.31 | chr3: 175446835-178263192 | 1 | NAALADL2§ | NAALADL2 |
| 17q25.3 | chr17: 78087533-78774742 | 8 | | ZNF750 |
| 19p12 | chr19: 21788507-34401877 | 12 | | ZNF492, ZNF99 |
| 12q23.1 | chr12: 97551177-99047626 | 3 | ANKS1B§ | ANKS1B |
| 4p16.3 | chr4: 1-435793 | 4 | | ZNF141 |
| 18p11.32 | chr18: 1-587750 | 4 | | COLEC12 |
| 2q33.2 | chr2: 204533830-206266883 | 1 | PARD3B§ | PARD3B |
| 8p21.2 | chr8: 22125332-30139123 | 63 | | DPYSL2, STMN4 |
| 8q11.22 | chr8: 42971602-72924037 | 86 | SNTG1§ | FLJ23356, ST18, RB1CC1 |
| 16q23.3 | chr16: 80759878-82408573 | 2 | CDH13§ | CDH13 |
| 11q14.1 | chr11: 82612034-85091467 | 6 | DLG2§ | CCDC89, CCDC90B, TMEM126A |
| 14q23.3 | chr14: 65275722-67085224 | 7 | | GPHN, MPP5 |
| 7p22.2 | chr7: 3046420-4279470 | 1 | SDK1§ | SDK1 |
| 13q34 | chr13: 111767404-114142980 | 25 | | TUBGCP3 |
| 17p12 | chr17: 10675416-12635879 | 5 | MAP2K4 | MAP2K4, ZNF18 |
| 21q22.2 | chr21: 38584860-42033506 | 19 | DSCAM§, TMPRSS2/ERG$ | DSCAM |
| 18q21.2 | chr18: 46172638-49935241 | 7 | SMAD4, DCC§ | DCC |
| 6q22.1 | chr6: 101000242-121511318 | 87 | | GTF3C6, TUBE1, ROS1 |
| 14q11.2 | chr14: 1-29140968 | 140 | | ZNF219, NDRG2 |

In various embodiments, it is contemplated to use the methods identified herein to identify CNVs of segments comprising the amplified regions or genes identified in Table 5 and/or to use the methods identified herein to identify CNVs of segments comprising the deleted regions or genes identified in 6.

In one embodiment, the methods described herein provide a means to assess the association between gene amplification and the extent of tumor evolution. Correlation between amplification and/or deletion and stage or grade of a cancer may be prognostically important because such information may contribute to the definition of a genetically based tumor grade that would better predict the future course of disease with more advanced tumors having the worst prognosis. In addition, information about early amplification and/or deletion events may be useful in associating those events as predictors of subsequent disease progression.

Gene amplification and deletions as identified by the method can be associated with other known parameters such as tumor grade, histology, Brd/Urd labeling index, hormonal status, nodal involvement, tumor size, survival duration and other tumor properties available from epidemiological and biostatistical studies. For example, tumor DNA to be tested by the method could include atypical hyperplasia, ductal carcinoma in situ, stage I-III cancer and metastatic lymph nodes in order to permit the identification of associations between amplifications and deletions and stage. The associations made may make possible effective therapeutic intervention. For example, consistently amplified regions may contain an overexpressed gene, the product of which may be able to be attacked therapeutically (for example, the growth factor receptor tyrosine kinase, $p185^{HER2}$).

In various embodiments, the methods described herein can be used to identify amplification and/or deletion events that are associated with drug resistance by determining the copy number variation of nucleic acid sequences from primary cancers to those of cells that have metastasized to other sites. If gene amplification and/or deletion is a manifestation of karyotypic instability that allows rapid development of drug resistance, more amplification and/or deletion in primary tumors from chemoresistant patients than in tumors in chemosensitive patients would be expected. For example, if amplification of specific genes is responsible for the development of drug resistance, regions surrounding those genes would be expected to be amplified consistently in tumor cells from pleural effusions of chemoresistant patients but not in the primary tumors. Discovery of associations between gene amplification and/or deletion and the development of drug resistance may allow the identification of patients that will or will not benefit from adjuvant therapy.

In a manner similar to that described for determining the presence or absence of complete and/or partial fetal chromosomal aneuploidies in a maternal sample, methods, apparatus, and systems described herein can be used to determine the presence or absence of complete and/or partial chromosomal aneuploidies in any patient sample comprising nucleic acids e.g. DNA or cfDNA (including patient samples that are not maternal samples). The patient sample can be any biological sample type as described elsewhere herein. Preferably, the sample is obtained by non-invasive procedures. For example, the sample can be a blood sample, or the serum and plasma fractions thereof. Alternatively, the sample can be a urine sample or a fecal sample. In yet other embodiments, the sample is a tissue biopsy sample. In all cases, the sample comprises nucleic acids e.g. cfDNA or genomic DNA, which is purified, and sequenced using any of the NGS sequencing methods described previously.

Both complete and partial chromosomal aneuploidies associated with the formation, and progression of cancer can be determined according to the present method.

In various embodiments, when using the methods described herein to determine the presence and/or increased risk of cancer normalization of the data can be made with respect to the chromosome(s) for which the CNV is determined. In certain embodiments normalization of the data can be made with respect to the chromosome arm(s) for which the CNV is determined. In certain embodiments, normalization of the data can be made with respect to the particular segment (s) for which the CNV is determined.

In addition to the role of CNV in cancer, CNVs have been associated with a growing number of common complex disease, including human immunodeficiency virus (HIV), autoimmune diseases and a spectrum of neuropsychiatric disorders.

CNVs in Infectious and Autoimmune Disease

To date a number of studies have reported association between CNV in genes involved in inflammation and the immune response and HIV, asthma, Crohn's disease and other autoimmune disorders (Fanciulli et al., Clin Genet 77:201-213 [2010]). For example, CNV in CCL3L1, has been implicated in HIV/AIDS susceptibility (CCL3L1, 17q11.2 deletion), rheumatoid arthritis (CCL3L1, 17q11.2 deletion), and Kawasaki disease (CCL3L1, 17q11.2 duplication); CNV in HBD-2, has been reported to predispose to colonic Crohn's disease (HDB-2, 8p23.1 deletion) and psoriasis (HDB-2, 8p23.1 deletion); CNV in FCGR3B, was shown to predispose to glomerulonephritis in systemic lupus erthematosous (FCGR3B, 1q23 deletion, 1q23 duplication), anti-neutrophil cytoplasmic antibody (ANCA)-associated vasculatis (FCGR3B, 1q23 deletion), and increase the risk of developing rheumatoid arthritis. There are at least two inflammatory or autoimmune diseases that have been shown to be associated with CNV at different gene loci. For example, Crohn's disease is associated with low copy number at HDB-2, but also with a common deletion polymorphism upstream of the IGRM gene that encodes a member of the p47 immunity-related GTPase family. In addition to the association with FCGR3B copy number, SLE susceptibility has also been reported to be significantly increased among subjects with a lower number of copies of complement component C4.

Associations between genomic deletions at the GSTM1 (GSTM1, 1q23deletion) and GSTT1 (GSTT1, 22q11.2 deletion) loci and increased risk of atopic asthma have been reported in a number of independent studies. In some embodiments, the methods described herein can be used to determine the presence or absence of a CNV associated with inflammation and/or autoimmune diseases. For example, the methods can be used to determine the presence of a CNV in a patient suspected to be suffering from HIV, asthma, or Crohn's disease. Examples of CNV associated with such diseases include without limitation deletions at 17q11.2, 8p23.1, 1q23, and 22q11.2, and duplications at 17q11.2, and 1q23. In some embodiments, the present method can be used to determine the presence of CNV in genes including but not limited to CCL3L1, HBD-2, FCGR3B, GSTM, GSTT1, C4, and IRGM.

CNV Diseases of the Nervous System

Associations between de novo and inherited CNV and several common neurological and psychiatric diseases have been reported in autism, schizophrenia and epilepsy, and some cases of neurodegenerative diseases such as Parkinson's disease, amyotrophic lateral sclerosis (ALS) and autosomal dominant Alzheimer's disease (Fanciulli et al., Clin Genet 77:201-213 [2010]). Cytogenetic abnormalities have been observed in patients with autism and autism spectrum disorders (ASDs) with duplications at 15q11-q13. According to the Autism Genome project Consortium, 154 CNV including several recurrent CNVs, either on chromosome 15q11-q13 or at new genomic locations including chromosome 2p16, 1q21 and at 17p12 in a region associated with Smith-Magenis syndrome that overlaps with ASD. Recurrent microdeletions or microduplications on chromosome 16p11.2 have highlighted the observation that de novo CNVs are detected at loci for genes such as SHANK3 (22q13.3 deletion), neurexin 1 (NRXN1, 2p16.3 deletion) and the neuroglins (NLGN4, Xp22.33 deletion) that are known to regulate synaptic differentiation and regulate glutaminergic neurotransmitter release. Schizophrenia has also been associated with multiple de novo CNVs. Microdeletions and microduplications associated with schizophrenia contain an overrepresentation of genes belonging to neurodevelopmental and glutaminergic pathways, suggesting that multiple CNVs affecting these genes may contribute directly to the pathogenesis of schizophrenia e.g. ERBB4, 2q34 deletion, SLC1A3, 5p13.3 deletion; RAPEGF4, 2q31.1 deletion; CIT, 12.24 deletion; and multiple genes with de novo CNV. CNVs have also been associated with other neurological disorders including epilepsy (CHRNA7, 15q13.3 deletion), Parkinson's disease (SNCA 4q22 duplication) and ALS (SMN1, 5q12.2.-q13.3 deletion; and SMN2 deletion). In some embodiments, the methods described herein can be used to determine the presence or absence of a CNV associated with diseases of the nervous system. For example, the methods can be used to determine the presence of a CNV in a patient suspected to be suffering from autisim, schizophrenia, epilepsy, neurodegenerative diseases such as Parkinson's disease, amyotrophic lateral sclerosis (ALS) or autosomal dominant Alzheimer's disease. The methods can be used to determine CNV of genes associated with diseases of the nervous system including without limitation any of the Autism Spectrum Disorders (ASD), schizophrenia, and epilepsy, and CNV of genes associated with neurodegenerative disorders such as Parkinson's disease. Examples of CNV associated with such diseases include without limitation duplications at 15q11-q13, 2p16, 1q21, 17p12, 16p11.2, and 4q22, and deletions at 22q13.3, 2p16.3, Xp22.33, 2q34, 5p13.3, 2q31.1, 12.24, 15q13.3, and 5q12.2. In some embodiments, the methods can be used to determine the presence of CNV in genes including but not limited to SHANK3, NLGN4, NRXN1, ERBB4, SLC1A3, RAPGEF4, CIT, CHRNA7, SNCA, SMN1, and SMN2.

CNV and Metabolic or Cardiovascular Diseases

The association between metabolic and cardiovascular traits, such as familial hypercholesterolemia (FH), atherosclerosis and coronary artery disease, and CNVs has been reported in a number of studies (Fanciulli et al., Clin Genet 77:201-213 [2010]). For example, germline rearrangements, mainly deletions, have been observed at the LDLR gene (LDLR, 19p13.2 deletion/duplication) in some FH patients who carry no other LDLR mutations. Another example is the LPA gene that encodes apolipoprotein(a) (apo(a)) whose plasma concentration is associated with risk of coronary artery disease, myocardial infarction (MI) and stroke. Plasma concentrations of the apo(a) containing lipoprotein Lp(a) vary over 1000-fold between individuals and 90% of this variability is genetically determined at the LPA locus, with plasma concentration and Lp(a) isoform size being proportional to a highly variable number of 'kringle 4' repeat sequences (range 5-50). These data indicate that CNV in at least two genes can be associated with cardiovascular risk. The methods described herein can be used in large studies to search specifically for CNV associations with cardiovascular disorders. In some embodiments, the present method can be used to determine the presence or absence of a CNV associated with metabolic or cardiovascular disease. For example, the present method can be used to determine the presence of a CNV in a patient suspected to be suffering from familial hypercholesterolemia. The methods described herein can be used to determine CNV of genes associated with metabolic or cardiovascular disease e.g. hypercholesterolemia. Examples of CNV associated with such diseases include without limitation 19p13.2 deletion/duplication of the LDLR gene, and multiplications in the LPA gene.

Determination of Complete Chromosomal Aneuploidies in Patient Samples

In one embodiment, method are provided for determining the presence or absence of any one or more different complete chromosomal aneuploidies in a patient test sample comprising nucleic acid molecules. In some embodiments, the method determines the presence or absence of any one or more different complete chromosomal aneuploidies. The steps of the method comprise (a) obtaining sequence information for the patient nucleic acids in the patient test sample; and (b) using the sequence information to identify a number of sequence tags for each of any one or more chromosomes of interest selected from chromosomes 1-22, X and Y and to identify a number of sequence tags for a normalizing chromosome sequence for each of the any one or more chromosomes of interest. The normalizing chromosome sequence can be a single chromosome, or it can be a group of chromosomes selected from chromosomes 1-22, X, and Y. The method further uses in step (c) the number of sequence tags identified for each of the any one or more chromosomes of interest and the number of sequence tags identified for each normalizing chromosome sequence to calculate a single chromosome dose for each of the any one or more chromosomes of interest; and (d) compares each of the single chromosome doses for each of the any one or more chromosomes of interest to a threshold value for each of the one or more chromosomes of interest, thereby determining the presence or absence of any one or more different complete patient chromosomal aneuploidies in the patient test sample.

In some embodiments, step (c) comprises calculating a single chromosome dose for each chromosomes of interest as the ratio of the number of sequence tags identified for each of the chromosomes of interest and the number of sequence tags identified for the normalizing chromosome for each of the chromosomes of interest.

In other embodiments, step (c) comprises calculating a single chromosome dose for each of the chromosomes of interest as the ratio of the number of sequence tags identified for each of the chromosomes of interest and the number of sequence tags identified for the normalizing chromosome for each of the chromosomes of interest. In other embodiments, step (c) comprises calculating a sequence tag ratio for a chromosome of interest by relating the number of sequence tags obtained for the chromosome of interest to the length of the chromosome of interest, and relating the number of tags for the corresponding normalizing chromosome sequence for the chromosome of interest to the length of the normalizing chromosome sequence, and calculating a chromosome dose for the chromosome of interest as a ratio of the sequence tags density of the chromosome of interest and the sequence tag density for the normalizing sequence. The calculation is repeated for each of all chromosomes of interest. Steps (a)-(d) can be repeated for test samples from different patients.

An example of the embodiment whereby one or more complete chromosomal aneuploidies are determined in a cancer patient test sample comprising cell-free DNA molecules, comprises: (a) sequencing at least a portion of cell-free DNA molecules to obtain sequence information for the patient cell-free DNA molecules in the test sample; (b) using the sequence information to identify a number of sequence tags for each of any twenty or more chromosomes of interest selected from chromosomes 1-22, X, and Y and to identify a number of sequence tags for a normalizing chromosome for each of the twenty or more chromosomes of interest; (c) using the number of sequence tags identified for each of the twenty or more chromosomes of interest and the number of sequence tags identified for each the normalizing chromosome to calculate a single chromosome dose for each of the twenty or more chromosomes of interest; and (d) comparing each of the single chromosome doses for each of the twenty or more chromosomes of interest to a threshold value for each of the twenty or more chromosomes of interest, and thereby determining the presence or absence of any twenty or more different complete chromosomal aneuploidies in the patient test sample.

In another embodiment, the method for determining the presence or absence of any one or more different complete chromosomal aneuploidies in a patient test sample as described above uses a normalizing segment sequence for determining the dose of the chromosome of interest. In this instance, the method comprises (a) obtaining sequence information for the nucleic acids in the sample; (b) using the sequence information to identify a number of sequence tags for each of any one or more chromosomes of interest selected from chromosomes 1-22, X and Y and to identify a number of sequence tags for a normalizing segment sequence for each of any one or more chromosomes of interest. The normalizing segment sequence can be a single segment of a chromosome or it can be a group of segments form one or more different chromosomes. The method further uses in step (c) the number of sequence tags identified for each of said any one or more chromosomes of interest and said number of sequence tags identified for said normalizing segment sequence to calculate a single chromosome dose for each of said any one or more chromosomes of interest; and (d) comparing each of said single chromosome doses for each of said any one or more chromosomes of interest to a threshold value for each of said one or more chromosomes of interest, and thereby determining the presence or absence of one or more different complete chromosomal aneuploidies in the patient sample.

In some embodiments, step (c) comprises calculating a single chromosome dose for each of said chromosomes of interest as the ratio of the number of sequence tags identified for each of said chromosomes of interest and the number of sequence tags identified for said normalizing segment sequence for each of said chromosomes of interest.

In other embodiments, step (c) comprises calculating a sequence tag ratio for a chromosome of interest by relating the number of sequence tags obtained for the chromosome of interest to the length of the chromosome of interest, and relating the number of tags for the corresponding normalizing segment sequence for the chromosome of interest to the length of the normalizing segment sequence, and calculating a chromosome dose for the chromosome of interest as a ratio of the sequence tags density of the chromosome of interest and the sequence tag density for the normalizing segment sequence. The calculation is repeated for each of all chromosomes of interest. Steps (a)-(d) can be repeated for test samples from different patients.

A means for comparing chromosome doses of different sample sets is provided by determining a normalized chromosome value (NCV), which relates the chromosome dose in a test sample to the mean of the of the corresponding chromosome dose in a set of qualified samples. The NCV is calculated as:

$$NCV_{ij} = \frac{x_{ij} - \hat{\mu}_j}{\hat{\sigma}_j}$$

where $\hat{\mu}_j$ and $\hat{\sigma}_j$ are the estimated mean and standard deviation, respectively, for the j-th chromosome dose in a set of qualified samples, and $x_{ij}$ is the observed j-th chromosome dose for test sample i.

In some embodiments, the presence or absence of one complete chromosomal aneuploidy is determined. In other embodiments, the presence or absence of two, three, four, five, six, seven, eight, nine, ten, eleven, twelve, thirteen, fourteen, fifteen, sixteen, seventeen, eighteen, nineteen, twenty, twenty-one, twenty-two, twenty-three, or twenty four complete chromosomal aneuploidies are determined in a sample, wherein twenty-two of the complete chromosomal aneuploidies correspond to complete chromosomal aneuploidies of any one or more of the autosomes; the twenty-third and twenty fourth chromosomal aneuploidy correspond to a complete chromosomal aneuploidy of chromosomes X and Y. As aneuploidies can comprise trisomies, tetrasomies, pentasomies and other polysomies, and the number of complete chromosomal aneuploidies varies in different diseases and in different stages of the same disease, the number of complete chromosomal aneuploidies that are determined according to the present method are at least 24, at least 25, at least 26, at least 27, at least 28, at least 29, at least 30 complete, at least 40, at least 50, at least 60, at least 70, at least 80, at least 90, at least 100 or more chromosomal aneuploidies. Systematic karyotyping of tumors has revealed that the chromosome number in cancer cells is highly variable, ranging from hypodiploidy (considerably fewer than 46 chromosomes) to tetraploidy and hypertetraploidy (up to 200 chromosomes) (Storchova and Kuffer J Cell Sci 121:3859-3866 [2008]). In some embodiments, the method comprises determining the presence or absence of up to 200 or more chromosomal aneuploidies in a sample form a patient suspected or known to be suffering from cancer e.g. colon cancer. The chromosomal aneuploidies include losses of one or more complete chromosomes (hypodiploidies), gains of complete chromosomes including trisomies, tetrasomies, pentasomies, and other polysomies. Gains and/or losses of segments of chromosomes can also be determined as described elsewhere herein. The method is applicable to determining the presence or absence of different aneuploidies in samples from patients suspected or known to be suffering from any cancer as described elsewhere herein.

In some embodiments, any one of chromosomes 1-22, X and Y, can be the chromosome of interest in determining the presence or absence of any one or more different complete chromosomal aneuploidies in a patient test sample as described above. In other embodiments, two or more chromosomes of interest are selected from any two or more of chromosomes 1, 2, 3, 4, 5, 6, 7, 8, 9, 10, 11, 12, 13, 14, 15, 16, 17, 18, 19, 20, 21, 22, X, or Y. In one embodiment, any one or more chromosomes of interest are selected from chromosomes 1-22, X, and Y comprise at least twenty chromosomes selected from chromosomes 1-22, X, and Y, and wherein the presence or absence of at least twenty different complete chromosomal aneuploidies is determined. In other embodiments, any one or more chromosomes of interest selected from chromosomes 1-22, X, and Y is all of chromosomes 1-22, X, and Y, and wherein the presence or absence of complete chromosomal aneuploidies of all of chromosomes 1-22, X, and Y is determined. Complete different chromosomal aneuploidies that can be determined include complete chromosomal monosomies of any one or more of chromosomes 1-22, X and Y; complete chromosomal trisomies of any one or more of chromosomes 1-22, X and Y; complete chromosomal tetrasomies of any one or more of chromosomes 1-22, X and Y; complete chromosomal pentasomies of any one or more of chromosomes 1-22, X and Y; and other complete chromosomal polysomies of any one or more of chromosomes 1-22, X and Y.

Determination of Partial Chromosomal Aneuploidies in Patient Samples

In another embodiment, methods for determining the presence or absence of any one or more different partial chromosomal aneuploidies in a patient test sample comprising nucleic acid molecules are provided. The steps of the method comprise (a) obtaining sequence information for the patient nucleic acids in the sample; and (b) using the sequence information to identify a number of sequence tags for each of any one or more segments of any one or more chromosomes of interest selected from chromosomes 1-22, X, and Y and to identify a number of sequence tags for a normalizing segment sequence for each of any one or more segments of any one or more chromosomes of interest. The normalizing segment sequence can be a single segment of a chromosome or it can be a group of segments form one or more different chromosomes. The method further uses in step (c) the number of sequence tags identified for each of any one or more segments of any one or more chromosomes of interest and the number of sequence tags identified for the normalizing segment sequence to calculate a single segment dose for each of any one or more segments of any one or more chromosome of interest; and (d) comparing each of the single chromosome doses for each of any one or more segments of any one or more chromosomes of interest to a threshold value for each of said any one or more chromosomal segments of any one or more chromosome of interest, and thereby determining the presence or absence of one or more different partial chromosomal aneuploidies in said sample.

In some embodiments, step (c) comprises calculating a single segment dose for each of any one or more segments of any one or more chromosomes of interest as the ratio of the number of sequence tags identified for each of any one or more segments of any one or more chromosomes of interest and the number of sequence tags identified for the normalizing segment sequence for each of any one or more segments of any one or more chromosomes of interest.

In other embodiments, step (c) comprises calculating a sequence tag ratio for a segment of interest by relating the number of sequence tags obtained for the segment of interest to the length of the segment of interest, and relating the number of tags for the corresponding normalizing segment sequence for the segment of interest to the length of the normalizing segment sequence, and calculating a segment dose for the segment of interest as a ratio of the sequence tags density of the segment of interest and the sequence tag density for the normalizing segment sequence. The calculation is repeated for each of all chromosomes of interest. Steps (a)-(d) can be repeated for test samples from different patients.

A means for comparing segment doses of different sample sets is provided by determining a normalized segment value (NSV), which relates the segment dose in a test sample to the mean of the of the corresponding segment dose in a set of qualified samples. The NSV is calculated as:

$$NSV_{ij} = \frac{x_{ij} - \hat{\mu}_j}{\hat{\sigma}_j}$$

where $\hat{\mu}_j$ and $\hat{\sigma}_j$ are the estimated mean and standard deviation, respectively, for the j-th segment dose in a set of qualified samples, and $x_{ij}$ is the observed j-th segment dose for test sample i.

In some embodiments, the presence or absence of one partial chromosomal aneuploidy is determined. In other embodiments, the presence or absence of two, three, four, five, six, seven, eight, nine, ten, fifteen, twenty, twenty-five, or more partial chromosomal aneuploidies are determined in a sample. In one embodiment, one segment of interest selected from any one of chromosomes 1-22, X, and Y is selected from chromosomes 1-22, X, and Y. In another embodiment, two or more segments of interest selected from chromosomes 1-22, X, and Y are selected from any two or more of chromosomes 1, 2, 3, 4, 5, 6, 7, 8, 9, 10, 11, 12, 13, 14, 15, 16, 17, 18, 19, 20, 21, 22, X, or Y. In one embodiment, any one or more segments of interest are selected from chromosomes 1-22, X, and Y comprise at least one, five, ten, 15, 20, 25, 50, 75, 100 or more segments selected from chromosomes 1-22, X, and Y, and wherein the presence or absence of at least one, five, ten, 15, 20, 25, 50, 75, 100, or more different partial chromosomal aneuploidies is determined. Different partial chromosomal aneuploidies that can be determined include chromosomal aneuploidies include partial duplications, partial multiplications, partial insertions and partial deletions.

Samples that can be used for determining the presence or absence of a chromosomal aneuploidy (partial or complete) in a patient can be any of the biological samples described elsewhere herein. The type of sample or samples that can be used for the determination of aneuploidy in a patient will depend on the type of disease from which the patient is known or suspected to be suffering. For example, a stool sample can be chosen as a source of DNA to determine the presence or absence of aneuploidies associated with colorectal cancer. The method is also applicable to tissue samples as described herein. Preferably, the sample is a biological sample that is obtained by non-invasive means e.g. a plasma sample. As described elsewhere herein, sequencing of the nucleic acids in the patient sample can be performed using next generation sequencing (NGS) as described elsewhere herein. In some embodiments, sequencing is massively parallel sequencing using sequencing-by-synthesis with reversible dye terminators. In other embodiments, sequencing is sequencing-by-ligation. In yet other embodiments, sequencing is single molecule sequencing. Optionally, an amplification step is performed prior to sequencing.

In some embodiments, the presence or absence of an aneuploidy is determined in a patient suspected to be suffering from a cancer as described elsewhere herein e.g. lung, breast, kidney, head and neck, ovary, cervix, colon, pancreas, esophagus, bladder and other organs, and blood cancers. Blood cancers include cancers of the bone marrow, blood, and lymphatic system, which includes lymph nodes, lymphatic vessels, tonsils, thymus, spleen, and digestive tract lymphoid tissue. Leukemia and myeloma, which start in the bone marrow, and lymphoma, which starts in the lymphatic system, are the most common types of blood cancer.

The determination of the presence or absence of one or more chromosomal aneuploidies in a patient sample can be made without limitation to determine the predisposition of the patient to a particular cancer, to determine the presence or absence of a cancer as part of routine screen in patients known and not known to be predisposed to the cancer in question, to provide a prognosis for the disease, to assess the need for adjuvant therapy, and to determine the progress or regress of the diseases.

Genetic Counseling

Fetal chromosome abnormalities are a major contributor to miscarriages, congenital anomalies, and perinatal deaths (Wellesley et al. Europ. J. Human Genet., 20: 521-526 [2012]; Nagaoka et al. Nature Rev. Genetics 13: 493-504 [2012]). Since the introduction of amniocentesis, followed by the introduction of chorionic villus sampling (CVS), pregnant women have had options to obtain information about fetal chromosome status (ACOG Practice Bulletin No. 77: Obstet Gynecol 109: 217-227 [2007]). Cytogenetic karyotyping of fetal cells or chorionic villi obtained from these procedures leads to diagnosis in the vast majority of cases with very high sensitivity and specificity (~99%) when adequate tissue is obtained (Hahnemann and Vejerslev, Prenat Diagn., 17: 801-820 1997; NICHD National Registry for Amniocentesis Study JAMA 236:1471-1476 [1976]). However, these procedures also pose risks to the fetus and pregnant woman (Odibo et al. Obstet Gynecol 112: 813-819 [2008]; Odibo et al. Obstet Gynecol 111: 589-595 [2008]).

To mitigate these risks, a series of prenatal screening algorithms have been developed to stratify women for their likelihood of the most common fetal trisomies—T21 (Down syndrome) and trisomy 18 (T18, Edwards syndrome) and to a lesser extent trisomy 13 (T13, Patau syndrome). The screens typically involve measurement of multiple biochemical analytes in the maternal serum at different time points combined with ultrasonographic measurement of the fetal nuchal translucency (NT) and incorporation of other maternal factors, such as age to generate a risk score. Based on their development and refinement over the years and depending on when the screening is administered (first or second trimester only, sequential, or fully integrated) and how the screening is administered (serum-only or serum combined with NT), a menu of options has evolved with variable detection rates (65 to 90%) and high screen positive rates (5%) (ACOG Practice Bulletin No. 77: Obstet Gynecol 109: 217-227 [2007]).

For patients, following this multi-step process, the resultant information or "risk score" can be confusing and anxiety provoking, particularly in the absence of comprehensive counseling. Ultimately, the results are weighed against the risks for miscarriage from an invasive procedure in a woman's decision-making. Better noninvasive means to obtain more definitive information on fetal chromosomal status facilitates decision making in this context. Such improved noninvasive means of obtaining more definitive information on fetal chromosomal status are believed to be provided by methods described herein.

In various embodiments, genetic counseling is contemplated as a component of the use of the assays described herein, particularly in a clinical context. Conversely, the aneuploidy detection methods described herein can comprise one option offered in the context of prenatal care and associated genetic counseling.

Accordingly, in various embodiments the methods described herein can offered as a primary screen (e.g., for women with an a priori pregnancy risk) or as a secondary screen to those women with a positive "conventional" screen. In certain embodiments, it is contemplated that the non-invasive prenatal testing (NIPT) methods described herein additionally comprise a genetic counseling component and/or that genetic counseling and pregnancy "management", optionally, or definitively incorporated the NIPT methods described herein.

For example, in certain embodiments, women present with one or more a priori pregnancy risks. Such risks include, but are not limited to one or more of the following:

1) Maternal age over 35 although it is noted that approximately 80% of children born with Down's syndrome are born to women under the age of 35.

2) Previous fetus/child with autosomal trisomy. It is believed that the recurrence rate is about 1.6 to about 8.2 times the maternal age risk depending on the type of trisomy, whether the previous pregnancy was spontaneously aborted, and the maternal age at the initial occurrence and the mother's age at subsequent prenatal diagnosis.

3) Previous fetus/child with sex chromosome abnormality—not all sex abnormalities have a maternal origin and not all have risk of recurrence. When they do, the recurrence rate is about 1.6 to about 1.5 times the maternal age risk.

4) Parental carrier of chromosomal translocation.

5) Parental carrier of chromosome inversion.

6) Parental aneuploidy or mosaicism.

7) Use of certain assisted reproductive technologies.

In such circumstances, the mother, e.g., in consultation with a physician, genetic counselor, and the like, may be offered use of the methods described herein for non-invasive determination of the presence or absence of a fetal aneuploidy (e.g., trisomy 21, trisomy 18, trisomy 13, monosomy X etc.) subject to the various considerations described below. In this regard, it is noted that the methods described herein are believed to be effective even in the first trimesters. Thus, in certain embodiments, use of the NIPT methods described herein is contemplated as early as 8 weeks, and in various embodiments at about 10 weeks or later.

In certain embodiments, the methods described herein can be offered as a secondary screen to those women with a positive "conventional" screen. For example, in certain embodiments, pregnant women may present with a structural abnormality such as fetal cystic hygroma, or increased nuchal translucency, e.g., as detected using ultrasonography. Typically ultrasound for structural defects is performed in weeks 18-22 and, particularly when an irregularity is observed, may be coupled with a fetal echocardiogram. It is contemplated that when an abnormality is observed (e.g., a positive "conventional" screen), the mother, e.g., in consultation with a physician, genetic counselor, and the like, may be offered use of the methods described herein for non-invasive determination of the presence or absence of a fetal aneuploidy (e.g., trisomy 21, trisomy 18, trisomy 13, monosomy X etc.) subject to the various considerations described below.

Thus, in various embodiments, genetic counseling is contemplated in which the (NIPT) assays described herein are offered as a component of prenatal care, the management of pregnancy and/or the development/design of a birth plan. By offering NIPT as a secondary screen to those women with a positive conventional screen (or other a priori risk), the number of unnecessary amniocentesis and CVS procedures are expected to decrease. However, the need for genetic counseling will increase, as informed consent is an important component of NIPT.

Since a positive NIPT result (using the methods described herein) is more similar to a positive result from amniocentesis or CVS, in genetic counseling women should be given the opportunity prior to this testing to decide whether they desire this degree of information. Pre-test genetic counseling for NIPT should also include discussion/recommendation for confirmation of abnormal test results via CVS, amniocentesis, cordocentesis, etc (depending upon gestational age), so that appropriate consideration can be given to the expected timing of results for post-test planning Per the National Society of Genetic Counselors (NSGC, USA) statements on the topic (see, e.g., Devers et al. Noninvasive Prenatal Testing/Noninvasive Prenatal Diagnosis: the position of the National Society of Genetic Counselors (by NSGC Public Policy Committee). NSGC Position Statements 2012; Benn et al. Prenat Diagn, 31: 519-522 [2011]), because NIPT does not presently screen for all chromosomal or genetic conditions, it may not replace standard risk assessment and prenatal diagnosis. It is contemplated that patients with other factors (e.g., certain abnormal ultrasound findings) suggestive of chromosome abnormality should receive genetic counseling in which they are provided the option of conventional confirmatory diagnostic testing, regardless of NIPT results. In genetic counseling women should also be made aware that for some patients an NIPT result may not be informative.

NIPT using the methods described herein is perhaps more similar to CVS than amniocentesis in that detection of aneuploidy is typically representative of the chromosomal constitution of the fetus, but in some instances may be representative of confined placental aneuploidy or confined placental mosaicism (CPM). CPM occurs in approximately 1-2% of cases of CVS results today, and some women undergo an amniocentesis at later gestational age after CVS to make the distinction between apparently isolated placental aneuploidy versus fetal aneuploidy. As NIPT is implemented more widely, cases of CPM are expected to cause some number of positive NIPT results that may not be subsequently confirmed by invasive procedure, particularly amniocentesis. Again, in various embodiments, it is contemplated that this information is presented to the patient in the context of genetic counseling (e.g., by physician, genetic counselor, etc.).

It will be recognized that in various embodiments, a component of genetic counseling may be to recommend confirmatory diagnostics, to inform regarding risk levels and timing for various confirmatory diagnostics can to provide input as to the value of the information provided by such confirmatory methods, particularly in the context of the timing of the pregnancy. In various embodiments the genetic counseling can also establish a plan to monitor the pregnancy (e.g., follow-up ultrasound, additional physician visits, and the like) and to set up a series of decision points where appropriate. In addition, the genetic counseling can suggest and aid in development of a birth plan that can include for example, decisions regarding the site of delivery (e.g., home, hospital, specialized facility, etc.), the staff involved at the site of delivery, available tertiary care for the infant, and the like.

While the foregoing discussion focuses on the methods described herein as a component (and perhaps secondary tool) in prenatal diagnosis, as clinical experience accumulates and if results are successful from comparative studies to conventional screening, it is possible that the NIPT methods described herein can replace current screening protocols and possibly serve as a primary tool.

It is also contemplated that the methods described herein will find use on pregnancies with multiple gestations.

Typically, it is expected that genetic counseling, e.g., as described above, may be provided by a physician (e.g., primary physician, obstetrician, etc.) and/or by a genetic counselor, or other qualified medical professional. In certain embodiments the counseling is provided face-to-face, however, it is recognized that in certain instances, the counseling can be provided through remote access (e.g., via text, cell phone, cell phone app, tablet app, internet, and the like).

It is also recognized, that in certain embodiments, the genetic counseling or a component thereof can be delivered by a computer system. For example, "smart advice" systems can be provided that in response to test results, instructions from a medical care provider, and/or in response to queries (e.g., from a patient) provide genetic counseling information (e.g., as described above). In certain embodiments the information will be specific to clinical information provided by the physician, healthcare system, and/or patient. In certain embodiments the information can provided in an iterative manner. Thus, for example, the patient can provide "what if" inquiries and the system can return information such as diagnostic options, risk factors, timing, and implication of various outcomes.

In certain embodiments the information can be provided in a transitory manner (e.g., presented on a computer screen). In certain embodiments, the information can be provided in a non-transitory manner. Thus, for example, the information can be printed out (e.g., as a list of options and/or recommendations optionally with associated timing, etc.) and/or stored on computer readable media (e.g., magnetic media such as a local hard drive, a server, etc., optical media, flash memory, and the like).

It will be appreciated that typically such systems will be configured to provide adequate security such that patient privacy is maintained, e.g., according to prevailing standards in the industry.

The foregoing discussion of genetic counseling is intended to be illustrative and not limiting. Genetic counseling is a well-established branch of medical science and incorporation of a counseling component with respect to the assays described herein is within the scope and skill of the practitioner. Moreover, it is recognized that as the field progresses, the nature of genetic counseling and associated information and recommendations is likely to alter.

Determination of Fetal Fraction

Methods of fetal fraction determination are disclosed in U.S. patent application Ser. No. 12/958,347 filed Dec. 1, 2010, U.S. patent application Ser. No. 13/365,240 filed Feb. 2, 2012, and U.S. patent application Ser. No. 13/445,778 filed Apr. 12, 2012, which are incorporated herein by reference in their entireties. A full discussion of the techniques for determining fetal fraction can be found in these documents.

The methods described herein enable determination of fetal fraction in a sample comprising a mixture of fetal and maternal nucleic acids, or more generally a mixture of nucleic acids having their origin in two different genomes. For purposes of this discussion, maternal and fetal nucleic acids will be described, but it should be understood that any two genomes can be substituted therefore. In some embodiments, fetal fraction is determined concurrently with determining the presence or absence of a copy number varation such as aneuploidy. As described more fully below, one set of tags of from a test sample may be employed to determine both fetal fraction and copy number variation.

Methods for quantifying fetal fraction rely on differences between the fetal and the maternal genome. In certain embodiments described herein, determination of fetal fraction of sample DNA relies on multiple DNA sequence readings at sequence sites known to harbor one or more polymorphisms. In some embodiments, the polymorphism sites or target nucleic acid sequences are discovered while aligning sequence tags to one another and/or a reference sequence. In certain embodiments, the fetal fraction of sample DNA is determined by considering copy number information for a particular chromosome or chromosome sequence where there is a copy number difference between the maternal chromosome and the fetal chromosome. In such embodiments, the fetal fraction of sample DNA is determined by considering the relative amounts of sample DNA from the mother and fetus that originated with a chromosome or segment determined or known to have a copy number variation. In such embodiments, fetal fraction may be calculated using copy number variations between maternal and fetal chromosomes. For this purpose, the method and apparatus may calculate a normalized chromosome value (NCV) as described below, or a similar metric.

Some methods are limited by the gender of the fetus, e.g., methods for quantifying fetal fraction that rely on the presence of sequences that are specific to the Y chromosome or determine the chromosome dose of X chromosome for a male fetus. In some embodiments, quantification of fetal DNA is directed toward fetal targets that have that either have no maternal counterparts e.g. Y chromosome sequences (Fan et al., Proc Natl Acad Sci 105:16266-16271 [2008] and US Patent Application Publication No. 2010/0112590, filed Nov. 6, 2009, Lo et al.) or the RHD1 gene in an RhD-negative mother, or differ from the maternal background by at multiple DNA base pairs. Other methods are independent of the gender of the fetus, and rely on polymorphic differences between the fetal and maternal genomes.

Allelic imbalances in polymorphisms can be detected and quantified by various techniques. In some embodiments, digital PCR is used to determine an allelic imbalance of polymorphisms e.g. a SNP on mRNA. Alternatively, capillary gel electrophoresis is used to detect differences in the size of the polymorphic region e.g. as in the case of an STR.

In some embodiments, epigenetic differences can be detected e.g. differential methylation of promoter regions, can be used alone or in combination with digital PCR to determine differences between the fetal and maternal genomes and quantity fetal fraction (Tong et al., Clin Chem 56:90-98 [2010]). Modifications of epigenetic methods are also included e.g. methylation-based DNA discrimination, (Erich et al., AJOG 204: pages 205.e1-205.e11[2011]). In some embodiments, the fetal fraction is estimated using sequencing of preselected panel(s) of polymorphic sequences as described elsewhere herein.

Methods for quantifying fetal DNA in maternal plasma include without limitation and in addition to the method of sequencing panels of preselected polymorphic sequences as described elsewhere herein, real-time qPCR, mass spectrometry, digital PCR including microfluidic digital PCR, capillary gel electrophoresis.

The discussion in this section initially considers fetal fraction as determined from one or more polymorphisms or other information from chromosomes or chromosome segments that do not (or are determined not to) have copy number variations. Fetal fraction determined by such techniques will be referred to herein as non-CNV fetal fraction or "NCNFF." Later in this section, techniques are described for calculating fetal fraction from chromosomes or chromosome segments determined to possess copy number variations. Fetal fraction determined from such techniques will be referred to herein as CNV fetal fraction or "CNFF."

In some embodiments, the fetal fraction is evaluated by determining the relative contribution of a polymorphic allele derived from the fetal genome and the contribution of the corresponding polymorphic allele derived from the maternal genome. In some embodiments, the fetal fraction is evaluated by determining the relative contribution of a polymorphic allele derived from the fetal genome to the total contribution of the corresponding polymorphic allele derived from both the fetal and the maternal genome.

Polymorphisms can be indicative, informative, or both. Indicative polymorphisms indicate the presence of fetal cell-free DNA ("cfDNA") in a maternal sample. Informative polymorphisms, such as informative SNPs, yield information about the fetus—for example, the presence or absence of a disease, genetic abnormality, or any other biological information such as the stage of gestation or gender. Informative polymorphisms in this instance are those which identify differences between the sequence of the mother and the fetus and are used in the methods disclosed herein. Stated another way, informative polymorphisms are polymorphisms in a nucleic acid sample that possess different sequences (i.e., they possess different alleles) and the sequences are present in different amounts. The different amounts of the sequences/alleles are used in some of the methods herein to determine fetal fraction, particularly NCNFF.

Polymorphic sites include, without limitation, single nucleotide polymorphisms (SNPs), tandem SNPs, small-scale multi-base deletions or insertions (IN-DELS or deletion insertion polymorphisms (DIPs)), Multi-Nucleotide Polymorphisms (MNPs), Short Tandem Repeats (STRs), restriction fragment length polymorphisms (RFLP), or any polymorphisms possessing any other allelic variation of sequence in a chromosome. In some embodiments, each target nucleic acid comprises two tandem SNPs. The tandem SNPs are analyzed as a single unit (e.g., as short haplotypes), and are provided herein as sets of two SNPs.

In some embodiments, the fetal fraction is determined by statistical and approximation techniques that evaluate the relative contributions of zygosities from the fetal and maternal genomes by using polymorphic sites to determine the relative contributions. The fetal fraction can also be determined by electrophoresis methods where certain types of polymorphic sites are electrophoretically separated and used to identify relative contribution of a polymorphic allele from the fetal genome and relative contribution of the corresponding polymorphic allele from the maternal genome.

Figure 6:
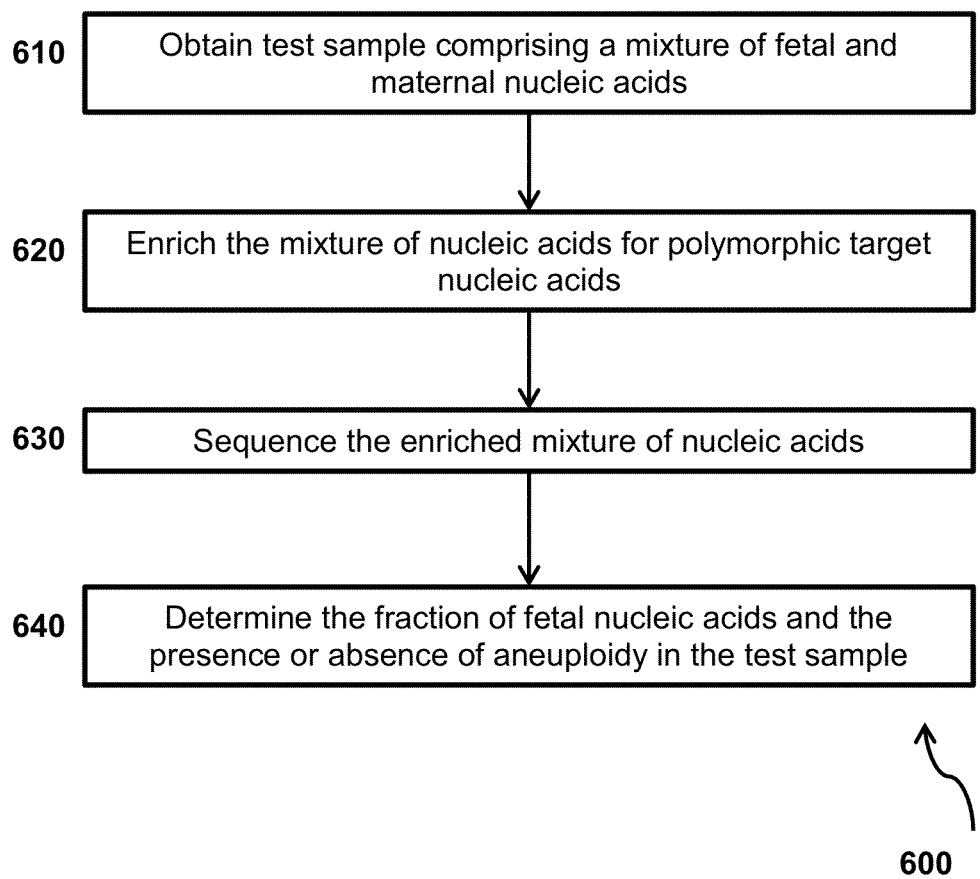
FIG. 6 is a flowchart of a method 600 for simultaneously determining the presence or absence of aneuploidy and the fetal fraction in a maternal test sample comprising a mixture of fetal and maternal nucleic acids.

In one embodiment shown in a process flow diagram in FIG. 6, fetal fraction is determined by a method 600 of first obtaining a test sample comprising a mixture of fetal and maternal nucleic acids in operation 610, enriching the mixture of nucleic acids for polymorphic target nucleic acids in operation 620, sequencing the enriched mixture of nucleic acids in operation 630, and determining the fetal fraction in the sample and aneuploidy simultaneously in operation 640.

Figure 7:
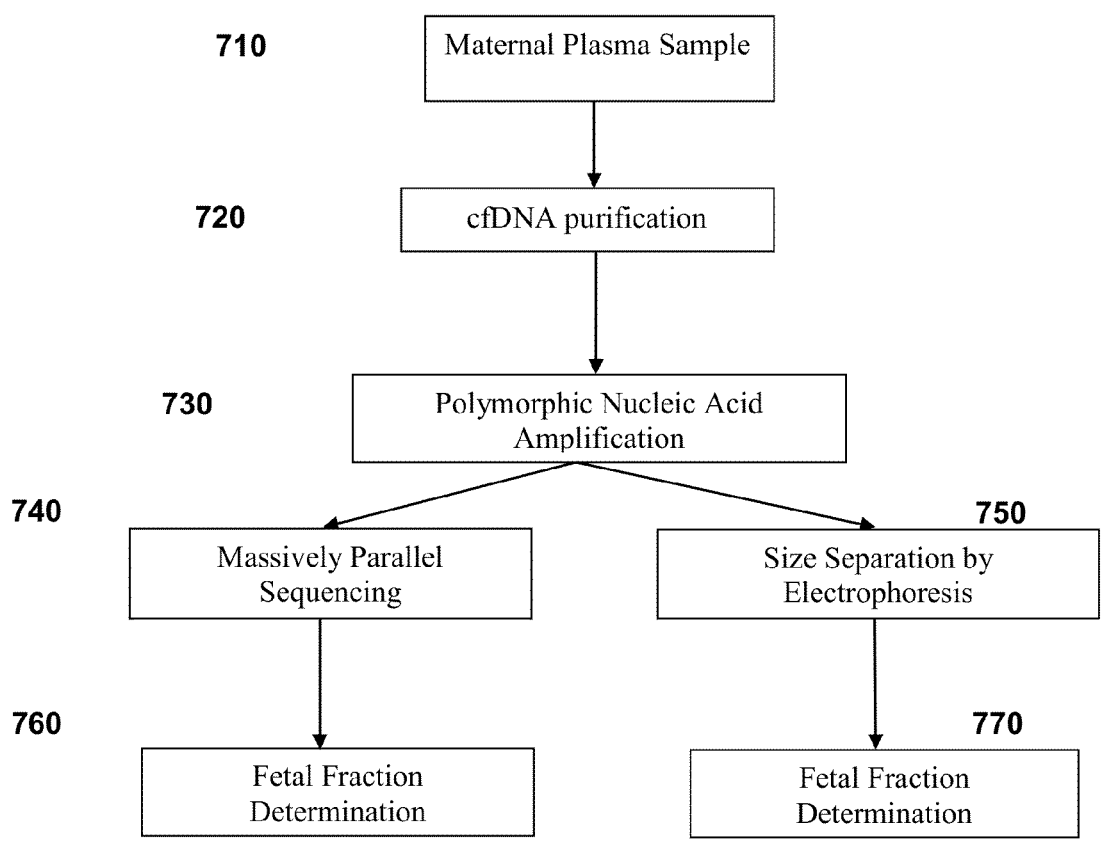
FIG. 7 is a flowchart of a method 700 for determining the fetal fraction in a maternal test sample comprising a mixture of fetal and maternal nucleic acids using massively parallel sequencing methods or size separation of polymorphic nucleic acid sequences.

FIG. 7 shows a process flow diagram for some embodiments. Fetal fraction is determined by: (i) obtaining a maternal plasma sample in operation 710, (ii) purifying the cfDNA in the sample in operation 720, (iii) amplifying the polymorphic nucleic acids in operation 730, (iv) using massively parallel sequencing methods to sequence the mixture in operation 740, and (v) calculating the fetal fraction in operation 760. In another embodiment, fetal fraction can be determined by (i) obtaining a maternal plasma sample in operation 710, (ii) purifying the cfDNA in the sample in operation 720, (iii) amplifying the polymorphic nucleic acids in operation 730, (iv) separating the nucleic acids by size using electrophoresis methods in operation 750, and (v) calculating the fetal fraction in sample 770.

Figure 8:
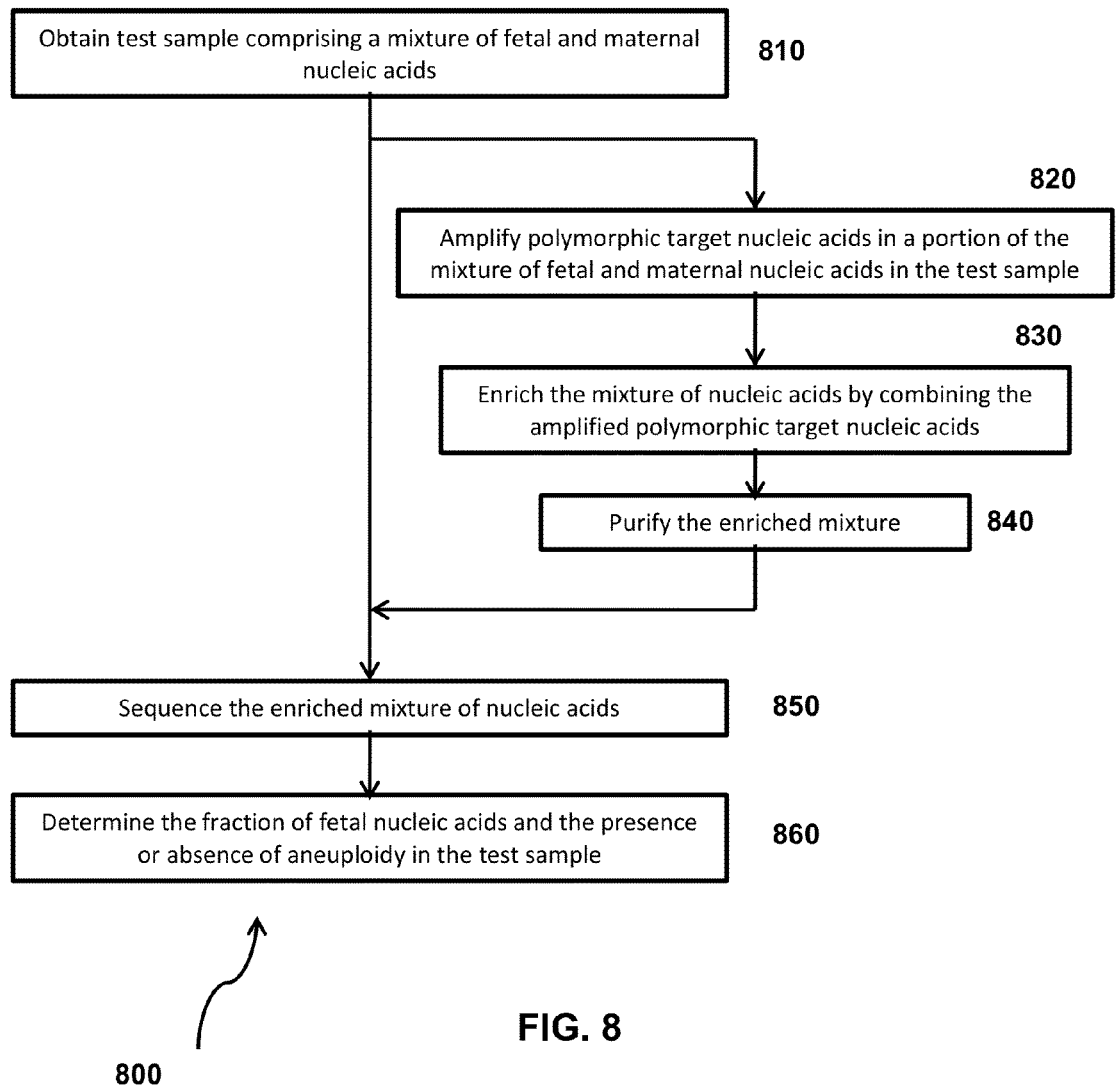
FIG. 8 is a flowchart of a method 800 for simultaneously determining the presence or absence of fetal aneuploidy and the fetal fraction in a maternal plasma test sample enriched for polymorphic nucleic acids.

In one embodiment shown in process flow diagram in FIG. 8, the fetal fraction is determined by: (i) obtaining a sample comprising a mixture of fetal and maternal nucleic acids in operation 810, (ii) amplifying the sample in operation 820, (iii) enriching the sample by combining the amplified sample with unamplified sample from the original mixture in operation 830, (iv) purifying the sample in operation 840, and (v) sequencing the sample to determine the fetal fraction using various methods in operation 850 to determine the fetal fraction and the presence or absence of aneuploidy simultaneously in operation 860.

Figure 9:
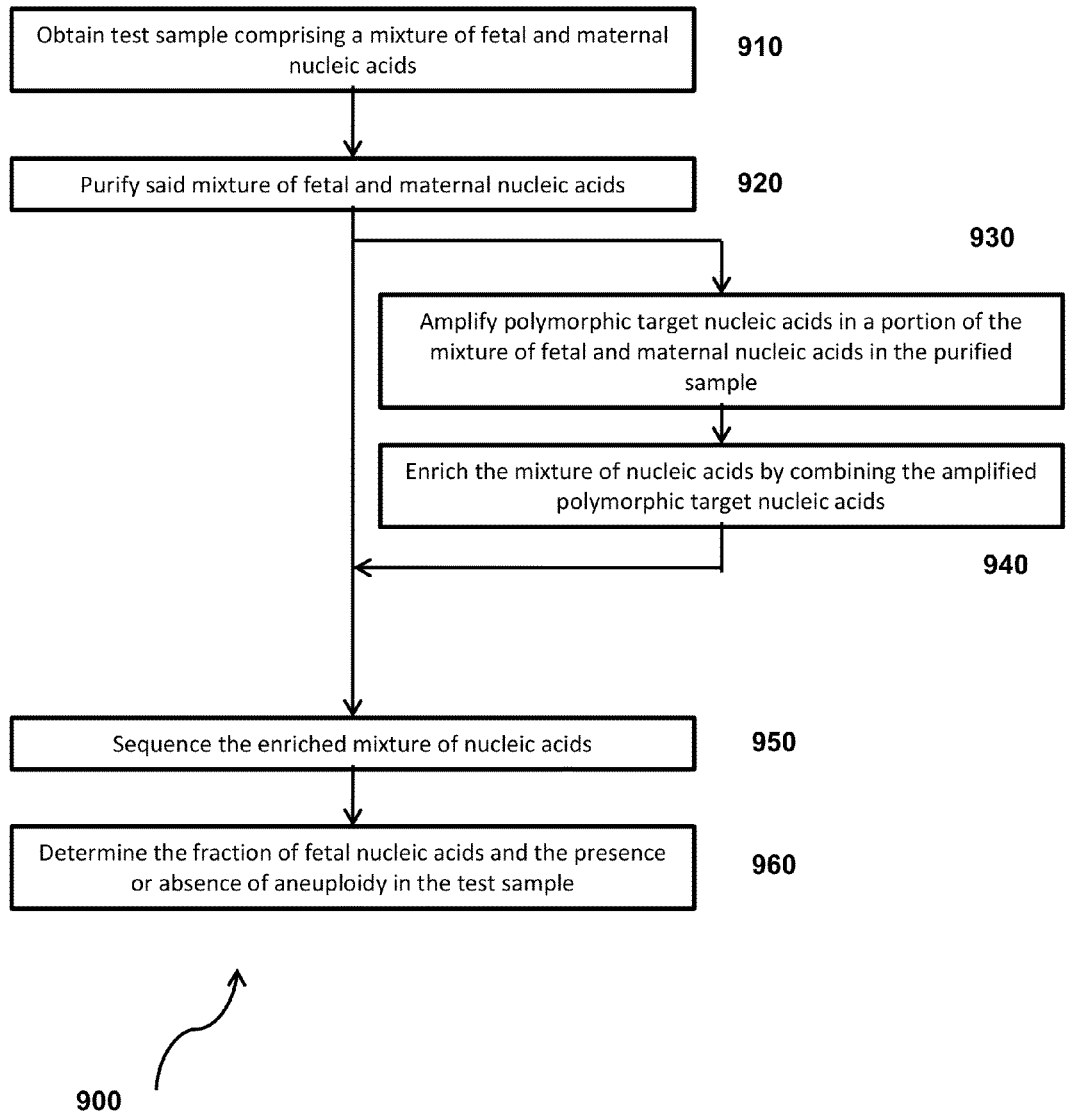
FIG. 9 is a flowchart of a method 900 for simultaneously determining the presence or absence of fetal aneuploidy and the fetal fraction in a maternal purified cfDNA test sample that has been enriched with polymorphic nucleic acids.

In another embodiment shown in the process flow diagram in FIG. 9, the fetal fraction is determined by: (i) obtaining a sample comprising a mixture of fetal and maternal nucleic acids in operation 910, (ii) purifying the sample in operation 920, (iii) amplifying a portion of the sample in operation 930, (iv) enriching the sample by combining the amplified sample with purified unamplified portion of the original sample from the original mixture in operation 940, and (v) sequencing the sample in operation 950 to determine the fetal fraction and the presence or absence of aneuploidy simultaneously in operation 960 using various methods.

Figure 10:
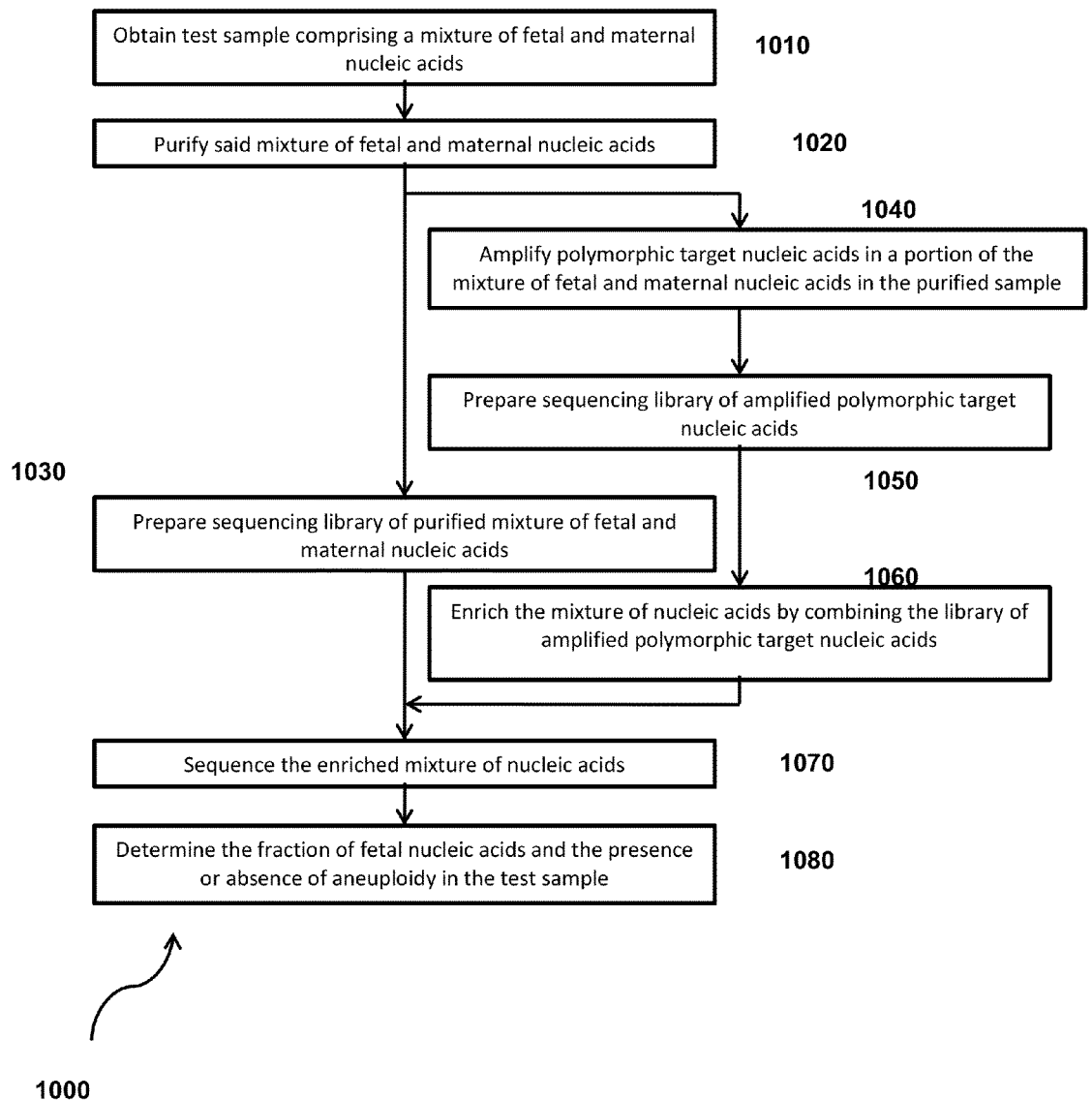
FIG. 10 is a flowchart of a method 1000 for simultaneously determining the presence or absence of fetal aneuploidy and the fetal fraction in a sequencing library constructed from fetal and maternal nucleic acids derived from a maternal test sample and enriched with polymorphic nucleic acids.

In another embodiment shown in the process flow diagram in FIG. 10, the fetal fraction is determined by: (i) obtaining a sample comprising a mixture of fetal and maternal nucleic acids in operation 1010, (ii) purifying the sample in operation 1020, (iii) amplifying a first portion of the sample in operation 1040, (iv) preparing a sequencing library of the amplified portion of the sample in operation 1050, (v) preparing a sequencing library of a second purified unamplified portion of the sample in operation 1030, (vi) enriching the mixture by combining the two sequencing libraries in operation 1060, and (vii) sequencing the mixture in operation 1070 to determine the fetal fraction and the presence or absence of aneuploidy simultaneously in operation 1080 using various methods.

In another embodiment, the fetal fraction is determined by: (i) obtaining a sample comprising a mixture of fetal and maternal nucleic acids, (ii) purifying the sample, (iii) amplifying the sample using labeled primers, and (iv) sequencing the sample using electrophoresis to determine the fetal fraction using various methods.

In another embodiment, the fetal fraction is determined by: (i) obtaining a sample comprising a mixture of fetal and maternal nucleic acids, (ii) purifying the sample, (iii) optionally enriching the sample by amplifying a portion of the sample, and (iv) sequencing the sample to determine the fetal fraction using various methods.

Purification of the original obtained sample, amplified sample, or amplified and enriched sample, or other nucleic acid samples relevant to the methods disclosed herein (such as in operations 720, 840, 920, and 1020) can be completed by any conventional technique. To separate cfDNA from cells, fractionation, centrifugation (e.g., density gradient centrifugation), DNA-specific precipitation, or high-throughput cell sorting, and/or separation methods can be used. Optionally, the sample obtained can be fragmented before purification or amplification. If the sample used comprises cfDNA, then fragmentation may not be required because cfDNA is fragmented in nature, with the fragments frequently of size around 150 to 200 bp.

In some of the above-described processes, selective amplification and enrichment is employed to increase the relative amount of nucleic acid from regions where polymorphisms are located. A similar result can be achieved by deep sequencing selected regions of the genome, particularly regions where polymorphisms are located.

Amplification

After obtaining a sample and purifying the sample, a portion of the purified mixture of fetal and maternal nucleic acids (e.g. cfDNA) is used to amplify a plurality of polymorphic target nucleic acids, each comprising a polymorphic site. Amplification of the target nucleic acids in the mixture of fetal and maternal nucleic acid is accomplished in some implementations by any method that uses PCR (polymerase chain reaction) or variations of the method, including but not limited to asymmetric PCR, helicase-dependent amplification, hot-start PCR, qPCR, solid phase PCR, and touchdown PCR. In some embodiments, the sample can be partially amplified to facilitate determining fetal fraction. In some embodiments, amplification is not performed. The disclosed methods of amplifications and other amplification techniques can be used in operations 730, 820, 930, and 1040.

Amplification of SNPs

A number of nucleic acid primers are available to amplify DNA fragments containing SNPs, and their sequences can be obtained, for example, from databases known by one skilled in the art. Additional primers can also be designed, for example, using a method similar to that published by Vieux, E. F., Kwok, P-Y and Miller, R. D. in BioTechniques (June 2002) Vol. 32, Supplement: "SNPs: Discovery of Marker Disease," pp. 28-32.

Sequence-specific primers are selected to amplify target nucleic acids. In one embodiment, target nucleic acids comprising a polymorphic site are amplified as amplicons. In another embodiment, target nucleic acids comprising two or more polymorphic sites, e.g. two tandem SNPs, are amplified as amplicons. The single or tandem SNPs are contained in amplified target nucleic acid amplicons of at least about 100 bp. The primers used for amplifying the target sequences comprising tandem SNPs are designed to encompass both SNP sites.

Amplification of STRs

Some nucleic acid primers are available to amplify DNA fragments containing STRs and such sequences can be obtained from databases known by one skilled in the art.

In some embodiments, a portion of the mixture of fetal and maternal nucleic acids is used as a template for amplifying target nucleic acids that have at least one STR. A comprehensive listing of references, facts and sequence information on STRs, published PCR primers, common multiplex systems, and related population data are compiled in STRBase, which may be accessed via the Internet at cstl.nist.gov/strbase. Sequence information from GenBank® at ncbi.nlm.nih.gov/genbank for commonly used STR loci is also accessible through STRBase.

STR multiplex systems allow the simultaneous amplification of multiple nonoverlapping loci in a single reaction, substantially increasing throughput. Because of the high polymorphisms of STRs, most individuals will be heterozygous. STRs can be used in electrophoresis analysis as described further below.

Amplification can also be done using miniSTRs to generate reduced-size amplicons to discern STR alleles that are shorter in length. The method of the disclosed embodiments encompasses determining the fraction of fetal nucleic acid in a maternal sample that has been enriched with target nucleic acids each comprising one miniSTR comprising quantifying at least one fetal and one maternal allele at a polymorphic miniSTR, which can be amplified to generate amplicons that are of lengths about the size of the circulating fetal DNA fragments. Any one pair or a combination of two or more pairs of miniSTR primers can be used to amplify at least one miniSTR.

Enrichment

Samples that are enriched may include: a plasma fraction of a blood sample; a sample of purified cfDNA that is extracted from plasma; a sequencing library sample prepared from a purified mixture of fetal and maternal nucleic acids; and others.

In certain embodiments, the sample comprising the mixture of DNA molecules is non-specifically enriched for the whole genome prior to whole genome sequencing i.e. whole genome amplification is performed prior to sequencing. Non-specific enrichment of the mixture of nucleic acids may refer to the whole genome amplification of the genomic DNA fragments of the DNA sample that can be used to increase the level of the sample DNA prior to identifying polymorphisms by sequencing. Non-specific enrichment can be the selective enrichment of one of the two genomes (fetal and maternal) present in the sample.

In other embodiments, the cfDNA in the sample is enriched specifically. Specific enrichment refers to the enrichment of a genomic sample for specific sequences, e.g. polymorphic target sequence, which is accomplished by methods that comprise specifically amplifying target nucleic acid sequences that comprise the polymorphic site.

In other embodiments, the mixture of nucleic acids present in the sample is enriched for polymorphic target nucleic acids each comprising a polymorphic site. Such enrichment can be used in operation 620. Enrichment of a mixture of fetal and maternal nucleic acids comprises amplifying target sequences from a portion of nucleic acids contained in the original maternal sample, and combining part or the entire amplified product with the remainder of the original maternal sample, such as in operations 830 and 940.

In yet another embodiment, the sample that is enriched is a sequencing library sample prepared from a purified mixture of fetal and maternal nucleic acids. The amount of amplified product that is used to enrich the original sample is selected to obtain sufficient sequencing information for determining the fetal fraction. At least about 3%, at least about 5%, at least about 7%, at least about 10%, at least about 15%, at least about 20%, at least about 25%, at least about 30% or more of the total number of sequence tags obtained from sequencing are mapped to determine the fetal fraction.

In one embodiment, in FIG. 10, enrichment includes amplifying the target nucleic acids that are contained in a portion of an original sample of a purified mixture of fetal and maternal nucleic acids (e.g. cfDNA that has been purified from a maternal plasma sample) in operation 1040. Similarly, the portion of purified unamplified cfDNA is used to prepare a primary sequencing library in operation 1050. In operation 1060, a portion of the target library is combined with the primary library generated from the unamplified mixture of nucleic acids, and the mixture of fetal and maternal nucleic acids comprised in the two libraries is sequenced in operation 1070. The enriched library may include at least about 5%, at least about 10%, at least about 15%, at least about 20%, or at least about 25% of the target library. In operation 1080, the data from the sequencing runs is analyzed and the simultaneous determination of the fetal fraction and presence or absence of aneuploidy is made as described in operation 640 of the embodiment depicted in FIG. 6.

Sequence Technology

The enriched mixture of fetal and maternal nucleic acids is sequenced. Sequence information that is needed for the determination of fetal fraction can be obtained using any of the known DNA sequencing methods, many of which are described elsewhere herein. Such sequencing methods include next generation sequencing (NGS), Sanger sequencing, Helicos True Single Molecule Sequencing (tSMS™), 454 sequencing (Roche), SOLiD technology (Applied Biosystems), Single Molecule Real-Time (SMRT™) sequencing technology (Pacific Biosciences), nanopore sequencing, chemical-sensitive field effect transistor (chemFET) array, Halcyon Molecular's method that uses transmission electron microscopy (TEM), ion torrent single molecule sequencing, sequencing by hybridization, and others. In some embodiments, massively parallel sequencing is adopted. In one embodiment, Illumina's sequencing-by-synthesis and reversible terminator-based sequencing chemistry is used. In some embodiments, partial sequencing is used.

The sequenced DNA is mapped to a reference genome. Reference genomes may be artificial or may be a human reference genome. Such reference genomes include: artificial target sequences genome comprising sequences of polymorphic target nucleic acids; an artificial SNP reference genome; an artificial STR reference genome; an artificial tandem-STR reference genome; the human reference genome NCBI36/hg18 sequence, which is available on the Internet at genome.ucsc.edu/cgi-bin/hgGateway?org=Human&db=hg18&hgsid=166260105; and the human reference genome NCBI36/hg18 sequence and an artificial target sequences genome, which includes the target polymorphic sequences e.g. a SNP genome. Some mismatch is allowed during the mapping process.

In one embodiment, sequencing information obtained in operation 630 is analyzed and the simultaneous determination of fetal fraction and determination of the presence or absence of aneuploidy is made.

As explained above, a plurality of sequence tags are obtained per sample. In some embodiments, at least about $3\times10^6$ sequence tags, at least about $5\times10^6$ sequence tags, at least about $8\times10^6$ sequence tags, at least about $10\times10^6$ sequence tags, at least about $15\times10^6$ sequence tags, at least about $20\times10^6$ sequence tags, at least about $30\times10^6$ sequence tags, at least about $40\times10^6$ sequence tags, or at least about $50\times10^6$ sequence tags comprising between 20 and 40 bp reads are obtained from mapping the reads to the reference genome per sample. In one embodiment, all the sequence reads are mapped to all regions of the reference genome. In one embodiment, the tags comprising reads that have been mapped to all regions e.g. all chromosomes, of the human reference genome are counted, and the fetal aneuploidy i.e. the over- or under-representation of a sequence of interest e.g. a chromosome or portion thereof, in the mixed DNA sample is determined, and the tags comprising reads that are mapped to the artificial target sequences genome are counted to determine the fetal fraction. The method does not require differentiation between the maternal and fetal genomes.

In one embodiment, the data from the sequencing runs is analyzed and the simultaneous determination of the fetal fraction and presence or absence of aneuploidy is made.

Sequencing Libraries

In some embodiments, a portion or all of the amplified polymorphic sequences is used to prepare a sequencing library for sequencing in a parallel fashion as described. In one embodiment, the library is prepared for sequencing-by-synthesis using Illumina's reversible terminator-based sequencing chemistry. A library can be prepared from purified cfDNA and includes at least about 10%, at least about 15%, at least about 20%, at least about 25%, at least about 30%, at least about 35%, at least about 40%, at least about 45%, or at least about 50% amplified product.

Figure 11:
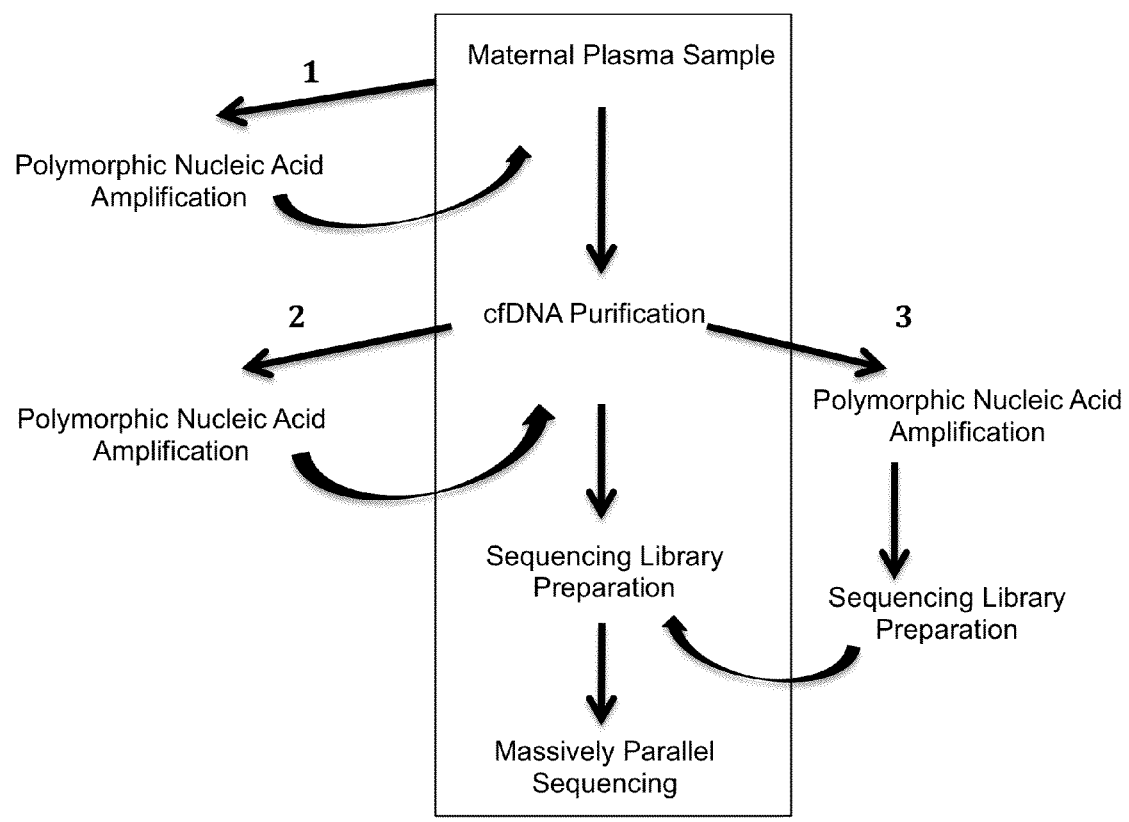
FIG. 11 is a flowchart outlining alternative embodiments of the method for determining fetal fraction by massively parallel sequencing shown in FIG. 7.

Sequencing of the library generated by any one of the methods depicted in FIG. 11 provides sequence tags derived from the amplified target nucleic acids and tags derived from the original unamplified maternal sample. Fetal fraction is calculated from the number of tags mapped to an artificial reference genome.

Calculation of Fetal Fraction

As explained, after sequencing the relevant DNA, computational methods can be used to map or align the sequence to a particular gene, chromosome, allele, or other structure. A number of computer algorithms exist to align sequences, including, without limitation, BLAST (Altschul et al., 1990), BLITZ (MPsrch) (Sturrock & Collins, 1993), FASTA (Pearson & Lipman, 1988), BOWTIE (Langmead et al., Genome Biology 10:R25.1-R25.10 [2009]), or ELAND (Illumina, Inc., San Diego, Calif., USA). In some embodiments, the sequences of the bins are found in nucleic acid databases known to those in the art, including, without limitation, GenBank, dbEST, dbSTS, EMBL (the European Molecular Biology Laboratory), and the DDBJ (the DNA Data Bank of Japan). BLAST or similar tools can be used to search the identified sequences against the sequence databases, and search hits can be used to sort the identified sequences into the appropriate bins. Alternatively, a Bloom filter or similar set membership tester may be employed to align reads to reference genomes. See U.S. Patent Application No. 61/552,374 filed Oct. 27, 2011 which is incorporated herein by reference in its entirety.

Figure 12:
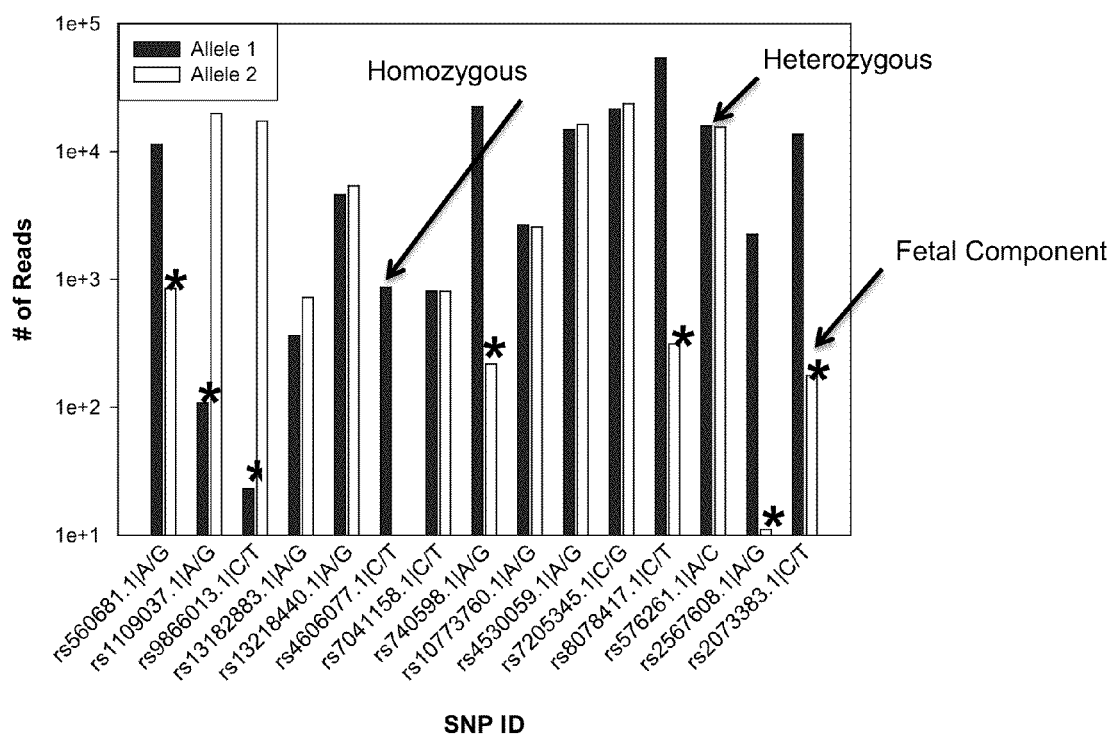
FIG. 12 is a bar diagram showing the identification of fetal and maternal polymorphic sequences (SNPs) used to determine fetal fraction in a test sample. The total number of sequence reads (Y-axis) mapped to the SNP sequences identified by rs numbers (X-axis), and the relative level of fetal nucleic acids (*) are shown.

As mentioned, the determination of the fetal fraction according to some embodiments, particularly NCNFF techniques, is based on the total number of tags that map to a first allele and the total number of tags that map to a second allele at an informative polymorphic site (e.g. a SNP) contained in a reference genome. The informative polymorphic site is identified by the difference in the allelic sequences and the amount of each of the possible alleles. Fetal cfDNA is often present at a concentration that is <10% of the maternal cfDNA. Thus, the presence of a minor contribution of an allele to the mixture of fetal and maternal nucleic acids relative to the major contribution of the maternal allele can be assigned to the fetus. Alleles that are derived from the maternal genome are herein referred to as major alleles, and alleles that are derived from the fetal genome are herein referred to as minor alleles. Alleles that are represented by similar levels of mapped sequence tags represent maternal alleles. The results of an exemplary multiplex amplification of target nucleic acids comprising SNPs derived from a maternal plasma sample are shown in FIG. 12.

Estimating Fetal Fraction Using Allele Ratios

The relative abundance of fetal cfDNA in the maternal sample can be determined as a parameter of the total number of unique sequence tags mapped to the target nucleic acid sequence on a reference genome for each of the two alleles of the predetermined polymorphic site. In one embodiment, the fraction of fetal nucleic acids in the mixture of fetal and maternal nucleic acids is calculated for each of the informative alleles (allele$_x$) as follows:

$$(\% \text{ fetal fraction allele}_x) = \left[ \frac{\sum (\text{fetal sequence tags for allele}_x)}{\sum (\text{maternal sequence tags for allele}_x)} \right] \times 100 \quad \text{Equation 1}$$

and fetal fraction for the sample is calculated as the average of the fetal fraction of all of the informative alleles. Optionally, the fraction of fetal nucleic acids in the mixture of fetal and maternal nucleic acids is calculated for each of the informative alleles (allelex) as follows:

$$(\% \text{ fetal fraction allele}_x) = \left[ \frac{2 \times \sum (\text{fetal sequence tags for allele}_x)}{\sum (\text{maternal sequence tags for allele}_x)} \right] \times 100 \quad \text{Equation 2}$$

to compensate for the presence of two fetal alleles, one being masked by the maternal background.

Estimating Fetal Fraction Using STR Sequences and Capillary Electrophoresis

Individuals have different lengths of STRs due to different number of repeats. Because of the high polymorphism of STRs, most individuals will be heterozygous i.e. most people will possess two alleles (versions)—one inherited from each parent—each with a different number of repeats. The non-maternally inherited fetal STR sequence will differ in the number of repeats from the maternal sequence. Amplification of these STR sequences can result in one or two major amplification products corresponding to the maternal alleles (and the maternally inherited fetal allele) and one minor product corresponding to the non-maternally inherited fetal allele. When sequenced, the collected samples can be correlated with the corresponding alleles and counted to determine relative fraction by using Equation 3.

PCR is performed on a purified sample by using fluorescently labeled primers. The PCR products comprising the STRs can be separated and detected using manual, semi-automated or automated electrophoresis methods. Semi-automated systems are gel-based and combine electrophoresis, detection, and analysis into one unit. On a semi-automated system, gel assembly and sample loading are still manual processes; however, once samples are loaded onto the gel, electrophoresis, detection and analysis proceed automatically. As the name implies, capillary electrophoresis is carried out in a microcapillary tube rather than between glass plates. Once samples, gel polymer, and buffer are loaded onto the instrument, the capillary is filled with gel polymer and the sample is loaded automatically. Data collection occurs in "real time" as fluorescently labeled fragments migrate past the detector at a fixed point and can be viewed as they are collected. The sequence obtained from capillary electrophoresis can be detected by a program to measure the wavelengths of the fluorescent labels. The calculation of fetal fraction is based on averaging all informative markers. Informative markers are identified by the presence of peaks on the electropherogram that fall within the parameters of preset bins for the STRs that are analyzed.

The fraction of the minor allele for any given informative marker is calculated by dividing the peak height of the minor component by the sum of the peak height for the major component, and the fraction is expressed as a percent for each informative locus as $$(\% \text{ fetal fraction}) = \left[ \frac{\text{peak height of minor allele(s)}}{\sum (\text{peak height of major allele(s)})} \right] \times 100 \quad \text{Equation 3}$$

The fetal fraction for a sample comprising two or more informative STRs would be calculated as the average of the fetal fractions calculated for the two or more informative markers.

Estimating Fetal Fraction Using Mixture Models

In embodiments disclosed herein, there are up to four different data types (the zygosity cases) that make up the minor allele frequency data for the polymorphisms under consideration.

Figure 13:
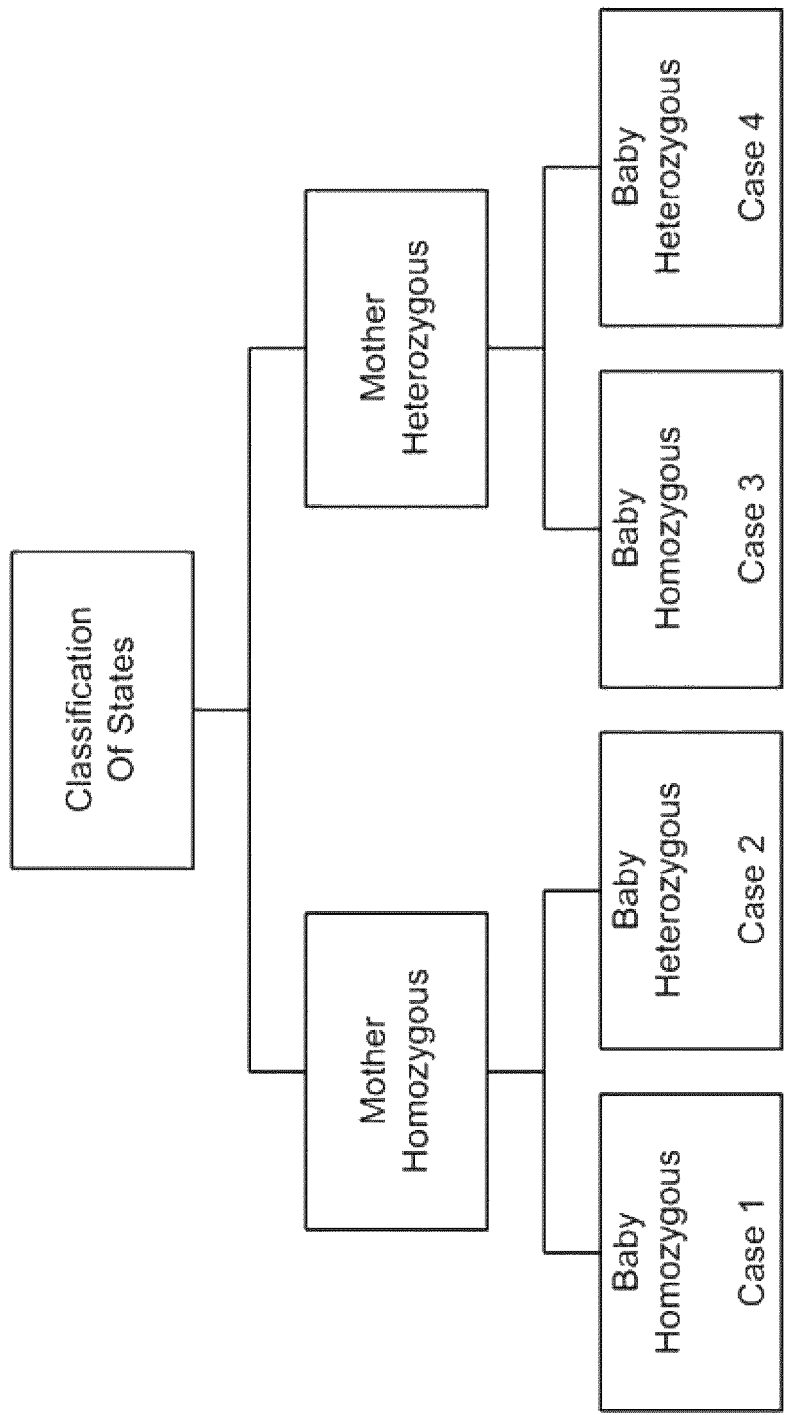
FIG. 13 is a block diagram depicting classification of fetal and maternal zygosity states for a given genomic position.

As indicated in FIG. 13, cases 1 and 2 are the polymorphism cases in which the mother is homozygous at a certain allele. In case 1, if the baby and the mother are both homozygous, the polymorphism is a case 1 polymorphism. This situation is typically not particularly interesting because the collected data will only have presence of one type of allele at the analyzed polymorphic site. In case 2, if the mother is homozygous and the baby is heterozygous, the fetal fraction, f, is nominally given by two times the ratio of the minor allele count to the coverage. Coverage is defined as the total number of reads or tags (both fetal and maternal) mapping to a particular site of a polymorphism. The equation for approximating the fetal fraction as a fraction of the fetal and maternal sample for case 2 is as follows:

$$2 \times \text{Ratio of minor allele count to coverage} = \qquad \text{Equation 4}$$

$$2 \times \left( \frac{\text{Minor allele count}}{\text{coverage}} \right)$$

In case 3, where the mother is heterozygous and the baby is homozygous, the fetal fraction is nominally one minus two times the ratio of the minor allele count to the coverage. The equation for approximating fetal fraction as a fraction of the total number of reads in both the fetal and maternal sample in case 3 is as follows:

$$1 - [2 \times \text{Ratio of minor allele count to coverage}] = \qquad \text{Equation 5}$$

$$1 - \left[ 2 \times \left( \frac{\text{Minor allele count}}{\text{coverage}} \right) \right]$$

Finally, in case 4 where both the mother and the fetus are heterozygous, the minor allele fraction should always be 0.5, barring error. The fetal fraction cannot be derived for polymorphisms falling into case 4.

Table 7 summarizes an example of estimating fetal fraction using Equations 4 and 5 if the number of reads of the major allele is 300 and the number of reads of the minor allele is 200. The coverage would be 500.

TABLE 7

Example of estimating fetal fraction using zygosity

| Case | Mom | Baby | Example |
|---|---|---|---|
| 1 | Homozygous | Homozygous | Cannot tell |
| 2 | Homozygous | Heterozygous | $2 \times \frac{200}{500} = \frac{4}{5} = 0.8^*$ |
| 3 | Heterozygous | Homozygous | $1 - \left[ 2 \times \frac{200}{500} \right] = \frac{1}{5} = 0.2$ |
| 4 | Heterozygous | Heterozygous | 0.5 | if coverage = 500, total number of reads: allele$_B$ = 300 (major), allele$_A$ = 200 (minor)
*This calculation of fetal fraction is for equation illustration purposes only and is not representative of actual fetal fraction values obtained from the methods in the disclosed embodiments.

In certain embodiments, a mixture model may be employed to classify a collection of polymorphisms into two or more of the presented zygosity cases and concurrently estimate the fetal DNA fraction from mean allele frequencies for each of these cases. Generally, a mixture model assumes that a particular collection of data is made up of a mixture of different types of data, each of which has its own expected distribution (e.g., a normal distribution). The process attempts to find the mean and possibly other characteristics for each type of data. In embodiments disclosed herein, there are up to four different data types (the zygosity cases) that make up the minor allele frequency data for the polymorphisms under consideration.

In certain embodiments employing mixture models, one or more factorial moments given by Equation 10 are calculated for the positions where polymorphisms are being considered. For example, a factorial moment $F_i$ (or a collection of factorial moments) is calculated using multiple SNP positions considered in the DNA sequence. As shown in Equation 10 below, each of the various factorial moments $F_i$ is a summation over all the various polymorphism positions under consideration for the ratio of minor allele frequency $a_i$ to coverage $d_i$ for a given position. As shown in Equation 11 below, these factorial moments are also related to the parameters $\alpha$ and $p_i$ associated with each of the four zygosity cases described above. Specifically, they related to the probability $p_i$ for each of the cases as well as the relative amounts of each of the four cases in the collection of polymorphisms under consideration given by $\alpha$. As explained, the probability $p_i$ is a function of the fraction of fetal DNA in the cell-free DNA in the mother's blood. As explained more fully below, by calculating a sufficient number of these factorial moments, the method provides a sufficient number of expressions to solve for all the unknowns. The unknowns in this case would be the relative amounts of each of the four cases in the population of polymorphisms under consideration as well as the probabilities (and hence fetal DNA fractions) associated with each of these four cases. Similar results can be obtained using other versions of mixture models. Some versions make use of only polymorphisms falling into cases 1 and 2, with polymorphisms for cases 3 and 4 being filtered by a thresholding technique.

Thus, the factorial moments may be used as part of a mixture model to identify the probabilities of any combination of the four cases of zygosity. And, as mentioned, these probabilities, or at least those for cases 2 and 3, are directly related to the fraction of fetal DNA in the total cell-free DNA in the mother's blood.

It should also be mentioned that sequencing error given by e may be employed to reduce the complexity of the system of factorial moment equations that must be solved. In this regard, it should be recognized that the sequencing error actually can have any one of four results (corresponding to each of the four possible bases at any given polymorphism position).

Let the major allele count at genomic position j be B, the first order statistic of counts (number of reads counted) at position j. The major allele, b, is the corresponding arg max. Subscripts are used when more than one SNP is being considered. The major allele count is given by:

$$B \equiv B_i \equiv \{b_j\} \equiv w_{j,i}^{(1)} = \max_{i \in \{1,1,3,4\}} \{w_{j,i}\} \qquad \text{Equation 6}$$

Let the minor allele count at position j be A, the second order statistic of counts (i.e. the second highest allele count) at position j:

$$A \equiv A_i \equiv \{a_j\} = w_{j,i}^{(2)} \qquad \text{Equation 7}$$

Coverage is defined as the total number of reads (both fetal and maternal) mapping to a particular site of a polymorphism. Let coverage at position j be defined as D:

$$D \equiv_j = \{d_i\} = A_j + B_j \qquad \text{Equation 8}$$

In this embodiment, the minor allele frequency A is a sum of four terms as shown in Equation 9. The four heterozygosity cases described suggest the following binomial mixture model for the distribution of $a_i$ minor allele counts in points $(a_i, d_i)$ where $d_i$ is the coverage:

$$A = \{a_i\} \sim \alpha_1 Bin(p_1, d_i) + \alpha_2 Bin(p_2, d_i) + \alpha_3 Bin(p_3, d_i) + \alpha_4 Bin(p_4, d_i) \qquad \text{Equation 9}$$

where
$1 = \alpha_1 + \alpha_2 + \alpha_3 + \alpha_4$
$m = 4$

Each term corresponds to one of the four zygosity cases. Each term is the product of a polymorphism fraction α and a binomial distribution of the minor allele frequency. The αs represent the fraction of the polymorphisms falling into each of the four cases. Each binominal distribution has an associated probability, p, and coverage, d. The minor allele probability for case 2, for example, is given by f/2 where f is the fetal fraction. Various models for relating $p_i$ to fetal fraction and sequencing error rates are described below. The parameters $\alpha_i$ relate to population specific parameters and the ability to let these values "float" gives these methods additional robustness with respect to factors like ethnicity and progeny of the parents.

The disclosed embodiments make use of factorial moments for the allele frequency data under consideration. As is well known, a distribution's mean is the first moment. It is the expected value of the minor allele frequency. The variance is the second moment. It is calculated from the expectation value of the allele frequency squared.

For various heterozygosity cases, Equation 9 above can be solved for fetal fraction. In certain embodiments, fetal fraction is solved through the method of factorial moments in which the mixture parameters can be expressed in terms of moments that can easily be estimated from the observed data.

The allele frequency data across all polymorphisms may be used to calculate i-th factorial moment $F_i$ (a first factorial moment $F_1$, a second factorial moment $F_2$, etc.) as shown in Equation 10. (SNPs are used for purposes of example only. Other types of polymorphisms may be used as discussed elsewhere herein.) Given n SNP positions, the factorial moments are defined as follows:

$$F_1 = \frac{1}{n}\sum_{i=1}^{n} \frac{a_i}{d_i}$$ Equation 10

$$F_2 = \frac{1}{n}\sum_{i=1}^{n} \frac{a_i(a_i - 1)}{d_i(d_1 - 1)}$$

...

$$F_j = \frac{1}{n}\sum_{i=1}^{n} \frac{a_i(a_i - 1) \ldots (a_i - j + 1)}{d_i(d_i - 1)(d_i - j + 1)}$$

As indicated by these equations, the factorial moments are summations of terms over i, the individual polymorphisms in the data set, where there are n such polymorphisms in the data set. The terms being summed are functions of the minor allele counts $a_i$ and coverage values $d_i$.

Usefully, the factorial moments have relationships with the values of $\alpha_i$ and $p_i$ as illustrated in Equation 11. Factorial moments can be related to the $\{\alpha_i, p_i\}$ such that $$F_1 \approx \sum_{i=1}^{m} \alpha_i p_i^1$$ Equation 11

$$F_2 \approx \sum_{i=1}^{m} \alpha_i p_i^2$$

...

$$F_j \approx \sum_{i=1}^{m} \alpha_i p_i^j$$

...

$$F_g \approx \sum_{i=1}^{m} \alpha_i p_i^g$$

From the probabilities $p_i$, one can determine the fetal fraction, f. For example, $$p_2 = \frac{f}{2}, \text{ and } p_3 = 1 - \frac{f}{2}.$$

Thus, the responsible logic can solve a system of equations relating the unknown α and p variables to the factorial moment expressions for minor allele fractions across the multiple polymorphisms under consideration. Of course, there are other techniques for solving the mixture models within the scope of the disclosed embodiments.

A solution can be identified by solving for the $\{\alpha_i, p_i\}$ in a system of equations derived from the above relation Equation 8 when n>2* (number of parameters to be estimated). Obviously, the problem becomes much more difficult mathematically for higher g as more $\{\alpha_i, p_i\}$ need to be estimated.

It is typically not possible to accurately discriminate between case 1 and 2 (or case 3 and 4) data by simple thresholds at lower fetal fractions. Case 1 and 2 data is easily separated from case 3 and 4 data by discriminating at point $$\left(\frac{2A}{D}\right) = T$$

where A is the minor allele count and D is the coverage and T is the threshold. Use of T=0.5 has been found to perform satisfactorily.

Note that the mixture model method employing Equations 10 and 11 makes use of the data for all polymorphisms but does not separately account for the sequencing error. Appropriate methods that separate data for the first and second cases from data for the third and fourth cases can account for sequencing error.

In further examples, the data set provided to a mixture model contains data for only case 1 and case 2 polymorphisms. These are polymorphisms for which the mother is homozygous. A threshold technique may be employed to remove the case 3 and 4 polymorphisms. For example, polymorphisms with minor allele frequencies greater than a particular threshold are eliminated before employing the mixture model. Using appropriately filtered data and factorial moments as reduced to Equations 13 and 14 below, one may calculate the fetal fraction, f, as shown in Equation 15. Note that Equation 13 is a restatement of Equation 9 for this implementation of a mixture model. Note also that in this particular example, the sequencing error associated with the machine reading is not known. As a consequence, the system of equations must separately be solved for the error, e.

Figure 14:
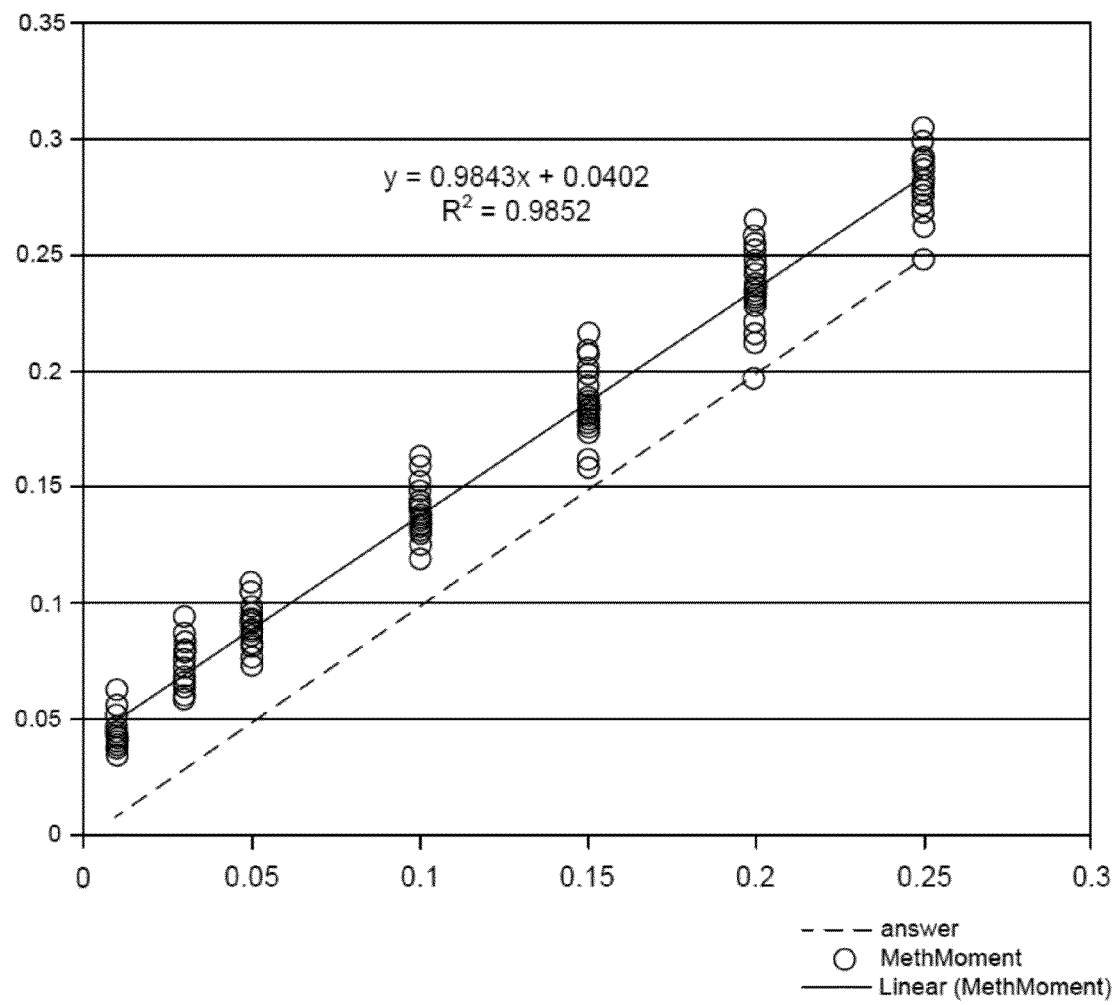
FIG. 14 shows a comparison of the results using a mixture model and the known fetal fraction and estimated fetal fraction.

FIG. 14 shows a comparison of the results using this mixture model and the known fetal fraction (x-axis) and estimated fetal fraction (y-axis). If the mixture model perfectly predicted the fetal fraction, the plotted results would follow the dashed line. Nevertheless, the estimated fractions are remarkably good, particularly considering that much of the data was eliminated prior to applying the mixture model.

To further elaborate, several other methods are available for parameter estimation of the model from Equation 7. In some cases, a tractable solution can be found by setting derivatives to zero of the chi-squared statistic. In cases where no easy solution can be found by direct differentiation, Taylor series expansion of the binomial probability distribution function (PDF) or other approximating polynomials can be effective. Minimum chi-square estimators are well-known to be efficient. The method of moments solutions from Equation 9 can be used as a starting point for the iteration. The following chi-square estimator can be used $$\chi^2(\alpha_i, p_i) = \sum_{i=1}^{n} \frac{(P_i - \sum \alpha_i \text{Binomial}(p_i, d_i))^2}{\text{Binomial}(n, p)} \quad \text{Equation 12}$$

where $P_i$ is the number of points of count i. An alternative method from Le Cam ["On the Asymptotic Theory of Estimation and Testing Hypotheses," Proceedings of the Third Berkeley Symposium on Mathematical Statistics and Probability, Vol. 1 Berkeley Calif.: University of CA Press, 1956, pp. 129-156] uses Ralph-Newton iteration of the likelihood function.

In accordance with another application, a method of resolving mixture models involving expectation maximization methods operating on mixtures of approximating Beta distributions is discussed.

Model 1: Cases 1 and 2, Sequencing Error Unknown

Consider a reduced model that only accounts for heterozygosity cases 1 and 2. In this case the mixture distribution can be written as $$A = \{a_i\} \sim \alpha_1 Bin(e, d_i) + \alpha_2 Bin(f/2, d_i) \quad \text{Equation 13}$$

where
$1 = \alpha_1 + \alpha_2$
$m = 4$
And the system $$F_1 = \alpha_1 e + (1-\alpha_1)(f/2)$$

$$F_2 = \alpha_1 e^2 + (1-\alpha_1)(f/2)^2$$

$$F_3 = \alpha_1 e^3 + (1-\alpha_1)(f/2)^3 \quad \text{Equation 14}$$

is solved for e (sequencing error rate), α (proportion of case 1 points), and f (fetal fraction), where the $F_i$ are defined as in Equation 10 above. A closed form solution for fetal fraction is chosen to be the real solution of $$f \approx \frac{(F_1 - 1)F_2 \pm \sqrt{F_2}\sqrt{4F_1^3 + F_2 - 3F_1(2 + F_1)F_2 + 4F_2^2}}{2(F_1^2 - F_2)} \quad \text{Equation 15}$$

that is between 0 and 1.

Figure 15:
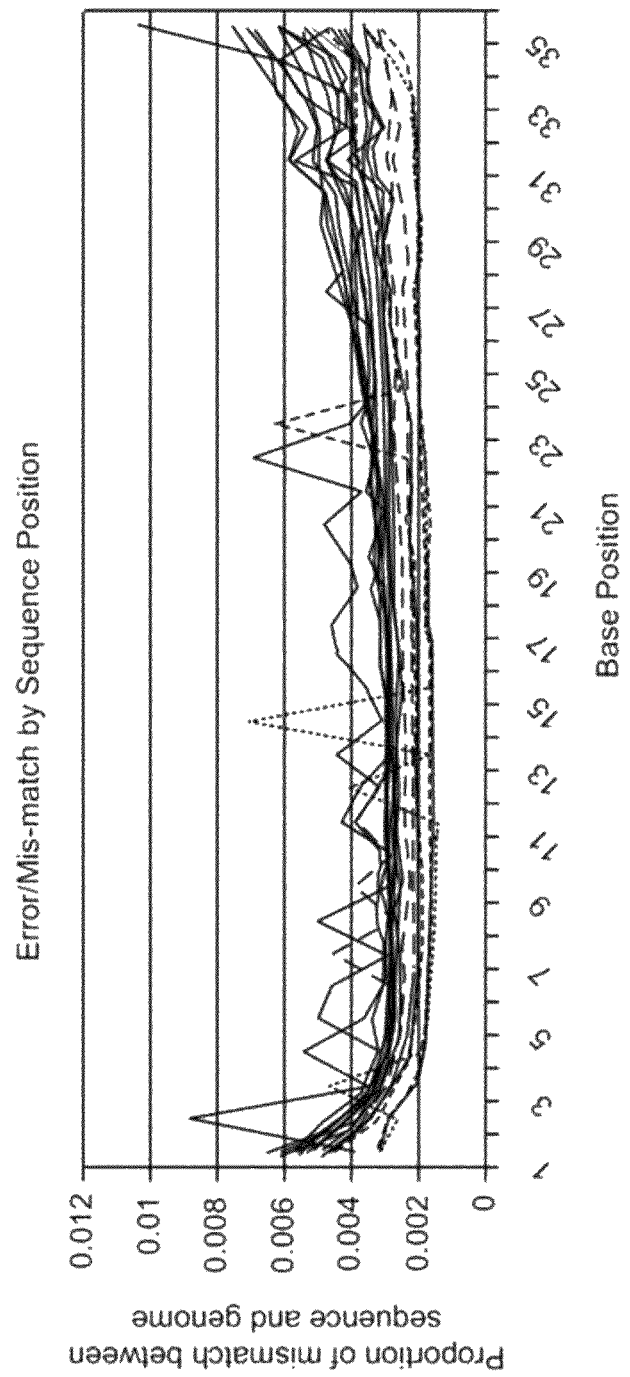
FIG. 15 presents error estimates by sequenced base position over 30 lanes of Illumina GA2 data aligned to human genome HG18 using Eland with default parameters.

To gauge the performance of estimators, a simulated dataset of Hardy-Weinberg Equilibrium points $(a_i, d_i)$ was constructed with fetal fraction designed to be {1%, 3%, 5%, 10%, 15%, 20%, and 25%} and a constant sequencing error rate of 1%. The 1% error rate is the currently accepted rate for the sequencing machines and protocols being used and is consistent with the graph of Illumina Genome analyzer II data shown in FIG. 15. Equation 15 was applied to the data and found, with the exception of a four point bias upwards, general agreement with the "known" fetal fraction. Interestingly, the sequencing error rate, e, is estimated to be just above 1%.

Model 2: Cases 1 and 2, Sequencing Error Known

Figure 16:
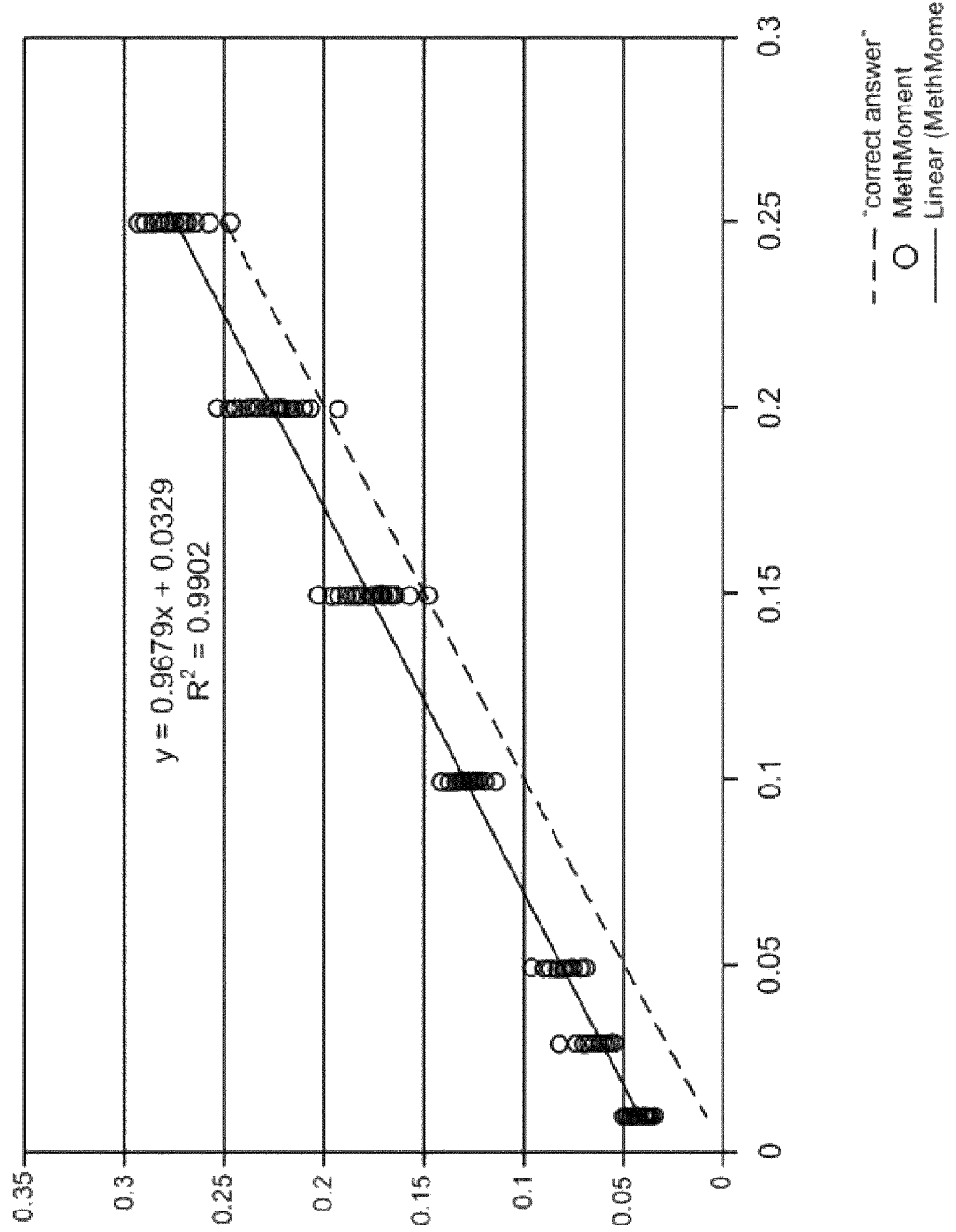
FIG. 16 shows that using the machine error rate as a known parameter reduces the upward bias by a point.

In the next mixture model example, thresholding or another filtering technique is again employed to remove data for polymorphisms falling into cases 3 and 4. However in this case, the sequencing error is known. This simplifies the resulting expression for fetal fraction, f, as shown in Equation 16. FIG. 16 shows that this version of a mixture model provided improved results compared to the approach employed with Equation 15. Let the sequencing machine error rate be e in the subsequent equations.

Figure 17:
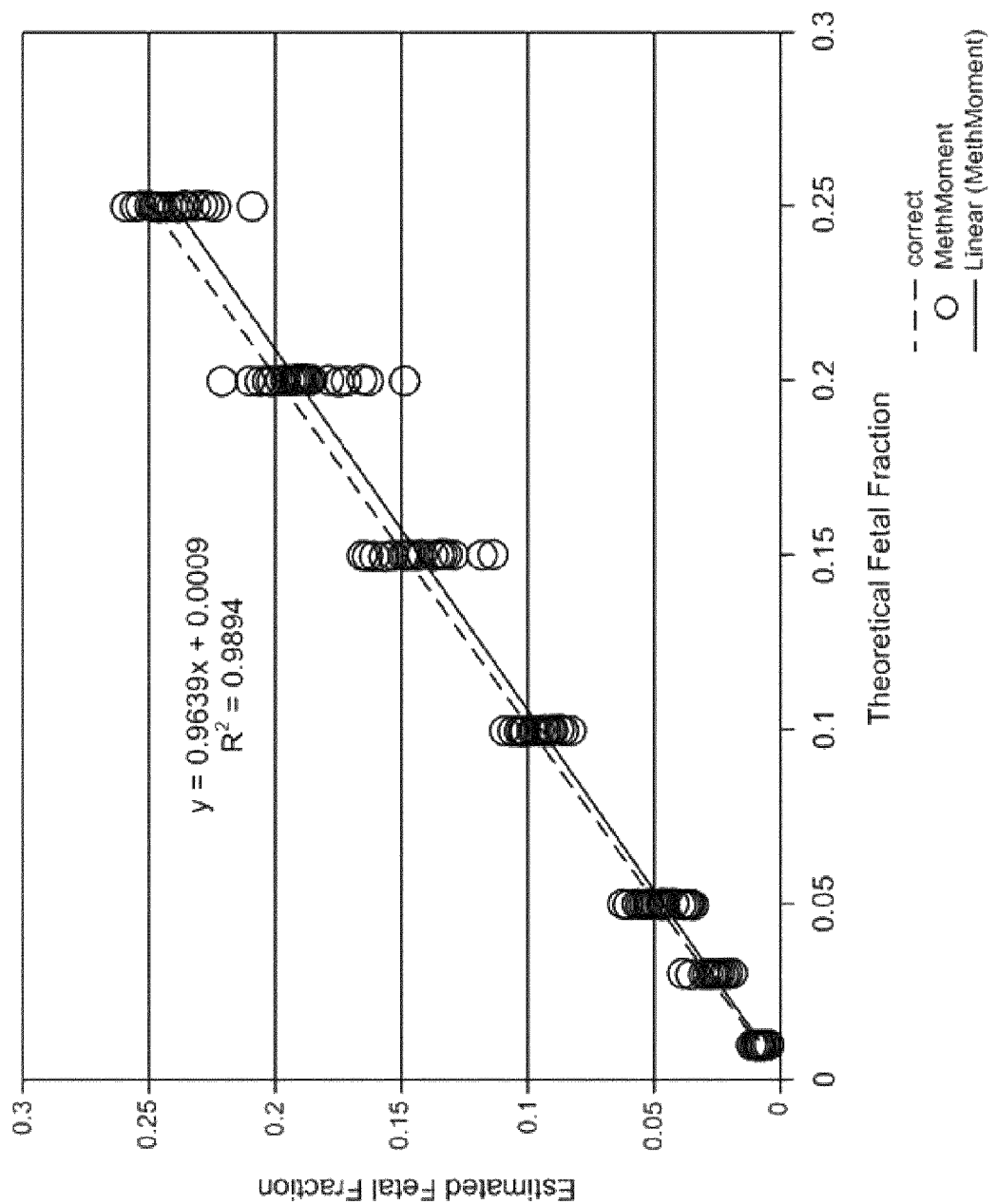
FIG. 17 shows that simulated data using the machine error rate as a known parameter enhancing the case 1 and 2 error models greatly reduces the upward bias to less than a point for fetal fraction below 0.2.

A similar approach is shown in Equations 17 and 18. This approach recognizes that only some sequencing errors add to the minor allele count. Rather, only one in every four sequencing errors should increase the minor allele count. FIG. 17 shows remarkably good agreement between the actual and estimated fetal fractions using this technique.

Since the sequencing error rate of the machines used is known to a great extent, the bias and complexity of calculations can be reduced by eliminating e as a variable to be solved. Thus we obtain the system of equations $$F_1 = \alpha_1 e + (1-\alpha_1)(f/2)$$

$$F_2 = \alpha_1 e^2 + (1-\alpha_1)(f/2)^2 \quad \text{Equation 16}$$

for fetal fraction f to obtain the solution:

$$f \approx \frac{2(eF_1 - F_2)}{(e - F_1)}$$

FIG. 16 shows that using the machine error rate as a known parameter reduces the upward bias by a point.

Model 3: Cases 1 and 2, Sequencing Error Known, Improved Error Models

To ameliorate bias in the model, we expanded the error model of the above equations to account for the fact that not every sequencing error event will add to minor allele count $A = a_i$ in heterozygosity case 1. Furthermore, we allow for the fact that sequencing error events may contribute to heterozygosity case 2 counts. Hence we determine fetal fraction f by solving for the following system of factorial moment relations:

$$F_1 = \alpha_1 e/4 + (1-\alpha_1)(e + f/2) \quad \text{Equation 17}$$

$$F_2 = \alpha_1 \left(\frac{e}{4}\right)^2 + (1-\alpha_1)(e + f/2)^2$$

The solution to the system is then:

$$f \approx \frac{-2(e^2 - 5eF_1 + 4F_2)}{(e - 4F_1)} \quad \text{Equation 18}$$

FIG. 17 shows that simulated data using the machine error rate as a known parameter, enhancing the case 1 and 2 error models, greatly reduces the upward bias to less than a point for fetal fraction below 0.2.

Using Fetal Fraction to Classify Affected Samples

In certain embodiments, fetal fraction estimates are employed to further characterize affected samples. In some cases, fetal fraction estimates allow an affected sample to be classified as a mosaic, a complete aneuploidy or a partial aneuploidy. One computer-implemented approach to obtaining this information is depicted with respect to the flowchart of FIG. 18A. This and related methods may be performed to provide simultaneous estimation of fetal fraction, determination of CNVs and classification of the CNVs. In other words, the same tags may be employed to perform any of three of these functions.

In order to use this method, two modes of estimating fetal fraction are employed. One mode produces a NCNFF value and the other mode produces a CNFF value. As explained, the CNFF value is obtained using a technique that relies on a chromosome or chromosome segment determined to possess a copy number variation. It need not rely on polymorphisms to calculate fetal fraction. An example of a non-polymorphic technique to calculate fetal fraction is described below in Example 17, which assumes that there is a duplication or deletion of a full chromosome and employs the following expression:

$$ff_{(i)} = 2 * NCV_{jA} CV_{jU} \qquad \text{Equation 25}$$

where j represents the identify of an aneuploidy chromosome and CV represents the coefficient of variation obtained from the qualified samples used to determine the mean and standard deviation in the expression for NCV.

The NCNFF value is obtained using a technique that relies on a chromosome or chromosome segment that does not have a copy number variation. Stated another way, the NCN fetal fraction is determined by a technique that reliably determines fetal fraction assuming normal ploidy of the portion of the genome used to calculate fetal fraction. The CN fetal fraction is determined by a technique that assumes the sample under consideration has a form of aneuploidy. The CNV of the affected chromosome or chromosome segment is used to calculate the CN fetal fraction. Techniques for its calculation are presented below.

By comparing the estimated value of NCN fetal fraction against the estimated value of CN fetal fraction, a method can determine the type of aneuploidy that may be present in a sample. Basically, if the NCN fetal fraction and the CN fetal fraction values match, the ploidy assumption in the techniques for estimating CN fetal fraction can be considered to be true. For example, if the method of calculating CN fetal fraction assumes that the sample has a complete chromosomal aneuploidy exhibiting either a single additional copy of a chromosome or a single deletion of a chromosome, and the NCN fetal fraction value matches the CN fetal fraction value, then the method may conclude that the sample exhibits a complete chromosomal aneuploidy. The basis for making the assumption is described in more detail below.

The NCN fetal fraction may be determined by various techniques. In some embodiments, the NCN fetal fraction is estimated using selected polymorphisms in a reference genome. Examples of these techniques were described above. In other embodiments, NCN fetal fraction is determined using the relative amount of X chromosome or Y chromosome (e.g., the chromosome dose of such chromosome) from a sample containing DNA from a pregnant mother carrying a son. The son's genome will not include a second copy of the X chromosome. Knowing this, the relative amount of X chromosome DNA can be used to provide a NCN value of fetal fraction.

Figure 18A:
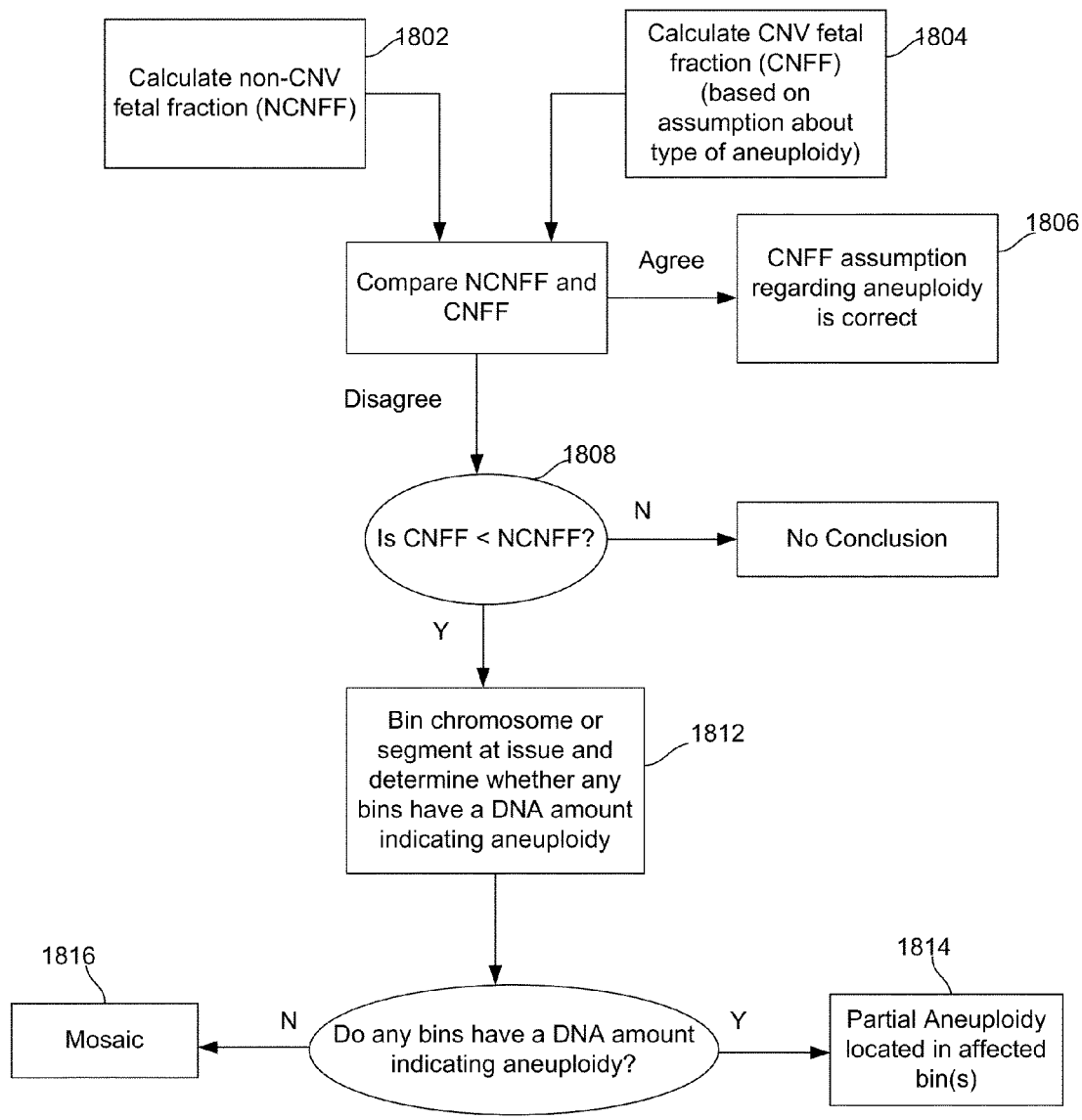
FIG. 18A is a flow chart depicting a method of classifying a CNV by comparing fetal fraction values calculated by two different techniques.

Turning to the flowchart 1800 of FIG. 18A, a NCN fetal fraction estimate 1802 and a CN fetal fraction estimate 1804 are compared. If they match as indicated at block 1806 the process is concluded and it is determined that the assumption implicit in the technique for estimating CN fetal fraction is true. In various embodiments, this assumption is that a trisomy or monosomy is present in one of the chromosomes of the fetus.

If, on the other hand, the comparison indicates that the two values of fetal fraction do not match (condition 1808) and in fact the estimation of CN fetal fraction is less than the NCN fetal fraction, then a second phase of the method is executed as indicated at block 1810.

In this second phase, the method determines whether the sample contains a partial aneuploidy or a mosaic. Further, if the sample includes a partial aneuploidy, the method determines where on the aneuploid chromosome the aneuploidy resides. In certain embodiments, this is accomplished by first binning the affected chromosome into multiple blocks. In one example, each block is about 1 million base pairs in length. Of course, other block lengths may be used such as about 1 kb, about 10 kb, about 100 kb, etc. The blocks do not overlap and span much or all of the length of the chromosome. The blocks or bins are compared to one another and this comparison provides insight about the condition. In one approach, for each block or bin, the mapped tags are counted and optionally converted to bin doses. These counts or bin doses will indicate which, if any of the bins or blocks is aneuploid. As part of the analysis of individual bins, it may be appropriate to normalize the information from each bin to account for inter-bin variations such as G-C content. The resulting normalized bins may be referred to as NBV for normalizing bin values; NBV is an example of a chromosome segment that is normalized to tags mapped to normalizing segments of GC content of segments with similar GC content (as in Example 19 below). In some embodiments, the fetal fraction is calculated for each bin and the individual values of fetal fraction values are compared. This sequential analysis of each bin is depicted in block 1812 of FIG. 18A. If any of the bins or blocks is identified as having aneuploidy (by considering tag densities, fetal fractions or other information), the method determines that the sample comprises a partial aneuploidy and additionally localizes the aneuploidy with the bin in which the tag count sufficiently deviates from an expected value. See block 1814.

If, however, when analyzing the individual the ends of the chromosome under consideration, the method does not identify any region of the chromosome exhibiting aneuploidy, the method determines that the sample contains a mosaic. See block 1816.

In related embodiments, copy number variations in portions of a genome are identified and classified in a process employing two independent calculations of fetal fraction, one from a portion of a genome preliminarily determined to harbor a copy number variation and another from elsewhere on the genome. An example of such process is depicted in the flow chart of FIGS. 18B and 18C.

Figure 18B:
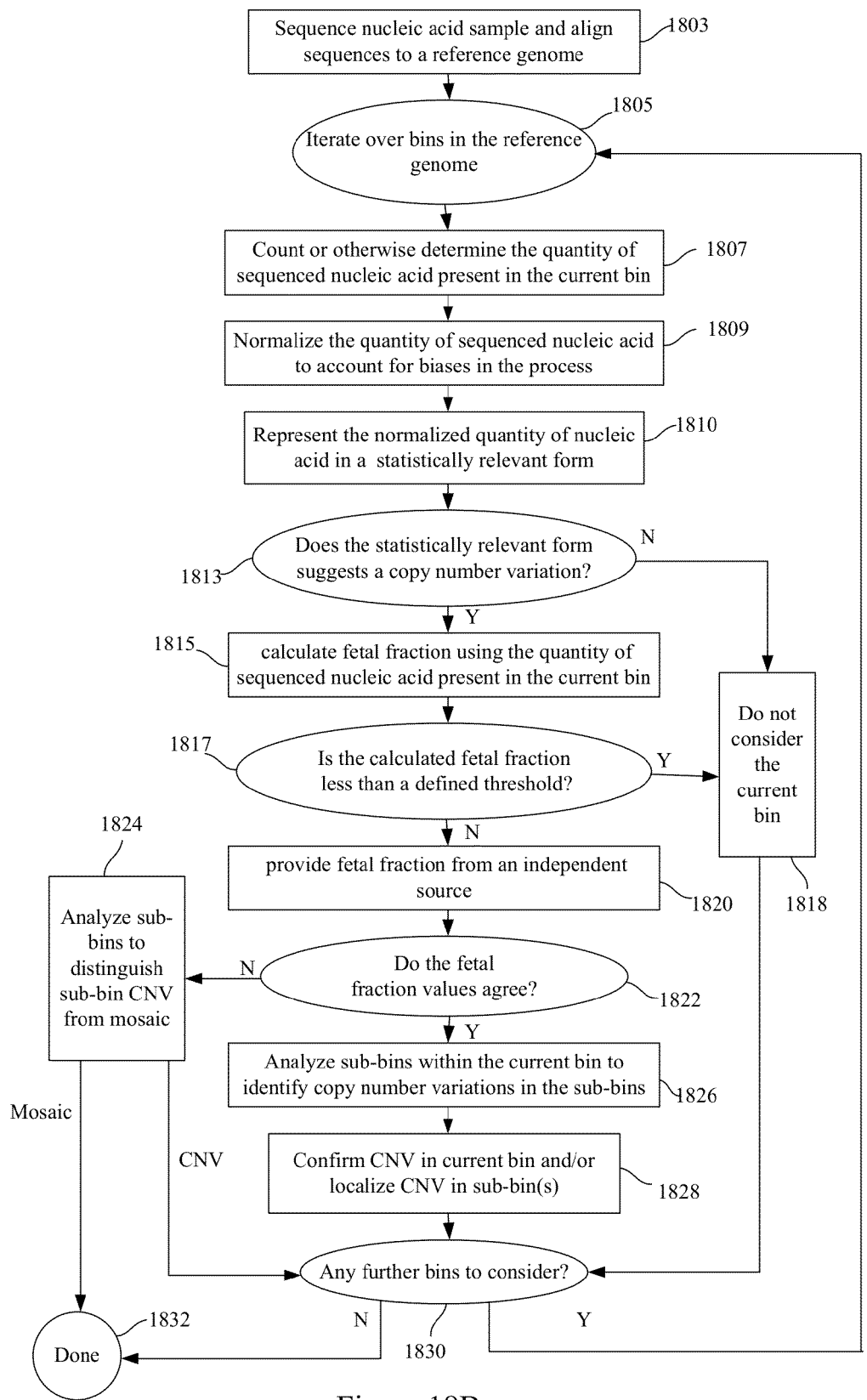
FIGS. 18B and 18C are together a flow chart depicting another method of classifying a CNV by comparing fetal fraction values calculated by two different techniques.

Turning to the flow chart shown in FIG. 18B, the depicted process begins at operation 1803 where a nucleic acid sample under consideration is sequenced and aligned to a reference genome sequence. As explained, the reference genome can be any one of many different nucleic acid sequences chosen for the sample under analysis. In a particular example, the reference genome is the human genome of a single individual or a consensus sequence of multiple individuals. In some examples, the reference genome is believed not to possess an aneuploidy or other significant copy number variation.

Sequencing can be accomplished by any one or more of various techniques. The chosen technique should provide a measure of the relative quantity or amount of all relevant portions of the reference genome present in the sample. In a particular embodiment, the sequencing technique is a massively parallel sequencing technique such as one of is described elsewhere herein. In some embodiments, massively parallel sequencing is performed on cell free DNA (cfDNA) obtained/extracted from the blood of a pregnant female. Of course, other samples containing a nucleic acid of interest may be employed. Generally, the sample is believed to contain nucleic acid originating from at least two distinct genomes (e.g. maternal and fetal genomes).

As depicted in FIG. 18B, the process employs multiple iterations, one for each of many "bins" within the reference genome. See item 1805 in the figure. In some cases, the reference genome is divided into bins of equal size, e.g. about 1 Mb in length. In other examples, the bins are of unequal size. In either case, each bin is separately considered to determine whether its sequence contains a copy number variation. In some embodiments, the bin boundaries are defined prior to alignment. In other embodiments, the bins are defined only after sequences from the sample are aligned to the reference genome. In some cases, bins are defined so that each bin contains an approximately equal amount of nucleic acid from the sample, in which case the bin boundaries are not defined until after alignment. The bin size is chosen based on the sequencing depth and other considerations, with sizes ranging from whole chromosomes (or even groups of chromosomes) to small segments (e.g., 100 kb bins or even as small as 1 kb). Small bin sizes may be appropriate when employing deep sequencing (e.g., more than 2 billion tags generated from sequencing).

Each iteration of the process described herein considers the sequences aligned to a single bin of the reference genome. As explained in more detail, each iteration determines not only whether the bin harbors a copy number variation but also the fetal fraction of the sample nucleic acid aligning to the bin.

It should be understood that while the process of FIG. 18B is described with reference to "fetal fraction," the concept of fetal fraction extends to fractions of any two distinct genomes contained in a sample. For example, if a sample contains DNA originating from somatic and cancerous cells, the fraction of nucleic acid in the sample originating from the cancer cells can be determined in a like manner as employed to determine the fetal fraction of DNA taken from the blood or other sample the pregnant mother.

As depicted in FIG. 18B, operations conducted in a single iteration for the bin under consideration involve counting sequence tags or otherwise determining the quantity of the nucleic acid present in the bin. See operation 1807. In the case of a massively parallel sequencing technique that produces reads and tags of a defined length (e.g., about 20 or 25 or 30 or 36 base pairs in length), the number of such tags aligning to the bin in question is simply counted. The count represents a quantity or mass of nucleic acid originating from the all genomes in the sample corresponding to the bin under consideration.

The quantity of sequenced nucleic acid determined to be present in the current bin is optionally normalized to account for biases that may have been introduced in the sample by collecting, sequencing, aligning, or other processing employed to determine the amount of nucleic acid in the current bin. See operation 1809. In some examples, normalization is performed on the basis of the relative amount of guanine and cytosine in the bin under consideration ("GC" content). See for example, U.S. patent application Ser. No. 13/009,708, filed Jan. 19, 2011, which is incorporated herein by reference in its entirety. GC content may be determined from the reference sequence or from the sample sequences themselves. In some cases, the quantity of a sample in a bin is normalized using the quantity of sample in one or more other bins determined to have GC contents similar to that of the bin under consideration. The BRVs described in the Example 20 are calculated in this manner. In certain embodiments, the reference sequence is initially divided into bins and each bin is ranked on the basis of its GC content so that bins having similar GC content can be immediately recognized for use in normalizing. In one embodiment, a bin ratio value is given by the number of tags in bin under consideration divided by the sum of numbers of tags in 10 other bins chosen to have the closest GC content to the bin under consideration.

More generally, the normalization can be conducted on the basis of empirically determined information or on the basis of a priori considerations. As an example, an empirical normalization process may employ the detected amount of one or more normalizing chromosomes or portions of chromosomes measured in the sample. Such normalizing chromosomes or portions may be identified experimentally to provide good discrimination of copy number. Such normalizing chromosomes or portions may be identified from qualified samples as described elsewhere herein. In some cases, the basis of normalization is a semi empirical consideration.

Returning to the flow chart of FIG. 18B, in an operation 1810 the quantity of nucleic acid in the current bin is transformed to facilitate a statistically relevant discrimination of samples possessing a genome with a copy number variation from samples which do not possess a copy number variation at the bin under consideration. In some cases, the copy number variation of interest exists only in the genome present in a low fraction (e.g., the fetal genome in a mixture of maternal and fetal DNA). Hence, operation 1810 may be employed to facilitate identification of copy number variation in samples where the variation exists only in a small fraction of the total nucleic acid in the sample. Generally, the value produced in operation 1810 is calculated from a difference between the normalized value of the quantity of nucleic acid and an expected value of the quantity for a bin having a known copy number. In one example, the statistically relevant form compares the quantity of nucleic acid identified in operations 1807 and/or 1809 with a median quantity of nucleic acid obtained from samples having normal copy numbers in the bin under consideration. In some embodiments, the difference in these quantities is scaled by a factor such as the median absolute deviation in the samples used to generate the median value. In one example, the amount of nucleic acid provided in operation 1810 takes the form of a z-score. Other forms include a t-test, log ratios, and related representations, any of which may be suggested by the distribution found in the sample.

Next, as illustrated at operation 1813, the method determines whether the amount of nucleic acid in the bin under consideration suggests a copy number variation for the bin under consideration. This maybe accomplished by simply determining whether the value calculated in operation 1810 is greater than or less than a certain magnitude associated with a normal copy number (e.g., 4 in the case of a z-score produced as described). If the evaluation conducted at operation 1813 indicates that the quantity of nucleic acid from the sample in the bin under consideration does not represent a copy number variation, then there is no reason to further consider the current bin. See block 1818 of the flowchart. From this juncture, the process typically returns to operation 1805 where the next bin in the reference genome is considered.

Assuming however that the evaluation conducted in operation 1813 indicates that the bin under consideration harbors a copy number variation, the process undertakes an operation 1815 which calculates a value of fetal fraction using the quantity of sequenced nucleic acid present in the current bin. Various techniques for calculating fetal fraction are suitable for use with this process. In some cases, the technique assumes that the copy number variation within the bin is of a particular type. For example, a copy number variation may be assumed to be a complete duplication or a complete deletion of the entire nucleic acid sequence contained in the current bin. In such case, the fetal fraction may be calculated according to equation 31 in the Example 20 (assuming that a z-score is used to provide a statistically meaningful representation of nucleic acid quantity). For example, the fetal fraction may be calculated as the absolute value of two times the z-score for the bin under consideration times the coefficient of variation. The coefficient of variation is obtained from the external samples used to calculate the median value of BRV and median absolute deviation for the bin under consideration.

If the calculated value of fetal fraction is less than a defined threshold (as indicated by the decision operation 1817), the process deems the information about the nucleic acid in the current bin unreliable and does not further consider the sequence in the current bin. In this case, the process continues through operation 1818 as described above. In one example, bins having a calculated fetal fraction value of less than about 4% are disregarded.

If the calculated value of fetal fraction determined in operation 1815 is greater than the defined threshold, the information about the bin is considered sufficiently reliable to continue with the evaluation. In such cases, process control is directed to an operation 1820 where a fetal fraction value from an independent source is considered. Such operation may be performed at the time the bin under consideration is evaluated or at an earlier time. In either case, the independent source typically does not employ the amount of nucleic acid in the bin under consideration as a basis for its calculation of fetal fraction. Examples of independent sources of information for the fetal fraction calculation include polymorphisms in nucleic acid sequences outside the bin under consideration, X chromosome counts in samples for male fetuses, etc. See U.S. patent application Ser. No. 12/958,347 filed Dec. 1, 2010; U.S. patent application Ser. No. 12/958,356 filed Dec. 1, 2010; and U.S. patent application Ser. No. 13/445,778 filed Apr. 12, 2012, each previously incorporated by reference.

Next, the two fetal fraction values are compared and it is determined whether or not they agree with one another. See decision operation 1822. If they agree, there is good evidence to conclude that the bin under consideration encompasses a copy number variation within at least one of the genomes present in the sample under evaluation.

In certain embodiments, however, the bin under consideration is further evaluated, with a finer resolution as indicated in operation 1826. In such cases, the process may analyze subregions within the current bin in order to identify copy number variations within the sub-bins. For example, if the bin size is 1 Mb, the sub-bins may each be 100 kb. To establish the presence of a copy number variation, the process may confirm that there are copy number variations in multiple sub-bins and that these copy number variations are clustered around a particular location or locations within the larger bin. See block 1828. For example, confirmation might require that at least two sub-bins within a group of four contiguous sub-bins possess copy number variations.

In certain embodiments, the sub-bins are analyzed for copy number variations using z-scores or a related representation as described above. In some implementations, the technique described in operations 1807, 1809, 1810, and 1813 may be used. For example, the process may require that at least two 100 kb bins within four contiguous bins have a z-score greater than 4 in order validate a copy number variation of the larger bin under consideration (e.g., a 1 Mb bin). In some implementations, the sub-bin analysis allows one to localize the copy number variation for the bin under consideration into one or more sub-regions under consideration.

Other techniques for confirming that the copy number variation in the current bin is supported by the copy number variations identified in the sub-bins may be employed. For example, fetal fraction values may be calculated based on the sub-bin z-scores (as described above for bins) and such fetal fraction values may be compared with an independently calculated fetal fraction value. Agreement can be checked on a per sub-bin basis. Sub-bins having fetal fraction values agreeing with the independently calculated fetal fraction value are deemed to possess a copy number variation.

When the two values fetal fraction compared in operation 1822 do not agree, the basis for the detected copy number variation is questioned. In the depicted process flow, this situation is addressed in operation 1824, which is further illustrated in FIG. 18C. In such cases, one may conclude that (1) the genome present in greater concentration (e.g., the maternal genome) has a copy number variation in the bin under consideration, (2) less than the entire sequence of the bin under considerations harbors the copy number variation, or (3) the fetus is a mosaic. When the copy number variation is present only in the genome present in greater concentration, the fetal fraction calculated using the copy number variation may be very large (e.g., 70% greater of lesser than calculated by an independent technique).

If operation 1824 determines that the sample contains nucleic acid from a mosaic, the process is concluded at 1832. In other words, no further bins are considered. However, if operation 1824 determines that one or more of the sub-bins possess a copy number variation, those sub-bins are noted and process control transfers to operation 1830, which determines whether any other bins remain to be considered. Similarly, after operation 1828 is completed, the evaluation of the nucleic acid in the bin under consideration is concluded and operation 1830 determines whether any further bins remain to be considered in the reference genome. If no further bins need to be considered, the process is completed as illustrated at 1832. If on the other hand, further bins need be considered, process control is directed back to operation 1805 where the next bin the reference genome is considered.

Information can be gleaned from contiguous bins having established copy number variations. For example, if all bins within a given chromosome have the same copy number variation, then it can be established that a full chromosomal aneuploidy exists (e.g., T21). If a subset of the bins in a chromosome have copy number variations, then a partial aneuploidy is established and localized. Bin or sub-bin analysis may also permit one to identify the origin of genomic material in an unbalanced translocation identified by karyotyping. See for example, Example 20 and the associated discussion of FIG. 71.

Figure 18C:
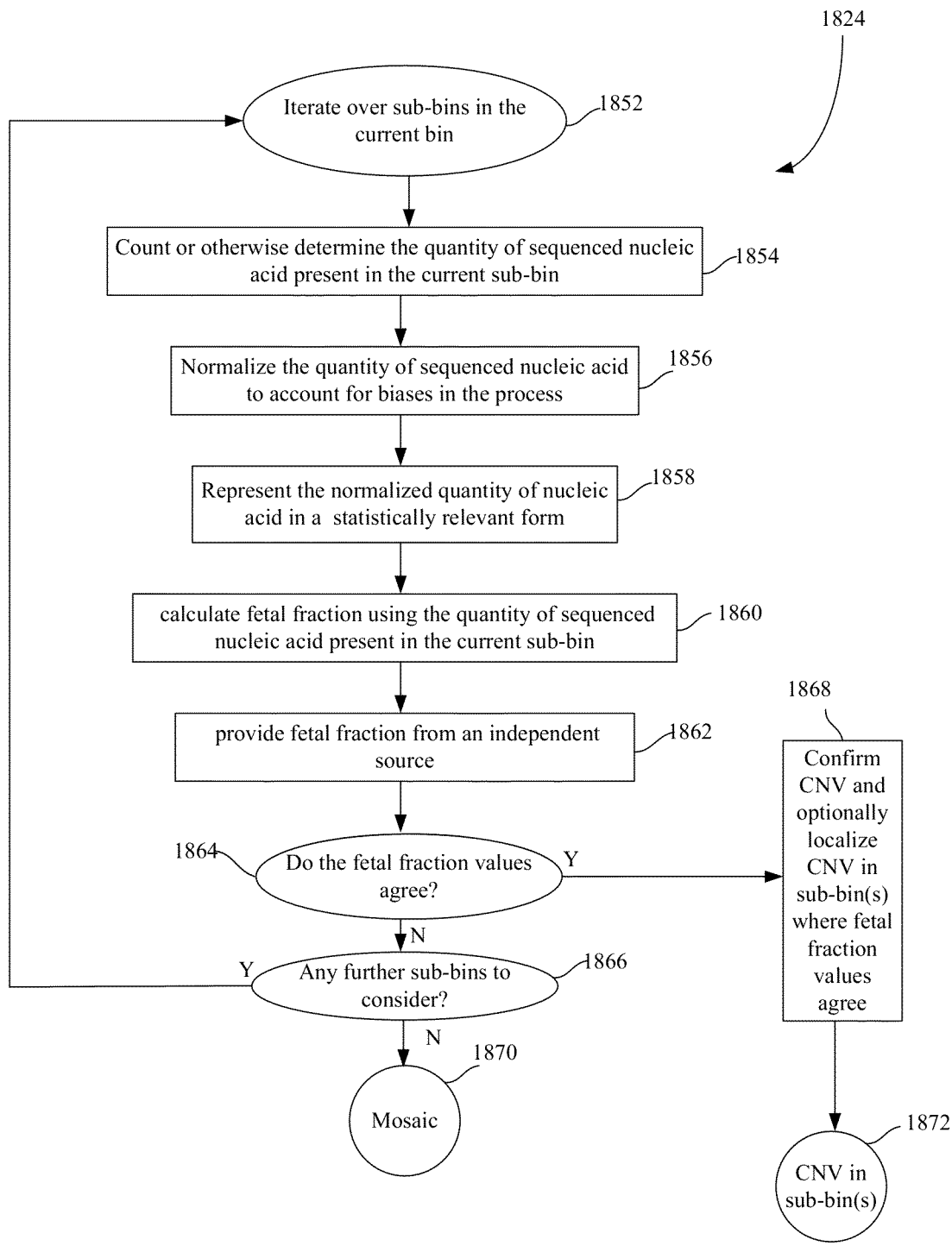

Turning now to FIG. 18C, one implementation of operation 1824 is described. As explained, the operation is triggered when the fetal fraction values compared in operation 1822 do not agree. This suggests that the bin under consideration contains only a partial copy number variation or the sample contains nucleic acid from a mosaic. Operation 1824 can distinguish these situations, and may also provide further insight into the location of copy number variation, if one is actually present in the bin under consideration.

As depicted in FIG. 18C, the process iterates over each of the sub-bins in the current bin. See process operation 1852. As an example, there may be 10 sub-bins in a 1 Mb bin, with each of the sub-bins being 100 kb in length. Each sub-bin is separately considered in process 1824.

Within each iteration, the process initially determines the quantity of sequenced nucleic acid present in the current sub-bin. This quantity may be obtained by counting the tags mapping to the current sub-bin as determined from, for example, the alignment operation performed in operation 1807 of FIG. 18B. Next, the quantity of sequenced nucleic acid in the current sub-bin is optionally normalized to account for biases in the process. This operation may be performed in a similar manner to that employed in operation 1809 of FIG. 18B. As an example, the quantity of nucleic acid in the current sub-bin may be normalized using the quantities of nucleic acid in 10 other sub-bins having GC contents similar to that of the sub-bin under consideration.

Next, as represented by block 1858 of FIG. 18C, the normalized quantity of nucleic acid in the current sub-bin is recast to a statistically relevant form such as a z-score. In certain embodiments, operation 1858 corresponds to operation 1810 of FIG. 18B, but is performed for sub-bin sized sequences. After operation 1858, a value of fetal fraction is calculated using the quantity of sequenced nucleic acid present in the current sub-bin. See operation 1860. This process may be performed in a similar manner as operation 1815 of FIG. 18B. Typically, the fetal fraction is calculated using an expression that assumes a complete duplication or deletion of the sequence within the boundaries of the current sub-bin. Equation 31 presented in Example 20 may be used for this purpose. Of course, the z-score and coefficient of variation values would need to be calculated using sub-bin sized sequences.

In operation 1862, fetal fraction from an independent source is provided for comparison with fetal fraction calculated in operation 1860. As an example, the fetal fraction provided in operation 1862 may be the same as that provided in operation 1820 of FIG. 18B. A comparison of these two values fetal fraction is made in operation 1864. An agreement in the fetal fraction values for a given sub-bin within the bin under consideration confirms a copy number variation in the bin under consideration. See block 1868. In other words, the assumption implicit in the method of calculating fetal fraction in operation 1860 is correct. That assumption may be that there is a complete duplication or complete deletion in the noted sub-bins. At this point, the process of FIG. 18C concludes as indicated at 1872. In such case, process control is direct to operation 1830 in FIG. 18B. Optionally, additional sub-bins are analyzed in the current bin to localize the copy number variation with high resolution. This allows the process to localize, with high-resolution, where the copy number variations exist in the bin under consideration.

As illustrated in FIG. 18C, if the fetal fraction values do not agree, as determined in operation 1864, the process determines whether there are any further sub-bins to consider within the current bin. See operation 1866. If additional sub-bins remain to be considered, process control is directed back to 1852 where the next sub-bin in the current bin is considered. If, on the other hand, no further sub-bins remain to be considered (operation 1866 is answered in the negative), the process concludes that no fetal fraction values considered in operation 1864 agree for any of the sub-bins considered in the bin under consideration. In this case, it is concluded that the sample under consideration includes nucleic acid from a mosaic. See item 1870. In other words, the fetus providing nucleic acid to the sample comprises two genomes, one of which harbors an aneuploidy. Process control returns to item 1832 in FIG. 18B.

A mosaic possesses two genomes. If neither genome possesses a copy number variation, then no surprising result should occur. In other words, operation 1813 of FIG. 18B would be answered in the negative. However, if one of the genomes in the mosaic contains a copy number variation, then that will be observed in operation 1813. However, the assumption that goes into producing the fetal fraction value for the bin under consideration will never be valid in the case of a mosaic, because the fetal DNA from the sample will include two genomes, one which is normal diploid and the other which is aneuploid. The relative ratio of these two genomes in the bin under consideration will influence the value of the fetal fraction. Because there is always some contribution from the normal diploid genome and some contribution from the aneuploidy genome, the assumption implicit in the calculation of fetal fraction (i.e., that the bin or sub-bin under consideration contains a complete deletion or complete duplication) will not be valid.

Calculating and Comparing True Fetal Fraction Using Polymorphisms e.g. SNPs on the Affected Sample's Chromosome of Interest and on a Chromosome Known not to be Aneuploid (e.g. Chromosome X) to Determine the Presence or Absence of Complete or Partial Aneuploidies in Male Fetuses As explained, the fetal fraction (FF) that is determined using informative polymorphic sequences e.g. informative SNPs, can be used to distinguish complete chromosomal aneuploidies from partial aneuploidies.

The presence or absence of an aneuploidy, whether partial or complete, can be determined from the value of fetal fraction that is determined using polymorphic target sequences present on a chromosome of interest and compared to the value of the fetal fraction determined using polymorphic target sequences present on a different chromosome in the sample. In samples where the fetus is a male, FF can be determined on a chromosome of interest, and compared to FF that is determined for chromosome X in the same sample. For example, given a maternal sample from a mother carrying a male fetus with trisomy 21, polymorphic sequences e.g. sequences comprising at least one informative SNP, are selected for being present on chromosome 21 and on chromosome X; the polymorphic target sequences are amplified, and sequenced, and the fetal fraction is determined as described elsewhere herein.

Given that the fetal fraction is proportional to the amount of a fetal chromosome in a sample, the fetal fraction determined using polymorphic sequences present on a trisomic chromosome in a maternal sample will be 1+½ times the fetal fraction determined using polymorphic sequences on a chromosome known not to be aneuploid e.g. chromosome X in a male fetus, in the same maternal sample. For example, in a normal sample, when fetal fraction is determined using a panel of polymorphisms on chromosome 21 ($FF_{21}$), and fetal fraction is determined using a panel of polymorphisms on chromosome X ($FF_X$), which is known to be unaffected in a male fetus, then $FF_{21}=FF_X$. However, if the fetus is trisomic for chromosome 21, then, the fetal fraction for a trisomic chromosome 21 ($FF_{21}$) will equal one and a half times the fetal fraction of chromosome X ($FF_X$) in the same sample ($FF_{21}=1.5*FF_X$). It follows that if $FF_{21}<FF_X$, the analysis logic can conclude that there is a partial deletion of chromosome 21 and/or the presence of masaicism. If $FF_{21}>FF_X$, the analysis logic can conclude that there is an increase in a portion of chromosome 21 e.g. a partial duplication or multiplication, or of a complete duplication of chromosome 21 that was not accounted for in the technique employed to calculate fetal fraction from chromosome 21. The difference between the two outcomes can be resolved as a partial duplication will result in a FF that is <$1.5*FF_X$. Alternatively, partial duplications, deletions or presence of mosaicism can be determined by e.g. increasing the number of polymorphic sequences on chromosome 21 to obtain multiple FF values along the length of the chromosome, such that a localized presence of a double or multiple value for the FF indicates an increase in a portion of the chromosome. Alternatively, as would be the case for a mosaic sample, the FF determined from the polymorphic sequences remains unchanged throughout the length of the chromosome, indicating an overall increase in the amount of the complete chromosome, but which increase is less than that for $FF_X$, as described above. In cases where there is a loss of an entire chromosome e.g. monosomy X, then the $FF_{monosomy}=\frac{1}{2}FF_x$. Fetal fraction values obtained from informative polymorphic sequences can be used in combination with sequence doses and their normalized dose values e.g. NCV, NSV, to confirm the presence of a complete aneuploidy.

Calculating Fetal Fraction from Chromosome Doses of Aneuploid Sequences

NCVs for the chromosome of interest were calculated according to the equation $$NCV_{ij} = \frac{x_{ij} - \hat{\mu}_j}{\hat{\sigma}_j} \qquad \text{Equation 19}$$

where $\hat{\mu}_j$ and $\hat{\sigma}_j$ are the estimated mean and standard deviation, respectively, for the j-th chromosome dose in a set of qualified samples, and $x_{ij}$ is the observed j-th chromosome dose for test sample i.

In general, the chromosome dose for trisomies will increase in proportion to the fetal fraction (ff). Therefore, the ff for a chromosome dose in a sample containing a trisomic chromosome will increase in proportion to the fetal fraction $$R_{jA} = \left(1 + \frac{ff}{2}\right) R_{jU} \qquad \text{Equation 20}$$

where $R_{jA}$ is the chromosome dose ($x_{ij}$) for chromosome j in an affected sample i, ff is the expected fetal fraction in the unaffected (qualified) sample U, and $R_{jU}$ is the chromosome dose in the unaffected sample. The factor "2" is included based on the assumption that there is one extra copy of the chromosome of interest. If other a different assumption is made (e.g., there this a partial duplication of the chromosome of interest, then the factor "2" does not represent reality. Substituting the chromosome dose $R_A$ in equation 19

$$NCV_{jA} = \frac{R_{jA} - \overline{R_{jU}}}{\sigma_{jU}} \qquad \text{Equation 21}$$

where $\overline{R_{jU}}$ is the equivalent of $\hat{\mu}_j$, and $\sigma_{jU}$ is the equivalent $\hat{\sigma}_j$; ff is solved as follows:

$$NCV_{jA} = \frac{\left(1 + \frac{ff}{2}\right)\overline{R_{jU}} - \overline{R_{jU}}}{\sigma_{jU}} \qquad \text{Equation 22}$$

$$NCV_{jA} = \frac{\left(\frac{ff}{2}\right)\overline{R_{jU}}}{\sigma_{jU}} \qquad \text{Equation 23}$$

$$NCV_{jA} = \frac{ff}{2CV_{jU}} \qquad \text{Equation 24}$$

Therefore, the percent "$ff_{(i)}$" can be determined for any chromosome as:

$$ff_{(i)} = 2 * NCV_{jA} CV_{jU} \qquad \text{Equation 25}$$

Using Fetal Fraction to Resolve No-Calls

The ability of determining significant differences in the representation of one or more sequences present in a mixture of two genomes is predicated on the relative contribution of sequences by the first genome relative to the contribution of the second genome. For example, noninvasive prenatal diagnosis using cfDNA in a maternal sample is challenging because only a small portion of the DNA sample is derived from the fetus. For prenatal diagnostic assays, the background of maternal DNA provides a practical limit on sensitivity, and therefore the fraction of fetal DNA present in the maternal sample is an important parameter. The sensitivity of fetal aneuploidy detection by counting DNA molecules depends on the fetal DNA fraction and the number of molecules that are counted.

Typically, about 1% of maternal test samples that analyzed for fetal aneuploidies by massively parallel sequencing are "no-call" samples for which insufficient sequencing information e.g. number of fetal sequence tags, precludes a confident determination of the presence or absence one or more fetal aneuploidies in the maternal sample. The "no-call" determination can result from levels of fetal cfDNA that are too low relative to the level of the maternal contribution to the sample to provide sequencing information that distinguishes the aneuploid sample from the sequencing information determined in qualified samples. To determine whether the "no-call" sample is or is not an aneuploid sample, fetal fraction determined empirically, and/or derived from, e.g., NVC values and used to confirm or deny the presence of chromosomal aneuploidies. As described elsewhere herein, ff can be used to characterize the type of aneuploidy present in a test sample. For example, for thresholds setting the "no-call" zone between 2.5 and 4 NCV values, a test sample having an NCV bordering the 4 NCV threshold and shown to have a low (e.g. less than 3%) fetal fraction is likely to be an affected sample. Conversely, a test sample having an NCV bordering the 2.5 NCV threshold and shown to have a high (e.g. greater than 40%) fetal fraction is likely to be an unaffected sample. Resolving the "no-call" samples can rely on one determination of fetal fraction. Preferably, the fetal fraction is determined according to two or more different methods, or from using NCVs determined from two or more different chromosomes in the sample using the same method. Similarly, fetal fraction can be used to assess whether samples with NCVs marginally greater than 4 or marginally smaller than NCVs of 2.5, may be false positive or false negative calls, respectively.

Apparatus and Systems for Determining CNV

Analysis of the sequencing data and the diagnosis derived therefrom are typically performed using various computer executed algorithms and programs. Therefore, certain embodiments employ processes involving data stored in or transferred through one or more computer systems or other processing systems. Embodiments of the invention also relate to apparatus for performing these operations. This apparatus may be specially constructed for the required purposes, or it may be a general-purpose computer (or a group of computers) selectively activated or reconfigured by a computer program and/or data structure stored in the computer. In some embodiments, a group of processors performs some or all of the recited analytical operations collaboratively (e.g., via a network or cloud computing) and/or in parallel. A processor or group of processors for performing the methods described herein may be of various types including microcontrollers and microprocessors such as programmable devices (e.g., CPLDs and FPGAs) and non-programmable devices such as gate array ASICs or general purpose microprocessors.

In addition, certain embodiments relate to tangible and/or non-transitory computer readable media or computer program products that include program instructions and/or data (including data structures) for performing various computer-implemented operations. Examples of computer-readable media include, but are not limited to, semiconductor memory devices, magnetic media such as disk drives, magnetic tape, optical media such as CDs, magneto-optical media, and hardware devices that are specially configured to store and perform program instructions, such as read-only memory devices (ROM) and random access memory (RAM). The computer readable media may be directly controlled by an end user or the media may be indirectly controlled by the end user. Examples of directly controlled media include the media located at a user facility and/or media that are not shared with other entities. Examples of indirectly controlled media include media that is indirectly accessible to the user via an external network and/or via a service providing shared resources such as the "cloud." Examples of program instructions include both machine code, such as produced by a compiler, and files containing higher level code that may be executed by the computer using an interpreter.

In various embodiments, the data or information employed in the disclosed methods and apparatus is provided in an electronic format. Such data or information may include reads and tags derived from a nucleic acid sample, counts or densities of such tags that align with particular regions of a reference sequence (e.g., that align to a chromosome or chromosome segment), reference sequences (including reference sequences providing solely or primarily polymorphisms), chromosome and segment doses, calls such as aneuploidy calls, normalized chromosome and segment values, pairs of chromosomes or segments and corresponding normalizing chromosomes or segments, counseling recommendations, diagnoses, and the like. As used herein, data or other information provided in electronic format is available for storage on a machine and transmission between machines. Conventionally, data in electronic format is provided digitally and may be stored as bits and/or bytes in various data structures, lists, databases, etc. The data may be embodied electronically, optically, etc.

In one embodiment, the invention provides a computer program product for generating an output indicating the presence or absence of an aneuploidy e.g. a fetal aneuploidy or cancer, in a test sample. The computer product may contain instructions for performing any one or more of the above-described methods for determining a chromosomal anomaly. As explained, the computer product may include a non-transitory and/or tangible computer readable medium having a computer executable or compilable logic (e.g., instructions) recorded thereon for enabling a processor to determine chromosome doses and, in some cases, whether a fetal aneuploidy is present or absent. In one example, the computer product comprises a computer readable medium having a computer executable or compilable logic (e.g., instructions) recorded thereon for enabling a processor to diagnose a fetal aneuploidy comprising: a receiving procedure for receiving sequencing data from at least a portion of nucleic acid molecules from a maternal biological sample, wherein said sequencing data comprises a calculated chromosome and/or segment dose; computer assisted logic for analyzing a fetal aneuploidy from said received data; and an output procedure for generating an output indicating the presence, absence or kind of said fetal aneuploidy.

The sequence information from the sample under consideration may be mapped to chromosome reference sequences to identify a number of sequence tags for each of any one or more chromosomes of interest and to identify a number of sequence tags for a normalizing segment sequence for each of said any one or more chromosomes of interest. In various embodiments, the reference sequences are stored in a database such as a relational or object database, for example.

It should be understood that it is not practical, or even possible in most cases, for an unaided human being to perform the computational operations of the methods disclosed herein. For example, mapping a single 30 bp read from a sample to any one of the human chromosomes might require years of effort without the assistance of a computational apparatus. Of course, the problem is compounded because reliable aneuploidy calls generally require mapping thousands (e.g., at least about 10,000) or even millions of reads to one or more chromosomes.

The methods disclosed herein can be performed using a computer-readable medium having stored thereon computer-readable instructions for carrying out a method for identifying any CNV e.g. chromosomal or partial aneuploidies. Thus, in one embodiment, the invention provides a computer-readable medium having stored thereon computer-readable instructions for carrying out a method for identifying complete and partial chromosomal aneuploidies e.g. fetal aneuploidies. Such instructions may include, for example, instructions for (a) obtaining and/or storing in a computer readable medium, at least temporarily, sequence information for fetal and maternal nucleic acids in a sample; (b) using the stored sequence information to computationally identify a number of sequence tags from the mixture of fetal and maternal nucleic acids for each of any one or more chromosomes of interest selected from chromosomes 1-22, X and Y, and to identify a number of sequence tags for at least one normalizing chromosome sequence for each of the one or more chromosomes of interest; and (c) computationally calculating, using the number of sequence tags identified for each of the one or more chromosomes of interest and the number of sequence tags identified for each normalizing chromosome sequence, a single chromosome dose for each of the chromosomes of interest. These instructions may be executed using one or more appropriately designed or configured processors. The instructions may additionally include comparing each of the chromosome doses to associated threshold values, and thereby determining the presence or absence of any four or more partial or complete different fetal chromosomal aneuploidies in the sample. As explained above, there are numerous variations on this process. All such variations can be implemented in using processing and storage features as described here.

In some embodiments, the instructions may further include automatically recording information pertinent to the method such as chromosome doses and the presence or absence of a fetal chromosomal aneuploidy in a patient medical record for a human subject providing the maternal test sample. The patient medical record may be maintained by, for example, a laboratory, physician's office, a hospital, a health maintenance organization, an insurance company, or a personal medical record website. Further, based on the results of the processor-implemented analysis, the method may further involve prescribing, initiating, and/or altering treatment of a human subject from whom the maternal test sample was taken. This may involve performing one or more additional tests or analyses on additional samples taken from the subject.

Disclosed methods can also be performed using a computer processing system which is adapted or configured to perform a method for identifying any CNV e.g. chromosomal or partial aneuploidies. Thus, in one embodiment, the invention provides a computer processing system which is adapted or configured to perform a method as described herein. In one embodiment, the apparatus comprises a sequencing device adapted or configured for sequencing at least a portion of the nucleic acid molecules in a sample to obtain the type of sequence information described elsewhere herein. The apparatus may also include components for processing the sample. Such components are described elsewhere herein.

Sequence or other data, can be input into a computer or stored on a computer readable medium either directly or indirectly. In one embodiment, a computer system is directly coupled to a sequencing device that reads and/or analyzes sequences of nucleic acids from samples. Sequences or other information from such tools are provided via interface in the computer system. Alternatively, the sequences processed by system are provided from a sequence storage source such as a database or other repository. Once available to the processing apparatus, a memory device or mass storage device buffers or stores, at least temporarily, sequences of the nucleic acids. In addition, the memory device may store tag counts for various chromosomes or genomes, etc. The memory may also store various routines and/or programs for analyzing the presenting the sequence or mapped data. Such programs/routines may include programs for performing statistical analyses, etc.

In one example, a user provides a sample into a sequencing apparatus. Data is collected and/or analyzed by the sequencing apparatus which is connected to a computer. Software on the computer allows for data collection and/or analysis. Data can be stored, displayed (via a monitor or other similar device), and/or sent to another location. The computer may be connected to the internet which is used to transmit data to a handheld device utilized by a remote user (e.g., a physician, scientist or analyst). It is understood that the data can be stored and/or analyzed prior to transmittal. In some embodiments, raw data is collected and sent to a remote user or apparatus that will analyze and/or store the data. Transmittal can occur via the internet, but can also occur via satellite or other connection. Alternately, data can be stored on a computer-readable medium and the medium can be shipped to an end user (e.g., via mail). The remote user can be in the same or a different geographical location including, but not limited to a building, city, state, country or continent.

In some embodiments, the methods also include collecting data regarding a plurality of polynucleotide sequences (e.g., reads, tags and/or reference chromosome sequences) and sending the data to a computer or other computational system. For example, the computer can be connected to laboratory equipment, e.g., a sample collection apparatus, a nucleotide amplification apparatus, a nucleotide sequencing apparatus, or a hybridization apparatus. The computer can then collect applicable data gathered by the laboratory device. The data can be stored on a computer at any step, e.g., while collected in real time, prior to the sending, during or in conjunction with the sending, or following the sending. The data can be stored on a computer-readable medium that can be extracted from the computer. The data collected or stored can be transmitted from the computer to a remote location, e.g., via a local network or a wide area network such as the internet. At the remote location various operations can be performed on the transmitted data as described below.

Among the types of electronically formatted data that may be stored, transmitted, analyzed, and/or manipulated in systems, apparatus, and methods disclosed herein are the following:

Reads obtained by sequencing nucleic acids in a test sample

Tags obtained by aligning reads to a reference genome or other reference sequence or sequences The reference genome or sequence Sequence tag density—Counts or numbers of tags for each of two or more regions (typically chromosomes or chromosome segments) of a reference genome or other reference sequences Identities of normalizing chromosomes or chromosome segments for particular chromosomes or chromosome segments of interest Doses for chromosomes or chromosome segments (or other regions) obtained from chromosomes or segments of interest and corresponding normalizing chromosomes or segments Thresholds for calling chromosome doses as either affected, non-affected, or no call The actual calls of chromosome doses Diagnoses (clinical condition associated with the calls)

Recommendations for further tests derived from the calls and/or diagnoses

Treatment and/or monitoring plans derived from the calls and/or diagnoses

These various types of data may be obtained, stored transmitted, analyzed, and/or manipulated at one or more locations using distinct apparatus. The processing options span a wide spectrum. At one end of the spectrum, all or much of this information is stored and used at the location where the test sample is processed, e.g., a doctor's office or other clinical setting. In other extreme, the sample is obtained at one location, it is processed and optionally sequenced at a different location, reads are aligned and calls are made at one or more different locations, and diagnoses, recommendations, and/or plans are prepared at still another location (which may be a location where the sample was obtained).

In various embodiments, the reads are generated with the sequencing apparatus and then transmitted to a remote site where they are processed to produce aneuploidy calls. At this remote location, as an example, the reads are aligned to a reference sequence to produce tags, which are counted and assigned to chromosomes or segments of interest. Also at the remote location, the counts are converted to doses using associated normalizing chromosomes or segments. Still further, at the remote location, the doses are used to generate aneuploidy calls.

Among the processing operations that may be employed at distinct locations are the following:

Sample collection

Sample processing preliminary to sequencing

Sequencing

Analyzing sequence data and deriving aneuploidy calls

Diagnosis

Reporting a diagnosis and/or a call to patient or health care provider

Developing a plan for further treatment, testing, and/or monitoring

Executing the plan

Counseling

Any one or more of these operations may be automated as described elsewhere herein. Typically, the sequencing and the analyzing of sequence data and deriving aneuploidy calls will be performed computationally. The other operations may be performed manually or automatically.

Examples of locations where sample collection may be performed include health practitioners' offices, clinics, patients' homes (where a sample collection tool or kit is provided), and mobile health care vehicles. Examples of locations where sample processing prior to sequencing may be performed include health practitioners' offices, clinics, patients' homes (where a sample processing apparatus or kit is provided), mobile health care vehicles, and facilities of aneuploidy analysis providers. Examples of locations where sequencing may be performed include health practitioners' offices, clinics, health practitioners' offices, clinics, patients' homes (where a sample sequencing apparatus and/or kit is provided), mobile health care vehicles, and facilities of aneuploidy analysis providers. The location where the sequencing takes place may be provided with a dedicated network connection for transmitting sequence data (typically reads) in an electronic format. Such connection may be wired or wireless and have and may be configured to send the data to a site where the data can be processed and/or aggregated prior to transmission to a processing site. Data aggregators can be maintained by health organizations such as Health Maintenance Organizations (HMOs).

The analyzing and/or deriving operations may be performed at any of the foregoing locations or alternatively at a further remote site dedicated to computation and/or the service of analyzing nucleic acid sequence data. Such locations include for example, clusters such as general purpose server farms, the facilities of an aneuploidy analysis service business, and the like. In some embodiments, the computational apparatus employed to perform the analysis is leased or rented. The computational resources may be part of an internet accessible collection of processors such as processing resources colloquially known as the cloud. In some cases, the computations are performed by a parallel or massively parallel group of processors that are affiliated or unaffiliated with one another. The processing may be accomplished using distributed processing such as cluster computing, grid computing, and the like. In such embodiments, a cluster or grid of computational resources collective form a super virtual computer composed of multiple processors or computers acting together to perform the analysis and/or derivation described herein. These technologies as well as more conventional supercomputers may be employed to process sequence data as described herein. Each is a form of parallel computing that relies on processors or computers. In the case of grid computing these processors (often whole computers) are connected by a network (private, public, or the Internet) by a conventional network protocol such as Ethernet. By contrast, a supercomputer has many processors connected by a local high-speed computer bus.

In certain embodiments, the diagnosis (e.g., the fetus has Downs syndrome or the patient has a particular type of cancer) is generated at the same location as the analyzing operation. In other embodiments, it is performed at a different location. In some examples, reporting the diagnosis is performed at the location where the sample was taken, although this need not be the case. Examples of locations where the diagnosis can be generated or reported and/or where developing a plan is performed include health practitioners' offices, clinics, internet sites accessible by computers, and handheld devices such as cell phones, tablets, smart phones, etc. having a wired or wireless connection to a network. Examples of locations where counseling is performed include health practitioners' offices, clinics, internet sites accessible by computers, handheld devices, etc.

In some embodiments, the sample collection, sample processing, and sequencing operations are performed at a first location and the analyzing and deriving operation is performed at a second location. However, in some cases, the sample collection is collected at one location (e.g., a health practitioner's office or clinic) and the sample processing and sequencing is performed at a different location that is optionally the same location where the analyzing and deriving take place.

In various embodiments, a sequence of the above-listed operations may be triggered by a user or entity initiating sample collection, sample processing and/or sequencing. After one or more these operations have begun execution the other operations may naturally follow. For example, the sequencing operation may cause reads to be automatically collected and sent to a processing apparatus which then conducts, often automatically and possibly without further user intervention, the sequence analysis and derivation of aneuploidy operation. In some implementations, the result of this processing operation is then automatically delivered, possibly with reformatting as a diagnosis, to a system component or entity that processes reports the information to a health professional and/or patient. As explained such information can also be automatically processed to produce a treatment, testing, and/or monitoring plan, possibly along with counseling information. Thus, initiating an early stage operation can trigger an end to end sequence in which the health professional, patient or other concerned party is provided with a diagnosis, a plan, counseling and/or other information useful for acting on a physical condition. This is accomplished even though parts of the overall system are physically separated and possibly remote from the location of, e.g., the sample and sequence apparatus.

Figure 19:
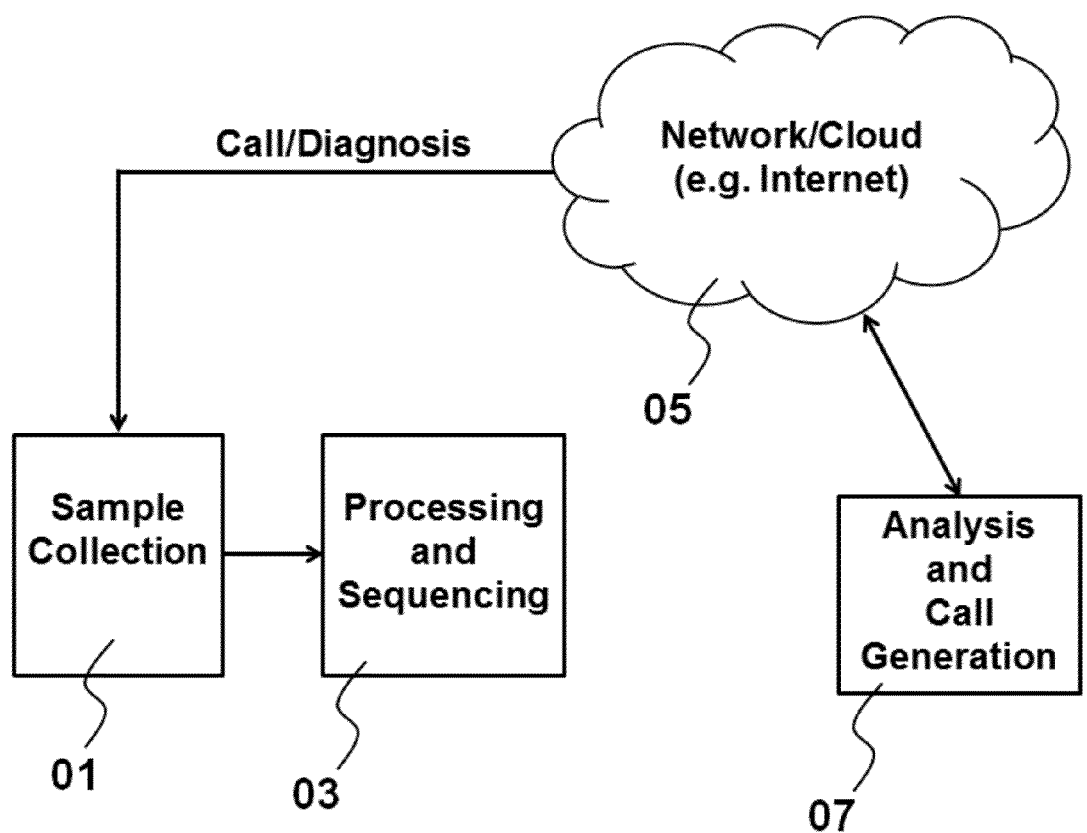
FIG. 19 is a block diagram of a dispersed system for processing a test sample and ultimately making a diagnosis.

FIG. 19 shows one implementation of a dispersed system for producing a call or diagnosis from a test sample. A sample collection location 01 is used for obtaining a test sample from a patient such as a pregnant female or a putative cancer patient. The samples then provided to a processing and sequencing location 03 where the test sample may be processed and sequenced as described above. Location 03 includes apparatus for processing the sample as well as apparatus for sequencing the processed sample. The result of the sequencing, as described elsewhere herein, is a collection of reads which are typically provided in an electronic format and provided to a network such as the Internet, which is indicated by reference number 05 in FIG. 19.

The sequence data is provided to a remote location 07 where analysis and call generation are performed. This location may include one or more powerful computational devices such as computers or processors. After the computational resources at location 07 have completed their analysis and generated a call from the sequence information received, the call is relayed back to the network 05. In some implementations, not only is a call generated at location 07 but an associated diagnosis is also generated. The call and or diagnosis are then transmitted across the network and back to the sample collection location 01 as illustrated in FIG. 19. As explained, this is simply one of many variations on how the various operations associated with generating a call or diagnosis may be divided among various locations. One common variant involves providing sample collection and processing and sequencing in a single location. Another variation involves providing processing and sequencing at the same location as analysis and call generation.

Figure 20:
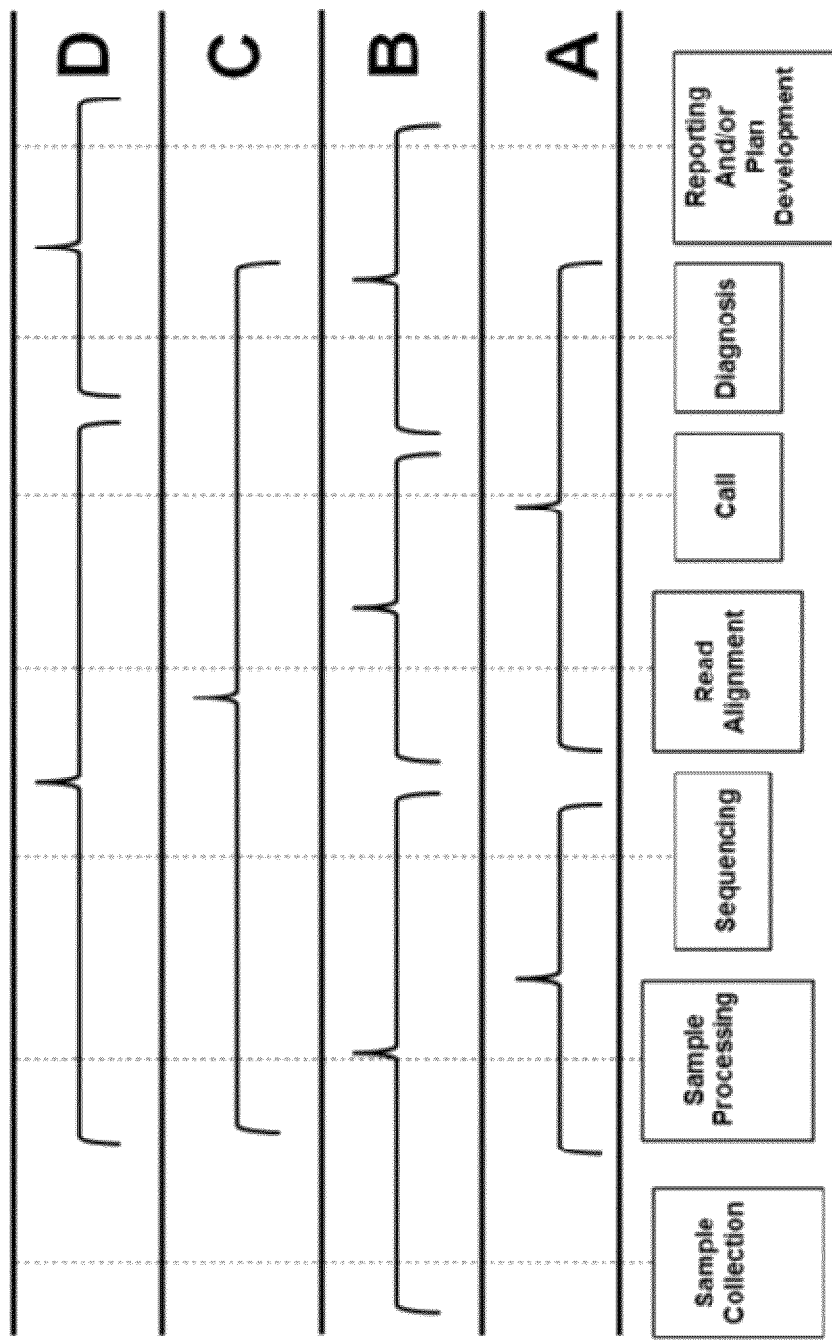
FIG. 20 schematically illustrates how different operations in processing test samples may be grouped to be handled by different elements of a system.

FIG. 20 elaborates on the options for performing various operations at distinct locations. In the most granular sense depicted in FIG. 20, each of the following operations is performed at a separate location: sample collection, sample processing, sequencing, read alignment, calling, diagnosis, and reporting and/or plan development.

In one embodiment that aggregates some of these operations, sample processing and sequencing are performed in one location and read alignment, calling, and diagnosis are performed at a separate location. See the portion of FIG. 20 identified by reference character A. In another implementation, that is identified by character B in FIG. 20, sample collection, sample processing, and sequencing are all performed at the same location. In this implementation, read alignment and calling are performed in a second location. Finally, diagnosis and reporting and/or plan development are performed in a third location. In the implementation depicted by character C in FIG. 20, sample collection is performed at a first location, sample processing, sequencing, read alignment, calling, and diagnosis are all performed together at a second location, and reporting and/or plan development are performed at a third location. Finally, in the implementation labeled D in FIG. 20, sample collection is performed at a first location, sample processing, sequencing, read alignment, and calling are all performed at a second location, and diagnosis and reporting and/or plan management are performed at a third location.

In one embodiment, the invention provides a system for use in determining the presence or absence of any one or more different complete fetal chromosomal aneuploidies in a maternal test sample comprising fetal and maternal nucleic acids, the system including a sequencer for receiving a nucleic acid sample and providing fetal and maternal nucleic acid sequence information from the sample; a processor; and a machine readable storage medium comprising instructions for execution on said processor, the instructions comprising:

(a) code for obtaining sequence information for said fetal and maternal nucleic acids in the sample;

(b) code for using said sequence information to computationally identify a number of sequence tags from the fetal and maternal nucleic acids for each of any one or more chromosomes of interest selected from chromosomes 1-22, X, and Y and to identify a number of sequence tags for at least one normalizing chromosome sequence or normalizing chromosome segment sequence for each of said any one or more chromosomes of interest;

(c) code for using said number of sequence tags identified for each of said any one or more chromosomes of interest and said number of sequence tags identified for each normalizing chromosome sequence or normalizing chromosome segment sequence to calculate a single chromosome dose for each of the any one or more chromosomes of interest; and (d) code for comparing each of the single chromosome doses for each of the any one or more chromosomes of interest to a corresponding threshold value for each of the one or more chromosomes of interest, and thereby determining the presence or absence of any one or more complete different fetal chromosomal aneuploidies in the sample.

In some embodiments, the code for calculating a single chromosome dose for each of the any one or more chromosomes of interest comprises code for calculating a chromosome dose for a selected one of the chromosomes of interest as the ratio of the number of sequence tags identified for the selected chromosome of interest and the number of sequence tags identified for a corresponding at least one normalizing chromosome sequence or normalizing chromosome segment sequence for the selected chromosome of interest.

In some embodiments, the system further comprises code for repeating the calculating of a chromosome dose for each of any remaining chromosome segments of the any one or more segments of any one or more chromosomes of interest.

In some embodiments, the one or more chromosomes of interest selected from chromosomes 1-22, X, and Y comprise at least twenty chromosomes selected from chromosomes 1-22, X, and Y, and wherein the instructions comprise instructions for determining the presence or absence of at least twenty different complete fetal chromosomal aneuploidies is determined.

In some embodiments, the at least one normalizing chromosome sequence is a group of chromosomes selected from chromosomes 1-22, X, and Y. In other embodiments, the at least one normalizing chromosome sequence is a single chromosome selected from chromosomes 1-22, X, and Y.

In another embodiment, the invention provides a system for use in determining the presence or absence of any one or more different partial fetal chromosomal aneuploidies in a maternal test sample comprising fetal and maternal nucleic acids, the system comprising: a sequencer for receiving a nucleic acid sample and providing fetal and maternal nucleic acid sequence information from the sample; a processor; and a machine readable storage medium comprising instructions for execution on said processor, the instructions comprising:

(a) code for obtaining sequence information for said fetal and maternal nucleic acids in said sample;

(b) code for using said sequence information to computationally identify a number of sequence tags from the fetal and maternal nucleic acids for each of any one or more segments of any one or more chromosomes of interest selected from chromosomes 1-22, X, and Y and to identify a number of sequence tags for at least one normalizing segment sequence for each of said any one or more segments of any one or more chromosomes of interest;

(c) code using said number of sequence tags identified for each of said any one or more segments of any one or more chromosomes of interest and said number of sequence tags identified for said normalizing segment sequence to calculate a single chromosome segment dose for each of said any one or more segments of any one or more chromosomes of interest; and (d) code for comparing each of said single chromosome segment doses for each of said any one or more segments of any one or more chromosomes of interest to a corresponding threshold value for each of said any one or more chromosome segments of any one or more chromosome of interest, and thereby determining the presence or absence of one or more different partial fetal chromosomal aneuploidies in said sample.

In some embodiments, the code for calculating a single chromosome segment dose comprises code for calculating a chromosome segment dose for a selected one of the chromosome segments as the ratio of the number of sequence tags identified for the selected chromosome segment and the number of sequence tags identified for a corresponding normalizing segment sequence for the selected chromosome segment.

In some embodiments, the system further comprises code for repeating the calculating of a chromosome segment dose for each of any remaining chromosome segments of the any one or more segments of any one or more chromosomes of interest.

In some embodiments, the system further comprises (i) code for repeating (a)-(d) for test samples from different maternal subjects, and (ii) code for determining the presence or absence of any one or more different partial fetal chromosomal aneuploidies in each of said samples.

In other embodiments of any of the systems provided herein, the code further comprises code for automatically recording the presence or absence of a fetal chromosomal aneuploidy as determined in (d) in a patient medical record for a human subject providing the maternal test sample, wherein the recording is performed using the processor.

In some embodiments of any of the systems provided herein, the sequencer is configured to perform next generation sequencing (NGS). In some embodiments, the sequencer is configured to perform massively parallel sequencing using sequencing-by-synthesis with reversible dye terminators. In other embodiments, the sequencer is configured to perform sequencing-by-ligation. In yet other embodiments, the sequencer is configured to perform single molecule sequencing.

Kits.

In various embodiments, kits are provided for practice of the methods described herein. In certain embodiments the kits comprise one or more positive internal controls for a full aneuploidy and/or for a partial aneuploidy. Typically, although not necessarily, the controls comprise internal positive controls comprising nucleic acid sequences of the type that are to be screened for. For example, a control for a test to determine the presence or absence of a fetal trisomy e.g. trisomy 21, in a maternal sample can comprises DNA characterized by trisomy 21 (e.g., DNA obtained from an individual with trisomy 21). In some embodiments, the control comprises a mixture of DNA obtained from two or more individuals with different aneuploidies. For example, for a test to determine the presence or absence of trisomy 13, trisomy 18, trisomy 21, and monosomy X, the control can comprise a combination of DNA samples obtained from pregnant women each carrying a fetus with one of the trisomys being tested. In addition to complete chromosomal aneuploidies, IPCs can be created to provide positive controls for tests to determine the presence or absence of partial aneuploidies.

In certain embodiments the positive control(s) comprise one or more nucleic acids comprising a trisomy 21 (T21), and/or a trisomy 18 (T18), and/or a trisomy 13 (T13). In certain embodiments the nucleic acid(s) comprising each of the trisomys present are T21 are provided in separate containers. In certain embodiments the nucleic acids comprising two or more trisomys are provided in a single container. Thus, for example, in certain embodiments, a container may contain T21 and T18, T21 and T13, T18 and T13. In certain embodiments, a container may contain T18, T21 and T13. In these various embodiments, the trisomys may be provided in equal quantity/concentration. In other embodiments, the trisomy may be provided in particular predetermined ratios. In various embodiments the controls can be provided as "stock" solutions of known concentration.

In certain embodiments the control for detecting an aneuploidy comprises a mixture of cellular genomic DNA obtained from a two subjects one being the contributor of the aneuploid genome. For example, as explained above, an internal positive control (IPC) that is created as a control for a test to determine a fetal trisomy e.g. trisomy 21, can comprise a combination of genomic DNA from a male or female subject carrying the trisomic chromosome with genomic DNA from a female subject known not to carry the trisomic chromosome. In certain embodiments the genomic DNA is sheared to provide fragments of between about 100-400 bp, between about 150-350 bp, or between about 200-300 bp to simulate the circulating cfDNA fragments in maternal samples.

In certain embodiments the proportion of fragmented DNA from the subject carrying the aneuploidy e.g. trisomy 21 in the control, is chosen to simulate the proportion of circulating fetal cfDNA found in maternal samples to provide an IPC comprising a mixture of fragmented DNA comprising about 5%, about 10%, about 15%, about 20%, about 25%, about 30%, of DNA from the subject carrying the aneuploidy. In certain embodiments the control comprise DNA from different subjects each carrying a different aneuploidy. For example, the IPC can comprise about 80% of the unaffected female DNA, and the remaining 20% can be DNA from three different subjects each carrying a trisomic chromosome 21, a trisomic chromosome 13, and a trisomic chromosome 18.

In certain embodiments the control(s) comprise cfDNA obtained from a mother known to carry a fetus with a known chromosomal aneuploidy. For example, the controls can comprise cfDNA obtained from a pregnant woman carrying a fetus with trisomy 21 and/or trisomy 18, and/or trisomy 13. The cfDNA can extracted from the maternal sample, and cloned into a bacterial vector and grown in bacteria to provide an ongoing source of the IPC. Alternatively, the cloned cfDNA can be amplified by e.g. PCR.

While the controls present in the kits are described above with respect to trisomies, they need not be so limited. It will be appreciated that the positive controls present in the kit can be created to reflect other partial aneuploidies including for example, various segment amplification and/or deletions. Thus, for example, where various cancers are known to be associated with particular amplifications or deletions of substantially complete chromosomal arms the positive control(s) can comprise a p arm or a q arm of any one or more of chromosomes 1-22, X and Y. In certain embodiments the control comprises an amplification of one or more arms selected from the group consisting of 1q, 3q, 4p, 4q, 5p, 5q, 6p, 6q, 7p, 7q, 8p, 8q, 9p, 9q, 10p, 10q, 12p, 12q, 13q, 14q, 16p, 17p, 17q, 18p, 18q, 19p, 19q, 20p, 20q, 21q, and/or 22q (see, e.g., Table 2).

In certain embodiments, the controls comprise aneuploidies for any regions known to be associated with particular amplifications or deletions (e.g., breast cancer associated with an amplification at 20Q13). Illustrative regions include, but are not limited to 17q23 (associated with breast cancer), 19q12 (associate with ovarian cancer), 1q21-1q23 (associated with sarcomas and various solid tumors), 8p11-p12 (associated with breast cancer), the ErbB2 amplicon, and so forth. In certain embodiments the controls comprise an amplification or a deletion of a chromosomal region as shown in any one of Tables 3-6. In certain embodiments the controls comprise an amplification or a deletion of a chromosomal region comprising a gene as shown in any one of Tables 3-6. In certain embodiments the controls comprise nucleic acid sequences comprising an amplification of a nucleic acid comprising one or more oncogenes In certain embodiments the controls comprise nucleic acid sequences comprising an amplification of a nucleic acid comprising one or more genes selected from the group consisting of MYC, ERBB2 (EFGR), CCND1 (Cyclin D1), FGFR1, FGFR2, HRAS, KRAS, MYB, MDM2, CCNE, KRAS, MET, ERBB1, CDK4, MYCB, ERBB2, AKT2, MDM2 and CDK4.

The foregoing controls are intended to be illustrative and not limiting. Using the teachings provided herein numerous other controls suitable for incorporation into a kit will be recognized by one of skill in the art.

In various embodiments in addition to the controls or instead of the controls, the kits comprise one or more nucleic acids and/or nucleic acid mimics that provide marker sequence(s) suitable for tracking and determining sample integrity. In certain embodiments the markers comprise an antigenomic sequence. In certain embodiments the marker sequences range in length from about 30 bp up to about 600 bp in length or about 100 bp to about 400 bp in length. In certain embodiments the marker sequence(s) are at least 30 bp (or nt) in length. In certain embodiments the marker is ligated to an adaptor and the length of the adaptor-ligated marker molecule is between about 200 bp (or nt) and about 600 bp (or nt), between about 250 bp (or nt) and 550 bp (or nt), between about 300 bp (or nt) and 500 bp (or nt), or between about 350 and 450. In certain embodiments, the length of the adaptor-ligated marker molecule is about 200 bp (or nt). In certain embodiments the length of a marker molecule can be about 150 bp (or nt), about 160 bp (or nt), 170 bp (or nt), about 180 bp (or nt), about 190 bp (or nt) or about 200 bp (or nt). In certain embodiments the length of marker ranges up to about 600 bp (or nt).

In certain embodiments the kit provides at least two, or at least three, or at least four, or at least five, or at least six, or at least seven, or at least eight, or at least nine, or at least ten, or at least 11, or at least 12, or at least 13, or at least 14, or at least 15, or at least 16, or at least 17 m, or at least 18, or at least 19, or at least 20, or at least 25, or at least 30, or at least 35, or at least 40, or at least 50 different sequences.

In various embodiments, the markers comprise one or more DNAs or the markers comprise one or more DNA mimetics. Suitable mimetics include, but are not limited to morpholino derivatives, peptide nucleic acids (PNA), and phosphorothioate DNA. In various embodiments the markers are incorporated into the controls. In certain embodiments the markers are incorporated into adaptor(s) and/or provided ligated to adaptors.

In certain embodiments the kit further includes one or more sequencing adaptors. Such adaptors include, but are not limited to indexed sequencing adaptors. In certain embodiments the adaptors comprise a single-stranded arm that include an index sequence and one or more PCR priming sites.

In certain embodiments the kit further comprises a sample collection device for collection of a biological sample. In certain embodiments the sample collection device comprises a device for collecting blood and, optionally a receptacle for containing blood. In certain embodiments the kit comprises a receptacle for containing blood and the receptacle comprises an anticoagulant and/or cell fixative, and/or one or more antigenomic marker sequence(s).

In certain embodiments the kit further comprises DNA extraction reagents (e.g., a separation matrix and/or an elution solution). The kits can also include reagents for sequencing library preparation. Such reagents include, but are not limited to a solution for end-repairing DNA, and/or a solution for dA-tailing DNA, and/or a solution for adaptor ligating DNA.

In addition, the kits optionally include labeling and/or instructional materials providing directions (e.g., protocols) for the use of the reagents and/or devices provided in the kit. For example, the instructional materials can teach the use of the reagents to prepare samples and/or to determine copy number variation in a biological sample. In certain embodiments the instructional materials teach the use of the materials to detect a trisomy. In certain embodiments the instructional materials teach the use of the materials to detect a cancer or a predisposition to a cancer.

While the instructional materials in the various kits typically comprise written or printed materials they are not limited to such. Any medium capable of storing such instructions and communicating them to an end user is contemplated herein. Such media include, but are not limited to electronic storage media (e.g., magnetic discs, tapes, cartridges, chips), optical media (e.g., CD ROM), and the like. Such media may include addresses to internet sites that provide such instructional materials.

The various method, apparatus, systems and uses are described in further detail in the following Examples which are not in any way intended to limit the scope of the invention as claimed. The attached Figures are meant to be considered as integral parts of the specification and description of the invention. The following examples are offered to illustrate, but not to limit the claimed invention.

EXPERIMENTAL

Example 1

Sample Processing and cfDNA Extraction

Peripheral blood samples were collected from pregnant women in their first or second trimester of pregnancy and who were deemed at risk for fetal aneuploidy. Informed consent was obtained from each participant prior to the blood draw. Blood was collected before amniocentesis or chorionic villus sampling. Karyotype analysis was performed using the chorionic villus or amniocentesis samples to confirm fetal karyotype.

Peripheral blood drawn from each subject was collected in ACD tubes. One tube of blood sample (approximately 6-9 mL/tube) was transferred into one 15-mL low speed centrifuge tube. Blood was centrifuged at 2640 rpm, 4° C. for 10 min using Beckman Allegra 6 R centrifuge and rotor model GA 3.8.

For cell-free plasma extraction, the upper plasma layer was transferred to a 15-ml high speed centrifuge tube and centrifuged at 16000×g, 4° C. for 10 min using Beckman Coulter Avanti J-E centrifuge, and JA-14 rotor. The two centrifugation steps were performed within 72 h after blood collection. Cell-free plasma comprising cfDNA was stored at −80° C. and thawed only once before amplification of plasma cfDNA or for purification of cfDNA.

Purified cell-free DNA (cfDNA) was extracted from cell-free plasma using the QIAamp Blood DNA Mini kit (Qiagen) essentially according to the manufacturer's instruction. One milliliter of buffer AL and 100 µl of Protease solution were added to 1 ml of plasma. The mixture was incubated for 15 minutes at 56° C. One milliliter of 100% ethanol was added to the plasma digest. The resulting mixture was transferred to QIAamp mini columns that were assembled with VacValves and VacConnectors provided in the QIAvac 24 Plus column assembly (Qiagen). Vacuum was applied to the samples, and the cfDNA retained on the column filters was washed under vacuum with 750 µl of buffer AW1, followed by a second wash with 750 µl of buffer AW24. The column was centrifuged at 14,000 RPM for 5 minutes to remove any residual buffer from the filter. The cfDNA was eluted with buffer AE by centrifugation at 14,000 RPM, and the concentration determined using Qubit™ Quantitation Platform (Invitrogen).

Example 2

Preparation and Sequencing of Primary and Enriched Sequencing Libraries a. Preparation of Sequencing Libraries—Abbreviated Protocol (ABB)

All sequencing libraries i.e. primary and enriched libraries, were prepared from approximately 2 ng of purified cfDNA that was extracted from maternal plasma. Library preparation was performed using reagents of the NEBNext™ DNA Sample Prep DNA Reagent Set 1 (Part No. E6000L; New England Biolabs, Ipswich, Mass.), for Illumina® as follows. Because cell-free plasma DNA is fragmented in nature, no further fragmentation by nebulization or sonication was done on the plasma DNA samples. The overhangs of approximately 2 ng purified cfDNA fragments contained in 40 µl were converted into phosphorylated blunt ends according to the NEBNext® End Repair Module by incubating in a 1.5 ml microfuge tube the cfDNA with 5 µl 10× phosphorylation buffer, 2 µl deoxynucleotide solution mix (10 mM each dNTP), 1 µl of a 1:5 dilution of DNA Polymerase I, 1 µl T4 DNA Polymerase and 1 µl T4 Polynucleotide Kinase provided in the NEBNext™ DNA Sample Prep DNA Reagent Set 1 for 15 minutes at 20° C. The enzymes were then heat inactivated by incubating the reaction mixture at 75° C. for 5 minutes. The mixture was cooled to 4° C., and dA tailing of the blunt-ended DNA was accomplished using 10 µl of the dA-tailing master mix containing the Klenow fragment (3' to 5' exo minus) (NEBNext™ DNA Sample Prep DNA Reagent Set 1), and incubating for 15 minutes at 37° C. Subsequently, the Klenow fragment was heat inactivated by incubating the reaction mixture at 75° C. for 5 minutes. Following the inactivation of the Klenow fragment, 1 µl of a 1:5 dilution of Illumina Genomic Adaptor Oligo Mix (Part No. 1000521; Illumina Inc., Hayward, Calif.) was used to ligate the Illumina adaptors (Non-Index Y-Adaptors) to the dA-tailed DNA using 4 µl of the T4 DNA ligase provided in the NEBNext™ DNA Sample Prep DNA Reagent Set 1, by incubating the reaction mixture for 15 minutes at 25° C. The mixture was cooled to 4° C., and the adaptor-ligated cfDNA was purified from unligated adaptors, adaptor dimers, and other reagents using magnetic beads provided in the Agencourt AMPure XP PCR purification system (Part No. A63881; Beckman Coulter Genomics, Danvers, Mass.). Eighteen cycles of PCR were performed to selectively enrich adaptor-ligated cfDNA (25 µl) using Phusion® High-Fidelity Master Mix (25 µl; Finnzymes, Woburn, Mass.) and Illumina's PCR primers (0.5 µM each) complementary to the adaptors (Part No. 1000537 and 1000537). The adaptor-ligated DNA was subjected to PCR (98° C. for 30 seconds; 18 cycles of 98° C. for 10 seconds, 65° C. for 30 seconds, and 72° C. for 30; final extension at 72° C. for 5 minutes, and hold at 4° C.) using Illumina Genomic PCR Primers (Part Nos. 100537 and 1000538) and the Phusion HF PCR Master Mix provided in the NEBNext™ DNA Sample Prep DNA Reagent Set 1, according to the manufacturer's instructions. The amplified product was purified using the Agencourt AMPure XP PCR purification system (Agencourt Bioscience Corporation, Beverly, Mass.) according to the manufacturer's instructions available at www.beckmangenomics.com/products/ AMPureXPProtocol_000387v001.pdf. The purified amplified product was eluted in 40 µl of Qiagen EB Buffer, and the concentration and size distribution of the amplified libraries was analyzed using the Agilent DNA 1000 Kit for the 2100 Bioanalyzer (Agilent technologies Inc., Santa Clara, Calif.).

b. Preparation of Sequencing Libraries—Full-Length Protocol

The full-length protocol described here is essentially the standard protocol provided by Illumina, and only differs from the Illumina protocol in the purification of the amplified library. The Illumina protocol instructs that the amplified library be purified using gel electrophoresis, while the protocol described herein uses magnetic beads for the same purification step. Approximately 2 ng of purified cfDNA extracted from maternal plasma was used to prepare a primary sequencing library using NEBNext™ DNA Sample Prep DNA Reagent Set 1 (Part No. E6000L; New England Biolabs, Ipswich, Mass.) for Illumina® essentially according to the manufacturer's instructions. All steps except for the final purification of the adaptor-ligated products, which was performed using Agencourt AMPure magnetic beads and reagents instead of the purification column, were performed according to the protocol accompanying the NEBNext™ Reagents for Sample Preparation for a genomic DNA library that is sequenced using the Illumina® GAIL The NEBNext™ protocol essentially follows that provided by Illumina, which is available at grcf.jhml.edu/hts/protocols/11257047_ChIP-_Sample Prep.pdf.

Figure 21A:
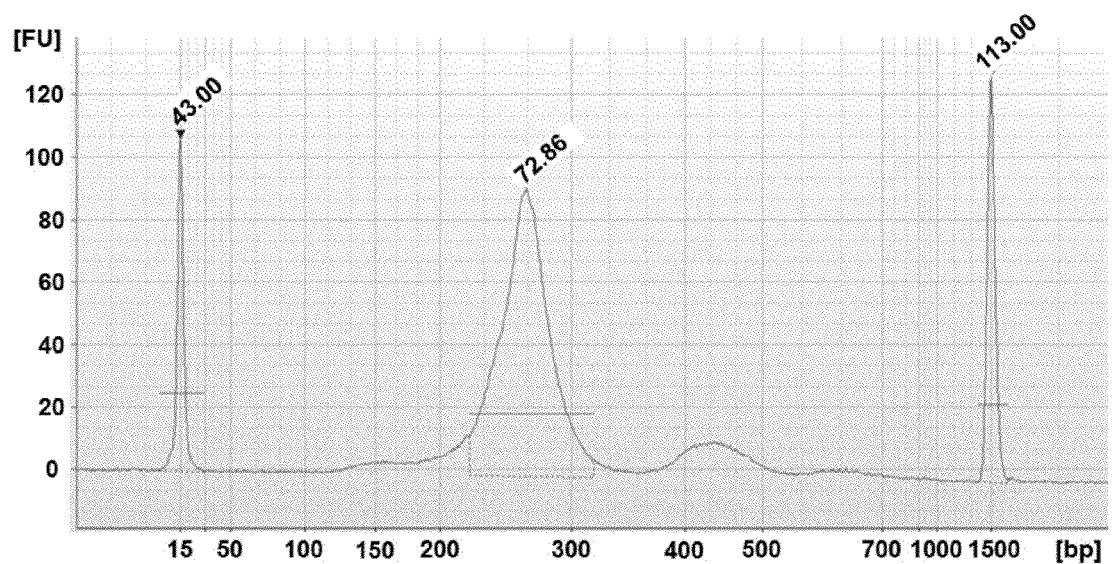
FIGS. 21A and 21B shows electropherograms of a cfDNA sequencing library prepared according to the abbreviated protocol described in Example 2a (FIG. 21A), and the protocol described in Example 2b (FIG. 21B).
Figure 21B:
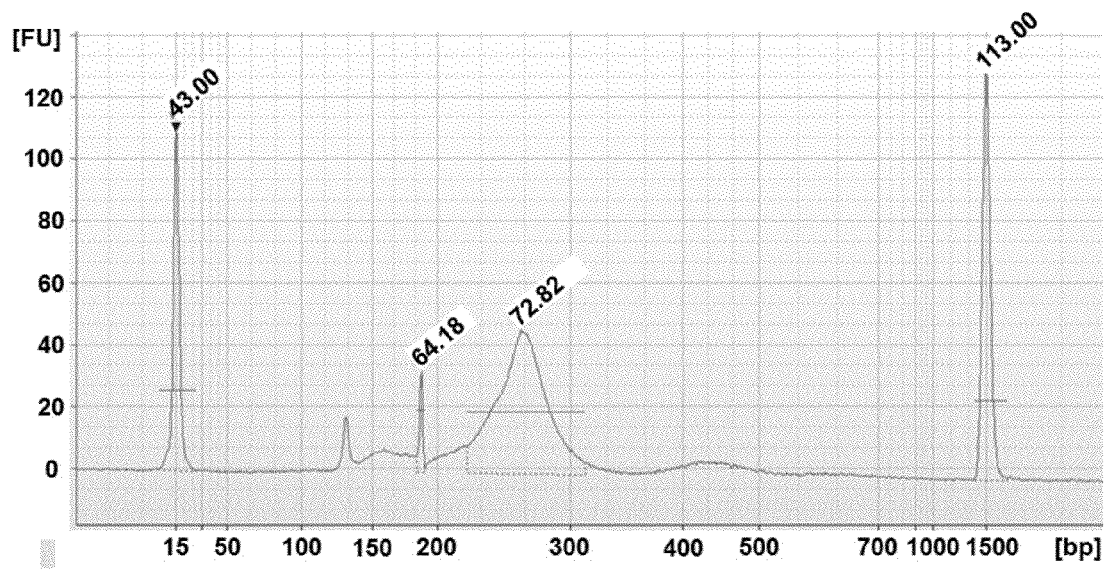

The overhangs of approximately 2 ng purified cfDNA fragments contained in 40 µl were converted into phosphorylated blunt ends according to the NEBNext® End Repair Module by incubating the 40 µl cfDNA with 5 µl 10× phosphorylation buffer, 2 µl deoxynucleotide solution mix (10 mM each dNTP), 1 µl of a 1:5 dilution of DNA Polymerase I, 1 µl T4 DNA Polymerase and 1 µl T4 Polynucleotide Kinase provided in the NEBNext™ DNA Sample Prep DNA Reagent Set 1 in a 200 µl microfuge tube in a thermal cycler for 30 minutes at 20° C. The sample was cooled to 4° C., and purified using a QIAQuick column provided in the QIAQuick PCR Purification Kit (QIAGEN Inc., Valencia, Calif.) as follows. The 50 µl reaction was transferred to 1.5 ml microfuge tube, and 250 µl of Qiagen Buffer PB were added. The resulting 300 µl were transferred to a QIAquick column, which was centrifuged at 13,000 RPM for 1 minute in a microfuge. The column was washed with 750 µl Qiagen Buffer PE, and re-centrifuged. Residual ethanol was removed by an additional centrifugation for 5 minutes at 13,000 RPM. The DNA was eluted in 39 µl Qiagen Buffer EB by centrifugation. dA tailing of 34 µl of the blunt-ended DNA was accomplished using 16 µl of the dA-tailing master mix containing the Klenow fragment (3' to 5' exo minus) (NEBNext™ DNA Sample Prep DNA Reagent Set 1), and incubating for 30 minutes at 37° C. according to the manufacturer's NEBNext® dA-Tailing Module. The sample was cooled to 4° C., and purified using a column provided in the MinElute PCR Purification Kit (QIAGEN Inc., Valencia, Calif.) as follows. The 50 µl reaction was transferred to 1.5 ml microfuge tube, and 250 µl of Qiagen Buffer PB were added. The 300 µl were transferred to the MinElute column, which was centrifuged at 13,000 RPM for 1 minute in a microfuge. The column was washed with 750 µl Qiagen Buffer PE, and re-centrifuged. Residual ethanol was removed by an additional centrifugation for 5 minutes at 13,000 RPM. The DNA was eluted in 15 µl Qiagen Buffer EB by centrifugation. Ten microliters of the DNA eluate were incubated with 1 µl of a 1:5 dilution of the Illumina Genomic Adapter Oligo Mix (Part No. 1000521), 15 µl of 2× Quick Ligation Reaction Buffer, and 4 µl Quick T4 DNA Ligase, for 15 minutes at 25° C. according to the NEB-Next® Quick Ligation Module. The sample was cooled to 4° C., and purified using a MinElute column as follows. One hundred and fifty microliters of Qiagen Buffer PE were added to the 30 µl reaction, and the entire volume was transferred to a MinElute column were transferred to a MinElute column, which was centrifuged at 13,000 RPM for 1 minute in a microfuge. The column was washed with 750 µl Qiagen Buffer PE, and re-centrifuged. Residual ethanol was removed by an additional centrifugation for 5 minutes at 13,000 RPM. The DNA was eluted in 28 µl Qiagen Buffer EB by centrifugation. Twenty three microliters of the adaptor-ligated DNA eluate were subjected to 18 cycles of PCR (98° C. for 30 seconds; 18 cycles of 98° C. for 10 seconds, 65° C. for 30 seconds, and 72° C. for 30; final extension at 72° C. for 5 minutes, and hold at 4° C.) using Illumina Genomic PCR Primers (Part Nos. 100537 and 1000538) and the Phusion HF PCR Master Mix provided in the NEBNext™ DNA Sample Prep DNA Reagent Set 1, according to the manufacturer's instructions. The amplified product was purified using the Agencourt AMPure XP PCR purification system (Agencourt Bioscience Corporation, Beverly, Mass.) according to the manufacturer's instructions available at www.beckmangenomics.com/products/AMPureXPProtocol_000387v001.pdf. The Agencourt AMPure XP PCR purification system removes unincorporated dNTPs, primers, primer dimers, salts and other contaminates, and recovers amplicons greater than 100 bp. The purified amplified product was eluted from the Agencourt beads in 40 µl of Qiagen EB Buffer and the size distribution of the libraries was analyzed using the Agilent DNA 1000 Kit for the 2100 Bioanalyzer (Agilent technologies Inc., Santa Clara, Calif.).

c. Analysis of Sequencing Libraries Prepared According to the Abbreviated (a) and the Full-Length (b) Protocols The electropherograms generated by the Bioanalyzer are shown in FIGS. 21A and 21B. FIG. 21A shows the electropherogram of library DNA prepared from cfDNA purified from plasma sample M24228 using the full-length protocol described in (a), and FIG. 21B shows the electropherogram of library DNA prepared from cfDNA purified from plasma sample M24228 using the full-length protocol described in (b). In both figures, peaks 1 and 4 represent the 15 bp Lower Marker, and the 1,500 Upper Marker, respectively; the numbers above the peaks indicate the migration times for the library fragments; and the horizontal lines indicate the set threshold for integration. The electropheregram in FIG. 21A shows a minor peak of fragments of 187 bp and a major peak of fragments of 263 bp, while the electropherogram in FIG. 21B shows only one peak at 265 bp. Integration of the peak areas resulted in a calculated concentration of 0.40 ng/µl for the DNA of the 187 bp peak in FIG. 21A, a concentration of 7.34 ng/µl for the DNA of the 263 bp peak in FIG. 21A, and a concentration of 14.72 ng/µl for the DNA of the 265 bp peak in FIG. 21B. The Illumina adaptors that were ligated to the cfDNA are known to be 92 bp, which when subtracted from the 265 bp, indicate that the peak size of the cfDNA is 173 bp. It is possible that the minor peak at 187 bp represents fragments of two primers that were ligated end-to-end. The linear two-primer fragments are eliminated from the final library product when the abbreviated protocol is used. The abbreviated protocol also eliminates other smaller fragments of less than 187 bp. In this example, the concentration of purified adaptor-ligated cfDNA is double that of the adaptor-ligated cfDNA produced using the full-length protocol. It has been noted that the concentration of the adaptor-ligated cfDNA fragments was always greater than that obtained using the full-length protocol (data not shown).

Thus, an advantage of preparing the sequencing library using the abbreviated protocol is that the library obtained consistently comprises only one major peak in the 262-267 bp range while the quality of the library prepared using the full-length protocol varies as reflected by the number and mobility of peaks other than that representing the cfDNA. Non-cfDNA products would occupy space on the flow cell and diminish the quality of the cluster amplification and subsequent imaging of the sequencing reactions, which underlies the overall assignment of the aneuploidy status. The abbreviated protocol was shown not to affect the sequencing of the library.

Another advantage of preparing the sequencing library using the abbreviated protocol is that the three enzymatic steps of blunt-ending, d-A tailing, and adaptor-ligation, take less than an hour to complete to support the validation and implementation of a rapid aneuploid diagnostic service.

Another advantage is that the three enzymatic steps of blunt-ending, d-A tailing, and adaptor ligation, are performed in the same reaction tube, thus avoiding multiple sample transfers that would potentially lead to loss of material, and more importantly to possible sample mix-up and sample contamination.

Example 3

Preparation of Sequencing Libraries from Unrepaired cfDNA: Adaptor Ligation in Solution To determine whether the abbreviated protocol could be further shortened to further expedite sample analysis, sequencing libraries were made from unrepaired cfDNA, and sequenced using the Illumina Genome Analyzer II as previously described.

cfDNA was prepared from peripheral blood samples as described herein. Blunt-ending and phosphorylation of the 5'-phosphate mandated by the published protocol for the Illumina platform were not performed to provide the unrepaired cfDNA sample.

Omitting DNA repair or DNA repair and phosphorylation was determined not to affect the quality or the yield of the sequencing library (data not shown).

2-Step in Solution Method for Non-Indexed Unrepaired DNA

In a first set of experiments, the unrepaired cfDNA was subjected to simultaneous dA tailing and adaptor ligation by combining both Klenow Exo- and T4-DNA ligase in the same reaction mixture as follows: Thirty microliters of cfDNA at a concentration between 20-150 pg/µl were dA-tailed (5 µl of 10×NEB buffer#2, 2 µl of 10 nM dNTP, 1 µl of 10 nM ATP, and 1 µl of 5000 U/ml of Klenow Exo-), and ligated to Illumina Y-adapters (1 µl of a 1:15 dilution of a 3 µM stock) using 1 µl of a 400,000 U/ml T4-DNA ligase, in a reaction volume of 50 µl. The non-indexed Y-adapters were from Illumina. The combined reactions were incubated at 25° C. for 30 minutes. The enzymes were heat inactivated at 75° C. for 5 minutes, and the reaction products were stored at 10° C.

The adaptor-ligated product was purified using SPRI beads (Agencourt AMPure XP PCR purification system, Beckman Coulter Genomics), and subjected to 18 cycles of PCR. The PCR-amplified library was subjected to purification using SPRI, and was sequenced using Illumina's Genome Analyzer IIx or HiSeq to obtain single-end reads of 36 bp according to the manufacturer's instructions. A large number of 36 bp reads were obtained, covering approximately 10% of the genome. Upon completion of sequencing of the sample, the Illumina "Sequencer Control Software/Real-time Analysis" transferred base call files in binary format to a network attached storage device for data analysis. Sequence data was analyzed by means of software designed to run on a Linux server that converts the binary format base calls into human readable text files using illumines "BCLConverter", then calls the Open Source "Bowtie" program to align sequences to the reference human genome that is derived from the hg18 genome provided by National Center for Biotechnology Information (NCBI36/hg18, available on the world wide web at http://genome.ucsc.edu/cgi-bin/hgGateway?org=Human&db=hg18&hgsid=166260105).

The software reads the sequence data generated from the above procedure that uniquely aligned to the genome from Bowtie output (bowtieout.txt files). Sequence alignments with up to 2 base mis-matches were allowed and included in alignment counts only if they aligned uniquely to the genome. Sequence alignments with identical start and end coordinates (duplicates) were excluded. Between about 5 and 25 million 36 bp tags with 2 or less mismatches were mapped uniquely to the human genome. All mapped tags were counted and included in the calculation of chromosome doses in both test and qualifying samples. Regions extending from base 0 to base 2×10⁶, base 10×10⁶ to base 13×10⁶, and base 23×10⁶ to the end of chromosome Y, were specifically excluded from the analysis because tags derived from either male or female fetuses map to these regions of the Y-chromosome.

Figure 22A:
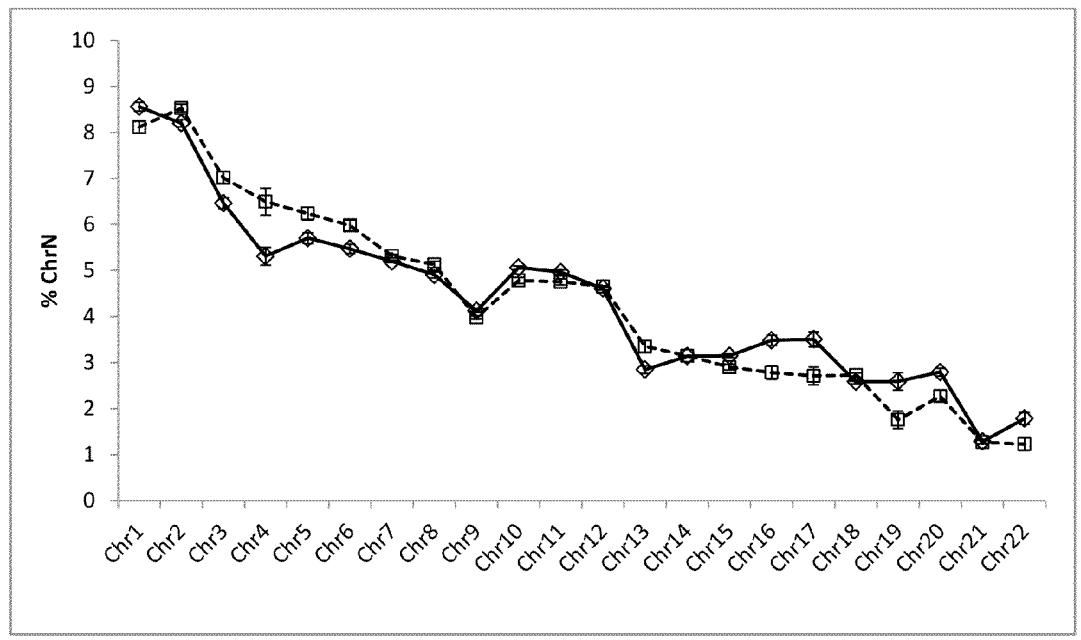
FIGS. 22A-22C provide graphs showing the average (n=16) of the percent of the total number of sequence tags that mapped to each human chromosome (% ChrN.
Figure 22B:
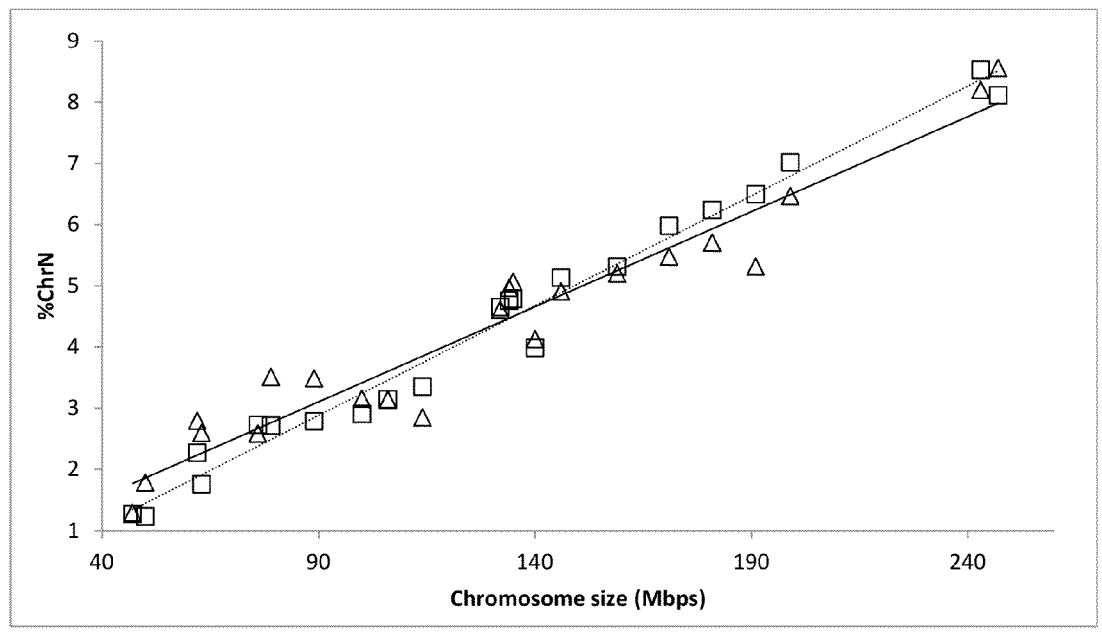

FIG. 22A shows the average (n=16) of the percent of the total number of sequence tags that mapped to each human chromosome (% ChrN) when the sequencing library was prepared according to the abbreviated protocol (ABB; ◇) and when the sequencing library was prepared according to the repair-free 2-STEP method (INSOL; □). These data show that preparing the sequencing library using the repair-free 2-STEP method resulted in a greater percent of tags mapped to chromosomes with lower GC content and a smaller percent of tags that mapped to chromosomes with greater GC content, when compared to the percent tags that mapped to the corresponding chromosomes when using the abbreviated method. FIG. 22B relates the percent sequence tags as a function of the size of the chromosome, and shows that the repair-free method decreases the bias of sequencing. The regression coefficient for mapped tags obtained from sequencing libraries prepared according to the abbreviated protocol (ABB; A), and the in solution repair-free protocol (2-STEP; □) were $R^2=0.9332$, and $R^2=0.9806$, respectively.

TABLE 8

Percent GC content/chromosome

| | Size (Mbps) | GC (%) |
|---|---|---|
| Chr1 | 247 | 41.37 |
| Chr2 | 243 | 39.44 |
| Chr3 | 199 | 38.74 |
| Chr4 | 191 | 38.60 |
| Chr5 | 181 | 39.35 |
| Chr6 | 171 | 39.94 |
| Chr7 | 159 | 39.78 |
| Chr8 | 146 | 40.30 |
| Chr9 | 140 | 40.17 |
| Chr10 | 135 | 40.43 |
| Chr11 | 134 | 41.37 |
| Chr12 | 132 | 40.59 |
| Chr13 | 114 | 38.24 |
| Chr14 | 106 | 40.85 |
| Chr15 | 100 | 41.80 |
| Chr16 | 89 | 44.64 |
| Chr17 | 79 | 45.01 |
| Chr18 | 76 | 39.66 |
| Chr19 | 63 | 48.21 |
| Chr20 | 62 | 42.05 |
| Chr21 | 47 | 40.68 |
| Chr22 | 50 | 47.64 |
| ChrX | 155 | 39.26 |
| ChrY | 58 | 37.74 |

Figure 22C:
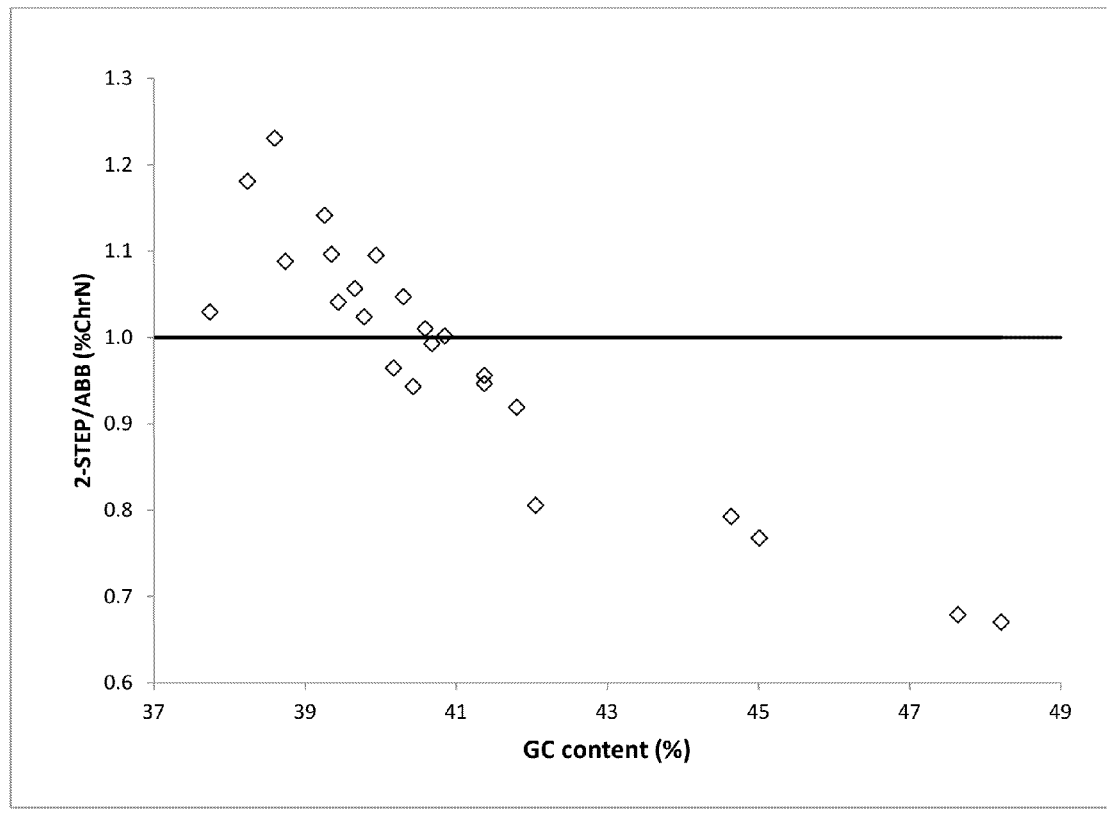

Comparison of the abbreviated to repair-free 2-STEP method was also viewed as a ratio of the percent tags mapped to individual chromosomes when using the repair-free method to the percent tags mapped to the individual chromosomes when using the abbreviated method as a function of the percent GC content of each chromosome. The percent GC content relative to chromosome size was calculated based on published information of chromosome sequences and binning of GC content (Constantini et al., Genome Res 16:536-541 [2006]) and provided in Table 8. The results are given in FIG. 22C, which shows that there was a noticeable decrease in the ratio for chromosomes having a high GC content, and an increase in the ratio for chromosomes having a low GC content. These data clearly show the normalizing effect that the repair-free method has for overcoming GC bias.

These data show that the repair-free method corrects for some of the GC bias that is known to be associated with sequencing of amplified DNA.

Figure 23A:
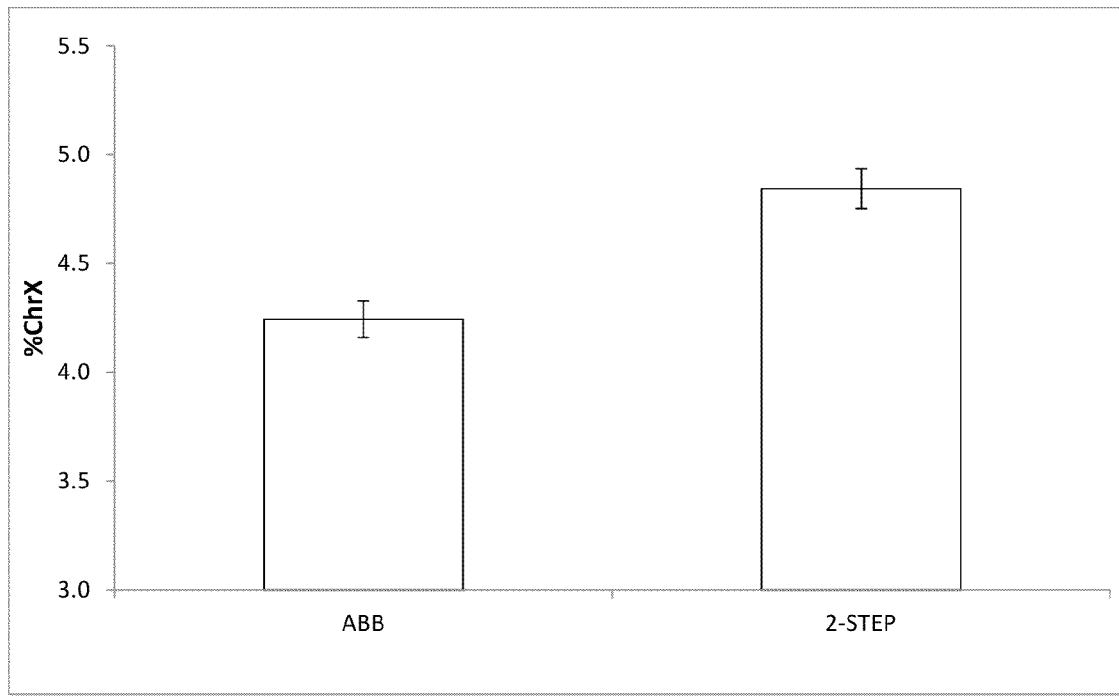
FIGS. 23A and 23B show bar diagrams providing mean and standard deviation of the percent of tags mapped to chromosomes X (FIG. 23A; % ChrX) and Y (FIG. 23B; % ChrY) obtained from sequencing 10 samples of cfDNA purified from plasma of 10 pregnant women.
Figure 23B:
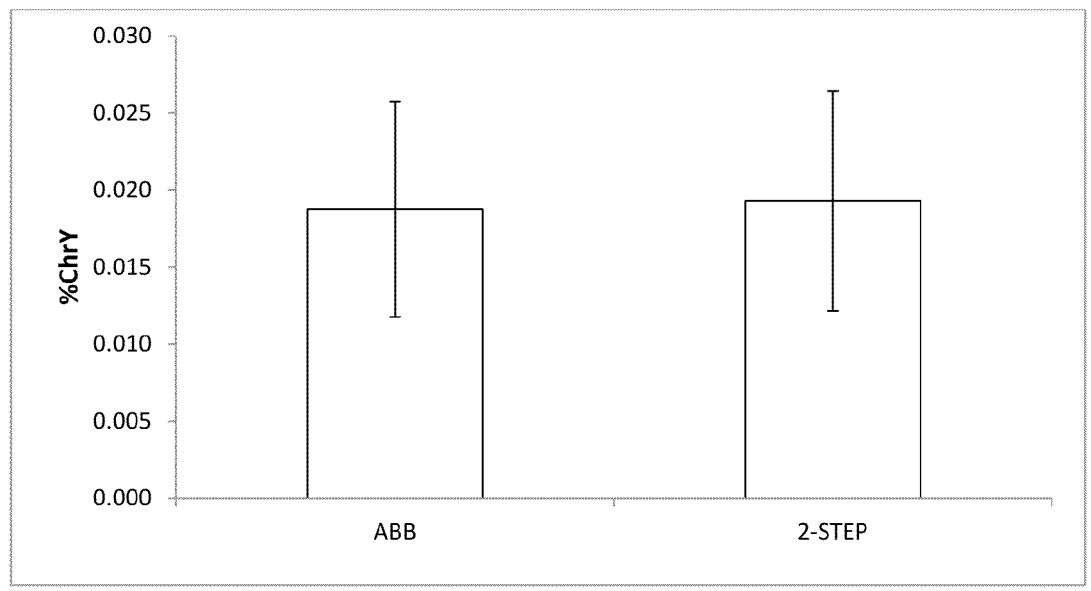

To determine whether the repair-free method affected the proportion of fetal versus maternal cfDNA that was sequenced, the percent number of tags that mapped to chromosomes x and Y were determined. FIGS. 23A and 23B show bar diagrams providing mean and standard deviation of the percent of tags mapped to chromosomes X (FIG. 23A; % ChrX) and Y (FIG. 23B; % ChrY) obtained from sequencing 10 samples of cfDNA purified from plasma of 10 pregnant women. FIG. 23A shows that a greater number of tags mapped to the X chromosome when using the repair-free method relative to that obtained using the abbreviated method. FIG. 23B shows that the percent tags that mapped to the Y chromosome when using the repair-free method was not different from that when using the abbreviated method.

These data show that the repair-free method does not introduce any bias for or against sequencing fetal versus maternal DNA i.e. the proportion of fetal sequences that were sequenced was not altered when using the repair-free method.

Taken together, these data show that the repair-free method does not adversely affect the quality of the sequencing library, nor the information obtained from sequencing the library. Excluding the DNA repair step required by published protocols lowers the cost of reagents, and expedites the preparation of the sequencing library.

2-Step in Solution Method for Indexed Unrepaired DNA

In a second set of experiments, the unrepaired cfDNA was subjected to dA tailing, followed by heat-inactivation of the Klenow Exo-, and adaptor ligation. Exclusion of the heat-inactivation of the Klenow Exo- did not affect either the yield or the quality of the sequencing library when non-indexed Illumina adaptors, (which carry a 21-base single-stranded arm) were used for the ligation.

To determine whether the repair-free method could be applied to multiplexed sequencing, home-made indexed Y adaptors comprising a 6 base index sequence, were used to generate the libraries by including or excluding heat-inactivation of the Klenow. Unlike non-indexed adapters, indexed-adapters comprise a 43-base single stranded arm which includes the index sequence and the PCR priming sites.

Twelve different indexed-adapters identical to Illumina TruSeq adapters were made starting with oligonucleotides obtained from Integrated DNA Technologies (Coralville, Iowa). Oligonucleotide sequences were obtained from published Illumina TruSeq Indexed-adapter sequences. Oligonucleotides were dissolved to obtain a 300 µM final concentration Annealing buffer (10 mM Tris, 1 mM EDTA, 50 mM NaCl, pH 7.5). Equimolar mixtures of oligonucleotides, typically 10 µl each at 300 µM, that comprise the two arms of any given indexed-adapter were mixed and allowed to anneal (95° C. for 6 minutes, followed by a slow, controlled cooling from 95° C. to 10° C.). The final 150 µM adapter was diluted to 7.5 µM in 10 mM Tris, 1 mM EDTA, pH 8 and stored at −20° C. until use.

The data showed that when indexed adaptors were used, the library preparation by the 2_STEP method did not work if active Klenow Exo- was present in the same reaction with ligase and indexed adapter. However, if Klenow Exo- was first heat-inactivated at 75° C. for 5 minutes prior to adding the ligase plus the indexed-adapter, the 2-STEP method worked well. It is likely that when indexed adapters and active Klenow Exo- are present together, the strand-displacement activity of the Klenow Exo- enzyme results in digestion of the long single-stranded DNA arms of the indexed-adaptors, eliminating the PCR primer sites. Electropherograms of sequencing libraries made using the same cfDNA and enzymes, without and with a heat-inactivation step after the Klenow Exo- reaction showed that including a heat-inactivation of the Klenow Exo- prior to adding ligase and the indexed-adapter in the 2-STEP method made a library with the expected profile, with the major peak at 290 bp (data not shown). Accordingly, as the repair-free method is applicable to multiplexed sequencing, all experiments using indexed-Y-adapters were amended to include the heat-inactivation of the Klenow Exo-.

Example 4

Preparation of Sequencing Libraries from Unrepaired cfDNA: Adaptor Ligation on a Solid Surface (SS)

1-Step Solid Surface Method for Non-Indexed DNA

To determine whether the repair-free library process could be simplified further, the repair-free sequencing library preparation method described in Example 3 was configured to be performed on a solid surface. Sequencing of the prepared libraries was performed as described in Example 3.

cfDNA was prepared from peripheral blood samples as described in Example 1. Polypropylene tubes were coated with streptavidin, washed and a first set of biotinylated indexed-adaptors were bound to the streptavidin-coated tubes as follows. Tubes of an 8-well PCR tube strip (USA Scientific, Ocala, Fla.) were coated with 0.5 nmoles of Streptavidin (Thermo Scientific, Rockford, Ill.) in 50 ul of PBS by incubating the SA overnight at 4° C. The tubes were washed four times with 200 µl each 1XTE. 7.5 pmoles, 3.75 pmoles, 1.8 pmoles and 0.9 pmoles of Biotinylated-Index1-adapters each in 50 µl TE were added in duplicate to the SA-coated tubes, and incubated at room temperature for 25 minutes. The unbound adaptors were removed and the tubes were washed four times with 200 µl of TE. Biotinylated Index1 adaptors were made as described in Example 3, using Biotinylated Universal Adapter Oligonucleotide purchased from IDT.

1-Step SS Method Using cfDNA from Non-Pregnant Subjects

In a second strip of PCR tubes control samples (NTC: no template control) or 30 µl of approximately 120 pg/µl, i.e. about 32 fmoles of purified cfDNA obtained from a non-pregnant woman were incubated at 37° C. for 15 minutes with 5 units Klenow Exo- in NEB Buffer #2 with 20 nmoles dNTP and 10 nmoles ATP in 50 µl reaction volume. Subsequently, the Klenow enzyme was deactivated by incubating the reaction mixture for 5 min at 75° C. The Klenow-DNA mixture was transferred to the corresponding tubes containing the SA-bound biotinylated adaptors, and the cfDNA was ligated to the immobilized adaptors by incubating the mixture with 400 units T4-DNA Ligase in 10 µl of 1xT4-DNA Ligase buffer at 25° C. for 15 minutes. Subsequently, 7.5 pmoles of non-biotinylated Index1-adapters were ligated to the solid-phase bound cfDNA by incubating it with 200 units of T4-DNA Ligase in 10 µl buffer at 25° C. for 15 minutes. The reaction mixture was removed, and the tubes were washed 5 times with 200 µl of TE buffer. The adaptor-ligated cfDNA was amplified by PCR using 50 µl of Phusion PCR mix [New England Biolabs)] containing 1 µM each P5 and P7 primers (IDT) and cycled as follows: [30 s @98° C., (10s@98° C., 10 s@50° C., 10 s@ 60° C., 10 s@72° C.)×18 cycles, 5' @72° C., 10° C. incubation]. The resulting library product was subjected to a SPRI cleaning [Beckman Coulter Genomics], and the quality of the library assessed from the profile obtained by analysis using a High Sensitivity Bioanalyzer chip [Agilent Technologies, Santa Clara, Calif.]]. The profiles showed that solid-phase sequencing library preparation of unrepaired cfDNA provides high-yield and high quality sequencing libraries (data not shown).

1-Step SS Method Using cfDNA from Pregnant Subjects

The solid-surface (SS) method was tested using cfDNA samples obtained from pregnant women.

The cfDNA was prepared from 8 peripheral blood samples obtained from pregnant women as described in Example 1, and sequencing libraries were prepared from the purified cfDNA as described above. The libraries were sequenced, and sequence information analyzed.

Figure 24:
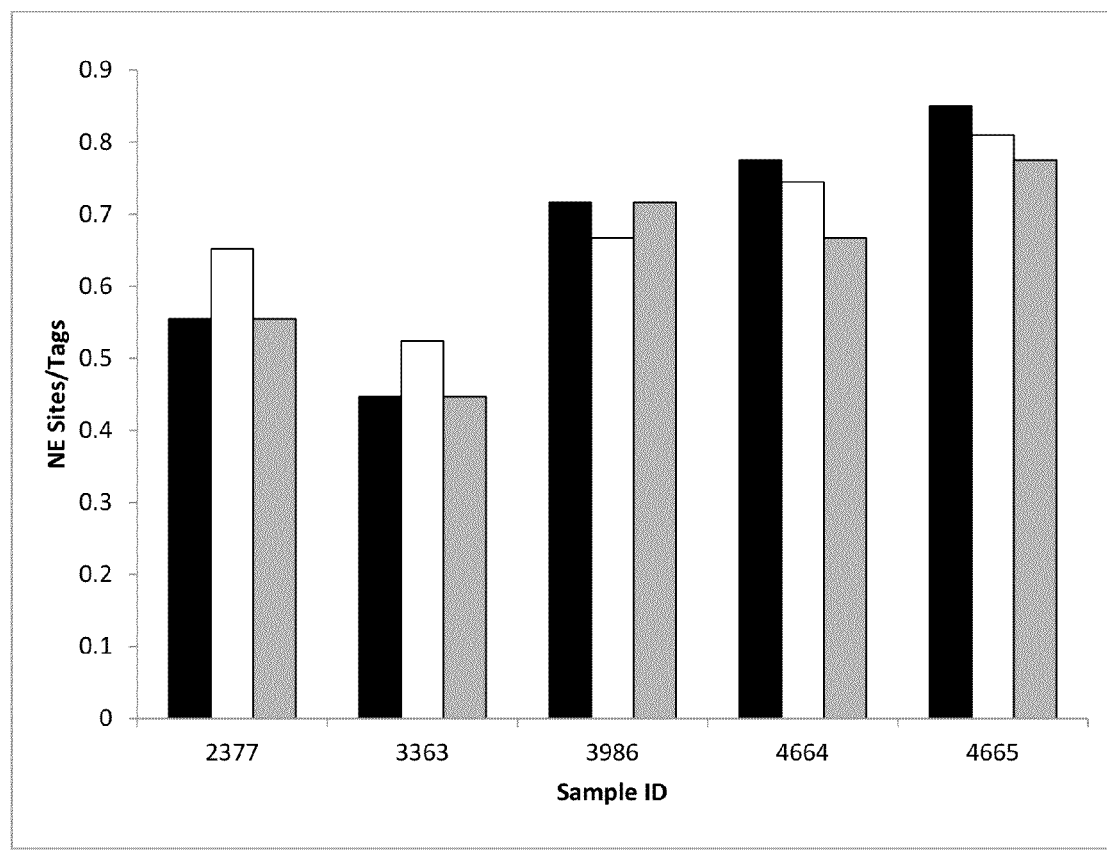
FIG. 24 shows the ratio of the number of non-excluded sites (NE sites) on the reference genome (hg18) to the total number of tags mapped to the non-excluded sites for each of 5 samples from which cfDNA was prepared and used to construct a sequencing library according to the abbreviated protocol (ABB) described in Example 2 (filled bars), the in solution repair-free protocol (2-STEP; empty bars), and the solid surface repair-free protocol (1-STEP; gray bars).

FIG. 24 shows the ratio of the number of non-excluded sites (NE sites) on the reference genome (hg18) and the total number of tags mapped to the non-excluded sites for each of 5 samples from which cfDNA was prepared and used to construct a sequencing library according to the abbreviated protocol (ABB) described in Example 2 (filled bars), the in solution repair-free protocol (2-STEP; empty bars) described in Example 18, and the solid surface repair-free protocol (1-STEP; gray bars) described in the present example.

The data shown in FIG. 24 shows that the representation of PCR-amplified sequences prepared according to the three protocols is comparable, indicating that the solid surface method does not skew the variety of sequences that are represented in the library.

Figure 25A:
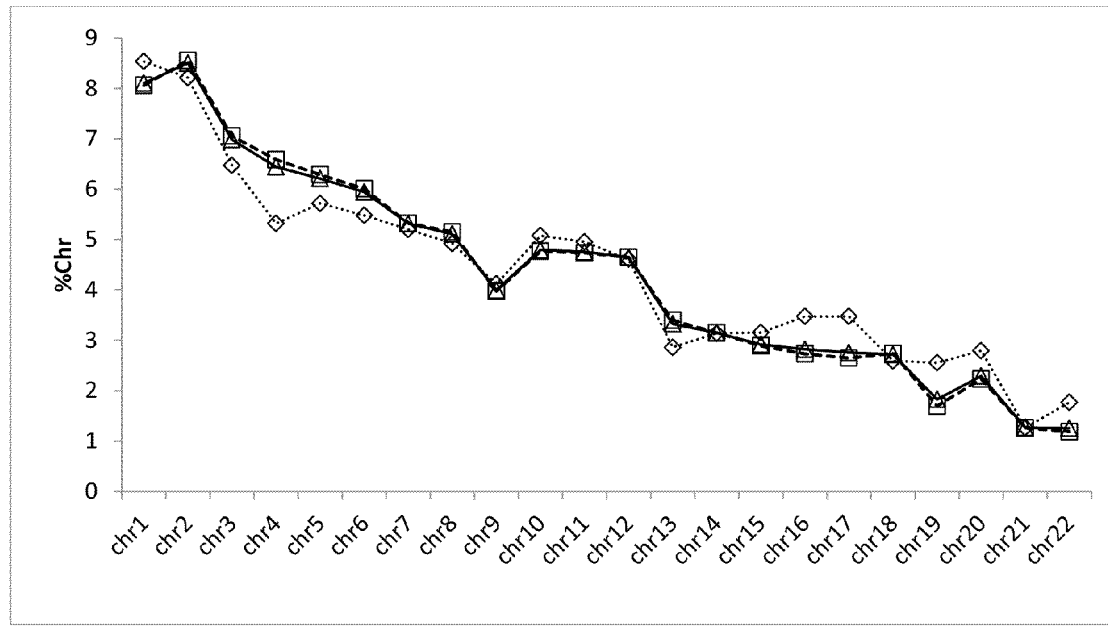
FIG. 25A) when the sequencing library was prepared on solid surface according to the abbreviated protocol (ABB; ◇), when the sequencing library was prepared according to the repair-free 2-STEP method (□), and when the library was prepared according to the repair-free 1-STEP method (Δ); and the percent sequence tags as a function of the size of the chromosome (FIG. 25B). The regression coefficient for mapped tags obtained from sequencing libraries prepared according to the abbreviated protocol (ABB; ◇), and the solid surface repair-free protocol (2-STEP; □).

FIG. 25A shows that the number of sequence tags uniquely mapped to each of the chromosomes when obtained from sequencing the library prepared according to the repair-free solid surface method is comparable to that obtained when using the in solution repair-free 2-STEP method described above. The data show that both repair-free methods decrease the GC bias of the sequencing data.

Figure 25B:
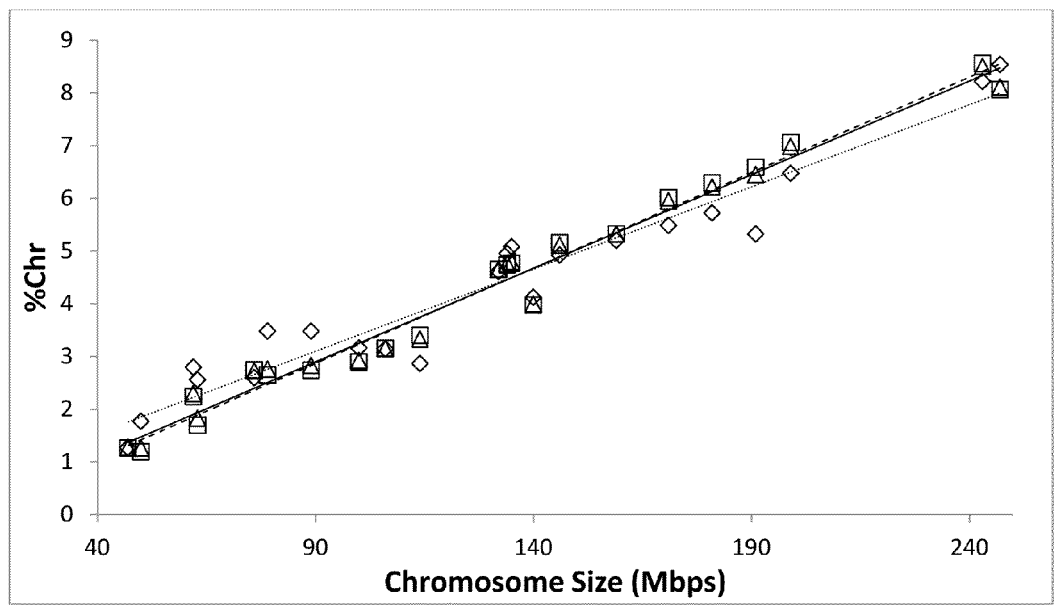

FIG. 25B shows the relationship between the number of tags mapped to the size of the chromosome to which the tags were mapped. The regression coefficient for mapped tags obtained from sequencing libraries prepared according to the abbreviated protocol (ABB), the in solution repair-free protocol (2-STEP), and the solid surface repair-free protocol (1-STEP) were $R^2=0.9352$, $R^2=0.9802$, and $R^2=0.9807$, respectively.

Figure 25C:
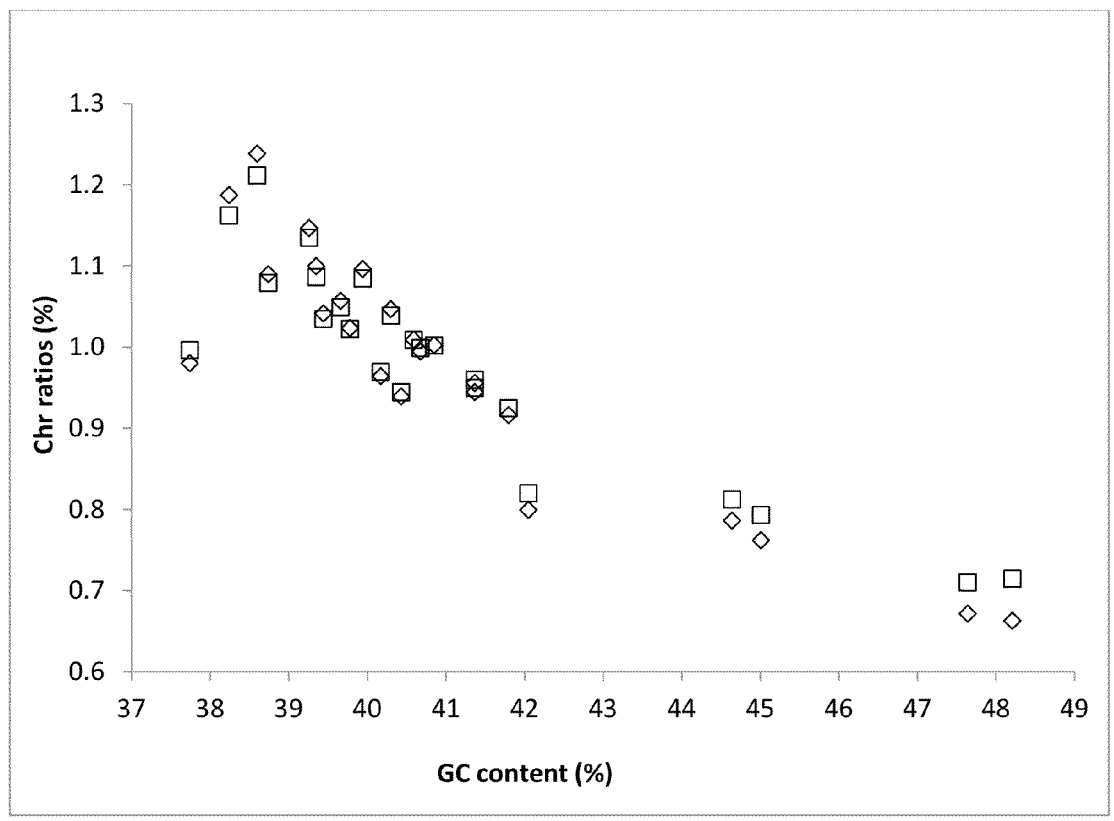
FIG. 25C shows the ratio of percent mapped sequence tags per chromosome obtained from sequencing libraries prepared according to the repair-free 2-STEP protocol and the tags per chromosome obtained sequencing libraries prepared according to the abbreviated protocol (ABB) as a function of the percent GC content of each chromosome (◇), and the ratio of percent mapped sequence tags per chromosome obtained from sequencing libraries prepared according to the repair-free 1-STEP protocol and the tags per chromosome obtained sequencing libraries prepared according to the abbreviated protocol (ABB) as a function of the percent GC content of each chromosome (□).

FIG. 25C shows the ratio of percent mapped sequence tags per chromosome obtained from sequencing libraries prepared according to the repair-free 2-STEP protocol and the tags per chromosome obtained sequencing libraries prepared according to the abbreviated protocol (ABB) as a function of the percent GC content of each chromosome (O), and the ratio of percent mapped sequence tags per chromosome obtained from sequencing libraries prepared according to the repair-free 1-STEP protocol and the tags per chromosome obtained sequencing libraries prepared according to the abbreviated protocol (ABB) as a function of the percent GC content of each chromosome (□). Taken together, the data in FIGS. 25B and 25C show that the 1-STEP and 2-STEP methods both show similar GC normalization effects because both omit the DNA repair step of the library process.

Figure 26A:
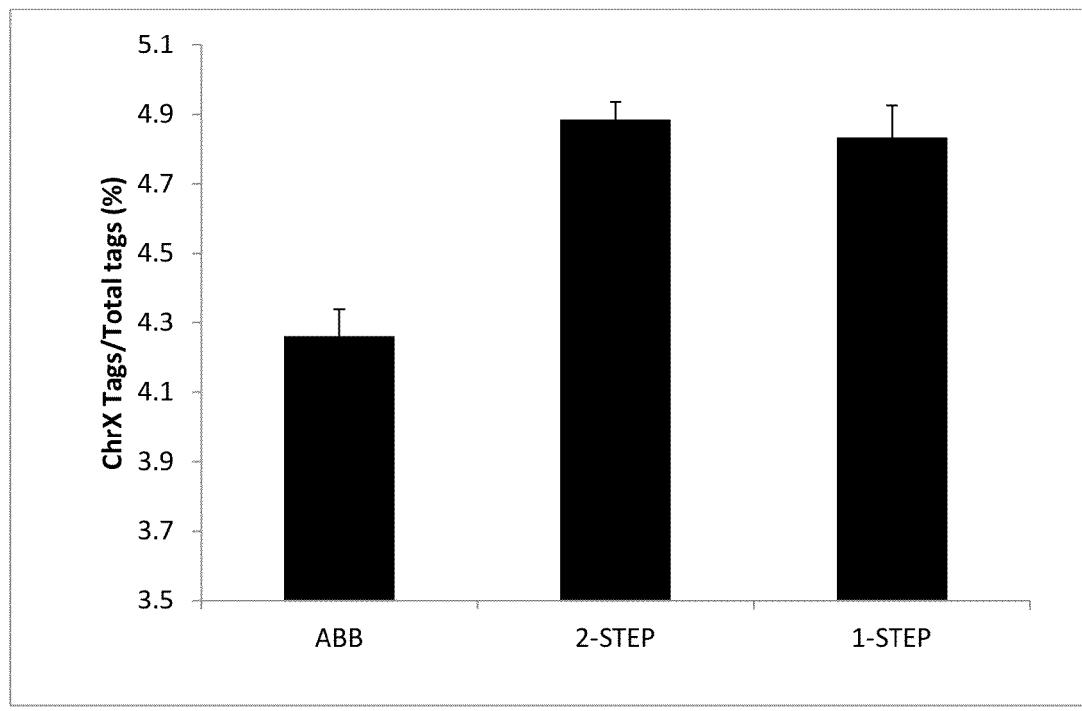
FIGS. 26A and 26B show a comparison of means and standard deviations of the percent of tags mapped to chromosomes X (FIG. 26A) and Y (FIG. 26B) obtained from sequencing 5 samples of cfDNA purified from plasma of 5 pregnant women from the ABB, 2-STEP and 1-STEP methods.
Figure 26B:
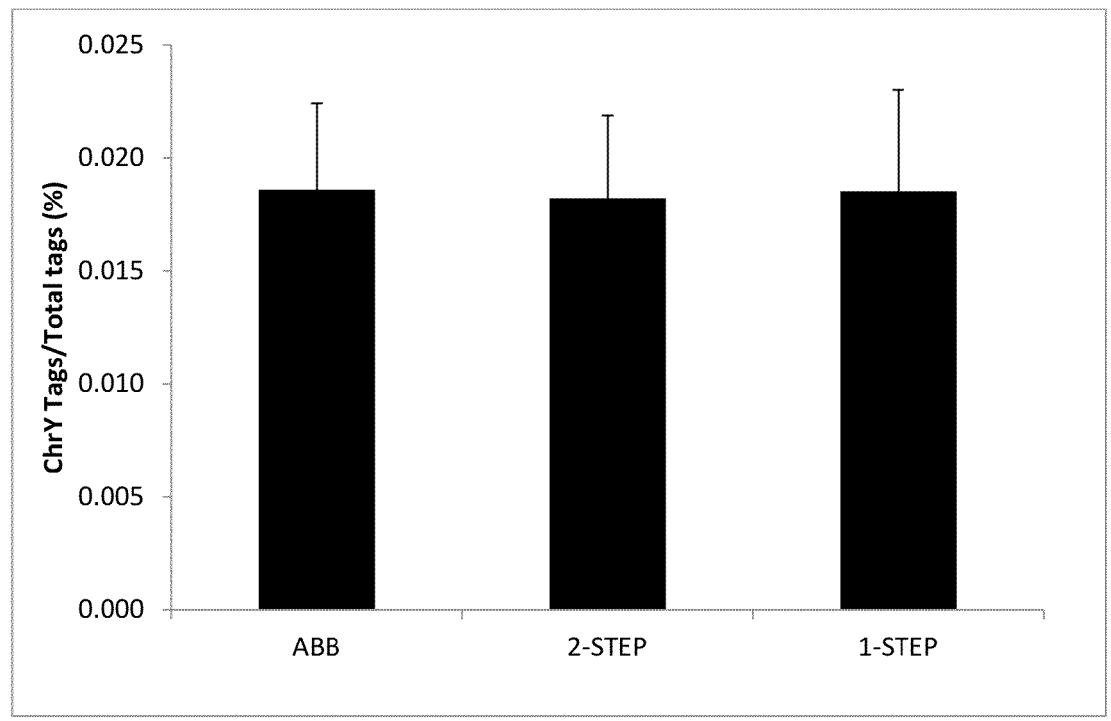

To determine whether the repair-free method affected the proportion of fetal versus maternal cfDNA that was sequenced, the percent number of tags that mapped to chromosomes x and Y were determined. FIGS. 26A and 26B shows a comparison of means and standard deviations of the percent of tags mapped to chromosomes X (FIG. 26A) and Y (FIG. 26B) obtained from sequencing 5 samples of cfDNA purified from plasma of 5 pregnant women from the ABB, 2-STEP and 1-STEP methods. FIG. 26A shows that a greater number of tags mapped to the X chromosome when using the repair-free methods (2-STEP and 1-STEP) relative to that obtained using the abbreviated method (filled bar). FIG. 26B shows that the percent tags that mapped to the Y chromosome when using the repair-free 2-STEP and 1-STEP methods was not different from that when using the abbreviated method.

These data show that the repair-free solid surface 1-STEP method does not introduce any bias for or against sequencing fetal versus maternal DNA i.e. the proportion of fetal sequences that were sequenced was not altered when using the repair-free solid surface method.

Taken together the data demonstrate that generating sequencing libraries on a solid surface is an easy and viable option for sequencing sample preparation.

Example 5

High-Throughput Compatibility of the Repair-Free Solid Surface 1-Step Library Preparation Method To determine whether the Repair-Free 1-STEP method for preparing libraries for sequencing by NGS technology, could be applied to high-throughput sample processing, 96 libraries of cfDNA from 96 peripheral blood samples were prepared in a 96 well PCR plate coated with SA-bound indexed adaptors. Sequencing of the prepared libraries was performed as described in Example 5.

Coating of a first PCR plate with SA, and ligation of biotinylated indexed adaptors was performed as described in Example 4. Each column of wells of the 96-well plate was coated with a biotinylated adaptor comprising a unique index. Using a second 96-well PCR plate, 37 different cfDNAs in 30 μl was subjected to dA tailing in the presence of 10 μl each of Klenow Master Mix at 37° C. for 15 minutes followed by inactivation of the Klenow enzyme at 75° C. for 5 minutes. Several cfDNAs were used in multiple wells for a total of 94 wells with cfDNA; 2 wells were used as no-template controls. The dA-tailed cfDNA mixture was transferred to the first PCR plate and ligated to the bound biotinylated adaptors in the presence of 10 μl Quick Ligase Master Mix 1 at 25° C. for 15 minutes using the PCT-225 Gradient Tetrad Thermal Cycler (BioRad, Hercules, Calif.). 10 μl of Ligation Master Mix2 customized for each indexed-adapter was added and ligated at 5° C. for 15 minutes. Unbound DNA was removed, and the bound DNA-biotinylated adaptor complexes washed five times with TE buffer. 50 μl of PCR master mix was added to each well, and the adaptor-ligated DNA was amplified and subjected to a SPRI cleaning as described in Example 4. The libraries were diluted and analyzed using HiSens BA chips.

Figure 27A:
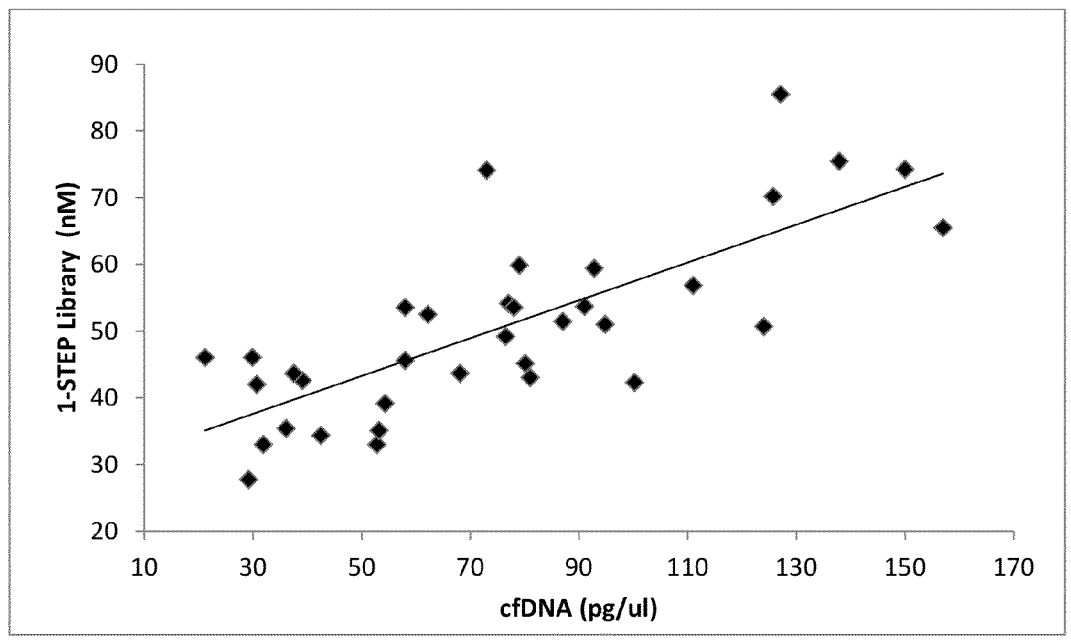
FIGS. 27A and 27B show a correlation between the amount of purified cfDNA used to prepare the sequencing libraries and the resulting amount of library product was made for 61 clinical samples prepared using the ABB method in solution (FIG. 27A), and 35 research samples prepared using the repair-free Solid Surface (SS) 1-STEP method (FIG. 27B).
Figure 27B:
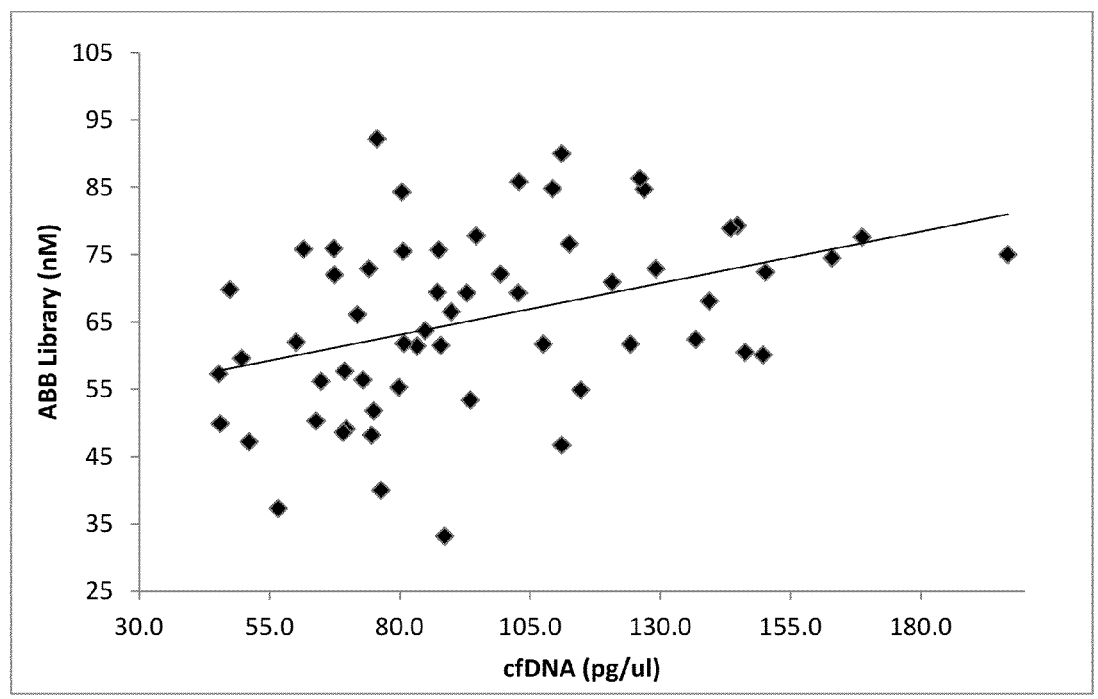
Figure 28:
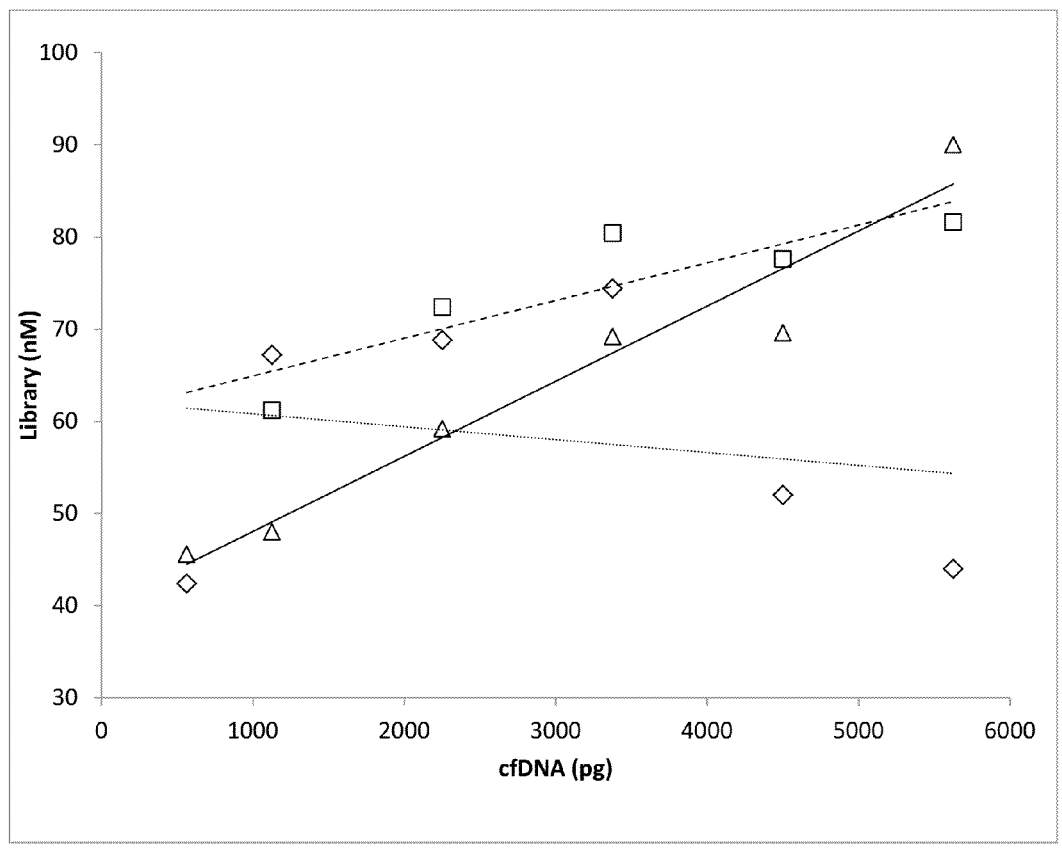
FIG. 28 shows the correlation between the amount of cfDNA used to make a library and the amount of library product obtained using the 2-STEP (□), the ABB (◇), and the 1-STEP (Δ) methods.

A correlation between the amount of purified cfDNA used to prepare the sequencing libraries and the resulting amount of library product was made for 61 clinical samples prepared using the ABB method (FIG. 27A), and 35 research samples prepared using the repair-free SS 1-STEP method (FIG. 27B). These data show that the correlation is considerably greater for libraries prepared using the Repair-Free SS 1-STEP method (R2=0.5826; FIG. 27A) when compared to that obtained for libraries prepared using the abbreviated method described in Example 2 (R2=0.1534; FIG. 27B). Note that the cfDNA samples in this comparison are not the same, because clinical samples are not available for R&D. However, these results indicate that the repair-free SS 1-STEP method has consistently greater correlation between cfDNA input and library output than the ABB method. The correlation was subsequently compared for the 3 methods i.e. ABB, repair-free 2-STEP, and repair-free SS 1-STEP methods using serially diluted amounts of the same purified cfDNA for all three methods. As is shown in FIG. 28, the best correlation was obtained when libraries were prepared according to the SS 1-STEP method ($R^2$=0.9457; Δ), followed by the 2-STEP method ($R^2$=0.7666; □), and the ABB method which had a significantly lower correlation ($R^2$=0.0386; ◊). These data show that repair-free methods, whether in solution or on a solid surface, provide consistent and predictable yields than either methods that end-modify [DNA repair and phosphorylation] cfDNA, whether including or excluding purification of the repaired DNA and of the dA tailed product.

The time taken for preparing the libraries according to the solid-surface method described in this example was several times less than that taken when the sequencing libraries were prepared according to the abbreviated method. For example, 10-14 samples can be prepared manually in approximately 4 hours using the ABB method, and 96 or 192 libraries can be prepared manually in 4 and 5 hours, respectively, when using the SS 1-STEP method. In addition, the SS 1-STEP method can be easily automated to prepare libraries in multiple of 96 for multiplexed sequencing using NGS technologies. Thus, the SS method would be suitable for commercial automated high-throughput analysis of samples.

Analysis of the DNA libraries showed that solid-phase sequencing library preparation of unrepaired cfDNA provides high-yield and high quality sequencing libraries that can be configured for automated processes to further expedite sample analysis requiring massively parallel sequencing using NGS technologies. The solid surface method is applicable to repaired DNA.

Example 6

Multiplex Sequencing of Libraries Prepared According to the 1-Step SS Method

Figure 29:
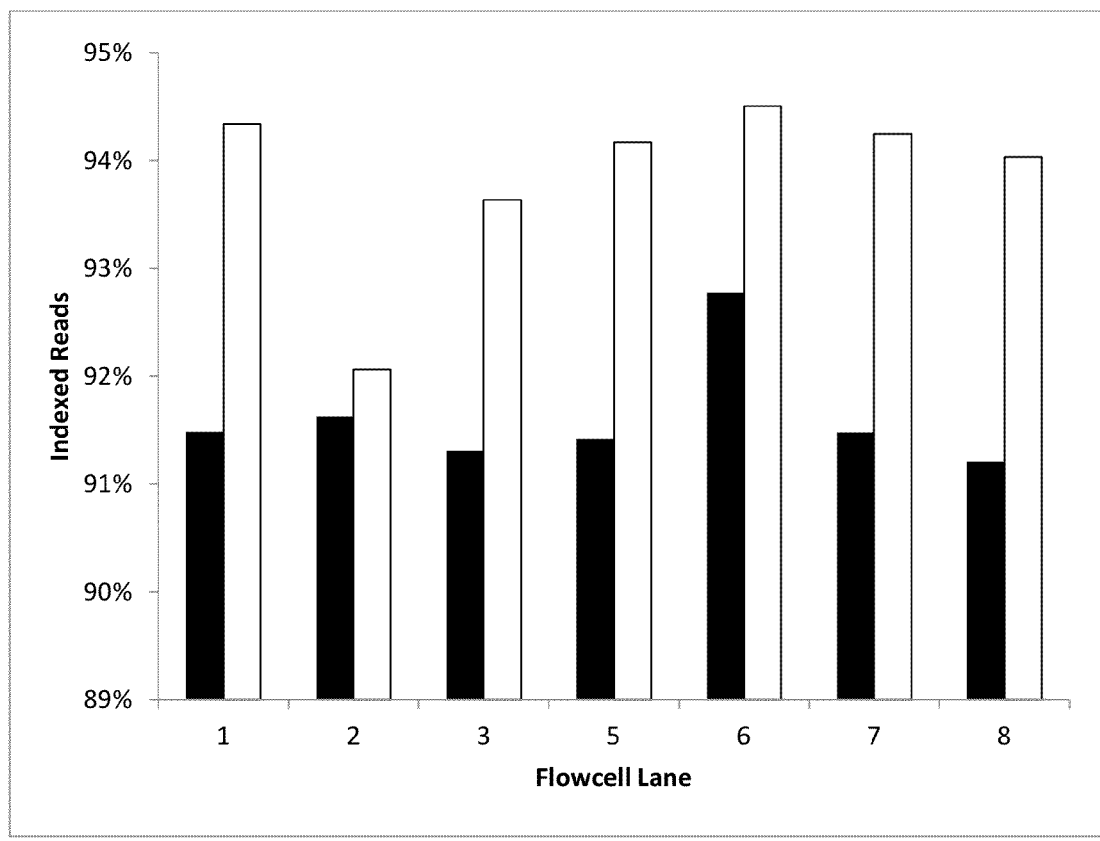
FIG. 29 shows the percent of indexed sequence reads that were obtained when indexed libraries were prepared using the 1-STEP (open bars) and the 2-STEP (filled bars) and sequenced as 6-plex i.e. 6 indexed samples/flow cell lane.
Figure 30A:
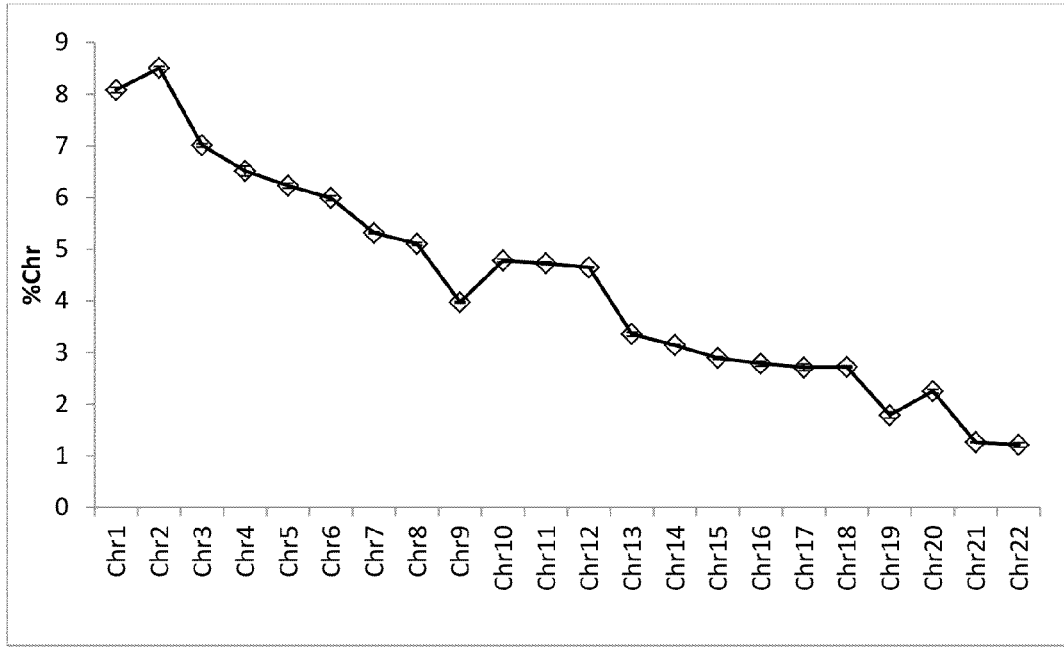
FIGS. 30A and 30B are graphs showing the average (n=42) of the percent of the total number of sequence tags that mapped to each human chromosome (% ChrN.
Figure 30B:
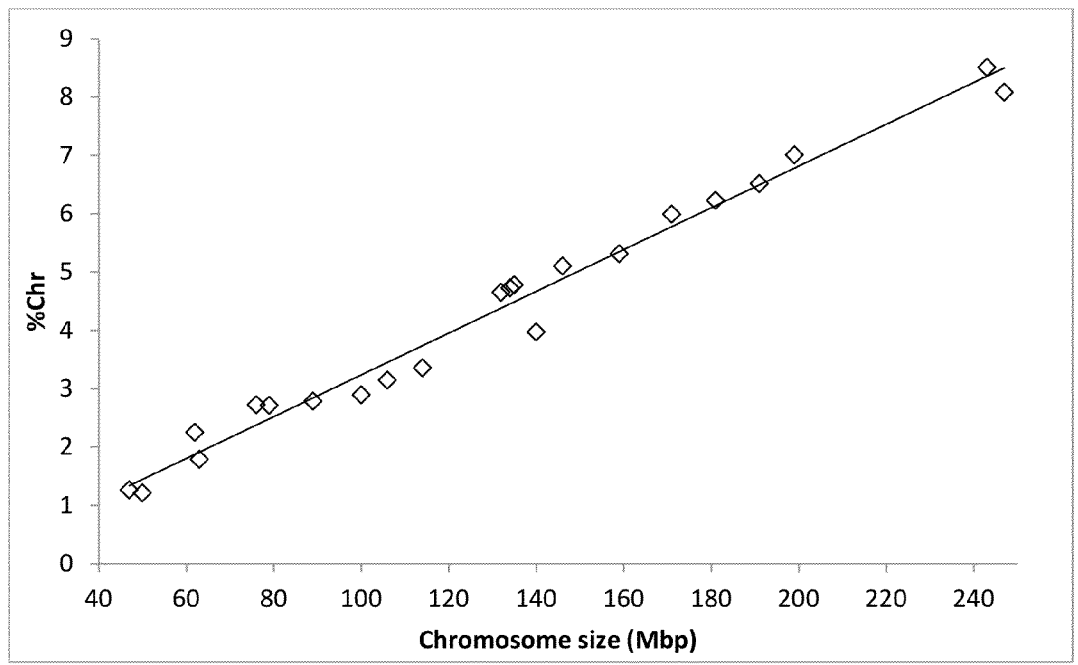

The library samples prepared on a 96-well plate by the SS 1-STEP method (Example 20) were sequenced in a multiplexed manner with six different indexed samples per lane of the Illumina HySeq sequencer flow cell. Sequencing of the prepared libraries was performed as described in Example 2. The data shown in FIG. 29 compares the efficiency of indexing as evaluated by multiplexed sequencing between the 2-STEP (filled bars) and SS 1-STEP (open bars). These data demonstrate that the efficiency of indexing is not compromised by preparing libraries on a solid surface. FIGS. 30A and 30B show the percent of the total number of sequence tags that mapped to each human chromosome (% ChrN; FIG. 30A) when the sequencing library was prepared according to the 1 step solid surface method; and FIG. 30B (R2=0.9807) shows the percent sequence tags as a function of the size of the chromosome. FIGS. 30A and 30B show that the GC bias of the SS 1-STEP method is same as that of the 2-STEP method, because both processes use the DNA repair-free sample preparation enzymatics.

Figure 31:
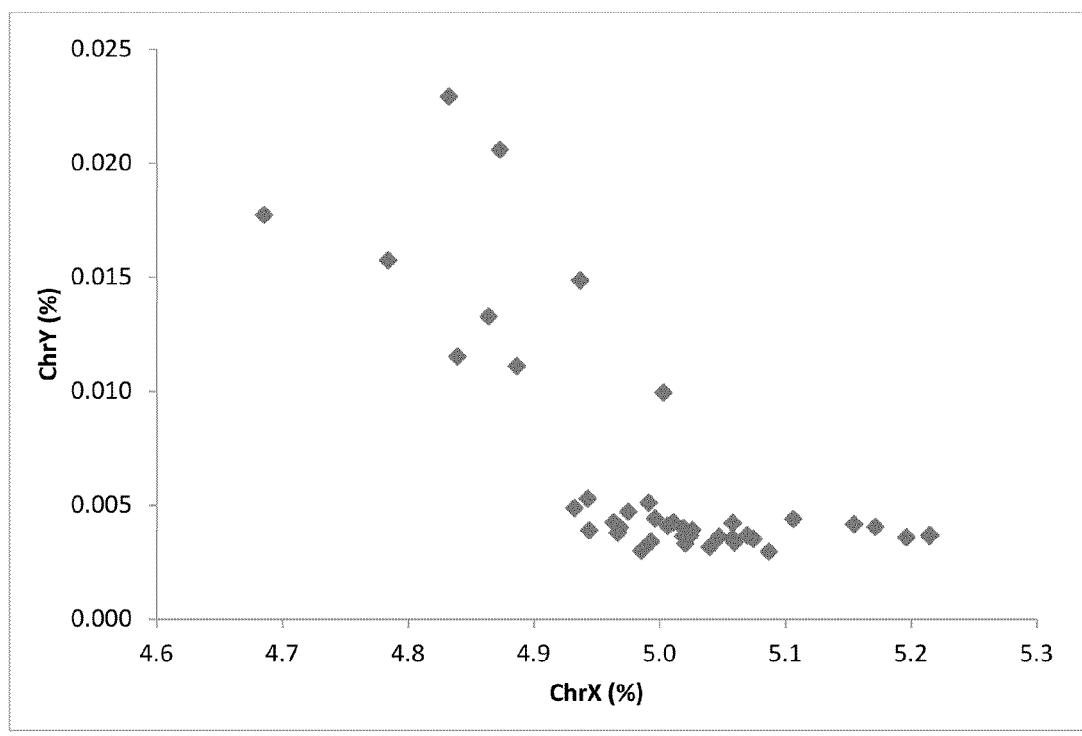
FIG. 31 shows the percent sequence tags mapped to the Y chromosome (ChrY) relative to the percent tags mapped to the X chromosome (ChrX).
Figure 32A:
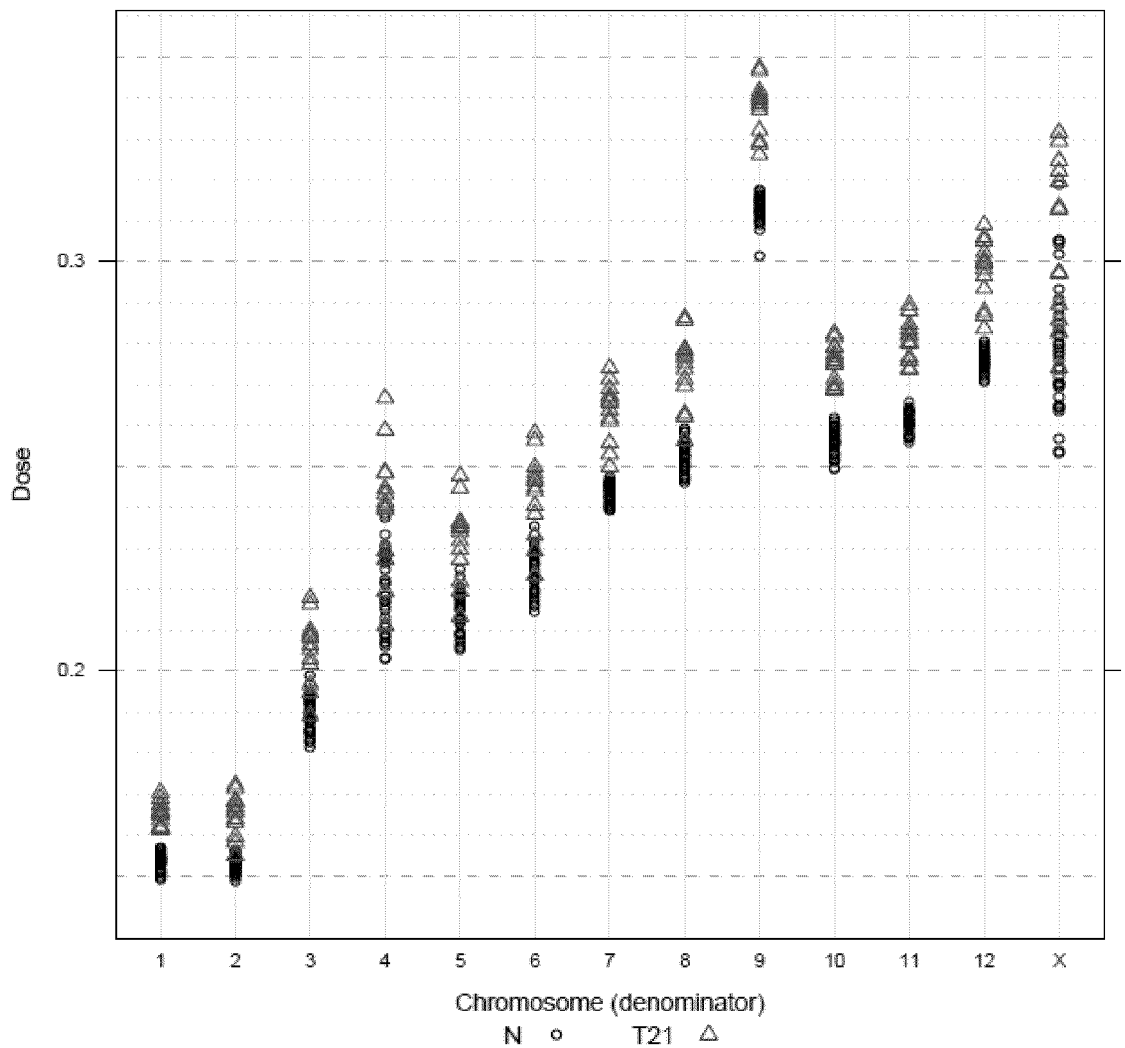
FIGS. 32A and 32B illustrate the distribution of the chromosome dose for chromosome 21 determined from sequencing cfDNA extracted from a set of 48 blood samples obtained from human subjects each pregnant with a male or a female fetus. Chromosome 21 doses for qualified i.e. normal for chromosome 21 (O), and trisomy 21 test samples are shown (Δ) for chromosomes 1-12 and X (FIG. 32A), and for chromosomes 1-22 and X (FIG. 32B).
Figure 32B:
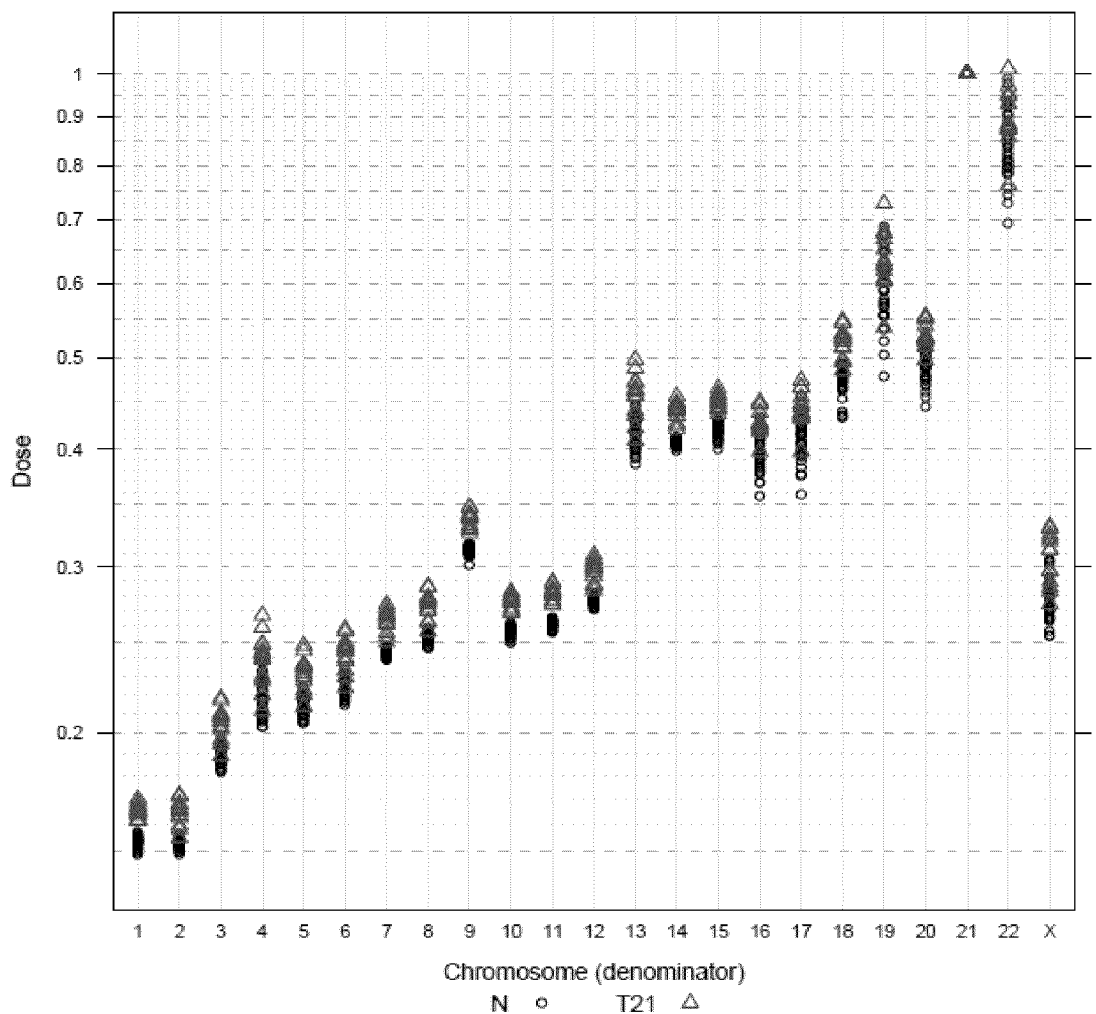

FIG. 31 shows the percent sequence tags that mapped to the Y-chromosome relative to the tags that mapped to the X-chromosome, obtained from sequencing 42 libraries that were prepared using the SS 1-STEP method with indexed adapters, and that were sequenced in a multiplexed manner using Illumina's sequencing by synthesis with reversible terminator technology. The data clearly differentiate samples obtained from pregnant women carrying male fetuses from those carrying female fetuses.

Example 7

Sample Processing and DNA Extraction

Peripheral blood samples were collected from pregnant women in their first or second trimester of pregnancy and who were deemed at risk for fetal aneuploidy. Informed consent was obtained from each participant prior to the blood draw. Blood was collected before amniocentesis or chorionic villus sampling. Karyotype analysis was performed using the chorionic villus or amniocentesis samples to confirm fetal karyotype.

Peripheral blood drawn from each subject was collected in ACD tubes. One tube of blood sample (approximately 6-9 mL/tube) was transferred into one 15-mL low speed centrifuge tube. Blood was centrifuged at 2640 rpm, 4° C. for 10 min using Beckman Allegra 6 R centrifuge and rotor model GA 3.8.

For cell-free plasma extraction, the upper plasma layer was transferred to a 15-ml high speed centrifuge tube and centrifuged at 16000×g, 4° C. for 10 min using Beckman Coulter Avanti J-E centrifuge, and JA-14 rotor. The two centrifugation steps were performed within 72 h after blood collection. Cell-free plasma was stored at −80° C. and thawed only once before DNA extraction.

Cell-free DNA was extracted from cell-free plasma by using QIAamp DNA Blood Mini kit (Qiagen) according to the manufacturer's instructions. Five milliliters of buffer AL and 500 µl of Qiagen Protease were added to 4.5 ml—5 ml of cell-free plasma. The volume was adjusted to 10 ml with phosphate buffered saline (PBS), and the mixture was incubated at 56° C. for 12 minutes. Multiple columns were used to separate the precipitated cfDNA from the solution by centrifugation at 8,000 RPM in a Beckman microcentrifuge. The columns were washed with AW1 and AW2 buffers, and the cfDNA was eluted with 55 µl of nuclease-free water. Approximately 3.5-7 ng of cfDNA was extracted from the plasma samples.

All sequencing libraries were prepared from approximately 2 ng of purified cfDNA that was extracted from maternal plasma. Library preparation was performed using reagents of the NEBNext™ DNA Sample Prep DNA Reagent Set 1 (Part No. E6000L; New England Biolabs, Ipswich, Mass.), for Illumina® as follows. Because cell-free plasma DNA is fragmented in nature, no further fragmentation by nebulization or sonication was done on the plasma DNA samples. The overhangs of approximately 2 ng purified cfDNA fragments contained in 40 µl were converted into phosphorylated blunt ends according to the NEBNext® End Repair Module by incubating in a 1.5 ml microfuge tube the cfDNA with 5 µl 10× phosphorylation buffer, 2 µl deoxynucleotide solution mix (10 mM each dNTP), 1 µl of a 1:5 dilution of DNA Polymerase I, 1 µl T4 DNA Polymerase and 1 µl T4 Polynucleotide Kinase provided in the NEBNext™ DNA Sample Prep DNA Reagent Set 1 for 15 minutes at 20° C. The enzymes were then heat inactivated by incubating the reaction mixture at 75° C. for 5 minutes. The mixture was cooled to 4° C., and dA tailing of the blunt-ended DNA was accomplished using 10 µl of the dA-tailing master mix containing the Klenow fragment (3' to 5' exo minus) (NEBNext™ DNA Sample Prep DNA Reagent Set 1), and incubating for 15 minutes at 37° C. Subsequently, the Klenow fragment was heat inactivated by incubating the reaction mixture at 75° C. for 5 minutes. Following the inactivation of the Klenow fragment, 1 µl of a 1:5 dilution of Illumina Genomic Adaptor Oligo Mix (Part No. 1000521; Illumina Inc., Hayward, Calif.) was used to ligate the Illumina adaptors (Non-Index Y-Adaptors) to the dA-tailed DNA using 4 µl of the T4 DNA ligase provided in the NEBNext™ DNA Sample Prep DNA Reagent Set 1, by incubating the reaction mixture for 15 minutes at 25° C. The mixture was cooled to 4° C., and the adaptor-ligated cfDNA was purified from unligated adaptors, adaptor dimers, and other reagents using magnetic beads provided in the Agencourt AMPure XP PCR purification system (Part No. A63881; Beckman Coulter Genomics, Danvers, Mass.). Eighteen cycles of PCR were performed to selectively enrich adaptor-ligated cfDNA using Phusion® High-Fidelity Master Mix (Finnzymes, Woburn, Mass.) and Illumina's PCR primers complementary to the adaptors (Part No. 1000537 and 1000537). The adaptor-ligated DNA was subjected to PCR (98° C. for 30 seconds; 18 cycles of 98° C. for 10 seconds, 65° C. for 30 seconds, and 72° C. for 30 seconds; final extension at 72° C. for 5 minutes, and hold at 4° C.) using Illumina Genomic PCR Primers (Part Nos. 100537 and 1000538) and the Phusion HF PCR Master Mix provided in the NEBNext™ DNA Sample Prep DNA Reagent Set 1, according to the manufacturer's instructions. The amplified product was purified using the Agencourt AMPure XP PCR purification system (Agencourt Bioscience Corporation, Beverly, Mass.) according to the manufacturer's instructions available at www.beckmangenomics.com/products/AMPureXPProtocol_000387v001.pdf. The purified amplified product was eluted in 40 µl of Qiagen EB Buffer, and the concentration and size distribution of the amplified libraries was analyzed using the Agilent DNA 1000 Kit for the 2100 Bioanalyzer (Agilent technologies Inc., Santa Clara, Calif.).

The amplified DNA was sequenced using Illumina's Genome Analyzer II to obtain single-end reads of 36 bp. Only about 30 bp of random sequence information are needed to identify a sequence as belonging to a specific human chromosome. Longer sequences can uniquely identify more particular targets. In the present case, a large number of 36 bp reads were obtained, covering approximately 10% of the genome. Upon completion of sequencing of the sample, the Illumina "Sequencer Control Software" transferred image and base call files to a Unix server running the Illumina "Genome Analyzer Pipeline" software version 1.51. The Illumina "Gerald" program was run to align sequences to the reference human genome that is derived from the hg18 genome provided by National Center for Biotechnology Information (NCBI36/hg18, available on the world wide web at http://genome.ucsc.edu/cgi-bin/hgGateway?org=Human&db=hg18&hgsid=166260105).

The sequence data generated from the above procedure that uniquely aligned to the genome was read from Gerald output (export.txt files) by a program (c2c.pl) running on a computer running the Linnux operating system. Sequence alignments with base mis-matches were allowed and included in alignment counts only if they aligned uniquely to the genome. Sequence alignments with identical start and end coordinates (duplicates) were excluded.

Between about 5 and 15 million 36 bp tags with 2 or less mismatches were mapped uniquely to the human genome. All mapped tags were counted and included in the calculation of chromosome doses in both test and qualifying samples. Regions extending from base 0 to base $2\times10^6$, base $10\times10^6$ to base $13\times10^6$, and base $23\times10^6$ to the end of chromosome Y, were specifically excluded from the analysis because tags derived from either male or female fetuses map to these regions of the Y-chromosome.

It was noted that some variation in the total number of sequence tags mapped to individual chromosomes across samples sequenced in the same run (inter-chromosomal variation), but substantially greater variation was noted to occur among different sequencing runs (inter-sequencing run variation).

Example 8

Dose and Variance for Chromosomes 13, 18, 21, X, and Y

To examine the extent of inter-chromosomal and inter-sequencing variation in the number of mapped sequence tags for all chromosomes, plasma cfDNA obtained from peripheral blood of 48 volunteer pregnant subjects was extracted and sequenced as described in Example 7, and analyzed as follows.

The total number of sequence tags that were mapped to each chromosome (sequence tag density) was determined. Alternatively, the number of mapped sequence tags may be normalized to the length of the chromosome to generate a sequence tag density ratio. The normalization to chromosome length is not a required step, and can be performed solely to reduce the number of digits in a number to simplify it for human interpretation. Chromosome lengths that can be used to normalize the sequence tags counts can be the lengths provided on the world wide web at genome.ucsc.edu/goldenPath/stats.html#hg18.

Figure 37:
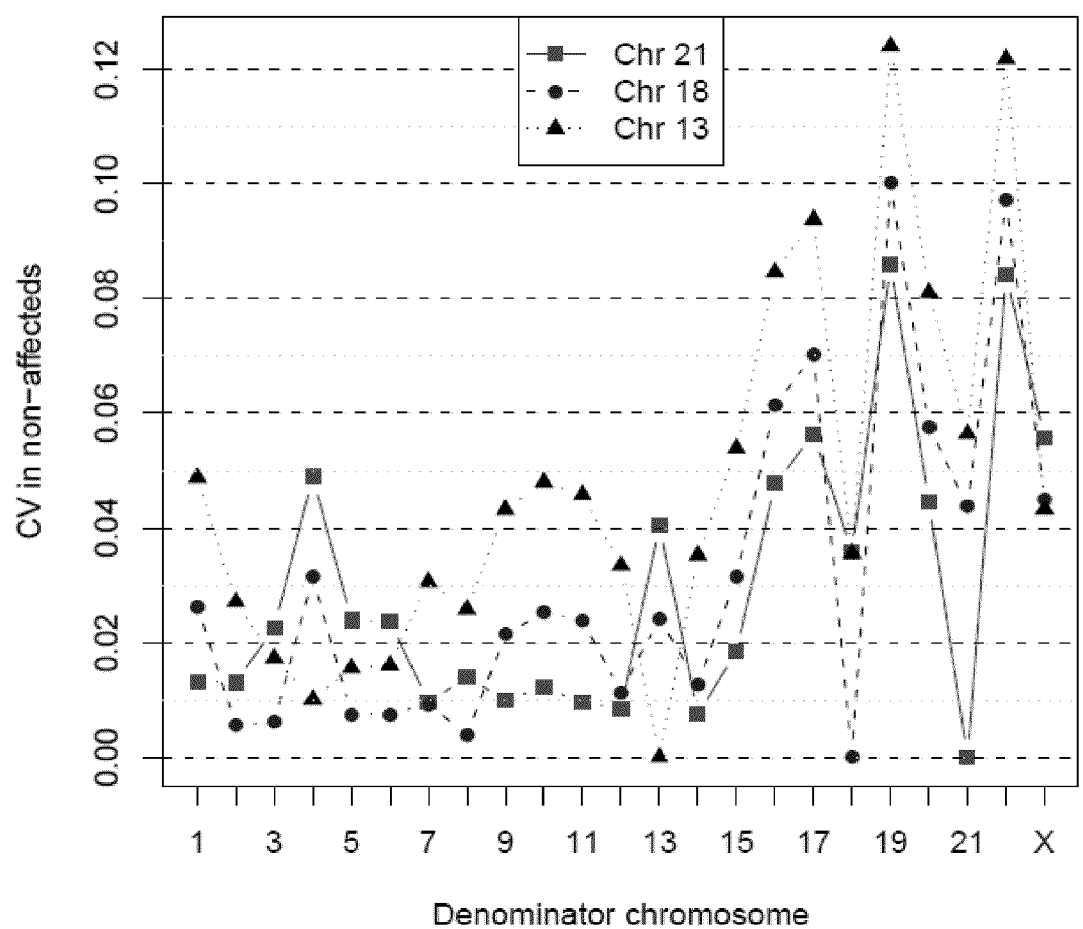
FIG. 37 shows the coefficient of variation (CV) for chromosomes 21 (■), 18 (●) and 13 (▲) that was determined from the doses shown in FIGS. 32A and 32B, 33A and 33B, and 34A and 34B, respectively.
Figure 38:
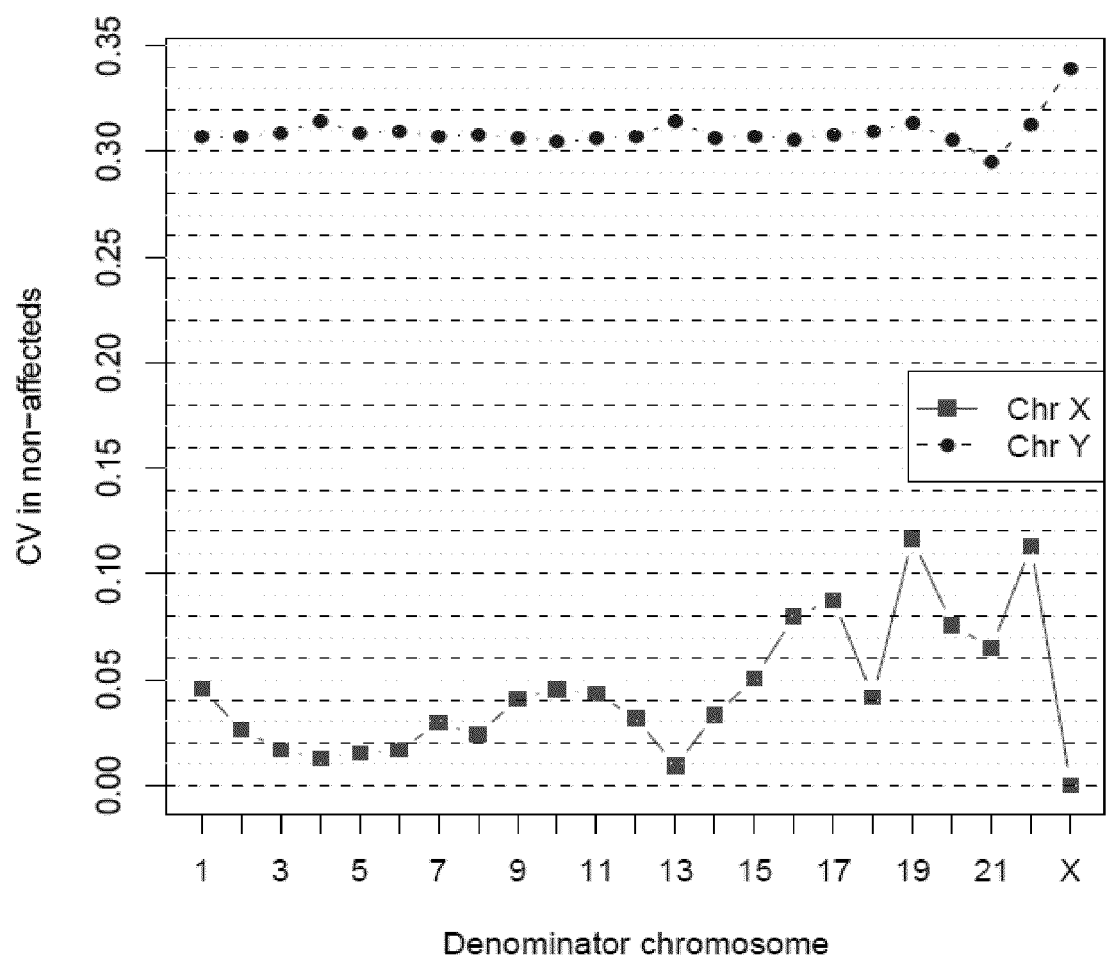
FIG. 38 shows the coefficient of variation (CV) for chromosomes X (■) and Y (●) that was determined from the doses shown in FIGS. 35A and 35B and 36A and 36B, respectively.
Figure 39:
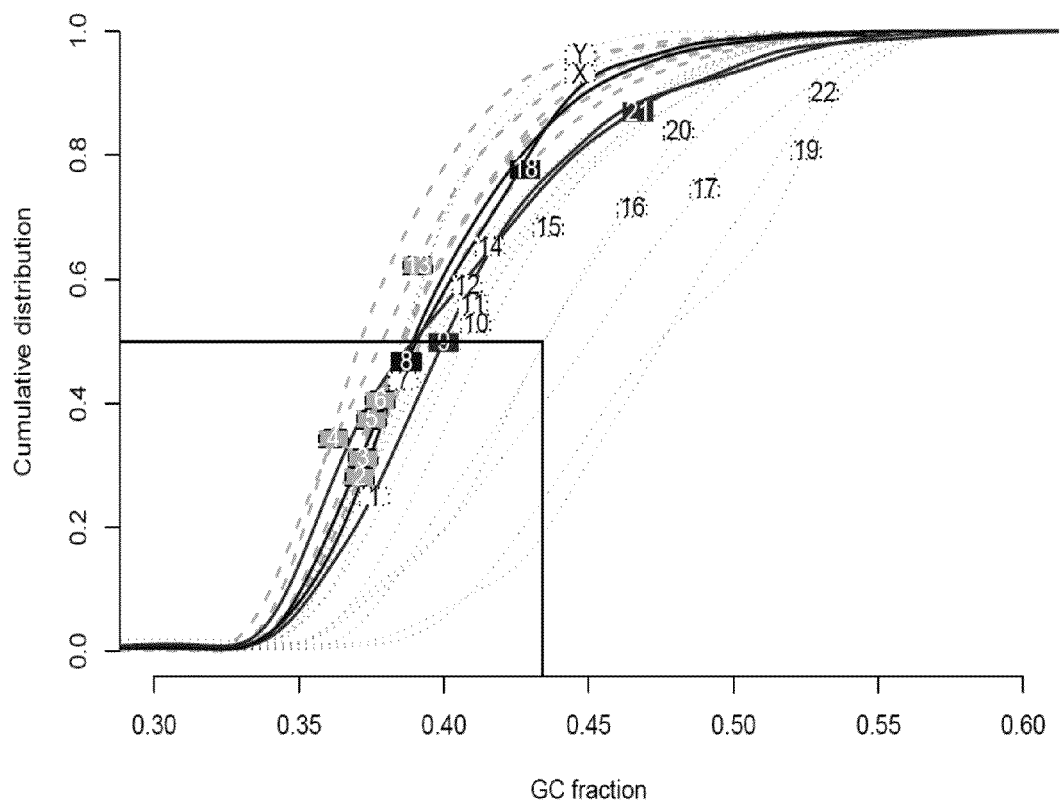
FIG. 39 shows the cumulative distribution of GC fraction by human chromosome. The vertical axis represents the frequency of the chromosome with GC content below the value shown on the horizontal axis.

The resulting sequence tag density for each chromosome was related to the sequence tag density of each of the remaining chromosomes to derive a qualified chromosome dose, which was calculated as the ratio of the sequence tag density for the chromosome of interest e.g. chromosome 21, and the sequence tag density of each of the remaining chromosomes i.e. chromosomes 1-20, 22 and X. Table 9 provides an example of the calculated qualified chromosome dose for chromosomes of interest 13, 18, 21, X, and Y, determined in one of the qualified samples. Chromosomes doses were determined for all chromosomes in all samples, and the average doses for chromosomes of interest 13, 18, 21, X and Y in the qualified samples are provided in Tables 10 and 11, and depicted in FIGS. 32-36. FIGS. 32-36 also depict the chromosome doses for the test samples. The chromosome doses for each of the chromosomes of interest in the qualified samples provides a measure of the variation in the total number of mapped sequence tags for each chromosome of interest relative to that of each of the remaining chromosomes. Thus, qualified chromosome doses can identify the chromosome or a group of chromosomes i.e. normalizing chromosome that has a variation among samples that is closest to the variation of the chromosome of interest, and that would serve as ideal sequences for normalizing values for further statistical evaluation. FIGS. 37 and 38 depict the calculated average chromosome doses determined in a population of qualified samples for chromosomes 13, 18, and 21, and chromosomes X and Y.

In some instances, the best normalizing chromosome may not have the least variation, but may have a distribution of qualified doses that best distinguishes a test sample or samples from the qualified samples i.e. the best normalizing chromosome may not have the lowest variation, but may have the greatest differentiability. Thus, differentiability accounts for the variation in chromosome dose and the distribution of the doses in the qualified samples.

Tables 10 and 11 provide the coefficient of variation as the measure of variability, and student t-test values as a measure of differentiability for chromosomes 18, 21, X and Y, wherein the smaller the T-test value, the greatest the differentiability. The differentiability for chromosome 13 was determined as the ratio of difference between the mean chromosome dose in the qualified samples and the dose for chromosome 13 in the only T13 test sample, and the standard deviation of mean of the qualified dose.

The qualified chromosome doses also serve as the basis for determining threshold values when identifying aneuploidies in test samples as described in the following.

TABLE 9

Qualified Chromosome Dose for Chromosomes 13, 18, 21, X and Y (n = 1; sample #11342, 46 XY)

| Chromosome | chr 21 | chr 18 | chr 13 | chr X | chrY |
| --- | --- | --- | --- | --- | --- |
| chr1 | 0.149901 | 0.306798 | 0.341832 | 0.490969 | 0.003958 |
| chr2 | 0.15413 | 0.315452 | 0.351475 | 0.504819 | 0.004069 |
| chr3 | 0.193331 | 0.395685 | 0.44087 | 0.633214 | 0.005104 |
| chr4 | 0.233056 | 0.476988 | 0.531457 | 0.763324 | 0.006153 |
| chr5 | 0.219209 | 0.448649 | 0.499882 | 0.717973 | 0.005787 |
| chr6 | 0.228548 | 0.467763 | 0.521179 | 0.748561 | 0.006034 |
| chr7 | 0.245124 | 0.501688 | 0.558978 | 0.802851 | 0.006472 |
| chr8 | 0.256279 | 0.524519 | 0.584416 | 0.839388 | 0.006766 |
| chr9 | 0.309871 | 0.634203 | 0.706625 | 1.014915 | 0.008181 |
| chr10 | 0.25122 | 0.514164 | 0.572879 | 0.822817 | 0.006633 |
| chr11 | 0.257168 | 0.526338 | 0.586443 | 0.8423 | 0.00679 |
| chr12 | 0.275192 | 0.563227 | 0.627544 | 0.901332 | 0.007265 |
| chr13 | 0.438522 | 0.897509 | 1 | 1.436285 | 0.011578 |
| chr14 | 0.405957 | 0.830858 | 0.925738 | 1.329624 | 0.010718 |
| chr15 | 0.406855 | 0.832697 | 0.927786 | 1.332566 | 0.010742 |
| chr16 | 0.376148 | 0.769849 | 0.857762 | 1.231991 | 0.009931 |
| chr17 | 0.383027 | 0.783928 | 0.873448 | 1.254521 | 0.010112 |
| chr18 | 0.488599 | 1 | 1.114194 | 1.600301 | 0.0129 |
| chr19 | 0.535867 | 1.096742 | 1.221984 | 1.755118 | 0.014148 |
| chr20 | 0.467308 | 0.956424 | 1.065642 | 1.530566 | 0.012338 |
| chr21 | 1 | 2.046668 | 2.280386 | 3.275285 | 0.026401 |
| chr22 | 0.756263 | 1.547819 | 1.724572 | 2.476977 | 0.019966 |
| chrX | 0.305317 | 0.624882 | 0.696241 | 1 | 0.008061 |
| chrY | 37.87675 | 77.52114 | 86.37362 | 124.0572 | 1 |

TABLE 10

Qualified Chromosome Dose, Variance and Differentiability for chromosomes 21, 18 and 13

| | 21 (n = 35) | | | | 18 (n = 40) | | | |
| --- | --- | --- | --- | --- | --- | --- | --- | --- |
| | Avg | Stdev | CV | T Test | Avg | Stdev | CV | T Test |
| chr1 | 0.15335 | 0.001997 | 1.30 | 3.18E−10 | 0.31941 | 0.008384 | 2.62 | 0.001675 |
| chr2 | 0.15267 | 0.001966 | 1.29 | 9.87E−07 | 0.31807 | 0.001756 | 0.55 | 4.39E−05 |
| chr3 | 0.18936 | 0.004233 | 2.24 | 1.04E−05 | 0.39475 | 0.002406 | 0.61 | 3.39E−05 |
| chr4 | 0.21998 | 0.010668 | 4.85 | 0.000501 | 0.45873 | 0.014292 | 3.12 | 0.001349 |
| chr5 | 0.21383 | 0.005058 | 2.37 | 1.43E−05 | 0.44582 | 0.003288 | 0.74 | 3.09E−05 |
| chr6 | 0.22435 | 0.005258 | 2.34 | 1.48E−05 | 0.46761 | 0.003481 | 0.74 | 2.32E−05 |
| chr7 | 0.24348 | 0.002298 | 0.94 | 2.05E−07 | 0.50765 | 0.004669 | 0.92 | 9.07E−05 |
| chr8 | 0.25269 | 0.003497 | 1.38 | 1.52E−06 | 0.52677 | 0.002046 | 0.39 | 4.89E−05 |
| chr9 | 0.31276 | 0.003095 | 0.99 | 3.83E−09 | 0.65165 | 0.013851 | 2.13 | 0.000559 |
| chr10 | 0.25618 | 0.003112 | 1.21 | 2.28E−10 | 0.53354 | 0.013431 | 2.52 | 0.002137 |
| chr11 | 0.26075 | 0.00247 | 0.95 | 1.08E−09 | 0.54324 | 0.012859 | 2.37 | 0.000998 |

TABLE 10-continued

Qualified Chromosome Dose, Variance and Differentiability for chromosomes 21, 18 and 13

| | 21 (n = 35) | | | | 18 (n = 40) | | | |
|---|---|---|---|---|---|---|---|---|
| | Avg | Stdev | CV | T Test | Avg | Stdev | CV | T Test |
| chr12 | 0.27563 | 0.002316 | 0.84 | 2.04E−07 | 0.57445 | 0.006495 | 1.13 | 0.000125 |
| chr13 | 0.41828 | 0.016782 | 4.01 | 0.000123 | 0.87245 | 0.020942 | 2.40 | 0.000164 |
| chr14 | 0.40671 | 0.002994 | 0.74 | 7.33E−08 | 0.84731 | 0.010864 | 1.28 | 0.000149 |
| chr15 | 0.41861 | 0.007686 | 1.84 | 1.85E−10 | 0.87164 | 0.027373 | 3.14 | 0.003862 |
| chr16 | 0.39977 | 0.018882 | 4.72 | 7.33E−06 | 0.83313 | 0.050781 | 6.10 | 0.075458 |
| chr17 | 0.41394 | 0.02313 | 5.59 | 0.000248 | 0.86165 | 0.060048 | 6.97 | 0.088579 |
| chr18 | 0.47236 | 0.016627 | 3.52 | 1.3E−07 | | | | |
| chr19 | 0.59435 | 0.05064 | 8.52 | 0.01494 | 1.23932 | 0.12315 | 9.94 | 0.231139 |
| chr20 | 0.49464 | 0.021839 | 4.42 | 2.16E−06 | 1.03023 | 0.058995 | 5.73 | 0.061101 |
| chr21 | | | | | 2.03419 | 0.08841 | 4.35 | 2.81E−05 |
| chr22 | 0.84824 | 0.070613 | 8.32 | 0.02209 | 1.76258 | 0.169864 | 9.64 | 0.181808 |
| chrX | 0.27846 | 0.015546 | 5.58 | 0.000213 | 0.58691 | 0.026637 | 4.54 | 0.064883 |

TABLE 11

Qualified Chromosome Dose, Variance and Differentiability for chromosomes 13, X, and Y

| | Avg | Stdev | CV | Diff | Avg | Stdev | CV | T Test |
|---|---|---|---|---|---|---|---|---|
| | 13 (n = 47) | | | | X (n = 19) | | | |
| chr1 | 0.36536 | 0.01775 | 4.86 | 1.904 | 0.56717 | 0.025988 | 4.58 | 0.001013 |
| chr2 | 0.36400 | 0.009817 | 2.70 | 2.704 | 0.56753 | 0.014871 | 2.62 | |
| chr3 | 0.45168 | 0.007809 | 1.73 | 3.592 | 0.70524 | 0.011932 | 1.69 | |
| chr4 | 0.52541 | 0.005264 | 1.00 | 3.083 | 0.82491 | 0.010537 | 1.28 | |
| chr5 | 0.51010 | 0.007922 | 1.55 | 3.944 | 0.79690 | 0.012227 | 1.53 | 1.29E−11 |
| chr6 | 0.53516 | 0.008575 | 1.60 | 3.758 | 0.83594 | 0.013719 | 1.64 | 2.79E−11 |
| chr7 | 0.58081 | 0.017692 | 3.05 | 2.445 | 0.90507 | 0.026437 | 2.92 | 7.41E−07 |
| chr8 | 0.60261 | 0.015434 | 2.56 | 2.917 | 0.93990 | 0.022506 | 2.39 | 2.11E−08 |
| chr9 | 0.74559 | 0.032065 | 4.30 | 2.102 | 1.15822 | 0.047092 | 4.07 | 0.000228 |
| chr10 | 0.61018 | 0.029139 | 4.78 | 2.060 | 0.94713 | 0.042866 | 4.53 | 0.000964 |
| chr11 | 0.62133 | 0.028323 | 4.56 | 2.081 | 0.96544 | 0.041782 | 4.33 | 0.000419 |
| chr12 | 0.65712 | 0.021853 | 3.33 | 2.380 | 1.02296 | 0.032276 | 3.16 | 3.95E−06 |
| chr13 | | | | | 1.56771 | 0.014258 | 0.91 | 2.47E−15 |
| chr14 | 0.96966 | 0.034017 | 3.51 | 2.233 | 1.50951 | 0.05009 | 3.32 | 8.24E−06 |
| chr15 | 0.99673 | 0.053512 | 5.37 | 1.888 | 1.54618 | 0.077547 | 5.02 | 0.002925 |
| chr16 | 0.95169 | 0.080007 | 8.41 | 1.613 | 1.46673 | 0.117073 | 7.98 | 0.114232 |
| chr17 | 0.98547 | 0.091918 | 9.33 | 1.484 | 1.51571 | 0.132775 | 8.76 | 0.188271 |
| chr18 | 1.13124 | 0.040032 | 3.54 | 2.312 | 1.74146 | 0.072447 | 4.16 | 0.001674 |
| chr19 | 1.41624 | 0.174476 | 12.32 | 1.306 | 2.16586 | 0.252888 | 11.68 | 0.460752 |
| chr20 | 1.17705 | 0.094807 | 8.05 | 1.695 | 1.81576 | 0.137494 | 7.57 | 0.08801 |
| chr21 | 2.33660 | 0.131317 | 5.62 | 1.927 | 3.63243 | 0.235392 | 6.48 | 0.00675 |
| chr22 | 2.01678 | 0.243883 | 12.09 | 1.364 | 3.08943 | 0.34981 | 11.32 | 0.409449 |
| chrX | 0.66679 | 0.028788 | 4.32 | 1.114 | | | | |
| chr2-6 | 0.46751 | 0.006762 | 1.45 | 4.066 | | | | |
| chr3-6 | 0.50332 | 0.005161 | 1.03 | 5.260 | | | | |
| chr_tot | | | | | 1.13209 | 0.038485 | 3.40 | 2.7E−05 |
| | | | | | Y (n = 26) | | | |
| Chr 1-22, X | | | | | 0.00734 | 0.002611 | 30.81 | 1.8E−12 |

Examples of diagnoses of T21, T13, T18 and a case of Turner syndrome obtained using the normalizing chromosomes, chromosome doses and differentiability for each of the chromosomes of interest are described in Example 9.

Example 9

Diagnosis of Fetal Aneuploidy Using Normalizing Chromosomes

To apply the use of chromosome doses for assessing aneuploidy in a biological test sample, maternal blood test samples were obtained from pregnant volunteers and cfDNA was prepared, sequenced and analyzed as described in Examples 1 and 2.

Trisomy 21

Table 12 provides the calculated dose for chromosome 21 in an exemplary test sample (#11403). The calculated threshold for the positive diagnosis of T21 aneuploidy was set at >2 standard deviations from the mean of the qualified (normal) samples. A diagnosis for T21 was given based on the chromosome dose in the test sample being greater than the set threshold. Chromosomes 14 and 15 were used as normalizing chromosomes in separate calculations to show that either a chromosome having the lowest variability e.g. chromosome 14, or a chromosome having the greatest differentiability e.g. chromosome 15, can be used to identify the aneuploidy. Thirteen T21 samples were identified using the calculated chromosome doses, and the aneuploidy samples were confirmed to be T21 bp karyotype.

TABLE 12

Chromosome Dose for a T21 aneuploidy (sample #11403, 47 XY + 21)

| Chromosome | Sequence Tag Density | Chromosome Dose for Chr 21 | Threshold |
|---|---|---|---|
| Chr21 | 333,660 | 0.419672 | 0.412696 |
| Chr14 | 795,050 | | |
| Chr21 | 333,660 | 0.441038 | 0.433978 |
| Chr15 | 756,533 | | |

Trisomy 18

Table 13 provides the calculated dose for chromosome 18 in a test sample (#11390). The calculated threshold for the positive diagnosis of T18 aneuploidy was set at 2 standard deviations from the mean of the qualified (normal) samples. A diagnosis for T18 was given based on the chromosome dose in the test sample being greater than the set threshold. Chromosome 8 was used as the normalizing chromosome. In this instance chromosome 8 had the lowest variability and the greatest differentiability. Eight T18 samples were identified using chromosome doses, and were confirmed to be T18 bp karyotype.

These data show that a normalizing chromosome can have both the lowest variability and the greatest differentiability.

TABLE 13

Chromosome Dose for a T18 aneuploidy (sample #11390, 47 XY + 18)

| Chromosome | Sequence Tag Density | Chromosome Dose for Chr 18 | Threshold |
|---|---|---|---|
| Chr18 | 602,506 | 0.585069 | 0.530867 |
| Chr8 | 1,029,803 | | |

Trisomy 13

Table 14 provides the calculated dose for chromosome 13 in a test sample (#51236). The calculated threshold for the positive diagnosis of T13 aneuploidy was set at 2 standard deviations from the mean of the qualified samples. A diagnosis for T13 was given based on the chromosome dose in the test sample being greater than the set threshold. The chromosome dose for chromosome 13 was calculated using either chromosome 5 or the group of chromosomes 3, 4, 5, and 6 as the normalizing chromosome. One T13 sample was identified.

TABLE 14

Chromosome Dose for a T13 aneuploidy (sample #51236, 47 XY + 13)

| Chromosome | Sequence Tag Density | Chromosome Dose for Chr 13 | Threshold |
|---|---|---|---|
| Chr13 | 692,242 | 0.541343 | 0.52594 |
| Chr5 | 1,278,749 | | |
| Chr13 | 692,242 | 0.530472 | 0.513647 |
| Chr3-6 [average] | 1,304,954 | | |

The sequence tag density for chromosomes 3-6 is the average tag counts for chromosomes 3-6.

The data show that the combination of chromosomes 3, 4, 5 and 6 provide a variability that is lower than that of chromosome 5, and the greatest differentiability than any of the other chromosomes.

Thus, a group of chromosomes can be used as the normalizing chromosome to determine chromosome doses and identify aneuploidies.

Turner Syndrome (Monosomy X)

Table 15 provides the calculated dose for chromosomes X and Y in a test sample (#51238). The calculated threshold for the positive diagnosis of Turner Syndrome (monosomy X) was set for the X chromosome at <−2 standard deviations from the mean, and for the absence of the Y chromosome at <−2 standard deviations from the mean for qualified (normal) samples.

TABLE 15

Chromosome Dose for a Turners (XO) aneuploidy (sample #51238, 45 X)

| Chromosome | Sequence Tag Density | Chromosome Dose for Chr X and Chr Y | Threshold |
|---|---|---|---|
| ChrX | 873,631 | 0.786642 | 0.803832 |
| Chr4 | 1,110,582 | | |
| ChrY | 1,321 | | |
| Chr_Total (1-22, X) (Average) | 856,623.6 | 0.001542101 | 0.00211208 |

A sample having an X chromosome dose less than that of the set threshold was identified as having less than one X chromosome. The same sample was determined to have a Y chromosome dose that was less than the set threshold, indicating that the sample did not have a Y chromosome. Thus, the combination of chromosome doses for X and Y were used to identify the Turner Syndrome (monosomy X) samples.

Thus, the method provided enables for the determination of CNV of chromosomes. In particular, the method enables for the determination of over- and under-representation chromosomal aneuploidies by massively parallel sequencing of maternal plasma cfDNA and identification of normalizing chromosomes for the statistical analysis of the sequencing data. The sensitivity and reliability of the method allow for accurate first and second trimester aneuploidy testing.

Example 10

Determination of Partial Aneuploidy

The use of sequence doses was applied for assessing partial aneuploidy in a biological test sample of cfDNA that was prepared from blood plasma, and sequenced as described in Example 7. The sample was confirmed by karyotyping to have been derived from a subject with a partial deletion of chromosome 11.

Figure 40:
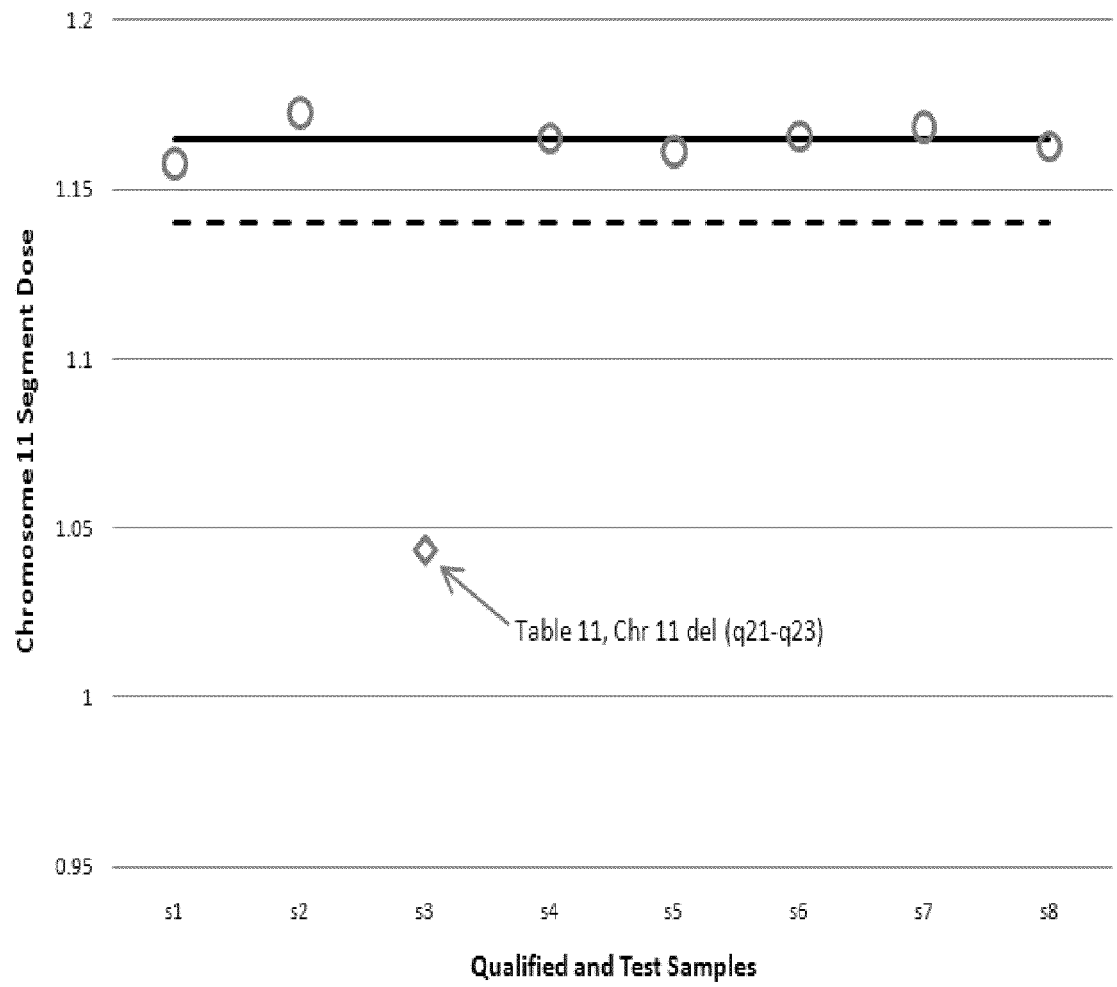
FIG. 40 from illustrates the sequence doses (Y-axis) for a segment of chromosome 11 (81000082-103000103 bp) determined from sequencing cfDNA extracted from a set of 7 qualified samples (O) obtained and 1 test sample (♦) from pregnant human subjects. A sample from a subject carrying a fetus with a partial aneuploidy of chromosome 11 (♦) was identified.

Analysis of the sequencing data for the partial aneuploidy (partial deletion of chromosome 11 i.e. q21-q23) was performed as described for the chromosomal aneuploidies in the previous examples. Mapping of the sequence tags to chromosome 11 in a test sample revealed a noticeable loss of tag counts between base pairs 81000082-103000103 in the q arm of the chromosome relative to the tag counts obtained for corresponding sequence on chromosome 11 in the qualified samples (data not shown). Sequence tags mapped to the sequence of interest on chromosome 11 (810000082-103000103 bp) in each of the qualified samples, and sequence tags mapped to all 20 megabase segments in the entire genome in the qualified samples i.e. qualified sequence tag densities, were used to determine qualified sequence doses as ratios of tag densities in all qualified samples. The average sequence dose, standard deviation, and coefficient of variation were calculated for all 20 megabase segments in the entire genome, and the 20-megabase sequence having the least variability was the identified normalizing sequence on chromosome 5 (13000014-33000033 bp) (See Table 16), which was used to calculate the dose for the sequence of interest in the test sample (see Table 17). Table 16 provides the sequence dose for the sequence of interest on chromosome 11 (810000082-103000103 bp) in the test sample that was calculated as the ratio of sequence tags mapped to the sequence of interest and the sequence tags mapped to the identified normalizing sequence. FIG. 40 shows the sequence doses for the sequence of interest in the 7 qualified samples (O) and the sequence dose for the corresponding sequence in the test sample (◇). The mean is shown by the solid line, and the calculated threshold for the positive diagnosis of partial aneuploidy that was set 5 standard deviations from the mean is shown by the dashed line. A diagnosis for partial aneuploidy was based on the sequence dose in the test sample being less than the set threshold. The test sample was verified by karyotyping to have deletion q21-q23 on chromosome 11.

Therefore, in addition to identifying chromosomal aneuploidies, the method of the invention can be used to identify partial aneuploidies.

TABLE 16

Qualified Normalizing Sequence, Dose and Variance for Sequence Chr11: 81000082-103000103 (qualified samples n = 7)

| | Chr11: 81000082-103000103 | | |
|---|---|---|---|
| | Avg | Stdev | CV |
| Chr5: 13000014-33000033 | 1.164702 | 0.004914 | 0.42 |

TABLE 17

Sequence Dose for Sequence of Interest (81000082-103000103) on Chromosome 11 (test sample 11206)

| Chromosome Segment | Sequence Tag Density | Chromosome Segment Dose for Chr 11 (q21-q23) | Threshold |
|---|---|---|---|
| Chr11: 81000082-103000103 | 27,052 | 1.0434313 | 1.1401347 |
| Chr5: 13000014-33000033 | 25,926 | | |

Example 11

Demonstration of Detection of Aneuploidy

Sequencing data obtained for the samples described in Examples 2 and 3, and shown in FIGS. 32-36 were further analyzed to illustrate the sensitivity of the method in successfully identifying aneuploidies in maternal samples. Normalized chromosome doses for chromosomes 21, 18, 13 X and Y were analyzed as a distribution relative to the standard deviation of the mean (Y-axis) and shown in FIGS. 41A-41E. The normalizing chromosome used is shown as the denominator (X-axis).

Figure 41A:
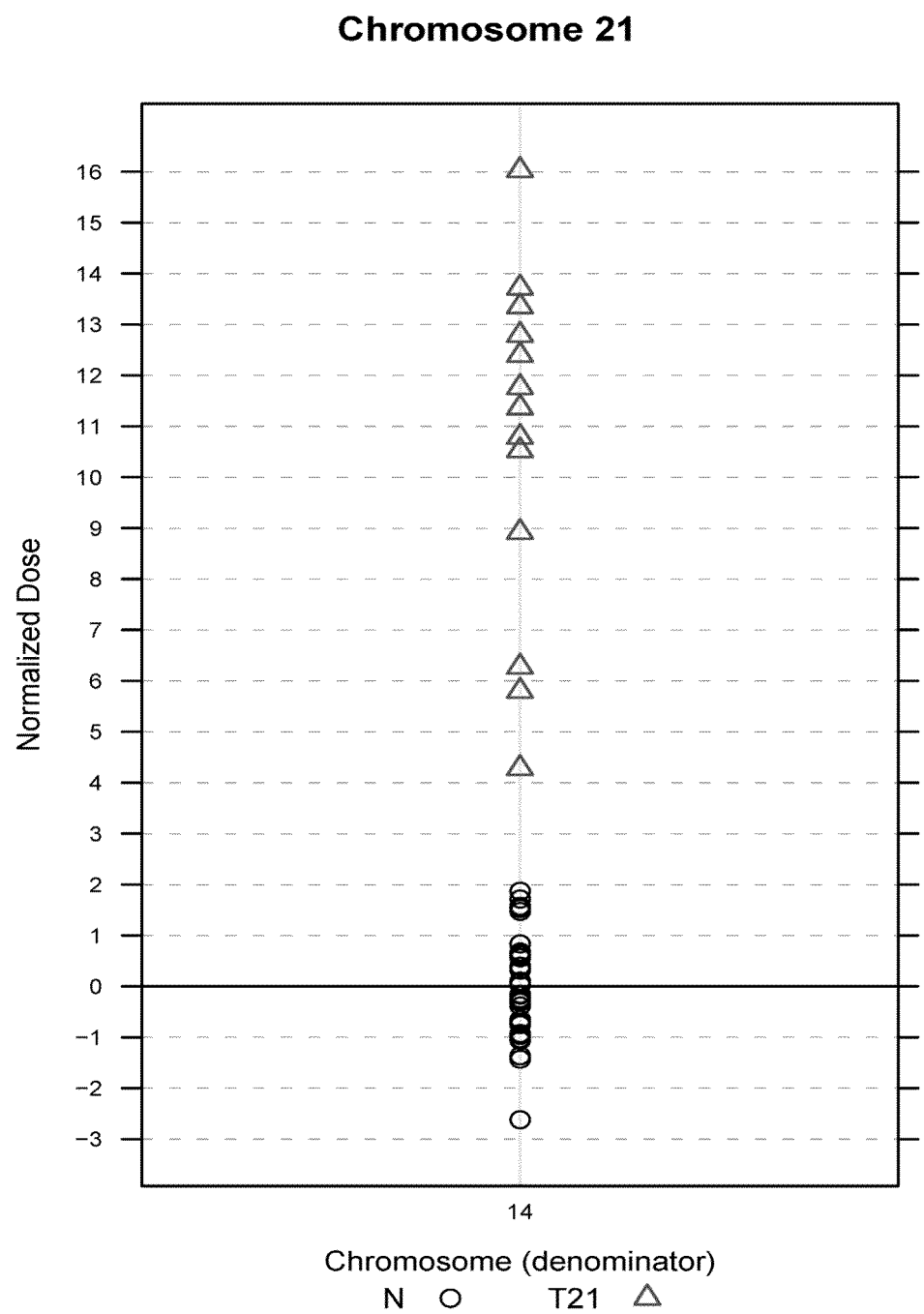
FIGS. 41A-41E illustrate the distribution of normalized chromosome doses for chromosome 21 (41A), chromosome 18 (41B), chromosome 13 (41C), chromosome X (41D) and chromosome Y (41E) relative to the standard deviation of the mean (Y-axis) for the corresponding chromosomes in the unaffected samples.
Figure 41B:
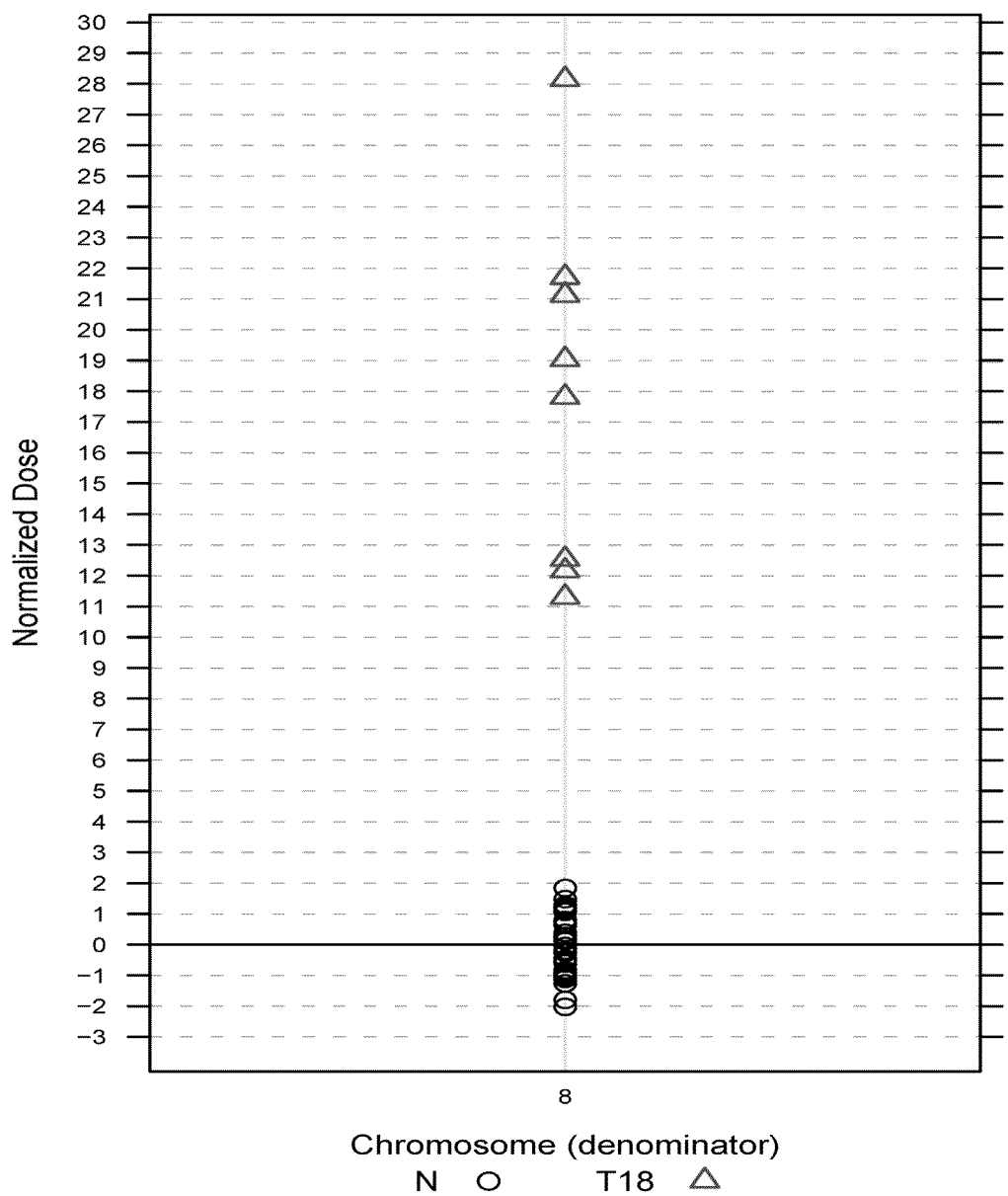
Figure 41C:
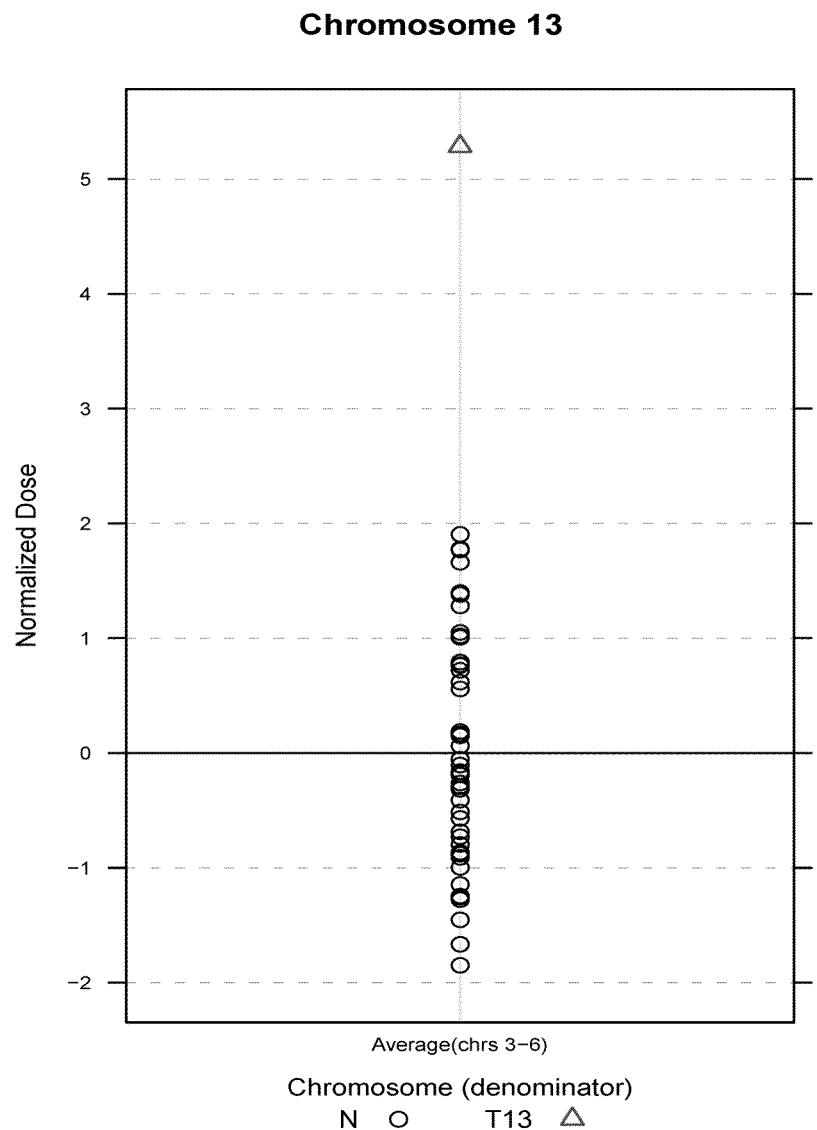
Figure 41D:
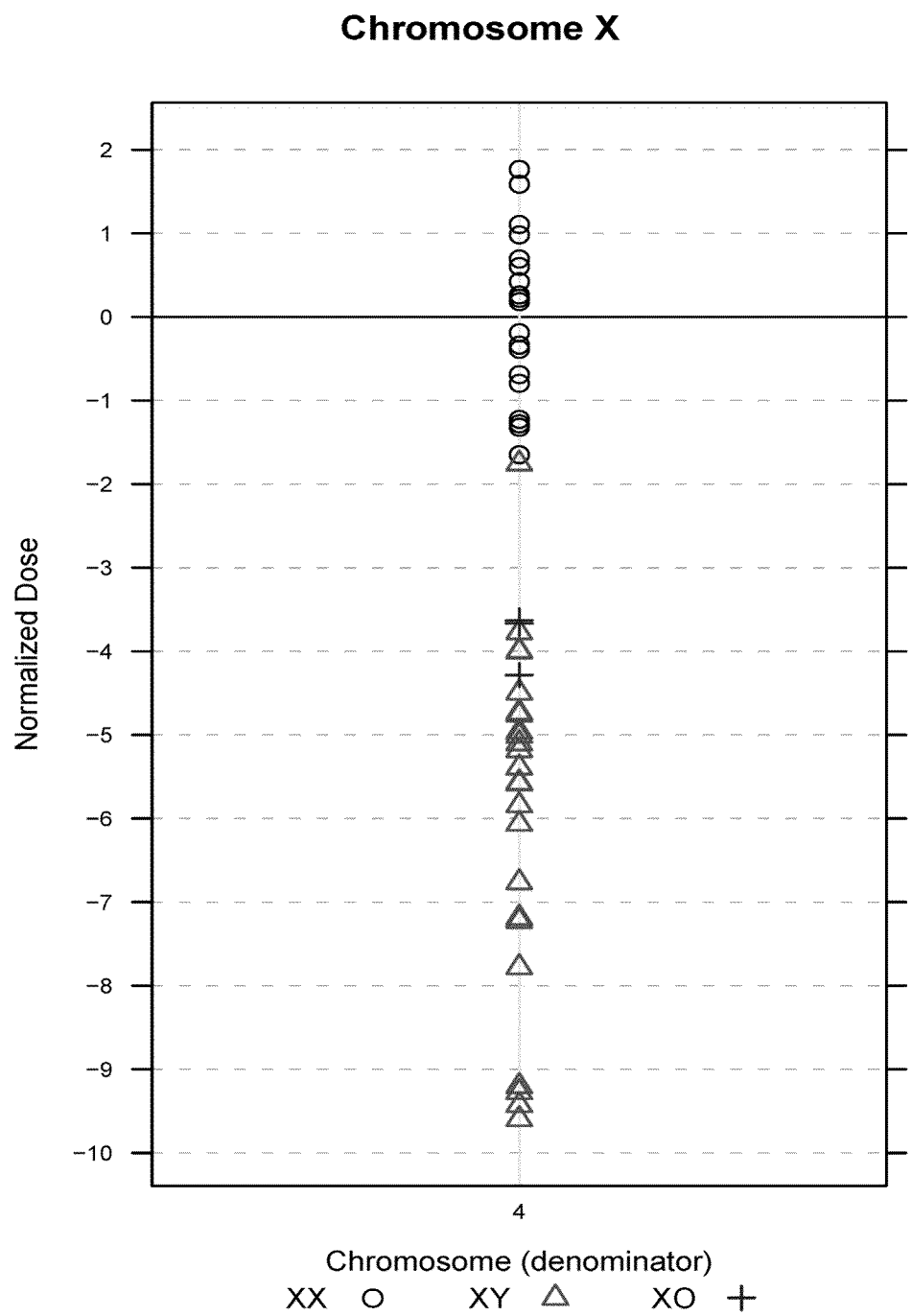
Figure 41E:
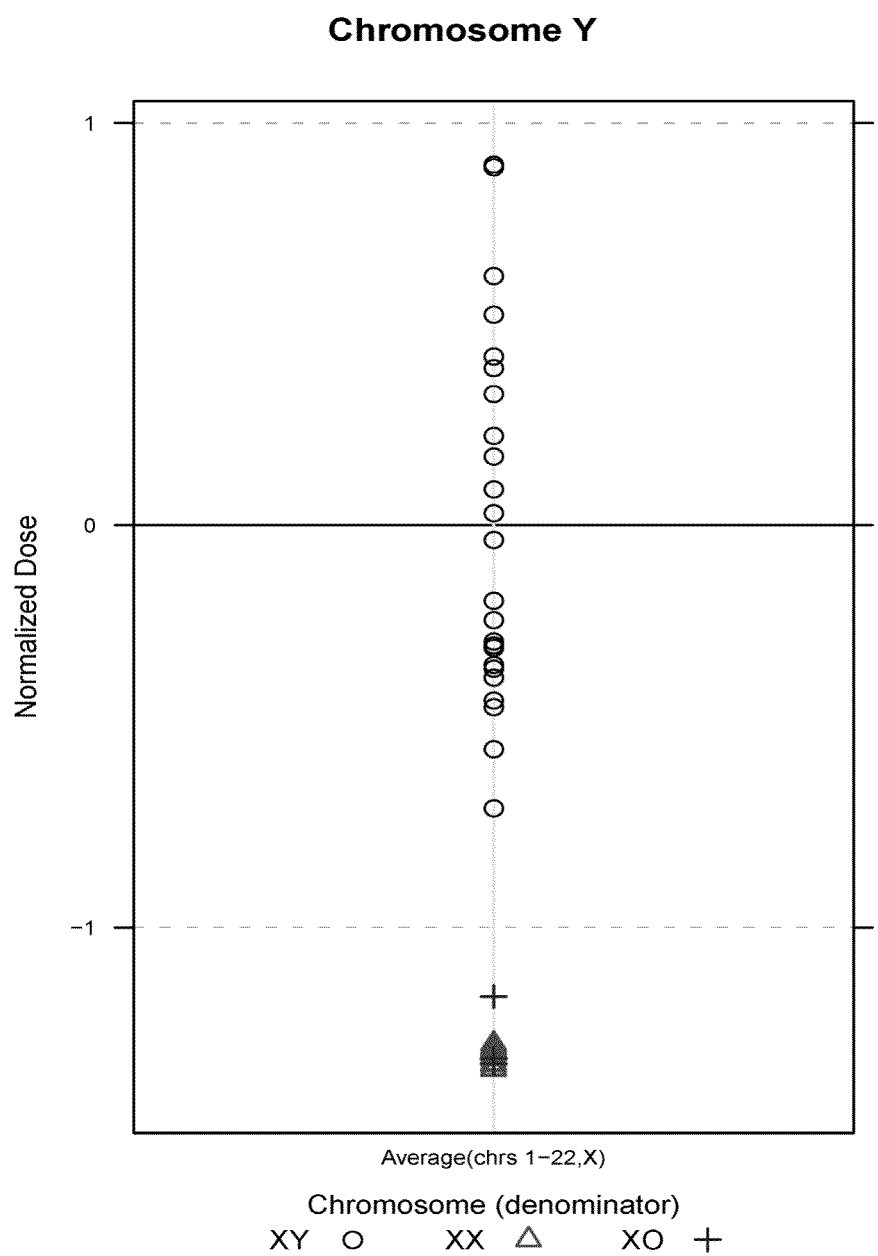

FIG. 41A shows the distribution of chromosome doses relative to the standard deviation from the mean for chromosome 21 dose in the unaffected samples (O) and the trisomy 21 samples (T21; Δ) when using chromosome 14 as the normalizing chromosome for chromosome 21. FIG. 41B shows the distribution of chromosome doses relative to the standard deviation from the mean for chromosome 18 dose in the unaffected samples (○) and the trisomy 18 samples (T18; Δ) when using chromosome 8 as the normalizing chromosome for chromosome 18. FIG. 41C shows the distribution of chromosome doses relative to the standard deviation from the mean for chromosome 13 dose in the unaffected samples (○) and the trisomy 13 samples (T13; Δ), using the average sequence tag density of the group of chromosomes 3, 4, 5, and 6 as the normalizing chromosome to determine the chromosome dose for chromosome 13. FIG. 41D shows the distribution of chromosome doses relative to the standard deviation from the mean for chromosome X dose in the unaffected female samples (○), the unaffected male samples (Δ), and the monosomy X samples (XO; +) when using chromosome 4 as the normalizing chromosome for chromosome X. FIG. 41E shows the distribution of chromosome doses relative to the standard deviation from the mean for chromosome Y dose in the unaffected male samples (o the unaffected female samples (Δ), and the monosomy X samples (+), when using the average sequence tag density of the group of chromosomes 1-22 and X as the normalizing chromosome to determine the chromosome dose for chromosome Y.

The data show that trisomy 21, trisomy 18, trisomy 13 were clearly distinguishable from the unaffected (normal) samples. The monosomy X samples were easily identifiable as having chromosome X dose that were clearly lower than those of unaffected female samples (FIG. 41D), and as having chromosome Y doses that were clearly lower than that of the unaffected male samples (FIG. 41E).

Therefore the method provided is sensitive and specific for determining the presence or absence of chromosomal aneuploidies in a maternal blood sample.

Example 12

Determination of Fetal Chromosomal Abnormalities Using Massively Parallel DNA Sequencing of Cell Free Fetal DNA from Maternal Blood: Test Set 1 Independent of Training Set 1

The study was conducted by qualified site clinical research personnel at 13 US clinic locations between April 2009 and July 2010 under a human subject protocol approved by institutional review boards (IRBs) at each institution. Informed written consent was obtained from each subject prior to study participation. The protocol was designed to provide blood samples and clinical data to support development of noninvasive prenatal genetic diagnostic methods. Pregnant women, age 18 years or older were eligible for inclusion. For patients undergoing clinically indicated CVS or amniocentesis blood was collected prior to performance of the procedure, and results of fetal karyotype was also collected. Peripheral blood samples (two tubes or ~20 mL total) were drawn from all subjects in acid citrate dextrose (ACD) tubes (Becton Dickinson). All samples were de-identified and assigned an anonymous patient ID number. Blood samples were shipped overnight to the laboratory in temperature controlled shipping containers provided for the study. Time elapsed between blood draw and sample receipt was recorded as part of the sample accessioning.

Site research coordinators entered clinical data relevant to the patient's current pregnancy and history into study case report forms (CRFs) using the anonymous patient ID number. Cytogenetic analysis of fetal karyotype from invasive prenatal procedure samples was performed per local laboratories and the results were also recorded in study CRFs. All data obtained on CRFs were entered into a clinical database the laboratory. Cell free plasma was obtained from individual blood tubes utilizing at two-step centrifugation process within 24-48 hours of sample of venipuncture. Plasma from a single blood tube was sufficient for sequencing analysis. Cell-free DNA was extracted from cell-free plasma by using QIAamp DNA Blood Mini kit (Qiagen) according to the manufacturer's instructions. Since the cell free DNA fragments are known to be approximately 170 base pairs (bp) in length (Fan et al., Clin Chem 56:1279-1286 [2010]) no fragmentation of the DNA was required prior to sequencing.

For the training set samples, cfDNA was sent to Prognosys Biosciences, Inc. (La Jolla, Calif.) for sequencing library preparation (cfDNA blunt ended and ligated to universal adapters) and sequencing using standard manufacturer protocols with the Illumina Genome Analyzer IIx instrumentation (http://www.illumina.com/). Single-end reads of 36 base pairs were obtained. Upon completion of the sequencing, all base call files were collected and analyzed. For the test set samples, sequencing libraries were prepared and sequencing carried out on Illumina Genome Analyzer IIx instrument. Sequencing library preparation was performed as follows. The full-length protocol described is essentially the standard protocol provided by Illumina, and only differs from the Illumina protocol in the purification of the amplified library: the Illumina protocol instructs that the amplified library be purified using gel electrophoresis, while the protocol described herein uses magnetic beads for the same purification step. Approximately 2 ng of purified cfDNA that had been extracted from maternal plasma was used to prepare a primary sequencing library using NEBNext™ DNA Sample Prep DNA Reagent Set 1 (Part No. E6000L; New England Biolabs, Ipswich, Mass.) for Illumina® essentially according to the manufacturer's instructions. All steps except for the final purification of the adaptor-ligated products, which was performed using Agencourt magnetic beads and reagents instead of the purification column, were performed according to the protocol accompanying the NEBNext™ Reagents for Sample Preparation for a genomic DNA library that is sequenced using the Illumina® GAIL The NEBNext™ protocol essentially follows that provided by Illumina, which is available at grcf.jhml.edu/hts/protocols/11257047_ChIP-_Sample_Prep.pdf.

The overhangs of approximately 2 ng purified cfDNA fragments contained in 40 µl were converted into phosphorylated blunt ends according to the NEBNext® End Repair Module by incubating the 40 µl cfDNA with 5 µl 10× phosphorylation buffer, 2 µl deoxynucleotide solution mix (10 mM each dNTP), 1 µl of a 1:5 dilution of DNA Polymerase I, 1 µl T4 DNA Polymerase and 1 µl T4 Polynucleotide Kinase provided in the NEBNext™ DNA Sample Prep DNA Reagent Set 1 in a 200 µl microfuge tube in a thermal cycler for 30 minutes at 20° C. The sample was cooled to 4° C., and purified using a QIAQuick column provided in the QIAQuick PCR Purification Kit (QIAGEN Inc., Valencia, Calif.) as follows. The 50 µl reaction was transferred to 1.5 ml microfuge tube, and 250 µl of Qiagen Buffer PB were added. The resulting 300 µl were transferred to a QIAquick column, which was centrifuged at 13,000 RPM for 1 minute in a microfuge. The column was washed with 750 µl Qiagen Buffer PE, and re-centrifuged. Residual ethanol was removed by an additional centrifugation for 5 minutes at 13,000 RPM. The DNA was eluted in 39 µl Qiagen Buffer EB by centrifugation. dA tailing of 34 µl of the blunt-ended DNA was accomplished using 16 µl of the dA-tailing master mix containing the Klenow fragment (3' to 5' exo minus) (NEBNext™ DNA Sample Prep DNA Reagent Set 1), and incubating for 30 minutes at 37° C. according to the manufacturer's NEBNext® dA-Tailing Module. The sample was cooled to 4° C., and purified using a column provided in the MinElute PCR Purification Kit (QIAGEN Inc., Valencia, Calif.) as follows. The 50 µl reaction was transferred to 1.5 ml microfuge tube, and 250 µl of Qiagen Buffer PB were added. The 300 µl were transferred to the MinElute column, which was centrifuged at 13,000 RPM for 1 minute in a microfuge. The column was washed with 750 µl Qiagen Buffer PE, and re-centrifuged. Residual ethanol was removed by an additional centrifugation for 5 minutes at 13,000 RPM. The DNA was eluted in 15 µl Qiagen Buffer EB by centrifugation. Ten microliters of the DNA eluate were incubated with 1 µl of a 1:5 dilution of the Illumina Genomic Adapter Oligo Mix (Part No. 1000521), 15 µl of 2× Quick Ligation Reaction Buffer, and 4 µl Quick T4 DNA Ligase, for 15 minutes at 25° C. according to the NEBNext® Quick Ligation Module. The sample was cooled to 4° C., and purified using a MinElute column as follows. One hundred and fifty microliters of Qiagen Buffer PE were added to the 30 µl reaction, and the entire volume was transferred to a MinElute column were transferred to a MinElute column, which was centrifuged at 13,000 RPM for 1 minute in a microfuge. The column was washed with 750 µl Qiagen Buffer PE, and re-centrifuged. Residual ethanol was removed by an additional centrifugation for 5 minutes at 13,000 RPM. The DNA was eluted in 28 µl Qiagen Buffer EB by centrifugation. Twenty three microliters of the adaptor-ligated DNA eluate were subjected to 18 cycles of PCR (98° C. for 30 seconds; 18 cycles of 98° C. for 10 seconds, 65° C. for 30 seconds, and 72° C. for 30; final extension at 72° C. for 5 minutes, and hold at 4° C.) using Illumina Genomic PCR Primers (Part Nos. 100537 and 1000538) and the Phusion HF PCR Master Mix provided in the NEBNext™ DNA Sample Prep DNA Reagent Set 1, according to the manufacturer's instructions. The amplified product was purified using the Agencourt AMPure XP PCR purification system (Agencourt Bioscience Corporation, Beverly, Mass.) according to the manufacturer's instructions available at www.beckmangenomics.com/products/AMPureXPProtocol_000387v001.pdf. The Agencourt AMPure XP PCR purification system removes unincorporated dNTPs, primers, primer dimers, salts and other contaminates, and recovers amplicons greater than 100 bp. The purified amplified product was eluted from the Agencourt beads in 40 µl of Qiagen EB Buffer and the size distribution of the libraries was analyzed using the Agilent DNA 1000 Kit for the 2100 Bioanalyzer (Agilent technologies Inc., Santa Clara, Calif.). For both the training and test sample sets, single-end reads of 36 base pairs were sequenced.

Data Analysis and Sample Classification

Sequence reads 36 bases in length were aligned to the human genome assembly hg18 obtained from the UCSC database (http://hgdownload.cse.ucsc.edu/goldenPath/hg18/bigZips/). Alignments were carried out utilizing the Bowtie short read aligner (version 0.12.5) allowing for up to two base mismatches during alignment (Langmead et al., Genome Biol 10:R25 [2009]. Only reads that unambiguously mapped to a single genomic location were included. Genomic sites where reads mapped were counted and included in the calculation of chromosome doses (see below). Regions on the Y chromosome where sequence tags from male and female fetuses map without any discrimination were excluded from the analysis (specifically, from base 0 to base 2×10⁶; base 10×10⁶ to base 13×10⁶; and base 23×10⁶ to the end of chromosome Y).

Intra-run and inter-run sequencing variation in the chromosomal distribution of sequence reads can obscure the effects of fetal aneuploidy on the distribution of mapped sequence sites. To correct for such variation, a chromosome dose was calculated as the count of mapped sites for a given chromosome of interest is normalized to counts observed on a predetermined normalizing chromosome sequence. As described previously, a normalized chromosome sequence can be composed of a single chromosome or a group of chromosomes. The normalizing chromosome sequence was first identified in a subset of samples in the training set of samples that were unaffected i.e. qualified samples having diploid karyotypes for chromosomes of interest 21, 18, 13 and X, considering each autosome as a potential denominator in a ratio of counts with our chromosomes of interest. Denominator chromosomes i.e. normalizing chromosome sequences were selected that minimized the variation of the chromosome doses within and between sequencing runs. Each chromosome of interest was determined to have a distinct normalizing chromosome sequence (denominator) (Table 18). No single chromosome could be identified as a normalizing chromosome sequence for chromosome 13 as no one chromosome was determined to reduce the variability in the dose of chromosome 13 across samples i.e. the spread of the NCV values for chromosome 13 was not reduced sufficiently to allow for a correct identification of a T13 aneuploidy. Chromosomes 2-6 were chosen randomly and tested for their ability as a group to mimic the behavior of chromosome 13. The group of chromosomes 2-6 was found to diminish substantially the variability in the dose for chromosome 13 in the training samples, and was thus chosen as the normalizing chromosome sequence for chromosome 13. As described above, the variability in chromosome dose for chromosome Y is greater than 30 independently of which single chromosome is used as the normalizing chromosome sequence in determining the chromosome Y dose. The group of chromosomes 2-6 was found to diminish substantially the variability in the dose for chromosome Y in the training samples, and was thus chosen as the normalizing chromosome sequence for chromosome Y.

The chromosome doses for each of the chromosomes of interest in the qualified samples provides a measure of the variation in the total number of mapped sequence tags for each chromosome of interest relative to that of each of the remaining chromosomes. Thus, qualified chromosome doses can identify the chromosome or a group of chromosomes i.e. normalizing chromosome sequence that has a variation among samples that is closest to the variation of the chromosome of interest, and that would serve as ideal sequences for normalizing values for further statistical evaluation.

Chromosome doses for all samples in the training set i.e. qualified and affected, also serve as the basis for determining threshold values when identifying aneuploidies in test samples as described in the following.

TABLE 18

Normalizing Chromosome Sequences for Determining Chromosome Doses

| Chromosome of Interest | Chromosome of Interest - Numerator (Chr mapped counts) | Normalizing Chromosome Sequence - Denominator (Chr mapped counts) |
|---|---|---|
| 21 | Chr 21 | Chr 9 |
| 18 | Chr 18 | Chr 8 |
| 13 | Chr 13 | Sum(Chr 2-6) |
| X | Chr X | Chr 6 |
| Y | Chr Y | Sum(Chr 2-6) |

For each chromosome of interest in each sample in the test set, a normalizing value was determined and used to determine the presence or absence of an aneuploidy. The normalizing value was calculated as a chromosome dose that can be further computed to provide a normalized chromosome value (NCV).

Chromosome Doses

For the test set, a chromosome dose was calculated for each chromosome of interest, 21, 18, 13, X and Y for every sample. As provided in Table 18 above, the chromosome dose for chromosome 21 was calculated as a ratio of the number of tags in the test sample that mapped to chromosome 21 in the test sample, and the number of tags in the test sample that mapped to chromosome 9; the chromosome dose for chromosome 18 was calculated as a ratio of the number of tags in the test sample that mapped to chromosome 18 in the test sample, and the number of tags in the test sample that mapped to chromosome 8; the chromosome dose for chromosome 13 was calculated as a ratio of the number of tags in the test sample that mapped to chromosome 13 in the test sample, and the number of tags in the test sample that mapped to chromosomes 2-6; the chromosome dose for chromosome X was calculated as a ratio of the number of tags in the test sample that mapped to chromosome X in the test sample, and the number of tags in the test sample that mapped to chromosome 6; and the chromosome dose for chromosome Y was calculated as a ratio of the number of tags in the test sample that mapped to chromosome Y in the test sample, and the number of tags in the test sample that mapped to chromosomes 2-6.

Normalized Chromosome Values

Using the chromosome dose for each of the chromosomes of interest in each of the test samples, and the mean of the corresponding chromosome dose determined in the qualified samples of the training set, a normalized chromosome value (NCV) was calculated using the equation:

$$NCV_{ij} = \frac{x_{ij} - \hat{\mu}_j}{\hat{\sigma}_j}$$

where $\hat{\mu}_j$ AND $\hat{\sigma}_j$ are the estimated training set mean and standard deviation respectively for the j-th chromosome dose, and $x_{ij}$ is the observed j-th chromosome dose for sample i. When chromosome doses are normally distributed, the NCV is equivalent to a statistical z-score for the doses. No significant departure from linearity is observed in a quantile-quantile plot of the NCVs from unaffected samples. In addition, standard tests of normality for the NCVs fail to reject the null hypothesis of normality.

For the test set, an NCV was calculated for each chromosome of interest, 21, 18, 13, X and Y for every sample. To insure a safe and effective classification scheme, conservative boundaries were chosen for aneuploidy classification. For classification of the autosomes' aneuploidy state, a NCV>4.0 was required to classify the chromosome as affected (i.e.

aneuploid for that chromosome) and a NCV<2.5 to classify a chromosome as unaffected. Samples with autosomes that have an NCV between 2.5 and 4.0 were classified as "no call".

Sex chromosome classification in the test was performed by sequential application of NCVs for both X and Y as follows:

If NCV Y>−2.0 standard deviations from the mean of male samples, then the sample was classified as male (XY).

If NCV Y<−2.0 standard deviations from the mean of male samples, and NCV X>−2.0 standard deviations from the mean of female samples, then the sample was classified as female (XX).

If NCV Y<−2.0 standard deviations from the mean of male samples, and NCV X<−3.0 standard deviations from the mean of female samples, then the sample was classified as monosomy X, i.e. Turner syndrome.

If the NCVs did not fit into any of the above criteria, then the sample was classified as a "no call" for sex.

Results

Study Population Demographics

A total of 1,014 patients were enrolled between April 2009 and July 2010. The patient demographics, invasive procedure type and karyotype results are summarized in Table 19. The average age of study participants was 35.6 yrs (range 17 to 47 yrs) and gestational age ranged between 6 weeks, 1 day to 38 weeks, 1 day (mean 15 weeks, 4 days). The overall incidence of abnormal fetal chromosome karyotypes was 6.8% with T21 incidence of 2.5%. Of 946 subjects with singleton pregnancies and karyotype, 906 (96%) showed at least one clinically recognized risk factor for fetal aneuploidy prior to prenatal procedure. Even eliminating those with advanced maternal age as their sole indication, the data demonstrates a very high false positive rate for current screening modalities. Ultrasound findings of increased nuchal translucency, cystic hygroma, or other structural congenital abnormality by ultrasound were most predictive of abnormal karyotype in this cohort.

TABLE 19

Patient Demographics

| | Total Enrolled (N = 1014) | Training Set (N = 71) | Test Set (N = 48) |
|---|---|---|---|
| Dates of Enrollment | April 2009-July 2010 | April 2009-December 2009 | January 2010-June 2010 |
| Number enrolled | 1014 | 435 | 575 |
| Maternal Age, yrs | | | |
| Mean (SD) | 35.6 (5.66) | 36.4 (6.05) | 34.2 (8.22) |
| Min/Max | 17/47 | 20/46 | 18/46 |
| Not Specified, N | 11 | 3 | 0 |
| Ethnicity, N (%) | | | |
| Caucasian | 636 (62.7) | 50 (70.4) | 24 (50.0) |
| Hispanic | 167 (16.5) | 6 (8.5) | 13 (27.0) |
| Asian | 63 (6.2) | 6 (8.5) | 5 (10.4) |
| Multi, more than one | 53 (5.2) | 6 (8.5) | 1 (2.1) |
| African American | 41 (4.0) | 1 (1.3) | 3 (6.3) |
| Other | 36 (3.6) | 2 (2.8) | 1 (2.1) |
| Native American | 9 (0.9) | 0 (0.0) | 1 (2.1) |
| Not Specified | 9 (0.9) | 0 (0.0) | 0 (0.0) |
| Gestational Age, wks, days | | | |
| Mean | 15 w 4 d | 14 w 5 d | 15 w 3 d |
| Min/Max | 6 w 1 d/38 w 1 d | 10 w 0 d/23 w 1 d | 10 w 4 d/28 w 3 d |

TABLE 19-continued

Patient Demographics

| | | | |
|---|---|---|---|
| Number of Fetus, N | | | |
| 1 | 982 | 67 | 47 |
| 2 | 30 | 4 | 1 |
| 3 | 2 | 0 | 0 |
| Prenatal Procedure, N (%) | | | |
| CVS | 430 (42.4) | 38 (53.5) | 28 (58.3) |
| Amniocentesis | 571 (56.3) | 32 (45.1) | 20 (41.7) |
| Not specified | 3 (0.3) | 1 (1.4) | 0 (0.0) |
| Not performed | 10 (1.0) | 0 (0.0) | 0 (0.0) |
| Fetal Karyotype, N (%) | | | |
| 46 XX | 453* (43.9) | 22* (29.7) | 7* (14.6) |
| 46 XY | 474* (45.9) | 26* (35.1) | 14 (29.2) |
| 47, +21, both sexes | 25* (2.4) | 10* (13.5) | 13 (27.1) |
| 47, +18, both sexes | 14 (1.4) | 5 (6.8) | 8 (16.7) |
| 47, +13, both sexes | 4 (0.4) | 2 (2.7) | 1 (2.1) |
| 45, X | 8 (0.8) | 3 (4.1) | 3 (6.3) |
| Complex, other | 18* (1.7) | 6 (8.1) | 2 (4.2) |
| Karyotype not available | 36 (3.5) | 0 (0.0) | 0 (0.0) |

| Prenatal Screening Risks for Karyotyped Singletons, N (%) | Non-sequenced N = 834 | Analyzed Training N = 65 | Analyzed Test N = 47 |
|---|---|---|---|
| AMA only (≥35 years) | 445 (53.4) | 27 (41.5) | 21 (44.7) |
| Screen positive (trisomy)** | 149 (17.9) | 18 (27.7) | 9 (19.1) |
| Increased NT | 35 (4.2) | 3 (4.6) | 5 (10.6) |
| Cystic Hygroma | 12 (1.4) | 5 (7.7) | 4 (8.5) |
| Cardiac Defect | 14 (1.7) | 0 (0.0) | 4 (8.5) |
| Other Congenital Abnormality | 78 (9.4) | 4 (6.2) | 3 (6.4) |
| Other Maternal Risk | 64 (7.7) | 5 (7.7) | 1 (2.1) |
| None specified | 37 (4.4) | 3 (4.6) | 0 (0.0) |

*Includes results of fetuses from multiple gestations,
**Assessed and reported by clinicians
Abbreviations:
AMA = Advanced Maternal Age,
NT = nuchal translucency The distribution of diverse ethnic backgrounds represented in this study population is also shown in Table 19. Overall, 63% of the patients in this study were Caucasian, 17% Hispanic, 6% Asian, 5% multi-ethnic, and 4% African American. It was noted that the ethnic diversity varied significantly from site to site. For example, one site enrolled 60% Hispanic and 26% Caucasian subjects while three clinics all located in the same state, enrolled no Hispanic subjects. As expected, there were no discernible differences observed in our results for different ethnicities.

Training Data Set 1

The training set study selected 71 samples from the initial sequential accumulation of 435 samples that were collected between April 2009 and December 2009. All subjects with affected fetus' (abnormal karyotypes) in this first series of subjects were included for sequencing and a random selection and number of non-affected subjects with adequate sample and data. Clinical characteristics of the training set patients were consistent with the overall study demographics as shown in Table 19. The gestational age range of the samples in the training set ranged from 10 weeks, 0 days to 23 weeks 1 day. Thirty-eight underwent CVS, 32 underwent amniocentesis and 1 patient did not have the invasive procedure type specified (an unaffected karyotype 46, XY). 70% of the patients were Caucasian, 8.5% Hispanic, 8.5% Asian, and 8.5% multi-ethnic. Six sequenced samples were removed from this set for the purposes of training: 4 samples from subjects with twin gestations (further discussed below), 1 sample with T18 that was contaminated during preparation, and 1 sample with a fetal karyotype 69,XXX, leaving 65 samples for the training set.

The number of unique sequence sites (i.e. tags identified with unique sites in the genome) varied from 2.2M in the early phases of the training set study to 13.7M in the latter phases due to improvements in sequencing technology over time. In order to monitor for any potential shifts in the chromosome doses over this 6-fold range in unique sites, different unaffected samples were run at the beginning and end of the study. For the first 15 unaffected samples run, the average number of unique sites was 3.8M and the average chromosome doses for chromosome 21 and chromosome 18 were 0.314 and 0.528, respectively. For the last 15 unaffected samples run, the average number of unique sites was 10.7M and the average chromosome doses for chromosome 21 and chromosome 18 were 0.316 and 0.529, respectively. There was no statistical difference between the chromosome doses for chromosome 21 and chromosome 18 over the time of the training set study.

Figure 42:
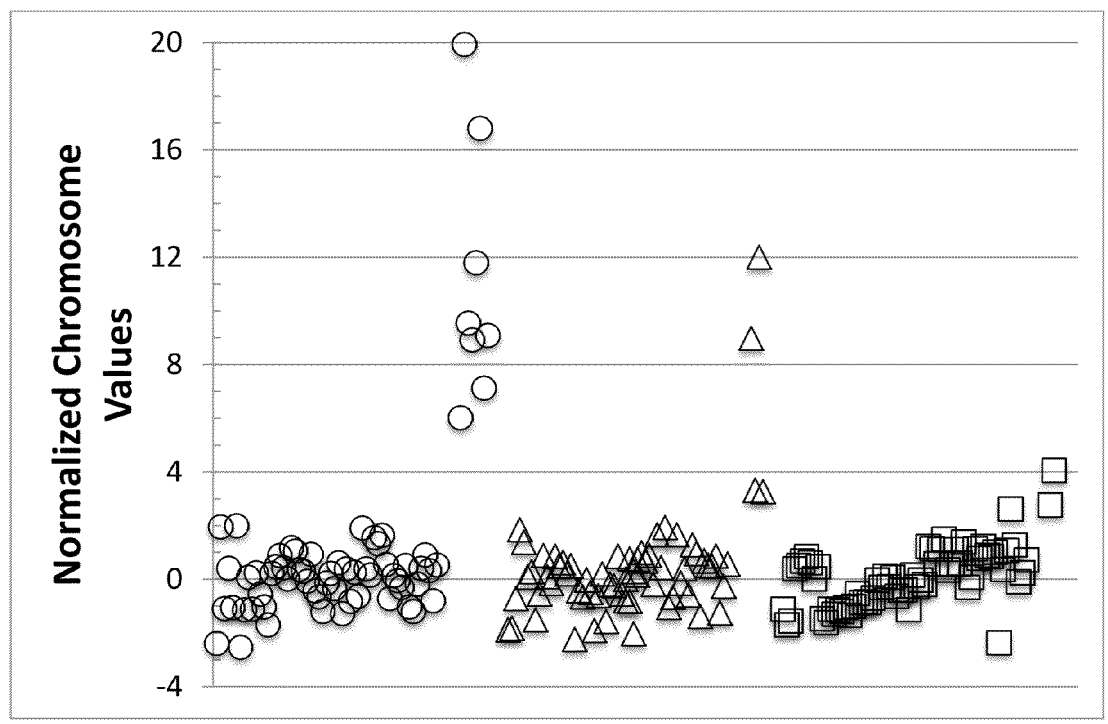
FIG. 42 shows normalized chromosome values for chromosomes 21 (O), 18 (Δ), and 13 (□) determined in samples from training set 1 using normalizing chromosomes as described in Example 12.

The training set NCVs for chromosomes 21, 18 and 13 are shown in FIG. 42. The results shown in FIG. 42 are consistent with an assumption of normality in that roughly 99% of the diploid NCVs would fall within ±2.5 standard deviations of the mean. Of this set of 65 samples, 8 samples with clinical karyotypes indicating T21 had NCVs ranging from 6 to 20. Four samples having clinical karyotypes indicative of fetal T18 had NCVs ranging from 3.3 to 12, and the two samples having karyotypes indicative of fetal trisomy 13 (T13) had NCVs of 2.6 and 4. The spread of the NCVs in affected samples is due to their dependence on the percentage of fetal cfDNA in the individual samples.

Similar to the autosomes, the means and standard deviations for the sex chromosomes were established in the training set. The sex chromosome thresholds allowed 100% identification of male and female fetuses in the training set.

Test Data Set 1

Having established chromosome doses means and standard deviations from the training set, a test set of 48 samples was selected from samples collected between January 2010 and June 2010 from 575 total samples. One of the samples from a twin gestation was removed from the final analysis leaving 47 samples in the test set. Personnel preparing samples for sequencing and operating the equipment were blinded to the clinical karyotype information. The gestational age range was similar to that seen in the training set (Table 19). 58% of the invasive procedures were CVS, higher than that of the overall procedural demographics, but also similar to the training set. 50% of subjects were Caucasian, 27% Hispanic, 10.4% Asian and 6.3% African American.

Figure 43:
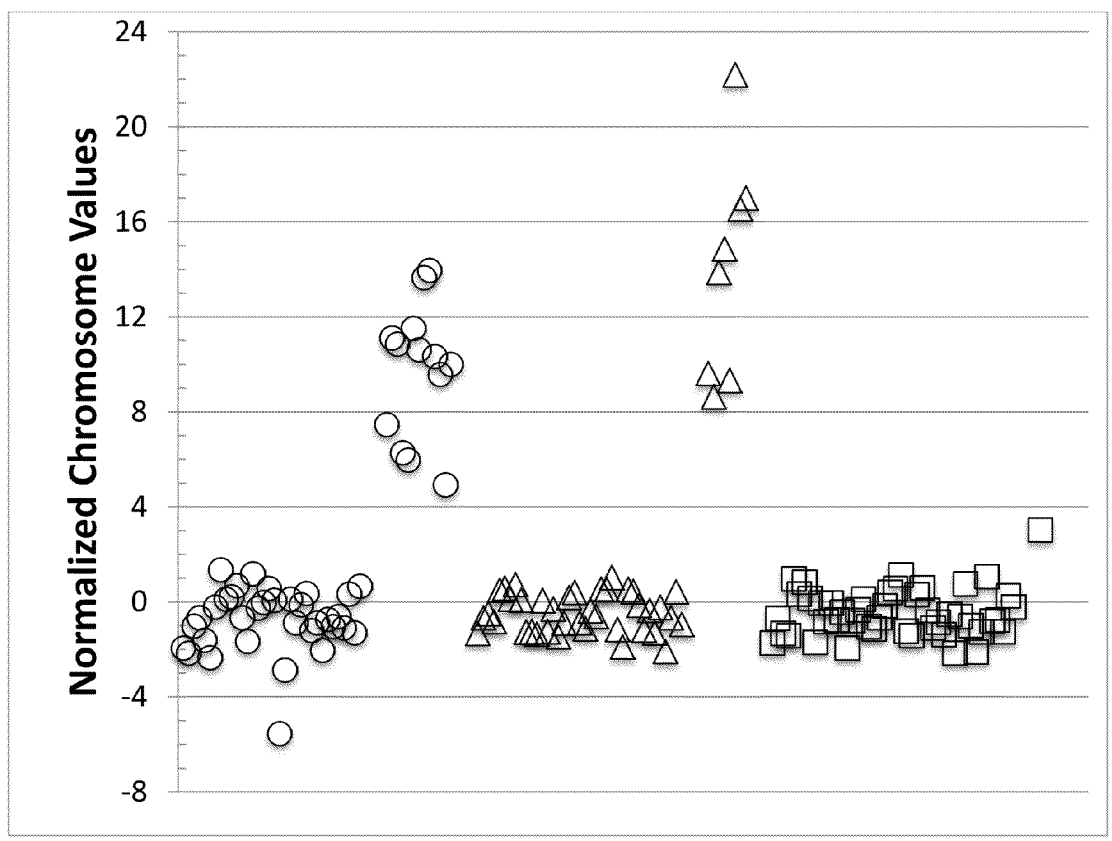
FIG. 43 shows normalized chromosome values for chromosomes 21 (O), 18 (Δ), and 13 (□) determined in samples from test set 1 using normalizing chromosomes as described in Example 12.

In the test set, the number of unique sequence tags varied from approximately 13M to 26M. For unaffected samples, the chromosome doses for chromosome 21 and chromosome 18 were 0.313 and 0.527, respectively. The test set NCVs for chromosome 21, chromosome 18 and chromosome 13 are shown in FIG. 43 and the classifications are given in Table 20.

TABLE 20

Test Set Classification Data Test Set Classification Data

T21 classification

| Karyotype | Unaffected for T21 | T21 | No Call |
|---|---|---|---|
| Unaffected for T21 | 34 | | |
| 47, XX or XY + 21 | | 13 | |

TABLE 20-continued

Test Set Classification Data Test Set Classification Data

T18 classification

| Karyotype | Unaffected for T18 | T18 | No Call |
|---|---|---|---|
| Unaffected for T18 | 39 | | |
| 47, XX or XY + 18 | | 8 | |

T13 classification

| Karyotype | Unaffected for T13 | T13 | No Call |
|---|---|---|---|
| Unaffected for T13 | 46 | | |
| 47, XX or XY + 13 | | | 1 |

Sex Chromosome Classification

| Karyotype | XY | XX | MX* | No Call |
|---|---|---|---|---|
| 46, XY | 24 | | | |
| 46, XX | | 18 | | 1 |
| 45, X | | | 2 | 1 |
| Cplx | 1 | | | |

*MX is monosomy in the X chromosome with no evidence of Y chromosome

In the test set, 13/13 subjects having clinical karyotypes that indicated fetal T21 were correctly identified having NCVs ranging from 5 to 14. Eight/eight subjects having karyotypes that indicated fetal T18 were correctly identified having NCVs ranging from 8.5 to 22. The single sample having a karyotype classified as T13 in this test set was classified as a no call with an NCV of approximately 3.

For the test data set, all male samples were correctly identified including a sample with complex karyotype, 46,XY+ marker chromosome (unidentifiable by cytogenetics) (Table 11). Nineteen of twenty female samples were correctly identified, and one female sample was categorized as a no call. For three samples in the test set with karyotype of 45,X, two of the three were correctly identified as monosomy X and 1 was classified as a no call (Table 20).

Twins

Four of the samples initially selected for the training set and one of the samples in the test set were from twin gestations. The thresholds being employed here could be confounded by the differing amount of cfDNA expected in the setting of a twin gestation. In the training set, the karyotype from one of the twin samples was monochorionic 47,XY+21. A second twin sample was fraternal and amniocentesis was carried out on each of the fetuses individually. In this twin gestation, one of the fetuses had a karyotype of 47,XY+21 while the other had a normal karyotype, 46,XX. In both of these cases the cell free classification based on the methods discussed above classified the sample as T21. The other two twin gestations in the training set were classified correctly as non-affected for T21 (all twins showed diploid karyotype for chromosome 21). For the twin gestation sample in the test set, karyotype was only established for Twin B (46,XX) and the algorithm correctly classified as non-affected for T21.

Conclusion

The data show that massively parallel sequencing can be used to determine a plurality abnormal fetal karyotypes from the blood of pregnant women. These data demonstrate that 100% correct classification of samples with trisomy 21 and trisomy 18 can be identified using independent test set data. Even in the case of fetuses with abnormal sex chromosome karyotypes, none of the samples were incorrectly classified with the algorithm of the method. Importantly, the algorithm also performed well in determining the presence of T21 in two sets of twin pregnancies having at least one affected fetus, which has never been shown previously. Furthermore, this study examined a variety of sequential samples from multiple centers representing not only the range of abnormal karyotypes that one is likely to witness in a commercial clinical setting, but showing the significance of accurately classifying pregnancies non-affected by common trisomies to address the unacceptably high false positive rates that remain in prenatal screening today. The data provide valuable insight into the vast capabilities of employing this method in the future. Analysis of subsets of the unique genomic sites showed increases in the variance consistent Poisson counting statistics.

The data build on the findings of Fan and Quake who demonstrated that the sensitivity of noninvasive prenatal determination of fetal aneuploidy from maternal plasma using massively parallel sequencing is only limited by the counting statistics (Fan and Quake, PLos One 5, e10439 [2010]). Because sequencing information was collected across the entire genome, this method is capable of determining any aneuploidy or other copy number variation including insertions and deletions. The karyotype from one of the samples had a small deletion in chromosome 11 between q21 and q23 that was observed as a ~10% decrease in the relative number of tags in a 25 Mb region starting at q21 when the sequencing data was analyzed in 500 kbase bins. In addition, in the training set, three of the samples had complex sex karyotypes due to mosaicism in the cytogenetic analysis. These karyotypes were: i) 47,XXX[9]/45,X[6], ii) 45,X [3]/46, XY[17], and iii) 47,XXX[13]/45,X[7]. Sample ii, which showed some XY-containing cells was correctly classified as XY. Samples i (from CVS procedure) and iii (from amniocentesis), which both showed a mixture of XXX and X cells by cytogenetic analysis (consistent with mosaic Turner syndrome), were classified as a no call and monosomy X, respectively.

In testing the algorithm, another interesting data point was observed having an NCV between −5 and −6 for chromosome 21 for one sample from the test set (FIG. 43). Although this sample was diploid in chromosome 21 bp cytogenetics, the karyotype showed mosaicism with partial triploidy for chromosome 9; 47, XX+9 [9]/46, XX [6]. Since chromosome 9 is used in the denominator to determine the chromosome dose for chromosome 21 (Table 18), this lowers the overall NCV value. The ability of the use of normalizing chromosomes to determine fetal trisomy 9 in this sample is evidenced by the results provided in Example 13 below.

Figure 44:
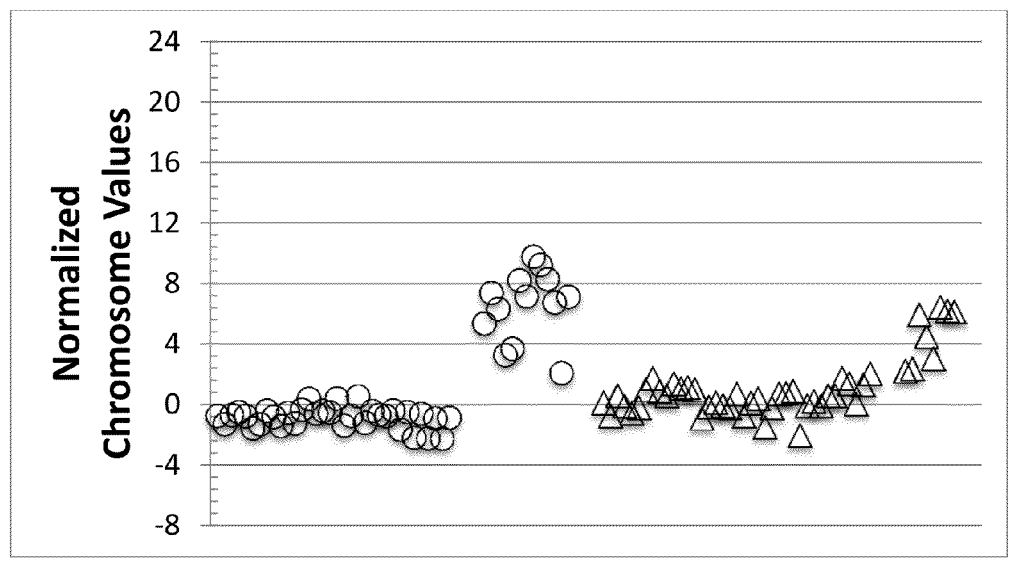
FIG. 44 shows normalized chromosome values for chromosomes 21 (O) and 18 (Δ) determined in samples from test set 1 using the normalizing method of Chiu et al. (normalizes the number of sequence tags identified for the chromosome of interest with the number of sequence tags obtained for the remaining chromosomes in the sample; see elsewhere herein Example 13).

The conclusion of Fan, et al regarding the sensitivity of these methods is only correct if the algorithms being utilized are able to account for any random or systematic biases introduced by the sequencing method. If the sequencing data is not properly normalized the resulting analysis will be inferior to the counting statistics. Chiu, et al noted in their recent paper that their measurement of chromosomes 18 and 13 using the massively parallel sequencing method was imprecise, and concluded that more research was necessary to apply the method to the determination of T18 and T13 (Chiu et al., BMJ 342:c7401 [2011]). The method utilized in the Chiu, et al paper simply uses the number of sequence tags on the chromosome of interest, in their case chromosome 21, normalized by the total number of tags in the sequencing run. The challenge for this approach is that the distribution of tags on each chromosome can vary from sequencing run to sequencing run, and thus increases the overall variation of the aneuploidy determination metric. In order to compare the results of the Chiu algorithm to the chromosome doses used in this example, the test data for chromosomes 21 and 18 was reanalyzed using the method recommended by Chiu, et al. as shown in FIG. 44. Overall, a compression in the range of NCV for each of the chromosomes 21 and 18 was observed as well as a decrease in the determination rate with 10/13 T21 and 5/8 of the T18 samples correctly identified from our test set utilizing an NCV threshold of 4.0 for aneuploidy classification.

Ehrich, et al also focused only on T21 and used the same algorithm as Chiu, et al., (Ehrich et al., Am J Obstet Gynecol 204:205 e1-e11 [2011]). In addition, after observing a shift in their test set z-score metric from the external reference data i.e. training set, they retrained on the test set to establish the classification boundaries. Although in principle this approach is feasible, in practice it would be challenging to decide how many samples are required to train and how often one would need to retrain to ensure that the classification boundaries are correct. One method of mitigating this issue is to include controls in every sequencing run that measure the baseline and calibrate for quantitative behavior.

The data obtained using the present method show that massively parallel sequencing is capable of determining multiple fetal chromosomal abnormalities from the plasma of pregnant women when the algorithm for normalizing the chromosome counting data is optimized. The present method for quantification not only minimizes random and systematic variations between sequencing runs, but also allows for effective classification of aneuploidies across the entire genome, most notably T21 and T18. Larger sample collections are required to test the algorithm for T13 determination. To this end, a prospective, blinded, multi-site clinical study to further demonstrate the diagnostic accuracy of the present method is being performed.

Example 13

Determination of the Presence or Absence of at Least 5 Different Chromosomal Aneuploidies in All Chromosomes of Individual Test Samples To demonstrate the capability of the method to determine the presence or absence of any chromosomal aneuploidy in each of a set of maternal test samples (test set 1; Example 12), systematically determined normalizing chromosome sequences were identified in unaffected samples of the training set (training set 1; Example 12), and used to calculate chromosome doses for all chromosomes in each of the test samples. Determination of the presence or absence of any one or more different complete fetal chromosomal aneuploidies in each of the test and training set samples was accomplished from sequencing information obtained from a single sequencing run on each individual sample.

Using the chromosome densities i.e. the number of sequence tags identified for each chromosome in each of the samples of the training set described in Example 12, a systematically determined normalizing chromosome sequence consisting of a single chromosome or a group of chromosomes was determined by calculating a single chromosome dose for each of chromosomes 1-22, X and Y. The systematically determined normalizing chromosome sequence for each of chromosomes 1-22, X, and Y was determined by systematically calculating chromosome doses for each chromosome using every possible combination of chromosomes as the denominator. For example, for chromosome 21 as the chromosome of interest, chromosome doses were calculated as a ratio of (i) the number of sequence tags obtained for chromosome 21 (chromosome of interest) and (ii) the number of sequence tags obtained for each of the remaining chromosomes, and the sum of the number of tags obtained for all possible combinations of the remaining chromosomes (excluding chromosome 21) i.e. 1, 2, 3, 4, 5, etc. up to 20, 21, 22, X, and Y; 1+2, 1+3, 1+4, 1+5, etc. up to 1+20, 1+22, 1+X, and 1+Y; 1+2+3, 1+2+4, 1+2+5 etc. up to 1+2+20, 1+2+22, 1+2+X, and 1+2+Y; 1+3+4, 1+3+5, 1+3+6 etc. up to 1+3+20, 1+3+22, 1+3+X, and 1+3+Y; 1+2+3+4, 1+2+3+5, 1+2+3+6 etc. up to 1+2+3+20, 1+2+3+22, 1+2+3+X, and 1+2+3+Y; and so on such that all possible combinations of all of chromosomes 1-20, 22, X and Y were used as a normalizing chromosome sequence (denominator) to determine all possible chromosome doses for each chromosome of interest in each of the qualified (aneuploid) samples in the training set. Chromosome doses were determined in the same manner for chromosome 21 in all training samples, and the systematically determined normalizing chromosome sequence for chromosome 21 was determined as the single or group of chromosomes resulting in a dose for chromosome 21 having the smallest variability across all training samples. The same analysis was repeated to determine the single chromosome or combination of chromosomes that would serve as the systematically determined normalizing chromosome sequence for each of the remaining chromosomes including chromosomes 13, 18, X and Y i.e. all possible combinations of chromosomes were used to determine the normalizing sequence (single chromosome or a group of chromosomes) for all other chromosomes of interest 1-12, 14-17, 19-20, 22, X and Y, in all training samples. Thus, all chromosomes were treated as chromosomes of interest, and a systematically determined normalizing sequence was determined for each of all chromosomes in each of the unaffected samples in the training set. Table 21 provides the single or the group of chromosomes that were identified as the systematically determined normalizing sequence for each of chromosomes of interest 1-22, X, and Y. As highlighted by Table 21, for some chromosomes of interest, the systematically determined normalizing chromosome sequence was determined to be a single chromosome (e.g. when chromosome 4 is the chromosome of interest), and for other chromosomes of interest, the systematically determined normalizing chromosome sequence was determined to be a group of chromosomes (e.g. when chromosome 21 is the chromosome of interest).

TABLE 21

Systematically Determined Normalizing Chromosome Sequences for All Chromosomes

| Chromosome of Interest | Systematically Determined Normalizing Sequence |
|---|---|
| 1 | 6 + 10 + 14 + 15 + 17 + 20 |
| 2 | 3 + 6 + 8 + 9 + 10 |
| 3 | 2 + 4 + 5 + 6 + 12 |
| 4 | 5 |
| 5 | 4 + 6 + 8 + 14 |
| 6 | 3 + 4 + 5 + 12 + 14 |
| 7 | 4 + 5 + 8 + 14 + 19 + 20 |
| 8 | 2 + 5 + 7 |
| 9 | 3 + 4 + 8 + 10 + 17 + 19 + 20 + 22 |
| 10 | 2 + 14 + 15 + 17 + 20 |
| 11 | 5 + 10 + 14 + 20 + 22 |
| 12 | 1 + 2 + 3 + 5 + 6 + 19 |
| 13 | 4 + 5 |
| 14 | 1 + 3 + 5 + 6 + 10 + 19 |
| 15 | 1 + 14 + 20 |
| 16 | 14 + 17 + 19 + 20 + 22 |
| 17 | 15 + 19 + 22 |
| 18 | 2 + 3 + 5 + 7 |

TABLE 21-continued

Systematically Determined Normalizing Chromosome Sequences for All Chromosomes

| Chromosome of Interest | Systematically Determined Normalizing Sequence |
|---|---|
| 19 | 22 |
| 20 | 10 + 16 + 17 + 22 |
| 21 | 4 + 14 + 16 + 20 + 22 |
| 22 | 19 |
| X | 4 + 8 |
| Y | 4 + 6 |

The mean, standard deviation (SD) and coefficient of variance (CV) for the systematically determined normalizing chromosome sequence determined for each of all chromosomes are given in Table 22.

TABLE 22

Mean, Standard Deviation and Coefficient of Variance for all systematically determined normalizing chromosome sequences

| Chromosome of interest | Mean | SD | CV |
|---|---|---|---|
| 1 | 0.36637 | 0.00266 | 0.72% |
| 2 | 0.31580 | 0.00068 | 0.22% |
| 3 | 0.21983 | 0.00055 | 0.18% |
| 4 | 0.98191 | 0.02509 | 2.56% |
| 5 | 0.30109 | 0.00076 | 0.25% |
| 6 | 0.21621 | 0.00059 | 0.27% |
| 7 | 0.21214 | 0.00044 | 0.21% |
| 8 | 0.25562 | 0.00068 | 0.27% |
| 9 | 0.12726 | 0.00034 | 0.27% |
| 10 | 0.24471 | 0.00098 | 0.40% |
| 11 | 0.26907 | 0.00098 | 0.36% |
| 12 | 0.12358 | 0.00029 | 0.23% |
| 13[a] | 0.26023 | 0.00122 | 0.47% |
| 14 | 0.09286 | 0.00028 | 0.30% |
| 15 | 0.21568 | 0.00147 | 0.68% |
| 16 | 0.25181 | 0.00134 | 0.53% |
| 17 | 0.46000 | 0.00248 | 0.54% |
| 18[a] | 0.10100 | 0.00038 | 0.38% |
| 19 | 1.43709 | 0.02899 | 2.02% |
| 20 | 0.19967 | 0.00123 | 0.62% |
| 21[a] | 0.07851 | 0.00053 | 0.67% |
| 22 | 0.69613 | 0.01391 | 2.00% |
| X[b] | 0.46865 | 0.00279 | 0.68% |
| Y[b] | 0.00028 | 0.00004 | 14.97% |

[a]Excluding trisomies
[b]Female fetus

The variance in chromosome doses across all training samples as reflected by the value of the CV, substantiates the use of systematically determined normalizing chromosome sequences to provide a large signal-to-noise ratio and dynamic range, allowing for the determination of the aneuploidies to be made with high sensitivity and high specificity, as shown in the following.

To demonstrate the sensitivity and specificity of the method, chromosome doses for all chromosomes of interest 1-22, X and Y were determined in each of the samples in the training set, and in each of all samples in the test set described in Example 11 using the corresponding systematically determined normalizing chromosome sequences provided in Table 21 above.

Using the systematically determined normalizing chromosome sequence for each of the chromosomes of interest, the presence or absence of any chromosomal aneuploidy was determined in each of the samples in the training set, and in each of the test samples i.e. it was determined whether each sample contained a complete fetal chromosomal aneuploidy of chromosome 1, 2, 3, 4, 5, 6, 7, 8, 9, 10, 11, 12, 13, 14, 15, 16, 17, 18, 19, 20, 21, 22, X, and Y. Sequence information i.e. the number of sequence tags, was obtained for all chromosomes in each of the samples in the training set, and in each of the test samples, and a single chromosome dose for each of the chromosomes in each of the training and test samples was calculated as described above using the number of sequence tags obtained for the systematically determined normalizing chromosome sequences corresponding to those determined in the trained set (Table 21). The number of sequence tags obtained in each of the training samples for the systematically determined normalizing chromosome sequences was used to determine the chromosome doses for each chromosome in each of the training samples, and the number of sequence tags obtained in each of the test samples for the systematically determined normalizing chromosome sequence was used to determine the chromosome dose for each chromosome for each of the test samples. To ensure safe and effective classification of aneuploidies, the same conservative boundaries were chosen as described in Example 12.

Training Set Results

Figure 45:
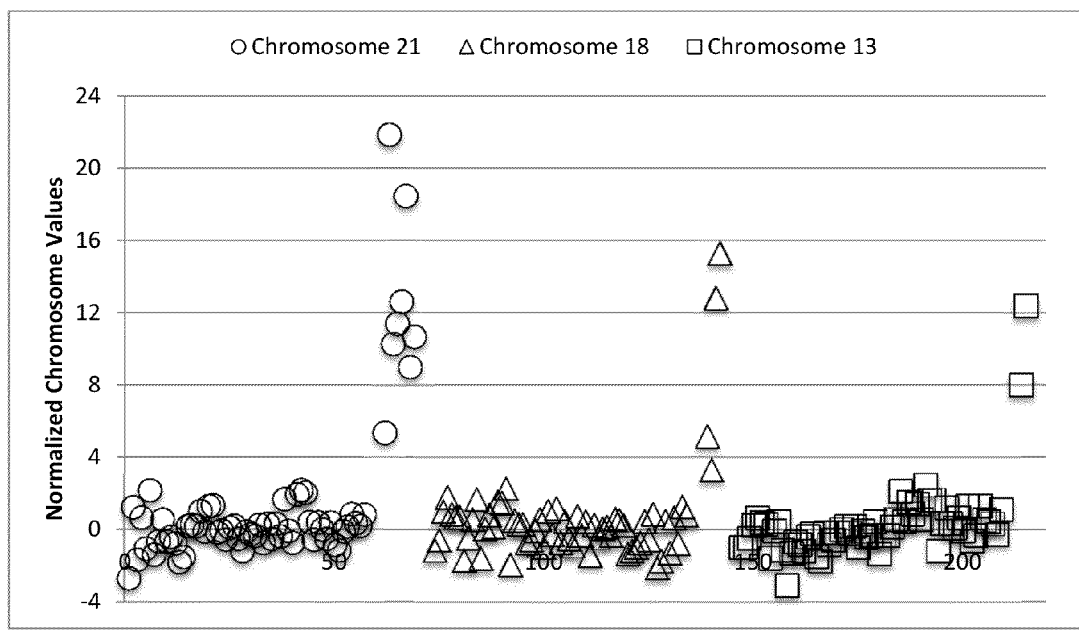
FIG. 45 shows normalized chromosome values for chromosomes 21 (O), 18 (Δ), and 13 (□) determined in samples from training set 1 using systematically determined normalizing chromosomes (as described in Example 13).

A plot of the chromosome doses for chromosomes 21, 18 and 13 in the training set of samples using the systematically determined normalizing chromosome sequence is given in FIG. 45. When using the systematically determined normalizing chromosome sequence i.e. the group of chromosomes 4+14+16+20+22, 8 samples with clinical karyotypes indicating T21 had NCVs between 5.4 and 21.5. When using the systematically determined normalizing chromosome sequence i.e. the group of chromosomes 2+3+5+7, 4 samples with clinical karyotypes indicating T18 had NCVs between 3.3 and 15.3. When using the systematically determined normalizing chromosome sequence i.e. the group of chromosomes 4+5, 2 samples with clinical karyotypes indicating T13 had NCVs of 8.0 and 12.4. The T21 samples of the training set are shown as the last 8 samples of the chromosome 21 data (O); the T18 samples of the training set are shown as the last 4 samples of the chromosome 18 data (Δ); and the T13 samples of the training set are shown as the last 2 samples of the chromosome 13 data (□).

These data show that normalizing chromosome sequences can be used to determine and correctly classify different complete fetal chromosomal aneuploidies with great confidence. Since all samples with affected karyotypes had NCVs greater than 3, there is less than approximately 0.1% probability that these samples are part of the unaffected distribution.

Figure 46A:
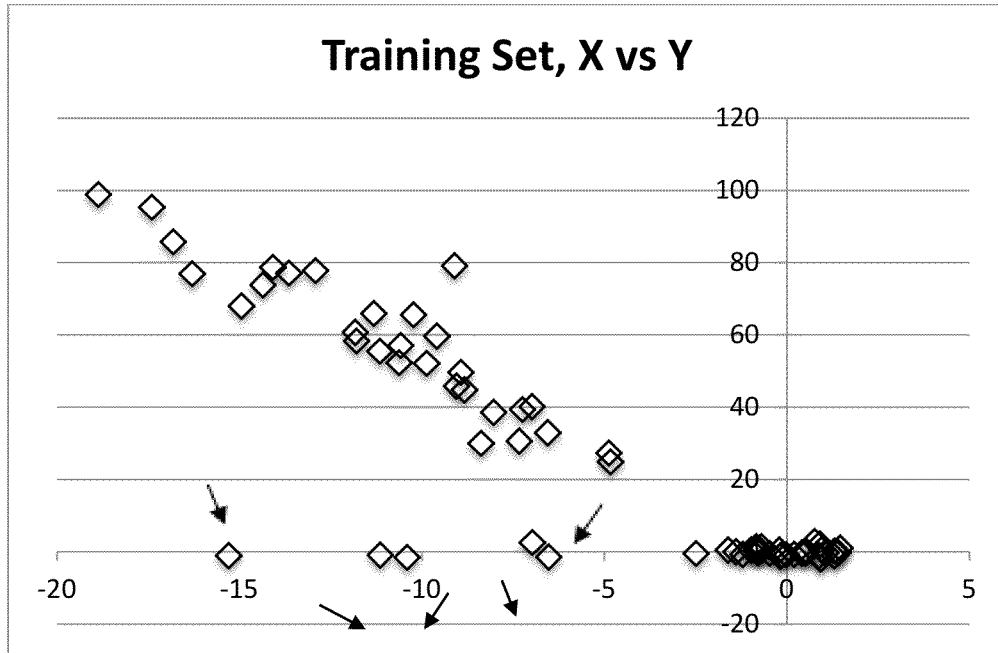
FIG. 46 shows normalized chromosome values for chromosomes X (X-axis) and Y (Y-axis). The arrows point to the 5 (FIG. 46A) and 3 (FIG. 46B) monosomy X samples that were identified in the training and test sets, respectively, as described in Example 13.

Similarly to the autosomes, when the systematically determined normalizing chromosome sequence (i.e. the group of chromosomes 4+8) was used for chromosome X, and when the systematically determined normalizing chromosome sequence (i.e. the group of chromosomes 4+6) was used for chromosome Y, all of the male and female fetuses in the training set were correctly identified. In addition, all 5 of the monosomy X samples were identified. FIG. 46A shows a plot of NCVs determined for the X chromosome (X-axis) and NCVs determined for the Y chromosome (Y axis) for each of the samples in the training set. All of the samples which are monosomy e X by karyotype have NCV values of less than −4.83. Those monosomy X samples that have karyotypes consistent with a 45,X karyotype (full or mosaic) have a Y NCV value close to zero as expected. Female samples cluster around NCV=0 for both X and Y.

Test Set Results

Figure 47:
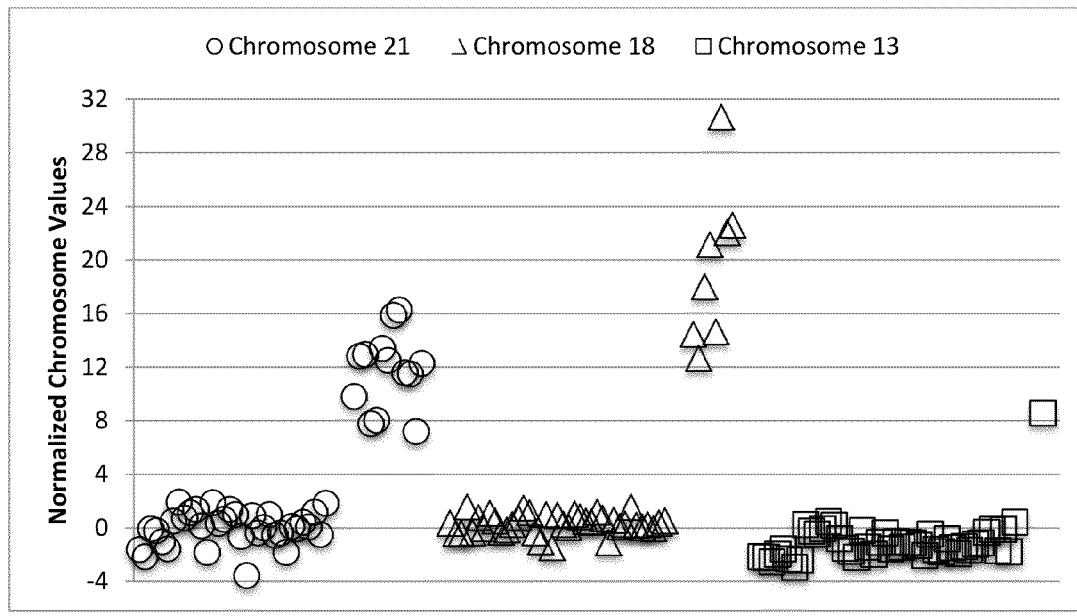
FIG. 47 shows normalized chromosome values for chromosomes 21 (O), 18 (Δ), and 13 (□) determined in samples from test set 1 using systematically determined normalizing chromosomes (as described in Example 13).

A plot of the chromosome doses for chromosomes 21, 18 and 13 in the test samples using the relevant systematically determined normalizing chromosome sequences is given in FIG. 47. When using the systematically determined normalizing chromosome sequence (i.e. the group of chromosomes 4+14+16+20+22), then 13 of 13 samples with clinical karyotypes indicating T21 were correctly identified with NCVs between 7.2 and 16.3. When using the systematically determined normalizing chromosome sequence (i.e. the group of chromosomes 2+3+5+7), then all 8 samples with clinical karyotypes indicating T18 were identified with NCVs between 12.7 and 30.7. When using the systematically determined normalizing chromosome sequence (i.e. the group of chromosomes 4+5), then the only one sample with clinical karyotypes indicating T13 was correctly identified with an NCV of 8.6. The T21 samples of the test set are shown as the last 13 samples of the chromosome 21 data (O); the T18 samples of the test set are shown as the last 8 samples of the chromosome 18 data (Δ); and the T13 sample of the test set is shown as the last sample of the chromosome 13 data (□).

These data show that systematically determined normalizing chromosome sequences can be used to determine and correctly classify different complete fetal chromosomal aneuploidies with great confidence. Similar to the training set, all samples with affected karyotypes had NCVs greater than 7, which indicated an infinitesimally small probability that these samples are part of the unaffected distribution (FIG. 47).

Figure 46B:
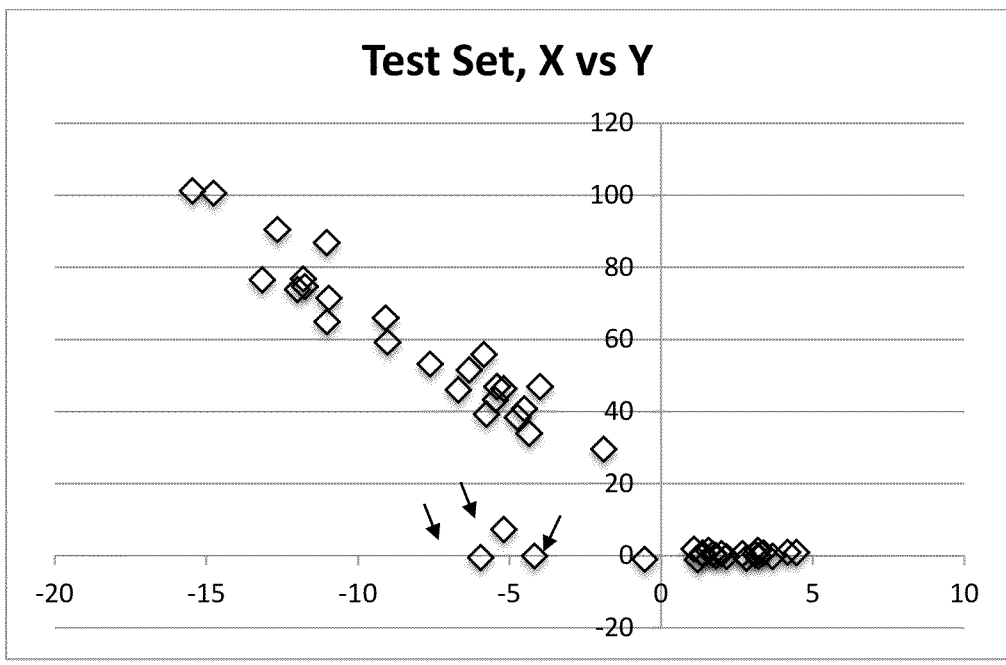

Similarly to the autosomes, when the systematically determined normalizing chromosome sequence (i.e. the group of chromosomes 4+8) was used for chromosome X, and when the systematically determined normalizing chromosome sequence (i.e. the group of chromosomes 4+6) was used for chromosome Y, all of the male and female fetuses in the test set were correctly identified. In addition, all 3 of the monosomy X samples were determined. FIG. 46B shows a plot of NCVs determined for the X chromosome (X-axis) and NCVs determined for the Y chromosome (Y axis) for each of the samples in the test set.

Figure 48:
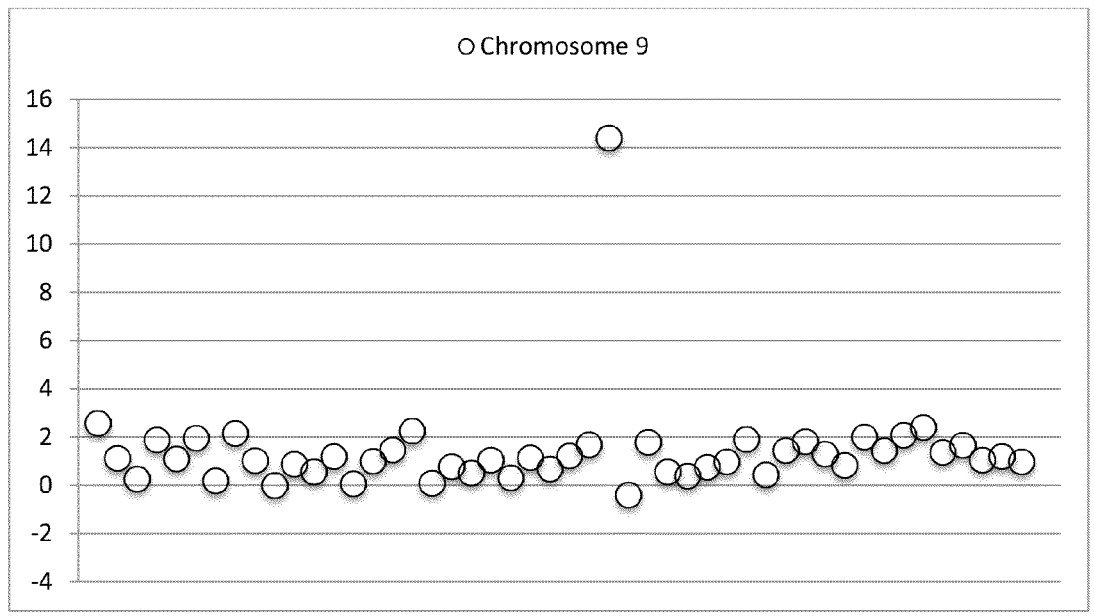
FIG. 48 shows normalized chromosome values for chromosome 9 (O) determined in samples from test set 1 using systematically determined normalizing chromosomes (as described in Example 13).

As previously described, the present method allows for determining the presence or absence of a complete, or partial, chromosomal aneuploidy of each of chromosomes 1-22, X, and Y in each sample. In addition to determining complete chromosomal aneuploidies T13, T18, T21, and monosomy X, the method determined the presence of a trisomy of chromosome 9 in one of the test samples. When using the systematically determined normalizing chromosome sequence (i.e. the group of chromosomes 3+4+8+10+17+19+20+22), for chromosome of interest 9, a sample having an NCV of 14.4 was identified (FIG. 48). This sample corresponded to the test sample in Example 12 that was suspected of being aneuploid for chromosome 9 following the calculation of an aberrantly low dose for chromosome 21 (for which chromosome 9 was used as the normalizing chromosome sequence in Example 12).

Figure 49:
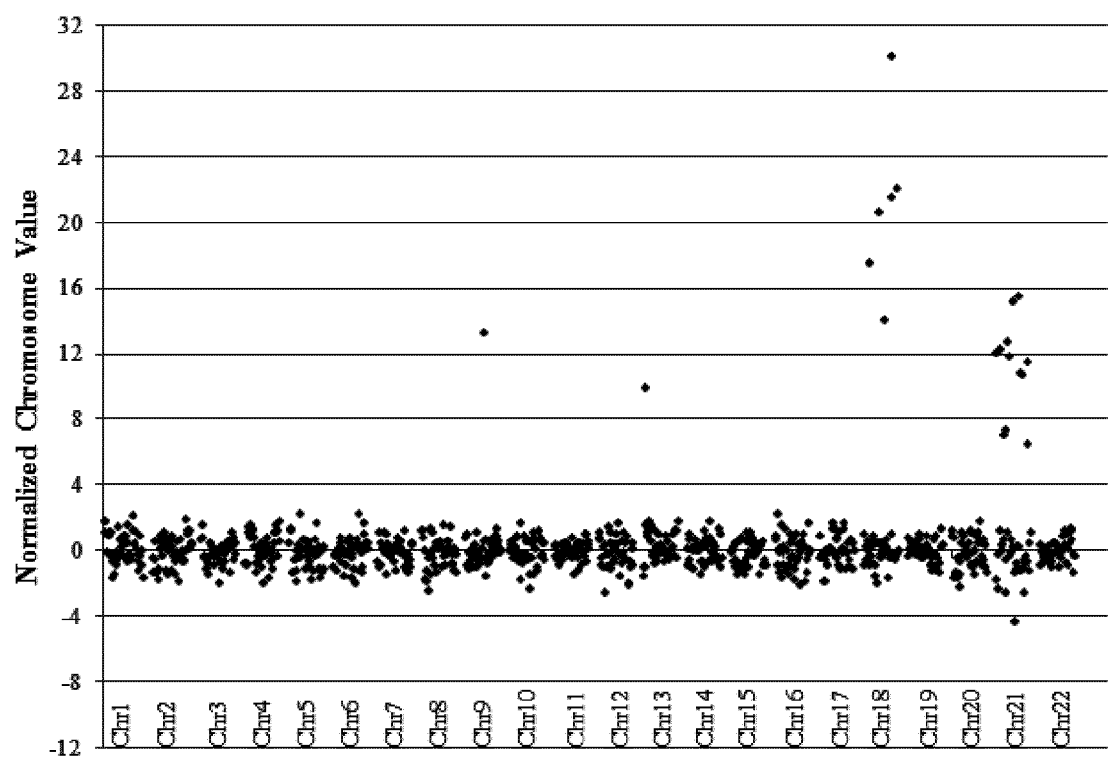
FIG. 49 shows normalized chromosome values for chromosomes 1-22 determined in samples from test set 1 using systematically determined normalizing chromosomes (as described in Example 13).

The data show that 100% of the samples having clinical karyotypes indicating T21, T13 T18, T9 and monosomy X were correctly identified. FIG. 49 shows a plot of the NCVs for each of chromosomes 1-22 in each of the 47 test samples. Medians of NCVs were normalized to zero. The data show that the method of the invention (including the use of systematically determined normalizing chromosome sequences) determined the presence of all 5 types of chromosomal aneuploidies that were present in this test set with 100% sensitivity and 100% specificity, and clearly indicate that the method can identify any complete chromosomal aneuploidy for any one of chromosomes 1-22, X, and Y, in any sample.

Example 14

Determination of the Presence or Absence of a Partial Fetal Chromosomal Aneuploidy

Determination of Cat Eye Syndrome

DiGeorge syndrome (22q11.2 deletion syndrome), a disorder caused by a defect in chromosome 22, results in the poor development of several body systems. Medical problems commonly associated with DiGeorge syndrome include heart defects, poor immune system function, a cleft palate, poor function of the parathyroid glands and behavioral disorders. The number and severity of problems associated with DiGeorge syndrome vary greatly. Almost everyone with DiGeorge syndrome needs treatment from specialists in a variety of fields.

To determine the presence or absence of a partial deletion of fetal chromosome 22, a blood sample is obtained by venipuncture for the mother, and cfDNA is prepared as described in the Examples above. The purified cfDNA is ligated to adaptors and subjected to cluster amplification using the Illumina cBot cluster station. Massively parallel sequencing is performed using reversible dye terminators to generate millions of 36 bp reads. The sequence reads are aligned to the human hg19 reference genome, and the reads that are uniquely mapped to the reference genome are counted as tags.

A set of qualified samples all known to be diploid for chromosome 22 i.e. chromosome 22 or any portion thereof is known to be present only in a diploid state, are first sequenced and analyzed to obtain a number of sequence tags for each of 1000 segments of 3 megabases (Mb) (excluding the region 22q11.2). Given that the human genome comprises approximately 3 billion bases (3 Gb), the 1000 segments of 3 Mb each approximately composes the remainder of the genome. Each of the 1000 segments can serve individually or as in a group of segment sequences that are used to determine the normalizing segment sequence for the segment of interest i.e. the 3 Mb region of 22q11.2. The number of sequence tags mapped to every single 1000 bp segment is used individually to compute segment doses for the 3 Mb region of 22q11.2. In addition, all possible combinations of two or more segments are used to determine segment doses for the segment of interest in all qualified samples. The single 3 Mb segment or the combination of two or more 3 Mb segments that result in the segment dose having the lowest variability across samples is chosen as the normalizing segment sequence.

The number of sequence tags mapped to the segment of interest in each of the qualified samples is used to determine a segment dose in each of the qualified samples. The mean and standard deviation of the segment doses in all qualified samples is calculated, and used to set threshold s to which segment doses determined in test samples can be compared. Preferably, normalized segment values (NSV) are calculated for all segments of interest in all qualified samples, and used to set the threshold values.

Subsequently, the number of tags mapped to the normalizing segment sequence in the corresponding test sample is used to determine the dose of the segment of interest in the test sample. A normalized segment value (NSV) is calculated for the segment in the test sample as described previously and the NCV of the segment of interest in the test sample is compared to the threshold determined using the qualified samples to determine the presence or absence of a deletion of 22q11.2 in the test sample.

A test NCV<−3, indicates that a loss in the segment of interest i.e. partial deletion of chromosome 22 (22q11.2) is present in the test sample.

Example 15

Stool DNA Testing for Prediction of Outcome for Stage II Colorectal Cancer Patients Around 30% of all stage II colon cancer patients will relapse and die of their disease. Stage II colon cancers of patients who had relapse of disease showed significantly more losses on chromosomes 4, 5, 15q, 17q and 18q. In particular, stage 11 colon cancer patients losses on 4q22.1-4-q35.2 have been shown to be associated with worse outcome. Determination of the presence or absence of these genomic alterations may aid in selecting patients for adjuvant therapy (Brosens et al., Analytical Cellular Pathology/Cellular Oncology 33: 95-104 [2010]).

To determine the presence or absence of one or more chromosomal deletions in the 4q22.1 to 4q35.2 region in patients with stage II colorectal cancer, stool and/or plasma samples are obtained from the patient(s). Stool DNA is prepared according to the method described by Chen et al., J Natl Cancer Inst 97:1124-1132 [2005]); and plasma DNA is prepared according to the method described in the Examples above. DNA is sequenced according to an NGS method described herein, and the sequence information for the patient (s) sample(s) is used to calculate segment doses for one or more segments spanning the 4q22.1 to 4q35.2 region. Segment doses are determined using normalizing segment sequences that are determined a priori by in a set of qualified stool and/or plasma samples, respectively. Segment doses in the test samples (patient samples) are calculated, and the presence or absence of one or more partial chromosomal deletions within the 4q22.1 to 4q35.2 region is determined by comparing the NSV for each of the segments of interest to the threshold set from the NSV in the set of qualified samples.

Example 16

Genome Wide Fetal Aneuploidy Detection by Sequencing of Maternal Plasma DNA

Diagnostic Accuracy in a Prospective, Blinded, Multicenter Study

The method for determining the presence or absence of aneuploidies in maternal test samples was used in a prospective study, and its diagnostic accuracy was shown as described below. The prospective study further demonstrates the efficacy of the method of the invention to detect fetal aneuploidy for multiple chromosomes across the genome. The blinded study emulates an actual population of pregnant women in which the fetal karyotype is unknown, and all samples with any abnormal karyotypes were selected for sequencing. Determinations of the classifications made according to the method of the invention were compared to fetal karyotypes from invasive procedures to determine the diagnostic performance of the method for multiple chromosomal aneuploidies. Summary of this Example.

Blood samples were collected in a prospective, blinded study from 2,882 women undergoing prenatal diagnostic procedures at 60 United States sites (clinicaltrials.gov NCT01122524).

An independent biostatistician selected all singleton pregnancies with any abnormal karyotype, and a balanced number of randomly selected pregnancies with euploid karyotypes. Chromosome classifications were made for each sample according the method of the invention and compared to fetal karyotype.

Within an analysis cohort of 532 samples, 89/89 trisomy 21 cases, (sensitivity 100% (95% CI 95.9-100)), 35/36 trisomy 18 cases (sensitivity 97.2%, (95% CI 85.5-99.9)), 11/14 trisomy 13 cases (sensitivity 78.6%, (95% CI 49.2-99.9)), 232/233 females (sensitivity 99.6%, (95% CI 97.6->99.9)), 184/184 males (sensitivity 100%, 95% CI 98.0-100)), and 15/16 monosomy X cases (sensitivity 93.8%, 95% CI 69.8-99.8)) were classified. There were no false positives for autosomal aneuploidies in unaffected subjects (100% specificity, (95% CI>98.5-100)). In addition, fetuses with mosaicism for trisomy 21 (3/3), trisomy 18 (1/1), and monosomy X (2/7), three cases of translocation trisomy, two cases of other autosomal trisomies (20 and 16) and other sex chromosome aneuploidies (XXX, XXY and XYY) were correctly classified.

The results further demonstrate the efficacy of the present method to detect fetal aneuploidy for multiple chromosomes across the genome using maternal plasma DNA. The high sensitivity and specificity for the detection of trisomies 21, 18, 13 and monosomy X suggest that the present method can be incorporated into existing aneuploidy screening algorithms to reduce unnecessary invasive procedures.

Materials and Methods

The MELISSA (MatErnal BLood IS Source to Accurately diagnose fetal aneuploidy) study was conducted as a prospective, multi-center observational study with blinded nested case: control analyses. Pregnant women, 18 years and older undergoing an invasive prenatal procedure to determine fetal karyotype were recruited (Clinicaltrials.gov NCT01122524). Eligibility criteria included pregnant women between 8 weeks, 0 days and 22 weeks, 0 days gestation who met at least one of the following additional criteria: age ≥38 years, positive screening test result (serum analytes and/or nuchal translucency (NT) measurement), presence of ultrasound markers associated with increased risk for fetal aneuploidy, or prior aneuploid fetus. Written informed consent was obtained from all women who agreed to participate.

Enrollment occurred at 60 geographically dispersed medical centers in 25 states per protocol approved by institutional review boards (IRB) at each institution. Two clinical research organizations (CROs) (Quintiles, Durham, N.C. and Emphusion, San Francisco, Calif.) were retained to maintain study blinding and provide clinical data management, data monitoring, biostatistics, and data analysis services.

Before any invasive procedure, a peripheral venous blood sample (17 mL) was collected in two acid citrate dextrose (ACD) tubes (Becton Dickinson) that were de-identified and labeled with a unique study number. Site research personnel entered study number, date, and time of blood draw into a secure electronic case report form (eCRF). Whole blood samples were shipped overnight in temperature-controlled containers from sites to the laboratory (Verinata Health, Inc., CA). Upon receipt and sample inspection, cell-free plasma was prepared per previously described methods (see Example 13) and stored frozen at −80° C. in 2 to 4 aliquots until time of sequencing. Date and time of sample receipt at the laboratory were recorded. A sample was determined to be eligible for analysis if it was received overnight, was cool to touch, and contained at least 7 mL blood. Samples that were eligible at receipt were reported to the CRO weekly and used for selection on a random sampling list (see below and FIG. 50). Clinical data from the woman's current pregnancy and fetal karyotype were entered into the eCRF by site research personnel and verified by CRO monitors through source document review.

Sample size determination was based on the precision of the estimates for a targeted range of performance characteristics (sensitivity and specificity) for the index test. Specifically, the number of affected (T21, T18, T13, male, female, or monosomy X) cases and unaffected (non-T21, non-T18, non-T13, not male, not female, or not monosomy X) controls were determined to estimate the sensitivity and specificity, respectively, to within a pre-specified small margin of error based on the normal approximation ($N=(1.96\sqrt{p(1-p)}/\text{margin of error})^2$, where p=the estimate of the sensitivity or specificity). Assuming a true sensitivity of 95% or greater, a sample size between 73 to 114 cases ensured that the precision of the estimate of sensitivity would be such that the lower bound of the 95% confidence interval (CI) would be 90% or greater (margin of error ≤5%). For smaller sample sizes, a larger estimated margin of error of the 95% CI for sensitivity was projected (from 6% to 13.5%). To estimate the specificity with greater precision a larger number of unaffected controls (~4:1 ratio to cases) were planned at the sampling stage. This ensured the precision of the estimate of specificity to at least 3%. Accordingly, as the sensitivity and/or specificity increased, the precision of the confidence interval would also increase.

Figure 50A:
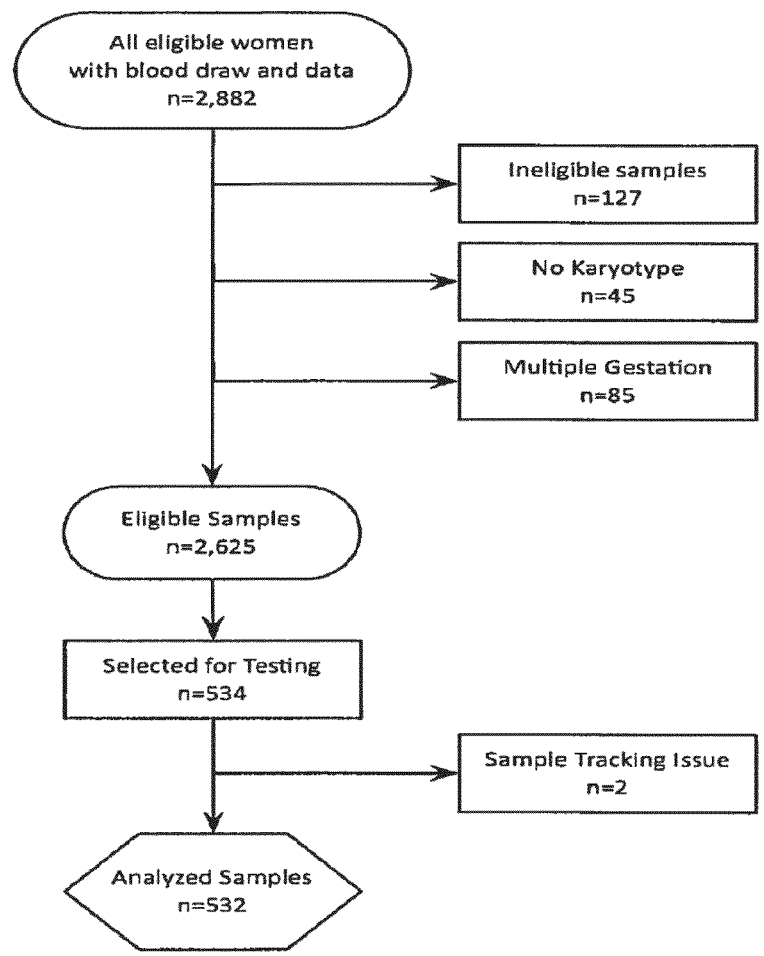
FIG. 50 shows a flow diagram of the design (A) and random sampling plan (B) for the study described in Example 16.

Based on sample size determination, a random sampling plan was devised for the CRO to generate lists of selected samples to sequence (minimum of 110 cases affected by T21, T18, or T13 and 400 non-affected for trisomy, allowing up to half of these to have karyotypes other than 46,XX or 46,XY). Subjects with a singleton pregnancy and an eligible blood sample were eligible for selection. Subjects with ineligible samples, no karyotype recorded, or a multiple gestation were excluded (FIG. 50). Lists were generated on a regular basis throughout the study and sent to the Verinata Health laboratory.

Each eligible blood sample was analyzed for six independent categories. The categories were aneuploidy status for chromosomes 21, 18 and 13, and gender status for male, female and monosomy X. While still blinded, one of three classifications (affected, unaffected, or unclassified) were generated prospectively for each of the six independent categories for each plasma DNA sample. Using this scenario, the same sample could be classified as affected in one analysis (e.g., aneuploidy for chromosome 21) and unaffected for another analysis (e.g., euploid for chromosome 18).

Conventional metaphase cytogenetic analysis of cells obtained by chorionic villus sampling (CVS) or amniocentesis was used as the reference standard in this study. Fetal karyotyping was performed in diagnostic laboratories routinely used by the participating sites. If after enrollment a patient underwent both CVS and amniocentesis, karyotype results from amniocentesis were used for study analysis. Fluorescence in situ hybridization (FISH) results for targeting chromosomes 21, 18, 13, X, and Y was allowed if a metaphase karyotype was not available (Table 24). All abnormal karyotype reports (i.e. other than 46, XX and 46, XY) were reviewed by a board-certified cytogeneticist and classified as affected or unaffected with respect to chromosomes 21, 18, and 13 and gender status for XX, XY and monosomy X.

Pre-specified protocol conventions defined the following abnormal karyotypes to be assigned a status of 'censored' for karyotype by the cytogeneticist: triploidy, tetraploidy, complex karyotypes other than trisomy (e.g., mosaicism) that involved chromosomes 21, 18, or 13, mosaics with mixed sex chromosomes, sex chromosome aneuploidy or karyotypes that could not be fully interpreted by the source document (e.g. marker chromosomes of unknown origin). Since the cytogenetic diagnosis was not known to the sequencing laboratory, all cytogenetically censored samples were independently analyzed and assigned a classification determined using sequencing information according to the method of the invention (Sequencing Classification), but were not included in the statistical analysis. Censored status pertained only to the relevant one or more of the six analyses (e.g., a mosaic T18 would be censored from chromosome 18 analysis, but considered 'unaffected' for other analyses, such as chromosomes 21, 13, X, and Y) (Table 25). Other abnormal and rare complex karyotypes, which could not be fully anticipated at the time of protocol design, were not censored from analysis (Table 26).

The data contained in the eCRF and clinical database were restricted to authorized users only (at the study sites, CROs, and contract clinical personnel). It was not accessible to any employees at Verinata Health until the time of unblinding.

After receiving random sample lists from the CRO, total cell-free DNA (a mixture of maternal and fetal) was extracted from thawed selected plasma samples as described in Example 13. Sequencing libraries were prepared utilizing the Illumina TruSeq kit v2.5. Sequencing was carried out (6-plex—i.e. 6 samples/lane) was performed on an Illumina HiSeq 2000 instrument in the Verinata Health laboratory. Single-end reads of 36 base pairs were obtained. The reads were mapped across the genome, and the sequence tags on each chromosome of interest were counted and used to classify the sample for independent categories as described above.

The clinical protocol required evidence of fetal DNA presence in order to report a classification result. A classification of male or aneuploid was considered sufficient evidence of fetal DNA. In addition, each sample was also tested for the presence of fetal DNA using two allele specific methods. In the first method, the AmpflSTR Minifiler kit (Life Technologies, San Diego, Calif.) was used to interrogate the presence of a fetal component in the cell free DNA. Electrophoresis of short tandem repeat (STR) amplicons was carried out on the ABI 3130 Genetic Analyzer following manufacturer's protocols. All nine STR loci in this kit were analyzed by comparing the intensity of each peak reported as a percentage of the sum of the intensities of all peaks, and the presence of minor peaks was used to provide evidence of fetal DNA. In cases in which no minor STR could be identified, an aliquot of the sample was examined with a single nucleotide polymorphism (SNP) panel of 15 SNPs with average heterozygosity ≥0.4 selected from the Kidd et al. panel (Kidd et al., Forensic Sci Int 164(1):20-32 [2006]). Allele specific methods that can be used to detect and/or quantify fetal DNA in maternal samples are described in U.S. Patent Publications 20120010085, 20110224087, and 20110201507, which are herein incorporated by reference.

Normalized chromosome values (NCVs) were determined by calculating all possible permutations of denominators for all autosomes and sex chromosomes as described in Example 13, however, because the sequencing is this study was carried out on a different instrument than our previous work with multiple samples/lane, new normalizing chromosome denominators had to be determined. The normalizing chromosome denominators in the current study were determined based on a training set of 110 independent (i.e. not from MELISSA eligible samples) unaffected samples (i.e. qualified samples) sequenced prior to analysis of the study samples. The new normalizing chromosomes denominators were determined by calculating all possible permutations of denominators for all autosomes and sex chromosomes that minimized the variation for the unaffected training set for all chromosomes across the genome (Table 23).

The NCV rules that were applied to provide the autosome classification of each test sample were those described in Example 12, i.e. for classification of aneuploidies of autosomes, a NCV>4.0 was required to classify the chromosome as affected (i.e. aneuploid for that chromosome) and a NCV<2.5 to classify a chromosome as unaffected. Samples with autosomes that have an NCV between 2.5 and 4.0 were named "unclassified".

Sex chromosome classification in the present test was performed by sequential application of NCVs for both X and Y as follows:

1. If NCV X<−4.0 AND NCV Y<2.5, then the sample was classified as monosomy X.
2. If NCV X>−2.5 AND NCV X<2.5 AND NCV Y<2.5, then the sample was classified as female (XX).
3. If NCV X>4.0 AND NCV Y<2.5, then the sample was classified as XXX.
4. If NCV X>−2.5 AND NCV X<2.5 AND NCV Y>33, then the sample was classified as XXY.
5. If NCV X<−4.0 AND NCV Y>4.0, then the sample was classified as male (XY).
6. If condition 5 was met, but NCV Y was approximately 2 times greater than expected for the measured NCV X value, then the sample was classified as XYY.
7. If the chromosome X and Y NCVs did not fit into any of the above criteria, then the sample was classified as unclassified for sex.

Because the laboratory was blinded to the clinical information, the sequencing results were not adjusted for any of the following demographic variables: maternal body mass index, smoking status, presence of diabetes, types of conception (spontaneous or assisted), prior pregnancies, prior aneuploidy, or gestational age. Neither maternal nor paternal samples were utilized for classification, and the classifications according to the present method did not depend on the measurement of specific loci or alleles.

The sequencing results were returned to an independent contract biostatistician prior to unblinding and analysis. Personnel at the study sites, CROs (including the biostatistician generating random sampling lists) and the contract cytogeneticist were blinded to sequencing results.

TABLE 23

Systematically Determined Normalizing Chromosome Sequences for All Chromosomes

| Chromosome of Interest | Systematically Determined Normalizing Sequence |
|---|---|
| 1 | 6 + 10 + 14 + 15 + 17 + 22 |
| 2 | 1 + 3 + 4 + 6 + 8 + 9 + 10 |
| 3 | +5 + 6 + 10 + 12 |
| 4 | 5 |
| 5 | 3 + 4 + 8 + 12 |
| 6 | 2 + 3 + 4 + 14 |
| 7 | 3 + 4 + 6 + 8 + 14 + 16 + 19 |
| 8 | 5 + 6 + 10 |
| 9 | 1 + 2 + 5 + 7 + 8 + 11 + 14 + 15 + 16 + 17 + 22 |
| 10 | 2 + 9 + 15 + 16 + 20 |
| 11 | 2 + 8 + 9 + 14 + 16 + 19 + 20 |
| 12 | 1 + 3 + 5 + 6 + 8 + 15 + 19 |
| 13 | 4 + 6 |
| 14 | 1 + 3 + 4 + 5 + 9 + 11 + 15 + 17 |

TABLE 23-continued

Systematically Determined Normalizing Chromosome Sequences for All Chromosomes

| Chromosome of Interest | Systematically Determined Normalizing Sequence |
|---|---|
| 15 | 1 + 10 + 20 |
| 16 | 20 |
| 17 | 15 + 19 + 22 |
| 18 | 5 + 8 |
| 19 | 22 |
| 20 | 15 + 16 + 17 + 22 |
| 21 | 4 + 17 + 22 |
| 22 | 19 |
| X | 4 + 5 + 8 |
| Y | 4 |

Statistical methods were documented in a detailed statistical analysis plan for the study. Point estimates for sensitivity and specificity along with exact 95% confidence intervals using the Clopper-Pearson method were computed for each of the six analysis categories. For all statistical estimation procedures performed, samples with no fetal DNA detected, 'censored' for complex karyotype (per protocol-defined conventions), or 'unclassified' by the sequencing test were removed.

Results

Between June 2010 and August 2011, 2,882 pregnant women were enrolled in the study. The characteristics of the eligible subjects and the selected cohort are given in Table 24. Subjects that enrolled and provided blood, but were later found during data monitoring to exceed inclusion criteria and have an actual gestational age at enrollment beyond 22 weeks, 0 days were allowed to remain in the study (n=22) Three of these samples were in the selected set. FIG. 50 shows the flow of samples between enrollment and analysis. There were 2,625 samples eligible for selection.

TABLE 24

Patient Demographics

|  | Eligible Patients (n = 2882) | Analyzed Patients (n = 534) | Affected Patients (n = 221) |
|---|---|---|---|
| Maternal Age, yrs |  |  |  |
| Mean (SD) | 35.8 (5.93) | 35.2 (6.40) | 34.4 (6.73) |
| Min/Max | 18/49 | 18/46 | 18/46 |
| Multiparous, N (%) | 2348 (81.5) | 425 (79.5) | 176 (79.6) |
| Pregnancy by Assisted Reproductive Techniques, N (%) | 247 (8.6) | 38 (7.1) | 17 (7.7) |
| Race, N (%) |  |  |  |
| White | 2078 (72.1) | 388 (72.7) | 161 (72.9) |
| African American | 338 (11.7) | 58 (10.9) | 28 (12.7) |
| Asian | 271 (9.4) | 53 (9.9) | 18 (8.1) |
| American Indian or Alaska Native | 22 (0.8) | 5 (0.9) | 2 (0.9) |
| Multi-racial | 173 (6.0) | 30 (5.6) | 12 (5.4) |
| BMI (kg/m$^2$) |  |  |  |
| Mean (SD) | 26.6 (5.89) | 26.2 (5.73) | 26.2 (5.64) |
| Min/Max | 15/76 | 17/59 | 18/56 |
| Current Smoker, N (%) | 165 (5.7) | 29 (5.4) | 6 (2.7) |
| Maternal Diabetes Mellitus, N (%) | 61 (2.1) | 11 (2.1) | 6 (2.7) |
| Trimester |  |  |  |
| First | 832 (28.9) | 165 (30.9) | 126 (57.0) |
| Second | 2050 (71.1) | 369 (69.1) | 95 (43.0) |
| Gestational Age (GA)*, wks, days |  |  |  |
| Mean | 15.5 (3.27) | 15.1 (3.16) | 14.8 (3.18) |
| Min/Max | 8/31 | 10/23 | 10/23 |
| Karyotype Source, N (%) |  |  |  |
| CVS | 1044 (36.8) | 228 (42.7) | 121 (54.8) |
| Amniocentesis | 1783 (62.8) | 301 (56.4) | 95 (43.0) |
| Products of Conception | 10 (0.4) | 5 (0.9) | 5 (2.2) |
| Amniocentesis after CVS, N (%) | 7 (0.2) | 1 (0.2) | 0 (0.0) |
| Karyotype by FISH-only, N (%) | 105 (3.6) | 18 (3.4) | 13 (5.9) |
| Number of Fetuses |  |  |  |
| 1 | 2797 (97.1) | 534 (100.0) | 221 (100.0) |
| 2 | 76 (2.6) | 0 (0.0) | 0 (0.0) |
| 3 | 7 (0.2) | 0 (0.0) | 0 (0.0) |
| 4 | 2 (0.2) | 0 (0.0) | 0 (0.0) |
| Prenatal Risk, N (%) |  |  |  |
| AMA only (≥38 years) | 1061 (36.8) | 152 (28.5) | 21 (9.5) |
| Positive screen risk | 622 (21.6) | 91 (17.0) | 14 (6.3) |

TABLE 24-continued

Patient Demographics

|  | Eligible Patients (n = 2882) | Analyzed Patients (n = 534) | Affected Patients (n = 221) |
|---|---|---|---|
| Ultrasound abnormality | 477 (6.6) | 122 (22.8) | 81 (36.7)** |
| Prior aneuploidy pregnancy | 82 (2.8) | 15 (2.8) | 4 (1.8) |
| More than 1 risk | 640 (22.2) | 154 (28.9) | 101 (45.7)** |
| Screening Risk Estimated By, N (%) | 1749 | 310 | 125 |
| Nuchal Translucency measure alone | 179 (10.2) | 53 (17.1) | 36 (28.8) |
| First Trimester Combined | 677 (38.7) | 117 (37.7) | 47 (37.6) |
| Second Trimester Triple or Quadruple | 414 (23.7) | 72 (23.3) | 16 (12.8) |
| Fully Integrated ($1^{st}$ and $2^{nd}$ Trimester) | 137 (7.8) | 14 (4.5) | 3 (2.4) |
| Sequential | 218 (12.5) | 32 (10.3) | 15 (12.0) |
| Other | 124 (7.1) | 22 (7.1) | 8 (6.4) |
| Abnormal Fetal Ultrasound, N (%) |  |  |  |
| One or more Soft Marker | 837 (29.0) | 242 (45.3) | 166 (75.1)** |
| One or more Major Marker | 719 (24.9) | 212 (39.7) | 143 (64.7) |
| IUGR (<$10^{th}$ percentile) | 228 (7.9) | 79 (15.8) | 65 (29.4) |
| Amniotic Fluid Volume | 26 (0.9) | 11 (2.1) | 11 (5.0) |
| Abnormality | 24 (0.8) | 7 (1.3) | 4 (1.8) |

Figure 50B:
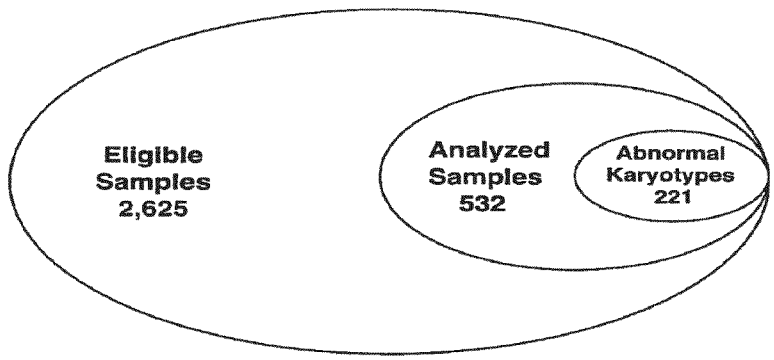

*GA at time of invasive procedure.
**Higher penetrance of ultrasound abnormalities in fetuses with abnormal karyotypes
Abbreviations:
BMI—Body Mass Index,
IUGR—Intrauterine growth retardation Per the random sampling plan, all eligible subjects with an abnormal karyotype were selected for analysis (FIG. 50B) as well as a set of subjects carrying euploid fetuses so that the total sequenced study population resulted in an approximately 4:1 ratio of unaffected to affected subjects for trisomies 21. From this process, 534 subjects were selected. Two samples were subsequently removed from analysis due to sample tracking issues in which a full chain of custody between sample tube and data acquisition did not pass quality audit (FIG. 50). This resulted in 532 subjects for analysis contributed by 53 of the 60 study sites. The demographics of the selected cohort were similar to the overall cohort.

Test Performance

Figure 51A:
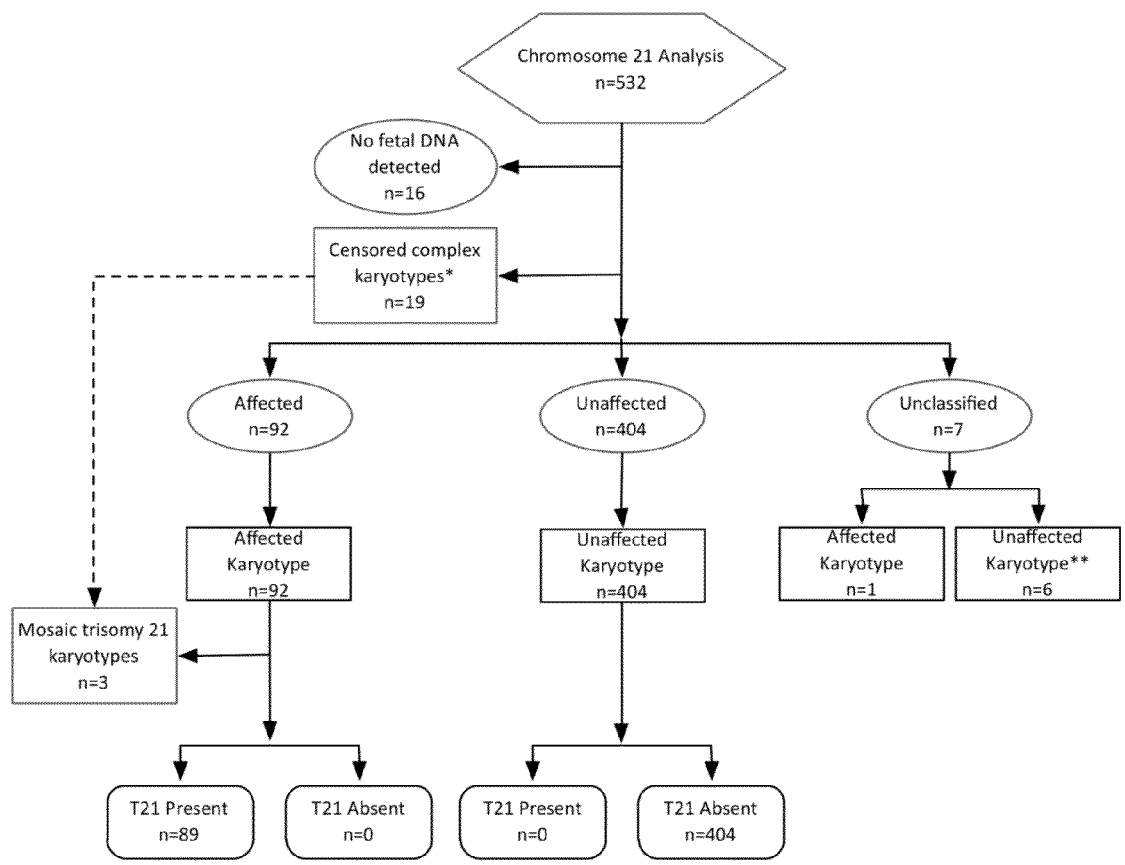
FIGS. 51A-51F show flow diagrams for the analyses for chromosomes 21, 18, and 13 (FIGS. 51A-51C, respectively), and gender analyses for female, male, and monosomy X (FIGS. 51D-51F, respectively). Ovals contain results obtained from sequencing information from the laboratory, rectangles contain karyotype results, and rectangles with rounded corners show comparative results used to determine test performance (sensitivity and specificity). The dashed lines in FIGS. 51A and 51B denote the relationship between mosaic samples for T21 (n=3) and T18 (n=1) that were censored from the analysis of chromosome 21 and 18, respectively, but were correctly determined as described in Example 16.
Figure 51B:
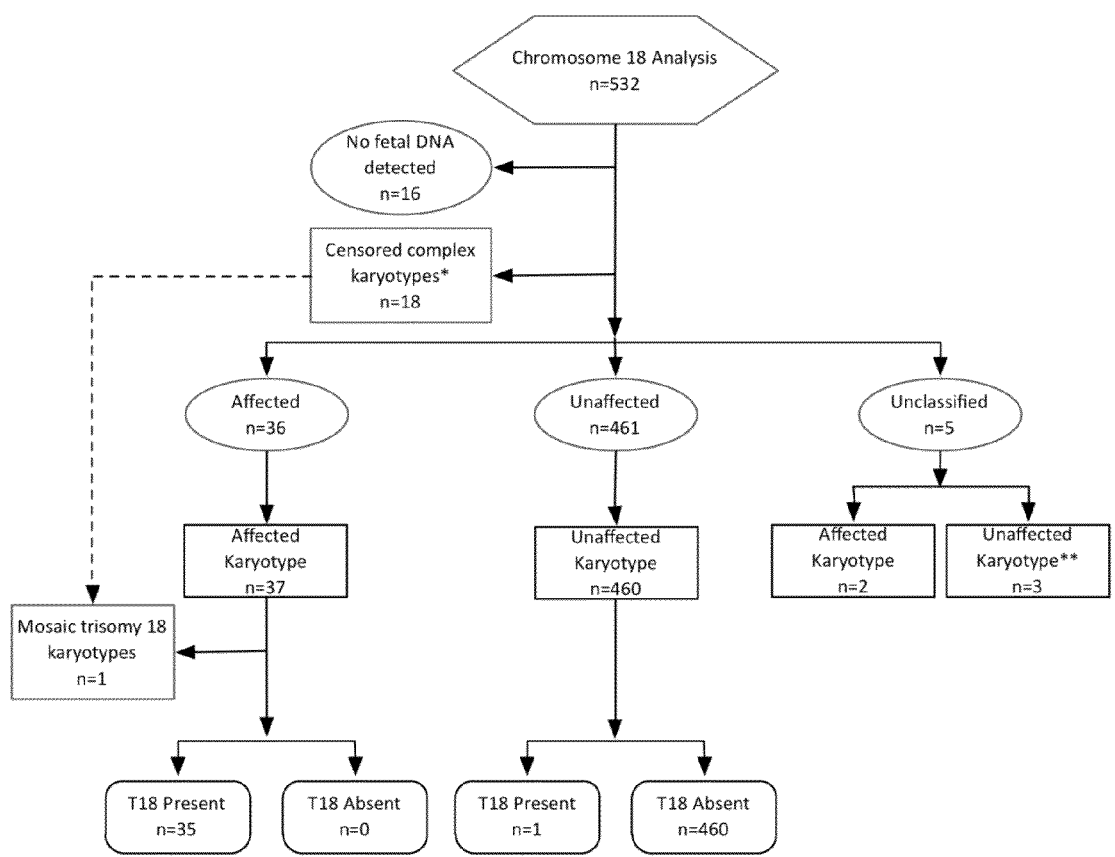
Figure 51C:
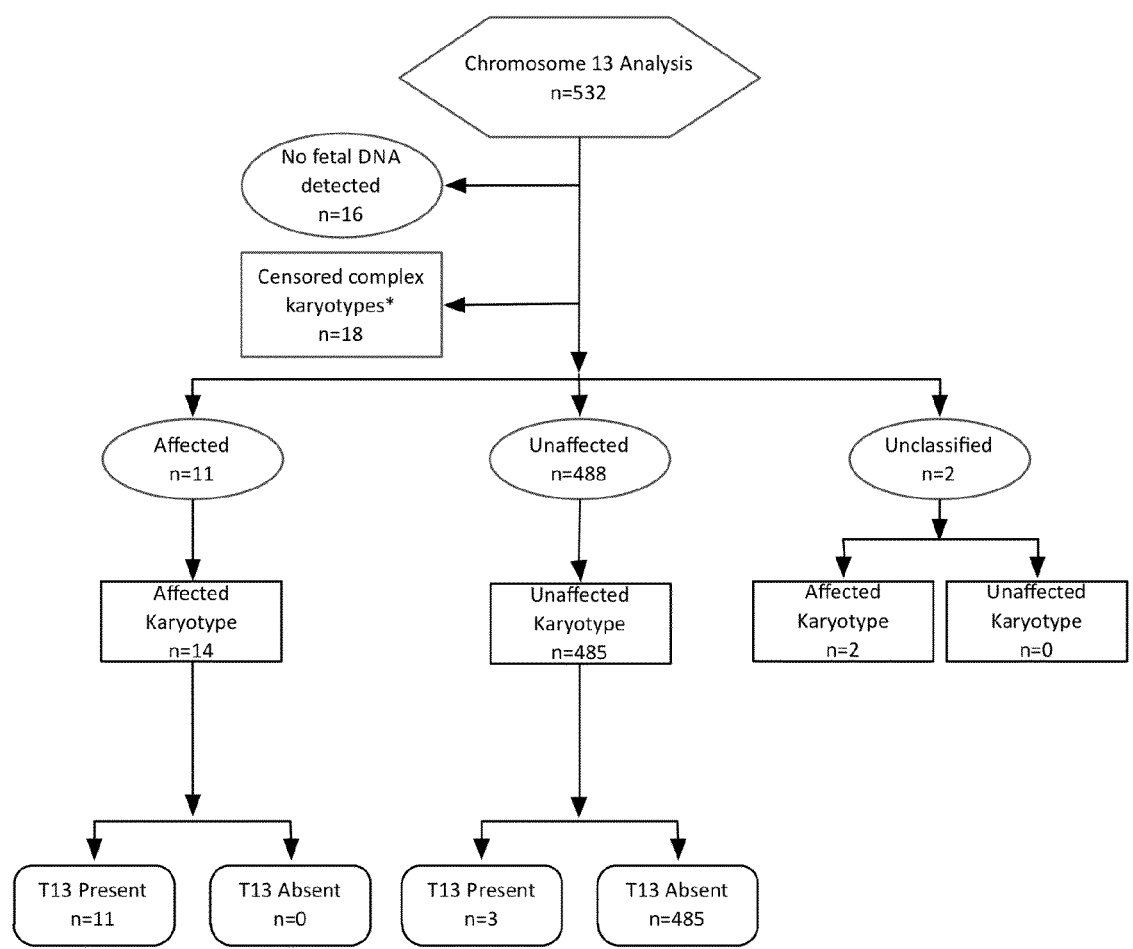
Figure 51D:
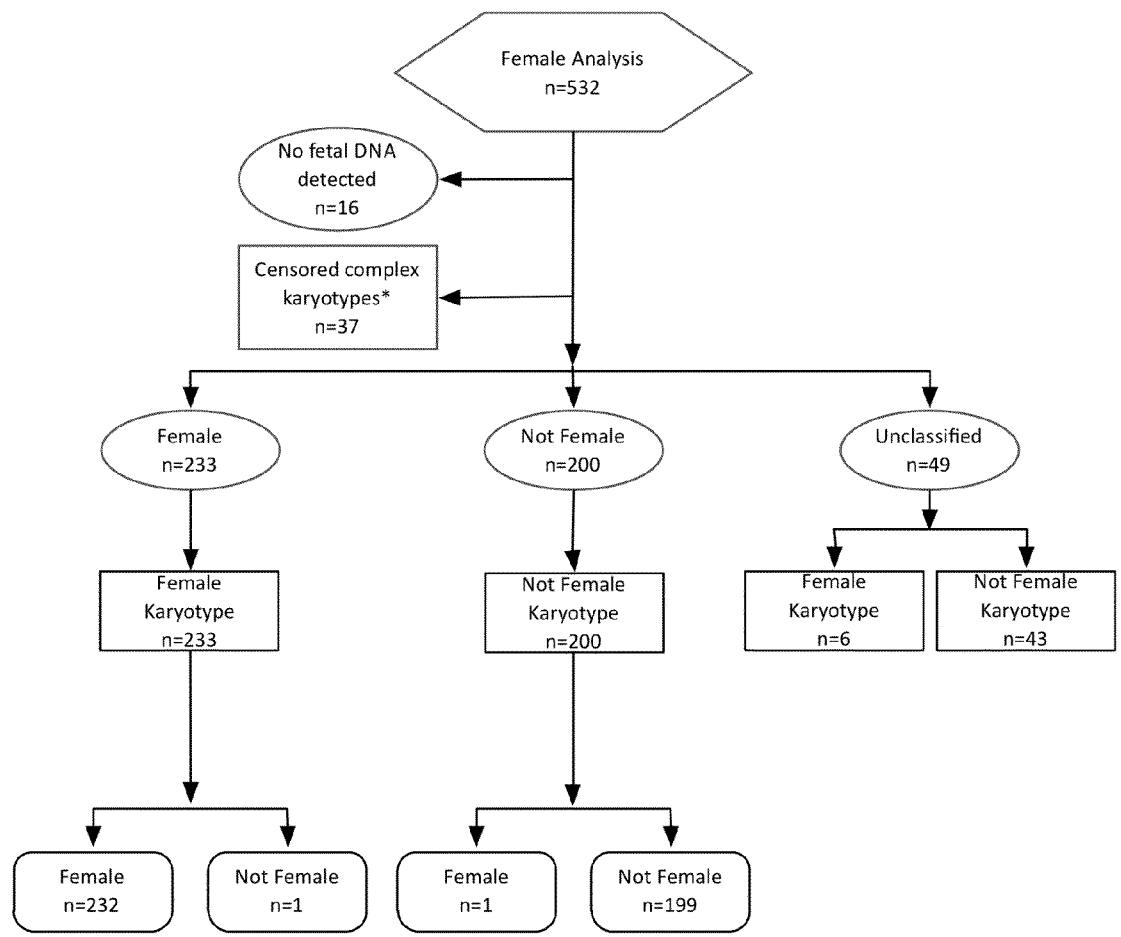
Figure 51E:
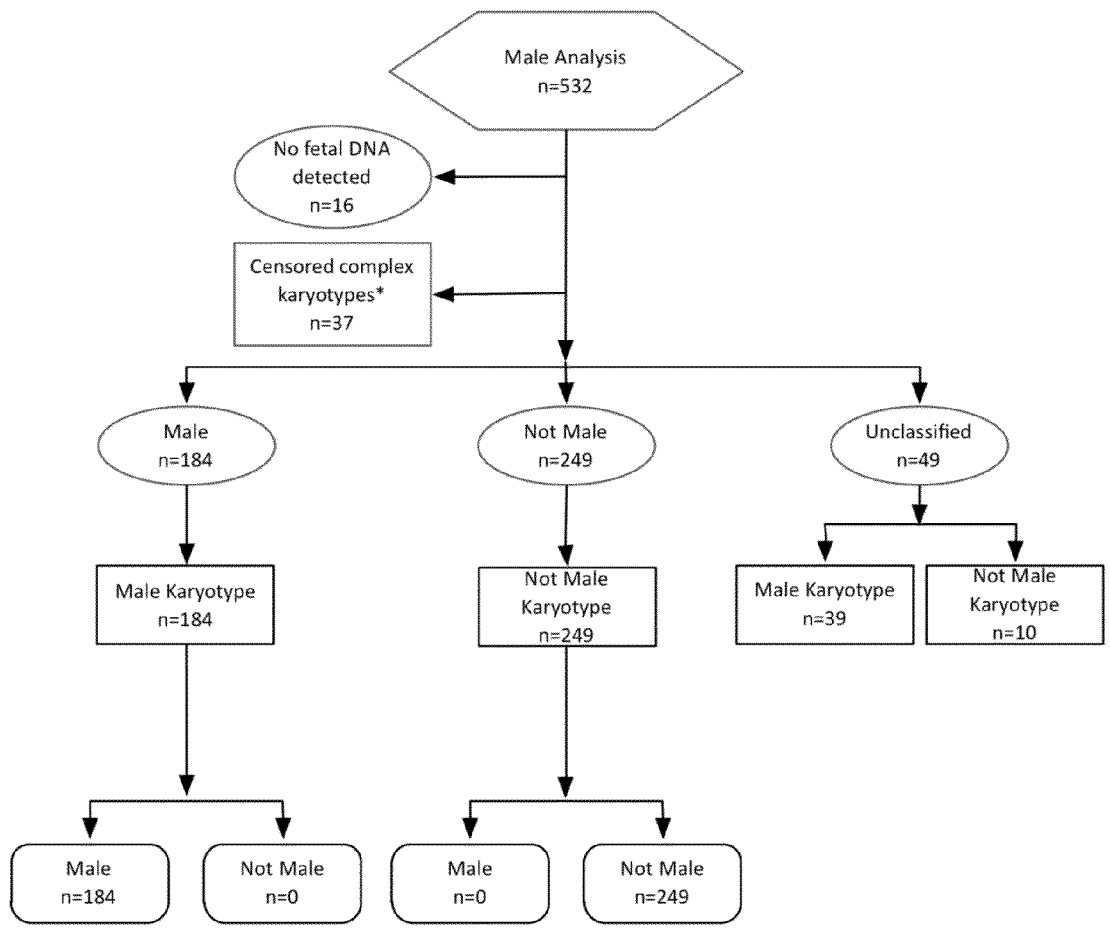
Figure 51F:
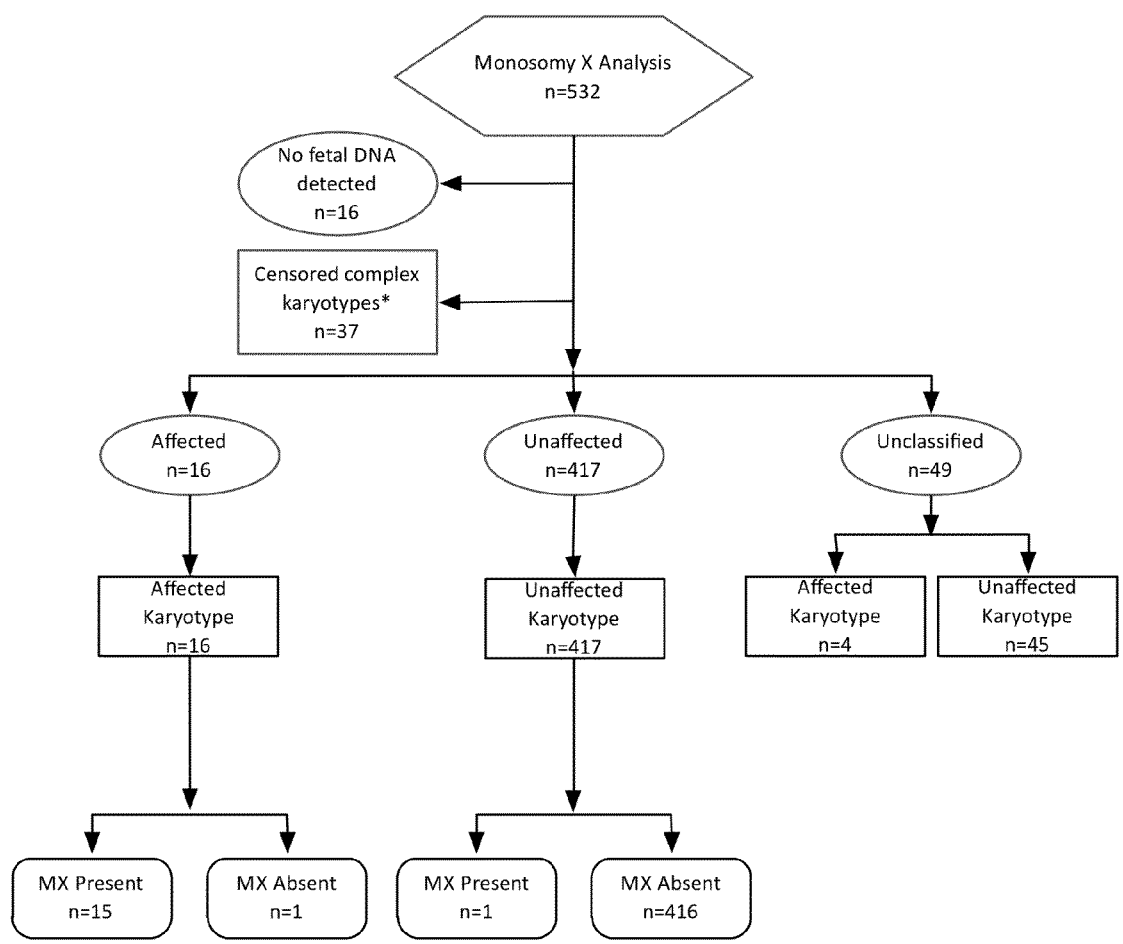
Figure 52:
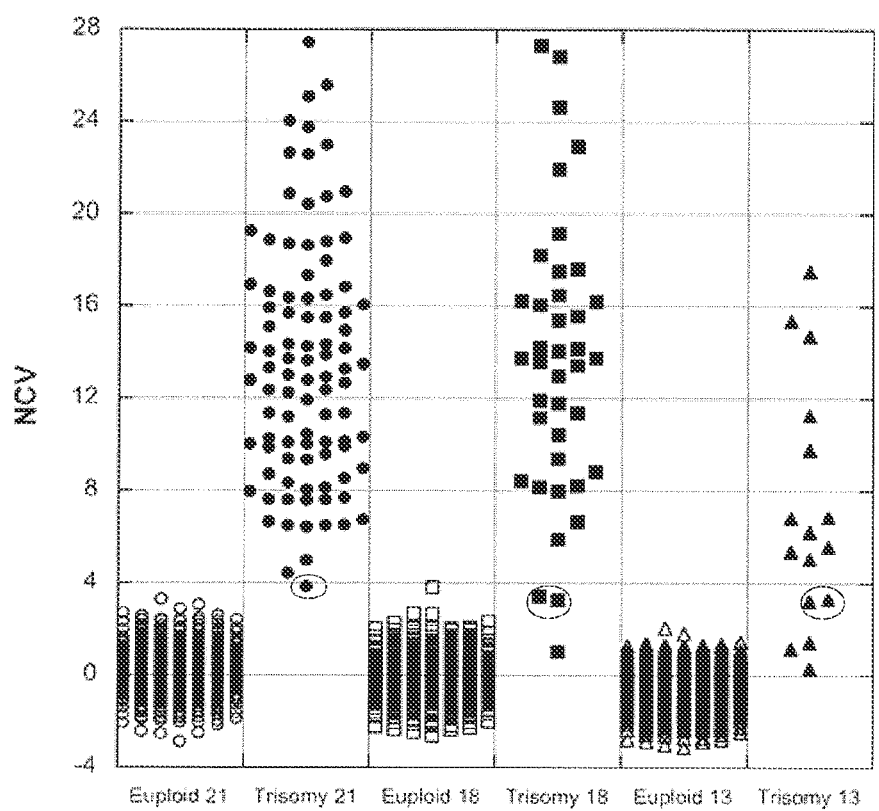
FIG. 52 shows normalized chromosome values (NCV) versus karyotype classifications for chromosomes 21 (●), 18 (■), and 13 (▲) for the test samples of the study described in Example 16. Circled samples denote unclassified samples with trisomy karyotype.
Figure 53:
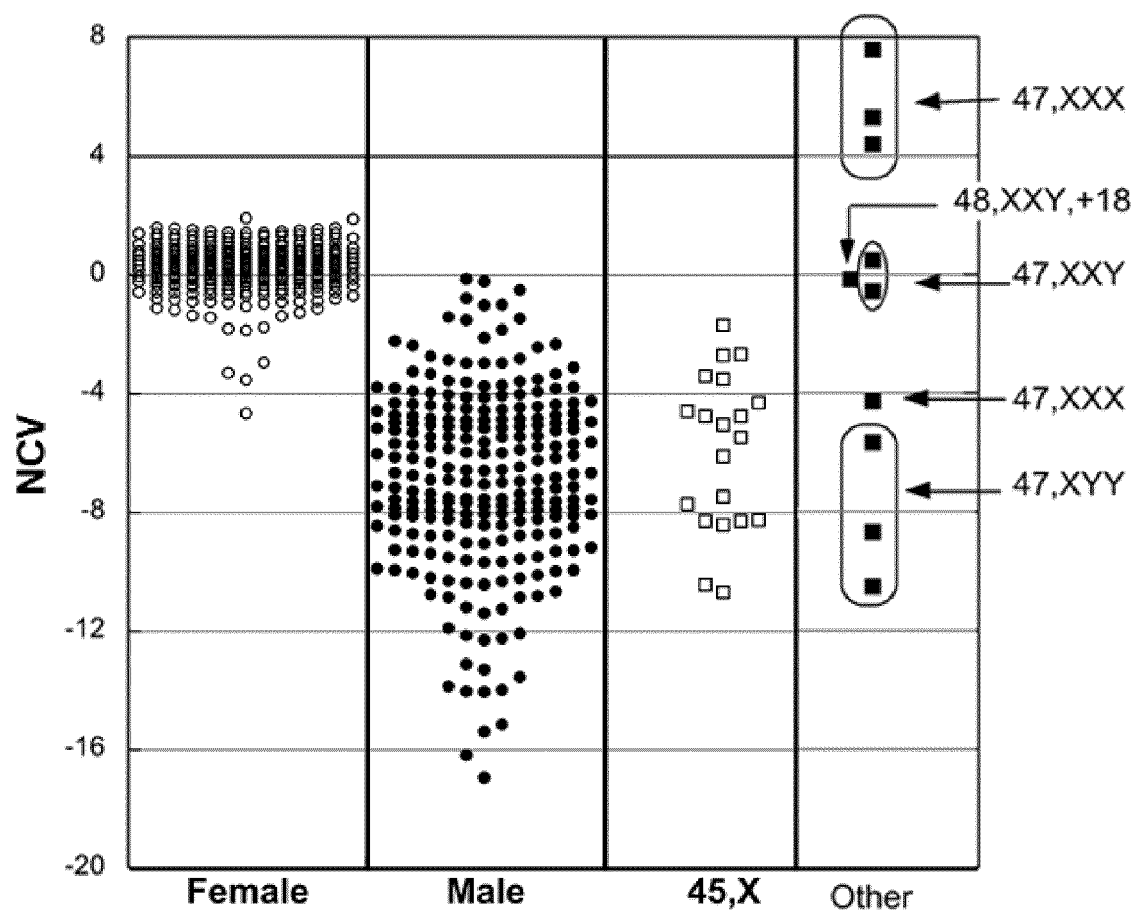
FIG. 53 shows normalized chromosome values for chromosome X (NCV) versus karyotype classifications for gender classifications of the test samples of the study described in Example 16. Samples with female karyotypes (○), samples with male karyotypes (●), samples with 45,X (□), and samples with other karyotypes i.e. XXX, XXY, and XYY (■) are shown.
Figure 54:
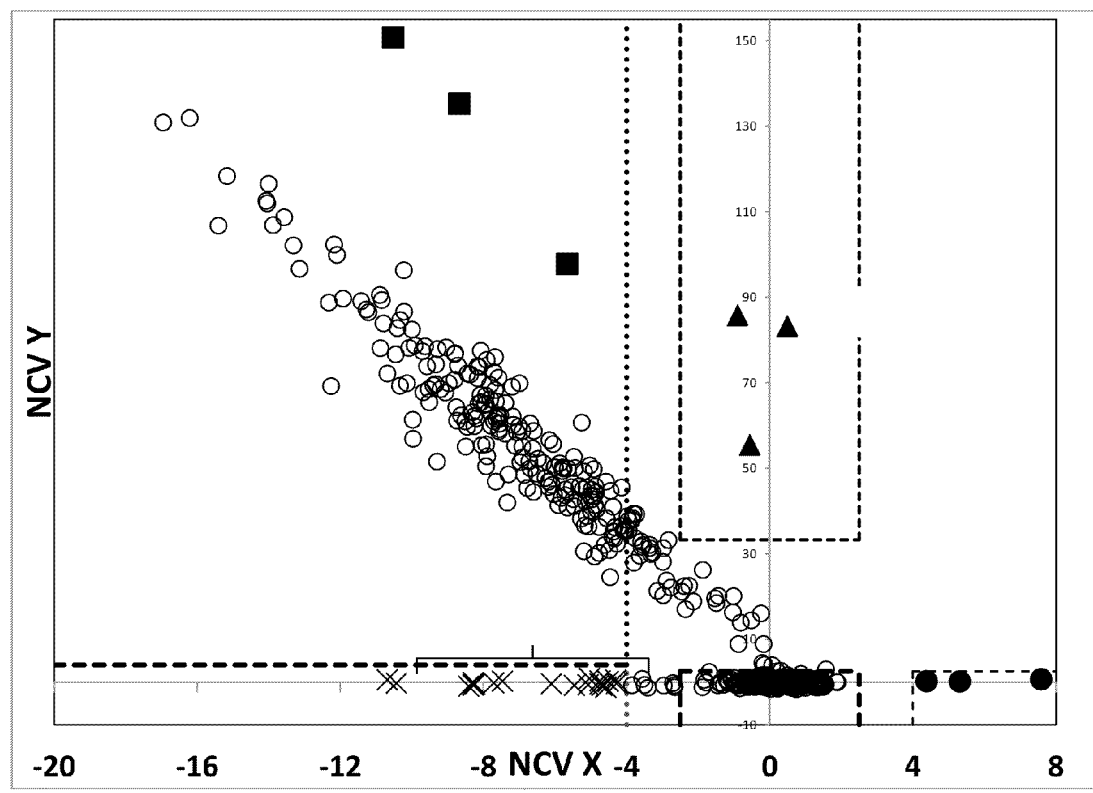
FIG. 54 shows a plot of normalized chromosome values for chromosome Y versus normalized chromosome values for chromosome X for the test samples of the clinical study described in Example 16. Euploid male and female samples (○), XXX samples (●), 45,X samples (X), XYY samples (■), and XXY samples (▲) are shown. The dashed lines show the threshold values used for classifying samples as described in Example 16.
Figure 55:
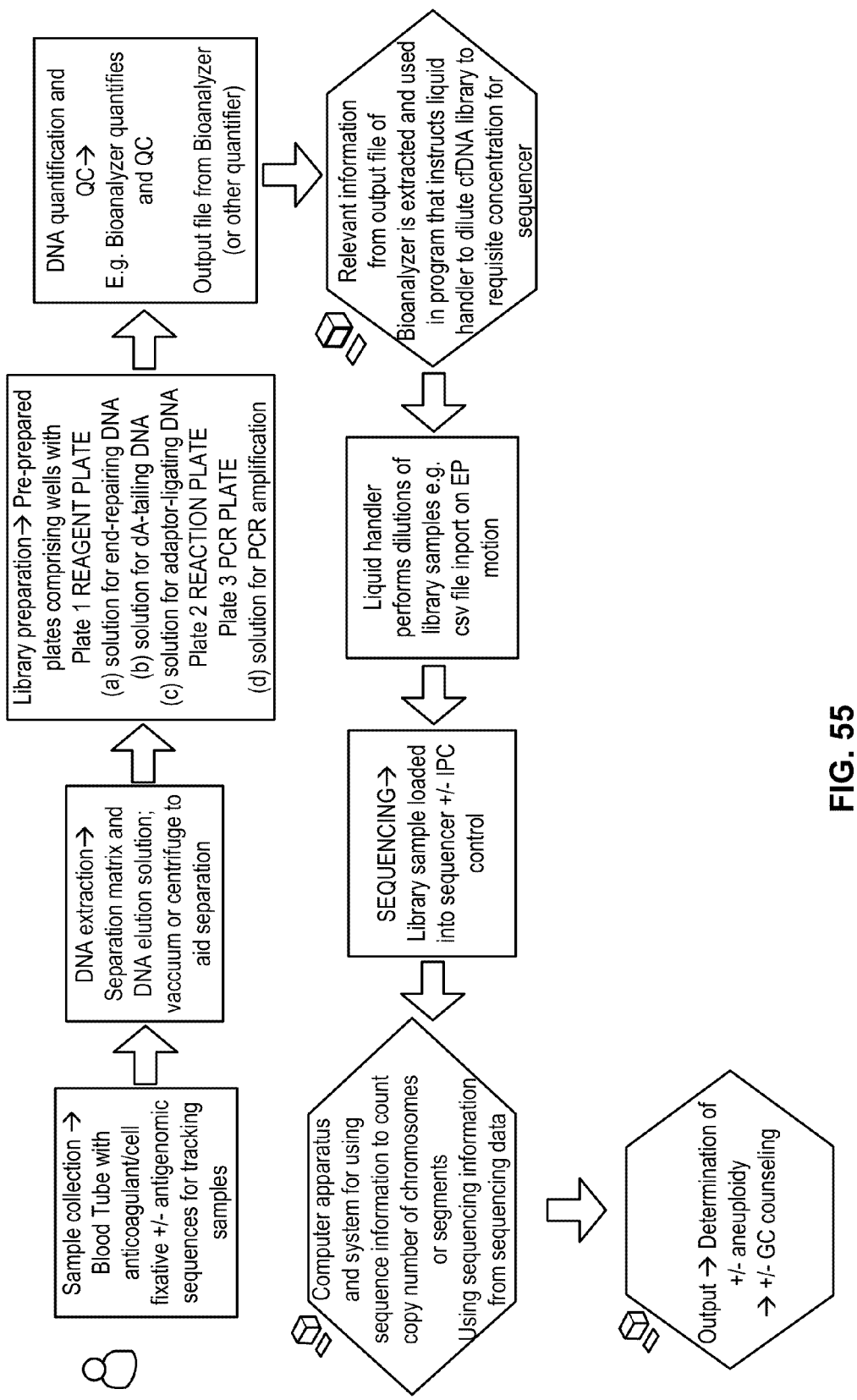
FIG. 55 schematically illustrates one embodiment of a CNV determination method described herein.

FIGS. 51A-51C show the flow diagram for aneuploidy analysis of chromosomes 21, 18 and 13 and FIGS. 51D-51F show gender analysis flow. Table 27 shows the sensitivity, specificity and confidence interval for each of the six analyses, and FIGS. 52, 53, and 54, show the graphical distribution of samples according to the NCVs following sequencing. In all 6 categories of analysis, 16 samples (3.0%) were removed due to no fetal DNA detected. After unblinding, there were no distinguishing clinical features for these samples. The number of censored karyotypes for each category was dependent on the condition being analyzed (fully detailed in FIG. 52).

Sensitivity and specificity of the method to detect T21 in the analysis population (n=493) were 100% (95% CI=95.9, 100.0) and 100% (95% CI=99.1, 100.0), respectively (Table 27 and FIG. 51A). This included correct classification for one complex T21 karyotype, 47, XX, inv(7)(p22q32), +21, and two translocation T21 arising from Robertsonian translocations one of which was also mosaic for monosomy X (45, X, +21,der(14; 21)q10;q10)[4]/46, XY, +21,der(14; 21)q10; q10)[17] and 46, XY, +21,der(21; 21)q10; q10).

Sensitivity and specificity to detect T18 in the analysis population (n=496) were 97.2% (85.5, 99.9) and 100% (99.2, 100.0) (Table 27 and FIG. 51B). Although censored (as per protocol) from the primary analysis, four samples with mosaic karyotype for T21 and T18 were all correctly classified by the method of the invention as 'affected' for aneuploidy (Table 25). Because they were correctly detected they are indicated on the left side of FIGS. 51A and 51B. All remaining censored samples were correctly classified as unaffected for trisomies 21, 18, and 13 (Table 25). Sensitivity and specificity to detect T13 in the analysis population were 78.6% (49.2, 99.9) and 100% (99.2, 100.0) (FIG. 51C). One T13 case detected arose from a Robertsonian translocation (46, XY, +13,der(13; 13)$_{q10}$;q10). There were seven unclassified samples in the chromosome 21 analysis (1.4%), five in the chromosome 18 analysis (1.0%), and two in the chromosome 13 analysis (0.4%) (FIG. 51A-51C). In all categories there was an overlap of three samples that had both a censored karyotype (69,XXX) and no fetal DNA detected. One unclassified sample in the chromosome 21 analysis was correctly identified as T13 in the chromosome 13 analysis and one unclassified sample in the chromosome 18 analysis was correctly identified as T21 in the chromosome 21 analysis.

TABLE 25

| | | Censored Karyotypes | |
|---|---|---|---|
| Karyotype | Censored Category | Sequencing Classification Aneuploidy | Sequencing Classification Gender |
| Mosaic Trisomy 21 and 18 (n = 4) | | | |
| 47, XY, +21[5]/46, XY[12] | 21 | Affected (T21) | Male |
| 47, XX, +21[4]/46, XX [5] | 21 | Affected (T21) | Unclassified |
| 47, XY, +21[21]/48, XY, +21 + mar[4]* | 21, 18, 13, gender | Affected (T21) | Male |
| 47, XX, +18 [42]/46, XX [8] | 18 | Affected (T18) | Female |
| Other Complex Mosaicism (n = 2) | | | |
| 45, XY, −13[5]/46, XY, r(13) (p11.1q22)[15] | 13 | Unaffected (21, 18, 13) | Male |
| 92, XXXX[20]/46, XX[61] | 21, 18, 13, gender | Unaffected (21, 18, 13) | Unclassified |
| Added material of uncertain origin (n = 5) | | | |
| 46, XX, add (X)(p22.1) | 21, 18, 13, gender | Unaffected (21, 18, 13) | Female |
| 46, XY, add(10)(q26) | 21, 18, 13, gender | Unaffected (21, 18, 13) | Male |
| 46, XY, add(15)(p11.2) | 21, 18, 13, gender | Unaffected (21, 18, 13) | Male |
| 47, XY, +mar/46, XY | 21, 18, 13, gender | Unaffected (21, 18, 13) | Male |
| 47, XX + mar [12]/46, XX[8] | 21, 18, 13, gender | Unaffected (21, 18, 13) | Female |
| Triploidy (n = 10) | | | |
| 69, XXY | 21, 18, 13, gender | Unaffected (21, 18, 13) | Unclassified sex |
| 69, XXX (n = 9) | 21, 18, 13, gender | Unaffected (21, 18, 13) (n = 6) Unclassified (n = 3) | Female (n = 5) Unclassified (n = 4) |
| Sex Chromosome Aneuploidy (n = 10) | | | |
| 47, XXX (n = 4) | gender | Unaffected (21, 18, 13) (n = 4) | XXX (n = 3) Monosomy X (n = 1) |
| 47, XXY (n = 3) | gender | Unaffected (21, 18, 13) (n = 2) Unclassified (18)** and Unaffected (21, 13) (n = 1) | XXY (n = 2) Unclassified (n = 1)** |
| 47, XYY (n = 3) | gender | Unaffected (21, 18, 13) (n = 3) | XYY (n = 3) |
| Mosaic Monosomy X (n = 7) | | | |
| 45, X/46, XX (n = 3) | gender | Unaffected (21, 18, 13) (n = 3) | Female (n = 2) Monosomy X (n = 1) |
| 45, X/47, XXX | gender | Unaffected (21, 18, 13) | Monosomy X |
| 45, X/46, XY (n = 2) | gender | Unaffected (21, 18, 13) (n = 2) | Male (n = 2) |
| 45, X, +21, der(14; 21)(q10; q10)[4]/46, XY, +21, der(14; 21)(q10; q10)[17] | gender | Affected (T21) and Unaffected (18, 13) | Male |
| Other Reasons (n = 3) | | | |
| Gender not disclosed in report (n = 2) | gender | Unaffected (21, 18, 13) | Female (n = 2) |
| 46, XY with maternal cell contamination (n = 1) | gender | Unaffected (21, 18, 13) | Male |

*Subject excluded from all analysis categories due to marker chromosome in one cell line.
**Subject with karyotype 48, XXY, +18 was unclassified in chromosome 18 analysis and sex aneuploidy was not detected.

TABLE 26

Abnormal and complex karyotypes that were not censored

| Karyotype | Sequencing Classification Aneuploidy | Sequencing Classification Gender |
|---|---|---|
| Monosomy X (n = 20) | | |
| 45, X (n = 15) | Unaffected (21, 18, 13) | Monosomy X |
| 45, X (n = 4) | Unaffected (21, 18, 13) | Unclassified |
| 45, X (n = 1) | Unaffected (21, 18, 13) | Female |
| Other Autosomal Trisomy or Partial Trisomy (n = 5) | | |
| 47, XX, +16 | Chromosome 16 aneuploidy | Unclassified |
| 47, XX, +20 | Chromosome 20 aneuploidy | Unclassified |
| Partial trisomy 6q12q16.3 and 6q16.3, no gender | Unaffected (21, 18, 13)* | Female |
| 47, XY, +22 | Unaffected (21, 18, 13) | Male |
| 47, XX, +22 | Unclassified (21, 18, 13) | Unclassified |
| Translocations (n = 7) | | |
| Balanced (n = 6) | Unaffected (21, 18, 13) | correct class (Male or Female) |
| Unbalanced (n = 1) | Unaffected (21, 18, 13) | Female |
| Other Complex Mosaicism (n = 4) | Unaffected (21, 18, 13) | correct class (Male or Female) |
| Other Complex Variants (n = 4) | Unaffected (21, 18, 13) | correct class (Male or Female) |

*An increased normalized chromosome value (NCV) of 3.6 was noticed from sequencing tags in chromosome 6 after unblinding.

Figure 33A:
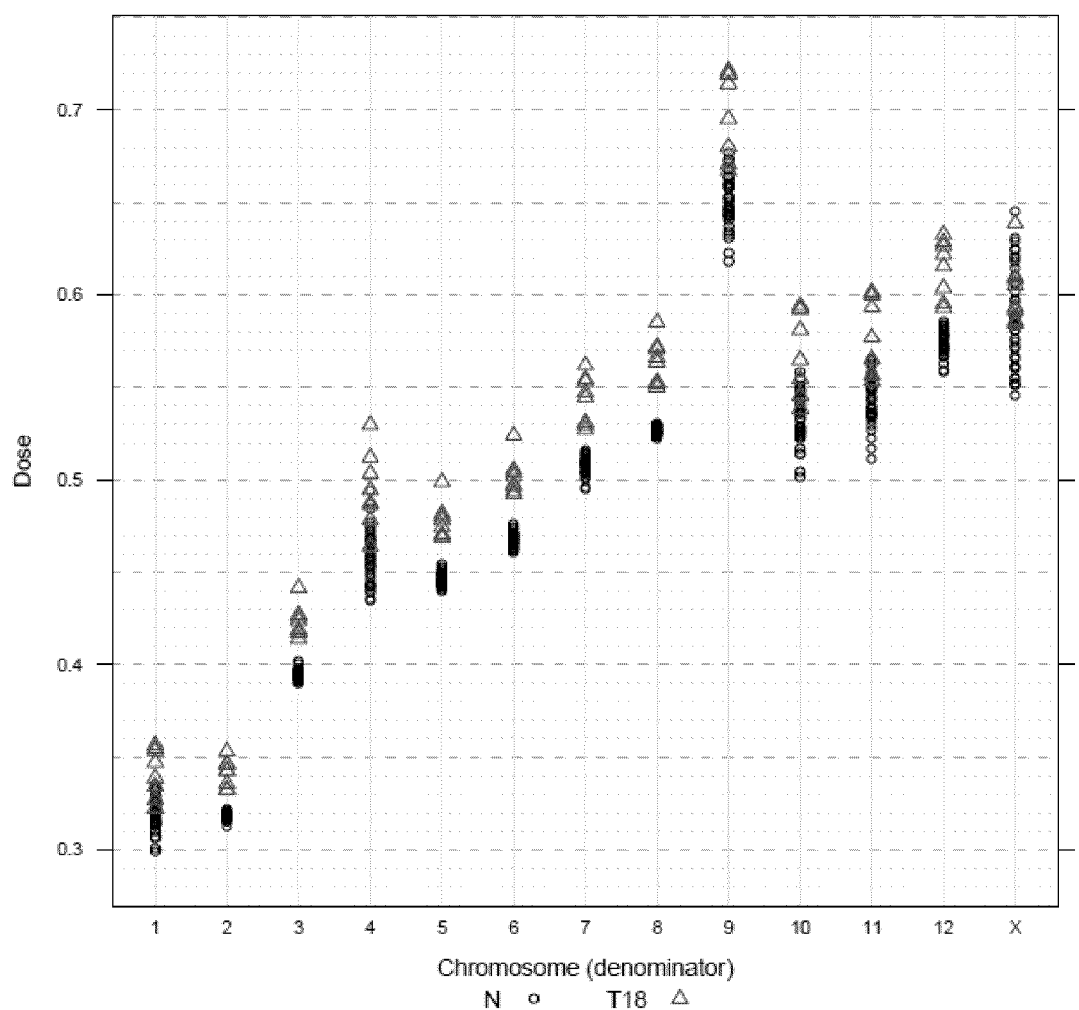
FIGS. 33A and 33B illustrate the distribution of the chromosome dose for chromosome 18 determined from sequencing cfDNA extracted from a set of 48 blood samples obtained from human subjects each pregnant with a male or a female fetus. Chromosome 18 doses for qualified i.e. normal for chromosome 18 (O), and trisomy 18 (Δ) test samples are shown for chromosomes 1-12 and X (FIG. 33A), and for chromosomes 1-22 and X (FIG. 33B).
Figure 33B:
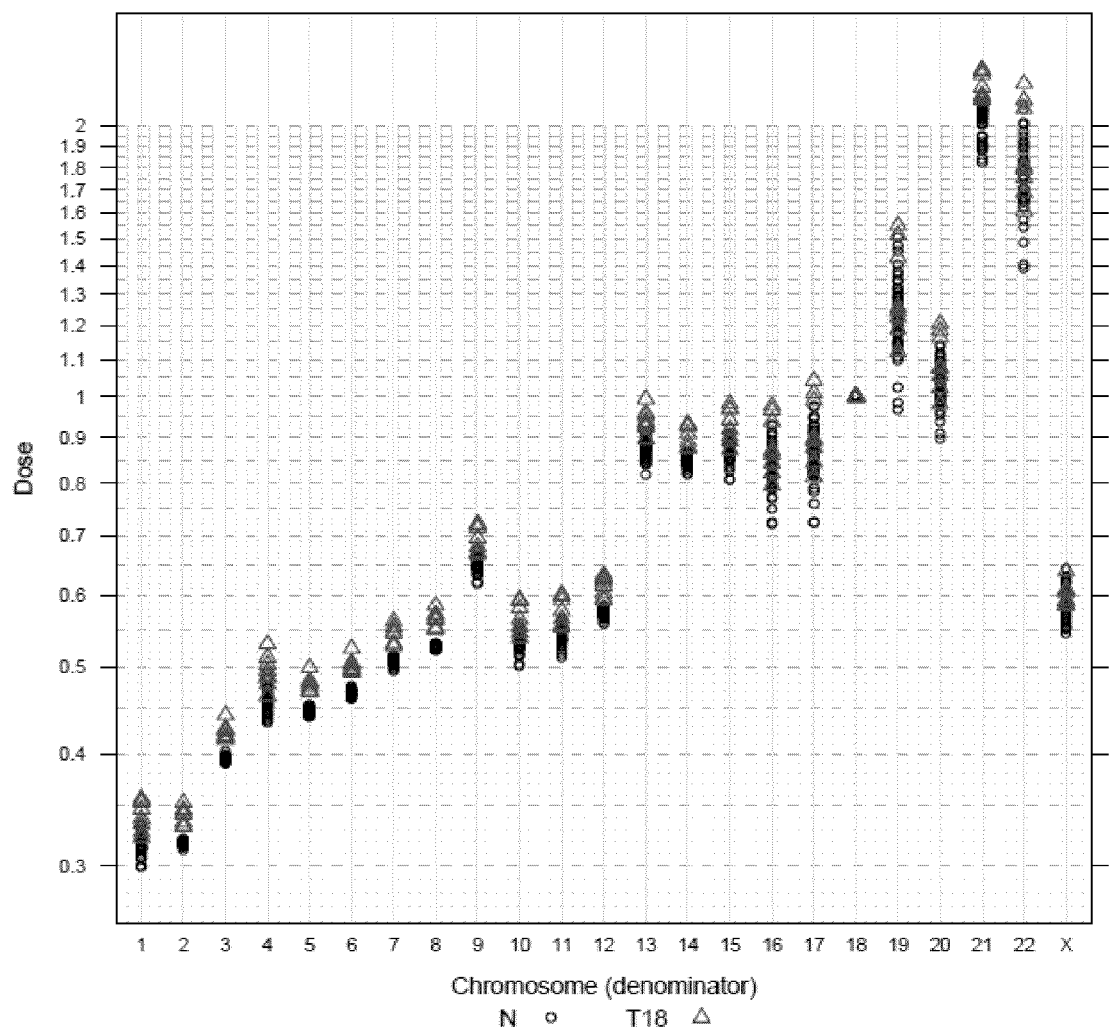
Figure 34A:
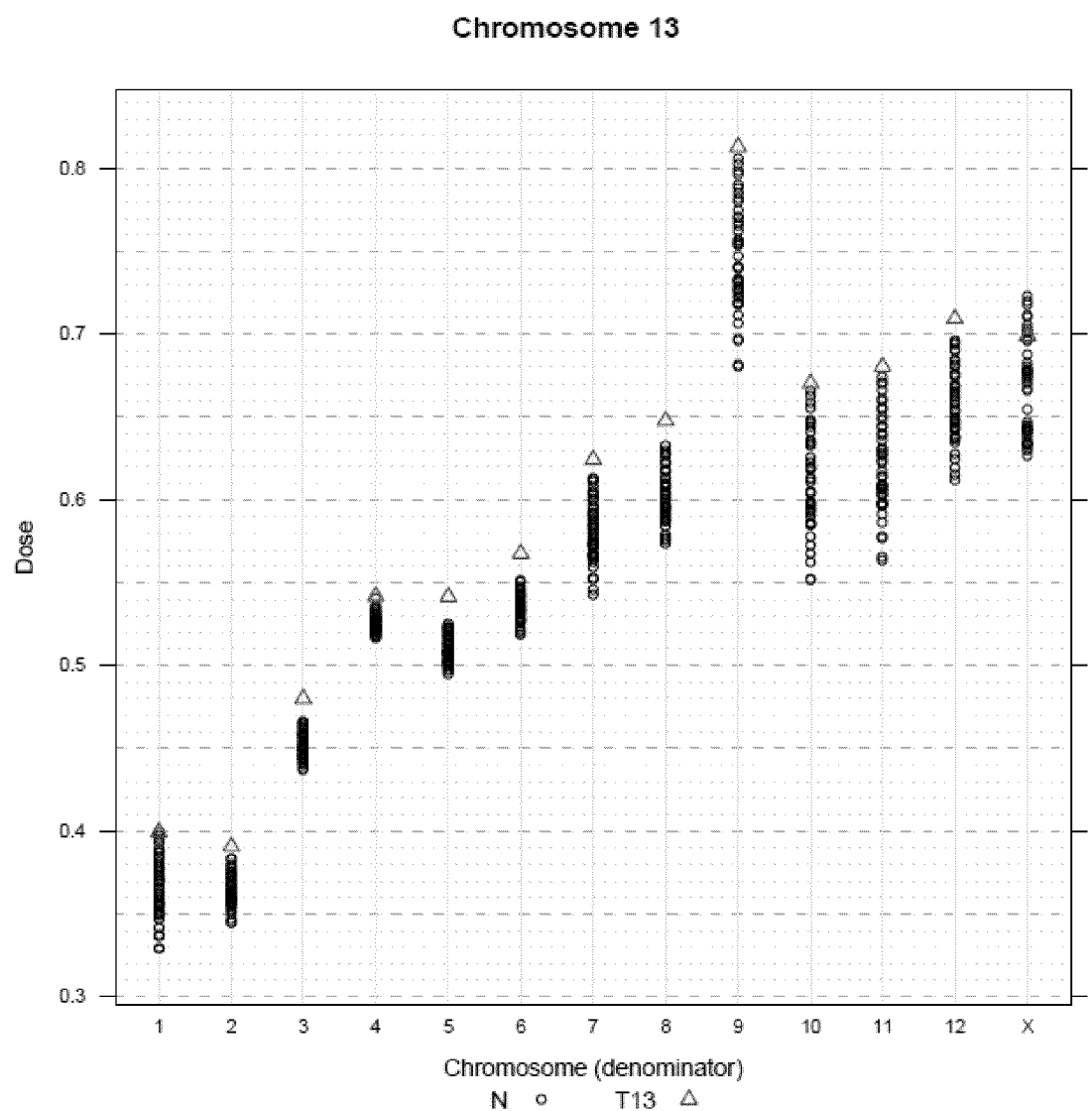
FIGS. 34A and 34B illustrate the distribution of the chromosome dose for chromosome 13 determined from sequencing cfDNA extracted from a set of 48 blood samples obtained from human subjects each pregnant with a male or a female fetus. Chromosome 13 doses for qualified i.e. normal for chromosome 13 (O), and trisomy 13 (Δ) test samples are shown for chromosomes 1-12 and X (FIG. 34A), and for chromosomes 1-22 and X (FIG. 34B).
Figure 34B:
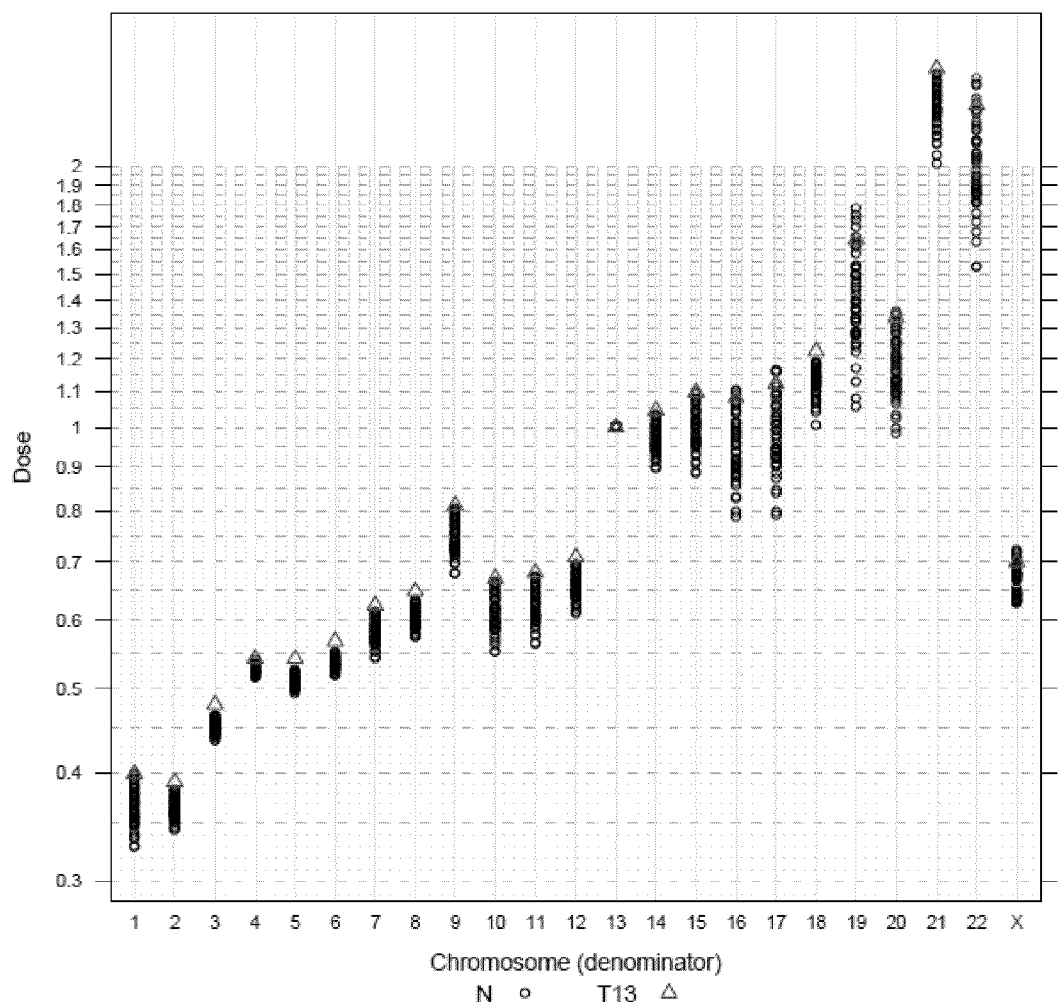
Figure 35A:
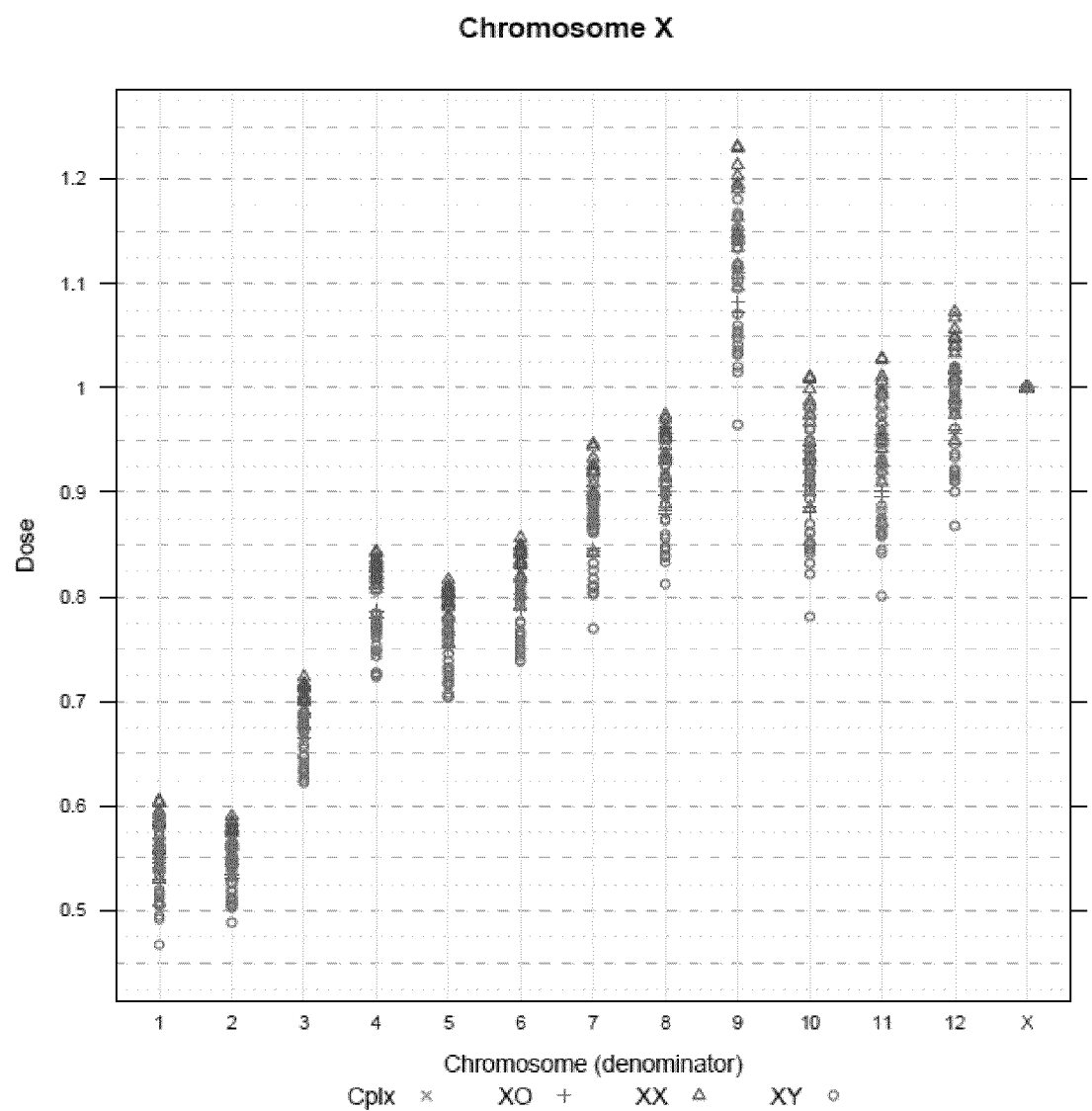
FIGS. 35A and 35B illustrate the distribution of the chromosome doses for chromosome X determined from sequencing cfDNA extracted from a set of 48 test blood samples obtained from human subjects each pregnant with a male or a female fetus. Chromosome X doses for males (46,XY; (O)), females (46,XX; (Δ)); monosomy X (45,X; (+)), and complex karyotypes (Cplx (X)) samples are shown for chromosomes 1-12 and X (FIG. 35A), and for chromosomes 1-22 and X (FIG. 35B).
Figure 35B:
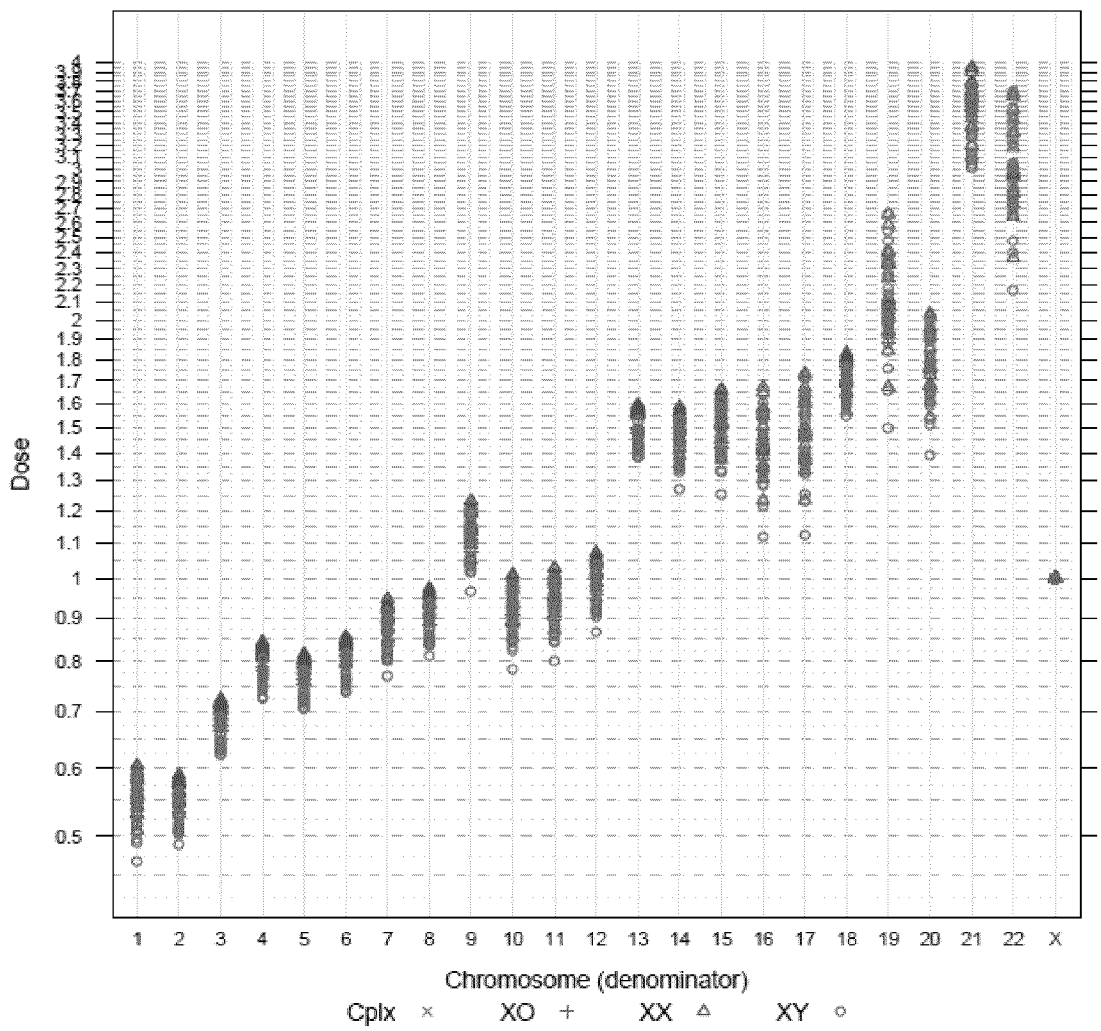
Figure 36A:
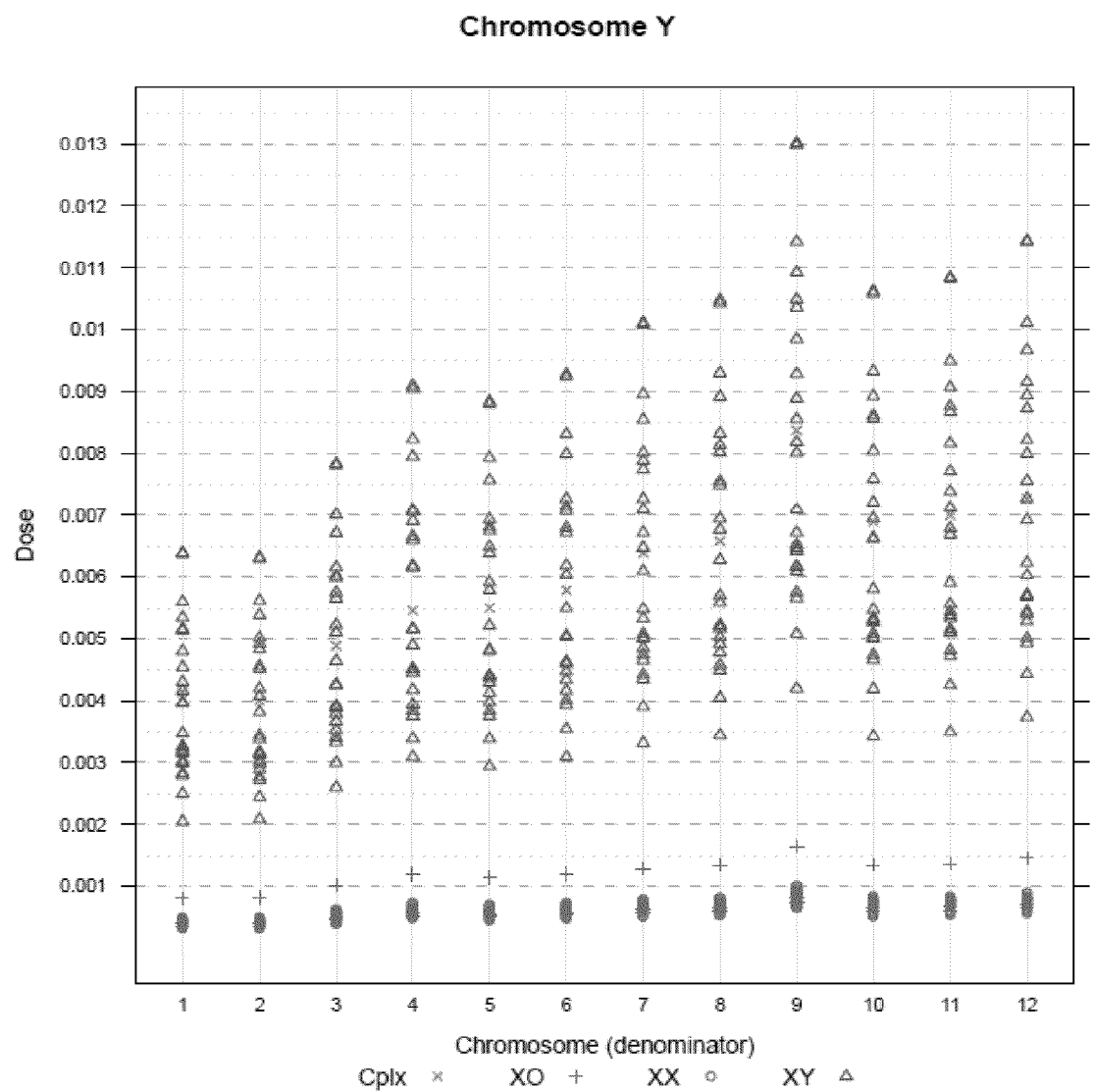
FIGS. 36A and 36B illustrate the distribution of the chromosome doses for chromosome Y determined from sequencing cfDNA extracted from a set of 48 test blood samples obtained from human subjects each pregnant with a male or a female fetus. Chromosome Y doses for males (46,XY; (Δ)), females (46,XX; (O)); monosomy X (45,X; (+)), and complex karyotypes (Cplx (X)) samples are shown for chromosomes 1-12 (FIG. 36A), and for chromosomes 1-22 (FIG. 36B).
Figure 36B:
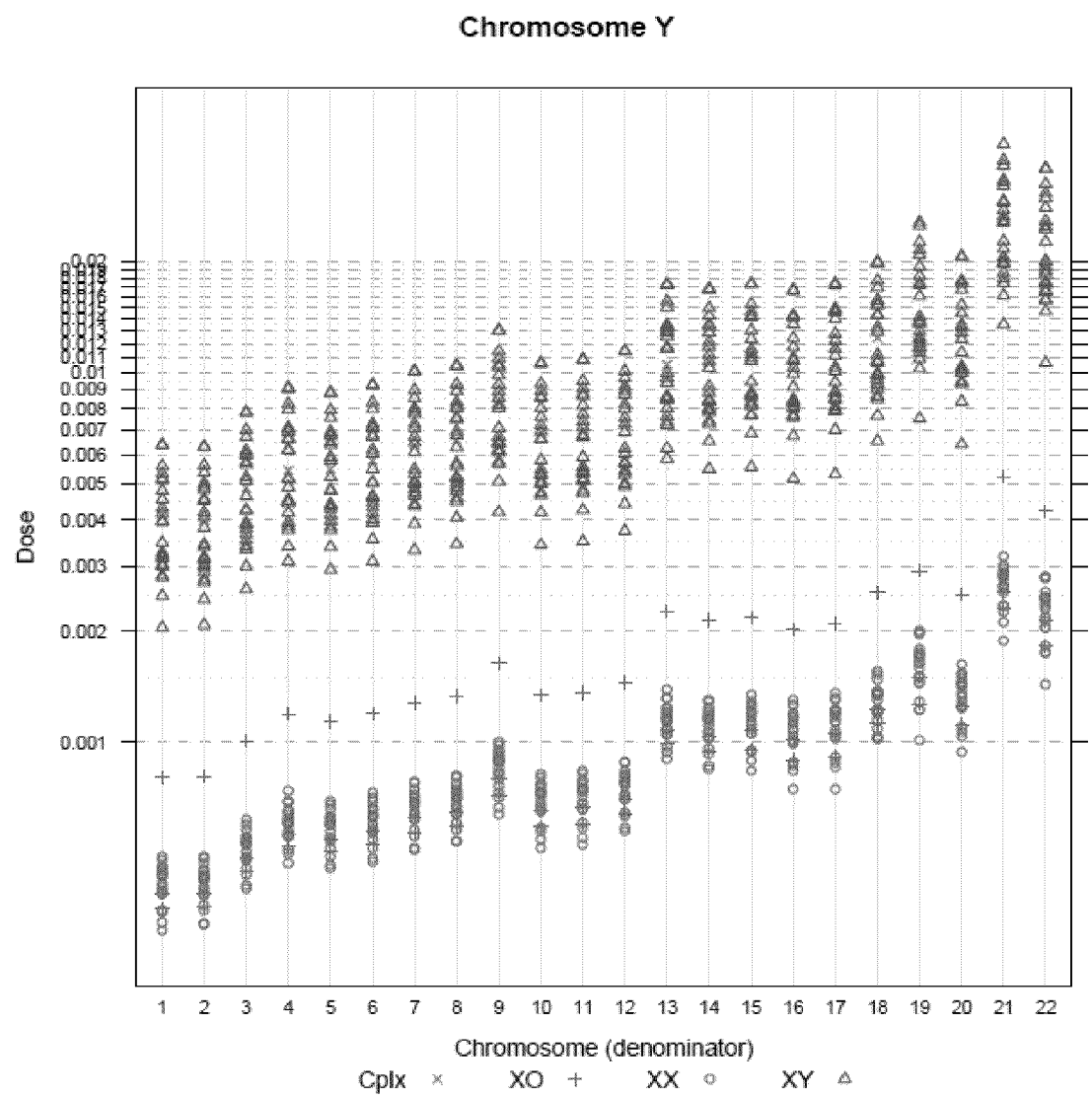

The sex chromosome analysis population for determining performance of the method (female, male, or monosomy X) was 433. Our refined algorithm for classifying the gender status, which allowed for accurate determination of sex chromosome aneuploidies, resulted in a higher number of unclassified results. Sensitivity and specificity for detecting diploid female state (XX) were 99.6% (95% CI=97.6, >99.9) and 99.5% (95% CI=97.2, >99.9), respectively; sensitivity and specificity to detect male (XY) were both 100% (95% CI=98.0, 100.0); and sensitivity and specificity for detecting monosomy X (45,X) were 93.8% (95% CI=69.8, 99.8) and 99.8% (95% CI=98.7, >99.9) (FIGS. 33D-f). Although censored from the analysis (as per protocol), the sequencing classifications of mosaic monosomy X karyotypes were as follows (Table 25): 2/7 classified as monosomy X, 3/7 classified with a Y chromosome component classified as XY and 2/7 with XX chromosome component classified as female. Two samples that were classified according to the method of the invention as monosomy X had karyotypes of 47,XXX and 46,XX. Eight of ten sex chromosome aneuploidies for karyotypes 47,XXX, 47,XXY and 47,XYY were correctly classified (Table 25). If the sex chromosome classifications had been limited to monosomy X, XY and XX, most of the unclassified samples would have been correctly classified as male, but the XXY and XYY sex aneuploidies would not have been identified.

In addition to accurately classifying trisomies 21, 18, 13 and gender, the sequencing results also correctly classified aneuploidy for chromosomes 16 and 20 in two samples (47, XX, +16 and 47,XX, +20) (Table 26). Interestingly, one sample with a clinically complex alteration of the long arm of chromosome 6 (6q) and two duplications, one of which was 37.5 Mb in size, showed an increased NCV from sequencing tags in chromosome 6 (NCV=3.6). In another sample, aneuploidy of chromosome 2 was detected according to the method of the invention but not observed in the fetal karyotype at amniocentesis (46,XX). Other complex karyotype variants shown in Tables 25 and 26 include samples from fetuses with chromosome inversions, deletions, translocations, triploidy and other abnormalities that were not detected here, but could potentially be classified at higher sequencing density and/or with further algorithm optimization using the method of the invention. In these cases, the method of the invention correctly classified the samples as unaffected for trisomy 21, 18, or 13 and as male or female.

In this study, 38/532 analyzed samples were from women who underwent assisted reproduction. Of these, 17/38 samples had chromosomal abnormalities; no false positives or false negatives were detected in this sub-population.

TABLE 27

Sensitivity and Specificity of the Method

| Performance | Sensitivity (%) | 95% CI | Specificity (%) | 95% CI |
|---|---|---|---|---|
| Trisomy 21 (n = 493) | 100.0 (89/89) | 95.9-100.0 | 100.0 (404/404) | 99.1-100.0 |
| Trisomy 18 (n = 496) | 97.2 (35/36) | 85.5-99.9 | 100 (460/460) | 99.2-100.0 |
| Trisomy 13 (n = 499) | 78.6 (11/14) | 49.2-99.9 | 100.0 (485/485) | 99.2-100.0 |
| Female (n = 433) | 99.6 (232/233) | 97.6->99.9 | 99.5 (199/200) | 97.2->99.9 |
| Male (n = 433) | 100.0 (184/184) | 98.0-100.0 | 100.0 (249/249) | 98.5-100.0 |
| Monosomy X (n = 433) | 93.8 (15/16) | 69.8-99.8 | 99.8 (416/417) | 98.7->99.9 |

Discussion

This prospective study to determine whole chromosome fetal aneuploidy from maternal plasma was designed to emulate the real world scenario of sample collection, processing and analysis. Whole blood samples were obtained at the enrollment sites, did not require immediate processing, and were shipped overnight to the sequencing laboratory. In contrast to a prior prospective study that only involved chromosome 21 (Palomaki et al., Genetics in Medicine 2011:1), in this study, all eligible samples with any abnormal karyotype were sequenced and analyzed. The sequencing laboratory did not have prior knowledge of which fetal chromosomes might be affected nor the ratio of aneuploid to euploid samples. The study design recruited a high-risk study population of pregnant women to assure a statistically significant prevalence of aneuploidy, and Tables 25 and 26 indicate the complexity of the karyotypes that were analyzed. The results demonstrate that: i) fetal aneuploidies (including those resulting from translocation trisomy, mosaicism, and complex variations) can be detected with high sensitivity and specificity and ii) aneuploidy in one chromosome does not affect the ability of the method of the invention to correctly identify the euploid status of other chromosomes. The algorithms utilized in the previous studies appear to be unable to effectively determine other aneuploidies that inevitably would be present in a general clinical population (Erich et al., Am J Obstet Gynecol 2011 March; 204(3):205 e1-11, Chiu et al., BMJ 2011; 342: c7401).

With regard to mosaicism, the analysis of sequencing information in this study was able to correctly classify samples that had mosaic karyotypes for chromosomes 21 and 18 in 4/4 affected samples. These results demonstrate the sensitivity of the analysis for detecting specific characteristics of cell free DNA in a complex mixture. In one case, the sequencing data for chromosome 2 indicated a whole or partial chromosome aneuploidy while the amniocentesis karyotype result for chromosome 2 was diploid. In two other examples, one sample with 47,XXX karyotype and another with a 46,XX karyotype, the method of the invention classified these samples as monosomy X. It is possible these are mosaic cases, or that the pregnant woman herself is mosaic. (It is important to remember that the sequencing is performed on total DNA, which is a combination of maternal and fetal DNA.) While cytogenetic analysis of amniocytes or villi from invasive procedures is currently the reference standard for aneuploidy classification, a karyotype performed on a limited number of cells cannot rule out low-level mosaicism. The current clinical study design did not include long term infant follow-up or access to placental tissue at delivery, so we are unable to determine if these were true or false positive results. We speculate that the specificity of the sequencing process, coupled with optimized algorithms according to the method of the invention to detect genome wide variation, may ultimately provide more sensitive identification of fetal DNA abnormalities, particularly in cases of mosaicism, than standard karyotyping.

The International Society for Prenatal Diagnosis has issued a Rapid Response Statement commenting on the commercial availability of massively parallel sequencing (MPS) for prenatal detection of Down syndrome (Benn et al., Prenat Diagn 2012 doi:10.1002/pd.2919). They state that before routine MPS-based population screening for fetal Down syndrome is introduced, evidence is needed that the test performs in some sub-populations, such as in women who conceive by in vitro fertilization. The results reported here suggest that the present method is accurate in this group of pregnant women, many of whom are at high risk for aneuploidy.

Although these results demonstrate the excellent performance of the present method with optimized algorithms for aneuploidy detection across the genome in singleton pregnancies from women at increased risk for aneuploidy, more experience, particularly in low-risk populations, is needed to build confidence in the diagnostic performance of the method when the prevalence is low and in multiple gestation. In the early stages of clinical implementation, classification of chromosomes 21, 18 and 13 using sequencing information according to the present method should be utilized after a positive first or second trimester screening result. This will reduce unnecessary invasive procedures caused by the false positive screening results, with a concomitant reduction in procedure related adverse events. Invasive procedures could be limited to confirmation of a positive result from sequencing. However, that there are clinical scenarios (e.g., advanced maternal age and infertility) in which pregnant women will want to avoid an invasive procedure; they may request this test as an alternative to the primary screen and/or invasive procedure. All patients should receive thorough pre-test counseling to ensure that they understand the limitations of the test and the implications of the results. As experience accumulates with more samples, it is possible that this test will replace current screening protocols and become a primary screening and ultimately a noninvasive diagnostic test for fetal aneuploidy.

Example 17

Determining Fetal Fraction from NCV to Distinguish the Presence of Complete or Partial Fetal Chromosomal Aneuploidies in Analytical Samples Given that the chromosome dose for a fetal chromosome of interest in a maternal sample increases proportionately with increasing fetal fraction, it is expected that a ff value that is based on the NCV value for a complete chromosome of interest would be determinative of the presence or absence of a complete fetal chromosomal aneuploidy. To demonstrate that ff determined from NCVs can be used to distinguish the presence of a complete chromosomal aneuploidy from a partial chromosomal aneuploidy or the contribution from a mosaic sample, genomic DNA from mothers and from their children were used to create artificial samples that simulated the mixture of fetal and maternal cfDNA found in the circulation of a pregnant woman. The NCV based value of fetal fraction is a form of putative fetal fraction described above.

The DNA of the mothers and children was purchased from Coriell Institute for Medical Research (Camden, N.J.). DNA identification and sample karyotype are given in Table 27.

TABLE 27

Example 17

| Artificial mixture # | Condition | Coriell ID | Family | Member | Comments | Clinical Pres | Karyotype |
|---|---|---|---|---|---|---|---|
| 1 | Whole trisomy; | NG09387 | 2139 | Mother | Normal | Normal | 46, XX |
|  |  | NG09394 | 2139 | Son | Affected T21 | Downs Syndrome | 47, XY, +21 |
| 2 | Deletion | NA10924 | 1313 | Mother | Normal | Normal | 46, XX |
|  |  | NA10925 | 1313 | Son | Deletion in 7 | Grieg Encephaly | 46, XY, del(7) (pter>p14:: p12>qter) |
| 3 | Mosaic | NA22629 | 2877 | Mother | Deletion in 11 | Affected | 46, XX, del(11) |
|  |  | NA22628 | 2877 | Son | Deletion in 11, Mos dup 15 | Affected mosaic | 47, XY, del(11) (pter-> p12::p11.2-> qter), +15[12]/ 46, XY, del(11) (pter-> p12::p11.2-> qter)[40].arr 11p12p11.12(41 392049- 49104319)x1 |
| 4 | Duplication | NA16368 | 1925 | Mother |  | Normal | 46, XX.arr(1- 22, X)x2 |

TABLE 27-continued

Example 17

| Artificial mixture # | Condition | Coriell ID | Family | Member | Comments | Clinical Pres | Karyotype |
|---|---|---|---|---|---|---|---|
| | | NA16363 | 1925 | Nor Twin Son | Monozygotic Twins, one normal, one affected | Normal | 46, XY |
| | | NA16362 | 1925 | Affected twin son; partial T22 | | Affected | 47, XY, +der(22) |

Samples comprising complete chromosomal or partial chromosomal aneuploidies were analyzed as follows.

In all cases, genomic DNA from the mother and genomic DNA from the child were sheared by sonication with a peak at 200 bp. Artificial samples comprising mothers' DNA with 0%, 5% or 10% w/w of the child's DNA spiked in were processed to prepare sequencing libraries, which were sequenced in a massively parallel fashion using sequencing-by-synthesis as described in Example 12. Each artificial DNA sample was sequenced four times using separate flow cells on the sequencer to provide 4 sets of sequence information for each of samples containing 0%, 5% and 10% child DNA. 36 bp reads were aligned to human reference genome hg19, and uniquely mapped tags were counted. Approximately $125 \times 10^6$ sequence tags were obtained for each of the 4 flow cell lanes used per sample.

Normalizing chromosomes (single or group of chromosomes) were identified in a set of qualified samples comprising 20 male and 20 female gDNA libraries, as described elsewhere herein. Normalizing chromosomes for chromosome 21 were identified chr4+chr16+chr22 normalizing chromosomes for chromosome 7 were identified as chr4+chr6+chr8+chr12+chr19+chr20normalizing chromosomes for chromosome 15 were identified as chr9+chr12+chr14+chr19+chr20, normalizing chromosome for chromosome 22 were identified as chr19 and normalizing chromosomes for chromosome X were identified as chr4+chr6+chr7+chr8. Sequence tags for the chromosome of interest and for the corresponding normalizing chromosome (single chromosome or group of chromosomes) obtained from sequencing the artificial samples were counted and used to calculate chromosome doses, and calculate NCVs.

In the instant example, the ff determined using NCV for chromosome 21 in a sample mixture (1) where $NCV_{21A}$ is the NCV value determined for chromosome 21 in the test sample (1), which comprises the triploid chromosome 21, and $CV_{21U}$ is the coefficient of variation for doses of chromosome 21 determined in the qualified samples (comprising diploid chromosome 21); and where $NCV_{XA}$ is the NCV value determined for chromosome X in the test sample (1), which comprises the triploid chromosome 21, and $CV_{XU}$ is the coefficient of variation for doses of chromosome X determined in the qualified samples (comprising diploid chromosome 21).

Figure 56:
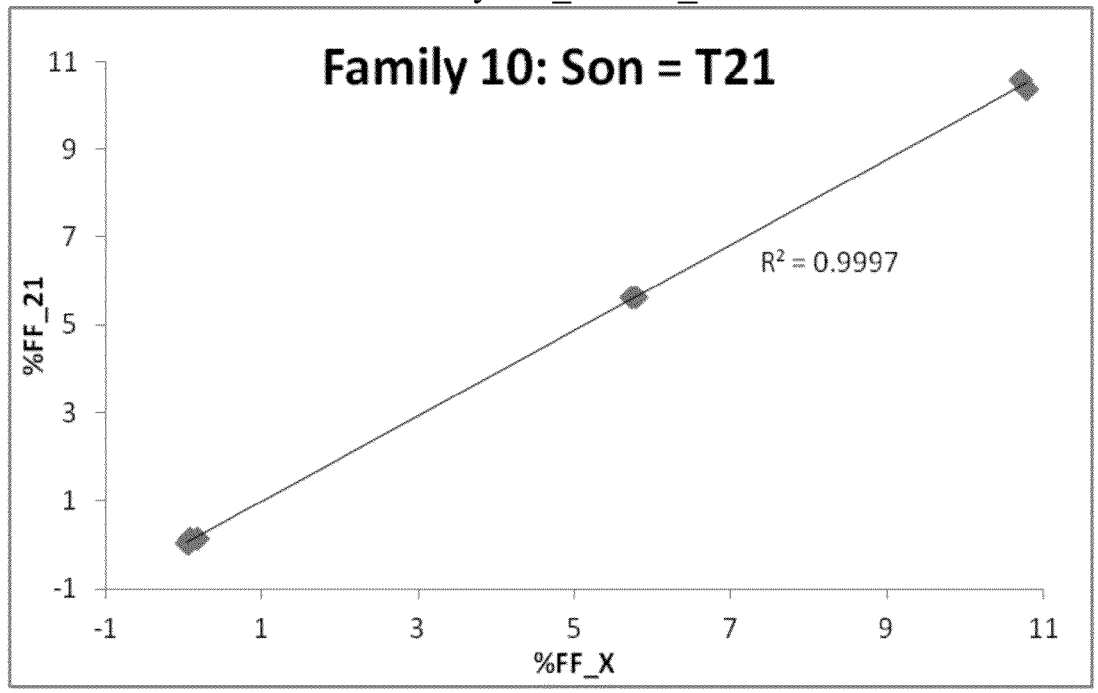
FIG. 56 shows a plot from Example 17 of the percent "ff" determined using doses of chromosome 21 ($ff_{21}$) as a function of the percent "ff" determined using doses of chromosome X ($ff_X$) in a synthetic maternal sample (1) comprising DNA from a child with trisomy 21

FIG. 56 shows a plot of the percent "ff" determined using doses of chromosome 21 ($ff_{21}$) as a function of the percent "ff" determined using doses of chromosome X ($ff_X$) in a synthetic maternal sample (1) comprising DNA from a child with trisomy 21.

The data shows that the chromosome doses and the NCVs derived therefrom increase in proportion with increasing ff, and that there is a 1:1 relationship between the percent ff determined using doses for the triploid chromosome i.e. chromosome 21, and the percent ff determined using doses for a chromosome known to be present as a single chromosome i.e. chromosome X.

Figure 57:
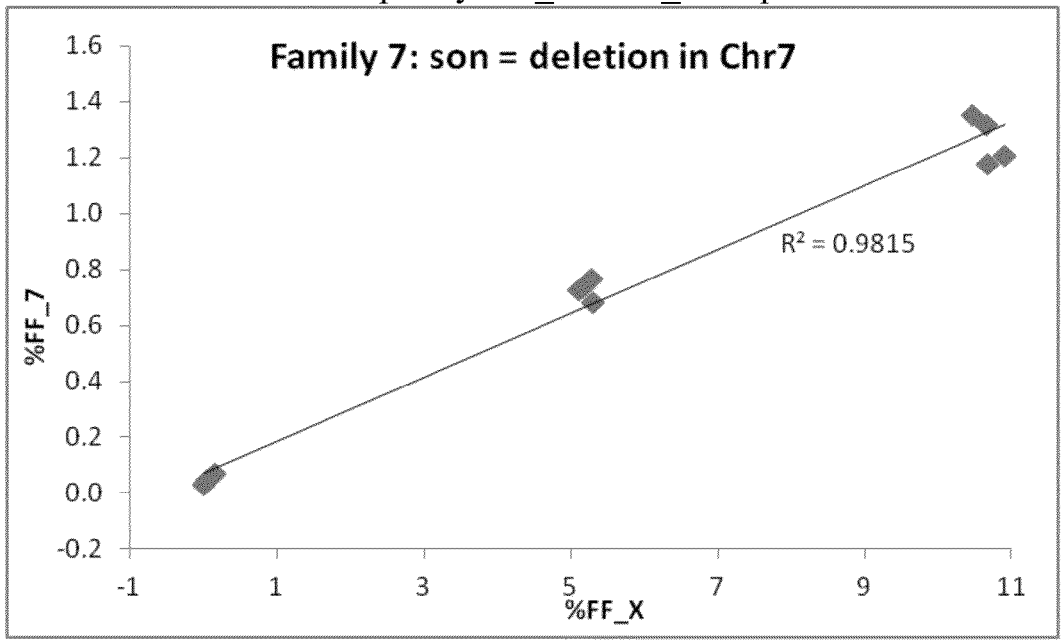
FIG. 57 shows a plot from Example 17 of the percent "ff" determined using doses of chromosome 7 ($ff_7$) as a function of the percent "ff" determined using doses of chromosome X ($ff_X$) in a synthetic maternal sample (2) comprising DNA from a euploid mother and her child who carries a partial deletion in chromosome 7.

FIG. 57 shows a plot of the percent "ff" determined using doses of chromosome 7 ($ff_7$) as a function of the percent "ff" determined using doses of chromosome X ($ff_X$) in a synthetic maternal sample (2) comprising DNA from a euploid mother and her child who carries a partial deletion in chromosome 7.

As was shown for samples (1) and (2), the data show that the chromosome doses and the NCVs derived therefrom increase in proportion with increasing ff. However, in a case where the aneuploidy is a partial chromosomal aneuploidy, the percent ff determined using chromosome doses of a partially aneuploid chromosome ($ff_7$) does not correspond to the percent ff determined using doses for chromosome X ($ff_X$). Therefore, deviation from the 1:1 relationship shown for a complete trisomic sample is indicative of the presence of a partial aneuploidy.

Figure 58:
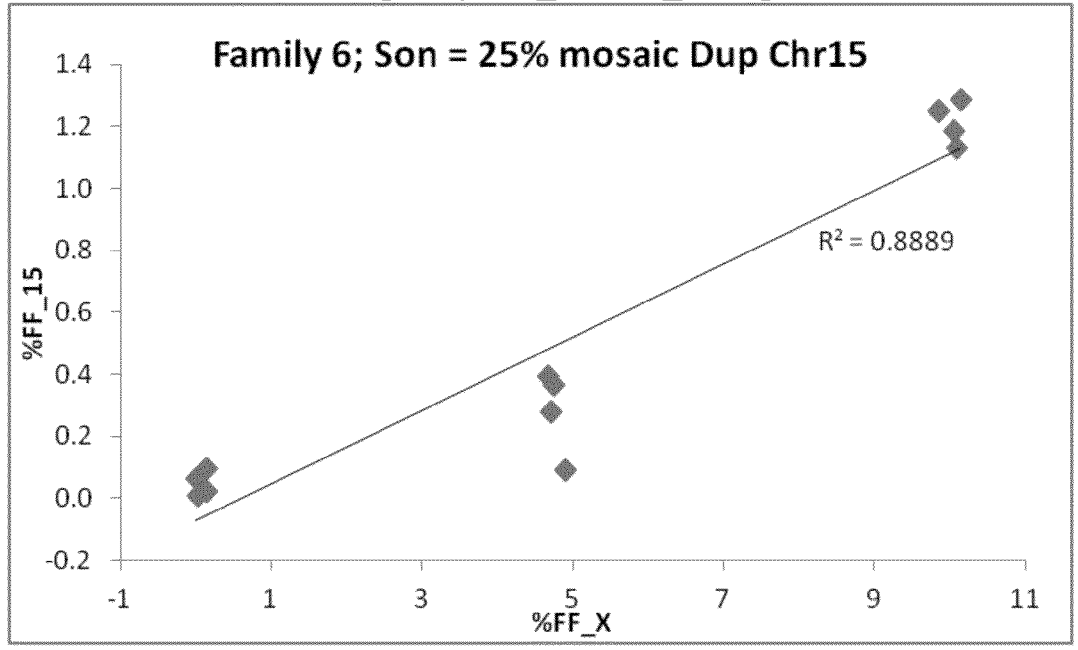
FIG. 58 shows a plot from Example 17 of the percent "ff" determined using doses of chromosome 15 ($ff_{15}$) as a function of the percent "ff" determined using doses of chromosome X ($ff_X$) in a synthetic maternal sample (3) comprising DNA from a euploid mother and her child who is 25% mosaic with a partial duplication of chromosome 15.

FIG. 58 shows a plot of the percent "ff" determined using doses of chromosome 15 ($ff_{15}$) as a function of the percent "ff" determined using doses of chromosome X ($ff_X$) in a synthetic maternal sample (3) comprising DNA from a euploid mother and her child who is 25% mosaic with a partial duplication of chromosome 15.

As was shown for samples (1) and (2), the ff determined using doses and the NCVs derived therefrom increase in proportion with increasing ff. As was shown in sample (2), sample (3) comprises a partial chromosomal aneuploidy, and the percent ff determined using chromosome doses of a partially aneuploid chromosome ($ff_{15}$) does not correspond to the percent ff determined using doses for chromosome X ($ff_X$). The lack of correspondence between the two ff is indicative of the presence of a partial aneuploidy rather than a complete chromosomal aneuploidy.

Figure 59:
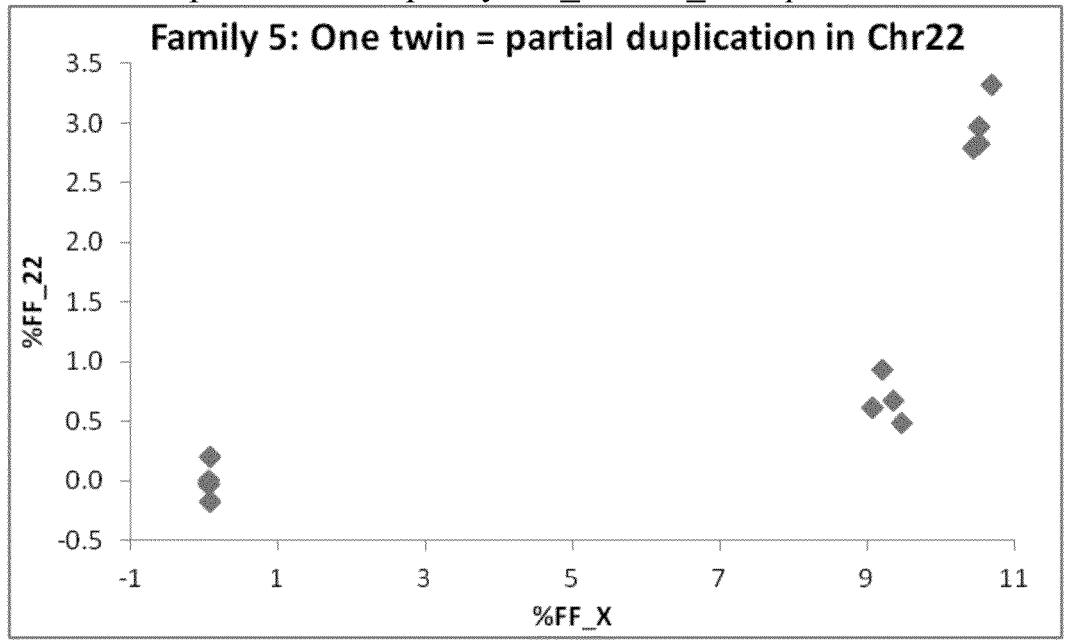
FIG. 59 shows a plot from Example 17 of the percent "ff" determined using doses of chromosome 22 ($ff_{22}$) and the NCVs derived therefrom in artificial sample (4) comprising 0% child DNA (i), and 10% DNA from an unaffected twin son known not to have a partial chromosomal aneuploidy of chromosome 22 (ii), and 10% DNA from the affected twin son known to have a partial chromosomal aneuploidy of chromosome 22 (iii).

FIG. 59 shows a plot of the percent "ff" determined using doses of chromosome 22 ($ff_{22}$) and the NCVs derived therefrom in artificial sample (4) comprising 0% child DNA (i), and 10% DNA from an unaffected twin son known not to have a partial chromosomal aneuploidy of chromosome 22 (ii), and 10% DNA from the affected twin son known to have a partial chromosomal aneuploidy of chromosome 22 (iii). The data show that the "ff" for the sample comprising the DNA from the unaffected twin and determined from the four NCVs calculated from doses of chromosome 22 are close to zero, indicating the absence of an aneuploidy of chromosome 22 in the unaffected child; and the "ff" of the unaffected twin when calculated from doses of chromosome X confirm that the "ff" for the unaffected twin sample is about 10%. The data also show that the "ff" for the sample comprising DNA from the affected twin and determined from the four NCVs calculated from doses of chromosome 22 ($ff_{22}$) is about 3%, indicating the presence of an aneuploidy in chromosome 22; while the "ff" when calculated from doses of chromosome X (ff$_X$) confirm that the "ff" for the unaffected twin sample is about 10%. The lack of correspondence between the ff$_{22}$ and ff$_X$ indicates that the aneuploidy of chromosome 22 in the affected twin is a partial chromosomal aneuploidy.

Therefore, the data shows that in maternal samples comprising cfDNA of a male fetus, the chromosome doses and the NCV values derived therefrom can be used to distinguish the presence of a complete trisomy from a partial aneuploidy and/or a complete or partial aneuploidy present in a mosaic sample. The partial aneuploidy can be an increase or a decrease of part of a chromosome. Optionally, resolution of the partial aneuploidy and/or mosaicism can be obtained by using chromosome doses and Estimated Fetal Fraction values as described in Example 12.

The fetal fraction methods described above can also be utilized to determine the likelihood that one or more of the fetus' in multi-gestational pregnancy has an aneuploidy. For example, in one case of fraternal twins the fetal fraction determined from the NCV$_X$ value was found to be 8.3% while that measured from the NCV$_{21}$ value was 5.0%. This suggested that only one of the pair of male fetuses had a T21 aneuploidy, and this result is confirmed by the karyotype result. In another example with maternal twins the fetal fraction determined from the X chromosome was 7.3% whereas fetal fraction determined from chromosome 18 was 8.9%. In this example, both twins were determined to be T18 males from karyotype.

Example 18

Determining Fetal Fraction from NCV to Identify the Presence of Complete Fetal Chromosomal Aneuploidies in Clinical Samples To demonstrate that a ff determined from NCVs (CNff) can be used to distinguish the presence of a complete chromosomal aneuploidy from a partial chromosomal aneuploidy in a clinical sample, chromosomes of interest 21, 13, and 18 were quantified in clinical samples using cfDNA obtained from the blood of pregnant women. The presence of trisomy was verified by karyotpe.

cfDNA was obtained from 46 maternal samples from pregnant women each carrying a male fetus with trisomy 21 (T21), 13 maternal samples from pregnant women each carrying a fetus with trisomy 18 (T18), and 3 maternal samples from pregnant women carrying a male fetus with trisomy 13 (T13). These clinical samples were samples from the clinical study described in Example 16. cfDNA was isolated, and sequencing libraries were prepared as described in Example 16, but using the new Illumina v3 chemistry.

Sequencing libraries made from cfDNA from qualified samples known to be unaffected for chromosomes 21, 18 and 13 were also sequenced using the Illumin v3 chemistry. Sequence reads obtained for the qualified samples were mapped to human reference genome hg19 and Sequence reads that uniquely mapped all chromosome sequences corresponding to human reference genome hg19 (non-repeat masked) were counted and used to systematically determine which chromosome or group of chromosomes would serve as the normalizing chromosome for each of chromosomes of interest 21, 18, and 13 in the test samples.

Table 28 below shows the normalizing chromosomes (denominator chromosomes) identified to be used to determine chromosome doses (ratios) for chromosomes 1-22, X and Y in each of the test samples.

TABLE 28

Example 18 - Normalizing chromosomes systematically identified for use in T21, T18, and T13 test samples

| chromosome | % cv_1 | mean_1 | stdv_1 | denominator_1 |
|---|---|---|---|---|
| chr1 | 0.17328043 | 0.40761174 | 0.00070631 | chr2 + chr10 + chr15 + chr20 + chr22 |
| chr2 | 0.12704695 | 0.28019322 | 0.00035598 | chr1 + chr4 + chr6 + chr8 + chr10 |
| chr3 | 0.15988408 | 0.40355832 | 0.00064523 | chr5 + chr6 + chr8 |
| chr4 | 1.74801104 | 1.01640701 | 0.01776691 | chr5 |
| chr5 | 0.12567875 | 0.26828505 | 0.00033718 | chr3 + chr4 + chr8 + chr12 |
| chr6 | 0.18609738 | 0.23679013 | 0.00044066 | chr2 + chr3 + chr4 + chr14 |
| chr7 | 0.15420267 | 0.14975583 | 0.00023093 | chr4 + chr5 + chr6 + chr8 + chr9 + chr12 + chr19 + chr22 |
| chr8 | 0.16386037 | 0.14886515 | 0.00024393 | chr3 + chr4 + chr5 + chr11 + chr12 + chr14 + chr20 |
| chr9 | 0.14260705 | 0.07866201 | 0.00011218 | chr1 + chr2 + chr5 + chr7 + chr8 + chr11 + chr14 + chr15 + chr16 + chr17 + chr22 |
| chr10 | 0.23668533 | 0.27352768 | 0.0006474 | chr1 + chr6 + chr20 + chr22 |
| chr11 | 0.15337497 | 0.18482929 | 0.00028348 | chr1 + chr5 + chr8 + chr16 + chr20 + chr22 |
| chr12 | 0.15469865 | 0.16993862 | 0.00026289 | chr3 + chr5 + chr6 + chr14 + chr17 + chr20 |
| chr13 | 0.43818368 | 0.26647091 | 0.00116763 | chr4 + chr6 |
| chr14 | 0.21119571 | 0.25952538 | 0.00054811 | chr5 + chr12 + chr22 |
| chr15 | 0.43655328 | 0.19120781 | 0.00083472 | chr1 + chr10 + chr20 |
| chr16 | 0.40796729 | 0.2909714 | 0.00118707 | chr15 + chr17 + chr19 + chr20 |
| chr17 | 0.43044876 | 0.42765351 | 0.00184083 | chr16 + chr20 + chr22 |
| chr18 | 0.2411015 | 0.23996728 | 0.00057856 | chr5 + chr8 |
| chr19 | 1.31524683 | 1.42233899 | 0.01870727 | chr22 |
| chr20 | 0.32975718 | 0.17240557 | 0.00056852 | chr10 + chr16 + chr17 + chr19 + chr22 |
| chr21 | 0.43611264 | 0.08516148 | 0.0003714 | chr4 + chr14 + chr16 + chr17 |
| chr22 | 1.31897082 | 0.70318839 | 0.00927485 | chr19 |
| chrx | 0.67161441 | 0.28361966 | 0.00190483 | chr4 + chr5 + chr8 |
| chry | 12.85179682 | 0.00035758 | 0.00004596 | chr4 + chr7 |

Having identified the normalizing chromosomes in the qualified samples, the test samples were sequenced, and sequence tags mapping to each of chromosomes 21, 18, 13, and corresponding normalizing chromosomes in the test samples were counted and used to calculate chromosome doses (ratios). NCV values were then calculated as described previously according to $$NCV_{jA} = \frac{R_{jA} - \overline{R_{jU}}}{\sigma_{jU}} \quad \text{Equation 21}$$

For each of the test samples, the fetal fraction was determined for chromosome x and for the chromosome of interest according to the equation $$ff_{(i)} = 2*NCV_{jA}CV_{jU} \quad \text{Equation 25}$$

described elsewhere in the specification.

Figure 60:
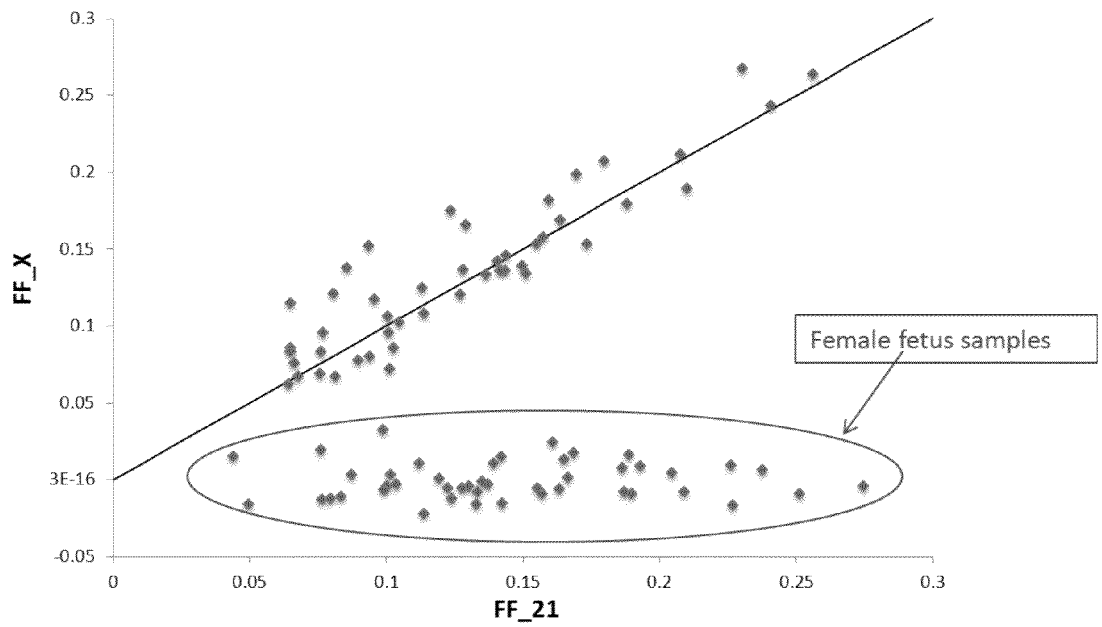
FIG. 60 shows a plot from Example 18 of the CNffx versus CNff21 determined in the samples comprising the fetal T21 trisomy.

FIG. 60 shows a plot of the CNffx versus CNff21 determined in the samples comprising the fetal T21 trisomy. As expected for a complete chromosomal aneuploidy, the CNffx matched that determined using NCVs from chromosome 21 (CNff21).

Figure 61:
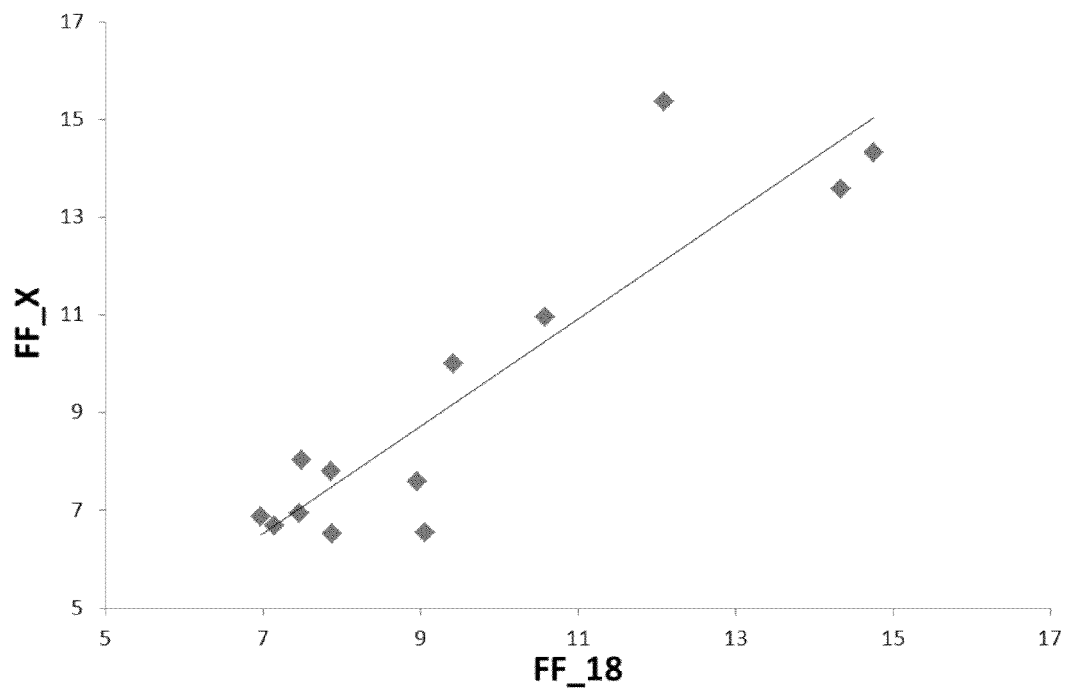
FIG. 61 shows a plot from Example 18 of the CNffx versus CNff18 determined in the samples comprising the fetal T18 trisomy.
Figure 62:
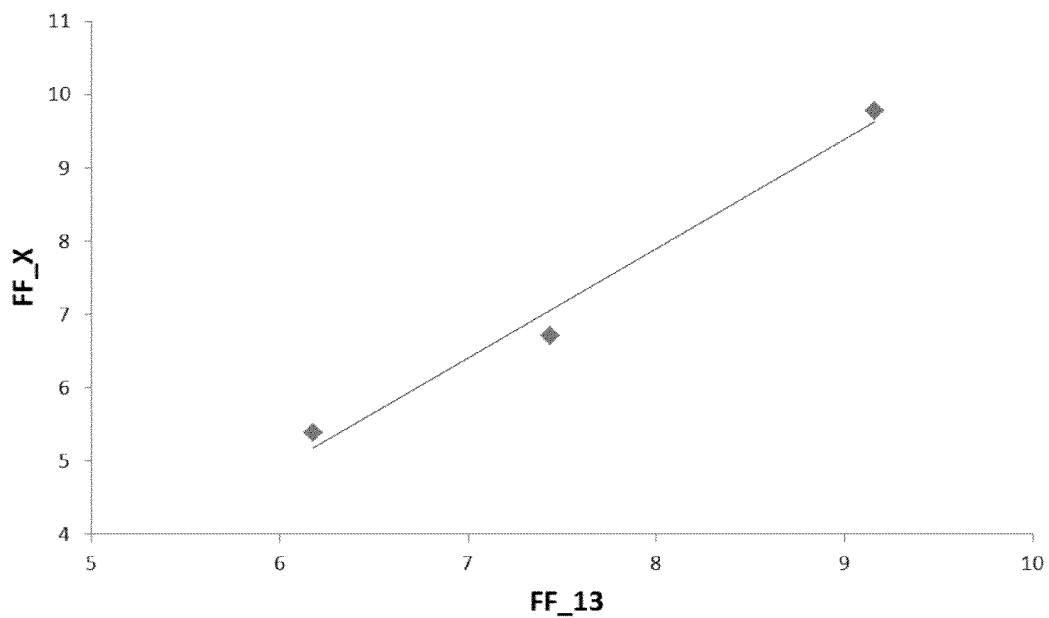
FIG. 62 shows a plot from Example 18 of the CNffx versus CNff13 determined in the samples comprising the fetal T13 trisomy.

Similarly, CNffx matched that determined using NCVs from chromosome 18 (CNff18) in the T18 test samples (FIG. 61), and CNffx matched that determined using NCVs from chromosome13 (CNff13) in the T13 test samples (FIG. 62).

FIG. 60 also shows the fetal fraction obtained for the samples with female fetuses affected by T21. As expected, CNff21 in these "female" samples could not be verified by comparison to chromosome X. In order to verify the CNff21 for the female samples, CNff can be determined for a chromosome known not to the aneuploid in a fetus e.g. chromosome 1. Alternatively, CNff21 for "female" samples can be confirmed by comparing it to a NCNff e.g. one determined by counting tags to polymorphic sequences, as described elsewhere herein.

Therefore, the number of sequence tags and the derived NCV values that identify copy number variations of complete chromosomes can be used to determine the corresponding fetal fraction in the aneuploid/affected samples. Correspondence in the CNff for a chromosome of interest with that of a chromosome known not to be aneuploid can be used to confirm the presence of a complete chromosomal trisomy.

Example 19

Determining Fetal Fraction from NCV to Identify the Presence of Partial Fetal Chromosomal Aneuploidies in Clinical Samples To demonstrate that a ff determined from NCVs (CNff) can be used to identify and localize the presence of a partial chromosomal aneuploidy from a partial chromosomal aneuploidy in a clinical sample, cfDNA from a clinical that had been identified as having an aneuploidy in chromosome 17, was sequenced and analyzed as described in Example 18.

Using sequence tags mapped to chromosome 17 in the test sample, and to normalizing chromosomes chr16+chr20+ chr22 that been identified in the set of qualified samples (Table 28 above), NCV values for each of chromosomes in the test sample were calculated.

Figure 63:
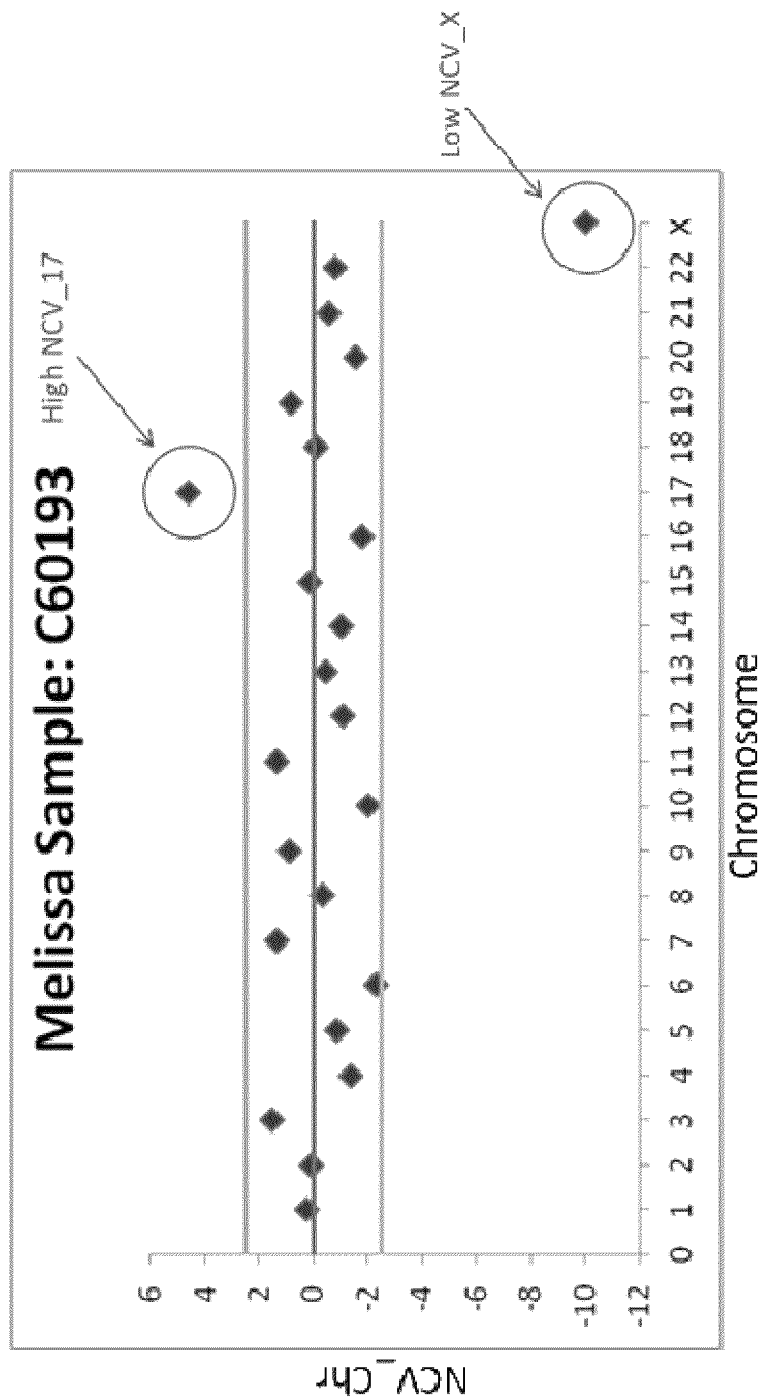
FIG. 63 shows a plot from Example 19 of NCV values for chromosomes 1-22 and X in the test sample.

FIG. 63 shows a plot of NCV values for chromosomes 1-22 and X in the test sample. As is shown in the plot, the NCV value for chromosome 17 was determined to have an NCV>4, which is the threshold that had been chosen for identifying aneuploid chromosomes. The plot also shows the NCV value for chromosome X, which as expected had a negative NCV.

The CNff for chromosome 17 and chromosome X were calculated according to $$ff_{(i)} = 2*NCV_{jA}CV_{jU} \quad \text{Equation 25}$$

and determined to be CNff17=3.9% and CNffX=13.5%.

The discrepancy between the CNff indicated the presence of either a partial aneuploidy or possibly of a mosaicism.

To distinguish the partial aneuploidy from a possible mosaicism, the number of tags counted for each of 100 Kbp consecutive blocks/bins on chromosome 17, and a normalized bin value (NBV) was calculated for each bin. Normalization of the number of tags in individual bins was performed by determining the ratio of tags/bin to the sum of the number of tags in 20 bins of identical size and having a GC content closest to that of the bin being analyzed. Thus, in this instance, normalization was related to GC content. Optionally, bin normalization can also be related to the variability in bin dose as determined in qualified samples as described for chromosome doses/ratios. In this example, the GCC Z-score is equivalent to the NBV value determined as $$NBV_{ij} = \frac{x_{ij} - M_j}{MAD} \quad \text{Equation 26}$$

where $M_j$ and $MAD_j$ are the estimated median and median adjusted deviation, respectively, for the j-th chromosome dose in a set of qualified samples, and $x_{ij}$ is the observed j-th chromosome dose for test sample i.

Figure 64:
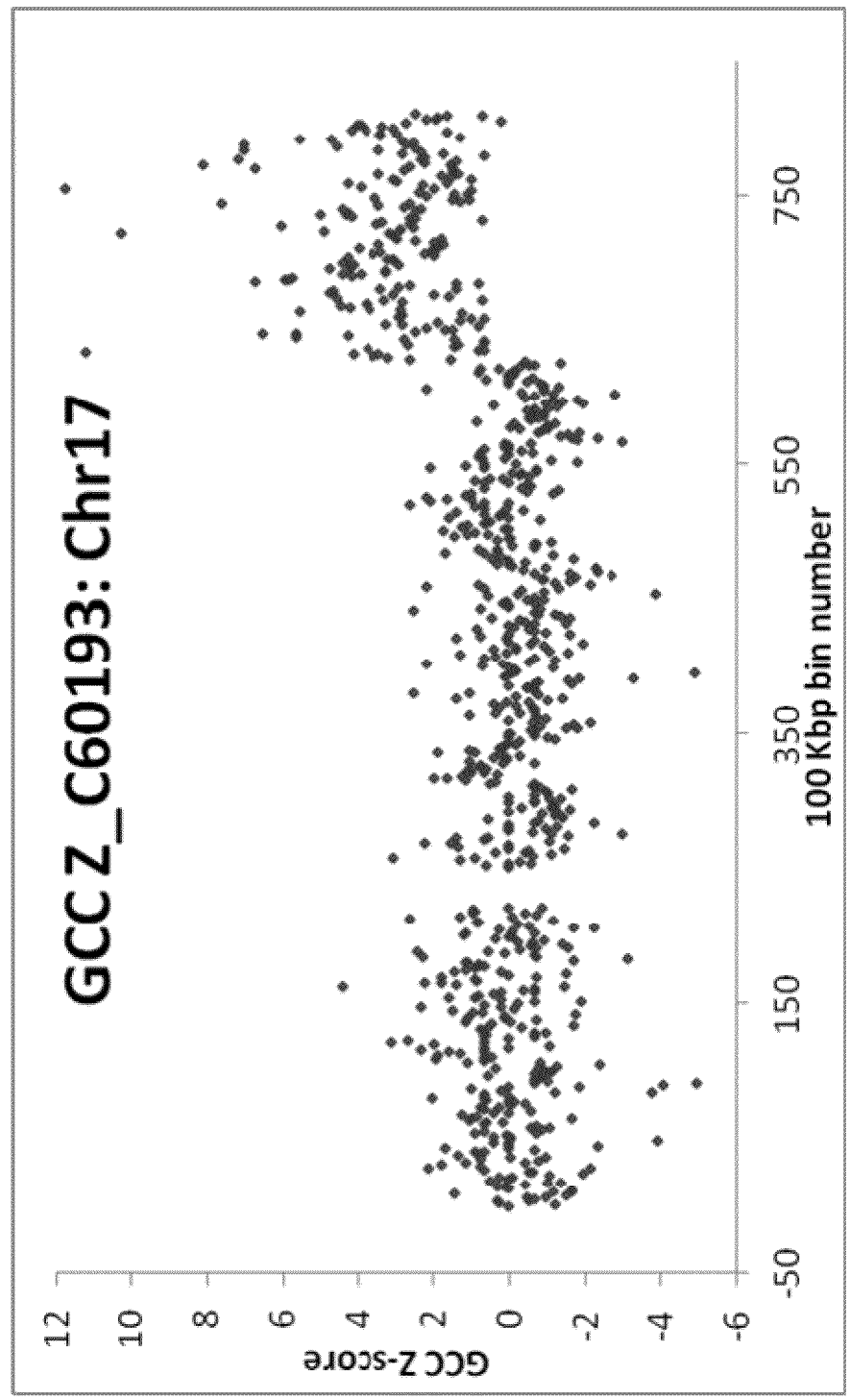
FIG. 64 shows the fetal fraction obtained in Example 18 for the samples with female fetuses affected by T21.

The normalized bin values (NBV) for each of the 100 Kbp bins along the length of chromosome 17 are shown on the Y-axis of FIG. 64 as GCC Z-score, indicating the GC normalization. The plot shown in FIG. 64 clearly shows an increase in copy number of the bins corresponding to approximately the last 200,000 bp of chromosome 17. This finding was in agreement with the karyotype provided for the sample indicating a duplication at the q ter of chromosome 17.

Therefore, CNff can be used to identify and to localize partial aneuploidies in chromosomes.

Example 20

Noninvasive Detection of Fetal Sub-Chromosome Abnormalities Using Deep Sequencing of Maternal Plasma Artificial Mixtures Artificial mixtures of 5% and 10% sheared genomic DNA were prepared using paired mother and child DNAs obtained from the Coriell Institute for Medical Research (Camden, N.J.). All children were males with karyotypes previously determined by metaphase cytogenetic analysis. The karyotypes of the four paired samples are shown in Table 29. The children's chromosome abnormalities were selected to represent different clinical scenarios, such as: a) whole chromosome aneuploidy (family 2139), b) sub-chromosomal deletion (family 1313), c) mosaic sub-chromosomal copy number change (family 2877, with an additional inherited deletion), and d) sub-chromosomal duplication (family 1925).

The genomic DNA samples were sheared to a size of ~200 bp using the Covaris S2 sonicator (Covaris, Woburn, Mass.) following the manufacturer's recommended protocols. DNA fragments smaller than 100 bp were removed using AmPure XP beads (Beckman Coulter Genomics, Danvers, Mass.). Sequencing libraries were generated with TruSeq v1 Sample Preparation kits (Illumina, San Diego, Calif.) from sheared DNA mixtures consisting of maternal DNA only and maternal+child DNA mixtures at 5% and 10% w/w. Samples were sequenced with single-ended 36 base pair (bp) reads on the Illumina HiSeq2000 instrument using TruSeq v3 chemistry. Each sample was sequenced on four lanes of a flow cell, resulting in $400 \times 10^6$ to $750 \times 10^6$ sequence tags per sample.

Maternal Plasma Samples

The MatErnal BLood IS Source to Accurately Diagnose Fetal Aneuploidy (MELISSA) trial was a registered clinical trial (NCT01122524) that recruited subjects and samples from 60 different centers in the United States. The study was designed to prospectively determine the accuracy of MPS (massively parallel sequencing) to detect whole chromosome fetal aneuploidy. During this trial, all samples with any abnormal karyotype were included to emulate the real clinical scenarios in which the fetal karyotype is not known at the time of sample acquisition. The results of this study have been previously published. Following completion of the MELISSA trial, the study database was assessed to identify ten samples that had complex karyotypes, including sub-chromosome abnormalities, material of unknown origin, or a marker chromosome (Table 30); also added was one MELISSA study sample with trisomy 20 as a control of performance in detection of whole chromosome aneuploidy. The karyotypes were performed for clinical indications and reflected local protocols. For example, some samples were analyzed with chromosome microarrays and some had metaphase analysis with or without FISH studies.

In the MELISSA study libraries were sequenced using single-end reads of 36 bp with 6 samples in a lane on an Illumina HiSeq2000 using TruSeq v2.5 chemistry. In the present example, the previously generated MELISSA libraries were re-sequenced using TruSeq v3 chemistry on an Illumina HiSeq 2000 with single-end reads of 25 bp. In this example, each of the 11 maternal samples was sequenced utilizing an entire flow cell, resulting in $600 \times 10^6$ to $1.3 \times 10^9$ sequence tags per sample. All sequencing was performed in the Verinata Health research laboratory (Redwood City, Calif.) by research laboratory personnel who were blinded to the fetal karyotype.

TABLE 29

Coriell samples used to generate artificial mixtures.

| amily ID | oriell ID | Member | Karyotype |
|---|---|---|---|
| 139 | G09387 | Mother | 46, XX |
|  | G09394 | Affected Son | 47, XY, +21 |
| 313 | A10924 | Mother | 46, XX |
|  | A10925 | Affected Son | 46, XY, del(7)(pter > p14::p12 > qter) |
| 877 | A22629 | Mother | 46, XX, del(11) |
|  | A22628 | Affected son | 47, XY, del(11)(pter-> p12::p11.2 > qter), +15[12]/ 46, XY, del(11)(pter->p12::p11.2->qter)[40] |
| 925 | A16268 | Mother | 46, XX |
|  | A16363 | Unaffected twin son | 46, XY |
|  | A16362 | Affected twin son | 47, XY, +der(22) |

TABLE 30

Karyotypes of clinical samples analyzed by MPS. Samples with shading are mosaic karyotypes.

| atient ID | Specimen | Procedure | Karyotype |
|---|---|---|---|
| 60715 | Chorionic villi | Metaphase and 20q12 FISH | 47, XX, +20 |
| 65104 | Cultured villi | Metaphase, 6q12, 6q16.3 FISH and microarray | arr 6q12q16.3(64, 075, 795-101, 594, 105)x3, 6q16.3(102, 176, 578-102, 827, 691)x3 |
| 61154 | Chorionic villi | Metaphase | 46, XY, del(7)(q36.1) |
| 61731 | Amniocytes | Metaphase and 22q FISH | 46, XX, del(8) (p23.1p23.2) |
| 62228 | Chorionic villi | Metaphase and Chr15 FISH | 45, XX, -15, der(21) t(15; 21) q15; p11.2) |
| 60193 | Amniocytes | Metaphase | 46, XY, add(10)(q26) |
| 61233 | Amniocytes | Metaphase | 46, XY, add (X) (p22.1) |
| 61183 | Amniocytes | Metaphase and FISH | 46, XY or 46, XY, add(15)(p11.2) |
| 65664 | Amniocytes | Metaphase | mos 46, XY, +i(20)(q10)[8]/ 46, XY[17] |
| 66515 | Chorionic villi | Metaphase and FISH | 47, XY, +der(14 or 22)[10]/46, XY[10] |
| 60552 | Chorionic villi | Metaphase | 47, XX + mar [12]/46, XX[8] |

Normalization and Analysis

Sequence reads were aligned to the human genome assembly hg19 obtained from the UCSC database (hgdownload.cse.ucsc.edu/goldenPath/hg19/bigZips/). Alignments were carried out utilizing the Bowtie short read aligner (version 0.12.5), allowing for up to two base mismatches during alignment. Only reads that unambiguously mapped to a single genomic location were included. Genomic sites at which reads mapped were counted as tags. Regions on the Y chromosome at which sequence tags from male and female samples mapped without any discrimination were excluded from the analysis (specifically, from base 0 to base $2 \times 10^6$; base $10 \times 10^6$ to base $13 \times 10^6$; and base $23 \times 10^6$ to the end of chromosome Y).

The genome was then further divided into 1 Mb and 100 kb bins and, for each sample, tags from both the positive and negative strand were assigned to individual bins for further analysis. The GC percentage of each bin was determined and bins were ranked by GC percentage across the entire genome. Each bin was individually normalized by calculating the ratio of tags within a bin to the sum of the number of tags in the 10 bins with the nearest GC percentages by equation (27):

$$BRV_{ij} = \frac{Tags_{ij}}{\sum Tags_{km}}$$

Where $BRV_{ij}$ is the "Bin Ratio Value" for the $j^{th}$ bin of chromosome i, and $Tags_{ij}$ is the number of tags in the $j^{th}$ bin of chromosome i. The sum runs over the 10 bins for the 1 Mb data and 40 bins for the 100 kb data for bins (kin) with the nearest GC percentage to bin ij.

In order to detect any sub-chromosomal differences, each of the BRVs were examined for deviations from the median values measured across multiple samples. The medians were determined from the four maternal only DNAs (Table 29) for the artificial samples and from the eleven maternal plasma samples (Table 30) for the clinical samples. Median absolute deviations (MADs) were calculated for each bin based on the medians and adjusted assuming a normal distribution for the number of tags in each bin. The adjusted MADs (aMADs) were utilized to calculate a z-score for each bin by equation (28):

$$z_{ij} = \frac{(BRV_{ij} - BRV_{Median_{ij}})}{aMAD_{ij}}$$

It was expected that $z_{ij}$ would be approximately ±3 for regions without any copy number variations (CNVs) and significantly greater than 3 when fetal CNVs were present.

The $z_{ij}$ values can be utilized to determine the relative fetal fraction (ff) present in the cfDNA. The value can then be compared to an independent measurement of ff to validate copy number detection, or suggest the presence of mosaicism. For a bin ratio containing a copy number change from normal, the $BRV_{ij}$ will increase (in the case of a duplication) or decrease (in the case of a deletion) by equation (29):

$$BRV_{ij} = \left(1 \pm \frac{ff_n}{2}\right) BRV_{Median_{ij}}$$

In this equation, $ff_n$ is the fetal fraction for sample n. If the coefficient of variation for each bin, $CV_{ij}$ is defined as equation (30):

$$CV_{ij} = \frac{aMAD_{ij}}{BRV_{Median_{ij}}}$$

then equation (31)

$$ff_n = \text{abs}(2 z_{ij} CV_{ij})$$

can be used to calculate $ff_n$ for sample n from $z_{ij}$ values.

Detection of a sub-chromosomal abnormality was a multi-step process for classifying specific regions as having a copy number variant. In step 1, $z_{ij}$ values from the 1 Mb bins that exceeded ±4 were identified. The calculated ff was then utilized and bins that had a ff of less than 4% were eliminated. For the samples with male fetuses, the ff was also calculated using all of the bins in chromosome X. This value was compared to the result obtained for putative copy number changes to validate a copy number change or suggest a mosaic result. Finally, in cases of a single 1 Mb bin that met the above criteria, the 100 kb bins data were examined and it was required that at least 2 bins (within a contiguous group of 4) indicated a $z_{ij}$ value that exceeded +4 or −4 before classifying a sample as having a copy number variant.

Results

Artificial Mixtures

Whole Chromosome Aneuploidy of Chromosome 21

Figure 65:
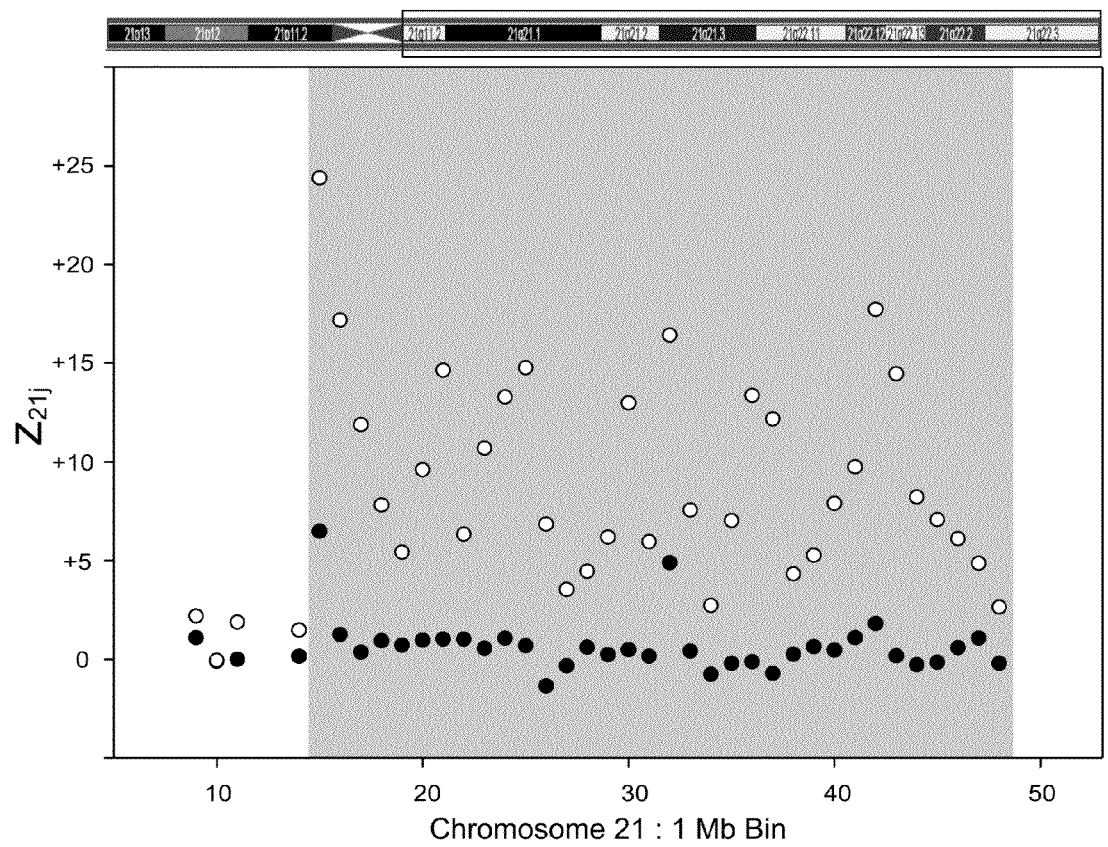
FIG. 65 shows the family 2139 $z_{21j}$ 1 Mb bin results for Chr 21 with 0% (solid circles) and 10% (empty circles) mixtures of the affected son's DNA mixed with the mother's DNA.

FIG. 65 shows the chromosome 21 $z_{21j}$ values (1 Mb bins) for an artificial mixture of family 2139 with 10% of the son's DNA (T21) mixed with the mother's DNA. In chromosome 21, there are approximately 38 Mb in the q arm that contain unique reference genome sequence in hg19. All of the chromosome 21 tags mapped to this region. With the exception of the first 4 Mb, FIG. 65 shows an over-representation of most of chromosome 21 in the 10% mixture, as would be expected with a full chromosome aneuploidy. Using equation (5) to calculate the ff from the average $z_{21j}$ values of the amplified regions, ffs of 7.0% and 12.7%, for the 5% and 10% mixtures, respectively, were obtained. Calculating the ff average using $z_{Xj}$ values, ffs of 4.2% and 9.0%, for the 5% and 10% mixtures, respectively, were obtained.

Sub-Chromosomal Deletion of Chromosome 7

Figure 66:
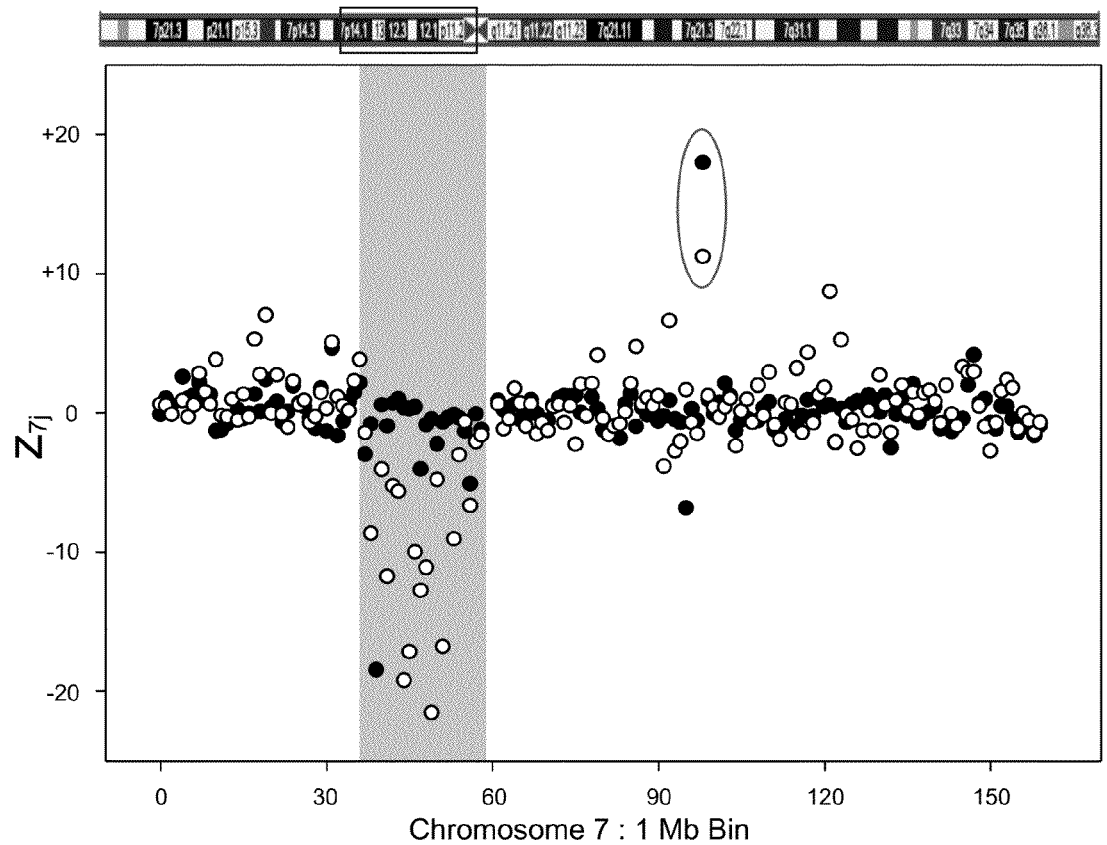
FIG. 66 shows the family 1313 $z_{7j}$ 1 Mb bin results for Chr 7 with 0% (solid circles) and 10% (empty circles) mixtures of the affected son's DNA mixed with the mother's DNA.

The method was next tested on Family 1313, in which the son has a sub-chromosomal deletion of chromosome 7. FIG. 66 shows the chromosome 7 $z_{7j}$ values (1 Mb bins) for the maternal sample mixed with 10% of her son's DNA. A deletion was observed beginning at bin 38 and continuing to bin 53. This reflects the approximately 15 Mb deletion documented in the metaphase karyotype. Fetal fraction values ffs of 6.1% and 10.5% were calculated for the 5% and 10% mixtures, respectively, for this sample. Calculating the ff average using $z_{Xj}$ values, ffs of 5.9% and 10.4% were obtained, respectively. Interestingly in this sample there appeared to be a duplication in the maternal sample at bin 98 of chromosome 7 (circle in FIG. 66), which did not appear in the son, i.e. was not inherited, and a concomitant value decrease was observed in the mixture. Bin 2 which had very high $z_{72}$ values of 43.9 and 28.5 for the maternal sample and 10% mixture, respectively (data not shown) also appeared to reflect a maternal duplication.

Mosaic Duplication of Chromosome 15

Figure 67:
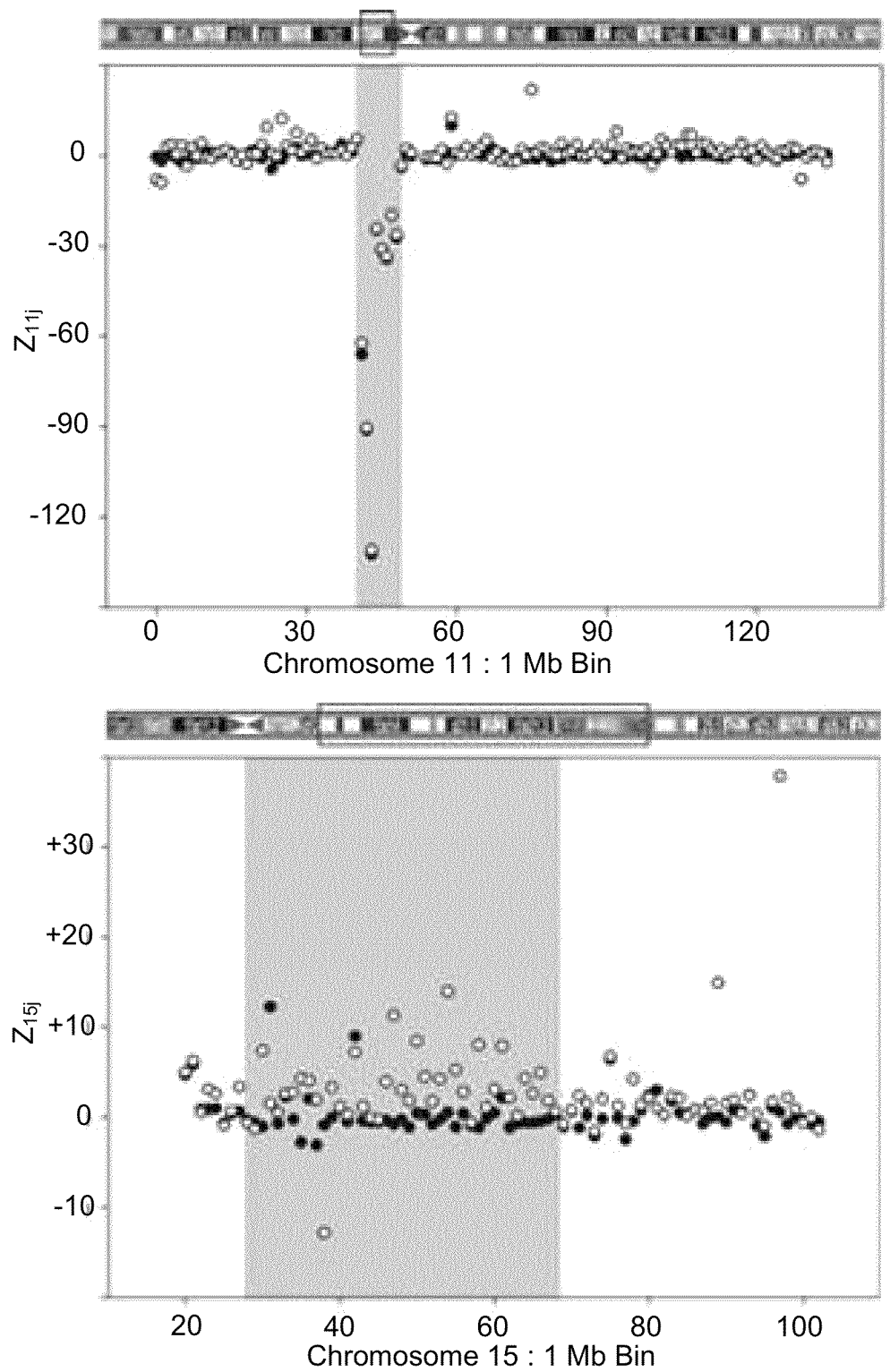
FIG. 67 shows the family 2877 $z_{ij}$ 1 Mb bin results for Chr 11 and 15 with 0% (solid circles) and 10% (empty circles) mixtures of the affected son's DNA mixed with the mother's DNA.

In Family 2877, the maternal sample has a deletion in chromosome 11 that was inherited by the son. In addition, the son has a duplication in chromosome 15 that was not maternally inherited, and is part of a mosaic karyotype in which the majority of cells are normal (Table 29). FIG. 67 shows both the chromosome 11 and chromosome 15 $z_{ij}$ values for the 1 Mb bins in the mixture with 10% of the son's DNA. As expected, the inherited deletion in chromosome 11 had a consistent set of values that did not change with fetal fraction. However, the chromosome 15 duplication was clearly detected between bins 28 and 65, albeit with more noise than observed in the other artificial samples. The noise results from the reduced apparent ff for this duplication due to the mosaicism. The ffs calculated from the duplication were 1.6% and 3.0% for the 5% and 10% mixtures, respectively. In contrast, the ffs calculated from chromosome X were 5.3% and 10.7%. The method was able to detect both the sub-chromosomal duplication with the low mosaic ff and to distinguish that the duplication was due to mosaicism by comparison of the ff result to an independent measurement of chromosome X.

Duplications of Chromosome 22

Family 1925 consisted of a mother and two male twins, one of which had two duplications of different sizes in chromosome 22. Ten percent mixtures of the affected twin's DNA and the mother were sequenced. The results indicated a 2 Mb and an 8 Mb duplication at bins 17 and 43, respectively. The ff for 10% mixture was calculated to be 11.2% from the 2 Mb duplication, 11.6% from the 8 Mb duplication, and 9.8% from chromosome X (data not shown).

Maternal Plasma Samples

Whole Chromosome Aneuploidy

Sample C60715 was previously reported in MELISSA study as detected for trisomy 20. The ff calculated from the whole chromosome 20 data (i.e. ~11 million tags without binning) was 4.7%. The 1 Mb bin results for this sample contain ~960 million tags across the genome. The extra copy of chromosome 20 was clearly detected and the ff calculated from the 1 Mb bin data is 4.4%, in agreement with the whole chromosome results.

Duplications and Deletions

Figure 68A:
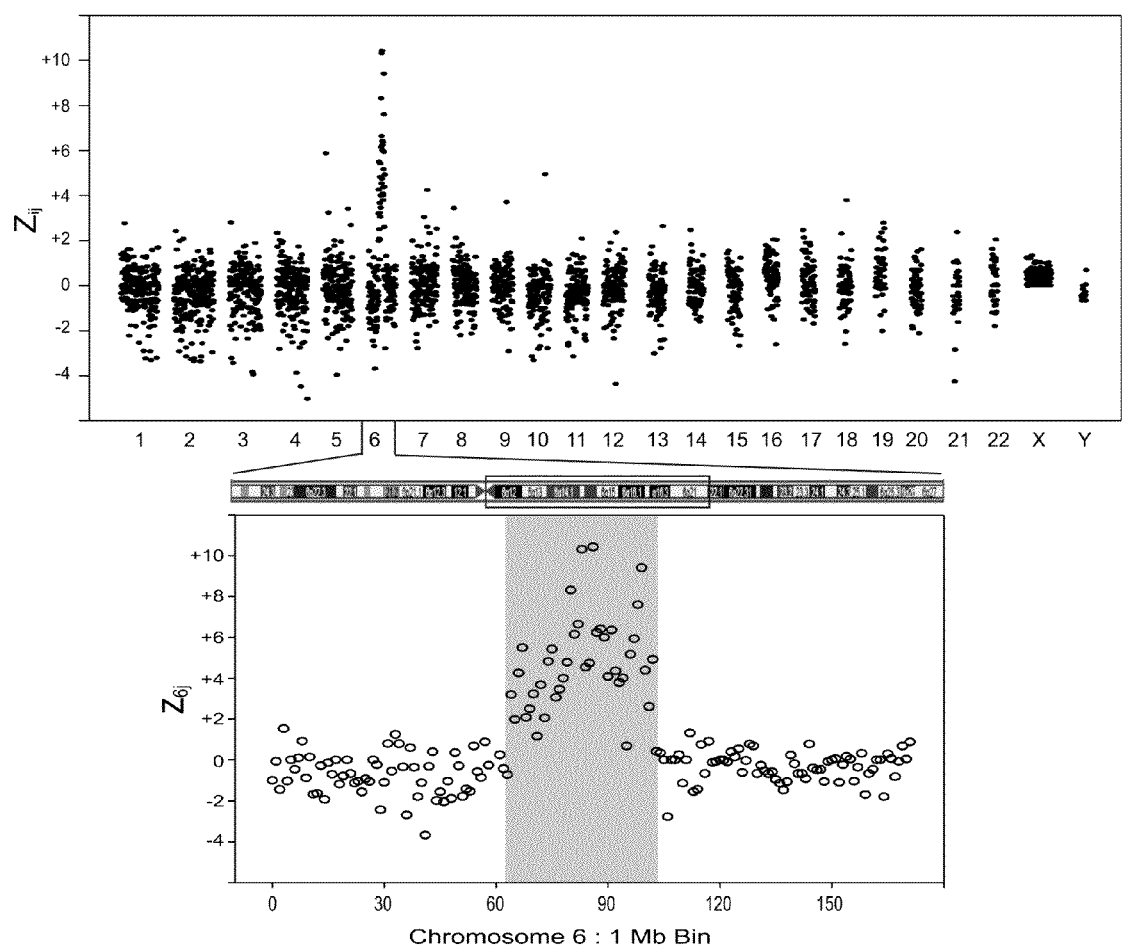
FIG. 68(a)-(b) show clinical sample C65104 $z_{ij}$ 1 Mb bin results with a karyotype with duplication in chromosome 6. Expanded regions show $z_{6j}$ 1 Mb bin and 100 kb bin results.
Figure 68B:
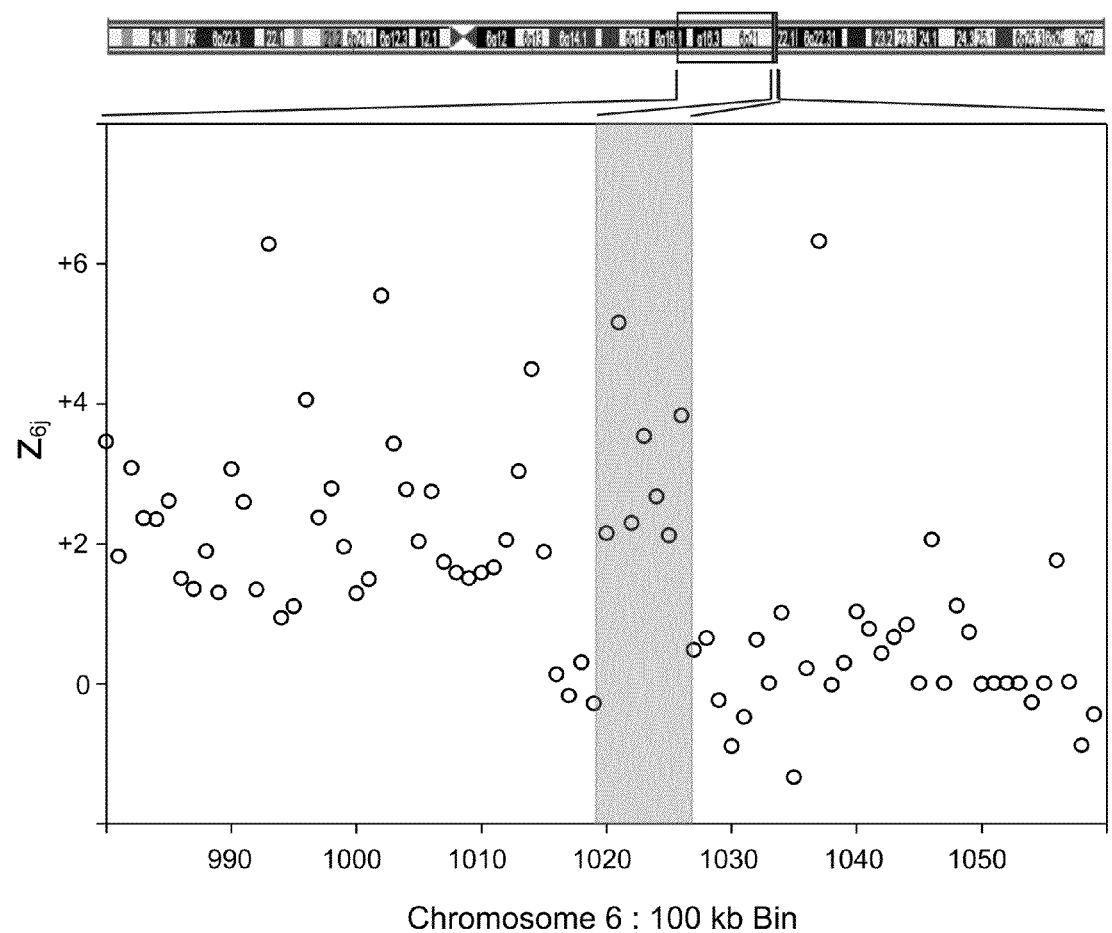

Sample C65104 (Table 31) had a complex fetal karyotype that involved the long arm of chromosome 6 (6q) and two duplications, one of which was 37.5 Mb in size. The second duplication was reported as approximately 650 kb from the chromosome microarray analysis of cultured villi. Using MPS it was previously reported that this sample showed an increased whole chromosome normalized chromosome value (NCV) in chromosome 6 (NCV=3.6). Bianchi, D. W., Platt, L. D., Goldberg, J. D., Abuhamad, A., Sehnert, A. J., Rava, R. P. (2012). Genome-wide fetal aneuploidy detection by maternal plasma DNA sequencing. Obstet. Gynecol. 119, 890-901. This value was insufficient to classify this sample as having a full chromosome aneuploidy, but it was consistent with the presence of a large duplication. FIG. 68 shows the 1 Mb bin results for this sample. All the chromosomes other than chromosome 6 showed z values that clustered around 0. By focusing only on chromosome 6 (FIG. 68), the exact region of the 38 Mb duplication was identified. This 38 Mb corresponded to the large duplication seen in the microarray karyotype, and the ff calculated from this duplication was 11.9%. The second duplication in the microarray karyotype was not detected a priori by our criteria; however, it can be clearly seen in the 100 kb bin expansion of the region (FIG. 68). Improved analytic methodology and/or deeper sequencing would clearly allow this duplication to be detected. Finally, a 300 kb gain in chromosome 7 at 7q22.1 was also identified by MPS in agreement with the microarray results (Table 31).

TABLE 31

MPS results on clinical samples that are congruent with the clinically reported karyotype.

| Patient ID | Affected Chr | Gain/ Loss | Start bin | End bin | Size (Mbp) | Chromosome region |
|---|---|---|---|---|---|---|
| C65104 | 6 | Gain | 64 | 102 | 38 | 6q12-6q16.3 |
|  | 7 | Gain | 98.1 | 98.3 | 0.3 | 7q22.1 |
| C61154 | 7 | Loss | 150.3 | 150.6 | 0.3 | 7q36.1 |
| C61731 | 8 | Loss | 2 | 12 | 10 | 8p23.2-8p23.2 |
| C62228 | 15 | Loss | 23 | 39 | 16 | 15q11.2-15q14 |
| C60193 | 17 | Gain | 62 | 81 | 19 | 17q23.3-17q25.3 |
|  | 10 | Loss | 134 | 135 | 2 | 10q26.3 |
| C61233 | 3 | Gain | 158 | 198 | 40 | 3q25.32-3q29 |
|  | X | Loss | 1 | 10 | 9 | Xp22.33-Xp22.31 |

Figure 69A:
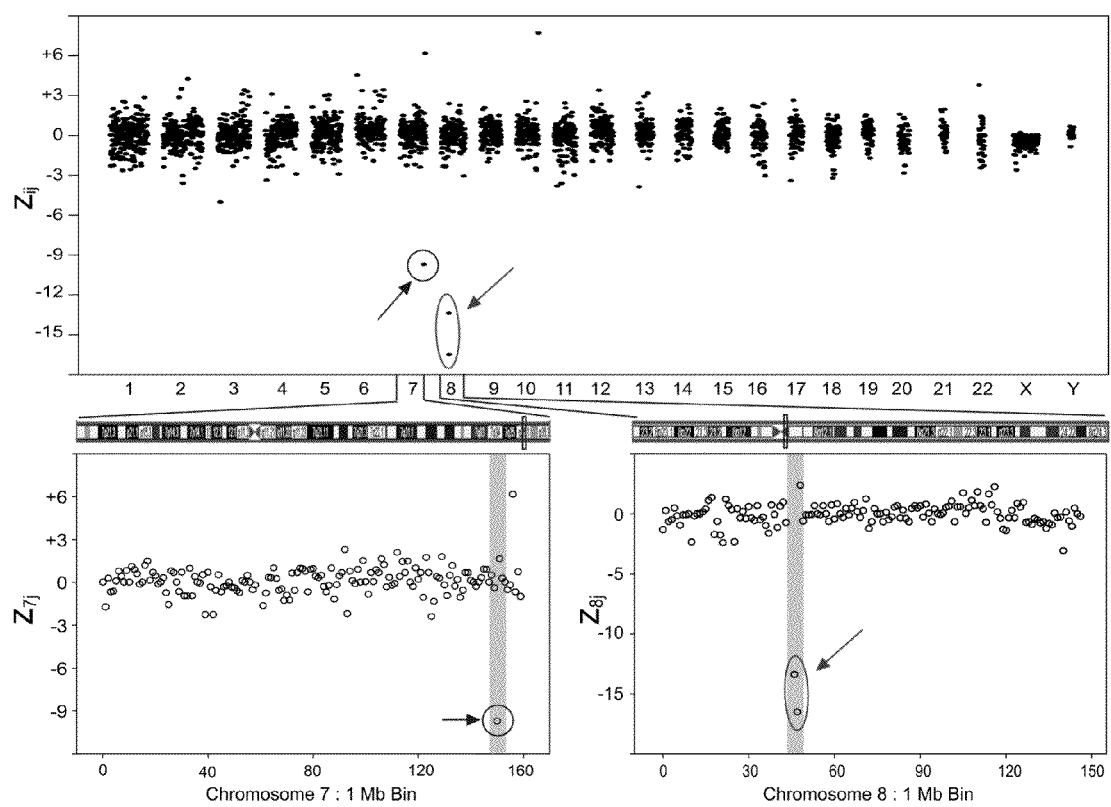
FIG. 69(a)-(b) show the clinical sample C61154 $z_{ij}$ 1 Mb bin results across the genome for clinical sample with a karyotype with a small deletion in chromosome 7 (circled). Another small deletion is detected in chromosome 8 (red circle). Expanded regions show $z_{7j}$ and $z_{8j}$ 100 kb bin data.
Figure 69B:
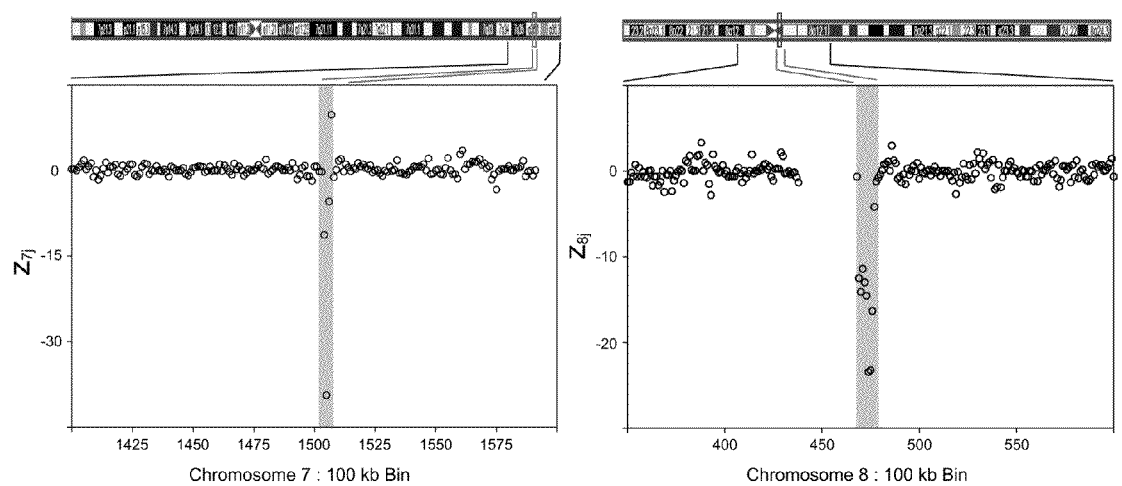

Sample C61154 came from a pregnant woman carrying a fetus with a 7q36.1 deletion detected by metaphase karyotype analysis of chorionic villi. FIG. 69 shows the 1 Mb bin results for this sample. Only chromosomes 7 and 8 showed 1 Mb bins with z values that met our criteria for classification. Chromosome 7 showed a single 1 Mb bin with a significant decrease in the z value at 7q36.1 (denoted by circle in FIG. 69). An examination of the data at higher resolution (100 kb bins) (FIG. 69) showed a deletion of approximately 300 kb, which was consistent with the karyotype report (Table 31). In this sample it was also observed an approximately 1 Mb deletion in both the 1 Mb and 100 kb bin data close to the centromere of chromosome 8 (as shown by the oval in FIG. 69). The chromosome 8 deletion was not reported in the karyotype obtained from chorionic villi (Table 32). The ffs calculated from the chromosome 7 and 8 deletions were 18.4% and 68.5%, respectively. The ff calculated from chromosome X was 2.8%. In this case, the high ff value for chromosome 8 indicated that this deletion, which was not reported in the fetal metaphase karyotype, was maternal in origin. In addition, the discordant value of the chromosome 7 compared to chromosome X ff values suggests that part of the signal could be due to the mother. The karyotype report indicated that the chromosome 7 "abnormality is most likely a derivative from a carrier parent," which is consistent with the MPS data.

Figure 70:
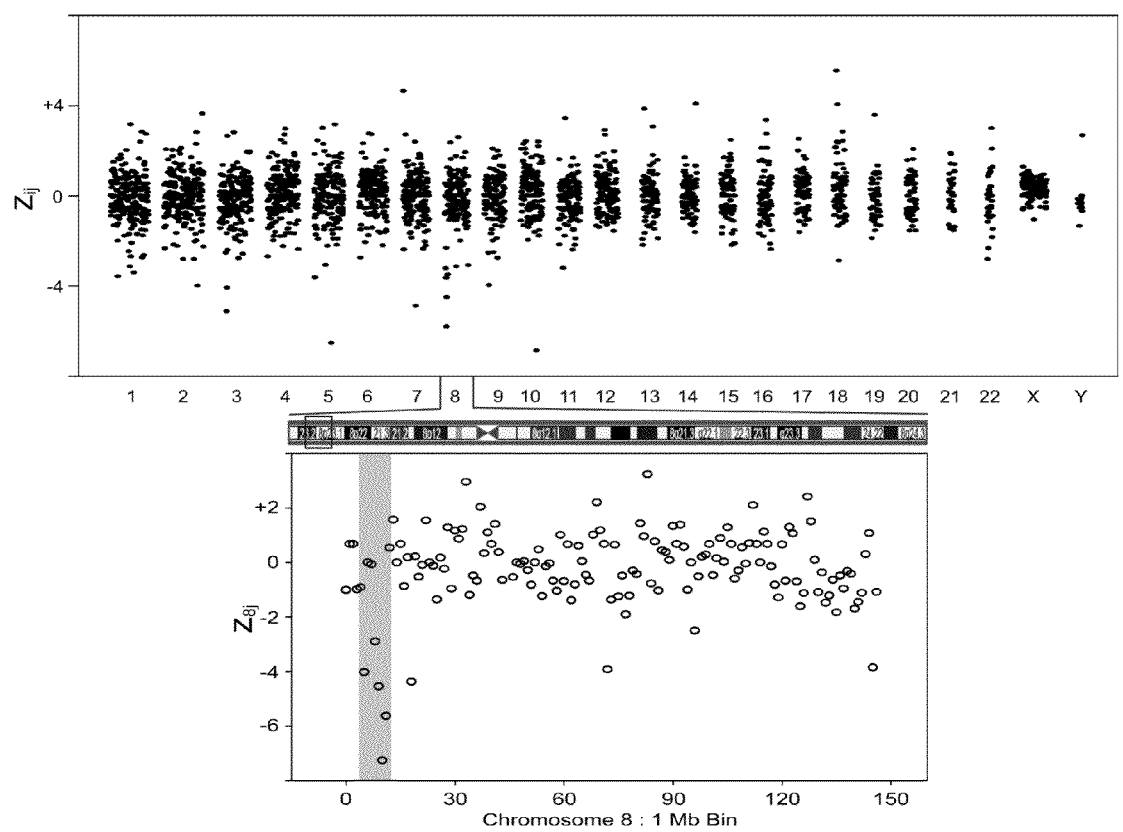
FIG. 70 shows the clinical sample C61731 $z_{ij}$ 1 Mb bin results across the genome for clinical sample with a karyotype with a small deletion in chromosome 8. Expanded region show $z_{8j}$ 1 Mb bin data.

Sample C61731 had a partial deletion of the short arm of chromosome 8. The 1 Mb bin results (FIG. 70) indicated an approximately 5 Mb deletion in the p-arm of chromosome 8 in agreement with the karyotype (Table 31). The fetal fraction calculated from this chromosome deletion was 8.4%.

Translocations

Figure 71:
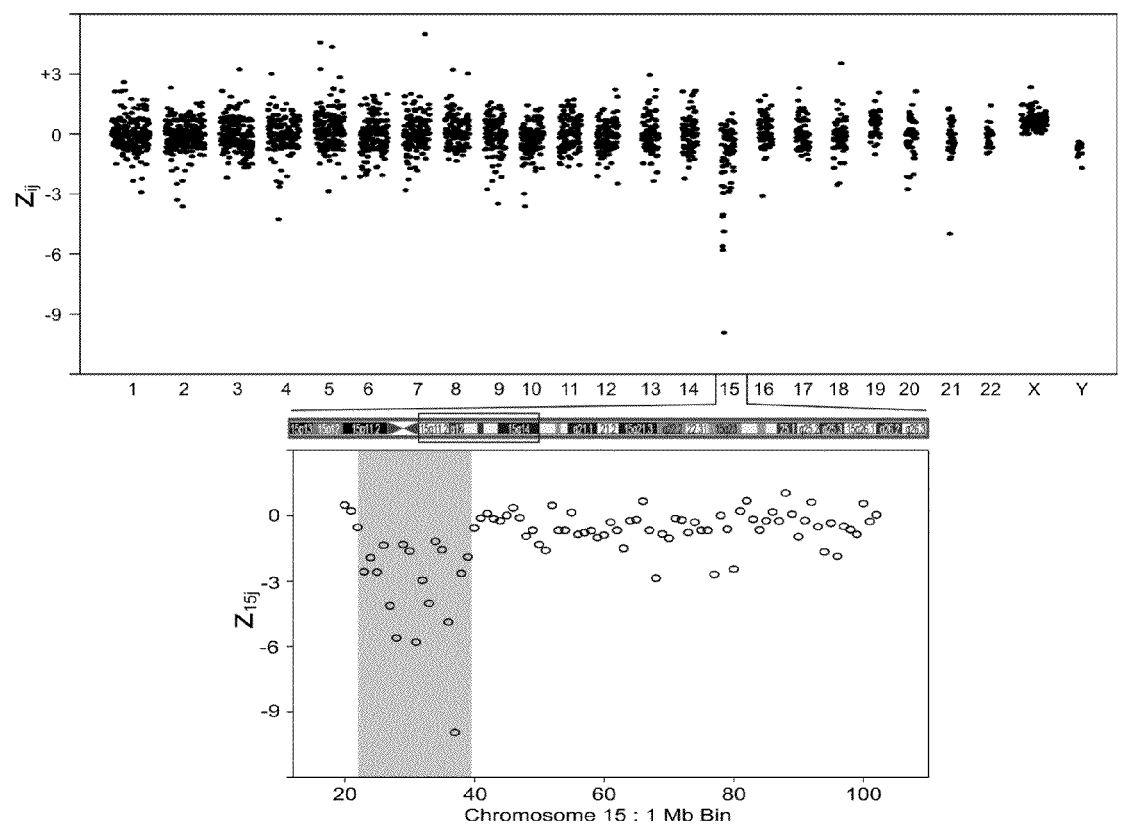
FIG. 71 shows the clinical sample C62228 $z_{ij}$ 1 Mb bin results across the genome for clinical sample with a karyotype with a deletion in chromosome 15. Expanded region show $z_{15j}$ 1 Mb bin data.

The fetal karyotype for sample C62228 showed an unbalanced translocation consisting of 45, XX, −15, der(21) t (15; 21) (q15;p11.2). The 1 Mb bin results for this sample are shown in FIG. 71. There was a clear 20 Mb deletion in chromosome 15 in agreement with the karyotype (Table 31). The ff calculated from the chromosome 15 deletion was 11.3%. No sub-chromosomal abnormalities were detected in the chromosome 21 data to indicate the translocation breakpoint.

Identification of Additional Material Not Identified by Karyotype

Figure 72:
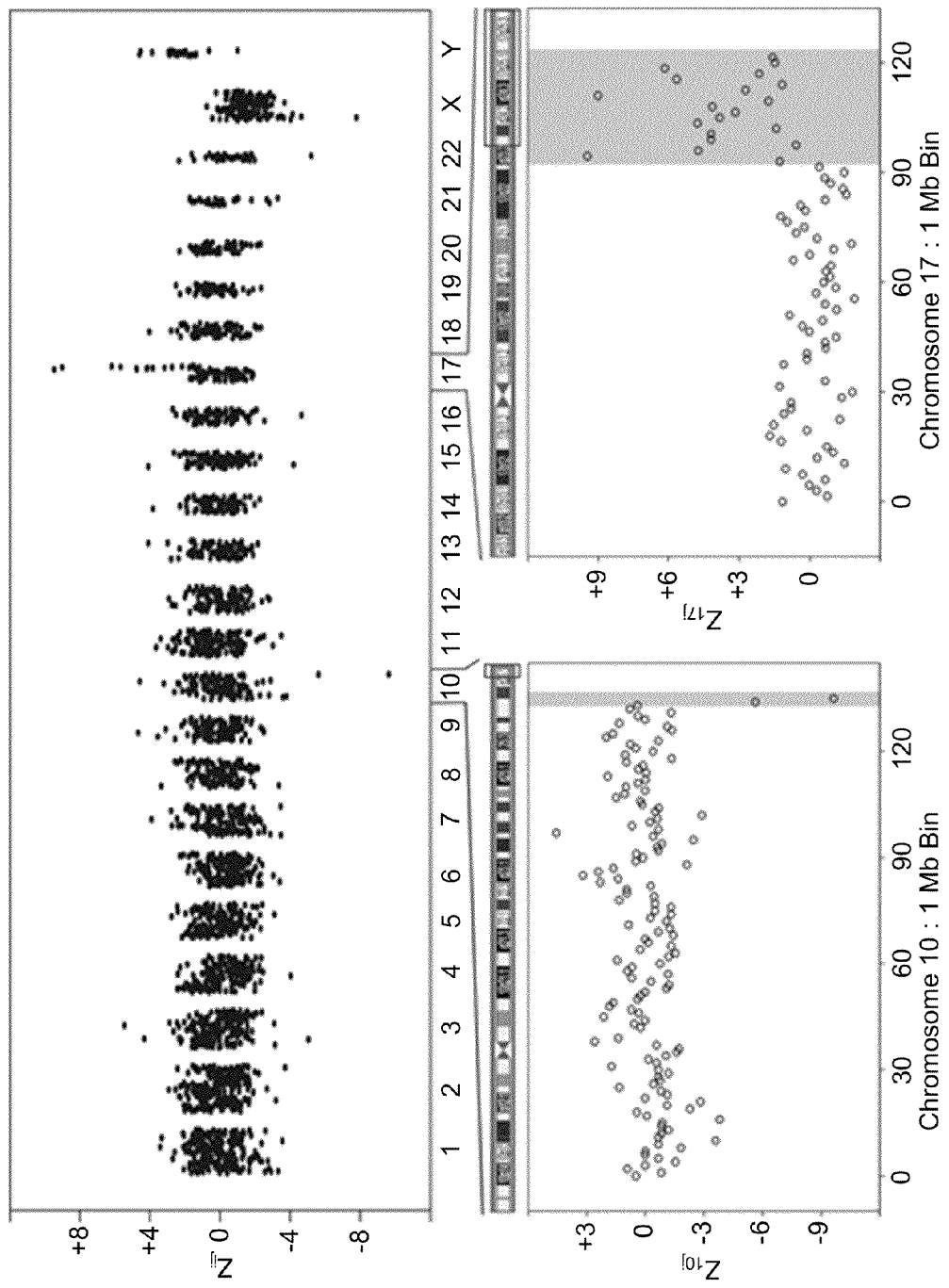
FIG. 72 shows the clinical sample C61093 $z_{ij}$ 1 Mb bin results across the genome with a karyotype 46, XY, add(10) (q26). Expanded regions show $z_{10j}$ and $z_{17j}$ 1 Mb bin data.

Two maternal samples had fetal karyotypes with added material of unknown origin at specific chromosomes. The 1 Mb bin results for sample C60193 are shown in FIG. 72. From the MPS data, the additional material of unknown origin on the long arm of chromosome 10 appeared to be derived from an approximately 17 Mb duplication at the q terminus of chromosome 17. There was also an approximately 2 Mb deletion at the q terminus of chromosome 10 that was confirmed by the 100 kb bin data. The ffs calculated from the chromosome 17 duplication and chromosome X (male fetus) were 12.5% and 9.4%, respectively. The 2 Mb deletion on chromosome 10 had a calculated ff of 19.4%. Finally, the MPS results for this sample indicated a small (300 kb) deletion in chromosome 7 that was not reported in the metaphase karyotype (Table 32).

Figure 73:
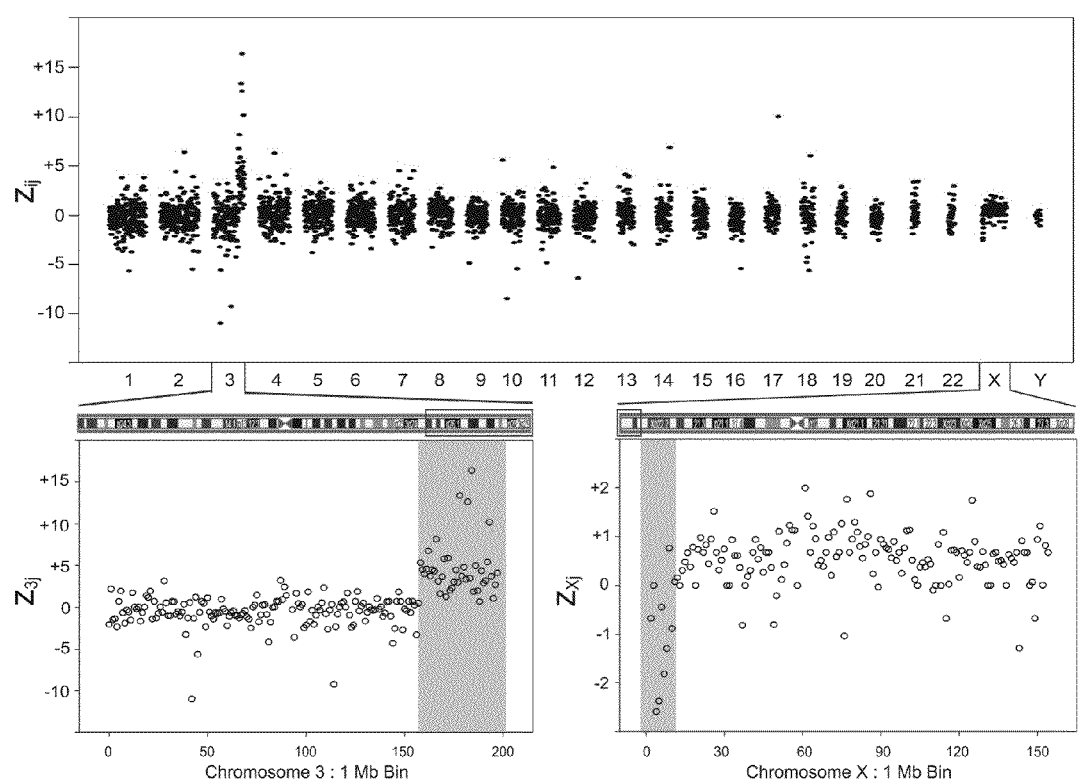
FIG. 73 shows the clinical sample C61233 $z_{ij}$ 1 Mb bin results across the genome with a karyotype 46,XX,add(X) (p22.1). Expanded regions show $z_{3j}$ and $z_{Xj}$ 1 Mb bin data.61233.

The 1 Mb bin results for sample C61233 are shown in FIG. 73. The karyotype for this sample indicated additional chromosomal material on the short arm of one of the X chromosomes. The additional material of unknown origin appeared to originate from a 40 Mb duplication at the q terminus of chromosome 3. There was also an approximately 9 Mb deletion on the p arm of chromosome X (Table 31). The ffs calculated from the chromosome 3 duplication and chromosome X deletion were 9.5% and 6.7%, respectively. The MPS results for this sample also indicated three small sub-chromosomal changes that were not reported in the metaphase karyotype (Table 32).

TABLE 32

Copy number variants detected by MPS that were not reported in the clinical karyotypes.

| Pat ID | Affected Chr | Gain/ Loss | Start bin | End bin | Size (Mbp) | Chromosome region |
|---|---|---|---|---|---|---|
| C60715 | 2 | Gain | 87.3 | 87.9 | 0.6 | 2p11.2 |
|  | 2 | Loss | 89.8 | 90.2 | 0.5 | 2p11.2 |
| C61154 | 8 | Loss | 46.9 | 47.7 | 0.9 | 8q11.1 |
| C60193 | 7 | Loss | 158.7 | 158.9 | 0.3 | 7q36.3 |
| C61233 | 3 | Loss | 114 | 114.5 | 0.6 | 3q13.31 |
|  | 11 | Loss | 55.5 | 85.4 | 0.2 | 11q11 |
|  | 17 | Gain | 81 | 81.1 | 0.2 | 17q25.3 |
| C61183 | 1 | Loss | 12.8 | 13 | 0.3 | 1p36.21 |
| C65664 | 7 | Loss | 39.3 | 40 | 0.8 | 7p14.1 |
|  | 14 | Loss | 58 | 58.1 | 0.2 | 14q23.1 |
| C66515 | 9 | Gain | 40.7 | 41 | 0.4 | 9p31.1 |
| C60552 | 6 | Loss | 151.4 | 151.5 | 0.2 | 6q25.1 |
|  | 22 | Gain | 25.6 | 25.9 | 0.4 | 22q11.23 |

Mosaic Karyotypes

Four of the samples listed in Table 30 (C61183, C65664, C66515, C60552) had mosaic karyotypes with sub-chromosomal abnormalities. Unfortunately for three of the samples (C61183, C66515, C60552) the putative sub-chromosomal abnormality originates in regions of the genome for which information is either unavailable in the genome build or highly repetitive and not be accessible for analysis. Thus, in this case, the process was unable to determine the sub-chromosomal abnormalities reported in these three samples. The $z_{ij}$ values were all close to and centered around zero. Sample C65664 had a mosaic karyotype with isochromosome 20q, an abnormality that is associated with an event secondary to post zygotic error. Chen, C.-P. (2003) Detection of mosaic isochromosome 20q in amniotic fluid in a pregnancy with fetal arthrogryposis multiplex congenita and normal karyotype in fetal blood and postnatal samples of placenta, skin, and liver. Prenat. Diagn. 23, 85-87. Since cfDNA primarily originates from placental cytotrophoblasts, it is not expected that this abnormality would be detected using MPS. There were 1-2 small sub-chromosomal changes detected in these samples by MPS that were not reported in the karyotypes (Table 32).

Further Discussion

This example demonstrates that in non-mosaic cases, it is possible to obtain a full fetal molecular karyotype using MPS of maternal plasma cfDNA that is equivalent to CMA (chromosomal microarray), and in some cases is better than a metaphase karyotype obtained from chorionic villi or amniocytes. Such a non-invasive test could have immediate clinical utility, particularly in rural areas where invasive procedures are not readily available.

Using 25-mer tags at ~$10^9$ tags/sample, the results indicate that sufficient precision can be obtained between sequencing runs to reliably achieve 100 kb resolution across the genome. Even greater resolution can be achieved with deeper sequencing. The improvements in the v3 sequencing chemistry allowed for the use of 25-mer tags, compared to the 36-mers used in previous work. Bianchi, D. W., Platt, L. D., Goldberg, J. D., Abuhamad, A., Sehnert, A. J., Rava, R. P. (2012). Genome-wide fetal aneuploidy detection by maternal plasma DNA sequencing. Obstet. Gynecol. 119, 890-901. These short tags mapped with high efficiency across the genome, and the quantitative behavior demonstrated with the artificial mixture analyses validates the methodology. At today's costs, this depth of sequencing is approximately $1,000 per sample. This is comparable to the cost of a chromosome microarray result, but employs a risk-free blood draw rather than an invasive procedure. Deeper sequencing would allow for even finer resolution at an additional cost. Thus, this type of analysis could be implemented today as a reflex test when other clinical factors are present (such as sonographically-detected anomalies that are not typical of whole chromosome aneuploidy) when the patient declines an invasive procedure or prefers a blood test.

The lack of results on the mosaic samples (except for the artificial mixture) highlights the current limitations of both the microarray and MPS approaches. Sub-chromosomal abnormalities that originate in regions of the genome for which information is either unavailable in the genome build or highly repetitive will not be accessible for analysis. Such inaccessible genome regions are typically focused in the telomeres and centromeres of different chromosomes and in the short arms of acrocentric chromosomes. Also, the lower fetal fraction for the mosaic portion will be more challenging for detection and may require even deeper sequencing for effective classification.

Metaphase cytogenetic analysis from cell cultures, while considered "standard," has some limitations that need to be considered. For example, the ability to detect sub-chromosomal abnormalities is typically limited to sizes of 5 Mb or greater. This constraint is what led to the recent recommendation of using CMAs as a first tier test in clinical practice. Cell culture is biased towards the detection of more stable chromosomal configurations over significant structural alterations. In the case of fluorescence in situ hybridization (FISH), only the regions of the genome that are addressed by design of the FISH probes can be analyzed. Finally, as shown here, in actual clinical practice metaphase karyotypes can be reported to contain "chromosomal material of unknown origin." The MPS methodology of measuring copy number variation introduced in this work overcomes these limitations of karyotyping Importantly, our results showed that MPS was able to identify the potential source of the material of unknown origin for clinical samples C60193 and C61233. In addition, the MPS data showed small deletions in the termini of the chromosomes that the metaphase karyotype indicated were the breakpoints for the unknown chromosomal material in each of these samples. Such deletions at the breakpoints of translocations have been reported repeatedly in the literature. Howarth, K. D., Pole, J. C. M, Beavis, J. C., Batty, E. M., Newman, S., Bignell, G. R., and Edwards, P. A. W. (2011) Large duplications at reciprocal translocation breakpoints that might be the counterpart of large deletions and could arise from stalled replication bubbles. Genome Res. 21, 525-534. Based on these results, MPS may have the capabilities to identify both the presence of a sub-chromosomal duplication and suggest a translocation position based on small deletions (or duplications) elsewhere in the genome.

The methodologies described in this example also have applications beyond the determination of fetal sub-chromosomal abnormalities from cfDNA in maternal plasma. Ultimately, MPS can be applied to any mixed biological sample in which one wishes to determine the sub-chromosomal abnormalities in the minor component, even when the minor component represents only a few percent of the total DNA in the specimen. In prenatal diagnostics, samples obtained from chorionic villi could be analyzed for mosaic karyotypes or maternal contamination. Outside of prenatal diagnosis, many different cancers have been associated with copy number changes that could potentially be detected from cfDNA in the blood of the patient or a solid tumor sample that contains both normal and cancer cells. As the cost of MPS continues to drop, it is expected that its application for detecting sub-chromosomal abnormalities in mixed samples will find broad clinical utility.

Determination of fetal sub-chromosome abnormalities using deep sequencing of maternal plasma allows for a full molecular karyotype of the fetus to be determined noninvasively.

What is claimed is:

1. A method for classifying a copy number variation in a fetal genome, the method comprising:
    (a) receiving sequence reads from fetal and maternal nucleic acids in a maternal test sample obtained from a mother carrying a fetus, wherein the sequence reads are provided in an electronic format;
    (b) aligning the sequence reads to one or more bins from a reference sequence using a computing apparatus and thereby providing sequence tags corresponding to the sequence reads, wherein each bin contains a subsequence within the reference sequence;

(c) computationally identifying a number of those sequence tags that are from one or more bins by using the computing apparatus and determining that a first bin of interest in the fetal genome harbors a copy number variation;

(d) calculating a first fetal fraction value by a first method that does not use information from sequence tags from the first bin of interest;

(e) calculating a second fetal fraction value by a second method that uses information from the sequence tags from the first bin of interest, wherein the second method includes a ploidy assumption that the fetal genome has a complete aneuploidy within the subsequence of the first bin of interest; and (f) comparing the first fetal fraction value and the second fetal fraction value and using the comparison to classify the copy number variation of the first bin of interest in the fetal genome as harboring a complete aneuploidy or another type of copy number variation.

2. The method of claim 1, wherein the comparing the first fetal fraction value and the second fetal fraction value comprises determining whether the two fetal fraction values are approximately equal.

3. The method of claim 2, further comprising determining that the two fetal fraction values are approximately equal, and thereby determining that the ploidy assumption of the second method is true.

4. The method of claim 2, wherein comparing the first fetal fraction value and the second fetal fraction value indicates that the two fetal fraction values are not approximately equal, and further comprising analyzing the tag information for the first bin of interest to determine whether (i) the first bin of interest harbors a partial aneuploidy, or (ii) the fetus is a mosaic.

5. The method of claim 4, wherein analyzing the tag information for the first bin of interest comprises:
dividing the sequence for the first bin of interest into a plurality of sub-bins;
determining whether any of said sub-bins contains significantly more or significantly less nucleic acid than one or more other sub-bins; and
if any of said plurality of sub-bins contain significantly more or significantly less nucleic acid than one or more other sub-bins, determining that the first bin of interest harbors a partial aneuploidy.

6. The method of claim 5, further comprising determining that a sub-bin of the first bin of interest containing significantly more or significantly less nucleic acid than one or more other sub-bins harbors the partial aneuploidy.

7. The method of claim 4, wherein analyzing the tag information for the first bin of interest comprises:
dividing the sequence for the first bin of interest into a plurality of sub-bins;
determining whether any of said sub-bins contains significantly more or significantly less nucleic acid than one or more other sub-bins; and
if none of said sub-bins contain significantly more or significantly less nucleic acid than one or more other sub-bins, determining that the fetus is a mosaic.

8. The method of claim 1, wherein if the first fetal fraction value is not approximately equal to the second fetal fraction value,
(i) determining whether the copy number variation results from a partial aneuploidy or a mosaic; and
(ii) if the copy number variation results from a partial aneuploidy, determining a locus of the partial aneuploidy on the first bin of interest.

9. The method of claim 8, wherein determining the locus of the partial aneuploidy on the first bin of interest comprises categorizing the sequence tags for the first bin of interest into sub-bins of blocks of nucleic acids in the first bin of interest; and counting sequence tags in each sub-bin.

10. The method of claim 1, further comprising sequencing cell free DNA from the maternal test sample to provide the sequence reads.

11. The method of claim 10, further comprising obtaining the maternal test sample from a pregnant organism.

12. The method of claim 1, wherein the aligning in (b) comprises using the computing apparatus to align at least about 1 million reads.

13. A computer program product comprising a non-transitory computer readable medium on which is provided program instructions for classifying a copy number variation in a fetal genome, the program instructions comprising:
(a) code for receiving sequence reads from fetal and maternal nucleic acids in a maternal test sample obtained from a mother carrying a fetus, wherein the sequence reads are provided in an electronic format;
(b) code for aligning the sequence reads to one or more bins from a reference sequence using a computing apparatus and thereby providing sequence tags corresponding to the sequence reads, wherein each bin contains a subsequence within the reference sequence;
(c) code for computationally identifying a number of those sequence tags that are from one or more bins by using the computing apparatus and determining that a first bin of interest in the fetal genome harbors a copy number variation;
(d) code for calculating a first fetal fraction value by a first method that does not use information from sequence tags from the first bin of interest;
(e) code for calculating a second fetal fraction value by a second method that uses information from the sequence tags from the first bin of interest, wherein the second method includes a ploidy assumption that the fetal genome has a complete aneuploidy within the subsequence of the first bin of interest; and
(f) code for comparing the first fetal fraction value and the second fetal fraction value and using the comparison to classify the copy number variation of the first bin of interest in the fetal genome as harboring a complete aneuploidy or another type of copy number variation.

14. A system for classifying a copy number variation in a fetal genome, the system comprising:
(a) an interface for receiving at least about 10,000 sequence reads from fetal and maternal nucleic acids in a maternal test sample obtained from a mother carrying a fetus, wherein the sequence reads are provided in an electronic format;
(b) memory for storing, at least temporarily, a plurality of said sequence reads;
(c) a processor designed or configured with p(i) aligning the sequence reads to one or more reference sequences and thereby providing sequence tags corresponding to the sequence reads;
(ii) identifying a number of those sequence tags that are from one or more bins of interest and determining that a first bin of interest in the fetal genome harbors a copy number variation, wherein each bin contains a subsequence within the reference sequence;
(iii) calculating a first fetal fraction value by a first method that does not use information from sequence tags from the first bin of interest;

(iv) calculating a second fetal fraction value by a second method that uses information from the sequence tags from the first bin of interest, wherein the second method includes a ploidy assumption that the fetal genome has a complete aneuploidy within the subsequence of the first bin of interest; and (v) comparing the first fetal fraction value and the second fetal fraction value and using the comparison to classify the copy number variation of the first bin of interest in the fetal genome as harboring a complete aneuploidy or another type of copy number variation.

15. The computer program product of claim 13, wherein the comparing the first fetal fraction value and the second fetal fraction value comprises determining whether the two fetal fraction values are approximately equal.

16. The computer program product of claim 15, the program instructions further comprising instructions for determining that the two fetal fraction values are approximately equal, and thereby determining that the ploidy assumption of the second method is true.

17. The computer program product of claim 15, the program instructions further comprising instructions for determining that the two fetal fraction values are not approximately equal, and analyzing the tag information for the first bin of interest to determine whether (i) the first bin of interest harbors a partial aneuploidy, or (ii) the fetus is a mosaic.

18. The computer program product of claim 17, wherein analyzing the tag information for the first bin of interest comprises:

dividing the sequence for the first bin of interest into a plurality of sub-bins;

determining whether any of said sub-bins contains significantly more or significantly less nucleic acid than one or more other sub-bins; and if any of said plurality of sub-bins contain significantly more or significantly less nucleic acid than one or more other sub-bins, determining that the first bin of interest harbors a partial aneuploidy.

19. The computer program product of claim 17, wherein analyzing the tag information for the first bin of interest comprises:

dividing the sequence for the first bin of interest into a plurality of sub-bins;

determining whether any of said sub-bins contains significantly more or significantly less nucleic acid than one or more other sub-bins; and if none of said sub-bins contain significantly more or significantly less nucleic acid than one or more other sub-bins, determining that the fetus is a mosaic.

20. The system of claim 14, wherein the comparing the first fetal fraction value and the second fetal fraction value comprises determining whether the two fetal fraction values are approximately equal.

21. The system of claim 20, the program instructions further comprising instructions for determining that the two fetal fraction values are approximately equal, and thereby determining that the ploidy assumption of the second method is true.

22. The system of claim 20, the program instructions further comprising instructions for determining that the two fetal fraction values are not approximately equal, and analyzing the tag information for the first bin of interest to determine whether (i) the first bin of interest harbors a partial aneuploidy, or (ii) the fetus is a mosaic.

23. The system of claim 22, wherein analyzing the tag information for the first bin of interest comprises:

dividing the sequence for the first bin of interest into a plurality of sub-bins;

determining whether any of said sub-bins contains significantly more or significantly less nucleic acid than one or more other sub-bins; and if any of said plurality of sub-bins contain significantly more or significantly less nucleic acid than one or more other sub-bins, determining that the first bin of interest harbors a partial aneuploidy.

24. The system of claim 22, wherein analyzing the tag information for the first bin of interest comprises:

dividing the sequence for the first bin of interest into a plurality of sub-bins;

determining whether any of said sub-bins contains significantly more or significantly less nucleic acid than one or more other sub-bins; and if none of said sub-bins contain significantly more or significantly less nucleic acid than one or more other sub-bins, determining that the fetus is a mosaic.

* * * * *